US012564191B2

(12) United States Patent
Garza Sanchez et al.

(10) Patent No.: US 12,564,191 B2
(45) Date of Patent: Mar. 3, 2026

(54) PESTICIDAL COMPOUNDS

(71) Applicant: BASF SE, Ludwigshafen (DE)

(72) Inventors: Rosario Aleyda Garza Sanchez, Ludwigshafen (DE); Arun Narine, Ludwigshafen (DE); Rupsha Chaudhuri, Navi Mumbai (IN); Pulakesh Maity, Navi Mumbai (IN)

(73) Assignee: BASF SE, Ludwigshafen (DE)

( * ) Notice: Subject to any disclaimer, the term of this patent is extended or adjusted under 35 U.S.C. 154(b) by 627 days.

(21) Appl. No.: 17/920,786

(22) PCT Filed: Apr. 23, 2021

(86) PCT No.: PCT/EP2021/060686

§ 371 (c)(1),
(2) Date: Oct. 22, 2022

(87) PCT Pub. No.: WO2021/219513

PCT Pub. Date: Nov. 4, 2021

(65) Prior Publication Data

US 2023/0157287 A1 May 25, 2023

(30) Foreign Application Priority Data

Apr. 28, 2020 (IN) ............................. 202021018239
Jun. 9, 2020 (EP) ..................................... 20178893

(51) Int. Cl.

| | |
|---|---|
| ***A01N 43/40*** | (2006.01) |
| ***A01N 43/54*** | (2006.01) |
| ***A01N 43/58*** | (2006.01) |
| ***A01N 43/78*** | (2006.01) |
| ***A01N 47/34*** | (2006.01) |
| ***C07D 213/75*** | (2006.01) |
| ***C07D 239/26*** | (2006.01) |
| ***C07D 239/28*** | (2006.01) |
| ***C07D 239/42*** | (2006.01) |
| ***C07D 417/12*** | (2006.01) |

(52) U.S. Cl.

CPC ............. *A01N 43/40* (2013.01); *A01N 43/54* (2013.01); *A01N 43/58* (2013.01); *A01N 43/78* (2013.01); *A01N 47/34* (2013.01); *C07D 213/75* (2013.01); *C07D 239/26* (2013.01); *C07D 239/28* (2013.01); *C07D 239/42* (2013.01); *C07D 417/12* (2013.01)

(58) Field of Classification Search

CPC ........ A01N 43/40; A01N 43/54; A01N 43/58; A01N 43/78; A01N 47/34; C07D 239/26; C07D 239/28; C07D 239/42; C07D 417/12; C07D 213/75

See application file for complete search history.

(56) References Cited

U.S. PATENT DOCUMENTS

| | | | |
|---|---|---|---|
| 3,296,272 | A | 1/1967 | Johnston |
| 3,325,503 | A | 6/1967 | Bimber |
| 4,617,303 | A | 10/1986 | Eicken et al. |
| 4,840,959 | A | 6/1989 | Oda et al. |
| 4,863,734 | A | 9/1989 | Pommer et al. |
| 4,914,128 | A | 4/1990 | Schirmer et al. |
| 5,026,417 | A | 6/1991 | Kucey |
| 5,091,539 | A | 2/1992 | Makisumi et al. |
| 5,268,488 | A | 12/1993 | Watanabe et al. |
| 6,313,147 | B1 | 11/2001 | Shaber et al. |
| 6,406,690 | B1 | 6/2002 | Peleg et al. |
| 6,448,228 | B1 | 9/2002 | Filippini et al. |
| 6,537,948 | B1 | 3/2003 | Tohyama et al. |
| 6,812,229 | B1 | 11/2004 | Ozaki et al. |
| 6,994,849 | B2 | 2/2006 | Droby |
| 8,445,255 | B2 | 5/2013 | Kloepper et al. |

(Continued)

FOREIGN PATENT DOCUMENTS

| | | |
|---|---|---|
| AU | 608221 B2 | 3/1991 |
| AU | 623996 B2 | 5/1992 |

(Continued)

OTHER PUBLICATIONS

International Application No. PCT/EP2021/060686, International Search Report and Written Opinion, mailed May 20, 2021.
Altug et al., Reactions of alkylidenepyrrolidines with a-chlorooximes and a-chlorohydrazones, Tetrahedron Letters, 50 (52) : 7392-7394 (2009).
Anastasiadis et al., The combined effect of the application of a biocontrol agent Paecilomyces lilacinus, with various practices for the control of root-knot nematodes, Crop Protection, 27(3-5):352-61 (2008).

(Continued)

*Primary Examiner* — Ali Soroush
*Assistant Examiner* — Andriae M Holt
(74) *Attorney, Agent, or Firm* — MARSHALL, GERSTEIN & BORUN LLP

(57) ABSTRACT

The present application relates to the compounds of formula (I), and the N-oxides, stereoisomers, tautomers and agriculturally or veterinarily acceptable salts thereof wherein the variables are defined in the claims. The compounds of formula (I), as well as the N-oxides, stereoisomers tautomers and agriculturally or veterinarily acceptable salts thereof are useful for combating or controlling invertebrate pests, in particular arthropod pests and nematodes. The application also relates to a method for controlling invertebrate pests by using these compounds and to plant propagation material and to an agricultural and a veterinary composition comprising said compounds.

(I)

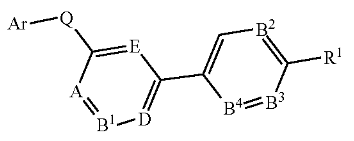

14 Claims, No Drawings

(56) References Cited

U.S. PATENT DOCUMENTS

| | | | |
|---|---|---|---|
| 2001/0007876 | A1 | 7/2001 | Alig et al. |
| 2001/0046994 | A1 | 11/2001 | Wu et al. |
| 2002/0102582 | A1 | 8/2002 | Levine |
| 2003/0097687 | A1 | 5/2003 | Trolinder et al. |
| 2003/0114311 | A1 | 6/2003 | Balko et al. |
| 2003/0120054 | A1 | 6/2003 | Chen et al. |
| 2003/0126634 | A1 | 7/2003 | Spencer et al. |
| 2004/0044040 | A1 | 3/2004 | Neubert et al. |
| 2004/0192672 | A1 | 9/2004 | Wegmann et al. |
| 2004/0204470 | A1 | 10/2004 | Elbe et al. |
| 2005/0032650 | A1 | 2/2005 | Tanaka et al. |
| 2005/0037925 | A1 | 2/2005 | Tsukamoto et al. |
| 2005/0070439 | A1 | 3/2005 | Kobori et al. |
| 2005/0143428 | A1 | 6/2005 | Dunkel et al. |
| 2005/0221989 | A1 | 10/2005 | Ehrenfreund et al. |
| 2006/0095986 | A1 | 5/2006 | Cavato et al. |
| 2006/0282911 | A1 | 12/2006 | Bull et al. |
| 2007/0292854 | A1 | 12/2007 | Behr et al. |
| 2008/0260932 | A1 | 10/2008 | Anderson et al. |
| 2009/0118346 | A1 | 5/2009 | Dunkel et al. |
| 2010/0222319 | A1 | 9/2010 | Bernhart et al. |
| 2010/0260735 | A1 | 10/2010 | Bais et al. |
| 2011/0067141 | A1 | 3/2011 | Froman et al. |
| 2011/0154523 | A1 | 6/2011 | Diehn et al. |
| 2012/0117676 | A1 | 5/2012 | Carlson et al. |
| 2012/0149571 | A1 | 6/2012 | Kloepper et al. |
| 2012/0202687 | A1 | 8/2012 | Crouse et al. |
| 2012/0289702 | A1 | 11/2012 | Shibayama et al. |
| 2013/0061346 | A1 | 3/2013 | Bard et al. |
| 2013/0203592 | A1 | 8/2013 | Fischer et al. |
| 2013/0236522 | A1 | 9/2013 | Misumi |
| 2014/0328994 | A1 | 11/2014 | Clark et al. |
| 2015/0196033 | A1 | 7/2015 | Crouse et al. |
| 2016/0222001 | A1 | 8/2016 | Barrow et al. |
| 2016/0330923 | A1 | 11/2016 | Weeks et al. |
| 2016/0345581 | A1 | 12/2016 | Soergel et al. |
| 2019/0161501 | A1 | 5/2019 | Tobinaga et al. |
| 2020/0077658 | A1 | 3/2020 | Sambasivan et al. |
| 2020/0163336 | A1 | 5/2020 | Nishio et al. |

FOREIGN PATENT DOCUMENTS

| | | | |
|---|---|---|---|
| AU | 642865 | B2 | 11/1993 |
| CA | 2471555 | A1 | 12/2005 |
| CN | 1309897 | A | 8/2001 |
| CN | 1456054 | A | 11/2003 |
| CN | 1907024 | A | 2/2007 |
| CN | 101715770 | A | 6/2010 |
| CN | 102126994 | A | 7/2011 |
| CN | 103387541 | A | 11/2013 |
| CN | 103814937 | A | 5/2014 |
| CN | 106167482 | A | 11/2016 |
| CN | 106928216 | A | 7/2017 |
| CN | 110291072 | A | 9/2019 |
| DE | 19650197 | A1 | 6/1998 |
| DE | 10021412 | A1 | 6/2001 |
| DE | 102005009458 | A1 | 9/2006 |
| EP | 0141317 | A2 | 5/1985 |
| EP | 0152031 | A2 | 8/1985 |
| EP | 0226917 | A1 | 7/1987 |
| EP | 0243970 | A1 | 11/1987 |
| EP | 0256503 | A2 | 2/1988 |
| EP | 0307510 | A2 | 3/1989 |
| EP | 0374753 | A2 | 6/1990 |
| EP | 0392225 | A2 | 10/1990 |
| EP | 0427529 | A1 | 5/1991 |
| EP | 0428941 | A1 | 5/1991 |
| EP | 0451878 | A1 | 10/1991 |
| EP | 0532022 | A1 | 3/1993 |
| EP | 0585215 | A1 | 3/1994 |
| EP | 0945453 | A1 | 9/1999 |
| EP | 1028125 | A1 | 8/2000 |
| EP | 1035122 | A1 | 9/2000 |
| EP | 1122244 | A1 | 8/2001 |
| EP | 1201648 | A1 | 5/2002 |
| EP | 2754659 | A1 | 7/2014 |
| EP | 2865265 | A1 | 4/2015 |
| EP | 2910126 | A1 | 8/2015 |
| JP | 2002-316902 | A | 10/2002 |
| NZ | 231804 | A | 3/1993 |
| WO | 91/02051 | A1 | 2/1991 |
| WO | 91/07481 | A1 | 5/1991 |
| WO | 93/07278 | A1 | 4/1993 |
| WO | 94/01546 | A1 | 1/1994 |
| WO | 95/17806 | A1 | 7/1995 |
| WO | 95/34656 | A1 | 12/1995 |
| WO | 96/21358 | A1 | 7/1996 |
| WO | 98/44140 | A1 | 10/1998 |
| WO | 98/46608 | A1 | 10/1998 |
| WO | 99/14187 | A1 | 3/1999 |
| WO | 99/24413 | A2 | 5/1999 |
| WO | 99/27783 | A1 | 6/1999 |
| WO | 00/26345 | A1 | 5/2000 |
| WO | 00/26356 | A1 | 5/2000 |
| WO | 00/29404 | A1 | 5/2000 |
| WO | 00/46148 | A1 | 8/2000 |
| WO | 00/65913 | A1 | 11/2000 |
| WO | 01/31042 | A2 | 5/2001 |
| WO | 01/41558 | A1 | 6/2001 |
| WO | 01/54501 | A2 | 8/2001 |
| WO | 01/56358 | A2 | 8/2001 |
| WO | 02/00163 | A2 | 1/2002 |
| WO | 02/15701 | A2 | 2/2002 |
| WO | 02/22583 | A2 | 3/2002 |
| WO | 02/34946 | A2 | 5/2002 |
| WO | 02/36831 | A2 | 5/2002 |
| WO | 02/40431 | A2 | 5/2002 |
| WO | 03/10149 | A1 | 2/2003 |
| WO | 03/11853 | A1 | 2/2003 |
| WO | 03/13224 | A2 | 2/2003 |
| WO | 03/14103 | A1 | 2/2003 |
| WO | 03/16286 | A1 | 2/2003 |
| WO | 03/16303 | A1 | 2/2003 |
| WO | 03/18810 | A2 | 3/2003 |
| WO | 03/52073 | A2 | 6/2003 |
| WO | 03/53145 | A1 | 7/2003 |
| WO | 03/61388 | A1 | 7/2003 |
| WO | 03/66609 | A1 | 8/2003 |
| WO | 03/74491 | A1 | 9/2003 |
| WO | 2004/011601 | A2 | 2/2004 |
| WO | 2004/039986 | A1 | 5/2004 |
| WO | 2004/049804 | A2 | 6/2004 |
| WO | 2004/072235 | A2 | 8/2004 |
| WO | 2004/074492 | A1 | 9/2004 |
| WO | 2004/083193 | A1 | 9/2004 |
| WO | 2004/099447 | A2 | 11/2004 |
| WO | 2005/059103 | A2 | 6/2005 |
| WO | WO-2005/054199 | A1 | 6/2005 |
| WO | 2005/061720 | A2 | 7/2005 |
| WO | 2005/063721 | A1 | 7/2005 |
| WO | 2005/087772 | A1 | 9/2005 |
| WO | 2005/087773 | A1 | 9/2005 |
| WO | 2005/103266 | A1 | 11/2005 |
| WO | 2005/103301 | A2 | 11/2005 |
| WO | 2005/120234 | A2 | 12/2005 |
| WO | 2005/123689 | A1 | 12/2005 |
| WO | 2005/123690 | A1 | 12/2005 |
| WO | 2006/015866 | A1 | 2/2006 |
| WO | 2006/039376 | A2 | 4/2006 |
| WO | 2006/043635 | A1 | 4/2006 |
| WO | WO-2006/067466 | A2 | 6/2006 |
| WO | 2006/087325 | A1 | 8/2006 |
| WO | 2006/087343 | A1 | 8/2006 |
| WO | 2006/089633 | A2 | 8/2006 |
| WO | 2006/098952 | A2 | 9/2006 |
| WO | 2006/108674 | A2 | 10/2006 |
| WO | 2006/108675 | A2 | 10/2006 |
| WO | 2006/128573 | A2 | 12/2006 |
| WO | 2006/130436 | A2 | 12/2006 |
| WO | 2007/006670 | A1 | 1/2007 |
| WO | 2007/017186 | A1 | 2/2007 |
| WO | 2007/043677 | A1 | 4/2007 |
| WO | 2007/082098 | A2 | 7/2007 |
| WO | 2007/090624 | A2 | 8/2007 |

(56) References Cited

FOREIGN PATENT DOCUMENTS

| | | | |
|---|---|---|---|
| WO | WO-2007/093599 | A1 | 8/2007 |
| WO | 2007/101369 | A1 | 9/2007 |
| WO | 2007/101540 | A1 | 9/2007 |
| WO | 2007/129454 | A1 | 11/2007 |
| WO | 2007/140256 | A1 | 12/2007 |
| WO | 2007/142840 | A2 | 12/2007 |
| WO | 2008/002872 | A2 | 1/2008 |
| WO | 2008/013622 | A2 | 1/2008 |
| WO | 2008/054747 | A2 | 5/2008 |
| WO | 2008/067911 | A1 | 6/2008 |
| WO | 2008/112019 | A2 | 9/2008 |
| WO | 2008/122406 | A1 | 10/2008 |
| WO | 2008/124849 | A2 | 10/2008 |
| WO | 2008/130953 | A2 | 10/2008 |
| WO | 2008/134969 | A1 | 11/2008 |
| WO | 2008/151780 | A1 | 12/2008 |
| WO | 2009/064652 | A1 | 5/2009 |
| WO | WO-2009/074749 | A2 | 6/2009 |
| WO | 2009/090181 | A2 | 7/2009 |
| WO | 2009/094442 | A2 | 7/2009 |
| WO | 2009/102873 | A1 | 8/2009 |
| WO | 2009/103049 | A2 | 8/2009 |
| WO | WO-2009/102736 | A1 | 8/2009 |
| WO | 2009/111263 | A1 | 9/2009 |
| WO | 2009/124707 | A2 | 10/2009 |
| WO | 2009/126473 | A1 | 10/2009 |
| WO | 2009/135299 | A1 | 11/2009 |
| WO | 2009/158026 | A1 | 12/2009 |
| WO | 2010/006713 | A2 | 1/2010 |
| WO | 2010/037016 | A1 | 4/2010 |
| WO | 2010/060379 | A1 | 6/2010 |
| WO | 2010/069882 | A1 | 6/2010 |
| WO | 2010/077816 | A1 | 7/2010 |
| WO | 2010/080829 | A1 | 7/2010 |
| WO | 2010/093764 | A1 | 8/2010 |
| WO | 2010/127926 | A1 | 11/2010 |
| WO | 2010/139271 | A1 | 12/2010 |
| WO | 2011/022469 | A2 | 2/2011 |
| WO | 2011/028657 | A1 | 3/2011 |
| WO | 2011/034704 | A1 | 3/2011 |
| WO | 2011/062904 | A1 | 5/2011 |
| WO | 2011/066384 | A1 | 6/2011 |
| WO | 2011/077514 | A1 | 6/2011 |
| WO | 2011/081174 | A1 | 7/2011 |
| WO | 2011/084621 | A1 | 7/2011 |
| WO | 2011/085575 | A1 | 7/2011 |
| WO | 2011/109395 | A2 | 9/2011 |
| WO | 2011/135833 | A1 | 11/2011 |
| WO | 2011/153186 | A1 | 12/2011 |
| WO | 2012/000896 | A2 | 1/2012 |
| WO | 2012/034403 | A1 | 3/2012 |
| WO | 2012/051199 | A2 | 4/2012 |
| WO | WO-2012/049190 | A1 | 4/2012 |
| WO | WO-2012/062844 | A1 | 5/2012 |
| WO | 2012/082548 | A2 | 6/2012 |
| WO | 2012/084812 | A1 | 6/2012 |
| WO | 2012/126766 | A1 | 9/2012 |
| WO | 2012/134808 | A1 | 10/2012 |
| WO | 2012/143317 | A1 | 10/2012 |
| WO | 2012/165511 | A1 | 12/2012 |
| WO | 2012/168188 | A1 | 12/2012 |
| WO | 2013/003558 | A1 | 1/2013 |
| WO | 2013/003977 | A1 | 1/2013 |
| WO | 2013/007767 | A1 | 1/2013 |
| WO | 2013/009791 | A1 | 1/2013 |
| WO | 2013/010862 | A1 | 1/2013 |
| WO | 2013/016516 | A1 | 1/2013 |
| WO | 2013/016527 | A1 | 1/2013 |
| WO | 2013/024009 | A1 | 2/2013 |
| WO | 2013/024010 | A1 | 2/2013 |
| WO | 2013/032693 | A2 | 3/2013 |
| WO | 2013/047441 | A1 | 4/2013 |
| WO | 2013/047749 | A1 | 4/2013 |
| WO | 2013/050317 | A1 | 4/2013 |
| WO | 2013/092224 | A1 | 6/2013 |
| WO | 2013/112527 | A1 | 8/2013 |
| WO | 2013/116052 | A1 | 8/2013 |
| WO | 2013/116053 | A1 | 8/2013 |
| WO | 2013/116251 | A2 | 8/2013 |
| WO | 2013/127704 | A1 | 9/2013 |
| WO | 2013/162072 | A1 | 10/2013 |
| WO | 2013/169923 | A2 | 11/2013 |
| WO | 2014/007217 | A1 | 1/2014 |
| WO | 2014/011429 | A1 | 1/2014 |
| WO | 2014/029697 | A1 | 2/2014 |
| WO | 2014/060177 | A1 | 4/2014 |
| WO | 2014/116854 | A1 | 7/2014 |
| WO | 2014/124369 | A1 | 8/2014 |
| WO | 2014/178910 | A1 | 11/2014 |
| WO | 2014/178913 | A1 | 11/2014 |
| WO | 2014/178941 | A1 | 11/2014 |
| WO | 2014/179276 | A1 | 11/2014 |
| WO | 2014/201235 | A2 | 12/2014 |
| WO | 2015/038503 | A1 | 3/2015 |
| WO | 2015/053998 | A1 | 4/2015 |
| WO | 2015/059039 | A1 | 4/2015 |
| WO | 2015/065922 | A1 | 5/2015 |
| WO | 2015/142571 | A1 | 9/2015 |
| WO | WO-2015169734 | A1 | 11/2015 |
| WO | 2015/190316 | A1 | 12/2015 |
| WO | 2016/020371 | A1 | 2/2016 |
| WO | WO-2016/116445 | A1 | 7/2016 |
| WO | 2016/123577 | A1 | 8/2016 |
| WO | 2016/150193 | A1 | 9/2016 |
| WO | WO-2016/156076 | A1 | 10/2016 |
| WO | WO-2016/167795 | A1 | 10/2016 |
| WO | 2016/183445 | A1 | 11/2016 |
| WO | 2017/062825 | A1 | 4/2017 |
| WO | 2017/062831 | A1 | 4/2017 |
| WO | 2017/198196 | A1 | 11/2017 |
| WO | 2017/209155 | A1 | 12/2017 |
| WO | 2017/214269 | A1 | 12/2017 |
| WO | 2018/021447 | A1 | 2/2018 |
| WO | 2018/052136 | A1 | 3/2018 |
| WO | 2018/059534 | A1 | 4/2018 |
| WO | 2018/084321 | A1 | 5/2018 |
| WO | 2018/110497 | A1 | 6/2018 |
| WO | 2018/177781 | A1 | 10/2018 |
| WO | 2018/177970 | A1 | 10/2018 |
| WO | WO-2020/083733 | A1 | 4/2020 |
| WO | WO-2020/109039 | A1 | 6/2020 |

OTHER PUBLICATIONS

Arias et al., Molecular evolution of herbicide resistance to phytoene desaturase inhibitors in Hydrilla verticillata and its potential use to generate herbicide-resistant crops, Pest Manag. Sci., 61(3):258-68 (2005).

Barcellos et al., Evidence of horizontal transfer of symbiotic genes from a Bradyrhizobium japonicum inoculant strain to indigenous diazotrophs Sinorhizobium (Ensifer) fredii and Bradyrhizobium elkanii in a Brazilian Savannah soil, Appl. Environ. Microbiol., 73(8):2635-43 (2007).

Beckie et al., Response of alfalfa to inoculation with Penicillium bilaii (Provide), Can. J. Plant Sci., 78(1):91-102 (1998).

Behrens et al., Dicamba resistance: enlarging and preserving biotechnology-based weed management strategies, Weed Sci., 316:1185-8 (2007).

Cassan et al., Azospirillum brasilense Az39 and Bradyrhizobium japonicum E109, inoculated singly or in combination, promote seed germination and early seedling growth in corn (*Zea mays* L.) and soybean (*Glycine max* L.), Eur. J. Soil Biol., 45(1):28-35 (2009).

Catalogue of Pesticide Formulation types and International Coding System, Croplife Technical Monograph No. 2, 6th Edition, May 2008.

Crimmin et al., Synthesis and coordination chemistry of tri-substituted benzamidrazones, Dalton Trans., 40 (2) : 514-522 (2011).

Dill et al., Glyphosate-resistant crops: adoption, use and future considerations, Pest Manag. Sci., 64(4):326-31 (2008).

Dunlap et al., Bacillus velezensis is not a later heterotypic synonym of Bacillus amyloliquefaciens; Bacillus methylotrophicus, Bacillus

(56) References Cited

OTHER PUBLICATIONS amyloliquefaciens subsp. plantarum and 'Bacillus oryzicola' are later heterotypic synonyms of Bacillus velezensis based on phylogenomics, International Journal of Systematic and Evolutionary Microbiology, 66(3) : 1212-1217(2016).
Fall et al., A Simple Method to Isolate Biofilm-forming Bacillus subtilis and Related Species from Plant Roots, System. Appl. Microbiol., 27:372-379 (2004).
Federal Register, 76(22) : 5679-6048 (2011).
Goos et al., Penicillium bilaji and phosphorus fertilization effects on the growth, development, yield and common root rot severity of spring wheat, Fertilizer Res., 39:97-103 (1994).
Green et al., New multiple-herbicide crop resistance and formulation technology to augment the utility of glyphosate, Pest Manag. Sci., 64(4):332-9 (2008).
Green, Evolution of glyphosate-resistant crop technology, Weed Sci., 57:108-17 (2009).
Hume et al., Superior Performance of The HUP-Bradyrhizobium japonicum Strain 532C in Ontario Soybean Field Trials, Can. J. Plant Sci., 70(3):661-66 (1990).
Hungria et al., Inoculation with selected strains of Azospirillum brasilense and A. lipoferum improves yields of maize and wheat in Brazil, Plant Soil, 331:413-25 (2010).
Intention to Grant, EP App. No. 21720500, Jan. 2, 2024, 7 pages.
International Application No. PCT/EP2021/060686, International Preliminary Report on Patentability, mailed Nov. 10, 2022.
Inui et al., Herbicide resistance in transgenic plants with mammalian P450 monooxygenase genes, Pest Manag. Sci., 61(3):286-91 (2005).
Krebs et al., Use of Bacillus subtilis as biocontrol agent. I. Activities and characterization of Bacillus subtillis strains, J. Plant Dis. Protection, 105(2): 181-97 (1998).
Laurent et al., Bisbenzamidines as Antifungal Agents. Are Both Amidine Functions Required to Observe an Anti-Pneumocystis carinii Activity?, Molecules, 15(6) : 4283-4293(2010).
Li et al., Development of PPO inhibitor-resistant cultures and crops, Pest Manag. Sci., 61(3):277-85 (2005).
Liu et al., The discovery of HNPC-A3066: a novel strobilurin acaricide, Pest. Manag. Sci., 65(3) : 229-234(2009).
Matringe et al., p-Hydroxyphenylpyruvate dioxygenase inhibitor-resistant plants, Pest Manag. Sci., 61(3):269-76 (2005).
Melchiorre et al., Evaluation of bradyrhizobia strains isolated from field-grown soybean plants in Argentina as improved inoculants, Biol. Fertil. Soils, 47(1):81-9 (2011).
Mills et al., Determination of selective action of fungicides on the microflora of barley seed, Plant Sci., 48(6):587-94 (1968).
Mollet and Grube-mann, Formulation technology, Wiley VCH, Weinheim, (pp. 30)2001.
Rowleys et al., Genetic variation and virulence of nucleopolyhedroviruses isolated worldwide from the heliothine pests Helicoverpa armigera, Helicoverpa zea, and Heliothis virescens, Journal of Invertebrate Pathology, 107(2):112-126 (2011).
Sanders et al., Metal-free sequential [3 + 2]-dipolar cycloadditions using cyclooctynes and 1,3-dipoles of different reactivity, J. Am. Chem. Soc., 133(4): 949-957(2011).
Stauderman et al., Evaluation of Isaria fumosorosea (Hypocreales: Cordycipitaceae) for control of the Asian citrus psyllid, Diaphorina citri (Hemiptera: Psyllidae), Biocontrol Science Technology, 22(7):747-61 (2012).
Tan et al., Imidazolinone-tolerant crops: history, current status and future, Pest Manag. Sci., 61:246-57 (2005).
Vitale et al., Evaluation of Trichoderma harzianum strain T22 as biological control agent of Calonectria pauciramosa, BioControl., 57:687-696 (2012).
Wehn et al., Facile Synthesis of Substituted 5-Amino- and 3-Amino-1,2,4-Thiadiazoles from a Common Precursor, Org. Lett., 11(24):5666-5669(2009).
Wei et al., Harpin, Elicitor of the Hypersensitive Response Produced by the Plant Pathogen Erwinia amylovora, Science, 257:85-88 (1992).
Williams et al., Differences in zoospore germination and host penetration in response to temperature among Western Australian isolates of Plasmopara viticola, Australian Journal of Agricultural Research, 58:702-710 (2007).
Arvanitis, et al., "Imidazo[4,5-b]pyridines as corticotropin releasing factor receptor ligands", Bioorganic & Medicinal Chemistry Letters, vol. 13, Issue 1, Jan. 2003, pp. 125-128.
Burns, et al., "Discovery of CYT997: a structurally novel orally active microtubule targeting agent", Bioorganic & Medicinal Chemistry Letters, vol. 19, Issue 16, Aug. 15, 2009, pp. 4639-4642.
European Search Report for EP Patent Application No. 20178893.2, Issued on Oct. 12, 2020, 9 pages.
Keche, et al., "A novel pyrimidine derivatives with aryl urea, thiourea and sulfonamide moieties: Synthesis, anti-inflammatory and antimicrobial evaluation", Bioorganic & Medicinal Chemistry Letters, vol. 22, Issue 10, May 22, 2012, pp. 3445-3448.

PESTICIDAL COMPOUNDS

CROSS-REFERENCE TO RELATED APPLICATIONS

This is the U.S. national phase of International Application No. PCT/EP2021/060686, filed Apr. 23, 2021, which claims the benefit of Indian Patent Application No. 202021018239, filed on Apr. 28, 2020, and European Patent Application No. 20178893.2, filed on Jun. 9, 2020.

Invertebrate pests and in particular insects, arachnids and nematodes destroy growing and harvested crops and attack wooden dwelling and commercial structures, thereby causing large economic loss to the food supply and to property. Accordingly, there is an ongoing need for new agents for combating invertebrate pests.

Carbamoylated and thiocarbamoylated oxime derivatives are known for pesticidal use, for example, in patent publications WO 2016/156076, semi-carbazones and thiosemicarbazones derivatives are known for pesticidal use in patent publication WO 2016/116445.

Due to the ability of target pests to develop resistance to pesticidally-active agents, there is an ongoing need to identify further compounds, which are suitable for combating invertebrate pests such as insects, arachnids and nematodes. Furthermore, there is a need for new compounds having a high pesticidal activity and showing a broad activity spectrum against a large number of different invertebrate pests, especially against difficult to control insects, arachnids and nematodes.

It is therefore an object of the present invention to identify and provide compounds, which exhibit a high pesticidal activity and have a broad activity spectrum against invertebrate pests.

It has been found that these objects can be achieved by substituted bicyclic compounds of formula I, as depicted and defined below, including their stereoisomers, their salts, in particular their agriculturally or veterinarily acceptable salts, their tautomers and their N-oxides.

In a first aspect, the present invention relates to the compounds of formula I,

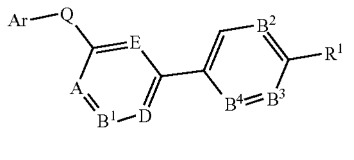

(I)

Wherein

A is N or $CR^A$;

$B^1$ is N or $CR^{B1}$;

D is N or $CR^D$;

E is N or $CR^E$;

wherein at least one of the A, $B^1$, E, and D is N; and when A and D are N, $B^1$ is $CR^{B1}$;

$B^2$ is N or $CR^{B2}$;

$B^3$ is N or $CR^{B3}$;

$B^4$ is N or $CR^{B4}$;

provided that at least one of the $B^2$, $B^3$, and $B^4$ is other than N;

$R^A$, $R^D$, $R^{B1}$, and $R^E$ independently of each other are H, halogen, $N_3$, OH, CN, $NO_2$, —SCN, —$SF_5$, $C_1$-$C_6$-alkyl, $C_1$-$C_6$-alkoxy, $C_2$-$C_6$-alkenyl, tri-$C_1$-$C_6$-alkylsilyl, $C_2$-$C_6$-alkynyl, $C_1$-$C_6$-alkoxy-$C_1$-$C_4$-alkyl, $C_1$-$C_6$-alkoxy-$C_1$-$C_4$-alkoxy, $C_3$-$C_6$-cycloalkyl, $C_3$-$C_6$-cycloalkoxy, $C_3$-$C_6$-cycloalkyl-$C_1$-$C_4$-alkyl, $C_1$-$C_4$-alkyl-$C_3$-$C_6$-cycloalkoxy, which moieties are unsubstituted or substituted with halogen, C(═O)—$OR^a$, $NR^bR^c$, $C_1$-$C_6$-alkylene-$NR^bR^c$, O—$C_1$-$C_6$-alkylene-$NR^bR^c$, $C_1$-$C_6$-alkylene-CN, NH—$C_1$-$C_6$-alkylene-$NR^bR^c$, C(═O)—$NR^bR^c$, C(═O)—$R^d$, $SO_2NR^bR^c$, or $S(═O)_mR^e$, phenyl, phenoxy, phenylcarbonyl, phenylthio, or —$CH_2$-phenyl, wherein the phenyl rings are unsubstituted or substituted with $R^f$;

$R^{B2}$, $R^{B3}$, and $R^{B4}$ independently of each other are H, halogen, $N_3$, OH, CN, $NO_2$, —SCN, —$SF_5$, $C_1$-$C_6$-alkyl, $C_1$-$C_6$-alkoxy, $C_2$-$C_6$-alkenyl, tri-$C_1$-$C_6$-alkylsilyl, $C_2$-$C_6$-alkynyl, $C_1$-$C_6$-alkoxy-$C_1$-$C_4$-alkyl, $C_1$-$C_6$-alkoxy-$C_1$-$C_4$-alkoxy, $C_3$-$C_6$-cycloalkyl, $C_3$-$C_6$-cycloalkoxy, $C_3$-$C_6$-cycloalkyl-$C_1$-$C_4$-alkyl, $C_1$-$C_4$-alkyl-$C_3$-$C_6$-cycloalkoxy, which moieties are unsubstituted or substituted with halogen, C(═O)—$OR^a$, $NR^bR^c$, $C_1$-$C_6$-alkylene-$NR^bR^c$, O—$C_1$-$C_6$-alkylene-$NR^bR^c$, $C_1$-$C_6$-alkylene-CN, NH—$C_1$-$C_6$-alkylene-$NR^bR^c$, C(═O)—$NR^bR^c$, C(═O)—$R^d$, $SO_2NR^bR^c$, or $S(═O)_mR^e$, phenyl, phenoxy, phenylcarbonyl, phenylthio, or —$CH_2$-phenyl, wherein the phenyl rings are unsubstituted or substituted with $R^f$;

Q is —$C(R^4R^5)$—O—, —C(═O)—O—, —$S(═O)_m$—$C(R^7R^8)$—, $N(R^2)$—$S(═O)_m$—, —$N(R^2)$—$C(R^9R^{10})$—, —C(═O)—$C(R^{19}R^{20})$—, —$N(R^2)$—, —$N(R^2)$—C(═O)—, —$N(R^2)$—C(═S)—, —$C(R^{13}R^{14})$—$C(R^{15}R^{16})$—, —N═C(X)—, —$N(R^2)$—C(═NR)—, or —$C(R^{17})$═$C(R^{18})$—; wherein Ar is bound to either side of Q;

m is 0, 1, or 2;

X is H, halogen, $SR^7$, $OR^8$, or $N(R^3)_2$;

R is H, CN, $C_1$-$C_6$-alkyl, $C_2$-$C_6$-alkenyl, $C_2$-$C_6$-alkynyl, or $C_3$-$C_6$-cycloalkyl, which moieties are unsubstituted or substituted with halogen, $OR^8$, $N(R^3)_2$;

$R^3$ is H, $C_1$-$C_6$-alkyl, or $C_1$-$C_6$-alkoxy-$C_1$-$C_4$-alkyl;

$R^2$ is H, $C_1$-$C_6$-alkyl, $C_2$-$C_6$-alkenyl, $C_2$-$C_6$-alkynyl, $C_1$-$C_6$-alkoxy-$C_1$-$C_4$-alkyl, $C_3$-$C_6$-cycloalkyl, $C_3$-$C_6$-cycloalkyl-$C_1$-$C_4$-alkyl, $C_3$-$C_6$-cycloalkoxy-$C_1$-$C_4$-alkyl, which moieties are unsubstituted or substituted with halogen, C(═O)—$OR^a$, $C_1$-$C_6$-alkylene-$NR^bR^c$, $C_1$-$C_6$-alkylene-CN, C(═O)—$NR^bR^c$, C(═O)—$R^d$, $SO_2NR^bR^c$, $S(═O)_mR^e$, phenyl, or —$CH_2$-phenyl, wherein the phenyl rings are unsubstituted or substituted with $R^f$;

$R^4$, $R^5$, $R^7$, $R^8$, $R^9$, $R^{10}$, $R^{13}$, $R^{14}$, $R^{15}$, $R^{16}$, $R^{17}$, $R^{18}$, $R^{19}$, $R^{20}$ are, identical or different, H, halogen, $C_1$-$C_6$-alkyl, $C_2$-$C_6$-alkenyl, $C_2$-$C_6$-alkynyl, $C_1$-$C_6$-alkoxy-$C_1$-$C_4$-alkyl, $C_3$-$C_6$-cycloalkyl, $C_3$-$C_6$-cycloalkyl-$C_1$-$C_4$-alkyl, $C_3$-$C_6$-cycloalkoxy-$C_1$-$C_4$-alkyl, which moieties are unsubstituted or substituted with halogen, C(═O)—$OR^a$, $C_1$-$C_6$-alkylene-$NR^bR^c$, $C_1$-$C_6$-alkylene-CN, C(═O)—$NR^bR^c$, C(═O)—$R^d$, $SO_2NR^bR^c$, $S(═O)_mR^e$, phenyl, or —$CH_2$-phenyl, wherein the phenyl rings are unsubstituted or substituted with $R^f$;

Ar is phenyl or 5- or 6-membered hetaryl or 1,3-benzodioxole, which are unsubstituted or substituted with $R^{Ar}$, wherein $R^{Ar}$ is halogen, $N_3$, OH, CN, $NO_2$, —SCN, —$SF_5$, $C_1$-$C_6$-alkyl, $C_1$-$C_6$-alkoxy, $C_2$-$C_6$-alkenyl, tri-$C_1$-$C_6$-alkylsilyl, $C_2$-$C_6$-alkynyl, $C_1$-$C_6$-alkoxy-$C_1$-$C_4$-alkyl, $C_1$-$C_6$-alkoxy-$C_1$-$C_4$-alkoxy, $C_3$-$C_6$-cycloalkyl, $C_3$-$C_6$-cycloalkoxy, $C_3$-$C_6$-cycloalkyl-$C_1$-$C_4$-alkyl, $C_3$-$C_6$- cycloalkoxy-$C_1$-$C_4$-alkyl, which moieties are unsubstituted or substituted with halogen, C(═O)—$OR^a$, $NR^bR^c$, $C_1$-$C_6$-alkylene-$NR^bR^c$, O—$C_1$-$C_6$-alkylene-$NR^bR^c$, $C_1$-$C_6$-alkylene-CN, NH—$C_1$-$C_6$-alkylene-$NR^bR^c$, C(═O)—$NR^bR^c$, C(═O)—$R^d$, $SO_2NR^bR^c$, or $S(═O)_mR^e$, phenyl, phenoxy, phenylcarbonyl, phenylthio or —$CH_2$-phenyl, wherein phenyl rings are unsubstituted or substituted with $R^f$;

$R^1$ is a moiety of formula Y—Z-T-$R^{11}$ or Y—Z-T-$R^{12}$; wherein

Y is —$CR^{ya}$═N—, wherein the N is bound to Z;
 —$NR^{yc}$—C(═O)—, wherein C(═O) is bound to Z; or
 —$NR^{yc}$—C(═S)—, wherein C(═S) is bound to Z;

Z is a single bond;
 —$NR^{zc}$—C(═O)—, wherein C(═O) is bound to T;
 —$NR^{zc}$—C(═S)—, wherein C(═S) is bound to T;
 —N═C(S—$R^{za}$)—, wherein T is bound to the carbon atom;
 —O—C(═O)—, wherein T is bound to the carbon atom; or
 —$NR^{zc}$—C(S—$R^{za}$)═, wherein T is bound to the carbon atom;
 Provided that when Y is —$NR^{yc}$—C(═O)— or —$NR^{yc}$—C(═S)—, then Z is other than a single bond;

T is O, N or N—$R^T$;

$R^{11}$ is $C_1$-$C_6$-alkyl, $C_2$-$C_6$-alkenyl, $C_2$-$C_6$-alkynyl, $C_1$-$C_6$-alkoxy-$C_1$-$C_4$-alkyl, $C_3$-$C_6$-cycloalkyl, $C_3$-$C_6$-cycloalkyl-$C_1$-$C_4$-alkyl, $C_1$-$C_4$-alkyl-$C_3$-$C_6$-cycloalkoxy, which moieties are unsubstituted or substituted with halogen, $C_1$-$C_6$-alkylene-$NR^bR^c$, $C_1$-$C_6$-alkylene-CN, C(═O)—$NR^bR^c$, C(═O)—$R^d$, aryl, aryl-carbonyl, aryl-$C_1$-$C_4$-alkyl, aryloxy-$C_1$-$C_4$-alkyl, hetaryl, carbonyl-hetaryl, hetaryl-$C_1$-$C_4$-alkyl or hetaryloxy-$C_1$-$C_4$-alkyl, wherein the phenyl and hetaryl rings are unsubstituted or substituted with $R^9$ and wherein the hetaryl is a 5- or 6-membered monocyclic hetaryl or a 8-, 9- or 10-membered bicyclic hetaryl;

$R^{12}$ is a radical of the formula $A^1$;

(A1)

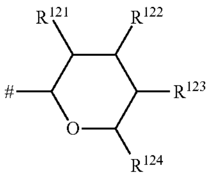

wherein # indicates the point of attachment to T;

$R^{121}$, $R^{122}$, $R^{123}$ are, identical or different, H, halogen, $C_1$-$C_6$-alkyl, $C_2$-$C_6$-alkenyl, $C_2$-$C_6$-alkynyl, $C_1$-$C_6$-alkoxy-$C_1$-$C_4$-alkyl, $C_1$-$C_6$-alkoxy, $C_2$-$C_6$-alkenyloxy, $C_2$-$C_6$-alkynyloxy, $C_1$-$C_6$-alkoxy-$C_1$-$C_4$-alkoxy, $C_1$-$C_6$-alkylcarbonlyoxy, $C_1$-$C_6$-alkenylcarbonlyoxy, $C_3$-$C_6$-cycloalkylcarbonlyoxy, which moieties are unsubstituted or substituted with halogen, or $NR^bR^c$, or one of $R^{121}$, $R^{122}$, $R^{123}$ may also be oxo;

$R^{124}$ is H, $C_1$-$C_6$-alkyl, $C_1$-$C_6$-alkoxy-$C_1$-$C_4$-alkyl, $C_1$-$C_6$-alkoxy, or $C_2$-$C_6$-alkenyloxy, which moieties are unsubstituted or substituted with halogen;

and where $R^{ya}$ is H, halogen, $C_1$-$C_6$-alkyl, $C_1$-$C_6$-alkoxy, $C_2$-$C_6$-alkenyl, $C_2$-$C_6$-alkynyl, $C_1$-$C_6$-alkoxy-$C_1$-$C_4$-alkyl, $C_3$-$C_6$-cycloalkyl, $C_1$-$C_4$-alkyl-$C_3$-$C_6$-cycloalkyl, $C_1$-$C_4$-alkyl-$C_3$-$C_6$-cycloalkoxy, which moieties are unsubstituted or substituted with halogen, C(═O)—$OR^a$, $C_1$-$C_6$-alkylene-$NR^bR^c$, $C_1$-$C_6$-alkylene-CN, C(═O)—$NR^bR^c$, C(═O)—$R^d$, $SO_2NR^bR^c$, $S(═O)_mR^e$, phenyl, or —$CH_2$-phenyl, wherein the phenyl rings are unsubstituted or substituted with $R^f$;

$R^{yc}$, $R^{zc}$ are, identical or different, H, $C_1$-$C_6$-alkyl, $C_2$-$C_6$-alkenyl, $C_2$-$C_6$-alkynyl, $C_1$-$C_4$-alkyl-$C_1$-$C_6$-alkoxy, $C_3$-$C_6$-cycloalkyl, $C_1$-$C_4$-alkyl-$C_3$-$C_6$-cycloalkyl, or $C_1$-$C_4$-alkyl-$C_3$-$C_6$-cycloalkoxy, which moieties are unsubstituted or substituted with halogen;

$R^T$ is H, $C_1$-$C_6$-alkyl, $C_2$-$C_6$-alkenyl, $C_2$-$C_6$-alkynyl, $C_1$-$C_4$-alkyl-$C_1$-$C_6$-alkoxy, $C_3$-$C_6$-cycloalkyl, $C_3$-$C_6$-cycloalkyl-$C_1$-$C_4$-alkyl, $C_3$-$C_6$-cycloalkoxy-$C_1$-$C_4$-alkyl, which moieties are unsubstituted or substituted with halogen, C(═O)—$OR^a$, $C_1$-$C_6$-alkylene-$NR^bR^c$, $C_1$-$C_6$-alkylene-CN, C(═O)—$NR^bR^c$, C(═O)—$R^d$, $SO_2NR^bR^c$, $S(═O)_mR^e$, phenyl, or —$CH_2$-phenyl, wherein the phenyl rings are unsubstituted or substituted with $R^f$;

$R^{zc}$ together with $R^T$ if present, may form $C_1$-$C_6$-alkylene or a linear $C_2$-$C_6$-alkenylene group, where in the linear $C_1$-$C_6$-alkylene and the linear $C_2$-$C_6$-alkenylene a $CH_2$ moiety may be replaced by a carbonyl or a C═N—R' and/or wherein 1 or 2 $CH_2$ moieties may be replaced by O or S and/or wherein the linear $C_1$-$C_6$-alkylene and the linear $C_2$-$C_6$-alkenylene may be unsubstituted or substituted with $R^h$;

$R^{za}$ is H, $C_1$-$C_6$-alkyl, $C_1$-$C_6$-alkoxy, $C_2$-$C_6$-alkenyl, tri-$C_1$-$C_6$-alkylsilyl, $C_2$-$C_6$-alkynyl, $C_1$-$C_4$-alkyl-$C_1$-$C_6$-alkoxy, $C_3$-$C_6$-cycloalkyl, $C_1$-$C_4$-alkyl-$C_3$-$C_6$-cycloalkoxy, $C_1$-$C_4$-alkyl-$C_3$-$C_6$-cycloalkyl, which moieties are unsubstituted or substituted with halogen, $C_1$-$C_6$-alkylene-$NR^bR^c$, $C_1$-$C_6$-alkylene-CN, C(═O)—$NR^bR^c$, C(═O)—$R^d$, phenyl, phenylcarbonyl, or —$CH_2$-phenyl, wherein the phenyl rings are unsubstituted or substituted with $R^f$;

$R^{za}$ together with $R^T$ if present, may form $C_1$-$C_6$-alkylene or a linear $C_2$-$C_6$-alkenylene group, where in the linear $C_1$-$C_6$-alkylene and the linear $C_2$-$C_6$-alkenylene a $CH_2$ moiety may be replaced by a carbonyl or a C═N—R' and/or wherein 1 or 2 $CH_2$ moieties may be replaced by O or S and/or wherein the linear $C_1$-$C_6$-alkylene and the linear $C_2$-$C_6$-alkenylene may be unsubstituted or substituted with $R^h$;

$R^a$, $R^b$ and $R^c$ are, identical or different, H, $C_1$-$C_6$-alkyl, $C_2$-$C_6$-alkenyl, $C_2$-$C_6$-alkynyl, $C_1$-$C_6$-alkoxy-$C_1$-$C_4$-alkyl, $C_3$-$C_6$-cycloalkyl, $C_3$-$C_6$-cycloalkyl-$C_1$-$C_4$-alkyl, $C_3$-$C_6$-cycloalkoxy-$C_1$-$C_4$-alkyl, which moieties are unsubstituted or substituted with halogen, $C_1$-$C_6$-alkylene-CN, phenyl, or —$CH_2$-phenyl, wherein the phenyl rings are unsubstituted or substituted with $R^f$;

$R^d$ is H, $C_1$-$C_6$-alkyl, $C_2$-$C_6$-alkenyl, $C_2$-$C_6$-alkynyl, $C_1$-$C_6$-alkoxy-$C_1$-$C_4$-alkyl, $C_3$-$C_6$-cycloalkyl, $C_3$-$C_6$-cycloalkyl-$C_1$-$C_4$-alkyl, $C_3$-$C_6$-cycloalkoxy-$C_1$-$C_4$-alkyl, which moieties are unsubstituted or substituted with halogen, phenyl, or —$CH_2$-phenyl, wherein the phenyl rings are unsubstituted or substituted with $R^f$;

$R^e$ is $C_1$-$C_6$-alkyl, $C_3$-$C_6$-cycloalkyl, $C_3$-$C_6$-cycloalkyl-$C_1$-$C_4$-alkyl, which moieties are unsubstituted or substituted with halogen, phenyl and —$CH_2$-phenyl, wherein the phenyl rings are unsubstituted or substituted with $R^f$;

$R^f$ is halogen, $N_3$, OH, CN, $NO_2$, —SCN, —$SF_5$, $C_1$-$C_6$-alkyl, $C_1$-$C_6$-alkoxy, $C_2$-$C_6$-alkenyl, tri-$C_1$-$C_6$-alkylsilyl, $C_2$-$C_6$-alkynyl, $C_1$-$C_6$-alkoxy-$C_1$-$C_4$-alkyl, $C_1$-$C_6$-alkoxy-$C_1$-$C_4$-alkoxy, $C_3$-$C_6$-cycloalkyl, $C_3$-$C_6$-cycloalkoxy, $C_3$-$C_6$-cycloalkyl-$C_1$-$C_4$-alkyl, $C_3$-$C_6$- cycloalkoxyx-$C_1$-$C_4$-alkyl, which moieties are unsubstituted or substituted with halogen, C(═O)—$OR^a$, $NR^bR^c$, $C_1$-$C_6$-alkylene-$NR^bR^c$, O—$C_1$-$C_6$-alkylene-$NR^bR^c$, $C_1$-$C_6$-alkylene-CN, NH—$C_1$-$C_6$-alkylene-$NR^bR^c$, C(═O)—$NR^bR^c$, C(═O)—$R^d$, $SO_2NR^bR^c$, or S(═O)$_m$$R^e$;

$R^9$ is halogen, $N_3$, OH, CN, $NO_2$, —SCN, —$SF_5$, $C_1$-$C_6$-alkyl, $C_1$-$C_6$-alkoxy, $C_2$-$C_6$-alkenyl, tri-$C_1$-$C_6$-alkylsilyl, $C_2$-$C_6$-alkynyl, $C_1$-$C_6$-alkoxy-$C_1$-$C_4$-alkyl, $C_1$-$C_6$-alkoxy-$C_1$-$C_4$-alkoxy, $C_3$-$C_6$-cycloalkyl, $C_3$-$C_6$-cycloalkoxy, $C_3$-$C_6$-cycloalkyl-$C_1$-$C_4$-alkyl, $C_3$-$C_6$-cycloalkoxy-$C_1$-$C_4$-alkyl, which moieties are unsubstituted or substituted with halogen, C(═O)—$OR^a$, $NR^bR^c$, $C_1$-$C_6$-alkylene-$NR^bR^c$, O—$C_1$-$C_6$-alkylene-$NR^bR^c$, $C_1$-$C_6$-alkylene-CN, NH—$C_1$-$C_6$-alkylene-$NR^bR^c$, C(═O)—$NR^bR^c$, C(═O)—$R^d$, $SO_2NR^bR^c$, or S(═O)$_m$$R^e$;

$R^h$ is halogen, OH, $C_1$-$C_6$-alkyl, $C_3$-$C_6$-cycloalkyl, or CN; and the N-oxides, stereoisomers, tautomers and agriculturally or veterinarily acceptable salts thereof.

Moreover, the present invention also relates to processes and intermediates for preparing compounds of formula I and to active compound combinations comprising them. Moreover, the present invention relates to agricultural or veterinary compositions comprising the compounds of formula I, and to the use of the compounds of formula I or compositions comprising them for combating or controlling invertebrate pests and/or for protecting crops, plants, plant propagation material and/or growing plants from attack and/or infestation by invertebrate pests. The present invention also relates to methods of applying the compounds of formula I. The present invention also relates to method for protecting crops, plants, plant propagation material and/or growing plants from attack or infestation by invertebrate pests comprising contacting or treating the crops, plants, plant propagation material and growing plants, or soil, material, surface, space, area or water in which the crops, plants, plant propagation material is stored or the plant is growing, with a pesticidally effective amount of at least one compound of formula (I) as defined above or a composition comprising at least one compound of formula (I);

Furthermore, the present invention relates to seed comprising compounds of formula I. Wherein the compounds of formula I includes N-oxides, stereoisomers, tautomers and agriculturally or veterinarily acceptable salts thereof.

General Procedure:

With due modification of the starting compounds, the compounds of formula I can be prepared by procedures as given in below schemes.

(I)

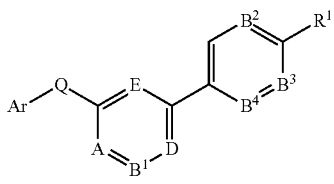

Compounds of the formula S1-2 can be prepared in amide coupling reactions between an aryl carboxylic acid (Ar-COOH) and compounds of the formula S1-1 using a coupling reagent such as HATU as described by, for example, Tobinaga, et al WO 2018/021447 (Scheme 1). Alternatively, an aryl carboxylic acid (ArCOOH) can be pre-activated as an acid chloride by reaction with, for example, $SOCl_2$, prior to reaction with an amine (S1-1) in the presence of a base (e.g. $Et_3N$) to form compounds of the formula S1-2. Compounds of the formula S1-3 can, in turn, be prepared by reaction of compounds of the formula S1-2 with a thionating reagent such at $P_2S_5$ as described by, for example, Carroll et al, WO 2008/130953. Compounds of the formula S1-4 can be synthesized by reaction of compounds of the formula S1-2 with a reducing agent such as $BH_3$.$SMe_2$ as described by, for example, Chen et al, WO 2009/135299.

Scheme 1

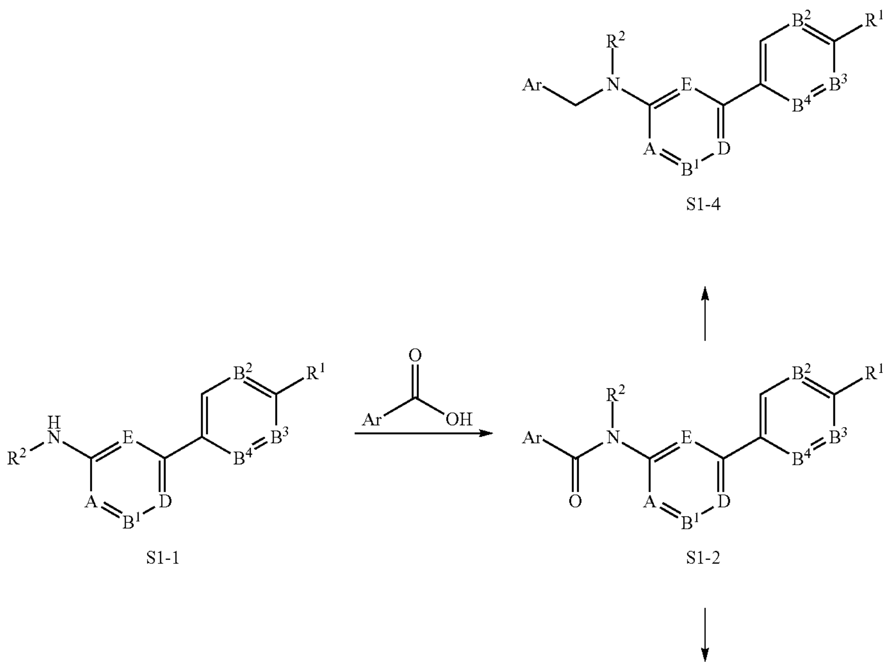

S1-4

S1-1

S1-2

-continued

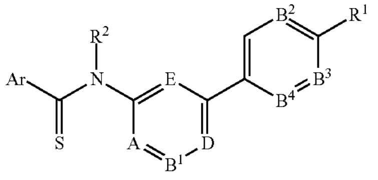

S1-3

Compounds of the formula S2-2 can be prepared from compounds of the formula S2-1 by reaction with, for example, hydroxylamine hydrochloride in the presence of a base (e.g. NaOH, pyridine, triethylamine, $K_2CO_3$, NaH) as described by, for example, Sanders et al, J. Am. Chem. Soc. 2011, 133, 949-957 (Scheme 2). Compounds of the formula S2-3 can be prepared from compounds of the formula S2-2 by reaction with a chlorinating reagent (e.g. N-chlorosuccinimide, NaOCl, t-butylhypochlorite) as described by, for example, Sanders et al, J. Am. Chem. Soc. 2011, 133, 949-957. Compounds of the formula S2-4 can be prepared from compounds of the formula S2-3 by reaction with an amine nucleophile ($ArNHR^2$) as described by, for example, Altug et al, Tetrahedron Lett. 2009, 50, 7392-7394. Compounds of the formula S2-5 can be prepared from compounds of the formula S2-4 by reaction with an electrophile (e.g. methyl iodide, cyanogen bromide, acetyl chloride etc.) in the presence of a base (e.g. NaOH, pyridine, triethylamine, $K_2CO_3$, NaH) as described by, for example, Lui et al, Pest. Manag. Sci. 2009, 65, 229-234.

Scheme 2

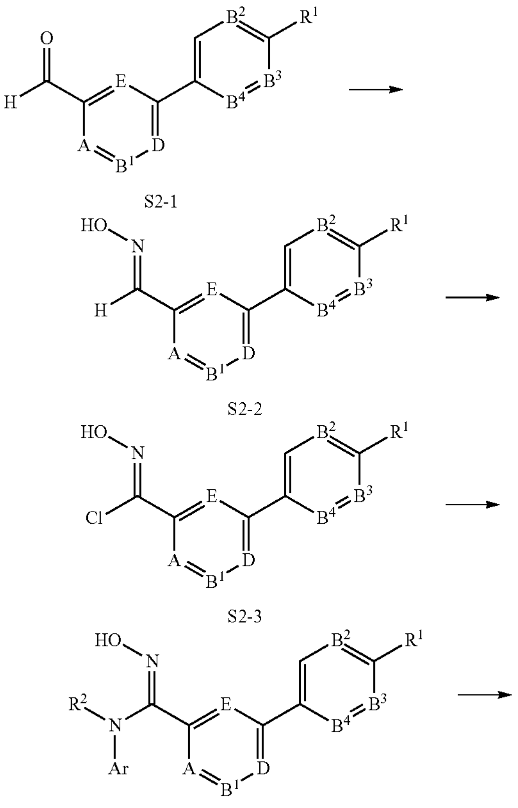

S2-1, S2-2, S2-3, S2-4

-continued

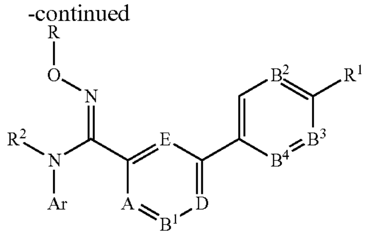

S2-5

Compounds of the formula S3-2 (R=Me, Et) can be prepared from compounds of the formula S3-1 by reaction with, for example, hydrochloric acid in methanol as described by, for example, Laurent et al, Molecules, 2010, 15, 4283-4293 (Scheme 3). Compounds of the formula S3-3 can be prepared from compounds of the formula S3-2 by reaction with an amine nucleophile ($ArNHR^2$) as described by, for example, Arnold et al, WO 2008/124849.

Scheme 3

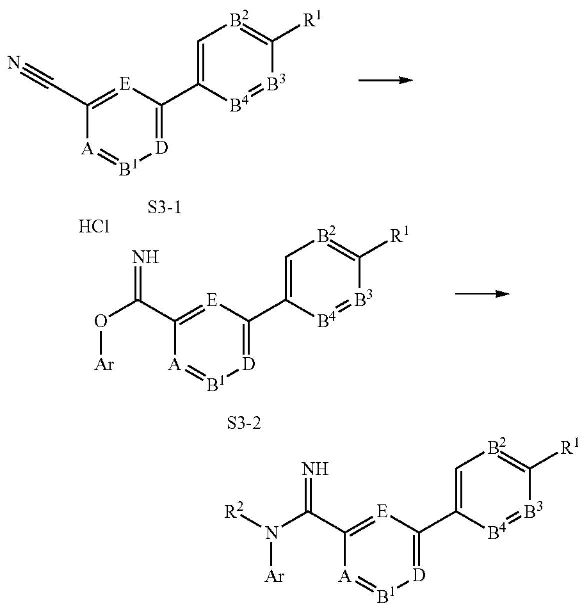

S3-1, S3-2, S3-3

Compounds of the formula S4-2 can be prepared via compounds of the formula S4-1 by reaction of compounds of the formula S1-2 with a chlorinating agent (e.g. N-chlorosuccinimide, NaOCl, t-butylhypochlorite) followed by a hydrazine $[H_2NN(R^3)_2]$ as described by, for example, Crimmin et al, Dalton Trans., 2011, 42, 514-522 (Scheme 4).

Compounds of the formula S4-2 can also be prepared from compounds of the formula S1-3 by reaction with, for example, a hydrazine $[H_2NN(R^3)_2]$ as described by, for example, Burlison et al, WO 2009/158026.

Scheme 4

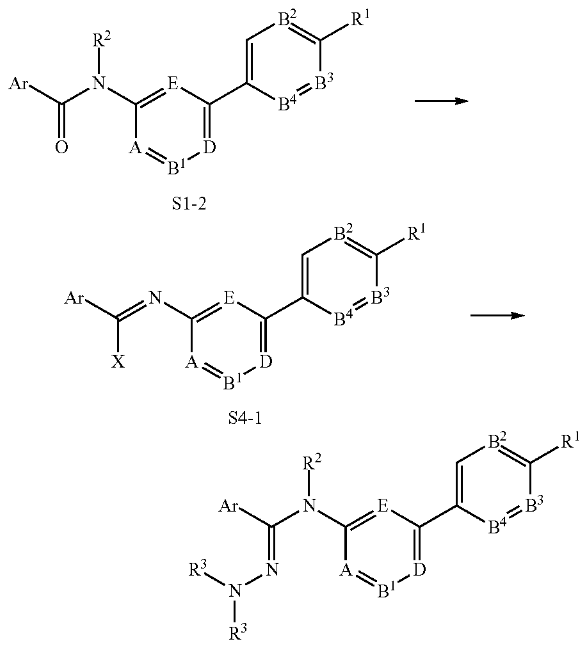

S1-2

S4-1

S4-2

-continued

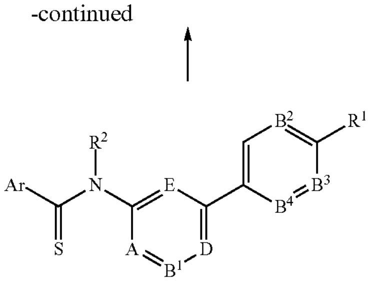

S1-3

Compounds of the formula S5-3 can be prepared by reaction of compounds of the formula S5-1 with a reducing agent, for example, $LiAlH_4$. The resultant compounds of the formula S5-2 can then by reacted with aryl alcohol (ArOH) under Mitsonobu conditions to form compounds of the formula S5-3 (Scheme 5). Compounds for the formula S5-5 can be prepared by reaction of compounds of the formula S5-2 with a chlorinating reagent (e.g. $SOCl_2$, $POCl_3$) as described by, for example, Miyahara et al, WO 2017/209155. The resultant compounds of the formula S5-4 can then be converted into compounds of the formula S5-2 by reaction with an arylthiol (ArSH). Compounds of the formula of the formula S5-6 can, in turn, be prepared by reaction of compounds of the formula S5-5 with an oxidizing agent (e.g. MCPBA). Compounds of the formula S1-4 can also be prepared by reducing compounds of the formula of the formula S5-1 with, e.g. DIBAL. The resultant compounds of the formula S2-1 can then be reacted with an amine ($ArNHR^2$) in a reductive amination with, e.g. $Na(CN)BH_3$ to form compounds of the formula S1-4.

Scheme 5

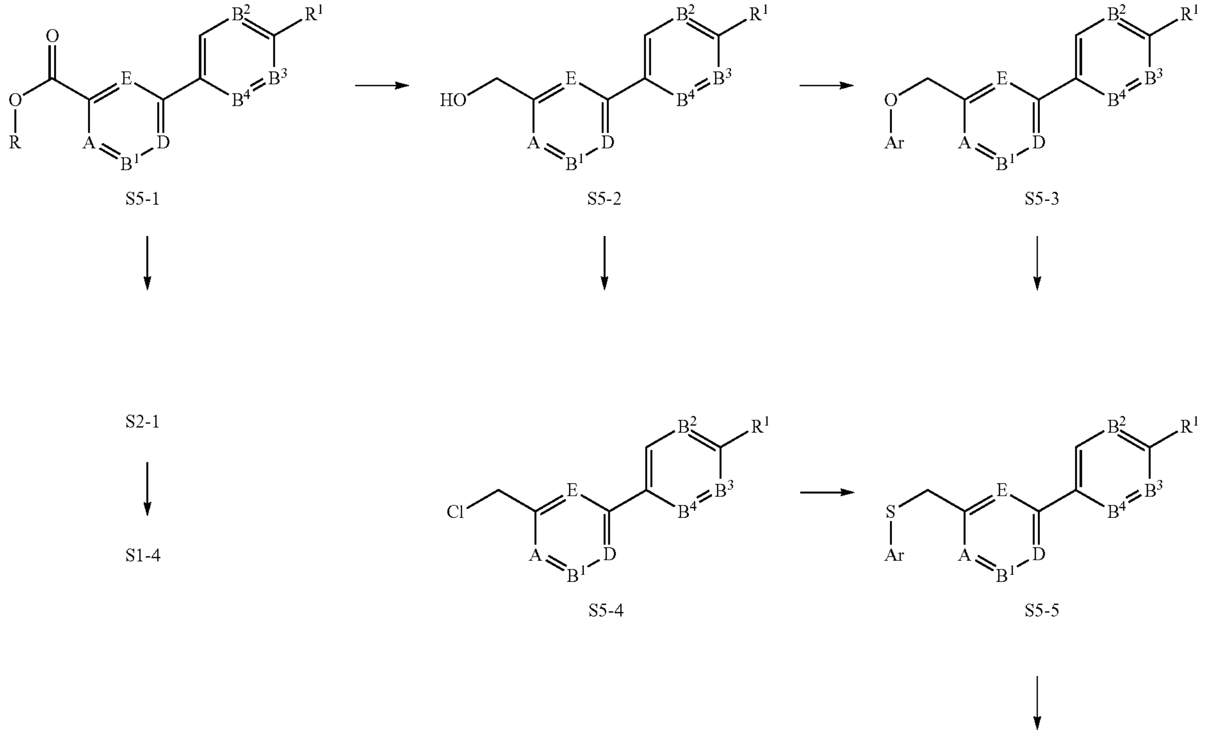

S5-1

S5-2

S5-3

S2-1

S1-4

S5-4

S5-5

-continued

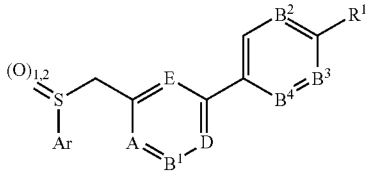

S5-6

Compounds of the formula S6-3 can be prepared by treating compounds of the formula S6-1 with a halogenating agent (e.g. $POCl_3$, $PBr_3$) (Scheme 6). The resultant compounds of the formula S6-2 can then be reacted with an amine ($R^2NH_2$) in an $S_NAr$ reaction or palladium-catalyzed amination as described by, for example, Ojida et al, WO 2018/084321 or Hatakeyama et al, WO 2018/110497, respectively. Alternatively, the resultant compounds of the formula S6-3 can be acylated with an aryl acid (or chloride) to form compounds of the formula S6-4.

Scheme 6

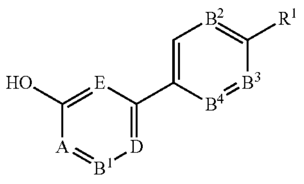

S6-1

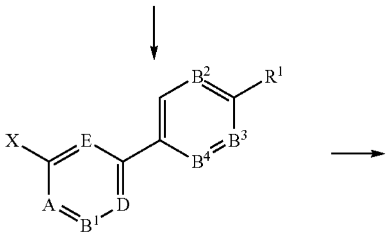

S6-2

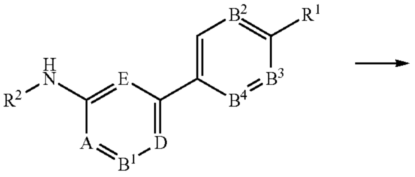

S6-3

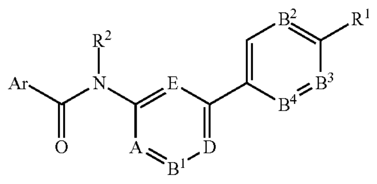

S6-4

Compounds of the formula S7-1, S7-2, S7-3 and S7-4 are isomers of compounds depicted in Scheme 1-4 and, as such, can be synthesized using analogous procedures are those described above (Scheme 7).

Scheme 7

S7-1

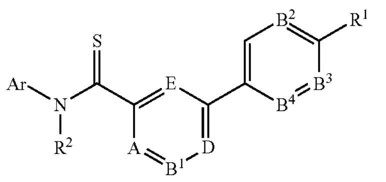

S7-2

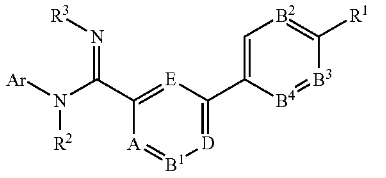

S7-3

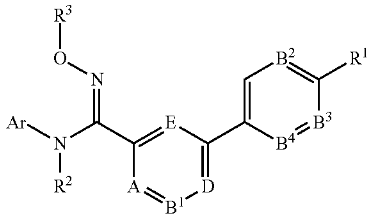

S7-4

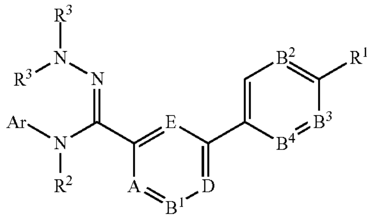

Compounds of the formula S8-1 can be prepared in analogy to compounds of the formula S6-3 (Scheme 8). Compounds of the formula S8-2 can be prepared from compounds of the formula S6-2 by reaction with an alcohol [$ArC(R^9)(R^{10})OH$] in an $S_NAr$ reaction or copper-catalyzed ether formation reaction as described by, for example, Long et al, WO 2018/059534 or Gao et al WO 2016/150193, respectively. Compounds of the formula S8-3 can be prepared from compounds of the formula S6-2 by reaction with a thiol [$ArC(R^9)(R^{10})SH$] in an $S_NAr$ reaction or palladium-catalyzed thioether formation reaction as described by, for example, Wang et al, WO 2017/198196 or Barrow et al, WO 2016/123577.

Scheme 8

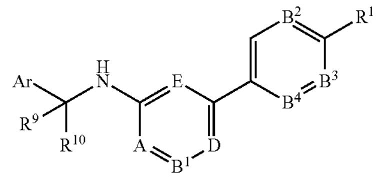

S8-1

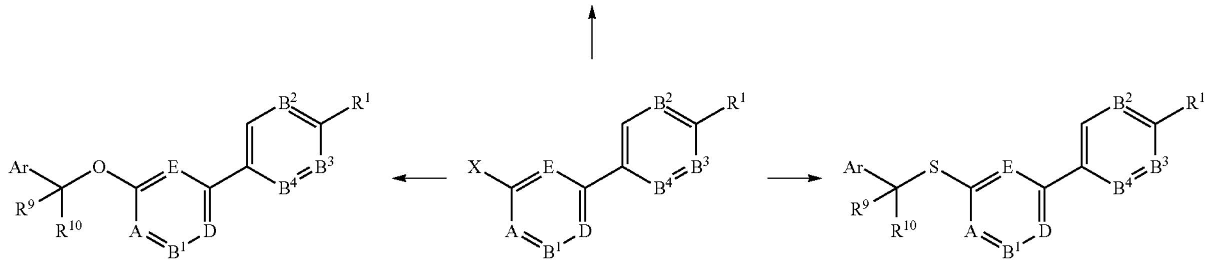

S8-2 S6-2 S8-3

Compounds of the formula S9-3 can also be prepared by a Suzuki-type aryl coupling reaction as depicted in scheme 9, where X is halogen such as chlorine or bromine and Lg is a boron containing radical such as $B(OH_2)$ or the corresponding di-$C_1$-$C_4$-alkyl ester. The reaction of the compound of formula S9-1 with the compound of formula S9-2 can be performed e.g. by analogy to the reaction described in WO 2014/007217 or in *Org. Lett.*, 2009, 11(24), 5666-5669 (Scheme 9).

Scheme 9

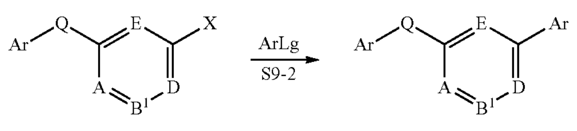

S9-1 S9-3

Similarly, compounds of the formula S10-3 can also be prepared by a Suzuki-type aryl coupling reaction as depicted in scheme 10, where X is halogen such as chlorine or bromine and Lg is a boron containing radical such as $B(OH_2)$ or the corresponding di-$C_1$-$C_4$-alkyl ester. The reaction of the compound of formula S10-1 with the compound of formula S10-2 can be performed e.g. by analogy to the reaction described in WO 2014/007217 or in *Org. Lett.*, 2009, 11(24), 5666-5669 (Scheme 10).

Scheme 10

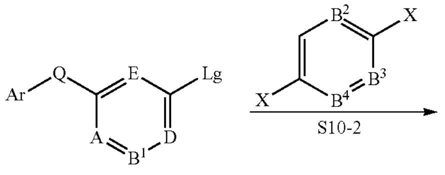

S10-1

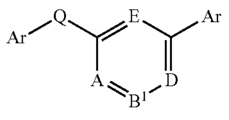

S10-3

Compounds of the formula S11-2 (R=Me, Et) can be prepared in a palladium-catalyzed carbonylation of compounds of the formula S11-1 using CO (g) and MeOH or EtOH as described by, for example, Evans et al, WO 2017/214269 (Scheme 11). Compounds of the formula S11-4 can, in turn, be prepared from Compounds of the formula S11-2 by, e.g. basic hydrolysis. Compounds of the formula S11-3 can also be prepared from compounds of the formula S11-2 by reduction with, e.g. DIBAL.

Scheme 11
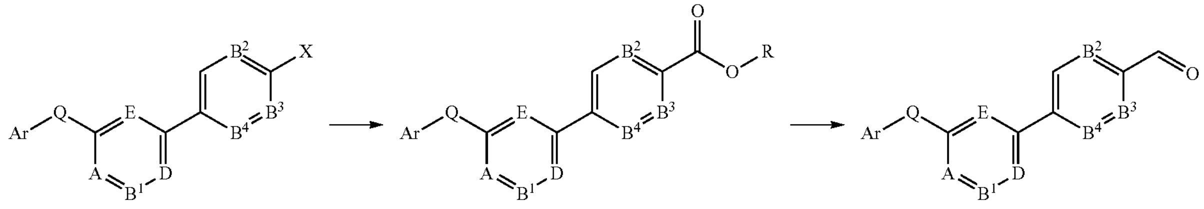
S11-1 S11-2 S11-3
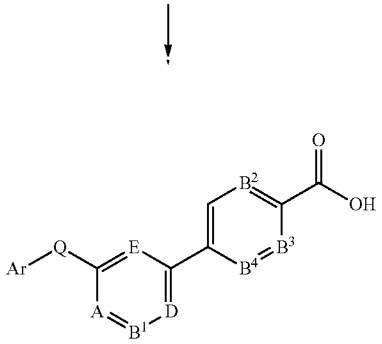
S11-4
Compounds of the formula S11-4, S11-3 and S12-1 can be converted in known syntheses into compounds on the formula (I) as described by, for example, Crouse et al, WO 2009/102736, Crouse et al, WO 2010/093764, Crouse et al, US 2012/0202687, Crouse et al, WO 2013/009791, Baum et al, WO 2013/116052, Fischer et al, WO 2013/116053, Crouse et al, WO 2014/011429, Jeanguenat et al, WO 2016/116445 and Narine et al, WO 2018/177781 (Scheme 12).
Scheme 12
S11-4
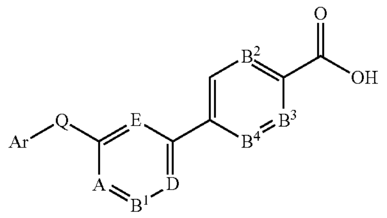
S11-3
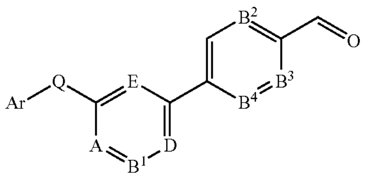
S12-1
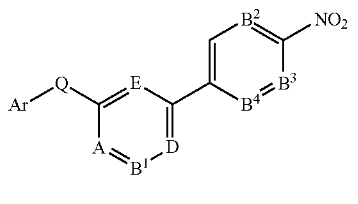
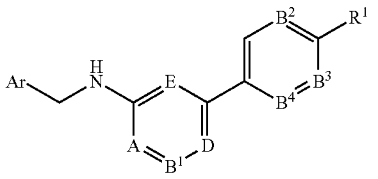
S1-4

-continued

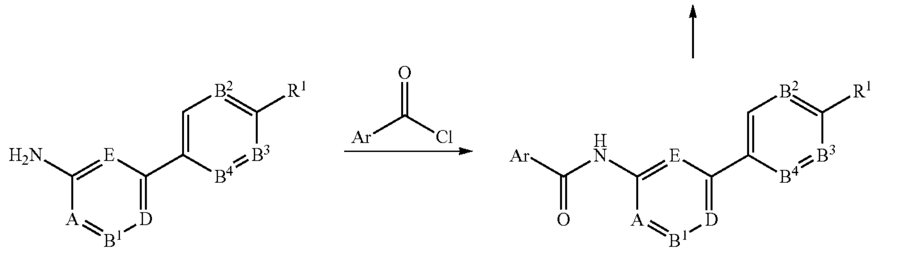

S1-1 S1-2

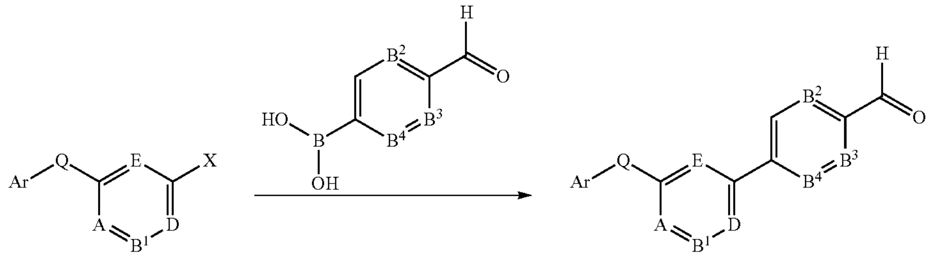

(S12-3)

Individual compounds of formula I can also be prepared by derivatisation of other compounds of formula I or the intermediates thereof.

If the synthesis yields mixtures of isomers, a separation is generally not necessarily required since in some cases the individual isomers can be interconverted during work-up for use or during application (for example under the action of light, acids or bases). Such conversions may also take place after use, for example in the treatment of plants in the treated plant, or in the harmful fungus to be controlled.

A skilled person will readily understand that the preferences for the substituents, also in particular the ones given in the tables below for the respective substituents, given herein in connection with compounds I apply for the intermediates accordingly. Thereby, the substituents in each case have independently of each other or more preferably in combination the meanings as defined herein.

Unless otherwise indicated, the term “compound(s) according to the invention” or “compound(s) of the invention” or “compound(s) of formula (I)”, refers to the compounds of formula I.

The term “compound(s) according to the invention”, or “compounds of formula I” comprises the compound(s) as defined herein as well as a stereoisomer, salt, tautomer or N-oxide thereof. The term “compound(s) of the present invention” is to be understood as equivalent to the term “compound(s) according to the invention”, therefore also comprising a stereoisomer, salt, tautomer or N-oxide thereof.

The term “composition(s) according to the invention” or “composition(s) of the present invention” encompasses composition(s) comprising at least one compound of formula I according to the invention as defined above. The compositions of the invention are preferably agricultural or veterinary compositions.

Depending on the substitution pattern, the compounds according to the invention may have one or more centers of chirality, in which case they are present as mixtures of enantiomers or diastereomers. The invention provides both the single pure enantiomers or pure diastereomers of the compounds according to the invention, and their mixtures and the use according to the invention of the pure enantiomers or pure diastereomers of the compounds according to the invention or their mixtures. Suitable compounds according to the invention also include all possible geometrical stereoisomers (cis/trans isomers) and mixtures thereof. Cis/trans isomers may be present with respect to an alkene, carbon-nitrogen double-bond or amide group. The term “stereoisomer(s)” encompasses both optical isomers, such as enantiomers or diastereomers, the latter existing due to more than one center of chirality in the molecule, as well as geometrical isomers (cis/trans isomers). The present invention relates to every possible stereoisomer of the compounds of formula I, i.e. to single enantiomers or diastereomers, as well as to mixtures thereof.

The compounds according to the invention may be amorphous or may exist in one or more different crystalline states (polymorphs) which may have different macroscopic properties such as stability or show different biological properties such as activities. The present invention relates to amorphous and crystalline compounds according to the invention, mixtures of different crystalline states of the respective compounds according to the invention, as well as amorphous or crystalline salts thereof.

The term “tautomers” encompasses isomers, which are derived from the compounds of formula I by the shift of an H-atom involving at least one H-atom located at a nitrogen, oxygen or sulphur atom. Examples of tautomeric forms are keto-enol forms, imine-enamine forms, urea-isourea forms, thiourea-isothiourea forms, (thio)amide-(thio)imidate forms etc.

The term “stereoisomers” encompasses both optical isomers, such as enantiomers or diastereomers, the latter existing due to more than one center of chirality in the molecule, as well as geometrical isomers (cis/trans isomers).

Depending on the substitution pattern, the compounds of the formula I may have one or more centers of chirality, in which case they are present as mixtures of enantiomers or diastereomers. One center of chirality is the carbon ring atom of the isothiazoline ring carrying radical $R^1$. The invention provides both the pure enantiomers or diastereomers and their mixtures and the use according to the invention of the pure enantiomers or diastereomers of the compound I or its mixtures. Suitable compounds of the formula I also include all possible geometrical stereoisomers (cis/trans isomers) and mixtures thereof.

The term N-oxides relates to a form of compounds I in which at least one nitrogen atom is present in oxidized form (as NO). To be more precise, it relates to any compound of the present invention which has at least one tertiary nitrogen atom that is oxidized to an N-oxide moiety. N-oxides of compounds I can in particular be prepared by oxidizing e.g. the ring nitrogen atom of an N-heterocycle, e.g. a pyridine or pyrimidine ring present in Ar or $R^{11}$, or an imino-nitrogen present in central tricyclic core, with a suitable oxidizing agent, such as peroxo carboxylic acids or other peroxides. The person skilled in the art knows if and in which positions compounds of the present invention may form N-oxides.

Salts of the compounds of the formula I are preferably agriculturally and veterinarily acceptable salts. They can be formed in a customary method, e.g. by reacting the compound with an acid of the anion in question if the compound of formula I has a basic functionality or by reacting an acidic compound of formula I with a suitable base.

Suitable agriculturally or veterinarily acceptable salts are especially the salts of those cations or the acid addition salts of those acids whose cations and anions, which are known and accepted in the art for the formation of salts for agricultural or veterinary use respectively, and do not have any adverse effect on the action of the compounds according to the present invention. Suitable cations are in particular the ions of the alkali metals, preferably lithium, sodium and potassium, of the alkaline earth metals, preferably calcium, magnesium and barium, and of the transition metals, preferably manganese, copper, zinc and iron, and also ammonium ($NH^{4+}$) and substituted ammonium in which one to four of the hydrogen atoms are replaced by $C_1$-$C_4$-alkyl, $C_1$-$C_4$-hydroxyalkyl, $C_1$-$C_4$-alkoxy, $C_1$-$C_4$-alkoxy-$C_1$-$C_4$-alkyl, hydroxy-$C_1$-$C_4$-alkoxy-$C_1$-$C_4$-alkyl, phenyl or —$CH_2$-phenyl. Examples of substituted ammonium ions comprise methylammonium, isopropylammonium, dimethylammonium, diisopropylammonium, trimethylammonium, tetramethylammonium, tetraethylammonium, tetrabutylammonium, 2-hydroxyethylammonium, 2-(2-hydroxyethoxy)ethylammonium, bis(2-hydroxyethyl)ammonium, benzyltrimethylammonium and benzyl-triethylammonium, furthermore phosphonium ions, sulfonium ions, preferably tri($C_1$-$C_4$-alkyl)sulfonium, and sulfoxonium ions, preferably tri($C_1$-$C_4$-alkyl)sulfoxonium. Suitable acid addition veterinarily acceptable salts, e.g. formed by compounds of formula I containing a basic nitrogen atom, e.g. an amino group, include salts with inorganic acids, for example hydrochlorides, sulphates, phosphates, and nitrates and salts of organic acids for example acetic acid, maleic acid, dimaleic acid, fumaric acid, difumaric acid, methane sulfenic acid, methane sulfonic acid, and succinic acid.

Anions of useful acid addition salts are primarily chloride, bromide, fluoride, hydrogen sulfate, sulfate, dihydrogen phosphate, hydrogen phosphate, phosphate, nitrate, hydrogen carbonate, carbonate, hexafluorosilicate, hexafluorophosphate, benzoate, and the anions of $C_1$-$C_4$-alkanoic acids, preferably formate, acetate, propionate and butyrate. They can be formed by reacting a compound of formulae I with an acid of the corresponding anion, preferably of hydrochloric acid, hydrobromic acid, sulfuric acid, phosphoric acid or nitric acid.

The term "invertebrate pest" as used herein encompasses animal populations, such as insects, arachnids and nematodes, which may attack plants, thereby causing substantial damage to the plants attacked, as well as ectoparasites which may infest animals, in particular warm blooded animals such as e.g. mammals or birds, or other higher animals such as reptiles, amphibians or fish, thereby causing substantial damage to the animals infested.

The term "plant propagation material" is to be understood to denote all the generative parts of the plant such as seeds and vegetative plant material such as cuttings and tubers (e. g. potatoes), which can be used for the multiplication of the plant. This includes seeds, roots, fruits, tubers, bulbs, rhizomes, shoots, sprouts and other parts of plants, including seedlings and young plants, which are to be transplanted after germination or after emergence from soil. The plant propagation materials may be treated prophylactically with a plant protection compound either at or before planting or transplanting. Said young plants may also be protected before transplantation by a total or partial treatment by immersion or pouring.

The term "plants" comprises any types of plants including "modified plants" and in particular "cultivated plants".

The term "modified plants" refers to any wild type species or related species or related genera of a cultivated plant.

The term "cultivated plants" is to be understood as including plants which have been modified by breeding, mutagenesis or genetic engineering including but not limiting to agricultural biotech products on the market or in development (cf. http://www.bio.org/speeches/pubs/er/agri_products.asp). Genetically modified plants are plants, which genetic material has been so modified by the use of recombinant DNA techniques that under natural circumstances cannot readily be obtained by cross breeding, mutations or natural recombination. Typically, one or more genes have been integrated into the genetic material of a genetically modified plant in order to improve certain properties of the plant. Such genetic modifications also include but are not limited to targeted post-translational modification of protein(s), oligo- or polypeptides e. g. by glycosylation or polymer additions such as prenylated, acetylated or farnesylated moieties or PEG moieties.

Plants that have been modified by breeding, mutagenesis or genetic engineering, e. g. have been rendered tolerant to applications of specific classes of herbicides, such as auxin herbicides such as dicamba or 2,4-D; bleacher herbicides such as hydroxylphenylpyruvate dioxygenase (HPPD) inhibitors or phytoene desaturase (PDS) inhibitors; acetolactate synthase (ALS) inhibitors such as sulfonyl ureas or imidazolinones; enolpyruvylshikimate-3-phosphate synthase (EPSPS) inhibitors, such as glyphosate; glutamine synthetase (GS) inhibitors such as glufosinate; protoporphyrinogen-IX oxidase inhibitors; lipid biosynthesis inhibitors such as acetyl CoA carboxylase (ACCase) inhibitors; or oxynil (i. e. bromoxynil or ioxynil) herbicides as a result of conventional methods of breeding or genetic engineering. Furthermore, plants have been made resistant to multiple classes of herbicides through multiple genetic modifications, such as resistance to both glyphosate and glufosinate or to both glyphosate and a herbicide from another class such as ALS inhibitors, HPPD inhibitors, auxin herbicides, or ACCase inhibitors. These herbicide resistance technologies are e. g. described in Pest Managem. Sci. 61, 2005, 246; 61, 2005, 258; 61, 2005, 277; 61, 2005, 269; 61, 2005, 286; 64, 2008, 326; 64, 2008, 332; Weed Sci. 57, 2009, 108; Austral. J. Agricult. Res. 58, 2007, 708; Science 316, 2007, 1185; and references quoted therein. Several cultivated plants have been rendered tolerant to herbicides by conventional methods of breeding (mutagenesis), e. g. Clearfield® summer rape (Canola, BASF SE, Germany) being tolerant to imidazolinones, e. g. imazamox, or ExpressSun® sunflowers (DuPont, USA) being tolerant to sulfonyl ureas, e. g. tribenuron. Genetic engineering methods have been used to render cultivated plants such as soybean, cotton, corn, beets and rape, tolerant to herbicides such as glyphosate and glufosinate, some of which are commercially available under the trade names RoundupReady® (glyphosate-tolerant, Monsanto, U.S.A.), Cultivance® (imidazolinone tolerant, BASF SE, Germany) and LibertyLink® (glufosinate-tolerant, Bayer CropScience, Germany).

Furthermore, plants are also covered that are by the use of recombinant DNA techniques capable to synthesize one or more insecticidal proteins, especially those known from the bacterial genus *Bacillus*, particularly from *Bacillus thuringiensis*, such as 5-endotoxins, e. g. CryIA(b), CryIA(c), CryIF, CryIF(a2), CryIIA(b), CryIIIA, CryIIIB(b1) or Cry9c; vegetative insecticidal proteins (VIP), e. g. VIP1, VIP2, VIP3 or VIP3A; insecticidal proteins of bacteria colonizing nematodes, e. g. *Photorhabdus* spp. or *Xenorhabdus* spp.; toxins produced by animals, such as scorpion toxins, arachnid toxins, wasp toxins, or other insect-specific neurotoxins; toxins produced by fungi, such Streptomycetes toxins, plant lectins, such as pea or barley lectins; agglutinins; proteinase inhibitors, such as trypsin inhibitors, serine protease inhibitors, patatin, cystatin or papain inhibitors; ribosome-inactivating proteins (RIP), such as ricin, maize-RIP, abrin, luffin, saporin or bryodin; steroid metabolism enzymes, such as 3-hydroxysteroid oxidase, ecdysteroid-IDP-glycosyl-transferase, cholesterol oxidases, ecdysone inhibitors or HMG-CoA-reductase; ion channel blockers, such as blockers of sodium or calcium channels; juvenile hormone esterase; diuretic hormone receptors (helicokinin receptors); stilben synthase, bibenzyl synthase, chitinases or glucanases. In the context of the present invention these insecticidal proteins or toxins are to be understood expressly also as pre-toxins, hybrid proteins, truncated or otherwise modified proteins. Hybrid proteins are characterized by a new combination of protein domains, (see, e. g. WO 02/015701). Further examples of such toxins or genetically modified plants capable of synthesizing such toxins are disclosed, e. g., in EP-A 374 753, WO 93/007278, WO 95/34656, EP-A 427 529, EP-A 451 878, WO 03/18810 und WO 03/52073. The methods for producing such genetically modified plants are generally known to the person skilled in the art and are described, e. g. in the publications mentioned above. These insecticidal proteins contained in the genetically modified plants impart to the plants producing these proteins tolerance to harmful pests from all taxonomic groups of athropods, especially to beetles (Coelop-tera), two-winged insects (Diptera), and moths (Lepidoptera) and to nematodes (Nematoda). Genetically modified plants capable to synthesize one or more insecticidal proteins are, e. g., described in the publications mentioned above, and some of which are commercially available such as YieldGard® (corn cultivars producing the Cry1Ab toxin), YieldGard® Plus (corn cultivars producing Cry1Ab and Cry3Bb1 toxins), Starlink® (corn cultivars producing the Cry9c toxin), Herculex® RW (corn cultivars producing Cry34Ab1, Cry35Ab1 and the enzyme Phosphinothricin-N-Acetyltransferase [PAT]); NuCOTN® 33B (cotton cultivars producing the Cry1Ac toxin), Bollgard® I (cotton cultivars producing the Cry1Ac toxin), Bollgard® II (cotton cultivars producing Cry1Ac and Cry2Ab2 toxins); VIPCOT® (cotton cultivars producing a VIP-toxin); NewLeaf® (potato cultivars producing the Cry3A toxin); Bt-Xtra®, NatureGard®, KnockOut®, BiteGard®, Protecta®, Bt11 (e. g. Agrisure® CB) and Bt176 from Syngenta Seeds SAS, France, (corn cultivars producing the Cry1Ab toxin and PAT enzyme), MIR604 from Syngenta Seeds SAS, France (corn cultivars producing a modified version of the Cry3A toxin, c.f. WO 03/018810), MON 863 from Monsanto Europe S.A., Belgium (corn cultivars producing the Cry3Bb1 toxin), IPC 531 from Monsanto Europe S.A., Belgium (cotton cultivars producing a modified version of the Cry1Ac toxin) and 1507 from Pioneer Overseas Corporation, Belgium (corn cultivars producing the Cry1F toxin and PAT enzyme).

Furthermore, plants are also covered that are by the use of recombinant DNA techniques capable to synthesize one or more proteins to increase the resistance or tolerance of those plants to bacterial, viral or fungal pathogens. Examples of such proteins are the so-called "pathogenesis-related proteins" (PR proteins, see, e. g. EP-A 392 225), plant disease resistance genes (e. g. potato cultivars, which express resistance genes acting against *Phytophthora infestans* derived from the mexican wild potato *Solanum bulbocastanum*) or T4-lysozym (e. g. potato cultivars capable of synthesizing these proteins with increased resistance against bacteria such as *Erwinia amylvora*). The methods for producing such genetically modified plants are generally known to the person skilled in the art and are described, e. g. in the publications mentioned above.

Furthermore, plants are also covered that are by the use of recombinant DNA techniques capable to synthesize one or more proteins to increase the productivity (e. g. bio mass production, grain yield, starch content, oil content or protein content), tolerance to drought, salinity or other growth-limiting environmental factors or tolerance to pests and fungal, bacterial or viral pathogens of those plants.

Furthermore, plants are also covered that contain by the use of recombinant DNA techniques a modified amount of substances of content or new substances of content, specifically to improve human or animal nutrition, e. g. oil crops that produce health-promoting long-chain omega-3 fatty acids or unsaturated omega-9 fatty acids (e. g. Nexera® rape, DOW Agro Sciences, Canada).

Furthermore, plants are also covered that contain by the use of recombinant DNA techniques a modified amount of substances of content or new substances of content, specifically to improve raw material production, e. g. potatoes that produce increased amounts of amylopectin (e. g. Amflora® potato, BASF SE, Germany).

The organic moieties mentioned in the above definitions of the variables are—like the term halogen—collective terms for individual listings of the individual members. The prefix $C_n$-$C_m$ indicates in each case the possible number of carbon atoms in the group.

The term halogen denotes in each case F, Br, Cl or I, in particular F, Cl or Br.

The term "alkyl" as used herein and in the alkyl moieties of alkoxy, alkylthio, and the like refers to saturated straight-chain or branched hydrocarbon radicals having 1 to 2 ("$C_1$-$C_2$-alkyl"), 1 to 3 ("$C_1$-$C_3$-alkyl"), 1 to 4 ("$C_1$-$C_4$-alkyl") or 1 to 6 ("$C_1$-$C_6$-alkyl") carbon atoms. $C_1$-$C_2$-Alkyl is $CH_3$ or $C_2H_5$. $C_1$-$C_3$-Alkyl is additionally propyl and isopropyl. $C_1$-$C_4$-Alkyl is additionally butyl, 1-methylpropyl (sec-butyl), 2-methylpropyl (isobutyl) or 1,1-dimethylethyl (tert-butyl). $C_1$-$C_6$-Alkyl is additionally also, for example, pentyl, 1-methylbutyl, 2-methylbutyl, 3-methylbutyl, 2,2-dimethylpropyl, 1-ethylpropyl, 1,1-dimethylpropyl, 1,2-dimethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, or 1-ethyl-2-methylpropyl.

The term "haloalkyl" as used herein, which is also expressed as "alkyl which is partially or fully halogenated", refers to straight-chain or branched alkyl groups having 1 to 2 ("$C_1$-$C_2$-haloalkyl"), 1 to 3 ("$C_1$-$C_3$-haloalkyl"), 1 to 4 ("$C_1$-$C_4$-haloalkyl") or 1 to 6 ("$C_1$-$C_6$-haloalkyl") carbon atoms (as mentioned above), where some or all of the hydrogen atoms in these groups are replaced by halogen atoms as mentioned above: in particular $C_1$-$C_2$-haloalkyl, such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl or pentafluoroethyl. $C_1$-$C_3$-haloalkyl is additionally, for example, 1-fluoropropyl, 2-fluoropropyl, 3-fluoropropyl, 1,1-difluoropropyl, 2,2-difluoropropyl, 1,2-difluoropropyl, 3,3-difluoropropyl, 3,3,3-trifluoropropyl, heptafluoropropyl, 1,1,1-trifluoroprop-2-yl, 3-chloropropyl and the like. Examples for $C_1$-$C_4$-haloalkyl are, apart those mentioned for $C_1$-$C_3$-haloalkyl, 4-chlorobutyl and the like.

The term "alkylene" (or alkanediyl) as used herein in each case denotes an alkyl radical as defined above, wherein one hydrogen atom at any position of the carbon backbone is replaced by one further binding site, thus forming a bivalent moiety. Alkylene has preferably 1 to 6 carbon atoms ($C_1$-$C_6$-alkylene), 2 to 6 carbon atoms ($C_2$-$C_6$-alkylene), in particular 1 to 4 carbon atoms ($C_1$-$C_4$-alkylene) or 2 to 4 carbon atoms ($C_2$-$C_4$-alkylene). Examples of alkylene are methylene (CH2), 1,1-ethandiyl, 1,2-ethandiyl, 1,3-propandiyl, 1,2-propandiyl, 2,2-propandiyl, 1,4-butandiyl, 1,2-butandiyl, 1,3-butandiyl, 2,3-butandiyl, 2,2-butandiyl, 1,5-pentandiyl, 2,2-dimethylpropan-1,3-diyl, 1,3-dimethyl-1,3-propandiyl, 1,6-hexandiyl etc.

The term "alkenyl" as used herein refers to monounsaturated straight-chain or branched hydrocarbon radicals having 2 to 3 ("$C_2$-$C_3$-alkenyl"), 2 to 4 ("$C_2$-$C_4$-alkenyl") or 2 to 6 ("$C_2$-$C_6$-alkenyl) carbon atoms and a double bond in any position, for example $C_2$-$C_3$-alkenyl, such as ethenyl, 1-propenyl, 2-propenyl or 1-methylethenyl; $C_2$-$C_4$-alkenyl, such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl or 2-methyl-2-propenyl; $C_2$-$C_6$-alkenyl, such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl, 1-ethyl-2-methyl-2-propenyl and the like.

The term "alkynyl" as used herein refers to straight-chain or branched hydrocarbon groups having 2 to 3 ("$C_2$-$C_3$-alkynyl"), 2 to 4 ("$C_2$-$C_4$-alkynyl") or 2 to 6 ("$C_2$-$C_6$-alkynyl") carbon atoms and one or two triple bonds in any position, for example $C_2$-$C_3$-alkynyl, such as ethynyl, 1-propynyl or 2-propynyl; $C_2$-$C_4$-alkynyl, such as ethynyl, 1-propynyl, 2-propynyl, 1-butynyl, 2-butynyl, 3-butynyl, 1-methyl-2-propynyl and the like, $C_2$-$C_6$-alkynyl, such as ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl, 1-ethyl-1-methyl-2-propynyl and the like;

The term "cycloalkyl" as used herein refers to mono- or bi- or polycyclic saturated hydrocarbon radicals having in particular 3 to 6 ("$C_3$-$C_6$-cycloalkyl") or 3 to 5 ("$C_3$-$C_5$-cycloalkyl") or 3 to 4 ("$C_3$-$C_4$-cycloalkyl") carbon atoms. Examples of monocyclic radicals having 3 to 4 carbon atoms comprise cyclopropyl and cyclobutyl. Examples of monocyclic radicals having 3 to 5 carbon atoms comprise cyclopropyl, cyclobutyl and cyclopentyl. Examples of monocyclic radicals having 3 to 6 carbon atoms comprise cyclopropyl, cyclobutyl, cyclopentyl and cyclohexyl. Examples of monocyclic radicals having 3 to 8 carbon atoms comprise cyclopropyl, cyclobutyl, cyclopentyl, cyclohexyl, cycloheptyl and cyclooctyl. Examples of bicyclic radicals having 7 or 8 carbon atoms comprise bicyclo[2.2.1]heptyl, bicyclo[3.1.1]heptyl, bicyclo[2.2.2]octyl and bicyclo[3.2.1]octyl. Preferably, the term cycloalkyl denotes a monocyclic saturated hydrocarbon radical.

The term "cycloalkoxy" as used herein refers to a cycloalkyl radical, in particular a monocyclic cycloalkyl radical, as defined above having in particular 3 to 6 ("$C_3$-$C_6$-cycloalkoxy") or 3 to 5 ("$C_3$-$C_5$-cycloalkoxy") or 3 to 4 ("$C_3$-$C_4$-cycloalksoxy") carbon atoms, which is bound via an oxygen atom to the remainder of the molecule.

The term "cycloalkyl-$C_1$-$C_4$-alkyl" refers to a $C_3$-$C_8$-cycloalkyl ("$C_3$-$C_8$-cycloalkyl-$C_1$-$C_4$-alkyl"), preferably a $C_3$-$C_6$-cycloalkyl ("$C_3$-$C_6$-cycloalkyl-$C_1$-$C_4$-alkyl"), more preferably a $C_3$-$C_4$-cycloalkyl ("$C_3$-$C_4$-cycloalkyl-$C_1$-$C_4$-alkyl") as defined above (preferably a monocyclic cycloalkyl group) which is bound to the remainder of the molecule via a $C_1$-$C_4$-alkyl group, as defined above. Examples for $C_3$-$C_4$-cycloalkyl-$C_1$-$C_4$-alkyl are cyclopropylmethyl, cyclopropylethyl, cyclopropylpropyl, cyclobutylmethyl, cyclobutylethyl and cyclobutylpropyl, Examples for $C_3$-$C_6$-cycloalkyl-$C_1$-$C_4$-alkyl, apart those mentioned for $C_3$-$C_4$-cycloalkyl-$C_1$-$C_4$-alkyl, are cyclopentylmethyl, cyclopentylethyl, cyclopentylpropyl, cyclohexylmethyl, cyclohexylethyl and cyclohexylpropyl.

The term "$C_1$-$C_2$-alkoxy" is a $C_1$-$C_2$-alkyl group, as defined above, attached via an oxygen atom. The term "$C_1$-$C_3$-alkoxy" is a $C_1$-$C_3$-alkyl group, as defined above, attached via an oxygen atom. The term "$C_1$-$C_4$-alkoxy" is a $C_1$-$C_4$-alkyl group, as defined above, attached via an oxygen atom. The term "$C_1$-$C_6$-alkoxy" is a $C_1$-$C_6$-alkyl group, as defined above, attached via an oxygen atom. The term "$C_1$-$C_{10}$-alkoxy" is a $C_1$-$C_{10}$-alkyl group, as defined above, attached via an oxygen atom. $C_1$-$C_2$-Alkoxy is $OCH_3$ or $OC_2H_5$. $C_1$-$C_3$-Alkoxy is additionally, for example, n-propoxy and 1-methylethoxy (isopropoxy). $C_1$-$C_4$-Alkoxy is additionally, for example, butoxy, 1-methylpropoxy (sec-butoxy), 2-methylpropoxy (isobutoxy) or 1,1-dimethylethoxy (tert-butoxy). $C_1$-$C_6$-Alkoxy is additionally, for example, pentoxy, 1-methylbutoxy, 2-methylbutoxy, 3-methylbutoxy, 1,1-dimethylpropoxy, 1,2-dimethylpropoxy, 2,2-dimethylpropoxy, 1-ethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy or 1-ethyl-2-methylpropoxy. $C_1$-$C_6$-Alkoxy is additionally, for example, heptyloxy, octyloxy, 2-ethylhexyloxy and positional isomers thereof. $C_1$-$C_{10}$-Alkoxy is additionally, for example, nonyloxy, decyloxy and positional isomers thereof.

The term "$C_1$-$C_2$-haloalkoxy" is a $C_1$-$C_2$-haloalkyl group, as defined above, attached via an oxygen atom. The term "$C_1$-$C_3$-haloalkoxy" is a $C_1$-$C_3$-haloalkyl group, as defined above, attached via an oxygen atom. The term "$C_1$-$C_4$-haloalkoxy" is a $C_1$-$C_4$-haloalkyl group, as defined above, attached via an oxygen atom. The term "$C_1$-$C_6$-haloalkoxy" is a $C_1$-$C_6$-haloalkyl group, as defined above, attached via an oxygen atom. $C_1$-$C_2$-Haloalkoxy is, for example, $OCH_2F$, $OCHF_2$, $OCF_3$, $OCH_2Cl$, $OCHCl_2$, $OCCl_3$, chlorofluoromethoxy, dichlorofluoromethoxy, chlorodifluoromethoxy, 2-fluoroethoxy, 2-chloroethoxy, 2-bromoethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy or $OC_2F_5$. $C_1$-$C_3$-Haloalkoxy is additionally, for example, 2-fluoropropoxy, 3-fluoropropoxy, 2,2-difluoropropoxy, 2,3-difluoropropoxy, 2-chloropropoxy, 3-chloropropoxy, 2,3-dichloropropoxy, 2-bromopropoxy, 3-bromopropoxy, 3,3,3-trifluoropropoxy, 3,3,3-trichloropropoxy, $OCH_2$—$C_2F_5$, $OCF_2$—$C_2F_5$, 1-($CH_2F$)-2-fluoroethoxy, 1-($CH_2Cl$)-2-chloroethoxy or 1-($CH_2Br$)-2-bromoethoxy. $C_1$-$C_4$-Haloalkoxy is additionally, for example, 4-fluorobutoxy, 4-chlorobutoxy, 4-bromobutoxy or nonafluorobutoxy. $C_1$-$C_6$-Haloalkoxy is additionally, for example, 5-fluoropentoxy, 5-chloropentoxy, 5-brompentoxy, 5-iodopentoxy, undecafluoropentoxy, 6-fluorohexoxy, 6-chlorohexoxy, 6-bromohexoxy, 6-iodohexoxy or dodecafluorohexoxy.

The term "$C_1$-$C_6$-alkoxy-$C_1$-$C_4$-alkyl" as used herein, refers to a straight-chain or branched alkyl having 1 to 4 carbon atoms, as defined above, where one hydrogen atom is replaced by a $C_1$-$C_6$-alkoxy group, as defined above. Examples are methoxymethyl, ethoxymethyl, propoxymethyl, isopropoxymethyl, n-butoxymethyl, sec-butoxymethyl, isobutoxymethyl, tert-butoxymethyl, 1-methoxyethyl, 1-ethoxyethyl, 1-propoxyethyl, 1-isopropoxyethyl, 1-n-butoxyethyl, 1-sec-butoxyethyl, 1-isobutoxyethyl, 1-tert-butoxyethyl, 2-methoxyethyl, 2-ethoxyethyl, 2-propoxyethyl, 2-isopropoxyethyl, 2-n-butoxyethyl, 2-sec-butoxyethyl, 2-isobutoxyethyl, 2-tert-butoxyethyl, 1-methoxypropyl, 1-ethoxypropyl, 1-propoxypropyl, 1-isopropoxypropyl, 1-n-butoxypropyl, 1-sec-butoxypropyl, 1-isobutoxypropyl, 1-tert-butoxypropyl, 2-methoxypropyl, 2-ethoxypropyl, 2-propoxypropyl, 2-isopropoxypropyl, 2-n-butoxypropyl, 2-sec-butoxypropyl, 2-isobutoxypropyl, 2-tert-butoxypropyl, 3-methoxypropyl, 3-ethoxypropyl, 3-propoxypropyl, 3-isopropoxypropyl, 3-n-butoxypropyl, 3-sec-butoxypropyl, 3-isobutoxypropyl, 3-tert-butoxypropyl and the like.

The term "alkoxyalkoxy" as used herein refers to an alkoxyalkyl radical, in particular a $C_1$-$C_6$-alkoxy-$C_1$-$C_4$-alkyl radical, as defined above, which is bound via an oxygen atom to the remainder of the molecule. Examples thereof are $OCH_2$—$OCH_3$, $OCH_2$—$OC_2H_5$, n-propoxymethoxy, $OCH_2$—$OCH(CH_3)_2$, n-butoxymethoxy, (1-methylpropoxy)methoxy, (2-methylpropoxy)methoxy, $OCH_2$—$OC(CH_3)_3$, 2-(methoxy)ethoxy, 2-(ethoxy)ethoxy, 2-(n-propoxy)ethoxy, 2-(1-methylethoxy)ethoxy, 2-(n-butoxy)ethoxy, 2-(1-methylpropoxy)ethoxy, 2-(2-methylpropoxy)ethoxy, 2-(1,1-dimethylethoxy)ethoxy, etc.

The substituent "oxo" replaces a $CH_2$ by a C(═O) group.

The term "aryl" relates to phenyl and bi- or polycyclic carbocycles having at least one fused phenylene ring, which is bound to the remainder of the molecule. Examples of bi- or polycyclic carbocycles having at least one phenylene ring include naphthyl, tetrahydronaphthyl, indanyl, indenyl, anthracenyl, fluorenyl etc.

The term "aryl-$C_1$-$C_4$-alkyl" relates to $C_1$-$C_4$-alkyl, as defined above, wherein one hydrogen atom has been replaced by an aryl radical, in particular a phenyl radical. Particular examples of aryl-$C_1$-$C_4$-alkyl include —$CH_2$-phenyl, 1-phenethyl, 2-phenetyl, 1-phenylpropyl, 2-phenylpropyl, 3-phenyl-1-propyl and 2-phenyl-2-propyl.

The term "aryloxy-$C_1$-$C_4$-alkyl" relates to $C_1$-$C_4$-alkyl, as defined above, wherein one hydrogen atom has been replaced by an aryloxy radical, in particular a phenoxy radical. Particular examples of aryloxy-$C_1$-$C_4$-alkyl include phenoxymethyl, 1-phenoxyethyl, 2-phenoxyetyl, 1-phenoxypropyl, 2-phenoxypropyl, 3-phenoxy-1-propyl and 2-phenoxy-2-propyl.

The term "aryl-$C_1$-$C_4$-carbonyl" relates to aryl as defined above, in particular a phenyl radical, which is bound by a carbonyl to the remainder of the molecule. Particular examples of arylcarbonyl include benzoyl, 1-naphthoyl and 2-naphthoyl.

The term "hetaryl" relates to aromatic heterocycles having either 5 or 6 ring atoms (5- or 6-membered hetaryl) and being monocyclic or 8, 9 or 10 ring atoms and bing bicyclic. Hetaryl will generally have at least one ring atom selected from O, S and N, which in case of N may be an imino-nitrogen or an amino-nitrogen, which carries hydrogen or a radical different from hydrogen. Hetaryl may have 1, 2, 3 or 4 further nitrogen atoms as ring members, which are imino nitrogens. Examples of 5- or 6-membered hetaryl include 2-furyl, 3-furyl, 2-thienyl, 3-thienyl, 1-pyrrolyl, 2-pyrrolyl, 3-pyrrolyl, 1-pyrazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 1-imidazolyl, 2-imidazolyl, 4-imidazolyl, 1,3,4-triazol-1-yl, 1,3,4-triazol-2-yl, 1,3,4-oxadiazolyl-2-yl, 1,3,4-thiadiazol-2-yl, 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl and 1,3,5-triazin-2-yl. Examples of 8-, 9- or 10-membered hetaryl include, for example, quinolinyl, isoquinolinyl, cinnolinyl, indolyl, indolizynyl, isoindolyl, indazolyl, benzofuryl, benzothienyl, benzo[b]thiazolyl, benzoxazolyl, benzthiazolyl, benzimidazolyl, imidazo[1,2-a]pyridine-2-yl, thieno[3,2-b]pyridine-5-yl, imidazo-[2,1-b]-thiazol-6-yl and 1,2,4-triazolo[1,5-a]pyridine-2-yl.

Examples of N-bound 5-, 6-, 7 or 8-membered saturated heterocycles include: pyrrolidin-1-yl, pyrazolidin-1-yl, imidazolidin-1-yl, oxazolidin-3-yl, isoxazolidin-2-yl, thiazolidin-3-yl, isothiazolidin-2-yl, piperidin-1-yl, piperazin-1-yl, morpholin-4-yl, thiomorpholin-4-yl, 1-oxothiomorpholin-4-yl, 1,1-dioxothiomorpholin-4-yl, azepan-1-yl and the like.

The term "hetaryl-$C_1$-$C_4$-alkyl" relates to $C_1$-$C_4$-alkyl, as defined above, wherein one hydrogen atom has been replaced by a hetaryl radical, in particular a pyridyl radical. Particular examples of hetaryl-$C_1$-$C_4$-alkyl include 2-pyridylmethyl, 3-pyridylmethyl, 4-pyridylmethyl, 1-(2-pyridyl)ethyl, 2-(2-pyridyl)ethyl, 1-(3-pyridyl)ethyl, 2-(3-pyridyl)ethyl, 1-(4-pyridyl)ethyl, 2-(4-pyridyl)ethyl etc.

The term "hetaryloxy-$C_1$-$C_4$-alkyl" relates to $C_1$-$C_4$-alkyl, as defined above, wherein one hydrogen atom has been replaced by an hetaryloxy radical, in particular a pyridyloxy radical. Particular examples of hetaryloxy-$C_1$-$C_4$-alkyl include 2-pyridyloxymethyl, 3-pyridyloxymethyl, 4-pyridyloxymethyl, 1-(2-pyridyloxy)ethyl, 2-(2-pyridyloxy)ethyl, 1-(3-pyridyloxy)ethyl, 2-(3-pyridyloxy)ethyl, 1-(4-pyridyloxy)ethyl, 2-(4-pyridyloxy)ethyl etc.

The term "hetaryl-$C_1$-$C_4$-carbonyl" relates to hetaryl as defined above, in particular a C-bound hetaryl radical, e.g. 2-, 3- or 4-pyridyl, 2- or 3-thienyl, 2- or 3-furyl, 1-, 2- or 3-pyrrolyl, 2- or 4-pyrimidinyl, pyridazinyl, 1-, 3- or 4-pyrazolyl, 1-, 2- or 4-imidazolyl radical, which is bound by a carbonyl to the remainder of the molecule.

The term "substituted" if not specified otherwise refers to substituted with 1, 2, or maximum possible number of substituents. If substituents as defined in compounds of formula I are more than one then they are independently from each other are same or different if not mentioned otherwise.

With respect to the variables, the embodiments of the compounds of the formula I are, In one preferred embodiment, A is N;

In another preferred embodiment, A and D are N;

In another preferred embodiment, $B^1$ is N;

In another preferred embodiment, $B^1$ and D are N;

In another preferred embodiment, E and D are N;

In another preferred embodiment, A is N, $B^1$ is $CR^{B1}$, E is $CR^E$, and D is $CR^D$;

In another preferred embodiment, A and D are N, $B^1$ is $CR^{B1}$, and E is $CR^E$.

In another preferred embodiment, $B^1$ is N, A is $CR^A$, D is $CR^D$, and E is $CR^E$.

In another preferred embodiment, $B^1$ and D are N, A is $CR^A$, and E is $CR^E$;

In another preferred embodiment, E and D are N, A is $CR^A$, and $B^1$ is $CR^{B1}$.

In one preferred embodiment, $B^2$ is $CR^{B2}$, $B^3$ is $CR^{B3}$, and $B^4$ is $CR^{B4}$;

In another preferred embodiment, $B^2$ is N, $B^3$ is $CR^{B3}$, $B^4$ is $CR^{B4}$;

In another preferred embodiment, $B^2$ is N, $B^3$ is N, $B^4$ is $CR^{B4}$;

In another preferred embodiment, $B^2$ is N, $B^3$ is $CR^{B3}$, $B^4$ is N;

In another preferred embodiment, $B^2$ is $CR^{B2}$, $B^3$ is N, $B^4$ is N;

In another preferred embodiment, A is N, $B^1$ is $CR^{B1}$, E is $CR^E$, D is $CR^D$, $B^2$ is $CR^{B2}$, $B^3$ is $CR^{B3}$, and $B^4$ is $CR^{B4}$;

In another preferred embodiment, A is N, $B^1$ is $CR^{B1}$, E is $CR^E$, D is $CR^D$, $B^2$ is N, $B^3$ is $CR^{B3}$, $B^4$ is $CR^{B4}$;

In another preferred embodiment, A is N, $B^1$ is $CR^{B1}$, E is $CR^E$, D is $CR^D$, $B^2$ is N, $B^3$ is N, $B^4$ is $CR^{B4}$;

In another preferred embodiment, A is N, $B^1$ is $CR^{B1}$, E is $CR^E$, D is $CR^D$, $B^2$ is N, $B^3$ is $CR^{B3}$, $B^4$ is N;

In another preferred embodiment, A is N, $B^1$ is $CR^{B1}$, E is $CR^E$, D is $CR^D$, $B^2$ is $CR^{B2}$, $B^3$ is N, $B^4$ is N:

In another preferred embodiment, A and D are N, $B^1$ is $CR^{B1}$, E is $CR^E$, $B^2$ is $CR^{B2}$, $B^3$ is $CR^{B3}$, and $B^4$ is $CR^{B4}$;

In another preferred embodiment, A and D are N, $B^1$ is $CR^{B1}$, E is $CR^E$, $B^2$ is N, $B^3$ is $CR^{B3}$, $B^4$ is $CR^{B4}$;

In another preferred embodiment, A and D are N, $B^1$ is $CR^{B1}$, E is $CR^E$, $B^2$ is N, $B^3$ is N, $B^4$ is $CR^{B4}$;

In another preferred embodiment, A and D are N, $B^1$ is $CR^{B1}$, E is $CR^E$, $B^2$ is N, $B^3$ is $CR^{B3}$, $B^4$ is N;

In another preferred embodiment, A and D are N, $B^1$ is $CR^{B1}$, E is $CR^E$, $B^2$ is $CR^{B2}$, $B^3$ is N, $B^4$ is N;

In another preferred embodiment, $B^1$ is N, A is $CR^A$, D is $CR^D$, E is $CR^E$, $B^2$ is $CR^{B2}$, $B^3$ is $CR^{B3}$, and $B^4$ is $CR^{B4}$;

In another preferred embodiment, $B^1$ is N, A is $CR^A$, D is $CR^D$, E is $CR^E$, $B^2$ is N, $B^3$ is $CR^{B3}$, $B^4$ is $CR^{B4}$;

In another preferred embodiment, $B^1$ is N, A is $CR^A$, D is $CR^D$, E is $CR^E$, $B^2$ is N, $B^3$ is N, $B^4$ is $CR^{B4}$;

In another preferred embodiment, $B^1$ is N, A is $CR^A$, D is $CR^D$, E is $CR^E$, $B^2$ is N, $B^3$ is $CR^{B3}$, $B^4$ is N;

In another preferred embodiment, $B^1$ is N, A is $CR^A$, D is $CR^D$, E is $CR^E$, $B^2$ is $CR^{B2}$, $B^3$ is N, $B^4$ is N;

In another preferred embodiment, $B^1$ and D are N, A is $CR^A$, E is $CR^E$, $B^2$ is $CR^{B2}$, $B^3$ is $CR^{B3}$, and $B^4$ is $CR^{B4}$;

In another preferred embodiment, $B^1$ and D are N, A is $CR^A$, E is $CR^E$, $B^2$ is N, $B^3$ is $CR^{B3}$, $B^4$ is $CR^{B4}$;

In another preferred embodiment, $B^1$ and D are N, A is $CR^A$, E is $CR^E$, $B^2$ is N, $B^3$ is N, $B^4$ is $CR^{B4}$;

In another preferred embodiment, $B^1$ and D are N, A is $CR^A$, E is $CR^E$, $B^2$ is N, $B^3$ is $CR^{B3}$, $B^4$ is N;

In another preferred embodiment, $B^1$ and D are N, A is $CR^A$, E is $CR^E$, $B^2$ is $CR^{B2}$, $B^3$ is N, $B^4$ is N;

In another preferred embodiment, E and D are N, A is $CR^A$, $B^1$ is $CR^{B1}$, $B^2$ is $CR^{B2}$, $B^3$ is $CR^{B3}$, and $B^4$ is $CR^{B4}$;

In another preferred embodiment, E and D are N, A is $CR^A$, $B^1$ is $CR^{B1}$, $B^2$ is N, $B^3$ is $CR^{B3}$, $B^4$ is $CR^{B4}$;

In another preferred embodiment, E and D are N, A is $CR^A$, $B^1$ is $CR^{B1}$, $B^2$ is N, $B^3$ is N, $B^4$ is $CR^{B4}$;

In another preferred embodiment, E and D are N, A is $CR^A$, $B^1$ is $CR^{B1}$, $B^2$ is N, $B^3$ is $CR^{B3}$, $B^4$ is N;

In another preferred embodiment, E and D are N, A is $CR^A$, $B^1$ is $CR^{B1}$, $B^2$ is $CR^{B2}$, $B^3$ is N, $B^4$ is N;

In one preferred embodiment, $R^A$ is H, halogen, OH, CN, $C_1$-$C_6$-alkyl, $C_1$-$C_6$-alkoxy, tri-$C_1$-$C_6$-alkylsilyl, $C_1$-$C_6$-alkoxy-$C_1$-$C_4$-alkyl, $C_3$-$C_6$-cycloalkyl, wherein the alkyl, alkoxy, cycloalkyl moieties are unsubstituted or substituted with halogen, C(═O)—$OR^a$, $NR^bR^c$, C(═O)—$NR^bR^c$, C(═O)—$R^d$, $SO_2NR^bR^c$, or $S(═O)_mR^e$;

In another preferred embodiment, $R^A$ is H, halogen, $C_1$-$C_6$-alkyl, $C_3$-$C_6$-cycloalkyl, wherein the alkyl or cycloalkyl moieties are unsubstituted or substituted with halogen.

In another preferred embodiment, $R^A$ is H, Cl, Br, F, $CH_3$, $C_2H_5$, n-$C_3H_7$, isopropyl, cyclopropyl, $CH_2F$, $CHF_2$, or $CF_3$.

In one preferred embodiment, $R^{B1}$, $R^{B2}$, $R^{B3}$, and $R^{B4}$ independently of each other are H, halogen, or $C_1$-$C_6$-alkyl;

In another preferred embodiment, $R^{B1}$, $R^{B2}$, $R^{B3}$, and $R^{B4}$ independently of each other are H, Cl, Br, F, $CH_3$, $C_2H_5$, n-$C_3H_7$, or isopropyl.

In one preferred embodiment, Q is —C($R^4R^5$)—O—, wherein C is bound to Ar.

In another preferred embodiment, Q is —C($R^4R^5$)—O—, wherein O is bound to Ar.

In another preferred embodiment, Q is —C(═O)—O—, wherein C is bound to Ar.

In another preferred embodiment, Q is —C(═O)—O—, wherein O is bound to Ar.

In another preferred embodiment, Q is —S(=O)$_m$—C($R^7R^8$)—, wherein S is bound to Ar.

In another preferred embodiment, Q is —S(=O)$_m$—C($R^7R^8$)—, wherein C is bound to Ar.

In another preferred embodiment, Q is —N($R^2$)—S(=O)$_m$ —, wherein N is bound to Ar.

In another preferred embodiment, Q is —N($R^2$)—S(=O)$_m$ —, wherein S is bound to Ar.

In another preferred embodiment, Q is —N($R^2$)—C($R^9R^{10}$)—, wherein N is bound to Ar.

In another preferred embodiment, Q is —N($R^2$)—C($R^9R^{10}$)—, wherein C is bound to Ar.

In another preferred embodiment, Q is —C(=O)—C($R^{19}R^{20}$)—, wherein C(=O) is bound to Ar.

In another preferred embodiment, Q is —C(=O)—C($R^{19}R^{20}$)—, wherein C($R^{19}R^{20}$) is bound to Ar.

In another preferred embodiment, Q is —N($R^2$)—C(=O)—, wherein N is bound to Ar.

In another preferred embodiment, Q is —N($R^2$)—, wherein N is bound to Ar.

In another preferred embodiment, Q is —N($R^2$)—C(=O)—, wherein C is bound to Ar.

In another preferred embodiment, Q is —N($R^2$)—C(=S)—, wherein N is bound to Ar.

In another preferred embodiment, Q is —N($R^2$)—C(=S)—, wherein C is bound to Ar.

In another preferred embodiment, Q is —N=C(X)—, wherein N is bound to Ar.

In another preferred embodiment, Q is —N=C(X)—, wherein C is bound to Ar.

In another preferred embodiment, Q is —N($R^2$)—C(=NR)—, wherein N is bound to Ar.

In another preferred embodiment, Q is —N($R^2$)—C(=NR)—, wherein C is bound to Ar.

In another preferred embodiment, Q is —C($R^{13}R^{14}$)—C($R^{15}R^{16}$)—.

In another preferred embodiment, Q is —C($R^{17}$)=C($R^{18}$)—.

In another preferred embodiment, Q is —C($R^4R^5$)—O—, —N($R^2$)—S(=O)$_m$—, —N($R^2$)—C($R^9R^{10}$)—, —N($R^2$)—C(=O)—, —N($R^2$)—C(=S)—, —N=C(X)—, or —N($R^2$)—C(=NR)—, wherein Ar is bound to either side of Q; In another preferred embodiment, Q is —C($R^4R^5$)—O—, —N($R^2$)—C($R^9R^{10}$)—, —N($R^2$)—, —N($R^2$)—C(=O)—, —N=C(X)—, or —N($R^2$)—C(=NR)—; wherein Ar is bound to either side of Q.

In another preferred embodiment, Q is —C($R^4R^5$)—O—, —N($R^2$)—C($R^9R^{10}$)—, —N($R^2$)—, —N($R^2$)—C(=O)—, or —N($R^2$)—C(=NR)—; wherein Ar is bound to either side of Q.

In another preferred embodiment, Q is —C($R^4R^5$)—O—, —N($R^2$)—C($R^9R^{10}$)—, —N($R^2$)—C(=O)—, —N($R^2$)—C(=NR)—, wherein Ar is bound to either side of Q;

In one preferred embodiment, X is H or N($R^3$)$_2$;

In another preferred embodiment, X is H;

In another preferred embodiment, X is N($R^3$)$_2$;

In one preferred embodiment, $R^3$ is H, $C_1$-$C_6$-alkyl, or $C_1$-$C_6$-alkoxy-$C_1$-$C_4$-alkyl;

In another preferred embodiment, $R^3$ is H, or $C_1$-$C_6$-alkyl;

In another preferred embodiment, $R^3$ is $C_1$-$C_6$-alkyl;

In another preferred embodiment, $R^3$ is H;

In one preferred embodiment, R is H, CN, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_3$-$C_6$-cycloalkyl, $C_3$-$C_6$-halocycloalkyl, $OR^8$, or N($R^3$)$_2$;

In another preferred embodiment, R is H, CN, $C_1$-$C_6$-alkyl, or $OR^8$;

In another preferred embodiment, R is H, or $C_1$-$C_6$-alkyl;

In another preferred embodiment, R is H, $CH_3$, $C_2H_5$, n-$C_3H_7$, or isopropyl;

In one preferred embodiment, $R^4$, $R^5$, $R^7$, $R^8$, $R^9$, $R^{10}$, $R^{13}$, $R^{14}$, $R^{15}$, $R^{16}$, $R^{17}$, $R^{18}$, $R^{19}$, $R^{20}$ are, identical or different, H, halogen, $C_1$-$C_6$-alkyl, $C_1$-$C_6$-haloalkylalkyl, $C_2$-$C_6$-alkenyl, $C_2$-$C_6$-alkynyl, $C_1$-$C_6$-alkoxy-$C_1$-$C_4$-alkyl, $C_3$-$C_6$-cycloalkyl, $C_3$-$C_6$-halocycloalkyl, $C_3$-$C_6$-cycloalkyl-$C_1$-$C_4$-alkyl, $C_3$-$C_6$-cycloalkoxy-$C_1$-$C_4$-alkyl, C(=O)—$OR^a$, C(=O)—$NR^bR^c$, C(=O)—$R^d$, $SO_2NR^bR^c$, S(=O)$_m$ $R^e$, phenyl, or —$CH_2$-phenyl, wherein the phenyl rings are unsubstituted or substituted with $R^f$;

In another preferred embodiment, $R^4$, $R^5$, $R^7$, $R^8$, $R^9$, $R^{10}$, $R^{13}$, $R^{14}$, $R^{15}$, $R^{16}$, $R^{17}$, $R^{18}$, $R^{19}$, $R^{20}$ are, identical or different, H, halogen, $C_1$-$C_6$-alkyl, $C_1$-$C_6$-haloalkylalkyl, $C_3$-$C_6$-cycloalkyl, $C_3$-$C_6$-halocycloalkyl, C(=O)—$OR^a$, C(=O)—$NR^bR^c$, C(=O)—$R^d$, phenyl, or —$CH_2$-phenyl, wherein the phenyl rings are unsubstituted or substituted with $R^f$;

In another preferred embodiment, $R^4$, $R^5$, $R^7$, $R^8$, $R^9$, $R^{10}$, $R^{13}$, $R^{14}$, $R^{15}$, $R^{16}$, $R^{17}$, $R^{18}$, $R^{19}$, $R^{20}$ are, identical or different, H, halogen, $C_1$-$C_6$-alkyl, or $C_1$-$C_6$-haloalkylalkyl;

In another preferred embodiment, $R^4$, $R^5$, $R^7$, $R^8$, $R^9$, $R^{10}$, $R^{13}$, $R^{14}$, $R^{15}$, $R^{16}$, $R^{17}$, $R^{18}$, $R^{19}$, $R^{20}$ are, identical or different, H, halogen, or $C_1$-$C_6$-alkyl;

In another preferred embodiment, $R^4$, $R^5$, $R^7$, $R^8$, $R^9$, $R^{10}$, $R^{13}$, $R^{14}$, $R^{15}$, $R^{16}$, $R^{17}$, $R^{18}$, $R^{19}$, $R^{20}$ are, identical or different, H or $C_1$-$C_6$-alkyl;

In one preferred embodiment, Ar is phenyl which is unsubstituted or substituted with $R^{Ar}$ In another preferred embodiment, Ar is 5- or 6-membered hetaryl, which is unsubstituted or substituted with $R^{Ar}$.

In more preferred embodiment, Ar is phenyl, pyrimidinyl, pyridazinyl, or pyridyl, which are unsubstituted or substituted with $R^{Ar}$.

In one preferred embodiment, $R^{Ar}$ is halogen, OH, CN, $NO_2$, SCN, $C_1$-$C_6$-alkyl, $C_1$-$C_6$-haloalkyl, $C_1$-$C_6$-alkoxy, $C_1$-$C_6$-haloalkoxy, or S—$R^e$.

In more preferred embodiment, $R^{Ar}$ is F, Cl, Br, OH, CN, $NO_2$, SCN, $CH_3$, $C_2H_5$, n-$C_3H_7$, isopropyl, $CH_2F$, $CHF_2$, $CF_3$, $CH_2CF_3$, $CF_2CHF_2$, $C_2F_5$, $CH_2CH_2CF_3$, $CH_2CF_2CHF_2$, $CH_2CF_2CF_3$, $OCH_3$, $OC_2H_5$, n-propyloxy, isopropyloxy, $OCH_2F$, $OCHF_2$, $OCF_3$, $OCH_2CF_3$, $OCF_2CHF_2$, $OC_2F_5$, $OCH_2CH_2CF_3$, $OCH_2CF_2CHF_2$, $OCH_2CF_2CF_3$, or S—$R^e$, where $R^e$ is $C_1$-$C_6$-alkyl, in particular $C_1$-$C_3$-alkyl such as $CH_3$, $C_2H_5$, n-$C_3H_7$ or isopropyl, or $C_1$-$C_6$-haloalkyl, in particular fluorinated $C_1$-$C_3$-alkyl such as $CH_2F$, $CHF_2$, $CF_3$, $CH_2CF_3$, $CF_2CHF_2$, $C_2F_5$, $CH_2CH_2CF_3$, $CH_2CF_2CHF_2$ or $CH_2CF_2CF_3$.

Particularly preferred Ar are listed in Table A below.

TABLE A

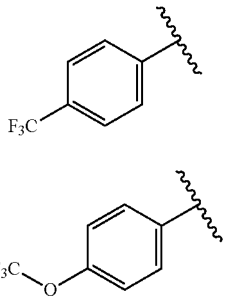

Ar-1

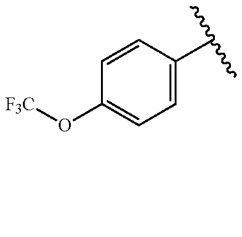 [SMILES: *c1ccc(OC(F)(F)F)cc1]

Ar-2

TABLE A-continued
Ar-3
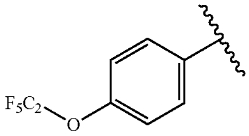
Ar-4
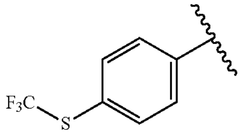 [SMILES: *c1ccc(SC(F)(F)F)cc1]
Ar-5
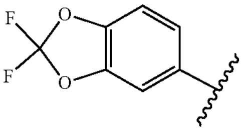 [SMILES: *c1ccc2c(c1)OC(F)(F)O2]
Ar-6
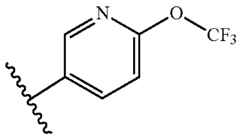 [SMILES: *c1ccc(OC(F)(F)F)nc1]
Ar-7
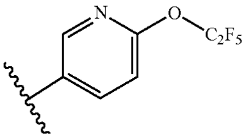
Ar-8
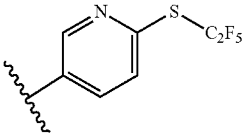
Ar-9
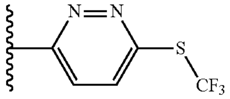
Ar-10
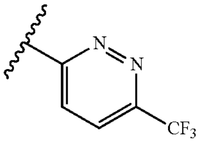
Ar-11
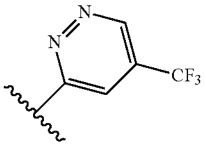 [SMILES: *c1cc(C(F)(F)F)cnn1]
Ar-12
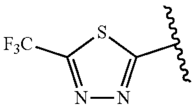 [SMILES: *c1nnc(C(F)(F)F)s1]
TABLE A-continued
Ar-13
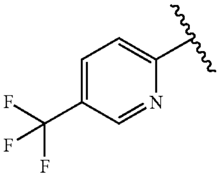 [SMILES: *c1ccc(C(F)(F)F)cn1]
Ar-14
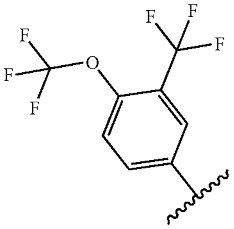 [SMILES: *c1ccc(OC(F)(F)F)c(C(F)(F)F)c1]
Ar-15
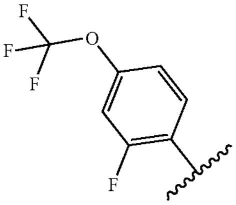 [SMILES: *c1ccc(OC(F)(F)F)cc1F]
Ar-16
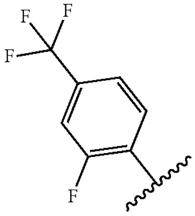 [SMILES: *c1ccc(C(F)(F)F)cc1F]
Ar-17
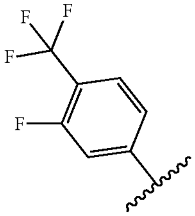 [SMILES: *c1ccc(C(F)(F)F)c(F)c1]
Ar-18
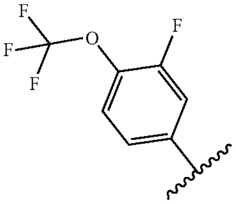 [SMILES: *c1ccc(OC(F)(F)F)c(F)c1]
Ar-19
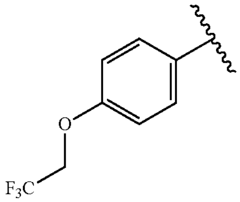 [SMILES: *c1ccc(OCC(F)(F)F)cc1]

TABLE A-continued

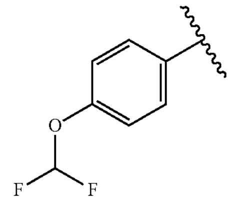 [SMILES: *c1ccc(OC(F)F)cc1]

Ar-20

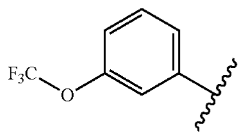 [SMILES: *c1cccc(OC(F)(F)F)c1]

Ar-21

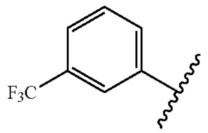 [SMILES: *c1cccc(C(F)(F)F)c1]

Ar-22

Particularly preferred Ar is selected from Ar-1 to Ar-20;
- also particularly preferred Ar is selected from Ar-1 to Ar-13;
- also particularly preferred Ar is selected from Ar-1 to Ar-13 and Ar-17 to Ar-18;
- also particularly preferred Ar is selected from Ar-1, Ar-2, Ar-3, Ar-4, Ar-10, Ar-17, and Ar-18.
- also particularly preferred Ar is selected from Ar-17 and Ar-18;
- also particularly preferred Ar is selected from Ar-1, Ar-2, Ar-5, Ar-21 and Ar-22;
- also particularly preferred Ar is Ar-17;
- also particularly preferred Ar is Ar-18;

In one preferred embodiment, $R^1$ is Y—Z-T-$R^{11}$.

In another preferred embodiment, $R^1$ is Y—Z-T-$R^{12}$.

In one preferred embodiment, Y is —$CR^{ya}$═N—, wherein the N is bound to Z.

In another preferred embodiment, Y is —$NR^{yc}$—C(═S)—, wherein C(═S) is bound to Z.

In another preferred embodiment, Y is —$NR^{yc}$—C(═O)—, wherein C(═O) is bound to Z.

In one preferred embodiment, Y is —$CR^{ya}$═N— and Z is a single bond;
- —$NR^{zc}$—C(═O)—, wherein C(═O) is bound to T;
- —$NR^{zc}$—C(═S)—, wherein C(═S) is bound to T;
- —N═C(S—$R^{za}$)—, wherein T is bound to the carbon atom; or
- —$NR^{zc}$—C(S—$R^{za}$)═, wherein T is bound to the carbon atom;

In another preferred embodiment, Z is —$NR^{zc}$—C(═S)—, wherein C(═S) is bound to T.

In another preferred embodiment, Z is —$NR^{zc}$—C(═O)—, wherein C(═O) is bound to T.

In another preferred embodiment, Z is-N═C(S—$R^{za}$)—, wherein T is bound to the carbon atom.

In another preferred embodiment, Z is-$NR^{zc}$—C(S—$R^{za}$)═, wherein T is bound to the carbon atom.

In another preferred embodiment, Z is —O—C(═O)—, wherein T is bound to the carbon atom;

In another preferred embodiment, Z is a single bond.

In one preferred embodiment, T is O.

In another preferred embodiment, T is N—$R^T$.

In another preferred embodiment, T is N.

In one preferred embodiment, $R^{ya}$ is H, halogen, $C_1$-$C_6$-alkyl, $C_1$-$C_6$-alkoxy, which are unsubstituted or substituted with halogen, phenyl, or —$CH_2$-phenyl, wherein the phenyl rings are unsubstituted or substituted with $R^f$.

In more preferred embodiment, $R^{ya}$ is H, halogen, $C_1$-$C_6$-alkyl, $C_1$-$C_6$-alkoxy, which are unsubstituted or substituted with halogen, or phenyl which is unsubstituted or substituted with $R^f$.

In most preferred embodiment, $R^{ya}$ is H, F, Cl, Br, $CH_3$, $C_2H_5$, n-$C_3H_7$, isopropyl, $CH_2F$, $CHF_2$, $CF_3$, $CH_2CF_3$, $CF_2CHF_2$, $C_2F_5$, $CH_2CH_2CF_3$, $CH_2CF_2CHF_2$, $CH_2CF_2CF_3$, $OCH_3$, $OC_2H_5$, n-propyloxy, isopropyloxy, $OCH_2F$, $OCHF_2$, $OCF_3$, $OCH_2CF_3$, $OCF_2CHF_2$, $OC_2F_5$, $OCH_2CH_2CF_3$, $OCH_2CF_2CHF_2$, $OCH_2CF_2CF_3$, or phenyl which is unsubstituted or substituted with $R^f$.

In further most preferred embodiment, $R^{ya}$ is H or $CH_3$;

In one embodiment, $R^{yc}$, $R^{zc}$ are H, $C_1$-$C_6$-alkyl, $C_3$-$C_6$-cycloalkyl, which are unsubstituted or substituted with halogen, phenyl, or —$CH_2$-phenyl, wherein the rings are unsubstituted or substituted with $R^f$.

In more preferred embodiment, $R^{yc}$ and $R^{zc}$ are H, $C_1$-$C_6$-alkyl, $C_1$-$C_6$-haloalkyl, or phenyl which is unsubstituted or substituted with $R^f$.

In most preferred embodiment, $R^{yc}$ and $R^{zc}$ are H, $CH_3$, $C_2H_5$, n-$C_3H_7$, isopropyl, $CH_2F$, $CHF_2$, $CF_3$, $CH_2CF_3$, $CF_2CHF_2$, $C_2F_5$, $CH_2CH_2CF_3$, $CH_2CF_2CHF_2$, $CH_2CF_2CF_3$, or phenyl which is unsubstituted or substituted with $R^f$.

In further most preferred embodiment, $R^{yc}$ and $R^{zc}$ are H or $CH_3$;

In one preferred embodiment, $R^T$ is H, $C_1$-$C_6$-alkyl, $C_2$-$C_6$-alkenyl, $C_2$-$C_6$-alkynyl, $C_1$-$C_4$-alkyl-$C_1$-$C_6$-alkoxy, which are unsubstituted or substituted with halogen, C(═O)—$NR^bR^c$, C(═O)—$R^d$, $SO_2NR^bR^c$, $S(═O)_mR^e$, phenyl, or —$CH_2$-phenyl, wherein the phenyl rings are unsubstituted or substituted with $R^f$.

In more preferred embodiment, $R^T$ is H, $C_1$-$C_6$-alkyl, $C_2$-$C_6$-alkenyl, $C_2$-$C_6$-alkynyl, $C_1$-$C_4$-alkyl-$C_1$-$C_6$-alkoxy, which are unsubstituted or substituted with halogen.

In most preferred embodiment, $R^T$ is H or $C_1$-$C_6$-alkyl.

In another preferred embodiment, $R^{zc}$ together with $R^T$ if present, forms $C_1$-$C_6$-alkylene or a linear $C_2$-$C_6$-alkenylene group, where in the linear $C_1$-$C_6$-alkylene and the linear $C_2$-$C_6$-alkenylene a $CH_2$ moiety may be replaced by a carbonyl or a C═N—R' and/or wherein 1 or 2 $CH_2$ moieties may be replaced by O or S and/or wherein the linear $C_1$-$C_6$-alkylene and the linear $C_2$-$C_6$-alkenylene may be unsubstituted or substituted with $R^h$.

In more preferred embodiment, $R^{zc}$ together with $R^T$ if present, forms $C_1$-$C_6$-alkylene or a linear $C_2$-$C_6$-alkenylene group, where in the linear $C_1$-$C_6$-alkylene and the linear $C_2$-$C_6$-alkenylene a $CH_2$ moiety is replaced by a carbonyl group.

In another more preferred embodiment, $R^{zc}$ together with $R^T$ if present, forms $C_1$-$C_6$-alkylene or a linear $C_2$-$C_6$-alkenylene group, where in the linear $C_1$-$C_6$-alkylene and the linear $C_2$-$C_6$-alkenylene a $CH_2$ moiety is replaced by a C═N—R' and wherein 1 or 2 $CH_2$ moieties may be replaced by O or S and/or wherein the linear $C_1$-$C_6$-alkylene and the linear $C_2$-$C_6$-alkenylene may be unsubstituted or substituted with $R^h$.

In another more preferred embodiment, $R^{zc}$ together with $R^T$ if present, forms $C_1$-$C_6$-alkylene or a linear $C_2$-$C_6$-alkenylene group, where in the linear $C_1$-$C_6$-alkylene and the linear $C_2$-$C_6$-alkenylene 1 or 2 $CH_2$ moieties are replaced by O or S and/or wherein the linear $C_1$-$C_6$-alkylene and the linear $C_2$-$C_6$-alkenylene may be unsubstituted or substituted with $R^h$.

In one preferred embodiment, $R^{za}$ is H, $C_1$-$C_6$-alkyl, $C_1$-$C_6$-haloalkyl, $C_1$-$C_6$-alkylene-$NR^bR^c$, $C_1$-$C_6$—C(═O)—$R^d$, phenyl, phenylcarbonyl, or —$CH_2$-phenyl, wherein the phenyl rings are unsubstituted or substituted with $R^f$;

In more preferred embodiment, $R^{za}$ is H, $C_1$-$C_6$-alkyl, or $C_1$-$C_6$-haloalkyl;

In most preferred embodiment, $R^{za}$ is H, $C_1$-$C_6$-alkyl.

In another preferred embodiment, $R^{za}$ together with $R^T$ if present, forms $C_1$-$C_6$-alkylene or a linear $C_2$-$C_6$-alkenylene group, where in the linear $C_1$-$C_6$-alkylene and the linear $C_2$-$C_6$-alkenylene a $CH_2$ moiety may be replaced by a carbonyl or a C═N—R' and/or wherein 1 or 2 $CH_2$ moieties may be replaced by O or S and/or wherein the linear $C_1$-$C_6$-alkylene and the linear $C_2$-$C_6$-alkenylene may be unsubstituted or substituted with $R^h$;

In more preferred embodiment, $R^{Za}$ together with $R^T$ if present, forms $C_1$-$C_6$-alkylene or a linear $C_2$-$C_6$-alkenylene group, where in the linear $C_1$-$C_6$-alkylene and the linear $C_2$-$C_6$-alkenylene a $CH_2$ moiety is replaced by a carbonyl group.

In another more preferred embodiment, $R^{za}$ together with $R^T$ if present, forms $C_1$-$C_6$-alkylene or a linear $C_2$-$C_6$-alkenylene group, where in the linear $C_1$-$C_6$-alkylene and the linear $C_2$-$C_6$-alkenylene a $CH_2$ moiety is replaced by a C═N—R' and wherein 1 or 2 $CH_2$ moieties may be replaced by O or S and/or wherein the linear $C_1$-$C_6$-alkylene and the linear $C_2$-$C_6$-alkenylene may be unsubstituted or substituted with $R^h$.

In another more preferred embodiment, $R^{za}$ together with $R^T$ if present, forms $C_1$-$C_6$-alkylene or a linear $C_2$-$C_6$-alkenylene group, where in the linear $C_1$-$C_6$-alkylene and the linear $C_2$-$C_6$-alkenylene 1 or 2 $CH_2$ moieties are replaced by O or S and/or wherein the linear $C_1$-$C_6$-alkylene and the linear $C_2$-$C_6$-alkenylene may be unsubstituted or substituted with $R^h$.

In a preferred embodiment, $R^a$, $R^b$ and $R^c$ are H, $C_1$-$C_6$-alkyl, $C_2$-$C_6$-alkenyl, $C_2$-$C_6$-alkynyl, which are unsubstituted or substituted with halogen, $C_1$-$C_6$-alkylene-CN, phenyl, or —$CH_2$-phenyl, wherein the phenyl rings are unsubstituted or substituted with $R^f$;

In more preferred embodiment, $R^a$, $R^b$ and $R^c$ are H, $C_1$-$C_6$-alkyl, $C_2$-$C_6$-alkenyl, $C_2$-$C_6$-alkynyl, which are unsubstituted or substituted with halogen, phenyl, or —$CH_2$-phenyl, wherein the phenyl rings are unsubstituted or substituted with $R^f$.

In a preferred embodiment, $R^d$ is H, $C_1$-$C_6$-alkyl, $C_2$-$C_6$-alkenyl, $C_2$-$C_6$-alkynyl, which are unsubstituted or substituted with halogen, phenyl, or —$CH_2$-phenyl, wherein the phenyl rings are unsubstituted or substituted with $R^f$.

In more preferred embodiment, $R^d$ is H, $C_1$-$C_6$-alkyl, $C_1$-$C_6$-haloalkyl, or phenyl which is unsubstituted or substituted with $R^f$.

In one preferred embodiment, $R^e$ is $C_1$-$C_6$-alkyl, $C_1$-$C_6$-haloalkyl, $C_3$-$C_6$-cycloalkyl, $C_3$-$C_6$-halocycloalkyl, phenyl, or —$CH_2$-phenyl, wherein the phenyl rings are unsubstituted or substituted with $R^f$.

In more preferred embodiment, $R^e$ is H, $C_1$-$C_6$-alkyl, $C_1$-$C_6$-haloalkyl, or phenyl unsubstituted or substituted with $R^f$.

In one preferred embodiment, $R^f$ is halogen, $N_3$, OH, CN, $NO_2$, —SCN, —$SF_5$, $C_1$-$C_6$-alkyl, $C_1$-$C_6$-alkoxy, $C_2$-$C_6$-alkenyl, $C_2$-$C_6$-alkynyl, $C_3$-$C_6$-cycloalkyl, $C_3$-$C_6$-cycloalkoxy, which are unsubstituted or substituted with halogen, C(═O)—$OR^a$, $NR^bR^c$, $C_1$-$C_6$-alkylene-$NR^bR^c$, $C_1$-$C_6$-alkylene-CN, C(═O)—$NR^bR^c$, C(═O)—$R^d$, $SO_2NR^bR^c$, or $S(═O)_mR^e$.

In more preferred embodiment, $R^f$ is halogen, $N_3$, OH, CN, $C_1$-$C_6$-alkyl, $C_1$-$C_6$-alkoxy, $C_2$-$C_6$-alkenyl, $C_2$-$C_6$-alkynyl, $C_3$-$C_6$-cycloalkyl, $C_3$-$C_6$-cycloalkoxy, which are unsubstituted or substituted with halogen, C(═O)—$OR^a$, $NR^bR^c$, $C_1$-$C_6$-alkylene-$NR^bR^c$, $C_1$-$C_6$-alkylene-CN, C(═O)—$NR^bR^c$, C(═O)—$R^d$, $SO_2NR^bR^c$, or $S(═O)_mR^e$.

In a preferred embodiment, $R^9$ is halogen, $N_3$, OH, CN, $NO_2$, —SCN, —$SF_5$, $C_1$-$C_6$-alkyl, $C_1$-$C_6$-alkoxy, $C_2$-$C_6$-alkenyl, $C_2$-$C_6$-alkynyl, $C_3$-$C_6$-cycloalkyl, $C_3$-$C_6$-cycloalkoxy, which are unsubstituted or substituted with halogen, C(═O)—$OR^a$, $NR^bR^c$, $C_1$-$C_6$-alkylene-$NR^bR^c$, NH—$C_1$-$C_6$-alkylene-$NR^bR^c$, C(═O)—$NR^bR^c$, C(═O)—$R^d$, $SO_2NR^bR^c$, or $S(═O)_mR^e$.

In more preferred embodiment, $R^9$ is halogen, $N_3$, OH, CN, $NO_2$, $C_1$-$C_6$-alkyl, $C_1$-$C_6$-alkoxy, $C_2$-$C_6$-alkenyl, $C_3$-$C_6$-cycloalkyl, $C_3$-$C_6$-cycloalkoxy, which are unsubstituted or substituted with halogen, C(═O)—$OR^a$, $NR^bR^c$, $C_1$-$C_6$-alkylene-$NR^bR^c$, C(═O)—$NR^bR^c$, C(═O)—$R^d$, $SO_2NR^bR^c$, or $S(═O)_mR^e$.

In one embodiment, m is 0.

In another embodiment, m is 1.

In another embodiment, m is 2.

In another embodiment, m is 0 or 1.

In another embodiment, m is 1 or 2.

In more preferred embodiment, $R^1$ are formulas Y-1 to Y-9 wherein  denotes attachment to the remaining part of the compound, D is $R^{11}$ or $R^{12}$ and wherein $R^T$, $R^{11}$, $R^{12}$, $R^{ya}$, $R^{yc}$, $R^{za}$ and $R^{zc}$ are as defined in compounds of formula I.

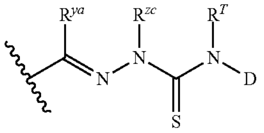

Y-1

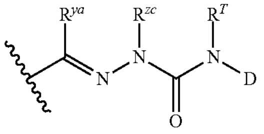

Y-2

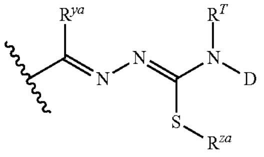

Y-3

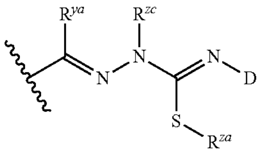

Y-4

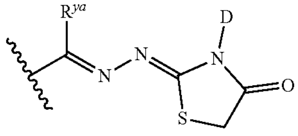

Y-5

-continued

Y-6

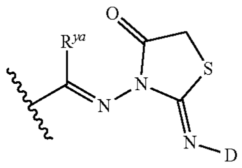

Y-8

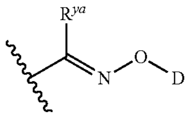

Y-9

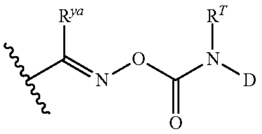

In more preferred embodiment, $R^1$ are formulas Y-1 to Y-8 wherein denotes attachment to use the remaining part of the compound, D is $R^{11}$ or $R^{12}$ and wherein $R^T$, $R^{11}$, $R^{12}$, $R^{ya}$, $R^{yc}$, $R^{za}$ and $R^{zc}$ are as defined in compounds of formula I.

Also in more preferred embodiment, $R^1$ are formulas Y-1, Y-5 or Y-6 wherein denotes attachment to the remaining part of the compound, D is $R^{11}$ or $R^{12}$ and wherein $R^T$, $R^{11}$, $R^{12}$, $R^{ya}$, $R^{yc}$, $R^{za}$ and $R^{zc}$ are as defined in compounds of formula I.

In another more preferred embodiment, $R^1$ are below formulas YZT-1 to YZT-9, wherein denotes attachment to the remaining part of the compound and $R^{11}$, $R^{12}$, $R^T$, $R^{ya}$, $R^{za}$ and $R^{zc}$ are as defined in compounds of formula I.

YZT-1

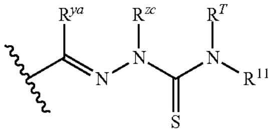

YZT-2

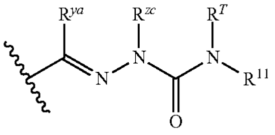

YZT-3

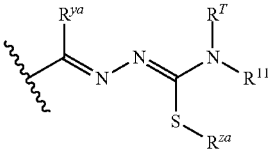

YZT-4

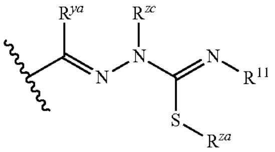

-continued

YZT-5

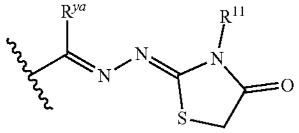

YZT-6

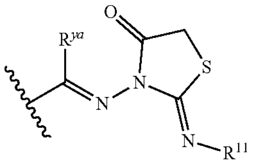

YZT-8

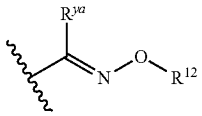

YZT-9

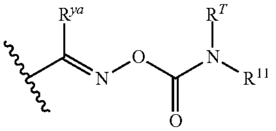

In another more preferred embodiment, $R^1$ are formulas YZT-1 to YZT-8, wherein denotes attachment to the remaining part of the compound and $R^{11}$, $R^{12}$, $R^T$, $R^{ya}$, $R^{za}$ and $R^{zc}$ are as defined in compounds of formula I.

In most preferred embodiment, $R^1$ are formulas Y-1A to Y-9A, wherein denotes attachment to the remaining part of the compound, D is $R^{11}$ or $R^{12}$.

Y-1A

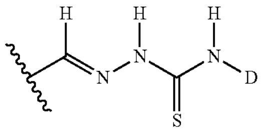

Y-1B

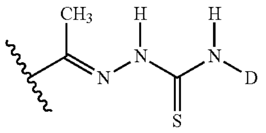

Y-2A

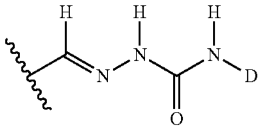

Y-2B

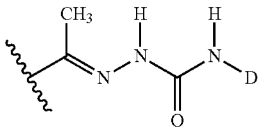

Y-3A

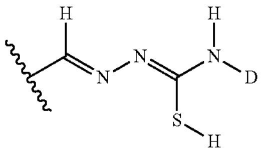

-continued

Y-3B

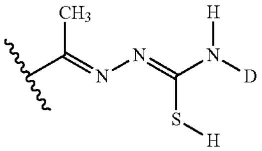

Y-3C

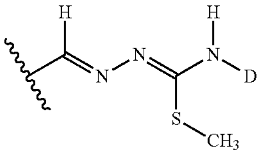

Y-3D

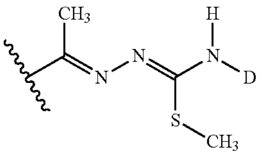

Y-4A

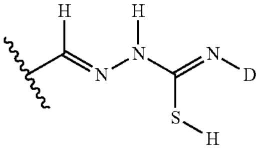

Y-4B

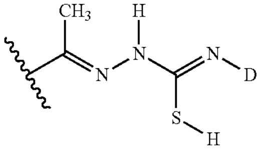

Y-4C

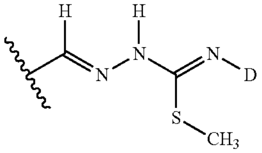

Y-4D

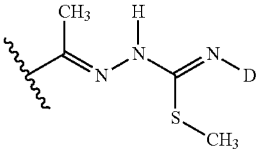

Y-5A

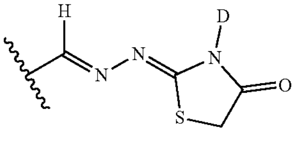

Y-5B

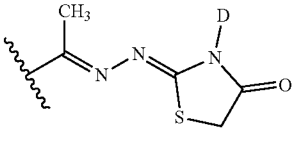

Y-6A

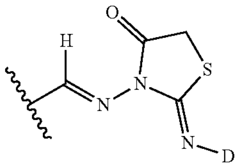

-continued

Y-6B

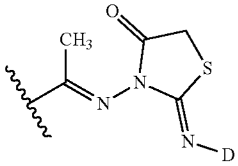

Y-8A

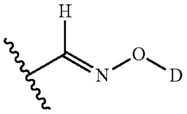

Y-8B

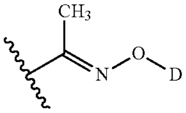

Y-9A

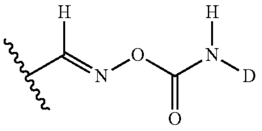

In most preferred embodiment, $R^1$ are formulas Y-1A to Y-8B, wherein  denotes attachment to the remaining part of the compound, D is $R^{11}$ or $R^{12}$.

In one preferred embodiment, $R^{11}$ is $C_1$-$C_6$-alkyl, $C_2$-$C_6$-alkenyl, $C_2$-$C_6$-alkynyl, $C_1$-$C_6$-alkoxy-$C_1$-$C_4$-alkyl, $C_3$-$C_6$-cycloalkyl, $C_3$-$C_6$-cycloalkyl-$C_1$-$C_4$-alkyl, $C_1$-$C_4$-alkyl-$C_3$-$C_6$-cycloalkoxy, which are unsubstituted or substituted with halogen, aryl, arylcarbonyl, aryl-$C_1$-$C_4$-alkyl, aryloxy-$C_1$-$C_4$-alkyl, hetaryl, carbonylhetaryl, $C_1$-$C_4$-alkyl-hetaryl and $C_1$-$C_4$-alkyl-hetaryloxy, wherein the aryl or hetaryl rings are unsubstituted or substituted with $R^9$ and wherein the hetaryl is a 5- or 6-membered monocyclic hetaryl or a 8-, 9- or 10-membered bicyclic hetaryl.

In more preferred embodiment, $R^{11}$ is $C_1$-$C_6$-alkyl, $C_2$-$C_6$-alkenyl, $C_2$-$C_6$-alkynyl, $C_3$-$C_6$-cycloalkyl, which are unsubstituted or substituted with halogen, aryl, arylcarbonyl, aryl-$C_1$-$C_4$-alkyl, aryloxy-$C_1$-$C_4$-alkyl, hetaryl, carbonyl-hetaryl, $C_1$-$C_4$-alkyl-hetaryl and $C_1$-$C_4$-alkyl-hetaryloxy, where the rings are unsubstituted or substituted with $R^g$ and wherein the hetaryl is a 5- or 6-membered monocyclic hetaryl or a 8-, 9- or 10-membered bicyclic hetaryl.

In most preferred embodiment, $R^{11}$ is aryl, aryl-$C_1$-$C_4$-alkyl, hetaryl, or hetaryl-$C_1$-$C_4$-alkyl, wherein the rings are unsubstituted or substituted with $R^g$ and where hetaryl in hetaryl or hetaryl-$C_1$-$C_4$-alkyl, is preferably a 5- or 6-membered monocyclic hetaryl such as pyridyl, pyrimidinyl, pyridazinyl, pyrrolyl, pyrazolyl, imidazolyl, oxazolyl, thiazolyl, isoxazolyl or isothiazolyl which is unsubstituted or substituted with $R^9$.

Examples of particularly preferred radicals $R^{11}$ are the radicals $R^{11}$-1 to $R^{11}$-29 summarized in Table A-1 below.

TABLE A-1

| | |
|---|---|
| 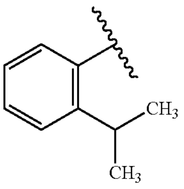 [SMILES: *c1ccccc1C(C)C] | $R^{11}$-1 |

TABLE A-1-continued
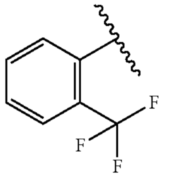 [SMILES: *c1ccccc1C(F)(F)F]
R11-2
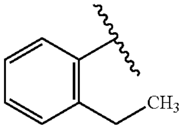 [SMILES: *c1ccccc1CC]
R11-3
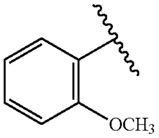 [SMILES: *c1ccccc1OC]
R11-4
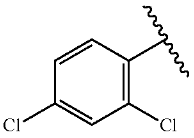 [SMILES: *c1ccc(Cl)cc1Cl]
R11-5
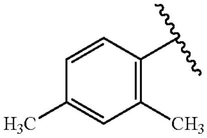
R11-6
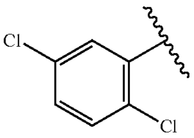 [SMILES: *c1cc(Cl)ccc1Cl]
R11-7
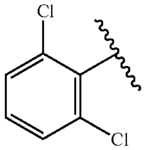 [SMILES: *c1c(Cl)cccc1Cl]
R11-8
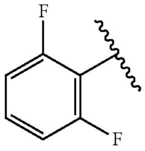 [SMILES: *c1c(F)cccc1F]
R11-9
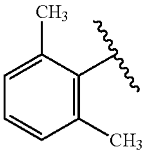
R11-10
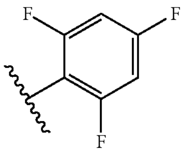 [SMILES: *c1c(F)cc(F)cc1F]
R11-11
TABLE A-1-continued
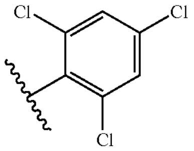 [SMILES: *c1c(Cl)cc(Cl)cc1Cl]
R11-12
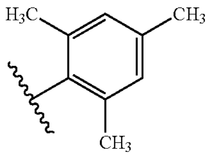
R11-13
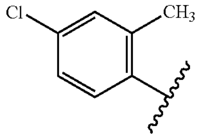 [SMILES: *c1ccc(Cl)cc1C]
R11-14
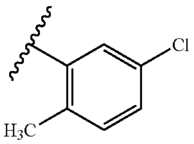
R11-15
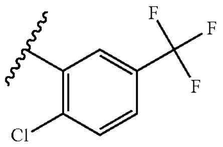 [SMILES: *c1cc(C(F)(F)F)ccc1Cl]
R11-16
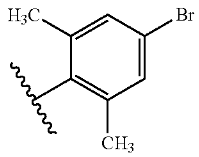 [SMILES: *c1c(C)cc(Br)cc1C]
R11-17
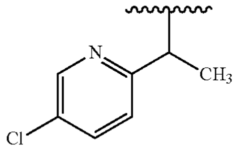 [SMILES: *C(C)c1ccc(Cl)cn1]
R11-18
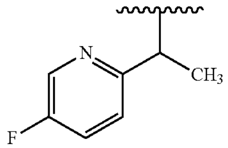 [SMILES: *C(C)c1ccc(F)cn1]
R11-19
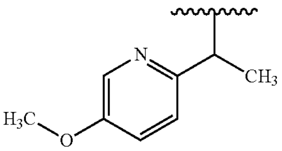 [SMILES: *C(C)c1ccc(OC)cn1]
R11-20
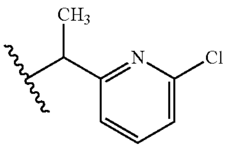 [SMILES: *C(C)c1cccc(Cl)n1]
R11-21

TABLE A-1-continued

| | |
|---|---|
| 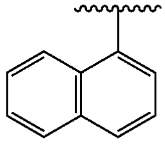 [SMILES: *c1cccc2ccccc12] | $R^{11}$-22 |
| 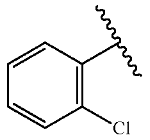 [SMILES: *c1ccccc1Cl] | $R^{11}$-23 |
| 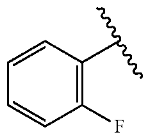 [SMILES: *c1ccccc1F] | $R^{11}$-24 |
| 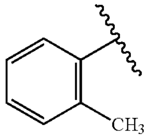 | $R^{11}$-25 |
| 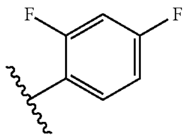 [SMILES: *c1ccc(F)cc1F] | $R^{11}$-26 |
| 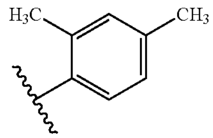 [SMILES: *c1ccc(C)cc1C] | $R^{11}$-27 |
| 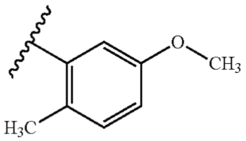 | $R^{11}$-28 |
| 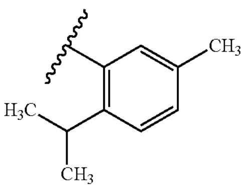 [SMILES: *c1cc(C)ccc1C(C)C] | $R^{11}$-29 |

In another preferred embodiment of the invention, $R^{11}$ is $R^{11}$-1, $R^{11}$-10, or $R^{11}$-29;

In one embodiment, $R^{12}$ is a radical of the formula ($A^1$),

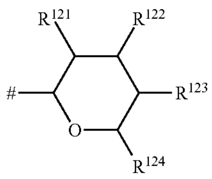

($A^1$)

wherein # indicates the point of attachment to T and wherein $R^{121}$, $R^{122}$, $R^{123}$ and $R^{124}$ are as defined above and wherein $R^{121}$, $R^{122}$, $R^{123}$ and $R^{124}$ independently of each other and especially in combination preferably have the following meanings:

$R^{121}$ is $C_1$-$C_4$-alkoxy, in particular $OCH_3$, $OC_2H_5$;

$R^{122}$ is $C_1$-$C_4$-alkoxy, such as $OCH_3$, $OC_2H_5$, n-propoxyx or isopropoxy, or $C_3$-$C_4$-alkenyloxy, such as allyloxy, with $R^{122}$ in particular being $OCH_3$, $OC_2H_5$, or n-propoxy;

$R^{123}$ is OH, $C_1$-$C_4$-alkoxy, such as $OCH_3$, $OC_2H_5$, or $C_3$-$C_4$-alkenyloxy, such as allyloxy, with $R^{123}$ in particular being $OCH_3$, $OC_2H_5$;

$R^{124}$ is $C_1$-$C_4$-alkyl, such as $CH_3$ or $C_2H_5$, or $C_1$-$C_4$-alkoxy-$C_1$-$C_4$-alkyl, such as methoxymethyl, ethoxymethyl, 2-methoxyethyl or 2-ethoxyethyl, with $R^{124}$ in particular being methyl.

In more preferred embodiment, $R^{12}$ is in particular a radical of the formula ($A^{11}$), e.g. ($A^{11}$-a) or ($A^{11}$-b)

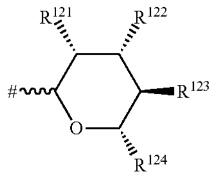

($A^{11}$)

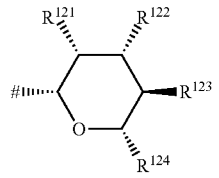

($A^{11}$-a)

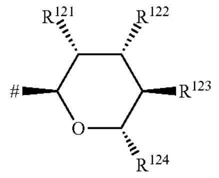

($A^{11}$-b)

wherein # indicates the point of attachment to T and wherein $R^{121}$, $R^{122}$, $R^{123}$ and $R^{124}$ are as defined above and wherein $R^{121}$, $R^{122}$, $R^{123}$ and $R^{124}$ independently of each other and especially in combination preferably have the following meanings:

$R^{121}$ is $C_1$-$C_4$-alkoxy, in particular $OCH_3$ or $OC_2H_5$;

$R^{122}$ is $C_1$-$C_4$-alkoxy, such as $OCH_3$, $OC_2H_5$, n-propoxyx or isopropoxy, or $C_3$-$C_4$-alkenyloxy, such as allyloxy, with $R^{122}$ in particular being $OCH_3$, $OC_2H_5$ or n-propoxy;

$R^{123}$ is OH, $C_1$-$C_4$-alkoxy, such as $OCH_3$ or $OC_2H_5$, or $C_3$-$C_4$-alkenyloxy, such as allyloxy, with $R^{123}$ in particular being $OCH_3$ or $OC_2H_5$;

$R^{124}$ is $C_1$-$C_4$-alkyl, such as $CH_3$ or $C_2H_5$, or $C_1$-$C_4$-alkoxy-$C_1$-$C_4$-alkyl, such as methoxymethyl, ethoxymethyl, 2-methoxyethyl or 2-ethoxyethyl, with $R^{124}$ in particular being methyl.

Particular examples of radicals $R^{12}$ are the following radicals $A^{11}$-1, $A^{11}$-1a, $A^{11}$-1b, $A^{11}$-2, $A^{11}$-2a, $A^{11}$-2b, $A^{11}$-3, $A^{11}$-3a and $A^{11}$-3b:

(A11-1)
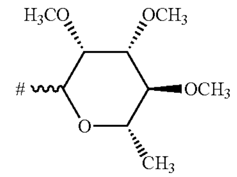
(A11-1a)
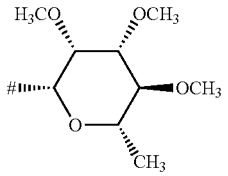
(A11-1b)
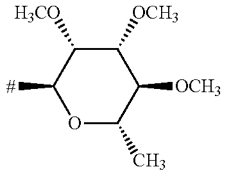
(A11-2)
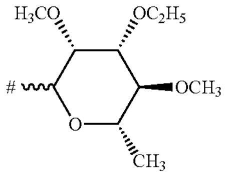
(A11-2a)
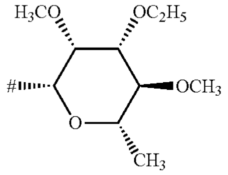
(A11-2b)
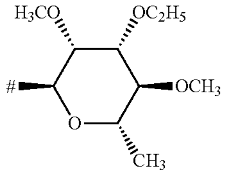
(A11-3)
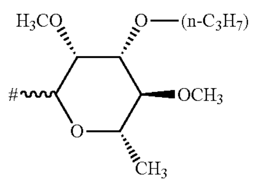
(A11-3a)
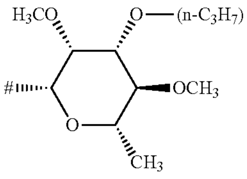
-continued
(A11-3b)
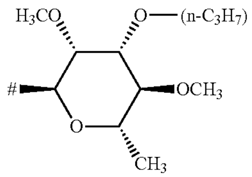
In a more preferred embodiment compounds of formula I are selected from compounds of formula A.1 to A.36.
A.1
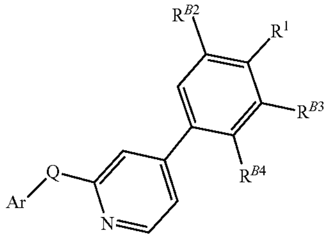
A.2
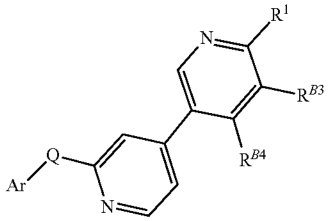
A.3
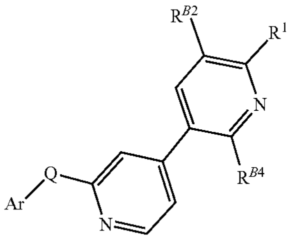
A.4
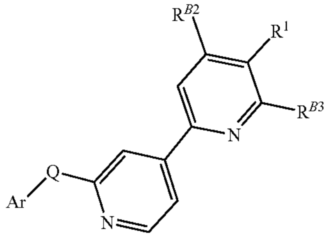
A.5
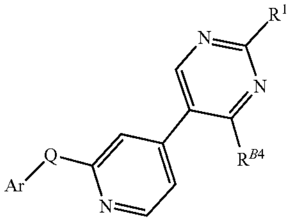

-continued
A.6
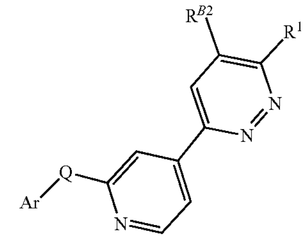
A.7
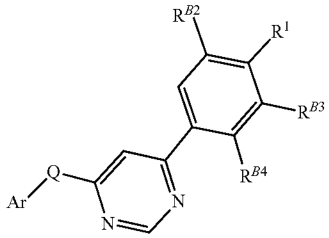
A.8
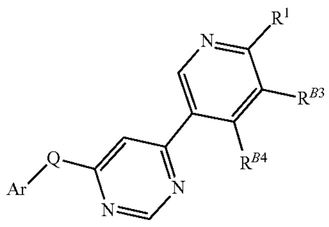
A.9
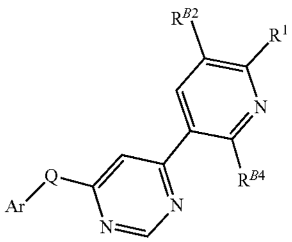
A.10
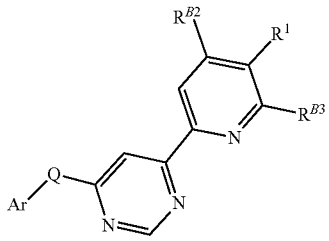
A.11
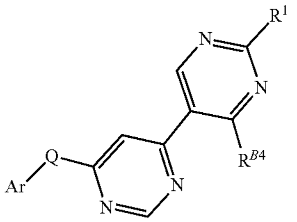
-continued
A.12
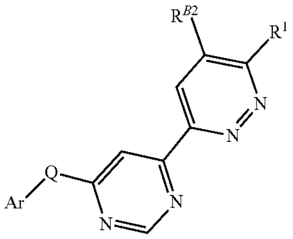
A.13
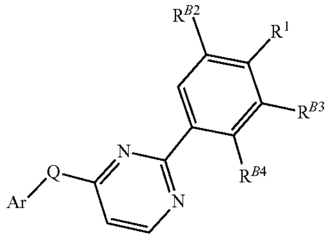
A.14
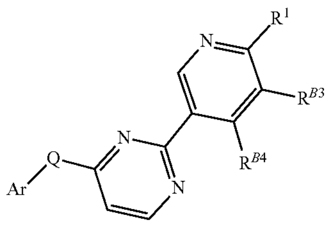
A.15
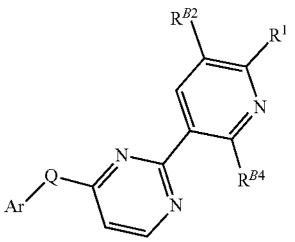
A.16
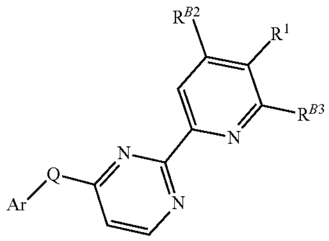
A.17
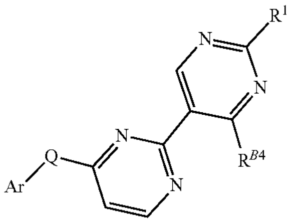

-continued
A.18
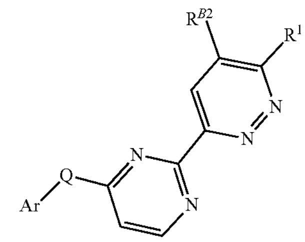
A.19
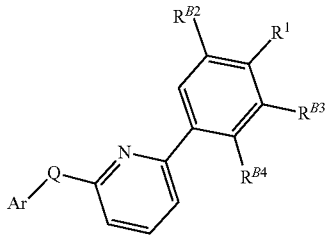
A.20
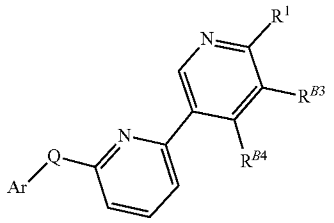
A.21
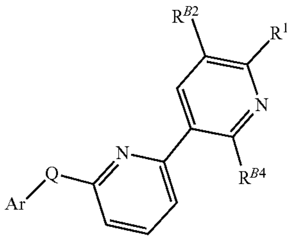
A.22
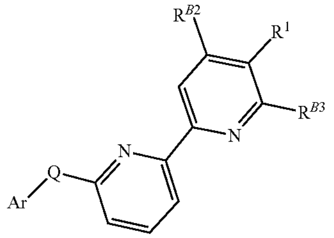
A.23
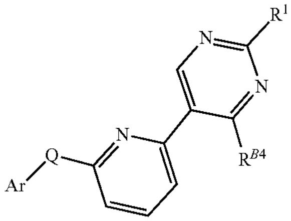
-continued
A.24
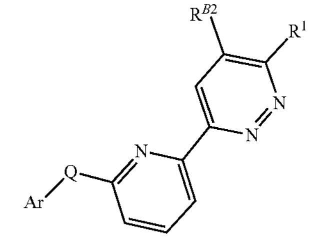
A.25
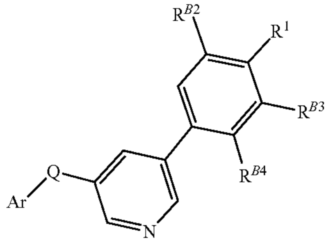
A.26
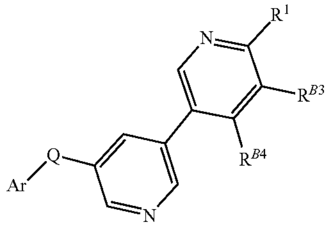
A.27
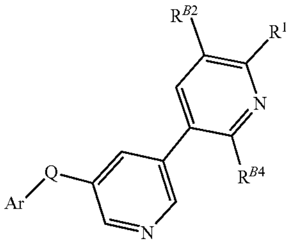
A.28
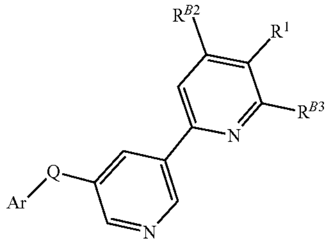
A.29
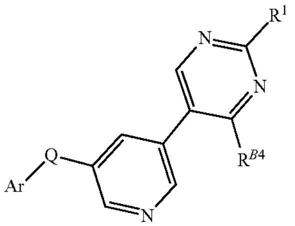

-continued

A.30

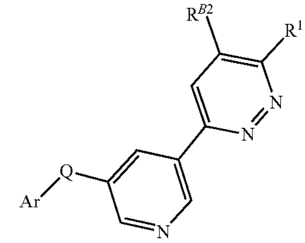

A.31

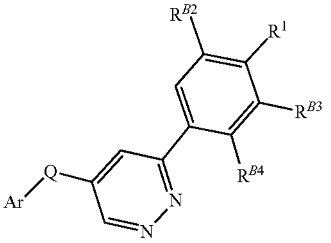

A.32

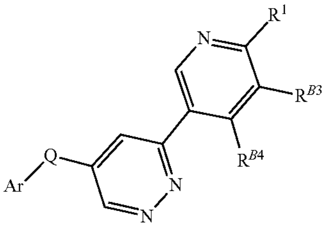

A.33

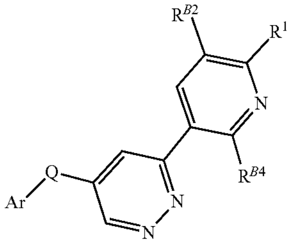

A.34

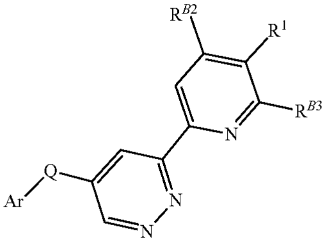

A.35

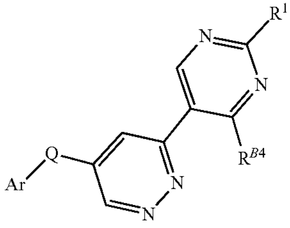

-continued

A.36

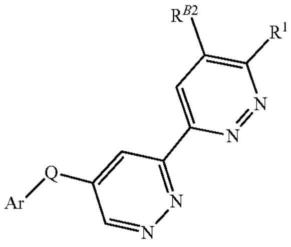

wherein, Ar is phenyl or 5- or 6-membered hetaryl ring which is substituted with $R^{Ar}$;

$R^{Ar}$ is halogen, OH, CN, $NO_2$, SCN, $C_1$-$C_6$-alkyl, $C_1$-$C_6$-alkoxy, or S—$R^e$, wherein the alkyl and alkoxy are unsubstituted or substituted with halogen;

$R^A$ is H, halogen, $C_1$-$C_6$-alkyl, $C_1$-$C_6$-haloalkyl, $C_3$-$C_6$-cycloalkyl, or $C_3$-$C_6$-halocycloalkyl;

$R^{B1}$, $R^{B2}$, $R^{B3}$, and $R^{B4}$ independently of each other are H, halogen, or $C_1$-$C_6$-alkyl;

Q is —$C(R^4R^5)$—O—, —$N(R^2)$—$S(=O)_m$—, —$N(R^2)$—$C(R^9R^{10})$—, —$N(R^2)$—C(=O)—, —$N(R^2)$—C(=S)—, —N=C(X)—, —$N(R^2)$—C(=NR)—; wherein Ar is bound to either side of Q;

X is $N(R^3)_2$;

and $R^1$ is Y—Z-T-$R^{11}$ or Y—Z-T-$R^{12}$, as defined in formula I.

more preferred compounds of formula I are compounds of formula I.1 to I.48, wherein $R^1$ is selected from Y-1A, Y-1B, Y-2A, Y-2B, Y-3A, Y-3B, Y-3C, Y-3D, Y-4A, Y-4B, Y-4C, Y-4D, Y-5A, Y-5B, Y-6A, Y-6B, Y-8A, and Y-8B; wherein D is $R^{11}$ or $R^{12}$, and other variables are as defined herein.

I.1

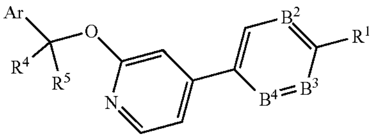

I.2

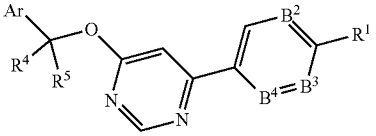

I.3

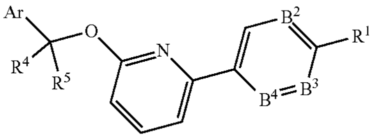

I.4

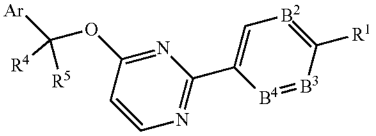

I.5

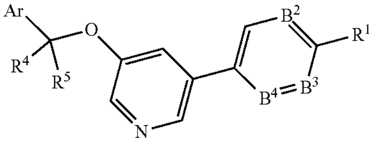

-continued
I.6
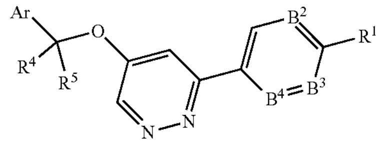
I.7
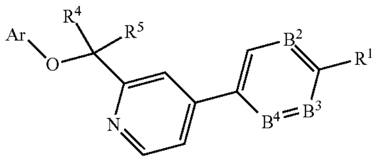
I-8
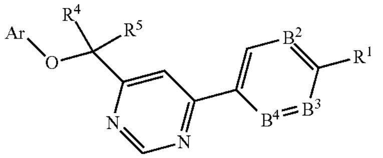
I-9
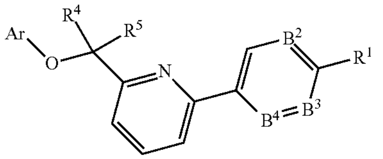
I-10
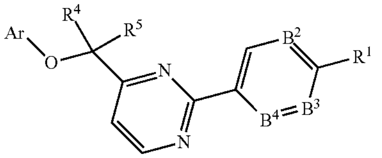
I-11
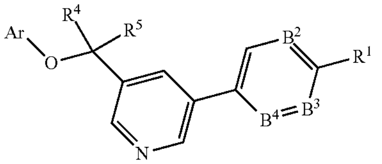
I.12
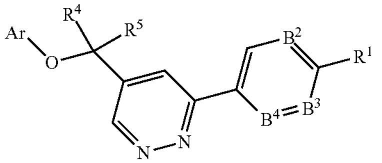
I.13
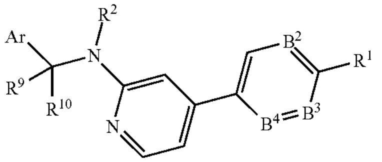
I.14
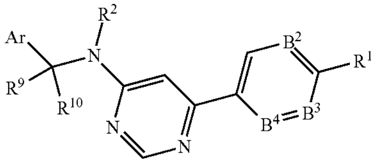
-continued
I.15
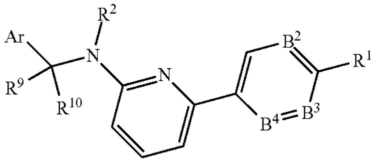
I.16
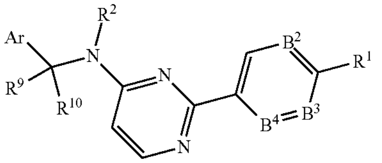
I.17
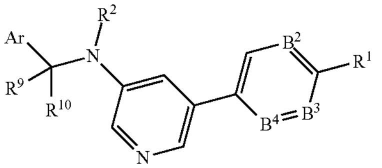
I.18
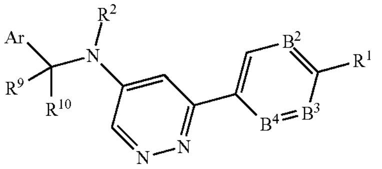
I.19
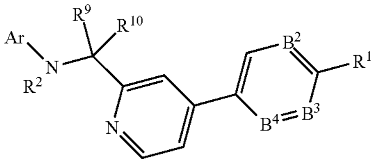
I.20
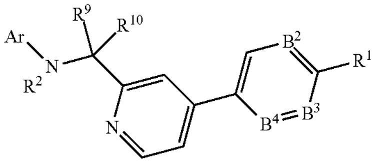
I.21
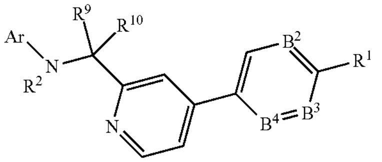
I.22
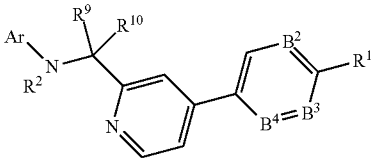
I.23
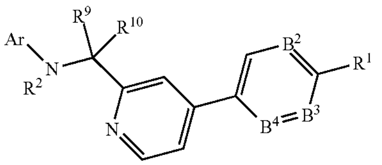

-continued
I.24
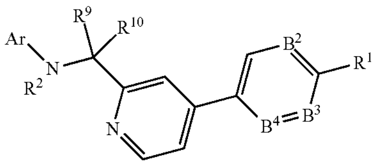
I.25
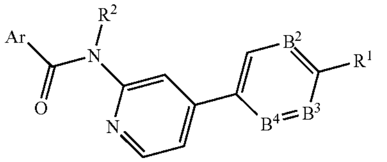
I.26
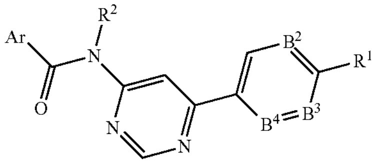
I.27
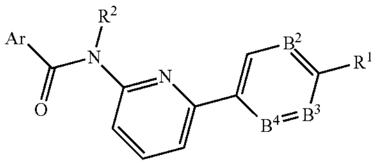
I.28
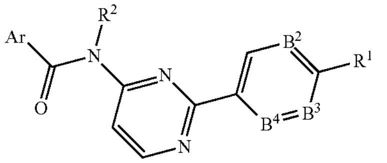
I.29
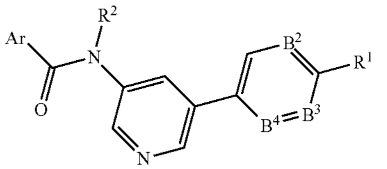
I.30
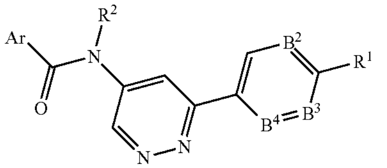
I.31
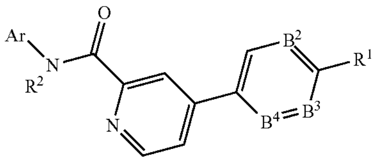
I.32
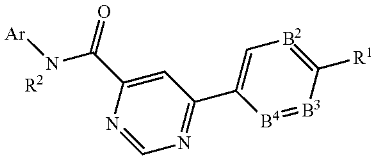
-continued
I.33
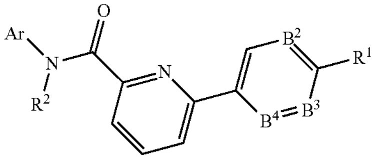
I.34
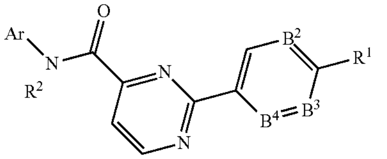
I.35
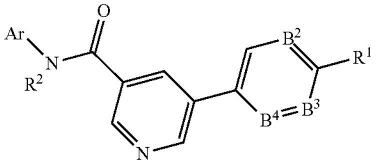
I.36
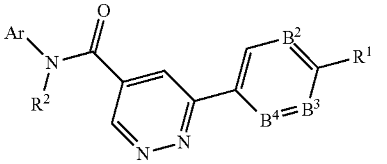
I.37
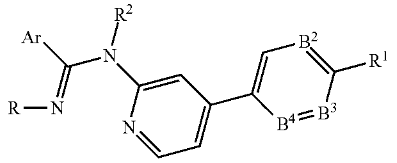
I.38
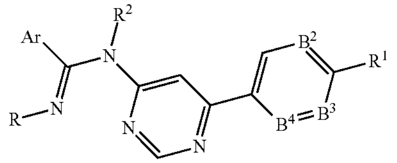
I.39
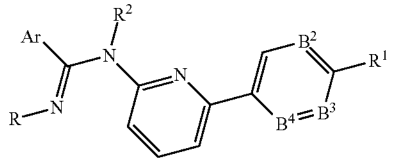
I.40
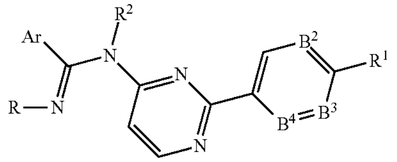
I.41
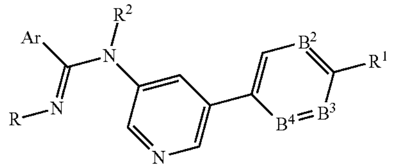

-continued

I.42

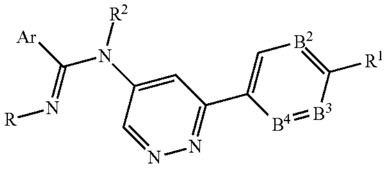

I.43

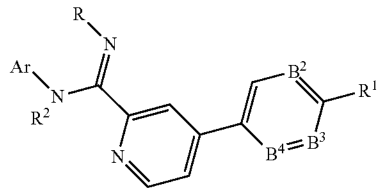

I.44

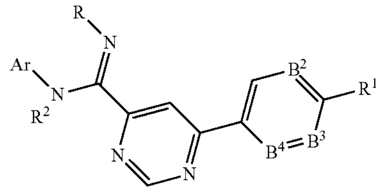

I.45

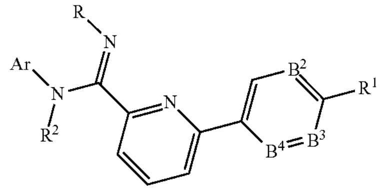

I.46

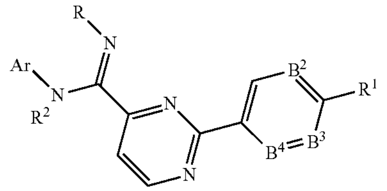

I.47

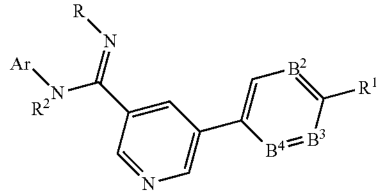

I.48

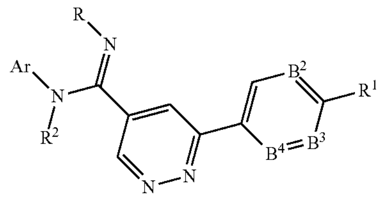

Also more preferred are the compound of formula I, wherein

A is N, $B^1$ is $CR^{B1}$, E is $CR^E$, D is $CR^D$, $B^2$ is $CR^{B2}$, $B^3$ is $CR^{B3}$, and $B^4$ is $CR^{B4}$;

$R^{B1}$, $R^E$, $R^D$ independently of each other are H, halogen, or $C_1$-$C_6$-alkyl;

$R^{B2}$, $R^{B3}$, and $R^{B4}$ independently of each other are H, halogen, $C_1$-$C_6$-alkyl;

Q is —$C(R^4R^5)$—O—, —$N(R^2)$—$C(R^9R^{10})$—, —$N(R^2)$—, —$N(R^2)$—C(═O)—, or —$N(R^2)$—C(═NR)—; wherein Ar is bound to either side of Q;

m is 0, 1, or 2;

R is H, CN, or $C_1$-$C_6$-alkyl;

$R^2$ is H or $C_1$-$C_6$-alkyl;

$R^4$, $R^5$, $R^9$, $R^{10}$, are identical or different H or $C_1$-$C_6$-alkyl;

Ar is $Ar^1$, $Ar^2$, $Ar^3$, $Ar^4$, $Ar^{10}$, $Ar^{17}$, or $Ar^{18}$;

$R^1$ is Y-1A, Y-3C, Y-5A, Y-6A, Y-8A, or Y-9A;

D is $R^{11}$ or $R^{12}$;

$R^{11}$ is $R^{11}$-1 or $R^{11}$-10;

$R^{12}$ is $A^1$-1b or $A^{11}$-3b;

Also more preferred are the compound of formula I, wherein

A and D are N, $B^1$ is $CR^{B1}$, E is $CR^E$, $B^2$ is $CR^{B2}$, $B^3$ is $CR^{B3}$, and $B^4$ is $CR^{B4}$;

$R^{B1}$, $R^E$, independently of each other are H, halogen, or $C_1$-$C_6$-alkyl;

$R^{B2}$, $R^{B3}$, and $R^{B4}$ independently of each other are H, halogen, $C_1$-$C_6$-alkyl;

Q is —$C(R^4R^5)$—O—, —$N(R^2)$—$C(R^9R^{10})$—, —$N(R^2)$—, —$N(R^2)$—C(═O)—, or —$N(R^2)$—C(═NR)—; wherein Ar is bound to either side of Q;

m is 0, 1, or 2;

R is H, CN, or $C_1$-$C_6$-alkyl;

$R^2$ is H or $C_1$-$C_6$-alkyl;

$R^4$, $R^5$, $R^9$, $R^{10}$, are identical or different H or $C_1$-$C_6$-alkyl;

Ar is $Ar^1$, $Ar^2$, $Ar^3$, $Ar^4$, $Ar^{10}$, $Ar^{17}$, or $Ar^{18}$;

$R^1$ is Y-1A, Y-3C, Y-5A, Y-6A, Y-8A, or Y-9A;

D is $R^{11}$ or $R^{12}$;

$R^{11}$ is $R^{11}$-1 or $R^{11}$-10;

$R^{12}$ is $A^1$-1b or $A^{11}$-3b;

Also more preferred are the compound of formula I, wherein $B^1$ is N, A is $CR^A$, O is $CR^D$, E is $CR^E$, $B^2$ is $CR^{B2}$, $B^3$ is $CR^{B3}$, and $B^4$ is $CR^{B4}$;

$R^A$, $R^E$, $R^D$ independently of each other are H, halogen, or $C_1$-$C_6$-alkyl;

$R^{B2}$, $R^{B3}$, and $R^{B4}$ independently of each other are H, halogen, $C_1$-$C_6$-alkyl;

Q is —$C(R^4R^5)$—O—, —$N(R^2)$—$C(R^9R^{10})$—, —$N(R^2)$—, —$N(R^2)$—C(═O)—, or —$N(R^2)$—C(═NR)—; wherein Ar is bound to either side of Q;

m is 0, 1, or 2;

R is H, CN, or $C_1$-$C_6$-alkyl;

$R^2$ is H or $C_1$-$C_6$-alkyl;

$R^4$, $R^5$, $R^9$, $R^{10}$, are identical or different H or $C_1$-$C_6$-alkyl;

Ar is $Ar^1$, $Ar^2$, $Ar^3$, $Ar^4$, $Ar^{10}$, $Ar^{17}$, or $Ar^{18}$;

$R^1$ is Y-1A, Y-3C, Y-5A, Y-6A, Y-8A, or Y-9A;

D is $R^{11}$ or $R^{12}$;

$R^{11}$ is $R^{11}$-1 or $R^{11}$-10;

$R^{12}$ is $A^1$-1b or $A^{11}$-3b;

Also more preferred are the compound of formula I, wherein $B^1$ and D are N, A is $CR^A$, E is $CR^E$, $B^2$ is $CR^{B2}$, $B^3$ is $CR^{B3}$, and $B^4$ is $CR^{B4}$;

$R^A$, $R^E$, independently of each other are H, halogen, or $C_1$-$C_6$-alkyl;

$R^{B2}$, $R^{B3}$, and $R^{B4}$ independently of each other are H, halogen, $C_1$-$C_6$-alkyl;

Q is —$C(R^4R^5)$—O—, —$N(R^2)$—$C(R^9R^{10})$—, —$N(R^2)$—, —$N(R^2)$—C(═O)—, or —$N(R^2)$—C(═NR)—; wherein Ar is bound to either side of Q;

m is 0, 1, or 2;

R is H, CN, or $C_1$-$C_6$-alkyl;

$R^2$ is H or $C_1$-$C_6$-alkyl;

$R^4$, $R^5$, $R^9$, $R^{10}$, are identical or different H or $C_1$-$C_6$-alkyl;

Ar is $Ar^1$, $Ar^2$, $Ar^3$, $Ar^4$, $Ar^{10}$, $Ar^{17}$, or $Ar^{18}$;

$R^1$ is Y-1A, Y-3C, Y-5A, Y-6A, Y-8A, or Y-9A;

D is $R^{11}$ or $R^{12}$;

$R^{11}$ is $R^{11}$-1 or $R^{11}$-10;

$R^{12}$ is $A^1$-1b or $A^{11}$-3b;

Also more preferred are the compound of formula I, wherein

E and D are N, A is $CR^A$, $B^1$ is $CR^{B1}$, $B^2$ is $CR^{B2}$, $B^3$ is $CR^{B3}$, and $B^4$ is $CR^{B4}$;

$R^A$, R $B^1$ independently of each other are H, halogen, or $C_1$-$C_6$-alkyl;

$R^{B2}$, $R^{B3}$, and $R^{B4}$ independently of each other are H, halogen, $C_1$-$C_6$-alkyl;

Q is —$C(R^4R^5)$—O—, —$N(R^2)$—$C(R^9R^{10})$—, —$N(R^2)$—, —$N(R^2)$—C(=O)—, or —$N(R^2)$—C(=NR)—; wherein Ar is bound to either side of Q;

m is 0, 1, or 2;

R is H, CN, or $C_1$-$C_6$-alkyl;

$R^2$ is H or $C_1$-$C_6$-alkyl;

$R^4$, $R^5$, $R^9$, $R^{10}$, are identical or different H or $C_1$-$C_6$-alkyl;

Ar is $Ar^1$, $Ar^2$, $Ar^3$, $Ar^4$, $Ar^{10}$, $Ar^{17}$, or $Ar^{18}$;

$R^1$ is Y-1A, Y-3C, Y-5A, Y-6A, Y-8A, or Y-9A;

D is $R^{11}$ or $R^{12}$;

$R^{11}$ is $R^{11}$-1 or $R^{11}$-10;

$R^{12}$ is $A^1$-1b or $A^{11}$-3b;

Also more preferred are the compound of formula I, wherein

A, $B^1$, E, D independently are selected from N or CH, wherein at least one of the A, $B^1$, E, and D is N; and when A and D are N, $B^1$ is CH;

$B^2$, $B^3$, $B^4$ are CH;

Q is —$C(R^4R^5)$—O—, —$N(R^2)$—$C(R^9R^{10})$—, —$N(R^2)$—, —$N(R^2)$—C(=O)—, —N=C(X)—, or —$N(R^2)$—C(=NR)—; wherein Ar is bound to either side of Q.

Ar is Ar-1 or Ar-2;

m is 0, 1, or 2;

R is H, CN, or $C_1$-$C_6$-alkyl;

$R^2$ is H or $C_1$-$C_6$-alkyl;

$R^4$, $R^5$, $R^9$, $R^{10}$, are identical or different H or $C_1$-$C_6$-alkyl;

Ar is $Ar^1$, $Ar^2$, $Ar^3$, $Ar^4$, $Ar^{10}$, $Ar^{17}$, or $Ar^{18}$;

$R^1$ is Y-1A, Y-5A, Y-6A or Y-8A;

D is $R^{11}$ or $R^{12}$;

$R^{11}$ is $R^{11}$-1 or $R^{11}$-29;

$R^{12}$ is $A^1$-1b or $A^{11}$-3b;

In another preferred embodiment, the compound of formula I are compounds of formula I.1 to I.48, wherein Ar is $Ar^1$, $Ar^2$, $Ar^3$, $Ar^4$, $Ar^{10}$, $Ar^{17}$, or $Ar^{18}$;

$B^4$ is N or CH;

$B^2$ is N or CH;

$B^3$ is N or CH;

$R^1$ is Y-1A, Y-1B, Y-2A, Y-2B, Y-3A, Y-3B, Y-3C, Y-3D, Y-4A, Y-4B, Y-4C, Y-4D, Y-5A, Y-5B, Y-6A, Y-6B, Y-8A, or Y-8B; wherein D is $R^{11}$ or $R^{12}$;

$R^{11}$ is $R^{11}$-1, $R^{11}$-2, $R^{11}$-3, $R^{11}$-5, $R^{11}$-6, $R^{11}$-7, $R^{11}$-8, $R^{11}$-9, $R^{11}$-10, $R^{11}$-11, $R^{11}$-12, $R^{11}$-13, $R^{11}$-14, $R^{11}$-15, $R^{11}$-16, $R^{11}$-17, $R^{11}$-18, $R^{11}$-19, $R^{11}$-20, $R^{11}$-21, $R^{11}$-22, $R^{11}$-23, $R^{11}$-25, $R^{11}$-26, $R^{11}$-27, $R^{11}$-28, or $R^{11}$-29;

$R^{12}$ is ($A^{11}$-1), ($A^{11}$-2), or ($A^{11}$-3).

$R^4$ and $R^5$ independently are H or $CH_3$, $R^9$ and $R^{10}$ independently are H or $CH_3$, $R^2$ is H, $CH_3$, or c-$C_3H_5$ R is NH, $NCH_3$, or NCN;

Particular compounds of formula I are the compounds of the formulae I.1 to I.48 that are compiled in the following tables 1 to 3888, wherein the combination of variables $B^2$, $B^3$, $B^4$, Ar, and D for each compound of tables 1 to 3888 corresponds to each line of Table B. Each of the groups mentioned for a substituent in the tables is furthermore per se, independently of the combination in which it is mentioned, a particularly preferred aspect of the substituent in question.

Table 1. Compounds of formula I.7 wherein $R^1$ is Y-1A, $R^4$ is H and $R^5$ is H.

Table 2. Compounds of formula I.7 wherein $R^1$ is Y-1B, $R^4$ is H and $R^5$ is H.

Table 3. Compounds of formula I.7 wherein $R^1$ is Y-2A, $R^4$ is H and $R^5$ is H.

Table 4. Compounds of formula I.7 wherein $R^1$ is Y-2B, $R^4$ is H and $R^5$ is H.

Table 5. Compounds of formula I.7 wherein $R^1$ is Y-3A, $R^4$ is H and $R^5$ is H.

Table 6. Compounds of formula I.7 wherein $R^1$ is Y-3B, $R^4$ is H and $R^5$ is H.

Table 7. Compounds of formula I.7 wherein $R^1$ is Y-3C, $R^4$ is H and $R^5$ is H.

Table 8. Compounds of formula I.7 wherein $R^1$ is Y-3D, $R^4$ is H and $R^5$ is H.

Table 9. Compounds of formula I.7 wherein $R^1$ is Y-4A, $R^4$ is H and $R^5$ is H.

Table 10. Compounds of formula I.7 wherein $R^1$ is Y-4B, $R^4$ is H and $R^5$ is H.

Table 11. Compounds of formula I.7 wherein $R^1$ is Y-4C, $R^4$ is H and $R^5$ is H.

Table 12. Compounds of formula I.7 wherein $R^1$ is Y-4D, $R^4$ is H and $R^5$ is H.

Table 13. Compounds of formula I.7 wherein $R^1$ is Y-5A, $R^4$ is H and $R^5$ is H.

Table 14. Compounds of formula I.7 wherein $R^1$ is Y-5B, $R^4$ is H and $R^5$ is H.

Table 15. Compounds of formula I.7 wherein $R^1$ is Y-6A, $R^4$ is H and $R^5$ is H.

Table 16. Compounds of formula I.7 wherein $R^1$ is Y-6B, $R^4$ is H and $R^5$ is H.

Table 17. Compounds of formula I.7 wherein $R^1$ is Y-8A, $R^4$ is H and $R^5$ is H.

Table 18. Compounds of formula I.7 wherein $R^1$ is Y-8B, $R^4$ is H and $R^5$ is H.

Table 19. Compounds of formula I.7 wherein $R^1$ is Y-1A, $R^4$ is $CH_3$ and $R^5$ is H.

Table 20. Compounds of formula I.7 wherein $R^1$ is Y-1B, $R^4$ is $CH_3$ and $R^5$ is H.

Table 21. Compounds of formula I.7 wherein $R^1$ is Y-2A, $R^4$ is $CH_3$ and $R^5$ is H.

Table 22. Compounds of formula I.7 wherein $R^1$ is Y-2B, $R^4$ is $CH_3$ and $R^5$ is H.

Table 23. Compounds of formula I.7 wherein $R^1$ is Y-3A, $R^4$ is $CH_3$ and $R^5$ is H.

Table 24. Compounds of formula I.7 wherein $R^1$ is Y-3B, $R^4$ is $CH_3$ and $R^5$ is H.

Table 25. Compounds of formula I.7 wherein $R^1$ is Y-3C, $R^4$ is $CH_3$ and $R^5$ is H.

Table 26. Compounds of formula I.7 wherein $R^1$ is Y-3D, $R^4$ is $CH_3$ and $R^5$ is H.

Table 27. Compounds of formula I.7 wherein $R^1$ is Y-4A, $R^4$ is $CH_3$ and $R^5$ is H.

Table 28. Compounds of formula I.7 wherein $R^1$ is Y-4B, $R^4$ is $CH_3$ and $R^5$ is H.

Table 29. Compounds of formula I.7 wherein $R^1$ is Y-4C, $R^4$ is $CH_3$ and $R^5$ is H.

Table 30. Compounds of formula I.7 wherein $R^1$ is Y-4D, $R^4$ is $CH_3$ and $R^5$ is H.

Table 31. Compounds of formula I.7 wherein $R^1$ is Y-5A, $R^4$ is $CH_3$ and $R^5$ is H.

Table 32. Compounds of formula I.7 wherein $R^1$ is Y-5B, $R^4$ is $CH_3$ and $R^5$ is H.

Table 33. Compounds of formula I.7 wherein $R^1$ is Y-6A, $R^4$ is $CH_3$ and $R^5$ is H.

Table 34. Compounds of formula I.7 wherein $R^1$ is Y-6B, $R^4$ is $CH_3$ and $R^5$ is H.

Table 35. Compounds of formula I.7 wherein $R^1$ is Y-8A, $R^4$ is $CH_3$ and $R^5$ is H.

Table 36. Compounds of formula I.7 wherein $R^1$ is Y-8B, $R^4$ is $CH_3$ and $R^5$ is H.

Table 37. Compounds of formula I.7 wherein $R^1$ is Y-1A, $R^4$ is $CH_3$ and $R^5$ is $CH_3$.

Table 38. Compounds of formula I.7 wherein $R^1$ is Y-1B, $R^4$ is $CH_3$ and $R^5$ is $CH_3$.

Table 39. Compounds of formula I.7 wherein $R^1$ is Y-2A, $R^4$ is $CH_3$ and $R^5$ is $CH_3$.

Table 40. Compounds of formula I.7 wherein $R^1$ is Y-2B, $R^4$ is $CH_3$ and $R^5$ is $CH_3$.

Table 41. Compounds of formula I.7 wherein $R^1$ is Y-3A, $R^4$ is $CH_3$ and $R^5$ is $CH_3$.

Table 42. Compounds of formula I.7 wherein $R^1$ is Y-3B, $R^4$ is $CH_3$ and $R^5$ is $CH_3$.

Table 43. Compounds of formula I.7 wherein $R^1$ is Y-3C, $R^4$ is $CH_3$ and $R^5$ is $CH_3$.

Table 44. Compounds of formula I.7 wherein $R^1$ is Y-3D, $R^4$ is $CH_3$ and $R^5$ is $CH_3$.

Table 45. Compounds of formula I.7 wherein $R^1$ is Y-4A, $R^4$ is $CH_3$ and $R^5$ is $CH_3$.

Table 46. Compounds of formula I.7 wherein $R^1$ is Y-4B, $R^4$ is $CH_3$ and $R^5$ is $CH_3$.

Table 47. Compounds of formula I.7 wherein $R^1$ is Y-4C, $R^4$ is $CH_3$ and $R^5$ is $CH_3$.

Table 48. Compounds of formula I.7 wherein $R^1$ is Y-4D, $R^4$ is $CH_3$ and $R^5$ is $CH_3$.

Table 49. Compounds of formula I.7 wherein $R^1$ is Y-5A, $R^4$ is $CH_3$ and $R^5$ is $CH_3$.

Table 50. Compounds of formula I.7 wherein $R^1$ is Y-5B, $R^4$ is $CH_3$ and $R^5$ is $CH_3$.

Table 51. Compounds of formula I.7 wherein $R^1$ is Y-6A, $R^4$ is $CH_3$ and $R^5$ is $CH_3$.

Table 52. Compounds of formula I.7 wherein $R^1$ is Y-6B, $R^4$ is $CH_3$ and $R^5$ is $CH_3$.

Table 53. Compounds of formula I.7 wherein $R^1$ is Y-8A, $R^4$ is $CH_3$ and $R^5$ is $CH_3$.

Table 54. Compounds of formula I.7 wherein $R^1$ is Y-8B, $R^4$ is $CH_3$ and $R^5$ is $CH_3$.

Table 55. Compounds of formula I.8 wherein $R^1$ is Y-1A, $R^4$ is H and $R^5$ is H.

Table 56. Compounds of formula I.8 wherein $R^1$ is Y-1B, $R^4$ is H and $R^5$ is H.

Table 57. Compounds of formula I.8 wherein $R^1$ is Y-2A, $R^4$ is H and $R^5$ is H.

Table 58. Compounds of formula I.8 wherein $R^1$ is Y-2B, $R^4$ is H and $R^5$ is H.

Table 59. Compounds of formula I.8 wherein $R^1$ is Y-3A, $R^4$ is H and $R^5$ is H.

Table 60. Compounds of formula I.8 wherein $R^1$ is Y-3B, $R^4$ is H and $R^5$ is H.

Table 61. Compounds of formula I.8 wherein $R^1$ is Y-3C, $R^4$ is H and $R^5$ is H.

Table 62. Compounds of formula I.8 wherein $R^1$ is Y-3D, $R^4$ is H and $R^5$ is H.

Table 63. Compounds of formula I.8 wherein $R^1$ is Y-4A, $R^4$ is H and $R^5$ is H.

Table 64. Compounds of formula I.8 wherein $R^1$ is Y-4B, $R^4$ is H and $R^5$ is H.

Table 65. Compounds of formula I.8 wherein $R^1$ is Y-4C, $R^4$ is H and $R^5$ is H.

Table 66. Compounds of formula I.8 wherein $R^1$ is Y-4D, $R^4$ is H and $R^5$ is H.

Table 67. Compounds of formula I.8 wherein $R^1$ is Y-5A, $R^4$ is H and $R^5$ is H.

Table 68. Compounds of formula I.8 wherein $R^1$ is Y-5B, $R^4$ is H and $R^5$ is H.

Table 69. Compounds of formula I.8 wherein $R^1$ is Y-6A, $R^4$ is H and $R^5$ is H.

Table 70. Compounds of formula I.8 wherein $R^1$ is Y-6B, $R^4$ is H and $R^5$ is H.

Table 71. Compounds of formula I.8 wherein $R^1$ is Y-8A, $R^4$ is H and $R^5$ is H.

Table 72. Compounds of formula I.8 wherein $R^1$ is Y-8B, $R^4$ is H and $R^5$ is H.

Table 73. Compounds of formula I.8 wherein $R^1$ is Y-1A, $R^4$ is $CH_3$ and $R^5$ is H.

Table 74. Compounds of formula I.8 wherein $R^1$ is Y-1B, $R^4$ is $CH_3$ and $R^5$ is H.

Table 75. Compounds of formula I.8 wherein $R^1$ is Y-2A, $R^4$ is $CH_3$ and $R^5$ is H.

Table 76. Compounds of formula I.8 wherein $R^1$ is Y-2B, $R^4$ is $CH_3$ and $R^5$ is H.

Table 77. Compounds of formula I.8 wherein $R^1$ is Y-3A, $R^4$ is $CH_3$ and $R^5$ is H.

Table 78. Compounds of formula I.8 wherein $R^1$ is Y-3B, $R^4$ is $CH_3$ and $R^5$ is H.

Table 79. Compounds of formula I.8 wherein $R^1$ is Y-3C, $R^4$ is $CH_3$ and $R^5$ is H.

Table 80. Compounds of formula I.8 wherein $R^1$ is Y-3D, $R^4$ is $CH_3$ and $R^5$ is H.

Table 81. Compounds of formula I.8 wherein $R^1$ is Y-4A, $R^4$ is $CH_3$ and $R^5$ is H.

Table 82. Compounds of formula I.8 wherein $R^1$ is Y-4B, $R^4$ is $CH_3$ and $R^5$ is H.

Table 83. Compounds of formula I.8 wherein $R^1$ is Y-4C, $R^4$ is $CH_3$ and $R^5$ is H.

Table 84. Compounds of formula I.8 wherein $R^1$ is Y-4D, $R^4$ is $CH_3$ and $R^5$ is H.

Table 85. Compounds of formula I.8 wherein $R^1$ is Y-5A, $R^4$ is $CH_3$ and $R^5$ is H.

Table 86. Compounds of formula I.8 wherein $R^1$ is Y-5B, $R^4$ is $CH_3$ and $R^5$ is H.

Table 87. Compounds of formula I.8 wherein $R^1$ is Y-6A, $R^4$ is $CH_3$ and $R^5$ is H.

Table 88. Compounds of formula I.8 wherein $R^1$ is Y-6B, $R^4$ is $CH_3$ and $R^5$ is H.

Table 89. Compounds of formula I.8 wherein $R^1$ is Y-8A, $R^4$ is $CH_3$ and $R^5$ is H.

Table 90. Compounds of formula I.8 wherein $R^1$ is Y-8B, $R^4$ is $CH_3$ and $R^5$ is H.

Table 91. Compounds of formula I.8 wherein $R^1$ is Y-1A, $R^4$ is $CH_3$ and $R^5$ is $CH_3$.

Table 92. Compounds of formula I.8 wherein $R^1$ is Y-1B, $R^4$ is $CH_3$ and $R^5$ is $CH_3$.

Table 93. Compounds of formula I.8 wherein $R^1$ is Y-2A, $R^4$ is $CH_3$ and $R^5$ is $CH_3$.

Table 94. Compounds of formula I.8 wherein $R^1$ is Y-2B, $R^4$ is $CH_3$ and $R^5$ is $CH_3$.

Table 95. Compounds of formula I.8 wherein $R^1$ is Y-3A, $R^4$ is $CH_3$ and $R^5$ is $CH_3$.

Table 96. Compounds of formula I.8 wherein $R^1$ is Y-3B, $R^4$ is $CH_3$ and $R^5$ is $CH_3$.

Table 97. Compounds of formula I.8 wherein $R^1$ is Y-3C, $R^4$ is $CH_3$ and $R^5$ is $CH_3$.

Table 98. Compounds of formula I.8 wherein $R^1$ is Y-3D, $R^4$ is $CH_3$ and $R^5$ is $CH_3$.

Table 99. Compounds of formula I.8 wherein $R^1$ is Y-4A, $R^4$ is $CH_3$ and $R^5$ is $CH_3$.

Table 100. Compounds of formula I.8 wherein $R^1$ is Y-4B, $R^4$ is $CH_3$ and $R^5$ is $CH_3$.

Table 101. Compounds of formula I.8 wherein $R^1$ is Y-4C, $R^4$ is $CH_3$ and $R^5$ is $CH_3$.

Table 102. Compounds of formula I.8 wherein $R^1$ is Y-4D, $R^4$ is $CH_3$ and $R^5$ is $CH_3$.

Table 103. Compounds of formula I.8 wherein $R^1$ is Y-5A, $R^4$ is $CH_3$ and $R^5$ is $CH_3$.

Table 104. Compounds of formula I.8 wherein $R^1$ is Y-5B, $R^4$ is $CH_3$ and $R^5$ is $CH_3$.

Table 105. Compounds of formula I.8 wherein $R^1$ is Y-6A, $R^4$ is $CH_3$ and $R^5$ is $CH_3$.

Table 106. Compounds of formula I.8 wherein $R^1$ is Y-6B, $R^4$ is $CH_3$ and $R^5$ is $CH_3$.

Table 107. Compounds of formula I.8 wherein $R^1$ is Y-8A, $R^4$ is $CH_3$ and $R^5$ is $CH_3$.

Table 108. Compounds of formula I.8 wherein $R^1$ is Y-8B, $R^4$ is $CH_3$ and $R^5$ is $CH_3$.

Table 109. Compounds of formula I.9 wherein $R^1$ is Y-1A, $R^4$ is H and $R^5$ is H.

Table 110. Compounds of formula I.9 wherein $R^1$ is Y-1B, $R^4$ is H and $R^5$ is H.

Table 111. Compounds of formula I.9 wherein $R^1$ is Y-2A, $R^4$ is H and $R^5$ is H.

Table 112. Compounds of formula I.9 wherein $R^1$ is Y-2B, $R^4$ is H and $R^5$ is H.

Table 113. Compounds of formula I.9 wherein $R^1$ is Y-3A, $R^4$ is H and $R^5$ is H.

Table 114. Compounds of formula I.9 wherein $R^1$ is Y-3B, $R^4$ is H and $R^5$ is H.

Table 115. Compounds of formula I.9 wherein $R^1$ is Y-3C, $R^4$ is H and $R^5$ is H.

Table 116. Compounds of formula I.9 wherein $R^1$ is Y-3D, $R^4$ is H and $R^5$ is H.

Table 117. Compounds of formula I.9 wherein $R^1$ is Y-4A, $R^4$ is H and $R^5$ is H.

Table 118. Compounds of formula I.9 wherein $R^1$ is Y-4B, $R^4$ is H and $R^5$ is H.

Table 119. Compounds of formula I.9 wherein $R^1$ is Y-4C, $R^4$ is H and $R^5$ is H.

Table 120. Compounds of formula I.9 wherein $R^1$ is Y-4D, $R^4$ is H and $R^5$ is H.

Table 121. Compounds of formula I.9 wherein $R^1$ is Y-5A, $R^4$ is H and $R^5$ is H.

Table 122. Compounds of formula I.9 wherein $R^1$ is Y-5B, $R^4$ is H and $R^5$ is H.

Table 123. Compounds of formula I.9 wherein $R^1$ is Y-6A, $R^4$ is H and $R^5$ is H.

Table 124. Compounds of formula I.9 wherein $R^1$ is Y-6B, $R^4$ is H and $R^5$ is H.

Table 125. Compounds of formula I.9 wherein $R^1$ is Y-8A, $R^4$ is H and $R^5$ is H.

Table 126. Compounds of formula I.9 wherein $R^1$ is Y-8B, $R^4$ is H and $R^5$ is H.

Table 127. Compounds of formula I.9 wherein $R^1$ is Y-1A, $R^4$ is $CH_3$ and $R^5$ is H.

Table 128. Compounds of formula I.9 wherein $R^1$ is Y-1B, $R^4$ is $CH_3$ and $R^5$ is H.

Table 129. Compounds of formula I.9 wherein $R^1$ is Y-2A, $R^4$ is $CH_3$ and $R^5$ is H.

Table 130. Compounds of formula I.9 wherein $R^1$ is Y-2B, $R^4$ is $CH_3$ and $R^5$ is H.

Table 131. Compounds of formula I.9 wherein $R^1$ is Y-3A, $R^4$ is $CH_3$ and $R^5$ is H.

Table 132. Compounds of formula I.9 wherein $R^1$ is Y-3B, $R^4$ is $CH_3$ and $R^5$ is H.

Table 133. Compounds of formula I.9 wherein $R^1$ is Y-3C, $R^4$ is $CH_3$ and $R^5$ is H.

Table 134. Compounds of formula I.9 wherein $R^1$ is Y-3D, $R^4$ is $CH_3$ and $R^5$ is H.

Table 135. Compounds of formula I.9 wherein $R^1$ is Y-4A, $R^4$ is $CH_3$ and $R^5$ is H.

Table 136. Compounds of formula I.9 wherein $R^1$ is Y-4B, $R^4$ is $CH_3$ and $R^5$ is H.

Table 137. Compounds of formula I.9 wherein $R^1$ is Y-4C, $R^4$ is $CH_3$ and $R^5$ is H.

Table 138. Compounds of formula I.9 wherein $R^1$ is Y-4D, $R^4$ is $CH_3$ and $R^5$ is H.

Table 139. Compounds of formula I.9 wherein $R^1$ is Y-5A, $R^4$ is $CH_3$ and $R^5$ is H.

Table 140. Compounds of formula I.9 wherein $R^1$ is Y-5B, $R^4$ is $CH_3$ and $R^5$ is H.

Table 141. Compounds of formula I.9 wherein $R^1$ is Y-6A, $R^4$ is $CH_3$ and $R^5$ is H.

Table 142. Compounds of formula I.9 wherein $R^1$ is Y-6B, $R^4$ is $CH_3$ and $R^5$ is H.

Table 143. Compounds of formula I.9 wherein $R^1$ is Y-8A, $R^4$ is $CH_3$ and $R^5$ is H.

Table 144. Compounds of formula I.9 wherein $R^1$ is Y-8B, $R^4$ is $CH_3$ and $R^5$ is H.

Table 145. Compounds of formula I.9 wherein $R^1$ is Y-1A, $R^4$ is $CH_3$ and $R^5$ is $CH_3$.

Table 146. Compounds of formula I.9 wherein $R^1$ is Y-1B, $R^4$ is $CH_3$ and $R^5$ is $CH_3$.

Table 147. Compounds of formula I.9 wherein $R^1$ is Y-2A, $R^4$ is $CH_3$ and $R^5$ is $CH_3$.

Table 148. Compounds of formula I.9 wherein $R^1$ is Y-2B, $R^4$ is $CH_3$ and $R^5$ is $CH_3$.

Table 149. Compounds of formula I.9 wherein $R^1$ is Y-3A, $R^4$ is $CH_3$ and $R^5$ is $CH_3$.

Table 150. Compounds of formula I.9 wherein $R^1$ is Y-3B, $R^4$ is $CH_3$ and $R^5$ is $CH_3$.

Table 151. Compounds of formula I.9 wherein $R^1$ is Y-3C, $R^4$ is $CH_3$ and $R^5$ is $CH_3$.

Table 152. Compounds of formula I.9 wherein $R^1$ is Y-3D, $R^4$ is $CH_3$ and $R^5$ is $CH_3$.

Table 153. Compounds of formula I.9 wherein $R^1$ is Y-4A, $R^4$ is $CH_3$ and $R^5$ is $CH_3$.

Table 154. Compounds of formula I.9 wherein $R^1$ is Y-4B, $R^4$ is $CH_3$ and $R^5$ is $CH_3$.

Table 155. Compounds of formula I.9 wherein $R^1$ is Y-4C, $R^4$ is $CH_3$ and $R^5$ is $CH_3$.

Table 156. Compounds of formula I.9 wherein $R^1$ is Y-4D, $R^4$ is $CH_3$ and $R^5$ is $CH_3$.

Table 157. Compounds of formula I.9 wherein $R^1$ is Y-5A, $R^4$ is $CH_3$ and $R^5$ is $CH_3$.

Table 158. Compounds of formula I.9 wherein $R^1$ is Y-5B, $R^4$ is $CH_3$ and $R^5$ is $CH_3$.

Table 159. Compounds of formula I.9 wherein $R^1$ is Y-6A, $R^4$ is $CH_3$ and $R^5$ is $CH_3$.

Table 160. Compounds of formula I.9 wherein $R^1$ is Y-6B, $R^4$ is $CH_3$ and $R^5$ is $CH_3$.

Table 161. Compounds of formula I.9 wherein $R^1$ is Y-8A, $R^4$ is $CH_3$ and $R^5$ is $CH_3$.

Table 162. Compounds of formula I.9 wherein $R^1$ is Y-8B, $R^4$ is $CH_3$ and $R^5$ is $CH_3$.

Table 163. Compounds of formula I.10 wherein $R^1$ is Y-1A, $R^4$ is H and $R^5$ is H.

Table 164. Compounds of formula I.10 wherein $R^1$ is Y-1B, $R^4$ is H and $R^5$ is H.

Table 165. Compounds of formula I.10 wherein $R^1$ is Y-2A, $R^4$ is H and $R^5$ is H.

Table 166. Compounds of formula I.10 wherein $R^1$ is Y-2B, $R^4$ is H and $R^5$ is H.

Table 167. Compounds of formula I.10 wherein $R^1$ is Y-3A, $R^4$ is H and $R^5$ is H.

Table 168. Compounds of formula I.10 wherein $R^1$ is Y-3B, $R^4$ is H and $R^5$ is H.

Table 169. Compounds of formula I.10 wherein $R^1$ is Y-3C, $R^4$ is H and $R^5$ is H.

Table 170. Compounds of formula I.10 wherein $R^1$ is Y-3D, $R^4$ is H and $R^5$ is H.

Table 171. Compounds of formula I.10 wherein $R^1$ is Y-4A, $R^4$ is H and $R^5$ is H.

Table 172. Compounds of formula I.10 wherein $R^1$ is Y-4B, $R^4$ is H and $R^5$ is H.

Table 173. Compounds of formula I.10 wherein $R^1$ is Y-4C, $R^4$ is H and $R^5$ is H.

Table 174. Compounds of formula I.10 wherein $R^1$ is Y-4D, $R^4$ is H and $R^5$ is H.

Table 175. Compounds of formula I.10 wherein $R^1$ is Y-5A, $R^4$ is H and $R^5$ is H.

Table 176. Compounds of formula I.10 wherein $R^1$ is Y-5B, $R^4$ is H and $R^5$ is H.

Table 177. Compounds of formula I.10 wherein $R^1$ is Y-6A, $R^4$ is H and $R^5$ is H.

Table 178. Compounds of formula I.10 wherein $R^1$ is Y-6B, $R^4$ is H and $R^5$ is H.

Table 179. Compounds of formula I.10 wherein $R^1$ is Y-8A, $R^4$ is H and $R^5$ is H.

Table 180. Compounds of formula I.10 wherein $R^1$ is Y-8B, $R^4$ is H and $R^5$ is H.

Table 181. Compounds of formula I.10 wherein $R^1$ is Y-1A, $R^4$ is $CH_3$ and $R^5$ is H.

Table 182. Compounds of formula I.10 wherein $R^1$ is Y-1B, $R^4$ is $CH_3$ and $R^5$ is H.

Table 183. Compounds of formula I.10 wherein $R^1$ is Y-2A, $R^4$ is $CH_3$ and $R^5$ is H.

Table 184. Compounds of formula I.10 wherein $R^1$ is Y-2B, $R^4$ is $CH_3$ and $R^5$ is H.

Table 185. Compounds of formula I.10 wherein $R^1$ is Y-3A, $R^4$ is $CH_3$ and $R^5$ is H.

Table 186. Compounds of formula I.10 wherein $R^1$ is Y-3B, $R^4$ is $CH_3$ and $R^5$ is H.

Table 187. Compounds of formula I.10 wherein $R^1$ is Y-3C, $R^4$ is $CH_3$ and $R^5$ is H.

Table 188. Compounds of formula I.10 wherein $R^1$ is Y-3D, $R^4$ is $CH_3$ and $R^5$ is H.

Table 189. Compounds of formula I.10 wherein $R^1$ is Y-4A, $R^4$ is $CH_3$ and $R^5$ is H.

Table 190. Compounds of formula I.10 wherein $R^1$ is Y-4B, $R^4$ is $CH_3$ and $R^5$ is H.

Table 191. Compounds of formula I.10 wherein $R^1$ is Y-4C, $R^4$ is $CH_3$ and $R^5$ is H.

Table 192. Compounds of formula I.10 wherein $R^1$ is Y-4D, $R^4$ is $CH_3$ and $R^5$ is H.

Table 193. Compounds of formula I.10 wherein $R^1$ is Y-5A, $R^4$ is $CH_3$ and $R^5$ is H.

Table 194. Compounds of formula I.10 wherein $R^1$ is Y-5B, $R^4$ is $CH_3$ and $R^5$ is H.

Table 195. Compounds of formula I.10 wherein $R^1$ is Y-6A, $R^4$ is $CH_3$ and $R^5$ is H.

Table 196. Compounds of formula I.10 wherein $R^1$ is Y-6B, $R^4$ is $CH_3$ and $R^5$ is H.

Table 197. Compounds of formula I.10 wherein $R^1$ is Y-8A, $R^4$ is $CH_3$ and $R^5$ is H.

Table 198. Compounds of formula I.10 wherein $R^1$ is Y-8B, $R^4$ is $CH_3$ and $R^5$ is H.

Table 199. Compounds of formula I.10 wherein $R^1$ is Y-1A, $R^4$ is $CH_3$ and $R^5$ is $CH_3$.

Table 200. Compounds of formula I.10 wherein $R^1$ is Y-1B, $R^4$ is $CH_3$ and $R^5$ is $CH_3$.

Table 201. Compounds of formula I.10 wherein $R^1$ is Y-2A, $R^4$ is $CH_3$ and $R^5$ is $CH_3$.

Table 202. Compounds of formula I.10 wherein $R^1$ is Y-2B, $R^4$ is $CH_3$ and $R^5$ is $CH_3$.

Table 203. Compounds of formula I.10 wherein $R^1$ is Y-3A, $R^4$ is $CH_3$ and $R^5$ is $CH_3$.

Table 204. Compounds of formula I.10 wherein $R^1$ is Y-3B, $R^4$ is $CH_3$ and $R^5$ is $CH_3$.

Table 205. Compounds of formula I.10 wherein $R^1$ is Y-3C, $R^4$ is $CH_3$ and $R^5$ is $CH_3$.

Table 206. Compounds of formula I.10 wherein $R^1$ is Y-3D, $R^4$ is $CH_3$ and $R^5$ is $CH_3$.

Table 207. Compounds of formula I.10 wherein $R^1$ is Y-4A, $R^4$ is $CH_3$ and $R^5$ is $CH_3$.

Table 208. Compounds of formula I.10 wherein $R^1$ is Y-4B, $R^4$ is $CH_3$ and $R^5$ is $CH_3$.

Table 209. Compounds of formula I.10 wherein $R^1$ is Y-4C, $R^4$ is $CH_3$ and $R^5$ is $CH_3$.

Table 210. Compounds of formula I.10 wherein $R^1$ is Y-4D, $R^4$ is $CH_3$ and $R^5$ is $CH_3$.

Table 211. Compounds of formula I.10 wherein $R^1$ is Y-5A, $R^4$ is $CH_3$ and $R^5$ is $CH_3$.

Table 212. Compounds of formula I.10 wherein $R^1$ is Y-5B, $R^4$ is $CH_3$ and $R^5$ is $CH_3$.

Table 213. Compounds of formula I.10 wherein $R^1$ is Y-6A, $R^4$ is $CH_3$ and $R^5$ is $CH_3$.

Table 214. Compounds of formula I.10 wherein $R^1$ is Y-6B, $R^4$ is $CH_3$ and $R^5$ is $CH_3$.

Table 215. Compounds of formula I.10 wherein $R^1$ is Y-8A, $R^4$ is $CH_3$ and $R^5$ is $CH_3$.

Table 216. Compounds of formula I.10 wherein $R^1$ is Y-8B, $R^4$ is $CH_3$ and $R^5$ is $CH_3$.

Table 217. Compounds of formula I.11 wherein $R^1$ is Y-1A, $R^4$ is H and $R^5$ is H.

Table 218. Compounds of formula I.11 wherein $R^1$ is Y-1B, $R^4$ is H and $R^5$ is H.

Table 219. Compounds of formula I.11 wherein $R^1$ is Y-2A, $R^4$ is H and $R^5$ is H.

Table 220. Compounds of formula I.11 wherein $R^1$ is Y-2B, $R^4$ is H and $R^5$ is H.

Table 221. Compounds of formula I.11 wherein $R^1$ is Y-3A, $R^4$ is H and $R^5$ is H.

Table 222. Compounds of formula I.11 wherein $R^1$ is Y-3B, $R^4$ is H and $R^5$ is H.

Table 223. Compounds of formula I.11 wherein $R^1$ is Y-3C, $R^4$ is H and $R^5$ is H.

Table 224. Compounds of formula I.11 wherein $R^1$ is Y-3D, $R^4$ is H and $R^5$ is H.

Table 225. Compounds of formula I.11 wherein $R^1$ is Y-4A, $R^4$ is H and $R^5$ is H.

Table 226. Compounds of formula I.11 wherein $R^1$ is Y-4B, $R^4$ is H and $R^5$ is H.

Table 227. Compounds of formula I.11 wherein $R^1$ is Y-4C, $R^4$ is H and $R^5$ is H.

Table 228. Compounds of formula I.11 wherein $R^1$ is Y-4D, $R^4$ is H and $R^5$ is H.

Table 229. Compounds of formula I.11 wherein $R^1$ is Y-5A, $R^4$ is H and $R^5$ is H.

Table 230. Compounds of formula I.11 wherein $R^1$ is Y-5B, $R^4$ is H and $R^5$ is H.

Table 231. Compounds of formula I.11 wherein $R^1$ is Y-6A, $R^4$ is H and $R^5$ is H.

Table 232. Compounds of formula I.11 wherein $R^1$ is Y-6B, $R^4$ is H and $R^5$ is H.

Table 233. Compounds of formula I.11 wherein $R^1$ is Y-8A, $R^4$ is H and $R^5$ is H.

Table 234. Compounds of formula I.11 wherein $R^1$ is Y-8B, $R^4$ is H and $R^5$ is H.

Table 235. Compounds of formula I.11 wherein $R^1$ is Y-1A, $R^4$ is $CH_3$ and $R^5$ is H.

Table 236. Compounds of formula I.11 wherein $R^1$ is Y-1B, $R^4$ is $CH_3$ and $R^5$ is H.

Table 237. Compounds of formula I.11 wherein $R^1$ is Y-2A, $R^4$ is $CH_3$ and $R^5$ is H.

Table 238. Compounds of formula I.11 wherein $R^1$ is Y-2B, $R^4$ is $CH_3$ and $R^5$ is H.

Table 239. Compounds of formula I.11 wherein $R^1$ is Y-3A, $R^4$ is $CH_3$ and $R^5$ is H.

Table 240. Compounds of formula I.11 wherein $R^1$ is Y-3B, $R^4$ is $CH_3$ and $R^5$ is H.

Table 241. Compounds of formula I.11 wherein $R^1$ is Y-3C, $R^4$ is $CH_3$ and $R^5$ is H.

Table 242. Compounds of formula I.11 wherein $R^1$ is Y-3D, $R^4$ is $CH_3$ and $R^5$ is H.

Table 243. Compounds of formula I.11 wherein $R^1$ is Y-4A, $R^4$ is $CH_3$ and $R^5$ is H.

Table 244. Compounds of formula I.11 wherein $R^1$ is Y-4B, $R^4$ is $CH_3$ and $R^5$ is H.

Table 245. Compounds of formula I.11 wherein $R^1$ is Y-4C, $R^4$ is $CH_3$ and $R^5$ is H.

Table 246. Compounds of formula I.11 wherein $R^1$ is Y-4D, $R^4$ is $CH_3$ and $R^5$ is H.

Table 247. Compounds of formula I.11 wherein $R^1$ is Y-5A, $R^4$ is $CH_3$ and $R^5$ is H.

Table 248. Compounds of formula I.11 wherein $R^1$ is Y-5B, $R^4$ is $CH_3$ and $R^5$ is H.

Table 249. Compounds of formula I.11 wherein $R^1$ is Y-6A, $R^4$ is $CH_3$ and $R^5$ is H.

Table 250. Compounds of formula I.11 wherein $R^1$ is Y-6B, $R^4$ is $CH_3$ and $R^5$ is H.

Table 251. Compounds of formula I.11 wherein $R^1$ is Y-8A, $R^4$ is $CH_3$ and $R^5$ is H.

Table 252. Compounds of formula I.11 wherein $R^1$ is Y-8B, $R^4$ is $CH_3$ and $R^5$ is H.

Table 253. Compounds of formula I.11 wherein $R^1$ is Y-1A, $R^4$ is $CH_3$ and $R^5$ is $CH_3$.

Table 254. Compounds of formula I.11 wherein $R^1$ is Y-1B, $R^4$ is $CH_3$ and $R^5$ is $CH_3$.

Table 255. Compounds of formula I.11 wherein $R^1$ is Y-2A, $R^4$ is $CH_3$ and $R^5$ is $CH_3$.

Table 256. Compounds of formula I.11 wherein $R^1$ is Y-2B, $R^4$ is $CH_3$ and $R^5$ is $CH_3$.

Table 257. Compounds of formula I.11 wherein $R^1$ is Y-3A, $R^4$ is $CH_3$ and $R^5$ is $CH_3$.

Table 258. Compounds of formula I.11 wherein $R^1$ is Y-3B, $R^4$ is $CH_3$ and $R^5$ is $CH_3$.

Table 259. Compounds of formula I.11 wherein $R^1$ is Y-3C, $R^4$ is $CH_3$ and $R^5$ is $CH_3$.

Table 260. Compounds of formula I.11 wherein $R^1$ is Y-3D, $R^4$ is $CH_3$ and $R^5$ is $CH_3$.

Table 261. Compounds of formula I.11 wherein $R^1$ is Y-4A, $R^4$ is $CH_3$ and $R^5$ is $CH_3$.

Table 262. Compounds of formula I.11 wherein $R^1$ is Y-4B, $R^4$ is $CH_3$ and $R^5$ is $CH_3$.

Table 263. Compounds of formula I.11 wherein $R^1$ is Y-4C, $R^4$ is $CH_3$ and $R^5$ is $CH_3$.

Table 264. Compounds of formula I.11 wherein $R^1$ is Y-4D, $R^4$ is $CH_3$ and $R^5$ is $CH_3$.

Table 265. Compounds of formula I.11 wherein $R^1$ is Y-5A, $R^4$ is $CH_3$ and $R^5$ is $CH_3$.

Table 266. Compounds of formula I.11 wherein $R^1$ is Y-5B, $R^4$ is $CH_3$ and $R^5$ is $CH_3$.

Table 267. Compounds of formula I.11 wherein $R^1$ is Y-6A, $R^4$ is $CH_3$ and $R^5$ is $CH_3$.

Table 268. Compounds of formula I.11 wherein $R^1$ is Y-6B, $R^4$ is $CH_3$ and $R^5$ is $CH_3$.

Table 269. Compounds of formula I.11 wherein $R^1$ is Y-8A, $R^4$ is $CH_3$ and $R^5$ is $CH_3$.

Table 270. Compounds of formula I.11 wherein $R^1$ is Y-8B, $R^4$ is $CH_3$ and $R^5$ is $CH_3$.

Table 271. Compounds of formula I.12 wherein $R^1$ is Y-1A, $R^4$ is H and $R^5$ is H.

Table 272. Compounds of formula I.12 wherein $R^1$ is Y-1B, $R^4$ is H and $R^5$ is H.

Table 273. Compounds of formula I.12 wherein $R^1$ is Y-2A, $R^4$ is H and $R^5$ is H.

Table 274. Compounds of formula I.12 wherein $R^1$ is Y-2B, $R^4$ is H and $R^5$ is H.

Table 275. Compounds of formula I.12 wherein $R^1$ is Y-3A, $R^4$ is H and $R^5$ is H.

Table 276. Compounds of formula I.12 wherein $R^1$ is Y-3B, $R^4$ is H and $R^5$ is H.

Table 277. Compounds of formula I.12 wherein $R^1$ is Y-3C, $R^4$ is H and $R^5$ is H.

Table 278. Compounds of formula I.12 wherein $R^1$ is Y-3D, $R^4$ is H and $R^5$ is H.

Table 279. Compounds of formula I.12 wherein $R^1$ is Y-4A, $R^4$ is H and $R^5$ is H.

Table 280. Compounds of formula I.12 wherein $R^1$ is Y-4B, $R^4$ is H and $R^5$ is H.

Table 281. Compounds of formula I.12 wherein $R^1$ is Y-4C, $R^4$ is H and $R^5$ is H.

Table 282. Compounds of formula I.12 wherein $R^1$ is Y-4D, $R^4$ is H and $R^5$ is H.

Table 283. Compounds of formula I.12 wherein $R^1$ is Y-5A, $R^4$ is H and $R^5$ is H.

Table 284. Compounds of formula I.12 wherein $R^1$ is Y-5B, $R^4$ is H and $R^5$ is H.

Table 285. Compounds of formula I.12 wherein $R^1$ is Y-6A, $R^4$ is H and $R^5$ is H.

Table 286. Compounds of formula I.12 wherein $R^1$ is Y-6B, $R^4$ is H and $R^5$ is H.

Table 287. Compounds of formula I.12 wherein $R^1$ is Y-8A, $R^4$ is H and $R^5$ is H.

Table 288. Compounds of formula I.12 wherein $R^1$ is Y-8B, $R^4$ is H and $R^5$ is H.

Table 289. Compounds of formula I.12 wherein $R^1$ is Y-1A, $R^4$ is $CH_3$ and $R^5$ is H.

Table 290. Compounds of formula I.12 wherein $R^1$ is Y-1B, $R^4$ is $CH_3$ and $R^5$ is H.

Table 291. Compounds of formula I.12 wherein $R^1$ is Y-2A, $R^4$ is $CH_3$ and $R^5$ is H.

Table 292. Compounds of formula I.12 wherein $R^1$ is Y-2B, $R^4$ is $CH_3$ and $R^5$ is H.

Table 293. Compounds of formula I.12 wherein $R^1$ is Y-3A, $R^4$ is $CH_3$ and $R^5$ is H.

Table 294. Compounds of formula I.12 wherein $R^1$ is Y-3B, $R^4$ is $CH_3$ and $R^5$ is H.

Table 295. Compounds of formula I.12 wherein $R^1$ is Y-3C, $R^4$ is $CH_3$ and $R^5$ is H.

Table 296. Compounds of formula I.12 wherein $R^1$ is Y-3D, $R^4$ is $CH_3$ and $R^5$ is H.

Table 297. Compounds of formula I.12 wherein $R^1$ is Y-4A, $R^4$ is $CH_3$ and $R^5$ is H.

Table 298. Compounds of formula I.12 wherein $R^1$ is Y-4B, $R^4$ is $CH_3$ and $R^5$ is H.

Table 299. Compounds of formula I.12 wherein $R^1$ is Y-4C, $R^4$ is $CH_3$ and $R^5$ is H.

Table 300. Compounds of formula I.12 wherein $R^1$ is Y-4D, $R^4$ is $CH_3$ and $R^5$ is H.

Table 301. Compounds of formula I.12 wherein $R^1$ is Y-5A, $R^4$ is $CH_3$ and $R^5$ is H.

Table 302. Compounds of formula I.12 wherein $R^1$ is Y-5B, $R^4$ is $CH_3$ and $R^5$ is H.

Table 303. Compounds of formula I.12 wherein $R^1$ is Y-6A, $R^4$ is $CH_3$ and $R^5$ is H.

Table 304. Compounds of formula I.12 wherein $R^1$ is Y-6B, $R^4$ is $CH_3$ and $R^5$ is H.

Table 305. Compounds of formula I.12 wherein $R^1$ is Y-8A, $R^4$ is $CH_3$ and $R^5$ is H.

Table 306. Compounds of formula I.12 wherein $R^1$ is Y-8B, $R^4$ is $CH_3$ and $R^5$ is H.

Table 307. Compounds of formula I.12 wherein $R^1$ is Y-1A, $R^4$ is $CH_3$ and $R^5$ is $CH_3$.

Table 308. Compounds of formula I.12 wherein $R^1$ is Y-1B, $R^4$ is $CH_3$ and $R^5$ is $CH_3$.

Table 309. Compounds of formula I.12 wherein $R^1$ is Y-2A, $R^4$ is $CH_3$ and $R^5$ is $CH_3$.

Table 310. Compounds of formula I.12 wherein $R^1$ is Y-2B, $R^4$ is $CH_3$ and $R^5$ is $CH_3$.

Table 311. Compounds of formula I.12 wherein $R^1$ is Y-3A, $R^4$ is $CH_3$ and $R^5$ is $CH_3$.

Table 312. Compounds of formula I.12 wherein $R^1$ is Y-3B, $R^4$ is $CH_3$ and $R^5$ is $CH_3$.

Table 313. Compounds of formula I.12 wherein $R^1$ is Y-3C, $R^4$ is $CH_3$ and $R^5$ is $CH_3$.

Table 314. Compounds of formula I.12 wherein $R^1$ is Y-3D, $R^4$ is $CH_3$ and $R^5$ is $CH_3$.

Table 315. Compounds of formula I.12 wherein $R^1$ is Y-4A, $R^4$ is $CH_3$ and $R^5$ is $CH_3$.

Table 316. Compounds of formula I.12 wherein $R^1$ is Y-4B, $R^4$ is $CH_3$ and $R^5$ is $CH_3$.

Table 317. Compounds of formula I.12 wherein $R^1$ is Y-4C, $R^4$ is $CH_3$ and $R^5$ is $CH_3$.

Table 318. Compounds of formula I.12 wherein $R^1$ is Y-4D, $R^4$ is $CH_3$ and $R^5$ is $CH_3$.

Table 319. Compounds of formula I.12 wherein $R^1$ is Y-5A, $R^4$ is $CH_3$ and $R^5$ is $CH_3$.

Table 320. Compounds of formula I.12 wherein $R^1$ is Y-5B, $R^4$ is $CH_3$ and $R^5$ is $CH_3$.

Table 321. Compounds of formula I.12 wherein $R^1$ is Y-6A, $R^4$ is $CH_3$ and $R^5$ is $CH_3$.

Table 322. Compounds of formula I.12 wherein $R^1$ is Y-6B, $R^4$ is $CH_3$ and $R^5$ is $CH_3$.

Table 323. Compounds of formula I.12 wherein $R^1$ is Y-8A, $R^4$ is $CH_3$ and $R^5$ is $CH_3$.

Table 324. Compounds of formula I.12 wherein $R^1$ is Y-8B, $R^4$ is $CH_3$ and $R^5$ is $CH_3$.

Table 325. Compounds of formula I.13 wherein $R^1$ is Y-1A, $R^2$ is H, $R^9$ is H and $R^{10}$ is H.

Table 326. Compounds of formula I.13 wherein $R^1$ is Y-1A, $R^2$ is H, $R^9$ is $CH_3$ and, $R^{10}$ is H.

Table 327. Compounds of formula I.13 wherein $R^1$ is Y-1A, $R^2$ is H, $R^9$ is $CH_3$ and $R^{10}$ is $CH_3$.

Table 328. Compounds of formula I.13 wherein $R^1$ is Y-1B, $R^2$ is H, $R^9$ is H and $R^{10}$ is H.

Table 329. Compounds of formula I.13 wherein $R^1$ is Y-1B, $R^2$ is H, $R^9$ is $CH_3$ and $R^{10}$ is H.

Table 330. Compounds of formula I.13 wherein $R^1$ is Y-1B, $R^2$ is H, $R^9$ is $CH_3$ and $R^{10}$ is $CH_3$.

Table 331. Compounds of formula I.13 wherein $R^1$ is Y-2A, $R^2$ is H, $R^9$ is H and $R^{10}$ is H.

Table 332. Compounds of formula I.13 wherein $R^1$ is Y-2A, $R^2$ is H, $R^9$ is $CH_3$ and $R^{10}$ is H.

Table 333. Compounds of formula I.13 wherein $R^1$ is Y-2A, $R^2$ is H, $R^9$ is $CH_3$ and $R^{10}$ is $CH_3$.

Table 334. Compounds of formula I.13 wherein $R^1$ is Y-2B, $R^2$ is H, $R^9$ is H and $R^{10}$ is H.

Table 335. Compounds of formula I.13 wherein $R^1$ is Y-2B, $R^2$ is H, $R^9$ is $CH_3$ and $R^{10}$ is H.

Table 336. Compounds of formula I.13 wherein $R^1$ is Y-2B, $R^2$ is H, $R^9$ is $CH_3$ and $R^{10}$ is $CH_3$.

Table 337. Compounds of formula I.13 wherein $R^1$ is Y-3A, $R^2$ is H, $R^9$ is H and $R^{10}$ is H.

Table 338. Compounds of formula I.13 wherein $R^1$ is Y-3A, $R^2$ is H, $R^9$ is $CH_3$ and $R^{10}$ is H.

Table 339. Compounds of formula I.13 wherein $R^1$ is Y-3A, $R^2$ is H, $R^9$ is $CH_3$ and $R^{10}$ is $CH_3$.

Table 340. Compounds of formula I.13 wherein $R^1$ is Y-3B, $R^2$ is H, $R^9$ is H and $R^{10}$ is H.

Table 341. Compounds of formula I.13 wherein $R^1$ is Y-3B, $R^2$ is H, $R^9$ is $CH_3$ and $R^{10}$ is H.

Table 342. Compounds of formula I.13 wherein $R^1$ is Y-3B, $R^2$ is H, $R^9$ is $CH_3$ and $R^{10}$ is $CH_3$.

Table 343. Compounds of formula I.13 wherein $R^1$ is Y-3C, $R^2$ is H, $R^9$ is H and $R^{10}$ is H.

Table 344. Compounds of formula I.13 wherein $R^1$ is Y-3C, $R^2$ is H, $R^9$ is $CH_3$ and $R^{10}$ is H.

Table 345. Compounds of formula I.13 wherein $R^1$ is Y-3C, $R^2$ is H, $R^9$ is $CH_3$ and $R^{10}$ is $CH_3$.

Table 346. Compounds of formula I.13 wherein $R^1$ is Y-3D, $R^2$ is H, $R^9$ is H and $R^{10}$ is H.

Table 347. Compounds of formula I.13 wherein $R^1$ is Y-3D, $R^2$ is H, $R^9$ is $CH_3$ and $R^{10}$ is H.

Table 348. Compounds of formula I.13 wherein $R^1$ is Y-3D, $R^2$ is H, $R^9$ is $CH_3$ and $R^{10}$ is $CH_3$.

Table 349. Compounds of formula I.13 wherein $R^1$ is Y-4A, $R^2$ is H, $R^9$ is H and $R^{10}$ is H.

Table 350. Compounds of formula I.13 wherein $R^1$ is Y-4A, $R^2$ is H, $R^9$ is $CH_3$ and $R^{10}$ is H.

Table 351. Compounds of formula I.13 wherein $R^1$ is Y-4A, $R^2$ is H, $R^9$ is $CH_3$ and $R^{10}$ is $CH_3$.

Table 352. Compounds of formula I.13 wherein $R^1$ is Y-4B, $R^2$ is H, $R^9$ is H and $R^{10}$ is H.

Table 353. Compounds of formula I.13 wherein $R^1$ is Y-4B, $R^2$ is H, $R^9$ is $CH_3$ and $R^{10}$ is H.

Table 354. Compounds of formula I.13 wherein $R^1$ is Y-4B, $R^2$ is H, $R^9$ is $CH_3$ and $R^{10}$ is $CH_3$.

Table 355. Compounds of formula I.13 wherein $R^1$ is Y-4C, $R^2$ is H, $R^9$ is H and $R^{10}$ is H.

Table 356. Compounds of formula I.13 wherein $R^1$ is Y-4C, $R^2$ is H, $R^9$ is $CH_3$ and $R^{10}$ is H.

Table 357. Compounds of formula I.13 wherein $R^1$ is Y-4C, $R^2$ is H, $R^9$ is $CH_3$ and $R^{10}$ is $CH_3$.

Table 358. Compounds of formula I.13 wherein $R^1$ is Y-4D, $R^2$ is H, $R^9$ is H and $R^{10}$ is H.

Table 359. Compounds of formula I.13 wherein $R^1$ is Y-4D, $R^2$ is H, $R^9$ is $CH_3$ and $R^{10}$ is H.

Table 360. Compounds of formula I.13 wherein $R^1$ is Y-4D, $R^2$ is H, $R^9$ is $CH_3$ and $R^{10}$ is $CH_3$.

Table 361. Compounds of formula I.13 wherein $R^1$ is Y-5A, $R^2$ is H, $R^9$ is H and $R^{10}$ is H.

Table 362. Compounds of formula I.13 wherein $R^1$ is Y-5A, $R^2$ is H, $R^9$ is $CH_3$ and $R^{10}$ is H.

Table 363. Compounds of formula I.13 wherein $R^1$ is Y-5A, $R^2$ is H, $R^9$ is $CH_3$ and $R^{10}$ is $CH_3$.

Table 364. Compounds of formula I.13 wherein $R^1$ is Y-5B, $R^2$ is H, $R^9$ is H and $R^{10}$ is H.

Table 365. Compounds of formula I.13 wherein $R^1$ is Y-5B, $R^2$ is H, $R^9$ is $CH_3$ and $R^{10}$ is H.

Table 366. Compounds of formula I.13 wherein $R^1$ is Y-5B, $R^2$ is H, $R^9$ is $CH_3$ and $R^{10}$ is $CH_3$.

Table 367. Compounds of formula I.13 wherein $R^1$ is Y-6A, $R^2$ is H, $R^9$ is H and $R^{10}$ is H.

Table 368. Compounds of formula I.13 wherein $R^1$ is Y-6A, $R^2$ is H, $R^9$ is $CH_3$ and $R^{10}$ is H.

Table 369. Compounds of formula I.13 wherein $R^1$ is Y-6A, $R^2$ is H, $R^9$ is $CH_3$ and $R^{10}$ is $CH_3$.

Table 370. Compounds of formula I.13 wherein $R^1$ is Y-6B, $R^2$ is H, $R^9$ is H and $R^{10}$ is H.

Table 371. Compounds of formula I.13 wherein $R^1$ is Y-6B, $R^2$ is H, $R^9$ is $CH_3$ and $R^{10}$ is H.

Table 372. Compounds of formula I.13 wherein $R^1$ is Y-6B, $R^2$ is H, $R^9$ is $CH_3$ and $R^{10}$ is $CH_3$.

Table 373. Compounds of formula I.13 wherein $R^1$ is Y-8A, $R^2$ is H, $R^9$ is H and $R^{10}$ is H.

Table 374. Compounds of formula I.13 wherein $R^1$ is Y-8A, $R^2$ is H, $R^9$ is $CH_3$ and $R^{10}$ is H.

Table 375. Compounds of formula I.13 wherein $R^1$ is Y-8A, $R^2$ is H, $R^9$ is $CH_3$ and $R^{10}$ is $CH_3$.

Table 376. Compounds of formula I.13 wherein $R^1$ is Y-8B, $R^2$ is H, $R^9$ is H and $R^{10}$ is H.

Table 377. Compounds of formula I.13 wherein $R^1$ is Y-8B, $R^2$ is H, $R^9$ is $CH_3$ and $R^{10}$ is H.

Table 378. Compounds of formula I.13 wherein $R^1$ is Y-8B, $R^2$ is H, $R^9$ is $CH_3$ and $R^{10}$ is $CH_3$.

Table 379. Compounds of formula I.13 wherein $R^1$ is Y-1A, $R^2$ is $CH_3$, $R^9$ is H and $R^{10}$ is H.

Table 380. Compounds of formula I.13 wherein $R^1$ is Y-1A, $R^2$ is $CH_3$, $R^9$ is $CH_3$ and $R^{10}$ is H.

Table 381. Compounds of formula I.13 wherein $R^1$ is Y-1A, $R^2$ is $CH_3$, $R^9$ is $CH_3$ and $R^{10}$ is $CH_3$.

Table 382. Compounds of formula I.13 wherein $R^1$ is Y-1B, $R^2$ is $CH_3$, $R^9$ is H and $R^{10}$ is H.

Table 383. Compounds of formula I.13 wherein $R^1$ is Y-1B, $R^2$ is $CH_3$, $R^9$ is $CH_3$ and $R^{10}$ is H.

Table 384. Compounds of formula I.13 wherein $R^1$ is Y-1B, $R^2$ is $CH_3$, $R^9$ is $CH_3$ and $R^{10}$ is $CH_3$.

Table 385. Compounds of formula I.13 wherein $R^1$ is Y-2A, $R^2$ is $CH_3$, $R^9$ is H and $R^{10}$ is H.

Table 386. Compounds of formula I.13 wherein $R^1$ is Y-2A, $R^2$ is $CH_3$, $R^9$ is $CH_3$ and $R^{10}$ is H.

Table 387. Compounds of formula I.13 wherein $R^1$ is Y-2A, $R^2$ is $CH_3$, $R^9$ is $CH_3$ and $R^{10}$ is $CH_3$.

Table 388. Compounds of formula I.13 wherein $R^1$ is Y-2B, $R^2$ is $CH_3$, $R^9$ is H and $R^{10}$ is H.

Table 389. Compounds of formula I.13 wherein $R^1$ is Y-2B, $R^2$ is $CH_3$, $R^9$ is $CH_3$ and $R^{10}$ is H.

Table 390. Compounds of formula I.13 wherein $R^1$ is Y-2B, $R^2$ is $CH_3$, $R^9$ is $CH_3$ and $R^{10}$ is $CH_3$.

Table 391. Compounds of formula I.13 wherein $R^1$ is Y-3A, $R^2$ is $CH_3$, $R^9$ is H and $R^{10}$ is H.

Table 392. Compounds of formula I.13 wherein $R^1$ is Y-3A, $R^2$ is $CH_3$, $R^9$ is $CH_3$ and $R^{10}$ is H.

Table 393. Compounds of formula I.13 wherein $R^1$ is Y-3A, $R^2$ is $CH_3$, $R^9$ is $CH_3$ and $R^{10}$ is $CH_3$.

Table 394. Compounds of formula I.13 wherein $R^1$ is Y-3B, $R^2$ is $CH_3$, $R^9$ is H and $R^{10}$ is H.

Table 395. Compounds of formula I.13 wherein $R^1$ is Y-3B, $R^2$ is $CH_3$, $R^9$ is $CH_3$ and $R^{10}$ is H.

Table 396. Compounds of formula I.13 wherein $R^1$ is Y-3B, $R^2$ is $CH_3$, $R^9$ is $CH_3$ and $R^{10}$ is $CH_3$.

Table 397. Compounds of formula I.13 wherein $R^1$ is Y-3C, $R^2$ is $CH_3$, $R^9$ is H and $R^{10}$ is H.

Table 398. Compounds of formula I.13 wherein $R^1$ is Y-3C, $R^2$ is $CH_3$, $R^9$ is $CH_3$ and $R^{10}$ is H.

Table 399. Compounds of formula I.13 wherein $R^1$ is Y-3C, $R^2$ is $CH_3$, $R^9$ is $CH_3$ and $R^{10}$ is $CH_3$.

Table 400. Compounds of formula I.13 wherein $R^1$ is Y-3D, $R^2$ is $CH_3$, $R^9$ is H and $R^{10}$ is H.

Table 401. Compounds of formula I.13 wherein $R^1$ is Y-3D, $R^2$ is $CH_3$, $R^9$ is $CH_3$ and $R^{10}$ is H.

Table 402. Compounds of formula I.13 wherein $R^1$ is Y-3D, $R^2$ is $CH_3$, $R^9$ is $CH_3$ and $R^{10}$ is $CH_3$.

Table 403. Compounds of formula I.13 wherein $R^1$ is Y-4A, $R^2$ is $CH_3$, $R^9$ is H and $R^{10}$ is H.

Table 404. Compounds of formula I.13 wherein $R^1$ is Y-4A, $R^2$ is $CH_3$, $R^9$ is $CH_3$ and $R^{10}$ is H.

Table 405. Compounds of formula I.13 wherein $R^1$ is Y-4A, $R^2$ is $CH_3$, $R^9$ is $CH_3$ and $R^{10}$ is $CH_3$.

Table 406. Compounds of formula I.13 wherein $R^1$ is Y-4B, $R^2$ is $CH_3$, $R^9$ is H and $R^{10}$ is H.

Table 407. Compounds of formula I.13 wherein $R^1$ is Y-4B, $R^2$ is $CH_3$, $R^9$ is $CH_3$ and $R^{10}$ is H.

Table 408. Compounds of formula I.13 wherein $R^1$ is Y-4B, $R^2$ is $CH_3$, $R^9$ is $CH_3$ and $R^{10}$ is $CH_3$.

Table 409. Compounds of formula I.13 wherein $R^1$ is Y-4C, $R^2$ is $CH_3$, $R^9$ is H and $R^{10}$ is H.

Table 410. Compounds of formula I.13 wherein $R^1$ is Y-4C, $R^2$ is $CH_3$, $R^9$ is $CH_3$ and $R^{10}$ is H.

Table 411. Compounds of formula I.13 wherein $R^1$ is Y-4C, $R^2$ is $CH_3$, $R^9$ is $CH_3$ and $R^{10}$ is $CH_3$.

Table 412. Compounds of formula I.13 wherein $R^1$ is Y-4D, $R^2$ is $CH_3$, $R^9$ is H and $R^{10}$ is H.

Table 413. Compounds of formula I.13 wherein $R^1$ is Y-4D, $R^2$ is $CH_3$, $R^9$ is $CH_3$ and $R^{10}$ is H.

Table 414. Compounds of formula I.13 wherein $R^1$ is Y-4D, $R^2$ is $CH_3$, $R^9$ is $CH_3$ and $R^{10}$ is $CH_3$.

Table 415. Compounds of formula I.13 wherein $R^1$ is Y-5A, $R^2$ is $CH_3$, $R^9$ is H and $R^{10}$ is H.

Table 416. Compounds of formula I.13 wherein $R^1$ is Y-5A, $R^2$ is $CH_3$, $R^9$ is $CH_3$ and $R^{10}$ is H.

Table 417. Compounds of formula I.13 wherein $R^1$ is Y-5A, $R^2$ is $CH_3$, $R^9$ is $CH_3$ and $R^{10}$ is $CH_3$.

Table 418. Compounds of formula I.13 wherein $R^1$ is Y-5B, $R^2$ is $CH_3$, $R^9$ is H and $R^{10}$ is H.

Table 419. Compounds of formula I.13 wherein $R^1$ is Y-5B, $R^2$ is $CH_3$, $R^9$ is $CH_3$ and $R^{10}$ is H.

Table 420. Compounds of formula I.13 wherein $R^1$ is Y-5B, $R^2$ is $CH_3$, $R^9$ is $CH_3$ and $R^{10}$ is $CH_3$.

Table 421. Compounds of formula I.13 wherein $R^1$ is Y-6A, $R^2$ is $CH_3$, $R^9$ is H and $R^{10}$ is H.

Table 422. Compounds of formula I.13 wherein $R^1$ is Y-6A, $R^2$ is $CH_3$, $R^9$ is $CH_3$ and $R^{10}$ is H.

Table 423. Compounds of formula I.13 wherein $R^1$ is Y-6A, $R^2$ is $CH_3$, $R^9$ is $CH_3$ and $R^{10}$ is $CH_3$.

Table 424. Compounds of formula I.13 wherein $R^1$ is Y-6B, $R^2$ is $CH_3$, $R^9$ is H and $R^{10}$ is H.

Table 425. Compounds of formula I.13 wherein $R^1$ is Y-6B, $R^2$ is $CH_3$, $R^9$ is $CH_3$ and $R^{10}$ is H.

Table 426. Compounds of formula I.13 wherein $R^1$ is Y-6B, $R^2$ is $CH_3$, $R^9$ is $CH_3$ and $R^{10}$ is $CH_3$. $CH_3$.

Table 427. Compounds of formula I.13 wherein $R^1$ is Y-8A, $R^2$ is $CH_3$, $R^9$ is H and $R^{10}$ is H.

Table 428. Compounds of formula I.13 wherein $R^1$ is Y-8A, $R^2$ is $CH_3$, $R^9$ is $CH_3$ and $R^{10}$ is H.

Table 429. Compounds of formula I.13 wherein $R^1$ is Y-8A, $R^2$ is $CH_3$, $R^9$ is $CH_3$ and $R^{10}$ is $CH_3$.

Table 430. Compounds of formula I.13 wherein $R^1$ is Y-8B, $R^2$ is $CH_3$, $R^9$ is H and $R^{10}$ is H.

Table 431. Compounds of formula I.13 wherein $R^1$ is Y-8B, $R^2$ is $CH_3$, $R^9$ is $CH_3$ and $R^{10}$ is H.

Table 432. Compounds of formula I.13 wherein $R^1$ is Y-8B, $R^2$ is $CH_3$, $R^9$ is $CH_3$ and $R^{10}$ is $CH_3$.

Table 433. Compounds of formula I.13 wherein $R^1$ is Y-1A, $R^2$ is $C_2H_5$, $R^9$ is H and $R^{10}$ is H.

Table 434. Compounds of formula I.13 wherein $R^1$ is Y-1A, $R^2$ is $C_2H_5$, $R^9$ is $CH_3$ and $R^{10}$ is H.

Table 435. Compounds of formula I.13 wherein $R^1$ is Y-1A, $R^2$ is $C_2H_5$, $R^9$ is $CH_3$ and $R^{10}$ is $CH_3$.

Table 436. Compounds of formula I.13 wherein $R^1$ is Y-1B, $R^2$ is $C_2H_5$, $R^9$ is H and $R^{10}$ is H.

Table 437. Compounds of formula I.13 wherein $R^1$ is Y-1B, $R^2$ is $C_2H_5$, $R^9$ is $CH_3$ and $R^{10}$ is H.

Table 438. Compounds of formula I.13 wherein $R^1$ is Y-1B, $R^2$ is $C_2H_5$, $R^9$ is $CH_3$ and $R^{10}$ is $CH_3$.

Table 439. Compounds of formula I.13 wherein $R^1$ is Y-2A, $R^2$ is $C_2H_5$, $R^9$ is H and $R^{10}$ is H.

Table 440. Compounds of formula I.13 wherein $R^1$ is Y-2A, $R^2$ is $C_2H_5$, $R^9$ is $CH_3$ and $R^{10}$ is H.

Table 441. Compounds of formula I.13 wherein $R^1$ is Y-2A, $R^2$ is $C_2H_5$, $R^9$ is $CH_3$ and $R^{10}$ is $CH_3$.

Table 442. Compounds of formula I.13 wherein $R^1$ is Y-2B, $R^2$ is $C_2H_5$, $R^9$ is H and $R^{10}$ is H.

Table 443. Compounds of formula I.13 wherein $R^1$ is Y-2B, $R^2$ is $C_2H_5$, $R^9$ is $CH_3$ and $R^{10}$ is H.

Table 444. Compounds of formula I.13 wherein $R^1$ is Y-2B, $R^2$ is $C_2H_5$, $R^9$ is $CH_3$ and $R^{10}$ is $CH_3$.

Table 445. Compounds of formula I.13 wherein $R^1$ is Y-3A, $R^2$ is $C_2H_5$, $R^9$ is H and $R^{10}$ is H.

Table 446. Compounds of formula I.13 wherein $R^1$ is Y-3A, $R^2$ is $C_2H_5$, $R^9$ is $CH_3$ and $R^{10}$ is H.

Table 447. Compounds of formula I.13 wherein $R^1$ is Y-3A, $R^2$ is $C_2H_5$, $R^9$ is $CH_3$ and $R^{10}$ is $CH_3$.

Table 448. Compounds of formula I.13 wherein $R^1$ is Y-3B, $R^2$ is $C_2H_5$, $R^9$ is H and $R^{10}$ is H.

Table 449. Compounds of formula I.13 wherein $R^1$ is Y-3B, $R^2$ is $C_2H_5$, $R^9$ is $CH_3$ and $R^{10}$ is H.

Table 450. Compounds of formula I.13 wherein $R^1$ is Y-3B, $R^2$ is $C_2H_5$, $R^9$ is $CH_3$ and $R^{10}$ is $CH_3$.

Table 451. Compounds of formula I.13 wherein $R^1$ is Y-3C, $R^2$ is $C_2H_5$, $R^9$ is H and $R^{10}$ is H.

Table 452. Compounds of formula I.13 wherein $R^1$ is Y-3C, $R^2$ is $C_2H_5$, $R^9$ is $CH_3$ and $R^{10}$ is H.

Table 453. Compounds of formula I.13 wherein $R^1$ is Y-3C, $R^2$ is $C_2H_5$, $R^9$ is $CH_3$ and $R^{10}$ is $CH_3$.

Table 454. Compounds of formula I.13 wherein $R^1$ is Y-3D, $R^2$ is $C_2H_5$, $R^9$ is H and $R^{10}$ is H.

Table 455. Compounds of formula I.13 wherein $R^1$ is Y-3D, $R^2$ is $C_2H_5$, $R^9$ is $CH_3$ and $R^{10}$ is H.

Table 456. Compounds of formula I.13 wherein $R^1$ is Y-3D, $R^2$ is $C_2H_5$, $R^9$ is $CH_3$ and $R^{10}$ is $CH_3$.

Table 457. Compounds of formula I.13 wherein $R^1$ is Y-4A, $R^2$ is $C_2H_5$, $R^9$ is H and $R^{10}$ is H.

Table 458. Compounds of formula I.13 wherein $R^1$ is Y-4A, $R^2$ is $C_2H_5$, $R^9$ is $CH_3$ and $R^{10}$ is H.

Table 459. Compounds of formula I.13 wherein $R^1$ is Y-4A, $R^2$ is $C_2H_5$, $R^9$ is $CH_3$ and $R^{10}$ is $CH_3$.

Table 460. Compounds of formula I.13 wherein $R^1$ is Y-4B, $R^2$ is $C_2H_5$, $R^9$ is H and $R^{10}$ is H.

Table 461. Compounds of formula I.13 wherein $R^1$ is Y-4B, $R^2$ is $C_2H_5$, $R^9$ is $CH_3$ and $R^{10}$ is H.

Table 462. Compounds of formula I.13 wherein $R^1$ is Y-4B, $R^2$ is $C_2H_5$, $R^9$ is $CH_3$ and $R^{10}$ is $CH_3$.

Table 463. Compounds of formula I.13 wherein $R^1$ is Y-4C, $R^2$ is $C_2H_5$, $R^9$ is H and $R^{10}$ is H.

Table 464. Compounds of formula I.13 wherein $R^1$ is Y-4C, $R^2$ is $C_2H_5$, $R^9$ is $CH_3$ and $R^{10}$ is H.

Table 465. Compounds of formula I.13 wherein $R^1$ is Y-4C, $R^2$ is $C_2H_5$, $R^9$ is $CH_3$ and $R^{10}$ is $CH_3$.

Table 466. Compounds of formula I.13 wherein $R^1$ is Y-4D, $R^2$ is $C_2H_5$, $R^9$ is H and $R^{10}$ is H.

Table 467. Compounds of formula I.13 wherein $R^1$ is Y-4D, $R^2$ is $C_2H_5$, $R^9$ is $CH_3$ and $R^{10}$ is H.

Table 468. Compounds of formula I.13 wherein $R^1$ is Y-4D, $R^2$ is $C_2H_5$, $R^9$ is $CH_3$ and $R^{10}$ is $CH_3$.

Table 469. Compounds of formula I.13 wherein $R^1$ is Y-5A, $R^2$ is $C_2H_5$, $R^9$ is H and $R^{10}$ is H.

Table 470. Compounds of formula I.13 wherein $R^1$ is Y-5A, $R^2$ is $C_2H_5$, $R^9$ is $CH_3$ and $R^{10}$ is H.

Table 471. Compounds of formula I.13 wherein $R^1$ is Y-5A, $R^2$ is $C_2H_5$, $R^9$ is $CH_3$ and $R^{10}$ is $CH_3$.

Table 472. Compounds of formula I.13 wherein $R^1$ is Y-5B, $R^2$ is $C_2H_5$, $R^9$ is H and $R^{10}$ is H.

Table 473. Compounds of formula I.13 wherein $R^1$ is Y-5B, $R^2$ is $C_2H_5$, $R^9$ is $CH_3$ and $R^{10}$ is H.

Table 474. Compounds of formula I.13 wherein $R^1$ is Y-5B, $R^2$ is $C_2H_5$, $R^9$ is $CH_3$ and $R^{10}$ is $CH_3$.

Table 475. Compounds of formula I.13 wherein $R^1$ is Y-6A, $R^2$ is $C_2H_5$, $R^9$ is H and $R^{10}$ is H.

Table 476. Compounds of formula I.13 wherein $R^1$ is Y-6A, $R^2$ is $C_2H_5$, $R^9$ is $CH_3$ and $R^{10}$ is H.

Table 477. Compounds of formula I.13 wherein $R^1$ is Y-6A, $R^2$ is $C_2H_5$, $R^9$ is $CH_3$ and $R^{10}$ is $CH_3$.

Table 478. Compounds of formula I.13 wherein $R^1$ is Y-6B, $R^2$ is $C_2H_5$, $R^9$ is H and $R^{10}$ is H.

Table 479. Compounds of formula I.13 wherein $R^1$ is Y-6B, $R^2$ is $C_2H_5$, $R^9$ is $CH_3$ and $R^{10}$ is H.

Table 480. Compounds of formula I.13 wherein $R^1$ is Y-6B, $R^2$ is $C_2H_5$, $R^9$ is $CH_3$ and $R^{10}$ is $CH_3$.

Table 481. Compounds of formula I.13 wherein $R^1$ is Y-8A, $R^2$ is $C_2H_5$, $R^9$ is H and $R^{10}$ is H.

Table 482. Compounds of formula I.13 wherein $R^1$ is Y-8A, $R^2$ is $C_2H_5$, $R^9$ is $CH_3$ and $R^{10}$ is H.

Table 483. Compounds of formula I.13 wherein $R^1$ is Y-8A, $R^2$ is $C_2H_5$, $R^9$ is $CH_3$ and $R^{10}$ is $CH_3$.

Table 484. Compounds of formula I.13 wherein $R^1$ is Y-8B, $R^2$ is $C_2H_5$, $R^9$ is H and $R^{10}$ is H.

Table 485. Compounds of formula I.13 wherein $R^1$ is Y-8B, $R^2$ is $C_2H_5$, $R^9$ is $CH_3$ and $R^{10}$ is H.

Table 486. Compounds of formula I.13 wherein $R^1$ is Y-8B, $R^2$ is $C_2H_5$, $R^9$ is $CH_3$ and $R^{10}$ is $CH_3$.

Table 487. Compounds of formula I.13 wherein $R^1$ is Y-1A, $R^2$ is c-$C_3H_5$, $R^9$ is H and $R^{10}$ is H.

Table 488. Compounds of formula I.13 wherein $R^1$ is Y-1A, $R^2$ is c-$C_3H_5$, $R^9$ is $CH_3$ and $R^{10}$ is H.

Table 489. Compounds of formula I.13 wherein $R^1$ is Y-1A, $R^2$ is c-$C_3H_5$, $R^9$ is $CH_3$ and $R^{10}$ is $CH_3$.

Table 490. Compounds of formula I.13 wherein $R^1$ is Y-1B, $R^2$ is c-$C_3H_5$, $R^9$ is H and $R^{10}$ is H.

Table 491. Compounds of formula I.13 wherein $R^1$ is Y-1B, $R^2$ is c-$C_3H_5$, $R^9$ is $CH_3$, $R^{10}$ is H.

Table 492. Compounds of formula I.13 wherein $R^1$ is Y-1B, $R^2$ is c-$C_3H_5$, $R^9$ is $CH_3$ and $R^{10}$ is $CH_3$.

Table 493. Compounds of formula I.13 wherein $R^1$ is Y-2A, $R^2$ is c-$C_3H_5$, $R^9$ is H and $R^{10}$ is H.

Table 494. Compounds of formula I.13 wherein $R^1$ is Y-2A, $R^2$ is c-$C_3H_5$, $R^9$ is $CH_3$ and $R^{10}$ is H.

Table 495. Compounds of formula I.13 wherein $R^1$ is Y-2A, $R^2$ is c-$C_3H_5$, $R^9$ is $CH_3$ and $R^{10}$ is $CH_3$.

Table 496. Compounds of formula I.13 wherein $R^1$ is Y-2B, $R^2$ is c-$C_3H_5$, $R^9$ is H and $R^{10}$ is H.

Table 497. Compounds of formula I.13 wherein $R^1$ is Y-2B, $R^2$ is c-$C_3H_5$, $R^9$ is $CH_3$ and $R^{10}$ is H.

Table 498. Compounds of formula I.13 wherein $R^1$ is Y-2B, $R^2$ is c-$C_3H_5$, $R^9$ is $CH_3$ and $R^{10}$ is $CH_3$.

Table 499. Compounds of formula I.13 wherein $R^1$ is Y-3A, $R^2$ is c-$C_3H_5$, $R^9$ is H and $R^{10}$ is H.

Table 500. Compounds of formula I.13 wherein $R^1$ is Y-3A, $R^2$ is c-$C_3H_5$, $R^9$ is $CH_3$ and $R^{10}$ is H.

Table 501. Compounds of formula I.13 wherein $R^1$ is Y-3A, $R^2$ is c-$C_3H_5$, $R^9$ is $CH_3$ and $R^{10}$ is $CH_3$.

Table 502. Compounds of formula I.13 wherein $R^1$ is Y-3B, $R^2$ is c-$C_3H_5$, $R^9$ is H and $R^{10}$ is H.

Table 503. Compounds of formula I.13 wherein $R^1$ is Y-3B, $R^2$ is c-$C_3H_5$, $R^9$ is $CH_3$ and $R^{10}$ is H.

Table 504. Compounds of formula I.13 wherein $R^1$ is Y-3B, $R^2$ is c-$C_3H_5$, $R^9$ is $CH_3$ and $R^{10}$ is $CH_3$.

Table 505. Compounds of formula I.13 wherein $R^1$ is Y-3C, $R^2$ is c-$C_3H_5$, $R^9$ is H and $R^{10}$ is H.

Table 506. Compounds of formula I.13 wherein $R^1$ is Y-3C, $R^2$ is c-$C_3H_5$, $R^9$ is $CH_3$ and $R^{10}$ is H.

Table 507. Compounds of formula I.13 wherein $R^1$ is Y-3C, $R^2$ is c-$C_3H_5$, $R^9$ is $CH_3$ and $R^{10}$ is $CH_3$.

Table 508. Compounds of formula I.13 wherein $R^1$ is Y-3D, $R^2$ is c-$C_3H_5$, $R^9$ is H and $R^{10}$ is H.

Table 509. Compounds of formula I.13 wherein $R^1$ is Y-3D, $R^2$ is c-$C_3H_5$, $R^9$ is $CH_3$ and $R^{10}$ is H.

Table 510. Compounds of formula I.13 wherein $R^1$ is Y-3D, $R^2$ is c-$C_3H_5$, $R^9$ is $CH_3$ and $R^{10}$ is $CH_3$.

Table 511. Compounds of formula I.13 wherein $R^1$ is Y-4A, $R^2$ is c-$C_3H_5$, $R^9$ is H and $R^{10}$ is H.

Table 512. Compounds of formula I.13 wherein $R^1$ is Y-4A, $R^2$ is c-$C_3H_5$, $R^9$ is $CH_3$ and $R^{10}$ is H.

Table 513. Compounds of formula I.13 wherein $R^1$ is Y-4A, $R^2$ is c-$C_3H_5$, $R^9$ is $CH_3$ and $R^{10}$ is $CH_3$.

Table 514. Compounds of formula I.13 wherein $R^1$ is Y-4B, $R^2$ is c-$C_3H_5$, $R^9$ is H and $R^{10}$ is H.

Table 515. Compounds of formula I.13 wherein $R^1$ is Y-4B, $R^2$ is c-$C_3H_5$, $R^9$ is $CH_3$ and $R^{10}$ is H.

Table 516. Compounds of formula I.13 wherein $R^1$ is Y-4B, $R^2$ is c-$C_3H_5$, $R^9$ is $CH_3$ and $R^{10}$ is $CH_3$.

Table 517. Compounds of formula I.13 wherein $R^1$ is Y-4C, $R^2$ is c-$C_3H_5$, $R^9$ is H and $R^{10}$ is H.

Table 518. Compounds of formula I.13 wherein $R^1$ is Y-4C, $R^2$ is c-$C_3H_5$, $R^9$ is $CH_3$ and $R^{10}$ is H.

Table 519. Compounds of formula I.13 wherein $R^1$ is Y-4C, $R^2$ is c-$C_3H_5$, $R^9$ is $CH_3$ and $R^{10}$ is $CH_3$.

Table 520. Compounds of formula I.13 wherein $R^1$ is Y-4D, $R^2$ is c-$C_3H_5$, $R^9$ is H and $R^{10}$ is H.

Table 521. Compounds of formula I.13 wherein $R^1$ is Y-4D, $R^2$ is c-$C_3H_5$, $R^9$ is $CH_3$ and $R^{10}$ is H.

Table 522. Compounds of formula I.13 wherein $R^1$ is Y-4D, $R^2$ is c-$C_3H_5$, $R^9$ is $CH_3$ and $R^{10}$ is $CH_3$.

Table 523. Compounds of formula I.13 wherein $R^1$ is Y-5A, $R^2$ is c-$C_3H_5$, $R^9$ is H and $R^{10}$ is H.

Table 524. Compounds of formula I.13 wherein $R^1$ is Y-5A, $R^2$ is c-$C_3H_5$, $R^9$ is $CH_3$ and $R^{10}$ is H.

Table 525. Compounds of formula I.13 wherein $R^1$ is Y-5A, $R^2$ is c-$C_3H_5$, $R^9$ is $CH_3$ and $R^{10}$ is $CH_3$.

Table 526. Compounds of formula I.13 wherein $R^1$ is Y-5B, $R^2$ is c-$C_3H_5$, $R^9$ is H and $R^{10}$ is H.

Table 527. Compounds of formula I.13 wherein $R^1$ is Y-5B, $R^2$ is c-$C_3H_5$, $R^9$ is $CH_3$ and $R^{10}$ is H.

Table 528. Compounds of formula I.13 wherein $R^1$ is Y-5B, $R^2$ is c-$C_3H_5$, $R^9$ is $CH_3$ and $R^{10}$ is $CH_3$.

Table 529. Compounds of formula I.13 wherein $R^1$ is Y-6A, $R^2$ is c-$C_3H_5$, $R^9$ is H and $R^{10}$ is H.

Table 530. Compounds of formula I.13 wherein $R^1$ is Y-6A, $R^2$ is c-$C_3H_5$, $R^9$ is $CH_3$ and $R^{10}$ is H.

Table 531. Compounds of formula I.13 wherein $R^1$ is Y-6A, $R^2$ is c-$C_3H_5$, $R^9$ is $CH_3$ and $R^{10}$ is $CH_3$.

Table 532. Compounds of formula I.13 wherein $R^1$ is Y-6B, $R^2$ is c-$C_3H_5$, $R^9$ is H and $R^{10}$ is H.

Table 533. Compounds of formula I.13 wherein $R^1$ is Y-6B, $R^2$ is c-$C_3H_5$, $R^9$ is $CH_3$ and $R^{10}$ is H.

Table 534. Compounds of formula I.13 wherein $R^1$ is Y-6B, $R^2$ is c-$C_3H_5$, $R^9$ is $CH_3$ and $R^{10}$ is $CH_3$.

Table 535. Compounds of formula I.13 wherein $R^1$ is Y-8A, $R^2$ is c-$C_3H_5$, $R^9$ is H and $R^{10}$ is H.

Table 536. Compounds of formula I.13 wherein $R^1$ is Y-8A, $R^2$ is c-$C_3H_5$, $R^9$ is $CH_3$ and $R^{10}$ is H.

Table 537. Compounds of formula I.13 wherein $R^1$ is Y-8A, $R^2$ is c-$C_3H_5$, $R^9$ is $CH_3$ and $R^{10}$ is $CH_3$.

Table 538. Compounds of formula I.13 wherein $R^1$ is Y-8B, $R^2$ is c-$C_3H_5$, $R^9$ is H and $R^{10}$ is H.

Table 539. Compounds of formula I.13 wherein $R^1$ is Y-8B, $R^2$ is c-$C_3H_5$, $R^9$ is $CH_3$ and $R^{10}$ is H.

Table 540. Compounds of formula I.13 wherein $R^1$ is Y-8B, $R^2$ is c-$C_3H_5$, $R^9$ is $CH_3$ and $R^{10}$ is $CH_3$.

Table 541. Compounds of formula I.14 wherein $R^1$ is Y-1A, $R^2$ is H, $R^9$ is H and $R^{10}$ is H.

Table 542. Compounds of formula I.14 wherein $R^1$ is Y-1A, $R^2$ is H, $R^9$ is $CH_3$ and, $R^{10}$ is H.

Table 543. Compounds of formula I.14 wherein $R^1$ is Y-1A, $R^2$ is H, $R^9$ is $CH_3$ and $R^{10}$ is $CH_3$.

Table 544. Compounds of formula I.14 wherein $R^1$ is Y-1B, $R^2$ is H, $R^9$ is H and $R^{10}$ is H.

Table 545. Compounds of formula I.14 wherein $R^1$ is Y-1B, $R^2$ is H, $R^9$ is $CH_3$ and $R^{10}$ is H.

Table 546. Compounds of formula I.14 wherein $R^1$ is Y-1B, $R^2$ is H, $R^9$ is $CH_3$ and $R^{10}$ is $CH_3$.

Table 547. Compounds of formula I.14 wherein $R^1$ is Y-2A, $R^2$ is H, $R^9$ is H and $R^{10}$ is H.

Table 548. Compounds of formula I.14 wherein $R^1$ is Y-2A, $R^2$ is H, $R^9$ is $CH_3$ and $R^{10}$ is H.

Table 549. Compounds of formula I.14 wherein $R^1$ is Y-2A, $R^2$ is H, $R^9$ is $CH_3$ and $R^{10}$ is $CH_3$.

Table 550. Compounds of formula I.14 wherein $R^1$ is Y-2B, $R^2$ is H, $R^9$ is H and $R^{10}$ is H.

Table 551. Compounds of formula I.14 wherein $R^1$ is Y-2B, $R^2$ is H, $R^9$ is $CH_3$ and $R^{10}$ is H.

Table 552. Compounds of formula I.14 wherein $R^1$ is Y-2B, $R^2$ is H, $R^9$ is $CH_3$ and $R^{10}$ is $CH_3$.

Table 553. Compounds of formula I.14 wherein $R^1$ is Y-3A, $R^2$ is H, $R^9$ is H and $R^{10}$ is H.

Table 554. Compounds of formula I.14 wherein $R^1$ is Y-3A, $R^2$ is H, $R^9$ is $CH_3$ and $R^{10}$ is H.

Table 555. Compounds of formula I.14 wherein $R^1$ is Y-3A, $R^2$ is H, $R^9$ is $CH_3$ and $R^{10}$ is $CH_3$.

Table 556. Compounds of formula I.14 wherein $R^1$ is Y-3B, $R^2$ is H, $R^9$ is H and $R^{10}$ is H.

Table 557. Compounds of formula I.14 wherein $R^1$ is Y-3B, $R^2$ is H, $R^9$ is $CH_3$ and $R^{10}$ is H.

Table 558. Compounds of formula I.14 wherein $R^1$ is Y-3B, $R^2$ is H, $R^9$ is $CH_3$ and $R^{10}$ is $CH_3$.

Table 559. Compounds of formula I.14 wherein $R^1$ is Y-3C, $R^2$ is H, $R^9$ is H and $R^{10}$ is H.

Table 560. Compounds of formula I.14 wherein $R^1$ is Y-3C, $R^2$ is H, $R^9$ is $CH_3$ and $R^{10}$ is H.

Table 561. Compounds of formula I.14 wherein $R^1$ is Y-3C, $R^2$ is H, $R^9$ is $CH_3$ and $R^{10}$ is $CH_3$.

Table 562. Compounds of formula I.14 wherein $R^1$ is Y-3D, $R^2$ is H, $R^9$ is H and $R^{10}$ is H.

Table 563. Compounds of formula I.14 wherein $R^1$ is Y-3D, $R^2$ is H, $R^9$ is $CH_3$ and $R^{10}$ is H.

Table 564. Compounds of formula I.14 wherein $R^1$ is Y-3D, $R^2$ is H, $R^9$ is $CH_3$ and $R^{10}$ is $CH_3$.

Table 565. Compounds of formula I.14 wherein $R^1$ is Y-4A, $R^2$ is H, $R^9$ is H and $R^{10}$ is H.

Table 566. Compounds of formula I.14 wherein $R^1$ is Y-4A, $R^2$ is H, $R^9$ is $CH_3$ and $R^{10}$ is H.

Table 567. Compounds of formula I.14 wherein $R^1$ is Y-4A, $R^2$ is H, $R^9$ is $CH_3$ and $R^{10}$ is $CH_3$.

Table 568. Compounds of formula I.14 wherein $R^1$ is Y-4B, $R^2$ is H, $R^9$ is H and $R^{10}$ is H.

Table 569. Compounds of formula I.14 wherein $R^1$ is Y-4B, $R^2$ is H, $R^9$ is $CH_3$ and $R^{10}$ is H.

Table 570. Compounds of formula I.14 wherein $R^1$ is Y-4B, $R^2$ is H, $R^9$ is $CH_3$ and $R^{10}$ is $CH_3$.

Table 571. Compounds of formula I.14 wherein $R^1$ is Y-4C, $R^2$ is H, $R^9$ is H and $R^{10}$ is H.

Table 572. Compounds of formula I.14 wherein $R^1$ is Y-4C, $R^2$ is H, $R^9$ is $CH_3$ and $R^{10}$ is H.

Table 573. Compounds of formula I.14 wherein $R^1$ is Y-4C, $R^2$ is H, $R^9$ is $CH_3$ and $R^{10}$ is $CH_3$.

Table 574. Compounds of formula I.14 wherein $R^1$ is Y-4D, $R^2$ is H, $R^9$ is H and $R^{10}$ is H.

Table 575. Compounds of formula I.14 wherein $R^1$ is Y-4D, $R^2$ is H, $R^9$ is $CH_3$ and $R^{10}$ is H.

Table 576. Compounds of formula I.14 wherein $R^1$ is Y-4D, $R^2$ is H, $R^9$ is $CH_3$ and $R^{10}$ is $CH_3$.

Table 577. Compounds of formula I.14 wherein $R^1$ is Y-5A, $R^2$ is H, $R^9$ is H and $R^{10}$ is H.

Table 578. Compounds of formula I.14 wherein $R^1$ is Y-5A, $R^2$ is H, $R^9$ is $CH_3$ and $R^{10}$ is H.

Table 579. Compounds of formula I.14 wherein $R^1$ is Y-5A, $R^2$ is H, $R^9$ is $CH_3$ and $R^{10}$ is $CH_3$.

Table 580. Compounds of formula I.14 wherein $R^1$ is Y-5B, $R^2$ is H, $R^9$ is H and $R^{10}$ is H.

Table 581. Compounds of formula I.14 wherein $R^1$ is Y-5B, $R^2$ is H, $R^9$ is $CH_3$ and $R^{10}$ is H.

Table 582. Compounds of formula I.14 wherein $R^1$ is Y-5B, $R^2$ is H, $R^9$ is $CH_3$ and $R^{10}$ is $CH_3$.

Table 583. Compounds of formula I.14 wherein $R^1$ is Y-6A, $R^2$ is H, $R^9$ is H and $R^{10}$ is H.

Table 584. Compounds of formula I.14 wherein $R^1$ is Y-6A, $R^2$ is H, $R^9$ is $CH_3$ and $R^{10}$ is H.

Table 585. Compounds of formula I.14 wherein $R^1$ is Y-6A, $R^2$ is H, $R^9$ is $CH_3$ and $R^{10}$ is $CH_3$.

Table 586. Compounds of formula I.14 wherein $R^1$ is Y-6B, $R^2$ is H, $R^9$ is H and $R^{10}$ is H.

Table 587. Compounds of formula I.14 wherein $R^1$ is Y-6B, $R^2$ is H, $R^9$ is $CH_3$ and $R^{10}$ is H.

Table 588. Compounds of formula I.14 wherein $R^1$ is Y-6B, $R^2$ is H, $R^9$ is $CH_3$ and $R^{10}$ is $CH_3$.

Table 589. Compounds of formula I.14 wherein $R^1$ is Y-8A, $R^2$ is H, $R^9$ is H and $R^{10}$ is H.

Table 590. Compounds of formula I.14 wherein $R^1$ is Y-8A, $R^2$ is H, $R^9$ is $CH_3$ and $R^{10}$ is H.

Table 591. Compounds of formula I.14 wherein $R^1$ is Y-8A, $R^2$ is H, $R^9$ is $CH_3$ and $R^{10}$ is $CH_3$.

Table 592. Compounds of formula I.14 wherein $R^1$ is Y-8B, $R^2$ is H, $R^9$ is H and $R^{10}$ is H.

Table 593. Compounds of formula I.14 wherein $R^1$ is Y-8B, $R^2$ is H, $R^9$ is $CH_3$ and $R^{10}$ is H.

Table 594. Compounds of formula I.14 wherein $R^1$ is Y-8B, $R^2$ is H, $R^9$ is $CH_3$ and $R^{10}$ is $CH_3$.

Table 595. Compounds of formula I.14 wherein $R^1$ is Y-1A, $R^2$ is $CH_3$, $R^9$ is H and $R^{10}$ is H.

Table 596. Compounds of formula I.14 wherein $R^1$ is Y-1A, $R^2$ is $CH_3$, $R^9$ is $CH_3$ and $R^{10}$ is H.

Table 597. Compounds of formula I.14 wherein $R^1$ is Y-1A, $R^2$ is $CH_3$, $R^9$ is $CH_3$ and $R^{10}$ is $CH_3$.

Table 598. Compounds of formula I.14 wherein $R^1$ is Y-1B, $R^2$ is $CH_3$, $R^9$ is H and $R^{10}$ is H.

Table 599. Compounds of formula I.14 wherein $R^1$ is Y-1B, $R^2$ is $CH_3$, $R^9$ is $CH_3$ and $R^{10}$ is H.

Table 600. Compounds of formula I.14 wherein $R^1$ is Y-1B, $R^2$ is $CH_3$, $R^9$ is $CH_3$ and $R^{10}$ is $CH_3$.

Table 601. Compounds of formula I.14 wherein $R^1$ is Y-2A, $R^2$ is $CH_3$, $R^9$ is H and $R^{10}$ is H.

Table 602. Compounds of formula I.14 wherein $R^1$ is Y-2A, $R^2$ is $CH_3$, $R^9$ is $CH_3$ and $R^{10}$ is H.

Table 603. Compounds of formula I.14 wherein $R^1$ is Y-2A, $R^2$ is $CH_3$, $R^9$ is $CH_3$ and $R^{10}$ is $CH_3$.

Table 604. Compounds of formula I.14 wherein $R^1$ is Y-2B, $R^2$ is $CH_3$, $R^9$ is H and $R^{10}$ is H.

Table 605. Compounds of formula I.14 wherein $R^1$ is Y-2B, $R^2$ is $CH_3$, $R^9$ is $CH_3$ and $R^{10}$ is H.

Table 606. Compounds of formula I.14 wherein $R^1$ is Y-2B, $R^2$ is $CH_3$, $R^9$ is $CH_3$ and $R^{10}$ is $CH_3$.

Table 607. Compounds of formula I.14 wherein $R^1$ is Y-3A, $R^2$ is $CH_3$, $R^9$ is H and $R^{10}$ is H.

Table 608. Compounds of formula I.14 wherein $R^1$ is Y-3A, $R^2$ is $CH_3$, $R^9$ is $CH_3$ and $R^{10}$ is H.

Table 609. Compounds of formula I.14 wherein $R^1$ is Y-3A, $R^2$ is $CH_3$, $R^9$ is $CH_3$ and $R^{10}$ is $CH_3$.

Table 610. Compounds of formula I.14 wherein $R^1$ is Y-3B, $R^2$ is $CH_3$, $R^9$ is H and $R^{10}$ is H.

Table 611. Compounds of formula I.14 wherein $R^1$ is Y-3B, $R^2$ is $CH_3$, $R^9$ is $CH_3$ and $R^{10}$ is H.

Table 612. Compounds of formula I.14 wherein $R^1$ is Y-3B, $R^2$ is $CH_3$, $R^9$ is $CH_3$ and $R^{10}$ is $CH_3$.

Table 613. Compounds of formula I.14 wherein $R^1$ is Y-3C, $R^2$ is $CH_3$, $R^9$ is H and $R^{10}$ is H.

Table 614. Compounds of formula I.14 wherein $R^1$ is Y-3C, $R^2$ is $CH_3$, $R^9$ is $CH_3$ and $R^{10}$ is H.

Table 615. Compounds of formula I.14 wherein $R^1$ is Y-3C, $R^2$ is $CH_3$, $R^9$ is $CH_3$ and $R^{10}$ is $CH_3$.

Table 616. Compounds of formula I.14 wherein $R^1$ is Y-3D, $R^2$ is $CH_3$, $R^9$ is H and $R^{10}$ is H.

Table 617. Compounds of formula I.14 wherein $R^1$ is Y-3D, $R^2$ is $CH_3$, $R^9$ is $CH_3$ and $R^{10}$ is H.

Table 618. Compounds of formula I.14 wherein $R^1$ is Y-3D, $R^2$ is $CH_3$, $R^9$ is $CH_3$ and $R^{10}$ is $CH_3$.

Table 619. Compounds of formula I.14 wherein $R^1$ is Y-4A, $R^2$ is $CH_3$, $R^9$ is H and $R^{10}$ is H.

Table 620. Compounds of formula I.14 wherein $R^1$ is Y-4A, $R^2$ is $CH_3$, $R^9$ is $CH_3$ and $R^{10}$ is H.

Table 621. Compounds of formula I.14 wherein $R^1$ is Y-4A, $R^2$ is $CH_3$, $R^9$ is $CH_3$ and $R^{10}$ is $CH_3$.

Table 622. Compounds of formula I.14 wherein $R^1$ is Y-4B, $R^2$ is $CH_3$, $R^9$ is H and $R^{10}$ is H.

Table 623. Compounds of formula I.14 wherein $R^1$ is Y-4B, $R^2$ is $CH_3$, $R^9$ is $CH_3$ and $R^{10}$ is H.

Table 624. Compounds of formula I.14 wherein $R^1$ is Y-4B, $R^2$ is $CH_3$, $R^9$ is $CH_3$ and $R^{10}$ is $CH_3$.

Table 625. Compounds of formula I.14 wherein $R^1$ is Y-4C, $R^2$ is $CH_3$, $R^9$ is H and $R^{10}$ is H.

Table 626. Compounds of formula I.14 wherein $R^1$ is Y-4C, $R^2$ is $CH_3$, $R^9$ is $CH_3$ and $R^{10}$ is H.

Table 627. Compounds of formula I.14 wherein $R^1$ is Y-4C, $R^2$ is $CH_3$, $R^9$ is $CH_3$ and $R^{10}$ is $CH_3$.

Table 628. Compounds of formula I.14 wherein $R^1$ is Y-4D, $R^2$ is $CH_3$, $R^9$ is H and $R^{10}$ is H.

Table 629. Compounds of formula I.14 wherein $R^1$ is Y-4D, $R^2$ is $CH_3$, $R^9$ is $CH_3$ and $R^{10}$ is H.

Table 630. Compounds of formula I.14 wherein $R^1$ is Y-4D, $R^2$ is $CH_3$, $R^9$ is $CH_3$ and $R^{10}$ is $CH_3$.

Table 631. Compounds of formula I.14 wherein $R^1$ is Y-5A, $R^2$ is $CH_3$, $R^9$ is H and $R^{10}$ is H.

Table 632. Compounds of formula I.14 wherein $R^1$ is Y-5A, $R^2$ is $CH_3$, $R^9$ is $CH_3$ and $R^{10}$ is H.

Table 633. Compounds of formula I.14 wherein $R^1$ is Y-5A, $R^2$ is $CH_3$, $R^9$ is $CH_3$ and $R^{10}$ is $CH_3$.

Table 634. Compounds of formula I.14 wherein $R^1$ is Y-5B, $R^2$ is $CH_3$, $R^9$ is H and $R^{10}$ is H.

Table 635. Compounds of formula I.14 wherein $R^1$ is Y-5B, $R^2$ is $CH_3$, $R^9$ is $CH_3$ and $R^{10}$ is H.

Table 636. Compounds of formula I.14 wherein $R^1$ is Y-5B, $R^2$ is $CH_3$, $R^9$ is $CH_3$ and $R^{10}$ is $CH_3$.

Table 637. Compounds of formula I.14 wherein $R^1$ is Y-6A, $R^2$ is $CH_3$, $R^9$ is H and $R^{10}$ is H.

Table 638. Compounds of formula I.14 wherein $R^1$ is Y-6A, $R^2$ is $CH_3$, $R^9$ is $CH_3$ and $R^{10}$ is H.

Table 639. Compounds of formula I.14 wherein $R^1$ is Y-6A, $R^2$ is $CH_3$, $R^9$ is $CH_3$ and $R^{10}$ is $CH_3$.

Table 640. Compounds of formula I.14 wherein $R^1$ is Y-6B, $R^2$ is $CH_3$, $R^9$ is H and $R^{10}$ is H.

Table 641. Compounds of formula I.14 wherein $R^1$ is Y-6B, $R^2$ is $CH_3$, $R^9$ is $CH_3$ and $R^{10}$ is H.

Table 642. Compounds of formula I.14 wherein $R^1$ is Y-6B, $R^2$ is $CH_3$, $R^9$ is $CH_3$ and $R^{10}$ is $CH_3$.

Table 643. Compounds of formula I.14 wherein $R^1$ is Y-8A, $R^2$ is $CH_3$, $R^9$ is H and $R^{10}$ is H.

Table 644. Compounds of formula I.14 wherein $R^1$ is Y-8A, $R^2$ is $CH_3$, $R^9$ is $CH_3$ and $R^{10}$ is H.

Table 645. Compounds of formula I.14 wherein $R^1$ is Y-8A, $R^2$ is $CH_3$, $R^9$ is $CH_3$ and $R^{10}$ is $CH_3$.

Table 646. Compounds of formula I.14 wherein $R^1$ is Y-8B, $R^2$ is $CH_3$, $R^9$ is H and $R^{10}$ is H.

Table 647. Compounds of formula I.14 wherein $R^1$ is Y-8B, $R^2$ is $CH_3$, $R^9$ is $CH_3$ and $R^{10}$ is H.

Table 648. Compounds of formula I.14 wherein $R^1$ is Y-8B, $R^2$ is $CH_3$, $R^9$ is $CH_3$ and $R^{10}$ is $CH_3$.

Table 649. Compounds of formula I.14 wherein $R^1$ is Y-1A, $R^2$ is $C_2H_5$, $R^9$ is H and $R^{10}$ is H.

Table 650. Compounds of formula I.14 wherein $R^1$ is Y-1A, $R^2$ is $C_2H_5$, $R^9$ is $CH_3$ and $R^{10}$ is H.

Table 651. Compounds of formula I.14 wherein $R^1$ is Y-1A, $R^2$ is $C_2H_5$, $R^9$ is $CH_3$ and $R^{10}$ is $CH_3$.

Table 652. Compounds of formula I.14 wherein $R^1$ is Y-1B, $R^2$ is $C_2H_5$, $R^9$ is H and $R^{10}$ is H.

Table 653. Compounds of formula I.14 wherein $R^1$ is Y-1B, $R^2$ is $C_2H_5$, $R^9$ is $CH_3$ and $R^{10}$ is H.

Table 654. Compounds of formula I.14 wherein $R^1$ is Y-1B, $R^2$ is $C_2H_5$, $R^9$ is $CH_3$ and $R^{10}$ is $CH_3$.

Table 655. Compounds of formula I.14 wherein $R^1$ is Y-2A, $R^2$ is $C_2H_5$, $R^9$ is H and $R^{10}$ is H.

Table 656. Compounds of formula I.14 wherein $R^1$ is Y-2A, $R^2$ is $C_2H_5$, $R^9$ is $CH_3$ and $R^{10}$ is H.

Table 657. Compounds of formula I.14 wherein $R^1$ is Y-2A, $R^2$ is $C_2H_5$, $R^9$ is $CH_3$ and $R^{10}$ is $CH_3$.

Table 658. Compounds of formula I.14 wherein $R^1$ is Y-2B, $R^2$ is $C_2H_5$, $R^9$ is H and $R^{10}$ is H.

Table 659. Compounds of formula I.14 wherein $R^1$ is Y-2B, $R^2$ is $C_2H_5$, $R^9$ is $CH_3$ and $R^{10}$ is H.

Table 660. Compounds of formula I.14 wherein $R^1$ is Y-2B, $R^2$ is $C_2H_5$, $R^9$ is $CH_3$ and $R^{10}$ is $CH_3$.

Table 661. Compounds of formula I.14 wherein $R^1$ is Y-3A, $R^2$ is $C_2H_5$, $R^9$ is H and $R^{10}$ is H.

Table 662. Compounds of formula I.14 wherein $R^1$ is Y-3A, $R^2$ is $C_2H_5$, $R^9$ is $CH_3$ and $R^{10}$ is H.

Table 663. Compounds of formula I.14 wherein $R^1$ is Y-3A, $R^2$ is $C_2H_5$, $R^9$ is $CH_3$ and $R^{10}$ is $CH_3$.

Table 664. Compounds of formula I.14 wherein $R^1$ is Y-3B, $R^2$ is $C_2H_5$, $R^9$ is H and $R^{10}$ is H.

Table 665. Compounds of formula I.14 wherein $R^1$ is Y-3B, $R^2$ is $C_2H_5$, $R^9$ is $CH_3$ and $R^{10}$ is H.

Table 666. Compounds of formula I.14 wherein $R^1$ is Y-3B, $R^2$ is $C_2H_5$, $R^9$ is $CH_3$ and $R^{10}$ is $CH_3$.

Table 667. Compounds of formula I.14 wherein $R^1$ is Y-3C, $R^2$ is $C_2H_5$, $R^9$ is H and $R^{10}$ is H.

Table 668. Compounds of formula I.14 wherein $R^1$ is Y-3C, $R^2$ is $C_2H_5$, $R^9$ is $CH_3$ and $R^{10}$ is H.

Table 669. Compounds of formula I.14 wherein $R^1$ is Y-3C, $R^2$ is $C_2H_5$, $R^9$ is $CH_3$ and $R^{10}$ is $CH_3$.

Table 670. Compounds of formula I.14 wherein $R^1$ is Y-3D, $R^2$ is $C_2H_5$, $R^9$ is H and $R^{10}$ is H.

Table 671. Compounds of formula I.14 wherein $R^1$ is Y-3D, $R^2$ is $C_2H_5$, $R^9$ is $CH_3$ and $R^{10}$ is H.

Table 672. Compounds of formula I.14 wherein $R^1$ is Y-3D, $R^2$ is $C_2H_5$, $R^9$ is $CH_3$ and $R^{10}$ is $CH_3$.

Table 673. Compounds of formula I.14 wherein $R^1$ is Y-4A, $R^2$ is $C_2H_5$, $R^9$ is H and $R^{10}$ is H.

Table 674. Compounds of formula I.14 wherein $R^1$ is Y-4A, $R^2$ is $C_2H_5$, $R^9$ is $CH_3$ and $R^{10}$ is H.

Table 675. Compounds of formula I.14 wherein $R^1$ is Y-4A, $R^2$ is $C_2H_5$, $R^9$ is $CH_3$ and $R^{10}$ is $CH_3$.

Table 676. Compounds of formula I.14 wherein $R^1$ is Y-4B, $R^2$ is $C_2H_5$, $R^9$ is H and $R^{10}$ is H.

Table 677. Compounds of formula I.14 wherein $R^1$ is Y-4B, $R^2$ is $C_2H_5$, $R^9$ is $CH_3$ and $R^{10}$ is H.

Table 678. Compounds of formula I.14 wherein $R^1$ is Y-4B, $R^2$ is $C_2H_5$, $R^9$ is $CH_3$ and $R^{10}$ is $CH_3$.

Table 679. Compounds of formula I.14 wherein $R^1$ is Y-4C, $R^2$ is $C_2H_5$, $R^9$ is H and $R^{10}$ is H.

Table 680. Compounds of formula I.14 wherein $R^1$ is Y-4C, $R^2$ is $C_2H_5$, $R^9$ is $CH_3$ and $R^{10}$ is H.

Table 681. Compounds of formula I.14 wherein $R^1$ is Y-4C, $R^2$ is $C_2H_5$, $R^9$ is $CH_3$ and $R^{10}$ is $CH_3$.

Table 682. Compounds of formula I.14 wherein $R^1$ is Y-4D, $R^2$ is $C_2H_5$, $R^9$ is H and $R^{10}$ is H.

Table 683. Compounds of formula I.14 wherein $R^1$ is Y-4D, $R^2$ is $C_2H_5$, $R^9$ is $CH_3$ and $R^{10}$ is H.

Table 684. Compounds of formula I.14 wherein $R^1$ is Y-4D, $R^2$ is $C_2H_5$, $R^9$ is $CH_3$ and $R^{10}$ is $CH_3$.

Table 685. Compounds of formula I.14 wherein $R^1$ is Y-5A, $R^2$ is $C_2H_5$, $R^9$ is H and $R^{10}$ is H.

Table 686. Compounds of formula I.14 wherein $R^1$ is Y-5A, $R^2$ is $C_2H_5$, $R^9$ is $CH_3$ and $R^{10}$ is H.

Table 687. Compounds of formula I.14 wherein $R^1$ is Y-5A, $R^2$ is $C_2H_5$, $R^9$ is $CH_3$ and $R^{10}$ is $CH_3$.

Table 688. Compounds of formula I.14 wherein $R^1$ is Y-5B, $R^2$ is $C_2H_5$, $R^9$ is H and $R^{10}$ is H.

Table 689. Compounds of formula I.14 wherein $R^1$ is Y-5B, $R^2$ is $C_2H_5$, $R^9$ is $CH_3$ and $R^{10}$ is H.

Table 690. Compounds of formula I.14 wherein $R^1$ is Y-5B, $R^2$ is $C_2H_5$, $R^9$ is $CH_3$ and $R^{10}$ is $CH_3$.

Table 691. Compounds of formula I.14 wherein $R^1$ is Y-6A, $R^2$ is $C_2H_5$, $R^9$ is H and $R^{10}$ is H.

Table 692. Compounds of formula I.14 wherein $R^1$ is Y-6A, $R^2$ is $C_2H_5$, $R^9$ is $CH_3$ and $R^{10}$ is H.

Table 693. Compounds of formula I.14 wherein $R^1$ is Y-6A, $R^2$ is $C_2H_5$, $R^9$ is $CH_3$ and $R^{10}$ is $CH_3$.

Table 694. Compounds of formula I.14 wherein $R^1$ is Y-6B, $R^2$ is $C_2H_5$, $R^9$ is H and $R^{10}$ is H.

Table 695. Compounds of formula I.14 wherein $R^1$ is Y-6B, $R^2$ is $C_2H_5$, $R^9$ is $CH_3$ and $R^{10}$ is H.

Table 696. Compounds of formula I.14 wherein $R^1$ is Y-6B, $R^2$ is $C_2H_5$, $R^9$ is $CH_3$ and $R^{10}$ is $CH_3$.

Table 697. Compounds of formula I.14 wherein $R^1$ is Y-8A, $R^2$ is $C_2H_5$, $R^9$ is H and $R^{10}$ is H.

Table 698. Compounds of formula I.14 wherein $R^1$ is Y-8A, $R^2$ is $C_2H_5$, $R^9$ is $CH_3$ and $R^{10}$ is H.

Table 699. Compounds of formula I.14 wherein $R^1$ is Y-8A, $R^2$ is $C_2H_5$, $R^9$ is $CH_3$ and $R^{10}$ is $CH_3$.

Table 700. Compounds of formula I.14 wherein $R^1$ is Y-8B, $R^2$ is $C_2H_5$, $R^9$ is H and $R^{10}$ is H.

Table 701. Compounds of formula I.14 wherein $R^1$ is Y-8B, $R^2$ is $C_2H_5$, $R^9$ is $CH_3$ and $R^{10}$ is H.

Table 702. Compounds of formula I.14 wherein $R^1$ is Y-8B, $R^2$ is $C_2H_5$, $R^9$ is $CH_3$ and $R^{10}$ is $CH_3$.

Table 703. Compounds of formula I.14 wherein $R^1$ is Y-1A, $R^2$ is c-$C_3H_5$, $R^9$ is H and $R^{10}$ is H.

Table 704. Compounds of formula I.14 wherein $R^1$ is Y-1A, $R^2$ is c-$C_3H_5$, $R^9$ is $CH_3$ and $R^{10}$ is H.

Table 705. Compounds of formula I.14 wherein $R^1$ is Y-1A, $R^2$ is c-$C_3H_5$, $R^9$ is $CH_3$ and $R^{10}$ is $CH_3$.

Table 706. Compounds of formula I.14 wherein $R^1$ is Y-1B, $R^2$ is c-$C_3H_5$, $R^9$ is H and $R^{10}$ is H.

Table 707. Compounds of formula I.14 wherein $R^1$ is Y-1B, $R^2$ is c-$C_3H_5$, $R^9$ is $CH_3$, $R^{10}$ is H.

Table 708. Compounds of formula I.14 wherein $R^1$ is Y-1B, $R^2$ is c-$C_3H_5$, $R^9$ is $CH_3$ and $R^{10}$ is $CH_3$.

Table 709. Compounds of formula I.14 wherein $R^1$ is Y-2A, $R^2$ is c-$C_3H_5$, $R^9$ is H and $R^{10}$ is H.

Table 710. Compounds of formula I.14 wherein $R^1$ is Y-2A, $R^2$ is c-$C_3H_5$, $R^9$ is $CH_3$ and $R^{10}$ is H.

Table 711. Compounds of formula I.14 wherein $R^1$ is Y-2A, $R^2$ is c-$C_3H_5$, $R^9$ is $CH_3$ and $R^{10}$ is $CH_3$.

Table 712. Compounds of formula I.14 wherein $R^1$ is Y-2B, $R^2$ is c-$C_3H_5$, $R^9$ is H and $R^{10}$ is H.

Table 713. Compounds of formula I.14 wherein $R^1$ is Y-2B, $R^2$ is c-$C_3H_5$, $R^9$ is $CH_3$ and $R^{10}$ is H.

Table 714. Compounds of formula I.14 wherein $R^1$ is Y-2B, $R^2$ is c-$C_3H_5$, $R^9$ is $CH_3$ and $R^{10}$ is $CH_3$.

Table 715. Compounds of formula I.14 wherein $R^1$ is Y-3A, $R^2$ is c-$C_3H_5$, $R^9$ is H and $R^{10}$ is H.

Table 716. Compounds of formula I.14 wherein $R^1$ is Y-3A, $R^2$ is c-$C_3H_5$, $R^9$ is $CH_3$ and $R^{10}$ is H.

Table 717. Compounds of formula I.14 wherein $R^1$ is Y-3A, $R^2$ is c-$C_3H_5$, $R^9$ is $CH_3$ and $R^{10}$ is $CH_3$.

Table 718. Compounds of formula I.14 wherein $R^1$ is Y-3B, $R^2$ is c-$C_3H_5$, $R^9$ is H and $R^{10}$ is H.

Table 719. Compounds of formula I.14 wherein $R^1$ is Y-3B, $R^2$ is c-$C_3H_5$, $R^9$ is $CH_3$ and $R^{10}$ is H.

Table 720. Compounds of formula I.14 wherein $R^1$ is Y-3B, $R^2$ is c-$C_3H_5$, $R^9$ is $CH_3$ and $R^{10}$ is $CH_3$.

Table 721. Compounds of formula I.14 wherein $R^1$ is Y-3C, $R^2$ is c-$C_3H_5$, $R^9$ is H and $R^{10}$ is H.

Table 722. Compounds of formula I.14 wherein $R^1$ is Y-3C, $R^2$ is c-$C_3H_5$, $R^9$ is $CH_3$ and $R^{10}$ is H.

Table 723. Compounds of formula I.14 wherein $R^1$ is Y-3C, $R^2$ is c-$C_3H_5$, $R^9$ is $CH_3$ and $R^{10}$ is $CH_3$.

Table 724. Compounds of formula I.14 wherein $R^1$ is Y-3D, $R^2$ is c-$C_3H_5$, $R^9$ is H and $R^{10}$ is H.

Table 725. Compounds of formula I.14 wherein $R^1$ is Y-3D, $R^2$ is c-$C_3H_5$, $R^9$ is $CH_3$ and $R^{10}$ is H.

Table 726. Compounds of formula I.14 wherein $R^1$ is Y-3D, $R^2$ is c-$C_3H_5$, $R^9$ is $CH_3$ and $R^{10}$ is $CH_3$.

Table 727. Compounds of formula I.14 wherein $R^1$ is Y-4A, $R^2$ is c-$C_3H_5$, $R^9$ is H and $R^{10}$ is H.

Table 728. Compounds of formula I.14 wherein $R^1$ is Y-4A, $R^2$ is c-$C_3H_5$, $R^9$ is $CH_3$ and $R^{10}$ is H.

Table 729. Compounds of formula I.14 wherein $R^1$ is Y-4A, $R^2$ is c-$C_3H_5$, $R^9$ is $CH_3$ and $R^{10}$ is $CH_3$.

Table 730. Compounds of formula I.14 wherein $R^1$ is Y-4B, $R^2$ is c-$C_3H_5$, $R^9$ is H and $R^{10}$ is H.

Table 731. Compounds of formula I.14 wherein $R^1$ is Y-4B, $R^2$ is c-$C_3H_5$, $R^9$ is $CH_3$ and $R^{10}$ is H.

Table 732. Compounds of formula I.14 wherein $R^1$ is Y-4B, $R^2$ is c-$C_3H_5$, $R^9$ is $CH_3$ and $R^{10}$ is $CH_3$.

Table 733. Compounds of formula I.14 wherein $R^1$ is Y-4C, $R^2$ is c-$C_3H_5$, $R^9$ is H and $R^{10}$ is H.

Table 734. Compounds of formula I.14 wherein $R^1$ is Y-4C, $R^2$ is c-$C_3H_5$, $R^9$ is $CH_3$ and $R^{10}$ is H.

Table 735. Compounds of formula I.14 wherein $R^1$ is Y-4C, $R^2$ is c-$C_3H_5$, $R^9$ is $CH_3$ and $R^{10}$ is $CH_3$.

Table 736. Compounds of formula I.14 wherein $R^1$ is Y-4D, $R^2$ is c-$C_3H_5$, $R^9$ is H and $R^{10}$ is H.

Table 737. Compounds of formula I.14 wherein $R^1$ is Y-4D, $R^2$ is c-$C_3H_5$, $R^9$ is $CH_3$ and $R^{10}$ is H.

Table 738. Compounds of formula I.14 wherein $R^1$ is Y-4D, $R^2$ is c-$C_3H_5$, $R^9$ is $CH_3$ and $R^{10}$ is $CH_3$.

Table 739. Compounds of formula I.14 wherein $R^1$ is Y-5A, $R^2$ is c-$C_3H_5$, $R^9$ is H and $R^{10}$ is H.

Table 740. Compounds of formula I.14 wherein $R^1$ is Y-5A, $R^2$ is c-$C_3H_5$, $R^9$ is $CH_3$ and $R^{10}$ is H.

Table 741. Compounds of formula I.14 wherein $R^1$ is Y-5A, $R^2$ is c-$C_3H_5$, $R^9$ is $CH_3$ and $R^{10}$ is $CH_3$.

Table 742. Compounds of formula I.14 wherein $R^1$ is Y-5B, $R^2$ is c-$C_3H_5$, $R^9$ is H and $R^{10}$ is H.

Table 743. Compounds of formula I.14 wherein $R^1$ is Y-5B, $R^2$ is c-$C_3H_5$, $R^9$ is $CH_3$ and $R^{10}$ is H.

Table 744. Compounds of formula I.14 wherein $R^1$ is Y-5B, $R^2$ is c-$C_3H_5$, $R^9$ is $CH_3$ and $R^{10}$ is $CH_3$.

Table 745. Compounds of formula I.14 wherein $R^1$ is Y-6A, $R^2$ is c-$C_3H_5$, $R^9$ is H and $R^{10}$ is H.

Table 746. Compounds of formula I.14 wherein $R^1$ is Y-6A, $R^2$ is c-$C_3H_5$, $R^9$ is $CH_3$ and $R^{10}$ is H.

Table 747. Compounds of formula I.14 wherein $R^1$ is Y-6A, $R^2$ is c-$C_3H_5$, $R^9$ is $CH_3$ and $R^{10}$ is $CH_3$.

Table 748. Compounds of formula I.14 wherein $R^1$ is Y-6B, $R^2$ is c-$C_3H_5$, $R^9$ is H and $R^{10}$ is H.

Table 749. Compounds of formula I.14 wherein $R^1$ is Y-6B, $R^2$ is c-$C_3H_5$, $R^9$ is $CH_3$ and $R^{10}$ is H.

Table 750. Compounds of formula I.14 wherein $R^1$ is Y-6B, $R^2$ is c-$C_3H_5$, $R^9$ is $CH_3$ and $R^{10}$ is $CH_3$.

Table 751. Compounds of formula I.14 wherein $R^1$ is Y-8A, $R^2$ is c-$C_3H_5$, $R^9$ is H and $R^{10}$ is H.

Table 752. Compounds of formula I.14 wherein $R^1$ is Y-8A, $R^2$ is c-$C_3H_5$, $R^9$ is $CH_3$ and $R^{10}$ is H.

Table 753. Compounds of formula I.14 wherein $R^1$ is Y-8A, $R^2$ is c-$C_3H_5$, $R^9$ is $CH_3$ and $R^{10}$ is $CH_3$.

Table 754. Compounds of formula I.14 wherein $R^1$ is Y-8B, $R^2$ is c-$C_3H_5$, $R^9$ is H and $R^{10}$ is H.

Table 755. Compounds of formula I.14 wherein $R^1$ is Y-8B, $R^2$ is c-$C_3H_5$, $R^9$ is $CH_3$ and $R^{10}$ is H.

Table 756. Compounds of formula I.14 wherein $R^1$ is Y-8B, $R^2$ is c-$C_3H_5$, $R^9$ is $CH_3$ and $R^{10}$ is $CH_3$.

Table 757. Compounds of formula I.15 wherein $R^1$ is Y-1A, $R^2$ is H, $R^9$ is H and $R^{10}$ is H.

Table 758. Compounds of formula I.15 wherein $R^1$ is Y-1A, $R^2$ is H, $R^9$ is $CH_3$ and, $R^{10}$ is H.

Table 759. Compounds of formula I.15 wherein $R^1$ is Y-1A, $R^2$ is H, $R^9$ is $CH_3$ and $R^{10}$ is $CH_3$.

Table 760. Compounds of formula I.15 wherein $R^1$ is Y-1B, $R^2$ is H, $R^9$ is H and $R^{10}$ is H.

Table 761. Compounds of formula I.15 wherein $R^1$ is Y-1B, $R^2$ is H, $R^9$ is $CH_3$ and $R^{10}$ is H.

Table 762. Compounds of formula I.15 wherein $R^1$ is Y-1B, $R^2$ is H, $R^9$ is $CH_3$ and $R^{10}$ is $CH_3$.

Table 763. Compounds of formula I.15 wherein $R^1$ is Y-2A, $R^2$ is H, $R^9$ is H and $R^{10}$ is H.

Table 764. Compounds of formula I.15 wherein $R^1$ is Y-2A, $R^2$ is H, $R^9$ is $CH_3$ and $R^{10}$ is H.

Table 765. Compounds of formula I.15 wherein $R^1$ is Y-2A, $R^2$ is H, $R^9$ is $CH_3$ and $R^{10}$ is $CH_3$.

Table 766. Compounds of formula I.15 wherein $R^1$ is Y-2B, $R^2$ is H, $R^9$ is H and $R^{10}$ is H.

Table 767. Compounds of formula I.15 wherein $R^1$ is Y-2B, $R^2$ is H, $R^9$ is $CH_3$ and $R^{10}$ is H.

Table 768. Compounds of formula I.15 wherein $R^1$ is Y-2B, $R^2$ is H, $R^9$ is $CH_3$ and $R^{10}$ is $CH_3$.

Table 769. Compounds of formula I.15 wherein $R^1$ is Y-3A, $R^2$ is H, $R^9$ is H and $R^{10}$ is H.

Table 770. Compounds of formula I.15 wherein $R^1$ is Y-3A, $R^2$ is H, $R^9$ is $CH_3$ and $R^{10}$ is H.

Table 771. Compounds of formula I.15 wherein $R^1$ is Y-3A, $R^2$ is H, $R^9$ is $CH_3$ and $R^{10}$ is $CH_3$.

Table 772. Compounds of formula I.15 wherein $R^1$ is Y-3B, $R^2$ is H, $R^9$ is H and $R^{10}$ is H.

Table 773. Compounds of formula I.15 wherein $R^1$ is Y-3B, $R^2$ is H, $R^9$ is $CH_3$ and $R^{10}$ is H.

Table 774. Compounds of formula I.15 wherein $R^1$ is Y-3B, $R^2$ is H, $R^9$ is $CH_3$ and $R^{10}$ is $CH_3$.

Table 775. Compounds of formula I.15 wherein $R^1$ is Y-3C, $R^2$ is H, $R^9$ is H and $R^{10}$ is H.

Table 776. Compounds of formula I.15 wherein $R^1$ is Y-3C, $R^2$ is H, $R^9$ is $CH_3$ and $R^{10}$ is H.

Table 777. Compounds of formula I.15 wherein $R^1$ is Y-3C, $R^2$ is H, $R^9$ is $CH_3$ and $R^{10}$ is $CH_3$.

Table 778. Compounds of formula I.15 wherein $R^1$ is Y-3D, $R^2$ is H, $R^9$ is H and $R^{10}$ is H.

Table 779. Compounds of formula I.15 wherein $R^1$ is Y-3D, $R^2$ is H, $R^9$ is $CH_3$ and $R^{10}$ is H.

Table 780. Compounds of formula I.15 wherein $R^1$ is Y-3D, $R^2$ is H, $R^9$ is $CH_3$ and $R^{10}$ is $CH_3$.

Table 781. Compounds of formula I.15 wherein $R^1$ is Y-4A, $R^2$ is H, $R^9$ is H and $R^{10}$ is H.

Table 782. Compounds of formula I.15 wherein $R^1$ is Y-4A, $R^2$ is H, $R^9$ is $CH_3$ and $R^{10}$ is H.

Table 783. Compounds of formula I.15 wherein $R^1$ is Y-4A, $R^2$ is H, $R^9$ is $CH_3$ and $R^{10}$ is $CH_3$.

Table 784. Compounds of formula I.15 wherein $R^1$ is Y-4B, $R^2$ is H, $R^9$ is H and $R^{10}$ is H.

Table 785. Compounds of formula I.15 wherein $R^1$ is Y-4B, $R^2$ is H, $R^9$ is $CH_3$ and $R^{10}$ is H.

Table 786. Compounds of formula I.15 wherein $R^1$ is Y-4B, $R^2$ is H, $R^9$ is $CH_3$ and $R^{10}$ is $CH_3$.

Table 787. Compounds of formula I.15 wherein $R^1$ is Y-4C, $R^2$ is H, $R^9$ is H and $R^{10}$ is H.

Table 788. Compounds of formula I.15 wherein $R^1$ is Y-4C, $R^2$ is H, $R^9$ is $CH_3$ and $R^{10}$ is H.

Table 789. Compounds of formula I.15 wherein $R^1$ is Y-4C, $R^2$ is H, $R^9$ is $CH_3$ and $R^{10}$ is $CH_3$.

Table 790. Compounds of formula I.15 wherein $R^1$ is Y-4D, $R^2$ is H, $R^9$ is H and $R^{10}$ is H.

Table 791. Compounds of formula I.15 wherein $R^1$ is Y-4D, $R^2$ is H, $R^9$ is $CH_3$ and $R^{10}$ is H.

Table 792. Compounds of formula I.15 wherein $R^1$ is Y-4D, $R^2$ is H, $R^9$ is $CH_3$ and $R^{10}$ is $CH_3$.

Table 793. Compounds of formula I.15 wherein $R^1$ is Y-5A, $R^2$ is H, $R^9$ is H and $R^{10}$ is H.

Table 794. Compounds of formula I.15 wherein $R^1$ is Y-5A, $R^2$ is H, $R^9$ is $CH_3$ and $R^{10}$ is H.

Table 795. Compounds of formula I.15 wherein $R^1$ is Y-5A, $R^2$ is H, $R^9$ is $CH_3$ and $R^{10}$ is $CH_3$.

Table 796. Compounds of formula I.15 wherein $R^1$ is Y-5B, $R^2$ is H, $R^9$ is H and $R^{10}$ is H.

Table 797. Compounds of formula I.15 wherein $R^1$ is Y-5B, $R^2$ is H, $R^9$ is $CH_3$ and $R^{10}$ is H.

Table 798. Compounds of formula I.15 wherein $R^1$ is Y-5B, $R^2$ is H, $R^9$ is $CH_3$ and $R^{10}$ is $CH_3$.

Table 799. Compounds of formula I.15 wherein $R^1$ is Y-6A, $R^2$ is H, $R^9$ is H and $R^{10}$ is H.

Table 800. Compounds of formula I.15 wherein $R^1$ is Y-6A, $R^2$ is H, $R^9$ is $CH_3$ and $R^{10}$ is H.

Table 801. Compounds of formula I.15 wherein $R^1$ is Y-6A, $R^2$ is H, $R^9$ is $CH_3$ and $R^{10}$ is $CH_3$.

Table 802. Compounds of formula I.15 wherein $R^1$ is Y-6B, $R^2$ is H, $R^9$ is H and $R^{10}$ is H.

Table 803. Compounds of formula I.15 wherein $R^1$ is Y-6B, $R^2$ is H, $R^9$ is $CH_3$ and $R^{10}$ is H.

Table 804. Compounds of formula I.15 wherein $R^1$ is Y-6B, $R^2$ is H, $R^9$ is $CH_3$ and $R^{10}$ is $CH_3$.

Table 805. Compounds of formula I.15 wherein $R^1$ is Y-8A, $R^2$ is H, $R^9$ is H and $R^{10}$ is H.

Table 806. Compounds of formula I.15 wherein $R^1$ is Y-8A, $R^2$ is H, $R^9$ is $CH_3$ and $R^{10}$ is H.

Table 807. Compounds of formula I.15 wherein $R^1$ is Y-8A, $R^2$ is H, $R^9$ is $CH_3$ and $R^{10}$ is $CH_3$.

Table 808. Compounds of formula I.15 wherein $R^1$ is Y-8B, $R^2$ is H, $R^9$ is H and $R^{10}$ is H.

Table 809. Compounds of formula I.15 wherein $R^1$ is Y-8B, $R^2$ is H, $R^9$ is $CH_3$ and $R^{10}$ is H.

Table 810. Compounds of formula I.15 wherein $R^1$ is Y-8B, $R^2$ is H, $R^9$ is $CH_3$ and $R^{10}$ is $CH_3$.

Table 811. Compounds of formula I.15 wherein $R^1$ is Y-1A, $R^2$ is $CH_3$, $R^9$ is H and $R^{10}$ is H.

Table 812. Compounds of formula I.15 wherein $R^1$ is Y-1A, $R^2$ is $CH_3$, $R^9$ is $CH_3$ and $R^{10}$ is H.

Table 813. Compounds of formula I.15 wherein $R^1$ is Y-1A, $R^2$ is $CH_3$, $R^9$ is $CH_3$ and $R^{10}$ is $CH_3$.

Table 814. Compounds of formula I.15 wherein $R^1$ is Y-1B, $R^2$ is $CH_3$, $R^9$ is H and $R^{10}$ is H.

Table 815. Compounds of formula I.15 wherein $R^1$ is Y-1B, $R^2$ is $CH_3$, $R^9$ is $CH_3$ and $R^{10}$ is H.

Table 816. Compounds of formula I.15 wherein $R^1$ is Y-1B, $R^2$ is $CH_3$, $R^9$ is $CH_3$ and $R^{10}$ is $CH_3$.

Table 817. Compounds of formula I.15 wherein $R^1$ is Y-2A, $R^2$ is $CH_3$, $R^9$ is H and $R^{10}$ is H.

Table 818. Compounds of formula I.15 wherein $R^1$ is Y-2A, $R^2$ is $CH_3$, $R^9$ is $CH_3$ and $R^{10}$ is H.

Table 819. Compounds of formula I.15 wherein $R^1$ is Y-2A, $R^2$ is $CH_3$, $R^9$ is $CH_3$ and $R^{10}$ is $CH_3$.

Table 820. Compounds of formula I.15 wherein $R^1$ is Y-2B, $R^2$ is $CH_3$, $R^9$ is H and $R^{10}$ is H.

Table 821. Compounds of formula I.15 wherein $R^1$ is Y-2B, $R^2$ is $CH_3$, $R^9$ is $CH_3$ and $R^{10}$ is H.
Table 822. Compounds of formula I.15 wherein $R^1$ is Y-2B, $R^2$ is $CH_3$, $R^9$ is $CH_3$ and $R^{10}$ is $CH_3$.
Table 823. Compounds of formula I.15 wherein $R^1$ is Y-3A, $R^2$ is $CH_3$, $R^9$ is H and $R^{10}$ is H.
Table 824. Compounds of formula I.15 wherein $R^1$ is Y-3A, $R^2$ is $CH_3$, $R^9$ is $CH_3$ and $R^{10}$ is H.
Table 825. Compounds of formula I.15 wherein $R^1$ is Y-3A, $R^2$ is $CH_3$, $R^9$ is $CH_3$ and $R^{10}$ is $CH_3$.
Table 826. Compounds of formula I.15 wherein $R^1$ is Y-3B, $R^2$ is $CH_3$, $R^9$ is H and $R^{10}$ is H.
Table 827. Compounds of formula I.15 wherein $R^1$ is Y-3B, $R^2$ is $CH_3$, $R^9$ is $CH_3$ and $R^{10}$ is H.
Table 828. Compounds of formula I.15 wherein $R^1$ is Y-3B, $R^2$ is $CH_3$, $R^9$ is $CH_3$ and $R^{10}$ is $CH_3$.
Table 829. Compounds of formula I.15 wherein $R^1$ is Y-3C, $R^2$ is $CH_3$, $R^9$ is H and $R^{10}$ is H.
Table 830. Compounds of formula I.15 wherein $R^1$ is Y-3C, $R^2$ is $CH_3$, $R^9$ is $CH_3$ and $R^{10}$ is H.
Table 831. Compounds of formula I.15 wherein $R^1$ is Y-3C, $R^2$ is $CH_3$, $R^9$ is $CH_3$ and $R^{10}$ is $CH_3$.
Table 832. Compounds of formula I.15 wherein $R^1$ is Y-3D, $R^2$ is $CH_3$, $R^9$ is H and $R^{10}$ is H.
Table 833. Compounds of formula I.15 wherein $R^1$ is Y-3D, $R^2$ is $CH_3$, $R^9$ is $CH_3$ and $R^{10}$ is H.
Table 834. Compounds of formula I.15 wherein $R^1$ is Y-3D, $R^2$ is $CH_3$, $R^9$ is $CH_3$ and $R^{10}$ is $CH_3$.
Table 835. Compounds of formula I.15 wherein $R^1$ is Y-4A, $R^2$ is $CH_3$, $R^9$ is H and $R^{10}$ is H.
Table 836. Compounds of formula I.15 wherein $R^1$ is Y-4A, $R^2$ is $CH_3$, $R^9$ is $CH_3$ and $R^{10}$ is H.
Table 837. Compounds of formula I.15 wherein $R^1$ is Y-4A, $R^2$ is $CH_3$, $R^9$ is $CH_3$ and $R^{10}$ is $CH_3$.
Table 838. Compounds of formula I.15 wherein $R^1$ is Y-4B, $R^2$ is $CH_3$, $R^9$ is H and $R^{10}$ is H.
Table 839. Compounds of formula I.15 wherein $R^1$ is Y-4B, $R^2$ is $CH_3$, $R^9$ is $CH_3$ and $R^{10}$ is H.
Table 840. Compounds of formula I.15 wherein $R^1$ is Y-4B, $R^2$ is $CH_3$, $R^9$ is $CH_3$ and $R^{10}$ is $CH_3$.
Table 841. Compounds of formula I.15 wherein $R^1$ is Y-4C, $R^2$ is $CH_3$, $R^9$ is H and $R^{10}$ is H.
Table 842. Compounds of formula I.15 wherein $R^1$ is Y-4C, $R^2$ is $CH_3$, $R^9$ is $CH_3$ and $R^{10}$ is H.
Table 843. Compounds of formula I.15 wherein $R^1$ is Y-4C, $R^2$ is $CH_3$, $R^9$ is $CH_3$ and $R^{10}$ is $CH_3$.
Table 844. Compounds of formula I.15 wherein $R^1$ is Y-4D, $R^2$ is $CH_3$, $R^9$ is H and $R^{10}$ is H.
Table 845. Compounds of formula I.15 wherein $R^1$ is Y-4D, $R^2$ is $CH_3$, $R^9$ is $CH_3$ and $R^{10}$ is H.
Table 846. Compounds of formula I.15 wherein $R^1$ is Y-4D, $R^2$ is $CH_3$, $R^9$ is $CH_3$ and $R^{10}$ is $CH_3$.
Table 847. Compounds of formula I.15 wherein $R^1$ is Y-5A, $R^2$ is $CH_3$, $R^9$ is H and $R^{10}$ is H.
Table 848. Compounds of formula I.15 wherein $R^1$ is Y-5A, $R^2$ is $CH_3$, $R^9$ is $CH_3$ and $R^{10}$ is H.
Table 849. Compounds of formula I.15 wherein $R^1$ is Y-5A, $R^2$ is $CH_3$, $R^9$ is $CH_3$ and $R^{10}$ is $CH_3$.
Table 850. Compounds of formula I.15 wherein $R^1$ is Y-5B, $R^2$ is $CH_3$, $R^9$ is H and $R^{10}$ is H.
Table 851. Compounds of formula I.15 wherein $R^1$ is Y-5B, $R^2$ is $CH_3$, $R^9$ is $CH_3$ and $R^{10}$ is H.
Table 852. Compounds of formula I.15 wherein $R^1$ is Y-5B, $R^2$ is $CH_3$, $R^9$ is $CH_3$ and $R^{10}$ is $CH_3$.
Table 853. Compounds of formula I.15 wherein $R^1$ is Y-6A, $R^2$ is $CH_3$, $R^9$ is H and $R^{10}$ is H.
Table 854. Compounds of formula I.15 wherein $R^1$ is Y-6A, $R^2$ is $CH_3$, $R^9$ is $CH_3$ and $R^{10}$ is H.
Table 855. Compounds of formula I.15 wherein $R^1$ is Y-6A, $R^2$ is $CH_3$, $R^9$ is $CH_3$ and $R^{10}$ is $CH_3$.
Table 856. Compounds of formula I.15 wherein $R^1$ is Y-6B, $R^2$ is $CH_3$, $R^9$ is H and $R^{10}$ is H.
Table 857. Compounds of formula I.15 wherein $R^1$ is Y-6B, $R^2$ is $CH_3$, $R^9$ is $CH_3$ and $R^{10}$ is H.
Table 858. Compounds of formula I.15 wherein $R^1$ is Y-6B, $R^2$ is $CH_3$, $R^9$ is $CH_3$ and $R^{10}$ is $CH_3$.
Table 859. Compounds of formula I.15 wherein $R^1$ is Y-8A, $R^2$ is $CH_3$, $R^9$ is H and $R^{10}$ is H.
Table 860. Compounds of formula I.15 wherein $R^1$ is Y-8A, $R^2$ is $CH_3$, $R^9$ is $CH_3$ and $R^{10}$ is H.
Table 861. Compounds of formula I.15 wherein $R^1$ is Y-8A, $R^2$ is $CH_3$, $R^9$ is $CH_3$ and $R^{10}$ is $CH_3$.
Table 862. Compounds of formula I.15 wherein $R^1$ is Y-8B, $R^2$ is $CH_3$, $R^9$ is H and $R^{10}$ is H.
Table 863. Compounds of formula I.15 wherein $R^1$ is Y-8B, $R^2$ is $CH_3$, $R^9$ is $CH_3$ and $R^{10}$ is H.
Table 864. Compounds of formula I.15 wherein $R^1$ is Y-8B, $R^2$ is $CH_3$, $R^9$ is $CH_3$ and $R^{10}$ is $CH_3$.
Table 865. Compounds of formula I.15 wherein $R^1$ is Y-1A, $R^2$ is $C_2H_5$, $R^9$ is H and $R^{10}$ is H.
Table 866. Compounds of formula I.15 wherein $R^1$ is Y-1A, $R^2$ is $C_2H_5$, $R^9$ is $CH_3$ and $R^{10}$ is H.
Table 867. Compounds of formula I.15 wherein $R^1$ is Y-1A, $R^2$ is $C_2H_5$, $R^9$ is $CH_3$ and $R^{10}$ is $CH_3$.
Table 868. Compounds of formula I.15 wherein $R^1$ is Y-1B, $R^2$ is $C_2H_5$, $R^9$ is H and $R^{10}$ is H.
Table 869. Compounds of formula I.15 wherein $R^1$ is Y-1B, $R^2$ is $C_2H_5$, $R^9$ is $CH_3$ and $R^{10}$ is H.
Table 870. Compounds of formula I.15 wherein $R^1$ is Y-1B, $R^2$ is $C_2H_5$, $R^9$ is $CH_3$ and $R^{10}$ is $CH_3$.
Table 871. Compounds of formula I.15 wherein $R^1$ is Y-2A, $R^2$ is $C_2H_5$, $R^9$ is H and $R^{10}$ is H.
Table 872. Compounds of formula I.15 wherein $R^1$ is Y-2A, $R^2$ is $C_2H_5$, $R^9$ is $CH_3$ and $R^{10}$ is H.
Table 873. Compounds of formula I.15 wherein $R^1$ is Y-2A, $R^2$ is $C_2H_5$, $R^9$ is $CH_3$ and $R^{10}$ is $CH_3$.
Table 874. Compounds of formula I.15 wherein $R^1$ is Y-2B, $R^2$ is $C_2H_5$, $R^9$ is H and $R^{10}$ is H.
Table 875. Compounds of formula I.15 wherein $R^1$ is Y-2B, $R^2$ is $C_2H_5$, $R^9$ is $CH_3$ and $R^{10}$ is H.
Table 876. Compounds of formula I.15 wherein $R^1$ is Y-2B, $R^2$ is $C_2H_5$, $R^9$ is $CH_3$ and $R^{10}$ is $CH_3$.
Table 877. Compounds of formula I.15 wherein $R^1$ is Y-3A, $R^2$ is $C_2H_5$, $R^9$ is H and $R^{10}$ is H.
Table 878. Compounds of formula I.15 wherein $R^1$ is Y-3A, $R^2$ is $C_2H_5$, $R^9$ is $CH_3$ and $R^{10}$ is H.
Table 879. Compounds of formula I.15 wherein $R^1$ is Y-3A, $R^2$ is $C_2H_5$, $R^9$ is $CH_3$ and $R^{10}$ is $CH_3$.
Table 880. Compounds of formula I.15 wherein $R^1$ is Y-3B, $R^2$ is $C_2H_5$, $R^9$ is H and $R^{10}$ is H.
Table 881. Compounds of formula I.15 wherein $R^1$ is Y-3B, $R^2$ is $C_2H_5$, $R^9$ is $CH_3$ and $R^{10}$ is H.
Table 882. Compounds of formula I.15 wherein $R^1$ is Y-3B, $R^2$ is $C_2H_5$, $R^9$ is $CH_3$ and $R^{10}$ is $CH_3$.
Table 883. Compounds of formula I.15 wherein $R^1$ is Y-3C, $R^2$ is $C_2H_5$, $R^9$ is H and $R^{10}$ is H.
Table 884. Compounds of formula I.15 wherein $R^1$ is Y-3C, $R^2$ is $C_2H_5$, $R^9$ is $CH_3$ and $R^{10}$ is H.
Table 885. Compounds of formula I.15 wherein $R^1$ is Y-3C, $R^2$ is $C_2H_5$, $R^9$ is $CH_3$ and $R^{10}$ is $CH_3$.
Table 886. Compounds of formula I.15 wherein $R^1$ is Y-3D, $R^2$ is $C_2H_5$, $R^9$ is H and $R^{10}$ is H.

Table 887. Compounds of formula I.15 wherein $R^1$ is Y-3D, $R^2$ is $C_2H_5$, $R^9$ is $CH_3$ and $R^{10}$ is H.

Table 888. Compounds of formula I.15 wherein $R^1$ is Y-3D, $R^2$ is $C_2H_5$, $R^9$ is $CH_3$ and $R^{10}$ is $CH_3$.

Table 889. Compounds of formula I.15 wherein $R^1$ is Y-4A, $R^2$ is $C_2H_5$, $R^9$ is H and $R^{10}$ is H.

Table 890. Compounds of formula I.15 wherein $R^1$ is Y-4A, $R^2$ is $C_2H_5$, $R^9$ is $CH_3$ and $R^{10}$ is H.

Table 891. Compounds of formula I.15 wherein $R^1$ is Y-4A, $R^2$ is $C_2H_5$, $R^9$ is $CH_3$ and $R^{10}$ is $CH_3$.

Table 892. Compounds of formula I.15 wherein $R^1$ is Y-4B, $R^2$ is $C_2H_5$, $R^9$ is H and $R^{10}$ is H.

Table 893. Compounds of formula I.15 wherein $R^1$ is Y-4B, $R^2$ is $C_2H_5$, $R^9$ is $CH_3$ and $R^{10}$ is H.

Table 894. Compounds of formula I.15 wherein $R^1$ is Y-4B, $R^2$ is $C_2H_5$, $R^9$ is $CH_3$ and $R^{10}$ is $CH_3$.

Table 895. Compounds of formula I.15 wherein $R^1$ is Y-4C, $R^2$ is $C_2H_5$, $R^9$ is H and $R^{10}$ is H.

Table 896. Compounds of formula I.15 wherein $R^1$ is Y-4C, $R^2$ is $C_2H_5$, $R^9$ is $CH_3$ and $R^{10}$ is H. Table 897. Compounds of formula I.15 wherein $R^1$ is Y-4C, $R^2$ is $C_2H_5$, $R^9$ is $CH_3$ and $R^{10}$ is $CH_3$.

Table 898. Compounds of formula I.15 wherein $R^1$ is Y-4D, $R^2$ is $C_2H_5$, $R^9$ is H and $R^{10}$ is H.

Table 899. Compounds of formula I.15 wherein $R^1$ is Y-4D, $R^2$ is $C_2H_5$, $R^9$ is $CH_3$ and $R^{10}$ is H.

Table 900. Compounds of formula I.15 wherein $R^1$ is Y-4D, $R^2$ is $C_2H_5$, $R^9$ is $CH_3$ and $R^{10}$ is $CH_3$.

Table 901. Compounds of formula I.15 wherein $R^1$ is Y-5A, $R^2$ is $C_2H_5$, $R^9$ is H and $R^{10}$ is H.

Table 902. Compounds of formula I.15 wherein $R^1$ is Y-5A, $R^2$ is $C_2H_5$, $R^9$ is $CH_3$ and $R^{10}$ is H.

Table 903. Compounds of formula I.15 wherein $R^1$ is Y-5A, $R^2$ is $C_2H_5$, $R^9$ is $CH_3$ and $R^{10}$ is $CH_3$.

Table 904. Compounds of formula I.15 wherein $R^1$ is Y-5B, $R^2$ is $C_2H_5$, $R^9$ is H and $R^{10}$ is H.

Table 905. Compounds of formula I.15 wherein $R^1$ is Y-5B, $R^2$ is $C_2H_5$, $R^9$ is $CH_3$ and $R^{10}$ is H.

Table 906. Compounds of formula I.15 wherein $R^1$ is Y-5B, $R^2$ is $C_2H_5$, $R^9$ is $CH_3$ and $R^{10}$ is $CH_3$.

Table 907. Compounds of formula I.15 wherein $R^1$ is Y-6A, $R^2$ is $C_2H_5$, $R^9$ is H and $R^{10}$ is H.

Table 908. Compounds of formula I.15 wherein $R^1$ is Y-6A, $R^2$ is $C_2H_5$, $R^9$ is $CH_3$ and $R^{10}$ is H.

Table 909. Compounds of formula I.15 wherein $R^1$ is Y-6A, $R^2$ is $C_2H_5$, $R^9$ is $CH_3$ and $R^{10}$ is $CH_3$.

Table 910. Compounds of formula I.15 wherein $R^1$ is Y-6B, $R^2$ is $C_2H_5$, $R^9$ is H and $R^{10}$ is H.

Table 911. Compounds of formula I.15 wherein $R^1$ is Y-6B, $R^2$ is $C_2H_5$, $R^9$ is $CH_3$ and $R^{10}$ is H.

Table 912. Compounds of formula I.15 wherein $R^1$ is Y-6B, $R^2$ is $C_2H_5$, $R^9$ is $CH_3$ and $R^{10}$ is $CH_3$.

Table 913. Compounds of formula I.15 wherein $R^1$ is Y-8A, $R^2$ is $C_2H_5$, $R^9$ is H and $R^{10}$ is H.

Table 914. Compounds of formula I.15 wherein $R^1$ is Y-8A, $R^2$ is $C_2H_5$, $R^9$ is $CH_3$ and $R^{10}$ is H.

Table 915. Compounds of formula I.15 wherein $R^1$ is Y-8A, $R^2$ is $C_2H_5$, $R^9$ is $CH_3$ and $R^{10}$ is $CH_3$.

Table 916. Compounds of formula I.15 wherein $R^1$ is Y-8B, $R^2$ is $C_2H_5$, $R^9$ is H and $R^{10}$ is H.

Table 917. Compounds of formula I.15 wherein $R^1$ is Y-8B, $R^2$ is $C_2H_5$, $R^9$ is $CH_3$ and $R^{10}$ is H.

Table 918. Compounds of formula I.15 wherein $R^1$ is Y-8B, $R^2$ is $C_2H_5$, $R^9$ is $CH_3$ and $R^{10}$ is $CH_3$.

Table 919. Compounds of formula I.15 wherein $R^1$ is Y-1A, $R^2$ is c-$C_3H_5$, $R^9$ is H and $R^{10}$ is H.

Table 920. Compounds of formula I.15 wherein $R^1$ is Y-1A, $R^2$ is c-$C_3H_5$, $R^9$ is $CH_3$ and $R^{10}$ is H.

Table 921. Compounds of formula I.15 wherein $R^1$ is Y-1A, $R^2$ is c-$C_3H_5$, $R^9$ is $CH_3$ and $R^{10}$ is $CH_3$.

Table 922. Compounds of formula I.15 wherein $R^1$ is Y-1B, $R^2$ is c-$C_3H_5$, $R^9$ is H and $R^{10}$ is H.

Table 923. Compounds of formula I.15 wherein $R^1$ is Y-1B, $R^2$ is c-$C_3H_5$, $R^9$ is $CH_3$, $R^{10}$ is H.

Table 924. Compounds of formula I.15 wherein $R^1$ is Y-1B, $R^2$ is c-$C_3H_5$, $R^9$ is $CH_3$ and $R^{10}$ is $CH_3$.

Table 925. Compounds of formula I.15 wherein $R^1$ is Y-2A, $R^2$ is c-$C_3H_5$, $R^9$ is H and $R^{10}$ is H.

Table 926. Compounds of formula I.15 wherein $R^1$ is Y-2A, $R^2$ is c-$C_3H_5$, $R^9$ is $CH_3$ and $R^{10}$ is H.

Table 927. Compounds of formula I.15 wherein $R^1$ is Y-2A, $R^2$ is c-$C_3H_5$, $R^9$ is $CH_3$ and $R^{10}$ is $CH_3$.

Table 928. Compounds of formula I.15 wherein $R^1$ is Y-2B, $R^2$ is c-$C_3H_5$, $R^9$ is H and $R^{10}$ is H.

Table 929. Compounds of formula I.15 wherein $R^1$ is Y-2B, $R^2$ is c-$C_3H_5$, $R^9$ is $CH_3$ and $R^{10}$ is H.

Table 930. Compounds of formula I.15 wherein $R^1$ is Y-2B, $R^2$ is c-$C_3H_5$, $R^9$ is $CH_3$ and $R^{10}$ is $CH_3$.

Table 931. Compounds of formula I.15 wherein $R^1$ is Y-3A, $R^2$ is c-$C_3H_5$, $R^9$ is H and $R^{10}$ is H.

Table 932. Compounds of formula I.15 wherein $R^1$ is Y-3A, $R^2$ is c-$C_3H_5$, $R^9$ is $CH_3$ and $R^{10}$ is H.

Table 933. Compounds of formula I.15 wherein $R^1$ is Y-3A, $R^2$ is c-$C_3H_5$, $R^9$ is $CH_3$ and $R^{10}$ is $CH_3$.

Table 934. Compounds of formula I.15 wherein $R^1$ is Y-3B, $R^2$ is c-$C_3H_5$, $R^9$ is H and $R^{10}$ is H.

Table 935. Compounds of formula I.15 wherein $R^1$ is Y-3B, $R^2$ is c-$C_3H_5$, $R^9$ is $CH_3$ and $R^{10}$ is H.

Table 936. Compounds of formula I.15 wherein $R^1$ is Y-3B, $R^2$ is c-$C_3H_5$, $R^9$ is $CH_3$ and $R^{10}$ is $CH_3$.

Table 937. Compounds of formula I.15 wherein $R^1$ is Y-3C, $R^2$ is c-$C_3H_5$, $R^9$ is H and $R^{10}$ is H.

Table 938. Compounds of formula I.15 wherein $R^1$ is Y-3C, $R^2$ is c-$C_3H_5$, $R^9$ is $CH_3$ and $R^{10}$ is H.

Table 939. Compounds of formula I.15 wherein $R^1$ is Y-3C, $R^2$ is c-$C_3H_5$, $R^9$ is $CH_3$ and $R^{10}$ is $CH_3$.

Table 940. Compounds of formula I.15 wherein $R^1$ is Y-3D, $R^2$ is c-$C_3H_5$, $R^9$ is H and $R^{10}$ is H.

Table 941. Compounds of formula I.15 wherein $R^1$ is Y-3D, $R^2$ is c-$C_3H_5$, $R^9$ is $CH_3$ and $R^{10}$ is H.

Table 942. Compounds of formula I.15 wherein $R^1$ is Y-3D, $R^2$ is c-$C_3H_5$, $R^9$ is $CH_3$ and $R^{10}$ is $CH_3$.

Table 943. Compounds of formula I.15 wherein $R^1$ is Y-4A, $R^2$ is c-$C_3H_5$, $R^9$ is H and $R^{10}$ is H.

Table 944. Compounds of formula I.15 wherein $R^1$ is Y-4A, $R^2$ is c-$C_3H_5$, $R^9$ is $CH_3$ and $R^{10}$ is H.

Table 945. Compounds of formula I.15 wherein $R^1$ is Y-4A, $R^2$ is c-$C_3H_5$, $R^9$ is $CH_3$ and $R^{10}$ is $CH_3$.

Table 946. Compounds of formula I.15 wherein $R^1$ is Y-4B, $R^2$ is c-$C_3H_5$, $R^9$ is H and $R^{10}$ is H.

Table 947. Compounds of formula I.15 wherein $R^1$ is Y-4B, $R^2$ is c-$C_3H_5$, $R^9$ is $CH_3$ and $R^{10}$ is H.

Table 948. Compounds of formula I.15 wherein $R^1$ is Y-4B, $R^2$ is c-$C_3H_5$, $R^9$ is $CH_3$ and $R^{10}$ is $CH_3$.

Table 949. Compounds of formula I.15 wherein $R^1$ is Y-4C, $R^2$ is c-$C_3H_5$, $R^9$ is H and $R^{10}$ is H.

Table 950. Compounds of formula I.15 wherein $R^1$ is Y-4C, $R^2$ is c-$C_3H_5$, $R^9$ is $CH_3$ and $R^{10}$ is H.

Table 951. Compounds of formula I.15 wherein $R^1$ is Y-4C, $R^2$ is c-$C_3H_5$, $R^9$ is $CH_3$ and $R^{10}$ is $CH_3$.

Table 952. Compounds of formula I.15 wherein $R^1$ is Y-4D, $R^2$ is c-$C_3H_5$, $R^9$ is H and $R^{10}$ is H.

Table 953. Compounds of formula I.15 wherein $R^1$ is Y-4D, $R^2$ is c-$C_3H_5$, $R^9$ is $CH_3$ and $R^{10}$ is H.

Table 954. Compounds of formula I.15 wherein $R^1$ is Y-4D, $R^2$ is c-$C_3H_5$, $R^9$ is $CH_3$ and $R^{10}$ is $CH_3$.

Table 955. Compounds of formula I.15 wherein $R^1$ is Y-5A, $R^2$ is c-$C_3H_5$, $R^9$ is H and $R^{10}$ is H.

Table 956. Compounds of formula I.15 wherein $R^1$ is Y-5A, $R^2$ is c-$C_3H_5$, $R^9$ is $CH_3$ and $R^{10}$ is H.

Table 957. Compounds of formula I.15 wherein $R^1$ is Y-5A, $R^2$ is c-$C_3H_5$, $R^9$ is $CH_3$ and $R^{10}$ is $CH_3$.

Table 958. Compounds of formula I.15 wherein $R^1$ is Y-5B, $R^2$ is c-$C_3H_5$, $R^9$ is H and $R^{10}$ is H.

Table 959. Compounds of formula I.15 wherein $R^1$ is Y-5B, $R^2$ is c-$C_3H_5$, $R^9$ is $CH_3$ and $R^{10}$ is H.

Table 960. Compounds of formula I.15 wherein $R^1$ is Y-5B, $R^2$ is c-$C_3H_5$, $R^9$ is $CH_3$ and $R^{10}$ is $CH_3$.

Table 961. Compounds of formula I.15 wherein $R^1$ is Y-6A, $R^2$ is c-$C_3H_5$, $R^9$ is H and $R^{10}$ is H.

Table 962. Compounds of formula I.15 wherein $R^1$ is Y-6A, $R^2$ is c-$C_3H_5$, $R^9$ is $CH_3$ and $R^{10}$ is H.

Table 963. Compounds of formula I.15 wherein $R^1$ is Y-6A, $R^2$ is c-$C_3H_5$, $R^9$ is $CH_3$ and $R^{10}$ is $CH_3$.

Table 964. Compounds of formula I.15 wherein $R^1$ is Y-6B, $R^2$ is c-$C_3H_5$, $R^9$ is H and $R^{10}$ is H.

Table 965. Compounds of formula I.15 wherein $R^1$ is Y-6B, $R^2$ is c-$C_3H_5$, $R^9$ is $CH_3$ and $R^{10}$ is H.

Table 966. Compounds of formula I.15 wherein $R^1$ is Y-6B, $R^2$ is c-$C_3H_5$, $R^9$ is $CH_3$ and $R^{10}$ is $CH_3$.

Table 967. Compounds of formula I.15 wherein $R^1$ is Y-8A, $R^2$ is c-$C_3H_5$, $R^9$ is H and $R^{10}$ is H.

Table 968. Compounds of formula I.15 wherein $R^1$ is Y-8A, $R^2$ is c-$C_3H_5$, $R^9$ is $CH_3$ and $R^{10}$ is H.

Table 969. Compounds of formula I.15 wherein $R^1$ is Y-8A, $R^2$ is c-$C_3H_5$, $R^9$ is $CH_3$ and $R^{10}$ is $CH_3$.

Table 970. Compounds of formula I.15 wherein $R^1$ is Y-8B, $R^2$ is c-$C_3H_5$, $R^9$ is H and $R^{10}$ is H.

Table 971. Compounds of formula I.15 wherein $R^1$ is Y-8B, $R^2$ is c-$C_3H_5$, $R^9$ is $CH_3$ and $R^{10}$ is H.

Table 972. Compounds of formula I.15 wherein $R^1$ is Y-8B, $R^2$ is c-$C_3H_5$, $R^9$ is $CH_3$ and $R^{10}$ is $CH_3$.

Table 973. Compounds of formula I.16 wherein $R^1$ is Y-1A, $R^2$ is H, $R^9$ is H and $R^{10}$ is H.

Table 974. Compounds of formula I.16 wherein $R^1$ is Y-1A, $R^2$ is H, $R^9$ is $CH_3$ and, $R^{10}$ is H.

Table 975. Compounds of formula I.16 wherein $R^1$ is Y-1A, $R^2$ is H, $R^9$ is $CH_3$ and $R^{10}$ is $CH_3$.

Table 976. Compounds of formula I.16 wherein $R^1$ is Y-1B, $R^2$ is H, $R^9$ is H and $R^{10}$ is H.

Table 977. Compounds of formula I.16 wherein $R^1$ is Y-1B, $R^2$ is H, $R^9$ is $CH_3$ and $R^{10}$ is H.

Table 978. Compounds of formula I.16 wherein $R^1$ is Y-1B, $R^2$ is H, $R^9$ is $CH_3$ and $R^{10}$ is $CH_3$.

Table 979. Compounds of formula I.16 wherein $R^1$ is Y-2A, $R^2$ is H, $R^9$ is H and $R^{10}$ is H.

Table 980. Compounds of formula I.16 wherein $R^1$ is Y-2A, $R^2$ is H, $R^9$ is $CH_3$ and $R^{10}$ is H.

Table 981. Compounds of formula I.16 wherein $R^1$ is Y-2A, $R^2$ is H, $R^9$ is $CH_3$ and $R^{10}$ is $CH_3$.

Table 982. Compounds of formula I.16 wherein $R^1$ is Y-2B, $R^2$ is H, $R^9$ is H and $R^{10}$ is H.

Table 983. Compounds of formula I.16 wherein $R^1$ is Y-2B, $R^2$ is H, $R^9$ is $CH_3$ and $R^{10}$ is H.

Table 984. Compounds of formula I.16 wherein $R^1$ is Y-2B, $R^2$ is H, $R^9$ is $CH_3$ and $R^{10}$ is $CH_3$.

Table 985. Compounds of formula I.16 wherein $R^1$ is Y-3A, $R^2$ is H, $R^9$ is H and $R^{10}$ is H.

Table 986. Compounds of formula I.16 wherein $R^1$ is Y-3A, $R^2$ is H, $R^9$ is $CH_3$ and $R^{10}$ is H.

Table 987. Compounds of formula I.16 wherein $R^1$ is Y-3A, $R^2$ is H, $R^9$ is $CH_3$ and $R^{10}$ is $CH_3$.

Table 988. Compounds of formula I.16 wherein $R^1$ is Y-3B, $R^2$ is H, $R^9$ is H and $R^{10}$ is H.

Table 989. Compounds of formula I.16 wherein $R^1$ is Y-3B, $R^2$ is H, $R^9$ is $CH_3$ and $R^{10}$ is H.

Table 990. Compounds of formula I.16 wherein $R^1$ is Y-3B, $R^2$ is H, $R^9$ is $CH_3$ and $R^{10}$ is $CH_3$.

Table 991. Compounds of formula I.16 wherein $R^1$ is Y-3C, $R^2$ is H, $R^9$ is H and $R^{10}$ is H.

Table 992. Compounds of formula I.16 wherein $R^1$ is Y-3C, $R^2$ is H, $R^9$ is $CH_3$ and $R^{10}$ is H.

Table 993. Compounds of formula I.16 wherein $R^1$ is Y-3C, $R^2$ is H, $R^9$ is $CH_3$ and $R^{10}$ is $CH_3$.

Table 994. Compounds of formula I.16 wherein $R^1$ is Y-3D, $R^2$ is H, $R^9$ is H and $R^{10}$ is H.

Table 995. Compounds of formula I.16 wherein $R^1$ is Y-3D, $R^2$ is H, $R^9$ is $CH_3$ and $R^{10}$ is H.

Table 996. Compounds of formula I.16 wherein $R^1$ is Y-3D, $R^2$ is H, $R^9$ is $CH_3$ and $R^{10}$ is $CH_3$.

Table 997. Compounds of formula I.16 wherein $R^1$ is Y-4A, $R^2$ is H, $R^9$ is H and $R^{10}$ is H.

Table 998. Compounds of formula I.16 wherein $R^1$ is Y-4A, $R^2$ is H, $R^9$ is $CH_3$ and $R^{10}$ is H.

Table 999. Compounds of formula I.16 wherein $R^1$ is Y-4A, $R^2$ is H, $R^9$ is $CH_3$ and $R^{10}$ is $CH_3$.

Table 1000. Compounds of formula I.16 wherein $R^1$ is Y-4B, $R^2$ is H, $R^9$ is H and $R^{10}$ is H.

Table 1001. Compounds of formula I.16 wherein $R^1$ is Y-4B, $R^2$ is H, $R^9$ is $CH_3$ and $R^{10}$ is H.

Table 1002. Compounds of formula I.16 wherein $R^1$ is Y-4B, $R^2$ is H, $R^9$ is $CH_3$ and $R^{10}$ is $CH_3$.

Table 1003. Compounds of formula I.16 wherein $R^1$ is Y-4C, $R^2$ is H, $R^9$ is H and $R^{10}$ is H.

Table 1004. Compounds of formula I.16 wherein $R^1$ is Y-4C, $R^2$ is H, $R^9$ is $CH_3$ and $R^{10}$ is H.

Table 1005. Compounds of formula I.16 wherein $R^1$ is Y-4C, $R^2$ is H, $R^9$ is $CH_3$ and $R^{10}$ is $CH_3$.

Table 1006. Compounds of formula I.16 wherein $R^1$ is Y-4D, $R^2$ is H, $R^9$ is H and $R^{10}$ is H.

Table 1007. Compounds of formula I.16 wherein $R^1$ is Y-4D, $R^2$ is H, $R^9$ is $CH_3$ and $R^{10}$ is H.

Table 1008. Compounds of formula I.16 wherein $R^1$ is Y-4D, $R^2$ is H, $R^9$ is $CH_3$ and $R^{10}$ is $CH_3$.

Table 1009. Compounds of formula I.16 wherein $R^1$ is Y-5A, $R^2$ is H, $R^9$ is H and $R^{10}$ is H.

Table 1010. Compounds of formula I.16 wherein $R^1$ is Y-5A, $R^2$ is H, $R^9$ is $CH_3$ and $R^{10}$ is H.

Table 1011. Compounds of formula I.16 wherein $R^1$ is Y-5A, $R^2$ is H, $R^9$ is $CH_3$ and $R^{10}$ is $CH_3$.

Table 1012. Compounds of formula I.16 wherein $R^1$ is Y-5B, $R^2$ is H, $R^9$ is H and $R^{10}$ is H.

Table 1013. Compounds of formula I.16 wherein $R^1$ is Y-5B, $R^2$ is H, $R^9$ is $CH_3$ and $R^{10}$ is H.

Table 1014. Compounds of formula I.16 wherein $R^1$ is Y-5B, $R^2$ is H, $R^9$ is $CH_3$ and $R^{10}$ is $CH_3$.

Table 1015. Compounds of formula I.16 wherein $R^1$ is Y-6A, $R^2$ is H, $R^9$ is H and $R^{10}$ is H.

Table 1016. Compounds of formula I.16 wherein $R^1$ is Y-6A, $R^2$ is H, $R^9$ is $CH_3$ and $R^{10}$ is H.

Table 1017. Compounds of formula I.16 wherein $R^1$ is Y-6A, $R^2$ is H, $R^9$ is $CH_3$ and $R^{10}$ is $CH_3$.

Table 1018. Compounds of formula I.16 wherein $R^1$ is Y-6B, $R^2$ is H, $R^9$ is H and $R^{10}$ is H.

Table 1019. Compounds of formula I.16 wherein $R^1$ is Y-6B, $R^2$ is H, $R^9$ is $CH_3$ and $R^{10}$ is H.

Table 1020. Compounds of formula I.16 wherein $R^1$ is Y-6B, $R^2$ is H, $R^9$ is $CH_3$ and $R^{10}$ is $CH_3$.

Table 1021. Compounds of formula I.16 wherein $R^1$ is Y-8A, $R^2$ is H, $R^9$ is H and $R^{10}$ is H.

Table 1022. Compounds of formula I.16 wherein $R^1$ is Y-8A, $R^2$ is H, $R^9$ is $CH_3$ and $R^{10}$ is H.

Table 1023. Compounds of formula I.16 wherein $R^1$ is Y-8A, $R^2$ is H, $R^9$ is $CH_3$ and $R^{10}$ is $CH_3$.

Table 1024. Compounds of formula I.16 wherein $R^1$ is Y-8B, $R^2$ is H, $R^9$ is H and $R^{10}$ is H.

Table 1025. Compounds of formula I.16 wherein $R^1$ is Y-8B, $R^2$ is H, $R^9$ is $CH_3$ and $R^{10}$ is H.

Table 1026. Compounds of formula I.16 wherein $R^1$ is Y-8B, $R^2$ is H, $R^9$ is $CH_3$ and $R^{10}$ is $CH_3$.

Table 1027. Compounds of formula I.16 wherein $R^1$ is Y-1A, $R^2$ is $CH_3$, $R^9$ is H and $R^{10}$ is H.

Table 1028. Compounds of formula I.16 wherein $R^1$ is Y-1A, $R^2$ is $CH_3$, $R^9$ is $CH_3$ and $R^{10}$ is H.

Table 1029. Compounds of formula I.16 wherein $R^1$ is Y-1A, $R^2$ is $CH_3$, $R^9$ is $CH_3$ and $R^{10}$ is $CH_3$.

Table 1030. Compounds of formula I.16 wherein $R^1$ is Y-1B, $R^2$ is $CH_3$, $R^9$ is H and $R^{10}$ is H.

Table 1031. Compounds of formula I.16 wherein $R^1$ is Y-1B, $R^2$ is $CH_3$, $R^9$ is $CH_3$ and $R^{10}$ is H.

Table 1032. Compounds of formula I.16 wherein $R^1$ is Y-1B, $R^2$ is $CH_3$, $R^9$ is $CH_3$ and $R^{10}$ is $CH_3$.

Table 1033. Compounds of formula I.16 wherein $R^1$ is Y-2A, $R^2$ is $CH_3$, $R^9$ is H and $R^{10}$ is H.

Table 1034. Compounds of formula I.16 wherein $R^1$ is Y-2A, $R^2$ is $CH_3$, $R^9$ is $CH_3$ and $R^{10}$ is H.

Table 1035. Compounds of formula I.16 wherein $R^1$ is Y-2A, $R^2$ is $CH_3$, $R^9$ is $CH_3$ and $R^{10}$ is $CH_3$.

Table 1036. Compounds of formula I.16 wherein $R^1$ is Y-2B, $R^2$ is $CH_3$, $R^9$ is H and $R^{10}$ is H.

Table 1037. Compounds of formula I.16 wherein $R^1$ is Y-2B, $R^2$ is $CH_3$, $R^9$ is $CH_3$ and $R^{10}$ is H.

Table 1038. Compounds of formula I.16 wherein $R^1$ is Y-2B, $R^2$ is $CH_3$, $R^9$ is $CH_3$ and $R^{10}$ is $CH_3$.

Table 1039. Compounds of formula I.16 wherein $R^1$ is Y-3A, $R^2$ is $CH_3$, $R^9$ is H and $R^{10}$ is H.

Table 1040. Compounds of formula I.16 wherein $R^1$ is Y-3A, $R^2$ is $CH_3$, $R^9$ is $CH_3$ and $R^{10}$ is H.

Table 1041. Compounds of formula I.16 wherein $R^1$ is Y-3A, $R^2$ is $CH_3$, $R^9$ is $CH_3$ and $R^{10}$ is $CH_3$.

Table 1042. Compounds of formula I.16 wherein $R^1$ is Y-3B, $R^2$ is $CH_3$, $R^9$ is H and $R^{10}$ is H.

Table 1043. Compounds of formula I.16 wherein $R^1$ is Y-3B, $R^2$ is $CH_3$, $R^9$ is $CH_3$ and $R^{10}$ is H.

Table 1044. Compounds of formula I.16 wherein $R^1$ is Y-3B, $R^2$ is $CH_3$, $R^9$ is $CH_3$ and $R^{10}$ is $CH_3$.

Table 1045. Compounds of formula I.16 wherein $R^1$ is Y-3C, $R^2$ is $CH_3$, $R^9$ is H and $R^{10}$ is H.

Table 1046. Compounds of formula I.16 wherein $R^1$ is Y-3C, $R^2$ is $CH_3$, $R^9$ is $CH_3$ and $R^{10}$ is H.

Table 1047. Compounds of formula I.16 wherein $R^1$ is Y-3C, $R^2$ is $CH_3$, $R^9$ is $CH_3$ and $R^{10}$ is $CH_3$.

Table 1048. Compounds of formula I.16 wherein $R^1$ is Y-3D, $R^2$ is $CH_3$, $R^9$ is H and $R^{10}$ is H.

Table 1049. Compounds of formula I.16 wherein $R^1$ is Y-3D, $R^2$ is $CH_3$, $R^9$ is $CH_3$ and $R^{10}$ is H.

Table 1050. Compounds of formula I.16 wherein $R^1$ is Y-3D, $R^2$ is $CH_3$, $R^9$ is $CH_3$ and $R^{10}$ is $CH_3$.

Table 1051. Compounds of formula I.16 wherein $R^1$ is Y-4A, $R^2$ is $CH_3$, $R^9$ is H and $R^{10}$ is H.

Table 1052. Compounds of formula I.16 wherein $R^1$ is Y-4A, $R^2$ is $CH_3$, $R^9$ is $CH_3$ and $R^{10}$ is H.

Table 1053. Compounds of formula I.16 wherein $R^1$ is Y-4A, $R^2$ is $CH_3$, $R^9$ is $CH_3$ and $R^{10}$ is $CH_3$.

Table 1054. Compounds of formula I.16 wherein $R^1$ is Y-4B, $R^2$ is $CH_3$, $R^9$ is H and $R^{10}$ is H.

Table 1055. Compounds of formula I.16 wherein $R^1$ is Y-4B, $R^2$ is $CH_3$, $R^9$ is $CH_3$ and $R^{10}$ is H.

Table 1056. Compounds of formula I.16 wherein $R^1$ is Y-4B, $R^2$ is $CH_3$, $R^9$ is $CH_3$ and $R^{10}$ is $CH_3$.

Table 1057. Compounds of formula I.16 wherein $R^1$ is Y-4C, $R^2$ is $CH_3$, $R^9$ is H and $R^{10}$ is H.

Table 1058. Compounds of formula I.16 wherein $R^1$ is Y-4C, $R^2$ is $CH_3$, $R^9$ is $CH_3$ and $R^{10}$ is H.

Table 1059. Compounds of formula I.16 wherein $R^1$ is Y-4C, $R^2$ is $CH_3$, $R^9$ is $CH_3$ and $R^{10}$ is $CH_3$.

Table 1060. Compounds of formula I.16 wherein $R^1$ is Y-4D, $R^2$ is $CH_3$, $R^9$ is H and $R^{10}$ is H.

Table 1061. Compounds of formula I.16 wherein $R^1$ is Y-4D, $R^2$ is $CH_3$, $R^9$ is $CH_3$ and $R^{10}$ is H.

Table 1062. Compounds of formula I.16 wherein $R^1$ is Y-4D, $R^2$ is $CH_3$, $R^9$ is $CH_3$ and $R^{10}$ is $CH_3$.

Table 1063. Compounds of formula I.16 wherein $R^1$ is Y-5A, $R^2$ is $CH_3$, $R^9$ is H and $R^{10}$ is H.

Table 1064. Compounds of formula I.16 wherein $R^1$ is Y-5A, $R^2$ is $CH_3$, $R^9$ is $CH_3$ and $R^{10}$ is H.

Table 1065. Compounds of formula I.16 wherein $R^1$ is Y-5A, $R^2$ is $CH_3$, $R^9$ is $CH_3$ and $R^{10}$ is $CH_3$.

Table 1066. Compounds of formula I.16 wherein $R^1$ is Y-5B, $R^2$ is $CH_3$, $R^9$ is H and $R^{10}$ is H.

Table 1067. Compounds of formula I.16 wherein $R^1$ is Y-5B, $R^2$ is $CH_3$, $R^9$ is $CH_3$ and $R^{10}$ is H.

Table 1068. Compounds of formula I.16 wherein $R^1$ is Y-5B, $R^2$ is $CH_3$, $R^9$ is $CH_3$ and $R^{10}$ is $CH_3$.

Table 1069. Compounds of formula I.16 wherein $R^1$ is Y-6A, $R^2$ is $CH_3$, $R^9$ is H and $R^{10}$ is H.

Table 1070. Compounds of formula I.16 wherein $R^1$ is Y-6A, $R^2$ is $CH_3$, $R^9$ is $CH_3$ and $R^{10}$ is H.

Table 1071. Compounds of formula I.16 wherein $R^1$ is Y-6A, $R^2$ is $CH_3$, $R^9$ is $CH_3$ and $R^{10}$ is $CH_3$.

Table 1072. Compounds of formula I.16 wherein $R^1$ is Y-6B, $R^2$ is $CH_3$, $R^9$ is H and $R^{10}$ is H.

Table 1073. Compounds of formula I.16 wherein $R^1$ is Y-6B, $R^2$ is $CH_3$, $R^9$ is $CH_3$ and $R^{10}$ is H. Table 1074. Compounds of formula I.16 wherein $R^1$ is Y-6B, $R^2$ is $CH_3$, $R^9$ is $CH_3$ and $R^{10}$ is $CH_3$.

Table 1075. Compounds of formula I.16 wherein $R^1$ is Y-8A, $R^2$ is $CH_3$, $R^9$ is H and $R^{10}$ is H.

Table 1076. Compounds of formula I.16 wherein $R^1$ is Y-8A, $R^2$ is $CH_3$, $R^9$ is $CH_3$ and $R^{10}$ is H.

Table 1077. Compounds of formula I.16 wherein $R^1$ is Y-8A, $R^2$ is $CH_3$, $R^9$ is $CH_3$ and $R^{10}$ is $CH_3$.

Table 1078. Compounds of formula I.16 wherein $R^1$ is Y-8B, $R^2$ is $CH_3$, $R^9$ is H and $R^{10}$ is H.

Table 1079. Compounds of formula I.16 wherein $R^1$ is Y-8B, $R^2$ is $CH_3$, $R^9$ is $CH_3$ and $R^{10}$ is H.

Table 1080. Compounds of formula I.16 wherein $R^1$ is Y-8B, $R^2$ is $CH_3$, $R^9$ is $CH_3$ and $R^{10}$ is $CH_3$.

Table 1081. Compounds of formula I.16 wherein $R^1$ is Y-1A, $R^2$ is $C_2H_5$, $R^9$ is H and $R^{10}$ is H.

Table 1082. Compounds of formula I.16 wherein $R^1$ is Y-1A, $R^2$ is $C_2H_5$, $R^9$ is $CH_3$ and $R^{10}$ is H.

Table 1083. Compounds of formula I.16 wherein $R^1$ is Y-1A, $R^2$ is $C_2H_5$, $R^9$ is $CH_3$ and $R^{10}$ is $CH_3$.

Table 1084. Compounds of formula I.16 wherein $R^1$ is Y-1B, $R^2$ is $C_2H_5$, $R^9$ is H and $R^{10}$ is H.

Table 1085. Compounds of formula I.16 wherein $R^1$ is Y-1B, $R^2$ is $C_2H_5$, $R^9$ is $CH_3$ and $R^{10}$ is H.

Table 1086. Compounds of formula I.16 wherein $R^1$ is Y-1B, $R^2$ is $C_2H_5$, $R^9$ is $CH_3$ and $R^{10}$ is $CH_3$.

Table 1087. Compounds of formula I.16 wherein $R^1$ is Y-2A, $R^2$ is $C_2H_5$, $R^9$ is H and $R^{10}$ is H.

Table 1088. Compounds of formula I.16 wherein $R^1$ is Y-2A, $R^2$ is $C_2H_5$, $R^9$ is $CH_3$ and $R^{10}$ is H.

Table 1089. Compounds of formula I.16 wherein $R^1$ is Y-2A, $R^2$ is $C_2H_5$, $R^9$ is $CH_3$ and $R^{10}$ is $CH_3$.

Table 1090. Compounds of formula I.16 wherein $R^1$ is Y-2B, $R^2$ is $C_2H_5$, $R^9$ is H and $R^{10}$ is H.

Table 1091. Compounds of formula I.16 wherein $R^1$ is Y-2B, $R^2$ is $C_2H_5$, $R^9$ is $CH_3$ and $R^{10}$ is H.

Table 1092. Compounds of formula I.16 wherein $R^1$ is Y-2B, $R^2$ is $C_2H_5$, $R^9$ is $CH_3$ and $R^{10}$ is $CH_3$.

Table 1093. Compounds of formula I.16 wherein $R^1$ is Y-3A, $R^2$ is $C_2H_5$, $R^9$ is H and $R^{10}$ is H.

Table 1094. Compounds of formula I.16 wherein $R^1$ is Y-3A, $R^2$ is $C_2H_5$, $R^9$ is $CH_3$ and $R^{10}$ is H.

Table 1095. Compounds of formula I.16 wherein $R^1$ is Y-3A, $R^2$ is $C_2H_5$, $R^9$ is $CH_3$ and $R^{10}$ is $CH_3$.

Table 1096. Compounds of formula I.16 wherein $R^1$ is Y-3B, $R^2$ is $C_2H_5$, $R^9$ is H and $R^{10}$ is H.

Table 1097. Compounds of formula I.16 wherein $R^1$ is Y-3B, $R^2$ is $C_2H_5$, $R^9$ is $CH_3$ and $R^{10}$ is H.

Table 1098. Compounds of formula I.16 wherein $R^1$ is Y-3B, $R^2$ is $C_2H_5$, $R^9$ is $CH_3$ and $R^{10}$ is $CH_3$.

Table 1099. Compounds of formula I.16 wherein $R^1$ is Y-3C, $R^2$ is $C_2H_5$, $R^9$ is H and $R^{10}$ is H.

Table 1100. Compounds of formula I.16 wherein $R^1$ is Y-3C, $R^2$ is $C_2H_5$, $R^9$ is $CH_3$ and $R^{10}$ is H.

Table 1101. Compounds of formula I.16 wherein $R^1$ is Y-3C, $R^2$ is $C_2H_5$, $R^9$ is $CH_3$ and $R^{10}$ is $CH_3$.

Table 1102. Compounds of formula I.16 wherein $R^1$ is Y-3D, $R^2$ is $C_2H_5$, $R^9$ is H and $R^{10}$ is H.

Table 1103. Compounds of formula I.16 wherein $R^1$ is Y-3D, $R^2$ is $C_2H_5$, $R^9$ is $CH_3$ and $R^{10}$ is H.

Table 1104. Compounds of formula I.16 wherein $R^1$ is Y-3D, $R^2$ is $C_2H_5$, $R^9$ is $CH_3$ and $R^{10}$ is $CH_3$.

Table 1105. Compounds of formula I.16 wherein $R^1$ is Y-4A, $R^2$ is $C_2H_5$, $R^9$ is H and $R^{10}$ is H.

Table 1106. Compounds of formula I.16 wherein $R^1$ is Y-4A, $R^2$ is $C_2H_5$, $R^9$ is $CH_3$ and $R^{10}$ is H.

Table 1107. Compounds of formula I.16 wherein $R^1$ is Y-4A, $R^2$ is $C_2H_5$, $R^9$ is $CH_3$ and $R^{10}$ is $CH_3$.

Table 1108. Compounds of formula I.16 wherein $R^1$ is Y-4B, $R^2$ is $C_2H_5$, $R^9$ is H and $R^{10}$ is H.

Table 1109. Compounds of formula I.16 wherein $R^1$ is Y-4B, $R^2$ is $C_2H_5$, $R^9$ is $CH_3$ and $R^{10}$ is H.

Table 1110. Compounds of formula I.16 wherein $R^1$ is Y-4B, $R^2$ is $C_2H_5$, $R^9$ is $CH_3$ and $R^{10}$ is $CH_3$.

Table 1111. Compounds of formula I.16 wherein $R^1$ is Y-4C, $R^2$ is $C_2H_5$, $R^9$ is H and $R^{10}$ is H.

Table 1112. Compounds of formula I.16 wherein $R^1$ is Y-4C, $R^2$ is $C_2H_5$, $R^9$ is $CH_3$ and $R^{10}$ is H.

Table 1113. Compounds of formula I.16 wherein $R^1$ is Y-4C, $R^2$ is $C_2H_5$, $R^9$ is $CH_3$ and $R^{10}$ is $CH_3$.

Table 1114. Compounds of formula I.16 wherein $R^1$ is Y-4D, $R^2$ is $C_2H_5$, $R^9$ is H and $R^{10}$ is H.

Table 1115. Compounds of formula I.16 wherein $R^1$ is Y-4D, $R^2$ is $C_2H_5$, $R^9$ is $CH_3$ and $R^{10}$ is H.

Table 1116. Compounds of formula I.16 wherein $R^1$ is Y-4D, $R^2$ is $C_2H_5$, $R^9$ is $CH_3$ and $R^{10}$ is $CH_3$.

Table 1117. Compounds of formula I.16 wherein $R^1$ is Y-5A, $R^2$ is $C_2H_5$, $R^9$ is H and $R^{10}$ is H.

Table 1118. Compounds of formula I.16 wherein $R^1$ is Y-5A, $R^2$ is $C_2H_5$, $R^9$ is $CH_3$ and $R^{10}$ is H.

Table 1119. Compounds of formula I.16 wherein $R^1$ is Y-5A, $R^2$ is $C_2H_5$, $R^9$ is $CH_3$ and $R^{10}$ is $CH_3$.

Table 1120. Compounds of formula I.16 wherein $R^1$ is Y-5B, $R^2$ is $C_2H_5$, $R^9$ is H and $R^{10}$ is H.

Table 1121. Compounds of formula I.16 wherein $R^1$ is Y-5B, $R^2$ is $C_2H_5$, $R^9$ is $CH_3$ and $R^{10}$ is H.

Table 1122. Compounds of formula I.16 wherein $R^1$ is Y-5B, $R^2$ is $C_2H_5$, $R^9$ is $CH_3$ and $R^{10}$ is $CH_3$.

Table 1123. Compounds of formula I.16 wherein $R^1$ is Y-6A, $R^2$ is $C_2H_5$, $R^9$ is H and $R^{10}$ is H.

Table 1124. Compounds of formula I.16 wherein $R^1$ is Y-6A, $R^2$ is $C_2H_5$, $R^9$ is $CH_3$ and $R^{10}$ is H.

Table 1125. Compounds of formula I.16 wherein $R^1$ is Y-6A, $R^2$ is $C_2H_5$, $R^9$ is $CH_3$ and $R^{10}$ is $CH_3$.

Table 1126. Compounds of formula I.16 wherein $R^1$ is Y-6B, $R^2$ is $C_2H_5$, $R^9$ is H and $R^{10}$ is H.

Table 1127. Compounds of formula I.16 wherein $R^1$ is Y-6B, $R^2$ is $C_2H_5$, $R^9$ is $CH_3$ and $R^{10}$ is H.

Table 1128. Compounds of formula I.16 wherein $R^1$ is Y-6B, $R^2$ is $C_2H_5$, $R^9$ is $CH_3$ and $R^{10}$ is $CH_3$.

Table 1129. Compounds of formula I.16 wherein $R^1$ is Y-8A, $R^2$ is $C_2H_5$, $R^9$ is H and $R^{10}$ is H.

Table 1130. Compounds of formula I.16 wherein $R^1$ is Y-8A, $R^2$ is $C_2H_5$, $R^9$ is $CH_3$ and $R^{10}$ is H.

Table 1131. Compounds of formula I.16 wherein $R^1$ is Y-8A, $R^2$ is $C_2H_5$, $R^9$ is $CH_3$ and $R^{10}$ is $CH_3$.

Table 1132. Compounds of formula I.16 wherein $R^1$ is Y-8B, $R^2$ is $C_2H_5$, $R^9$ is H and $R^{10}$ is H.

Table 1133. Compounds of formula I.16 wherein $R^1$ is Y-8B, $R^2$ is $C_2H_5$, $R^9$ is $CH_3$ and $R^{10}$ is H.

Table 1134. Compounds of formula I.16 wherein $R^1$ is Y-8B, $R^2$ is $C_2H_5$, $R^9$ is $CH_3$ and $R^{10}$ is $CH_3$.

Table 1135. Compounds of formula I.16 wherein $R^1$ is Y-1A, $R^2$ is c-$C_3H_5$, $R^9$ is H and $R^{10}$ is H.

Table 1136. Compounds of formula I.16 wherein $R^1$ is Y-1A, $R^2$ is c-$C_3H_5$, $R^9$ is $CH_3$ and $R^{10}$ is H.

Table 1137. Compounds of formula I.16 wherein $R^1$ is Y-1A, $R^2$ is c-$C_3H_5$, $R^9$ is $CH_3$ and $R^{10}$ is $CH_3$.

Table 1138. Compounds of formula I.16 wherein $R^1$ is Y-1B, $R^2$ is c-$C_3H_5$, $R^9$ is H and $R^{10}$ is H.

Table 1139. Compounds of formula I.16 wherein $R^1$ is Y-1B, $R^2$ is c-$C_3H_5$, $R^9$ is $CH_3$, $R^{10}$ is H.

Table 1140. Compounds of formula I.16 wherein $R^1$ is Y-1B, $R^2$ is c-$C_3H_5$, $R^9$ is $CH_3$ and $R^{10}$ is $CH_3$.

Table 1141. Compounds of formula I.16 wherein $R^1$ is Y-2A, $R^2$ is c-$C_3H_5$, $R^9$ is H and $R^{10}$ is H.

Table 1142. Compounds of formula I.16 wherein $R^1$ is Y-2A, $R^2$ is c-$C_3H_5$, $R^9$ is $CH_3$ and $R^{10}$ is H.

Table 1143. Compounds of formula I.16 wherein $R^1$ is Y-2A, $R^2$ is c-$C_3H_5$, $R^9$ is $CH_3$ and $R^{10}$ is $CH_3$.

Table 1144. Compounds of formula I.16 wherein $R^1$ is Y-2B, $R^2$ is c-$C_3H_5$, $R^9$ is H and $R^{10}$ is H.

Table 1145. Compounds of formula I.16 wherein $R^1$ is Y-2B, $R^2$ is c-$C_3H_5$, $R^9$ is $CH_3$ and $R^{10}$ is H.

Table 1146. Compounds of formula I.16 wherein $R^1$ is Y-2B, $R^2$ is c-$C_3H_5$, $R^9$ is $CH_3$ and $R^{10}$ is $CH_3$.

Table 1147. Compounds of formula I.16 wherein $R^1$ is Y-3A, $R^2$ is c-$C_3H_5$, $R^9$ is H and $R^{10}$ is H.

Table 1148. Compounds of formula I.16 wherein $R^1$ is Y-3A, $R^2$ is c-$C_3H_5$, $R^9$ is $CH_3$ and $R^{10}$ is H.

Table 1149. Compounds of formula I.16 wherein $R^1$ is Y-3A, $R^2$ is c-$C_3H_5$, $R^9$ is $CH_3$ and $R^{10}$ is $CH_3$.

Table 1150. Compounds of formula I.16 wherein $R^1$ is Y-3B, $R^2$ is c-$C_3H_5$, $R^9$ is H and $R^{10}$ is H.

Table 1151. Compounds of formula I.16 wherein $R^1$ is Y-3B, $R^2$ is c-$C_3H_5$, $R^9$ is $CH_3$ and $R^{10}$ is H.

Table 1152. Compounds of formula I.16 wherein $R^1$ is Y-3B, $R^2$ is c-$C_3H_5$, $R^9$ is $CH_3$ and $R^{10}$ is $CH_3$.

Table 1153. Compounds of formula I.16 wherein $R^1$ is Y-3C, $R^2$ is c-$C_3H_5$, $R^9$ is H and $R^{10}$ is H.

Table 1154. Compounds of formula I.16 wherein $R^1$ is Y-3C, $R^2$ is c-$C_3H_5$, $R^9$ is $CH_3$ and $R^{10}$ is H.

Table 1155. Compounds of formula I.16 wherein $R^1$ is Y-3C, $R^2$ is c-$C_3H_5$, $R^9$ is $CH_3$ and $R^{10}$ is $CH_3$.

Table 1156. Compounds of formula I.16 wherein $R^1$ is Y-3D, $R^2$ is c-$C_3H_5$, $R^9$ is H and $R^{10}$ is H.

Table 1157. Compounds of formula I.16 wherein $R^1$ is Y-3D, $R^2$ is c-$C_3H_5$, $R^9$ is $CH_3$ and $R^{10}$ is H.

Table 1158. Compounds of formula I.16 wherein $R^1$ is Y-3D, $R^2$ is c-$C_3H_5$, $R^9$ is $CH_3$ and $R^{10}$ is $CH_3$.

Table 1159. Compounds of formula I.16 wherein $R^1$ is Y-4A, $R^2$ is c-$C_3H_5$, $R^9$ is H and $R^{10}$ is H.

Table 1160. Compounds of formula I.16 wherein $R^1$ is Y-4A, $R^2$ is c-$C_3H_5$, $R^9$ is $CH_3$ and $R^{10}$ is H.

Table 1161. Compounds of formula I.16 wherein $R^1$ is Y-4A, $R^2$ is c-$C_3H_5$, $R^9$ is $CH_3$ and $R^{10}$ is $CH_3$.

Table 1162. Compounds of formula I.16 wherein $R^1$ is Y-4B, $R^2$ is c-$C_3H_5$, $R^9$ is H and $R^{10}$ is H.

Table 1163. Compounds of formula I.16 wherein $R^1$ is Y-4B, $R^2$ is c-$C_3H_5$, $R^9$ is $CH_3$ and $R^{10}$ is H.

Table 1164. Compounds of formula I.16 wherein $R^1$ is Y-4B, $R^2$ is c-$C_3H_5$, $R^9$ is $CH_3$ and $R^{10}$ is $CH_3$.

Table 1165. Compounds of formula I.16 wherein $R^1$ is Y-4C, $R^2$ is c-$C_3H_5$, $R^9$ is H and $R^{10}$ is H.

Table 1166. Compounds of formula I.16 wherein $R^1$ is Y-4C, $R^2$ is c-$C_3H_5$, $R^9$ is $CH_3$ and $R^{10}$ is H.

Table 1167. Compounds of formula I.16 wherein $R^1$ is Y-4C, $R^2$ is c-$C_3H_5$, $R^9$ is $CH_3$ and $R^{10}$ is $CH_3$.

Table 1168. Compounds of formula I.16 wherein $R^1$ is Y-4D, $R^2$ is c-$C_3H_5$, $R^9$ is H and $R^{10}$ is H.

Table 1169. Compounds of formula I.16 wherein $R^1$ is Y-4D, $R^2$ is c-$C_3H_5$, $R^9$ is $CH_3$ and $R^{10}$ is H.

Table 1170. Compounds of formula I.16 wherein $R^1$ is Y-4D, $R^2$ is c-$C_3H_5$, $R^9$ is $CH_3$ and $R^{10}$ is $CH_3$.

Table 1171. Compounds of formula I.16 wherein $R^1$ is Y-5A, $R^2$ is c-$C_3H_5$, $R^9$ is H and $R^{10}$ is H.

Table 1172. Compounds of formula I.16 wherein $R^1$ is Y-5A, $R^2$ is c-$C_3H_5$, $R^9$ is $CH_3$ and $R^{10}$ is H.

Table 1173. Compounds of formula I.16 wherein $R^1$ is Y-5A, $R^2$ is c-$C_3H_5$, $R^9$ is $CH_3$ and $R^{10}$ is $CH_3$.

Table 1174. Compounds of formula I.16 wherein $R^1$ is Y-5B, $R^2$ is c-$C_3H_5$, $R^9$ is H and $R^{10}$ is H.

Table 1175. Compounds of formula I.16 wherein $R^1$ is Y-5B, $R^2$ is c-$C_3H_5$, $R^9$ is $CH_3$ and $R^{10}$ is H.

Table 1176. Compounds of formula I.16 wherein $R^1$ is Y-5B, $R^2$ is c-$C_3H_5$, $R^9$ is $CH_3$ and $R^{10}$ is $CH_3$.

Table 1177. Compounds of formula I.16 wherein $R^1$ is Y-6A, $R^2$ is c-$C_3H_5$, $R^9$ is H and $R^{10}$ is H.

Table 1178. Compounds of formula I.16 wherein $R^1$ is Y-6A, $R^2$ is c-$C_3H_5$, $R^9$ is $CH_3$ and $R^{10}$ is H.

Table 1179. Compounds of formula I.16 wherein $R^1$ is Y-6A, $R^2$ is c-$C_3H_5$, $R^9$ is $CH_3$ and $R^{10}$ is $CH_3$.

Table 1180. Compounds of formula I.16 wherein $R^1$ is Y-6B, $R^2$ is c-$C_3H_5$, $R^9$ is H and $R^{10}$ is H.

Table 1181. Compounds of formula I.16 wherein $R^1$ is Y-6B, $R^2$ is c-$C_3H_5$, $R^9$ is $CH_3$ and $R^{10}$ is H.

Table 1182. Compounds of formula I.16 wherein $R^1$ is Y-6B, $R^2$ is c-$C_3H_5$, $R^9$ is $CH_3$ and $R^{10}$ is $CH_3$.

Table 1183. Compounds of formula I.16 wherein $R^1$ is Y-8A, $R^2$ is c-$C_3H_5$, $R^9$ is H and $R^{10}$ is H.

Table 1184. Compounds of formula I.16 wherein $R^1$ is Y-8A, $R^2$ is c-$C_3H_5$, $R^9$ is $CH_3$ and $R^{10}$ is H.

Table 1185. Compounds of formula I.16 wherein $R^1$ is Y-8A, $R^2$ is c-$C_3H_5$, $R^9$ is $CH_3$ and $R^{10}$ is $CH_3$.

Table 1186. Compounds of formula I.16 wherein $R^1$ is Y-8B, $R^2$ is c-$C_3H_5$, $R^9$ is H and $R^{10}$ is H.

Table 1187. Compounds of formula I.16 wherein $R^1$ is Y-8B, $R^2$ is c-$C_3H_5$, $R^9$ is $CH_3$ and $R^{10}$ is H.

Table 1188. Compounds of formula I.16 wherein $R^1$ is Y-8B, $R^2$ is c-$C_3H_5$, $R^9$ is $CH_3$ and $R^{10}$ is $CH_3$.

Table 1189. Compounds of formula I.17 wherein $R^1$ is Y-1A, $R^2$ is H, $R^9$ is H and $R^{10}$ is H.

Table 1190. Compounds of formula I.17 wherein $R^1$ is Y-1A, $R^2$ is H, $R^9$ is $CH_3$ and, $R^{10}$ is H.

Table 1191. Compounds of formula I.17 wherein $R^1$ is Y-1A, $R^2$ is H, $R^9$ is $CH_3$ and $R^{10}$ is $CH_3$.

Table 1192. Compounds of formula I.17 wherein $R^1$ is Y-1B, $R^2$ is H, $R^9$ is H and $R^{10}$ is H.

Table 1193. Compounds of formula I.17 wherein $R^1$ is Y-1B, $R^2$ is H, $R^9$ is $CH_3$ and $R^{10}$ is H.

Table 1194. Compounds of formula I.17 wherein $R^1$ is Y-1B, $R^2$ is H, $R^9$ is $CH_3$ and $R^{10}$ is $CH_3$.

Table 1195. Compounds of formula I.17 wherein $R^1$ is Y-2A, $R^2$ is H, $R^9$ is H and $R^{10}$ is H.

Table 1196. Compounds of formula I.17 wherein $R^1$ is Y-2A, $R^2$ is H, $R^9$ is $CH_3$ and $R^{10}$ is H.

Table 1197. Compounds of formula I.17 wherein $R^1$ is Y-2A, $R^2$ is H, $R^9$ is $CH_3$ and $R^{10}$ is $CH_3$.

Table 1198. Compounds of formula I.17 wherein $R^1$ is Y-2B, $R^2$ is H, $R^9$ is H and $R^{10}$ is H.

Table 1199. Compounds of formula I.17 wherein $R^1$ is Y-2B, $R^2$ is H, $R^9$ is $CH_3$ and $R^{10}$ is H.

Table 1200. Compounds of formula I.17 wherein $R^1$ is Y-2B, $R^2$ is H, $R^9$ is $CH_3$ and $R^{10}$ is $CH_3$.

Table 1201. Compounds of formula I.17 wherein $R^1$ is Y-3A, $R^2$ is H, $R^9$ is H and $R^{10}$ is H.

Table 1202. Compounds of formula I.17 wherein $R^1$ is Y-3A, $R^2$ is H, $R^9$ is $CH_3$ and $R^{10}$ is H.

Table 1203. Compounds of formula I.17 wherein $R^1$ is Y-3A, $R^2$ is H, $R^9$ is $CH_3$ and $R^{10}$ is $CH_3$.

Table 1204. Compounds of formula I.17 wherein $R^1$ is Y-3B, $R^2$ is H, $R^9$ is H and $R^{10}$ is H.

Table 1205. Compounds of formula I.17 wherein $R^1$ is Y-3B, $R^2$ is H, $R^9$ is $CH_3$ and $R^{10}$ is H.

Table 1206. Compounds of formula I.17 wherein $R^1$ is Y-3B, $R^2$ is H, $R^9$ is $CH_3$ and $R^{10}$ is $CH_3$.

Table 1207. Compounds of formula I.17 wherein $R^1$ is Y-3C, $R^2$ is H, $R^9$ is H and $R^{10}$ is H.

Table 1208. Compounds of formula I.17 wherein $R^1$ is Y-3C, $R^2$ is H, $R^9$ is $CH_3$ and $R^{10}$ is H.

Table 1209. Compounds of formula I.17 wherein $R^1$ is Y-3C, $R^2$ is H, $R^9$ is $CH_3$ and $R^{10}$ is $CH_3$.

Table 1210. Compounds of formula I.17 wherein $R^1$ is Y-3D, $R^2$ is H, $R^9$ is H and $R^{10}$ is H.

Table 1211. Compounds of formula I.17 wherein $R^1$ is Y-3D, $R^2$ is H, $R^9$ is $CH_3$ and $R^{10}$ is H.

Table 1212. Compounds of formula I.17 wherein $R^1$ is Y-3D, $R^2$ is H, $R^9$ is $CH_3$ and $R^{10}$ is $CH_3$.

Table 1213. Compounds of formula I.17 wherein $R^1$ is Y-4A, $R^2$ is H, $R^9$ is H and $R^{10}$ is H.

Table 1214. Compounds of formula I.17 wherein $R^1$ is Y-4A, $R^2$ is H, $R^9$ is $CH_3$ and $R^{10}$ is H.

Table 1215. Compounds of formula I.17 wherein $R^1$ is Y-4A, $R^2$ is H, $R^9$ is $CH_3$ and $R^{10}$ is $CH_3$.

Table 1216. Compounds of formula I.17 wherein $R^1$ is Y-4B, $R^2$ is H, $R^9$ is H and $R^{10}$ is H.

Table 1217. Compounds of formula I.17 wherein $R^1$ is Y-4B, $R^2$ is H, $R^9$ is $CH_3$ and $R^{10}$ is H.

Table 1218. Compounds of formula I.17 wherein $R^1$ is Y-4B, $R^2$ is H, $R^9$ is $CH_3$ and $R^{10}$ is $CH_3$.

Table 1219. Compounds of formula I.17 wherein $R^1$ is Y-4C, $R^2$ is H, $R^9$ is H and $R^{10}$ is H.

Table 1220. Compounds of formula I.17 wherein $R^1$ is Y-4C, $R^2$ is H, $R^9$ is $CH_3$ and $R^{10}$ is H.

Table 1221. Compounds of formula I.17 wherein $R^1$ is Y-4C, $R^2$ is H, $R^9$ is $CH_3$ and $R^{10}$ is $CH_3$.

Table 1222. Compounds of formula I.17 wherein $R^1$ is Y-4D, $R^2$ is H, $R^9$ is H and $R^{10}$ is H.

Table 1223. Compounds of formula I.17 wherein $R^1$ is Y-4D, $R^2$ is H, $R^9$ is $CH_3$ and $R^{10}$ is H.

Table 1224. Compounds of formula I.17 wherein $R^1$ is Y-4D, $R^2$ is H, $R^9$ is $CH_3$ and $R^{10}$ is $CH_3$.

Table 1225. Compounds of formula I.17 wherein $R^1$ is Y-5A, $R^2$ is H, $R^9$ is H and $R^{10}$ is H.

Table 1226. Compounds of formula I.17 wherein $R^1$ is Y-5A, $R^2$ is H, $R^9$ is $CH_3$ and $R^{10}$ is H.

Table 1227. Compounds of formula I.17 wherein $R^1$ is Y-5A, $R^2$ is H, $R^9$ is $CH_3$ and $R^{10}$ is $CH_3$.

Table 1228. Compounds of formula I.17 wherein $R^1$ is Y-5B, $R^2$ is H, $R^9$ is H and $R^{10}$ is H.

Table 1229. Compounds of formula I.17 wherein $R^1$ is Y-5B, $R^2$ is H, $R^9$ is $CH_3$ and $R^{10}$ is H.

Table 1230. Compounds of formula I.17 wherein $R^1$ is Y-5B, $R^2$ is H, $R^9$ is $CH_3$ and $R^{10}$ is $CH_3$.

Table 1231. Compounds of formula I.17 wherein $R^1$ is Y-6A, $R^2$ is H, $R^9$ is H and $R^{10}$ is H.

Table 1232. Compounds of formula I.17 wherein $R^1$ is Y-6A, $R^2$ is H, $R^9$ is $CH_3$ and $R^{10}$ is H.

Table 1233. Compounds of formula I.17 wherein $R^1$ is Y-6A, $R^2$ is H, $R^9$ is $CH_3$ and $R^{10}$ is $CH_3$.

Table 1234. Compounds of formula I.17 wherein $R^1$ is Y-6B, $R^2$ is H, $R^9$ is H and $R^{10}$ is H.

Table 1235. Compounds of formula I.17 wherein $R^1$ is Y-6B, $R^2$ is H, $R^9$ is $CH_3$ and $R^{10}$ is H.

Table 1236. Compounds of formula I.17 wherein $R^1$ is Y-6B, $R^2$ is H, $R^9$ is $CH_3$ and $R^{10}$ is $CH_3$.

Table 1237. Compounds of formula I.17 wherein $R^1$ is Y-8A, $R^2$ is H, $R^9$ is H and $R^{10}$ is H.

Table 1238. Compounds of formula I.17 wherein $R^1$ is Y-8A, $R^2$ is H, $R^9$ is $CH_3$ and $R^{10}$ is H.

Table 1239. Compounds of formula I.17 wherein $R^1$ is Y-8A, $R^2$ is H, $R^9$ is $CH_3$ and $R^{10}$ is $CH_3$.

Table 1240. Compounds of formula I.17 wherein $R^1$ is Y-8B, $R^2$ is H, $R^9$ is H and $R^{10}$ is H.

Table 1241. Compounds of formula I.17 wherein $R^1$ is Y-8B, $R^2$ is H, $R^9$ is $CH_3$ and $R^{10}$ is H.

Table 1242. Compounds of formula I.17 wherein $R^1$ is Y-8B, $R^2$ is H, $R^9$ is $CH_3$ and $R^{10}$ is $CH_3$.

Table 1243. Compounds of formula I.17 wherein $R^1$ is Y-1A, $R^2$ is $CH_3$, $R^9$ is H and $R^{10}$ is H.

Table 1244. Compounds of formula I.17 wherein $R^1$ is Y-1A, $R^2$ is $CH_3$, $R^9$ is $CH_3$ and $R^{10}$ is H.

Table 1245. Compounds of formula I.17 wherein $R^1$ is Y-1A, $R^2$ is $CH_3$, $R^9$ is $CH_3$ and $R^{10}$ is $CH_3$.

Table 1246. Compounds of formula I.17 wherein $R^1$ is Y-1B, $R^2$ is $CH_3$, $R^9$ is H and $R^{10}$ is H.

Table 1247. Compounds of formula I.17 wherein $R^1$ is Y-1B, $R^2$ is $CH_3$, $R^9$ is $CH_3$ and $R^{10}$ is H.

Table 1248. Compounds of formula I.17 wherein $R^1$ is Y-1B, $R^2$ is $CH_3$, $R^9$ is $CH_3$ and $R^{10}$ is $CH_3$.

Table 1249. Compounds of formula I.17 wherein $R^1$ is Y-2A, $R^2$ is $CH_3$, $R^9$ is H and $R^{10}$ is H.

Table 1250. Compounds of formula I.17 wherein $R^1$ is Y-2A, $R^2$ is $CH_3$, $R^9$ is $CH_3$ and $R^{10}$ is H.

Table 1251. Compounds of formula I.17 wherein $R^1$ is Y-2A, $R^2$ is $CH_3$, $R^9$ is $CH_3$ and $R^{10}$ is $CH_3$.

Table 1252. Compounds of formula I.17 wherein $R^1$ is Y-2B, $R^2$ is $CH_3$, $R^9$ is H and $R^{10}$ is H.

Table 1253. Compounds of formula I.17 wherein $R^1$ is Y-2B, $R^2$ is $CH_3$, $R^9$ is $CH_3$ and $R^{10}$ is H.

Table 1254. Compounds of formula I.17 wherein $R^1$ is Y-2B, $R^2$ is $CH_3$, $R^9$ is $CH_3$ and $R^{10}$ is $CH_3$.

Table 1255. Compounds of formula I.17 wherein $R^1$ is Y-3A, $R^2$ is $CH_3$, $R^9$ is H and $R^{10}$ is H.

Table 1256. Compounds of formula I.17 wherein $R^1$ is Y-3A, $R^2$ is $CH_3$, $R^9$ is $CH_3$ and $R^{10}$ is H.

Table 1257. Compounds of formula I.17 wherein $R^1$ is Y-3A, $R^2$ is $CH_3$, $R^9$ is $CH_3$ and $R^{10}$ is $CH_3$.

Table 1258. Compounds of formula I.17 wherein $R^1$ is Y-3B, $R^2$ is $CH_3$, $R^9$ is H and $R^{10}$ is H.

Table 1259. Compounds of formula I.17 wherein $R^1$ is Y-3B, $R^2$ is $CH_3$, $R^9$ is $CH_3$ and $R^{10}$ is H.

Table 1260. Compounds of formula I.17 wherein $R^1$ is Y-3B, $R^2$ is $CH_3$, $R^9$ is $CH_3$ and $R^{10}$ is $CH_3$.

Table 1261. Compounds of formula I.17 wherein $R^1$ is Y-3C, $R^2$ is $CH_3$, $R^9$ is H and $R^{10}$ is H.

Table 1262. Compounds of formula I.17 wherein $R^1$ is Y-3C, $R^2$ is $CH_3$, $R^9$ is $CH_3$ and $R^{10}$ is H.

Table 1263. Compounds of formula I.17 wherein $R^1$ is Y-3C, $R^2$ is $CH_3$, $R^9$ is $CH_3$ and $R^{10}$ is $CH_3$.

Table 1264. Compounds of formula I.17 wherein $R^1$ is Y-3D, $R^2$ is $CH_3$, $R^9$ is H and $R^{10}$ is H.

Table 1265. Compounds of formula I.17 wherein $R^1$ is Y-3D, $R^2$ is $CH_3$, $R^9$ is $CH_3$ and $R^{10}$ is H.

Table 1266. Compounds of formula I.17 wherein $R^1$ is Y-3D, $R^2$ is $CH_3$, $R^9$ is $CH_3$ and $R^{10}$ is $CH_3$.

Table 1267. Compounds of formula I.17 wherein $R^1$ is Y-4A, $R^2$ is $CH_3$, $R^9$ is H and $R^{10}$ is H.

Table 1268. Compounds of formula I.17 wherein $R^1$ is Y-4A, $R^2$ is $CH_3$, $R^9$ is $CH_3$ and $R^{10}$ is H.

Table 1269. Compounds of formula I.17 wherein $R^1$ is Y-4A, $R^2$ is $CH_3$, $R^9$ is $CH_3$ and $R^{10}$ is $CH_3$.

Table 1270. Compounds of formula I.17 wherein $R^1$ is Y-4B, $R^2$ is $CH_3$, $R^9$ is H and $R^{10}$ is H.

Table 1271. Compounds of formula I.17 wherein $R^1$ is Y-4B, $R^2$ is $CH_3$, $R^9$ is $CH_3$ and $R^{10}$ is H.

Table 1272. Compounds of formula I.17 wherein $R^1$ is Y-4B, $R^2$ is $CH_3$, $R^9$ is $CH_3$ and $R^{10}$ is $CH_3$.

Table 1273. Compounds of formula I.17 wherein $R^1$ is Y-4C, $R^2$ is $CH_3$, $R^9$ is H and $R^{10}$ is H.

Table 1274. Compounds of formula I.17 wherein $R^1$ is Y-4C, $R^2$ is $CH_3$, $R^9$ is $CH_3$ and $R^{10}$ is H.

Table 1275. Compounds of formula I.17 wherein $R^1$ is Y-4C, $R^2$ is $CH_3$, $R^9$ is $CH_3$ and $R^{10}$ is $CH_3$.

Table 1276. Compounds of formula I.17 wherein $R^1$ is Y-4D, $R^2$ is $CH_3$, $R^9$ is H and $R^{10}$ is H.

Table 1277. Compounds of formula I.17 wherein $R^1$ is Y-4D, $R^2$ is $CH_3$, $R^9$ is $CH_3$ and $R^{10}$ is H.

Table 1278. Compounds of formula I.17 wherein $R^1$ is Y-4D, $R^2$ is $CH_3$, $R^9$ is $CH_3$ and $R^{10}$ is $CH_3$.

Table 1279. Compounds of formula I.17 wherein $R^1$ is Y-5A, $R^2$ is $CH_3$, $R^9$ is H and $R^{10}$ is H.

Table 1280. Compounds of formula I.17 wherein $R^1$ is Y-5A, $R^2$ is $CH_3$, $R^9$ is $CH_3$ and $R^{10}$ is H.

Table 1281. Compounds of formula I.17 wherein $R^1$ is Y-5A, $R^2$ is $CH_3$, $R^9$ is $CH_3$ and $R^{10}$ is $CH_3$.

Table 1282. Compounds of formula I.17 wherein $R^1$ is Y-5B, $R^2$ is $CH_3$, $R^9$ is H and $R^{10}$ is H.

Table 1283. Compounds of formula I.17 wherein $R^1$ is Y-5B, $R^2$ is $CH_3$, $R^9$ is $CH_3$ and $R^{10}$ is H.

Table 1284. Compounds of formula I.17 wherein $R^1$ is Y-5B, $R^2$ is $CH_3$, $R^9$ is $CH_3$ and $R^{10}$ is $CH_3$.

Table 1285. Compounds of formula I.17 wherein $R^1$ is Y-6A, $R^2$ is $CH_3$, $R^9$ is H and $R^{10}$ is H.

Table 1286. Compounds of formula I.17 wherein $R^1$ is Y-6A, $R^2$ is $CH_3$, $R^9$ is $CH_3$ and $R^{10}$ is H.

Table 1287. Compounds of formula I.17 wherein $R^1$ is Y-6A, $R^2$ is $CH_3$, $R^9$ is $CH_3$ and $R^{10}$ is $CH_3$.

Table 1288. Compounds of formula I.17 wherein $R^1$ is Y-6B, $R^2$ is $CH_3$, $R^9$ is H and $R^{10}$ is H.

Table 1289. Compounds of formula I.17 wherein $R^1$ is Y-6B, $R^2$ is $CH_3$, $R^9$ is $CH_3$ and $R^{10}$ is H.

Table 1290. Compounds of formula I.17 wherein $R^1$ is Y-6B, $R^2$ is $CH_3$, $R^9$ is $CH_3$ and $R^{10}$ is $CH_3$.

Table 1291. Compounds of formula I.17 wherein $R^1$ is Y-8A, $R^2$ is $CH_3$, $R^9$ is H and $R^{10}$ is H.

Table 1292. Compounds of formula I.17 wherein $R^1$ is Y-8A, $R^2$ is $CH_3$, $R^9$ is $CH_3$ and $R^{10}$ is H.

Table 1293. Compounds of formula I.17 wherein $R^1$ is Y-8A, $R^2$ is $CH_3$, $R^9$ is $CH_3$ and $R^{10}$ is $CH_3$.

Table 1294. Compounds of formula I.17 wherein $R^1$ is Y-8B, $R^2$ is $CH_3$, $R^9$ is H and $R^{10}$ is H.

Table 1295. Compounds of formula I.17 wherein $R^1$ is Y-8B, $R^2$ is $CH_3$, $R^9$ is $CH_3$ and $R^{10}$ is H.

Table 1296. Compounds of formula I.17 wherein $R^1$ is Y-8B, $R^2$ is $CH_3$, $R^9$ is $CH_3$ and $R^{10}$ is $CH_3$.

Table 1297. Compounds of formula I.17 wherein $R^1$ is Y-1A, $R^2$ is $C_2H_5$, $R^9$ is H and $R^{10}$ is H.

Table 1298. Compounds of formula I.17 wherein $R^1$ is Y-1A, $R^2$ is $C_2H_5$, $R^9$ is $CH_3$ and $R^{10}$ is H.

Table 1299. Compounds of formula I.17 wherein $R^1$ is Y-1A, $R^2$ is $C_2H_5$, $R^9$ is $CH_3$ and $R^{10}$ is $CH_3$.

Table 1300. Compounds of formula I.17 wherein $R^1$ is Y-1B, $R^2$ is $C_2H_5$, $R^9$ is H and $R^{10}$ is H.

Table 1301. Compounds of formula I.17 wherein $R^1$ is Y-1B, $R^2$ is $C_2H_5$, $R^9$ is $CH_3$ and $R^{10}$ is H.

Table 1302. Compounds of formula I.17 wherein $R^1$ is Y-1B, $R^2$ is $C_2H_5$, $R^9$ is $CH_3$ and $R^{10}$ is $CH_3$.

Table 1303. Compounds of formula I.17 wherein $R^1$ is Y-2A, $R^2$ is $C_2H_5$, $R^9$ is H and $R^{10}$ is H.

Table 1304. Compounds of formula I.17 wherein $R^1$ is Y-2A, $R^2$ is $C_2H_5$, $R^9$ is $CH_3$ and $R^{10}$ is H.

Table 1305. Compounds of formula I.17 wherein $R^1$ is Y-2A, $R^2$ is $C_2H_5$, $R^9$ is $CH_3$ and $R^{10}$ is $CH_3$.

Table 1306. Compounds of formula I.17 wherein $R^1$ is Y-2B, $R^2$ is $C_2H_5$, $R^9$ is H and $R^{10}$ is H.

Table 1307. Compounds of formula I.17 wherein $R^1$ is Y-2B, $R^2$ is $C_2H_5$, $R^9$ is $CH_3$ and $R^{10}$ is H.

Table 1308. Compounds of formula I.17 wherein $R^1$ is Y-2B, $R^2$ is $C_2H_5$, $R^9$ is $CH_3$ and $R^{10}$ is $CH_3$.

Table 1309. Compounds of formula I.17 wherein $R^1$ is Y-3A, $R^2$ is $C_2H_5$, $R^9$ is H and $R^{10}$ is H.

Table 1310. Compounds of formula I.17 wherein $R^1$ is Y-3A, $R^2$ is $C_2H_5$, $R^9$ is $CH_3$ and $R^{10}$ is H.

Table 1311. Compounds of formula I.17 wherein $R^1$ is Y-3A, $R^2$ is $C_2H_5$, $R^9$ is $CH_3$ and $R^{10}$ is $CH_3$.

Table 1312. Compounds of formula I.17 wherein $R^1$ is Y-3B, $R^2$ is $C_2H_5$, $R^9$ is H and $R^{10}$ is H.

Table 1313. Compounds of formula I.17 wherein $R^1$ is Y-3B, $R^2$ is $C_2H_5$, $R^9$ is $CH_3$ and $R^{10}$ is H.

Table 1314. Compounds of formula I.17 wherein $R^1$ is Y-3B, $R^2$ is $C_2H_5$, $R^9$ is $CH_3$ and $R^{10}$ is $CH_3$.

Table 1315. Compounds of formula I.17 wherein $R^1$ is Y-3C, $R^2$ is $C_2H_5$, $R^9$ is H and $R^{10}$ is H.

Table 1316. Compounds of formula I.17 wherein $R^1$ is Y-3C, $R^2$ is $C_2H_5$, $R^9$ is $CH_3$ and $R^{10}$ is H.

Table 1317. Compounds of formula I.17 wherein $R^1$ is Y-3C, $R^2$ is $C_2H_5$, $R^9$ is $CH_3$ and $R^{10}$ is $CH_3$.

Table 1318. Compounds of formula I.17 wherein $R^1$ is Y-3D, $R^2$ is $C_2H_5$, $R^9$ is H and $R^{10}$ is H.

Table 1319. Compounds of formula I.17 wherein $R^1$ is Y-3D, $R^2$ is $C_2H_5$, $R^9$ is $CH_3$ and $R^{10}$ is H.

Table 1320. Compounds of formula I.17 wherein $R^1$ is Y-3D, $R^2$ is $C_2H_5$, $R^9$ is $CH_3$ and $R^{10}$ is $CH_3$.

Table 1321. Compounds of formula I.17 wherein $R^1$ is Y-4A, $R^2$ is $C_2H_5$, $R^9$ is H and $R^{10}$ is H.

Table 1322. Compounds of formula I.17 wherein $R^1$ is Y-4A, $R^2$ is $C_2H_5$, $R^9$ is $CH_3$ and $R^{10}$ is H.

Table 1323. Compounds of formula I.17 wherein $R^1$ is Y-4A, $R^2$ is $C_2H_5$, $R^9$ is $CH_3$ and $R^{10}$ is $CH_3$.

Table 1324. Compounds of formula I.17 wherein $R^1$ is Y-4B, $R^2$ is $C_2H_5$, $R^9$ is H and $R^{10}$ is H.

Table 1325. Compounds of formula I.17 wherein $R^1$ is Y-4B, $R^2$ is $C_2H_5$, $R^9$ is $CH_3$ and $R^{10}$ is H.

Table 1326. Compounds of formula I.17 wherein $R^1$ is Y-4B, $R^2$ is $C_2H_5$, $R^9$ is $CH_3$ and $R^{10}$ is $CH_3$.

Table 1327. Compounds of formula I.17 wherein $R^1$ is Y-4C, $R^2$ is $C_2H_5$, $R^9$ is H and $R^{10}$ is H.

Table 1328. Compounds of formula I.17 wherein $R^1$ is Y-4C, $R^2$ is $C_2H_5$, $R^9$ is $CH_3$ and $R^{10}$ is H.

Table 1329. Compounds of formula I.17 wherein $R^1$ is Y-4C, $R^2$ is $C_2H_5$, $R^9$ is $CH_3$ and $R^{10}$ is $CH_3$.

Table 1330. Compounds of formula I.17 wherein $R^1$ is Y-4D, $R^2$ is $C_2H_5$, $R^9$ is H and $R^{10}$ is H.

Table 1331. Compounds of formula I.17 wherein $R^1$ is Y-4D, $R^2$ is $C_2H_5$, $R^9$ is $CH_3$ and $R^{10}$ is H.

Table 1332. Compounds of formula I.17 wherein $R^1$ is Y-4D, $R^2$ is $C_2H_5$, $R^9$ is $CH_3$ and $R^{10}$ is $CH_3$.

Table 1333. Compounds of formula I.17 wherein $R^1$ is Y-5A, $R^2$ is $C_2H_5$, $R^9$ is H and $R^{10}$ is H. Table 1334. Compounds of formula I.17 wherein $R^1$ is Y-5A, $R^2$ is $C_2H_5$, $R^9$ is $CH_3$ and $R^{10}$ is H.

Table 1335. Compounds of formula I.17 wherein $R^1$ is Y-5A, $R^2$ is $C_2H_5$, $R^9$ is $CH_3$ and $R^{10}$ is $CH_3$.

Table 1336. Compounds of formula I.17 wherein $R^1$ is Y-5B, $R^2$ is $C_2H_5$, $R^9$ is H and $R^{10}$ is H.

Table 1337. Compounds of formula I.17 wherein $R^1$ is Y-5B, $R^2$ is $C_2H_5$, $R^9$ is $CH_3$ and $R^{10}$ is H.

Table 1338. Compounds of formula I.17 wherein $R^1$ is Y-5B, $R^2$ is $C_2H_5$, $R^9$ is $CH_3$ and $R^{10}$ is $CH_3$.

Table 1339. Compounds of formula I.17 wherein $R^1$ is Y-6A, $R^2$ is $C_2H_5$, $R^9$ is H and $R^{10}$ is H.

Table 1340. Compounds of formula I.17 wherein $R^1$ is Y-6A, $R^2$ is $C_2H_5$, $R^9$ is $CH_3$ and $R^{10}$ is H.

Table 1341. Compounds of formula I.17 wherein $R^1$ is Y-6A, $R^2$ is $C_2H_5$, $R^9$ is $CH_3$ and $R^{10}$ is $CH_3$.

Table 1342. Compounds of formula I.17 wherein $R^1$ is Y-6B, $R^2$ is $C_2H_5$, $R^9$ is H and $R^{10}$ is H.

Table 1343. Compounds of formula I.17 wherein $R^1$ is Y-6B, $R^2$ is $C_2H_5$, $R^9$ is $CH_3$ and $R^{10}$ is H.

Table 1344. Compounds of formula I.17 wherein $R^1$ is Y-6B, $R^2$ is $C_2H_5$, $R^9$ is $CH_3$ and $R^{10}$ is $CH_3$.

Table 1345. Compounds of formula I.17 wherein $R^1$ is Y-8A, $R^2$ is $C_2H_5$, $R^9$ is H and $R^{10}$ is H.

Table 1346. Compounds of formula I.17 wherein $R^1$ is Y-8A, $R^2$ is $C_2H_5$, $R^9$ is $CH_3$ and $R^{10}$ is H.

Table 1347. Compounds of formula I.17 wherein $R^1$ is Y-8A, $R^2$ is $C_2H_5$, $R^9$ is $CH_3$ and $R^{10}$ is $CH_3$.

Table 1348. Compounds of formula I.17 wherein $R^1$ is Y-8B, $R^2$ is $C_2H_5$, $R^9$ is H and $R^{10}$ is H.

Table 1349. Compounds of formula I.17 wherein $R^1$ is Y-8B, $R^2$ is $C_2H_5$, $R^9$ is $CH_3$ and $R^{10}$ is H.

Table 1350. Compounds of formula I.17 wherein $R^1$ is Y-8B, $R^2$ is $C_2H_5$, $R^9$ is $CH_3$ and $R^{10}$ is $CH_3$.

Table 1351. Compounds of formula I.17 wherein $R^1$ is Y-1A, $R^2$ is c-$C_3H_5$, $R^9$ is H and $R^{10}$ is H.

Table 1352. Compounds of formula I.17 wherein $R^1$ is Y-1A, $R^2$ is c-$C_3H_5$, $R^9$ is $CH_3$ and $R^{10}$ is H.

Table 1353. Compounds of formula I.17 wherein $R^1$ is Y-1A, $R^2$ is c-$C_3H_5$, $R^9$ is $CH_3$ and $R^{10}$ is $CH_3$.

Table 1354. Compounds of formula I.17 wherein $R^1$ is Y-1B, $R^2$ is c-$C_3H_5$, $R^9$ is H and $R^{10}$ is H.

Table 1355. Compounds of formula I.17 wherein $R^1$ is Y-1B, $R^2$ is c-$C_3H_5$, $R^9$ is $CH_3$, $R^{10}$ is H.

Table 1356. Compounds of formula I.17 wherein $R^1$ is Y-1B, $R^2$ is c-$C_3H_5$, $R^9$ is $CH_3$ and $R^{10}$ is $CH_3$.

Table 1357. Compounds of formula I.17 wherein $R^1$ is Y-2A, $R^2$ is c-$C_3H_5$, $R^9$ is H and $R^{10}$ is H.

Table 1358. Compounds of formula I.17 wherein $R^1$ is Y-2A, $R^2$ is c-$C_3H_5$, $R^9$ is $CH_3$ and $R^{10}$ is H.

Table 1359. Compounds of formula I.17 wherein $R^1$ is Y-2A, $R^2$ is c-$C_3H_5$, $R^9$ is $CH_3$ and $R^{10}$ is $CH_3$.

Table 1360. Compounds of formula I.17 wherein $R^1$ is Y-2B, $R^2$ is c-$C_3H_5$, $R^9$ is H and $R^{10}$ is H.

Table 1361. Compounds of formula I.17 wherein $R^1$ is Y-2B, $R^2$ is c-$C_3H_5$, $R^9$ is $CH_3$ and $R^{10}$ is H.

Table 1362. Compounds of formula I.17 wherein $R^1$ is Y-2B, $R^2$ is c-$C_3H_5$, $R^9$ is $CH_3$ and $R^{10}$ is $CH_3$.

Table 1363. Compounds of formula I.17 wherein $R^1$ is Y-3A, $R^2$ is c-$C_3H_5$, $R^9$ is H and $R^{10}$ is H.

Table 1364. Compounds of formula I.17 wherein $R^1$ is Y-3A, $R^2$ is c-$C_3H_5$, $R^9$ is $CH_3$ and $R^{10}$ is H.

Table 1365. Compounds of formula I.17 wherein $R^1$ is Y-3A, $R^2$ is c-$C_3H_5$, $R^9$ is $CH_3$ and $R^{10}$ is $CH_3$.

Table 1366. Compounds of formula I.17 wherein $R^1$ is Y-3B, $R^2$ is c-$C_3H_5$, $R^9$ is H and $R^{10}$ is H.

Table 1367. Compounds of formula I.17 wherein $R^1$ is Y-3B, $R^2$ is c-$C_3H_5$, $R^9$ is $CH_3$ and $R^{10}$ is H.

Table 1368. Compounds of formula I.17 wherein $R^1$ is Y-3B, $R^2$ is c-$C_3H_5$, $R^9$ is $CH_3$ and $R^{10}$ is $CH_3$.

Table 1369. Compounds of formula I.17 wherein $R^1$ is Y-3C, $R^2$ is c-$C_3H_5$, $R^9$ is H and $R^{10}$ is H.

Table 1370. Compounds of formula I.17 wherein $R^1$ is Y-3C, $R^2$ is c-$C_3H_5$, $R^9$ is $CH_3$ and $R^{10}$ is H.

Table 1371. Compounds of formula I.17 wherein $R^1$ is Y-3C, $R^2$ is c-$C_3H_5$, $R^9$ is $CH_3$ and $R^{10}$ is $CH_3$.

Table 1372. Compounds of formula I.17 wherein $R^1$ is Y-3D, $R^2$ is c-$C_3H_5$, $R^9$ is H and $R^{10}$ is H.

Table 1373. Compounds of formula I.17 wherein $R^1$ is Y-3D, $R^2$ is c-$C_3H_5$, $R^9$ is $CH_3$ and $R^{10}$ is H.

Table 1374. Compounds of formula I.17 wherein $R^1$ is Y-3D, $R^2$ is c-$C_3H_5$, $R^9$ is $CH_3$ and $R^{10}$ is $CH_3$.

Table 1375. Compounds of formula I.17 wherein $R^1$ is Y-4A, $R^2$ is c-$C_3H_5$, $R^9$ is H and $R^{10}$ is H.

Table 1376. Compounds of formula I.17 wherein $R^1$ is Y-4A, $R^2$ is c-$C_3H_5$, $R^9$ is $CH_3$ and $R^{10}$ is H.

Table 1377. Compounds of formula I.17 wherein $R^1$ is Y-4A, $R^2$ is c-$C_3H_5$, $R^9$ is $CH_3$ and $R^{10}$ is $CH_3$.

Table 1378. Compounds of formula I.17 wherein $R^1$ is Y-4B, $R^2$ is c-$C_3H_5$, $R^9$ is H and $R^{10}$ is H.

Table 1379. Compounds of formula I.17 wherein $R^1$ is Y-4B, $R^2$ is c-$C_3H_5$, $R^9$ is $CH_3$ and $R^{10}$ is H.

Table 1380. Compounds of formula I.17 wherein $R^1$ is Y-4B, $R^2$ is c-$C_3H_5$, $R^9$ is $CH_3$ and $R^{10}$ is $CH_3$.

Table 1381. Compounds of formula I.17 wherein $R^1$ is Y-4C, $R^2$ is c-$C_3H_5$, $R^9$ is H and $R^{10}$ is H.

Table 1382. Compounds of formula I.17 wherein $R^1$ is Y-4C, $R^2$ is c-$C_3H_5$, $R^9$ is $CH_3$ and $R^{10}$ is H.

Table 1383. Compounds of formula I.17 wherein $R^1$ is Y-4C, $R^2$ is c-$C_3H_5$, $R^9$ is $CH_3$ and $R^{10}$ is $CH_3$.

Table 1384. Compounds of formula I.17 wherein $R^1$ is Y-4D, $R^2$ is c-$C_3H_5$, $R^9$ is H and $R^{10}$ is H.

Table 1385. Compounds of formula I.17 wherein $R^1$ is Y-4D, $R^2$ is c-$C_3H_5$, $R^9$ is $CH_3$ and $R^{10}$ is H.

Table 1386. Compounds of formula I.17 wherein $R^1$ is Y-4D, $R^2$ is c-$C_3H_5$, $R^9$ is $CH_3$ and $R^{10}$ is $CH_3$.

Table 1387. Compounds of formula I.17 wherein $R^1$ is Y-5A, $R^2$ is c-$C_3H_5$, $R^9$ is H and $R^{10}$ is H.

Table 1388. Compounds of formula I.17 wherein $R^1$ is Y-5A, $R^2$ is c-$C_3H_5$, $R^9$ is $CH_3$ and $R^{10}$ is H.

Table 1389. Compounds of formula I.17 wherein $R^1$ is Y-5A, $R^2$ is c-$C_3H_5$, $R^9$ is $CH_3$ and $R^{10}$ is $CH_3$.

Table 1390. Compounds of formula I.17 wherein $R^1$ is Y-5B, $R^2$ is c-$C_3H_5$, $R^9$ is H and $R^{10}$ is H.

Table 1391. Compounds of formula I.17 wherein $R^1$ is Y-5B, $R^2$ is c-$C_3H_5$, $R^9$ is $CH_3$ and $R^{10}$ is H.

Table 1392. Compounds of formula I.17 wherein $R^1$ is Y-5B, $R^2$ is c-$C_3H_5$, $R^9$ is $CH_3$ and $R^{10}$ is $CH_3$.

Table 1393. Compounds of formula I.17 wherein $R^1$ is Y-6A, $R^2$ is c-$C_3H_5$, $R^9$ is H and $R^{10}$ is H.

Table 1394. Compounds of formula I.17 wherein $R^1$ is Y-6A, $R^2$ is c-$C_3H_5$, $R^9$ is $CH_3$ and $R^{10}$ is H.

Table 1395. Compounds of formula I.17 wherein $R^1$ is Y-6A, $R^2$ is c-$C_3H_5$, $R^9$ is $CH_3$ and $R^{10}$ is $CH_3$.

Table 1396. Compounds of formula I.17 wherein $R^1$ is Y-6B, $R^2$ is c-$C_3H_5$, $R^9$ is H and $R^{10}$ is H.

Table 1397. Compounds of formula I.17 wherein $R^1$ is Y-6B, $R^2$ is c-$C_3H_5$, $R^9$ is $CH_3$ and $R^{10}$ is H.

Table 1398. Compounds of formula I.17 wherein $R^1$ is Y-6B, $R^2$ is c-$C_3H_5$, $R^9$ is $CH_3$ and $R^{10}$ is $CH_3$.

Table 1399. Compounds of formula I.17 wherein $R^1$ is Y-8A, $R^2$ is c-$C_3H_5$, $R^9$ is H and $R^{10}$ is H.

Table 1400. Compounds of formula I.17 wherein $R^1$ is Y-8A, $R^2$ is c-$C_3H_5$, $R^9$ is $CH_3$ and $R^{10}$ is H.

Table 1401. Compounds of formula I.17 wherein $R^1$ is Y-8A, $R^2$ is c-$C_3H_5$, $R^9$ is $CH_3$ and $R^{10}$ is $CH_3$.

Table 1402. Compounds of formula I.17 wherein $R^1$ is Y-8B, $R^2$ is c-$C_3H_5$, $R^9$ is H and $R^{10}$ is H.

Table 1403. Compounds of formula I.17 wherein $R^1$ is Y-8B, $R^2$ is c-$C_3H_5$, $R^9$ is $CH_3$ and $R^{10}$ is H.

Table 1404. Compounds of formula I.17 wherein $R^1$ is Y-8B, $R^2$ is c-$C_3H_5$, $R^9$ is $CH_3$ and $R^{10}$ is $CH_3$.

Table 1405. Compounds of formula I.18 wherein $R^1$ is Y-1A, $R^2$ is H, $R^9$ is H and $R^{10}$ is H.

Table 1406. Compounds of formula I.18 wherein $R^1$ is Y-1A, $R^2$ is H, $R^9$ is $CH_3$ and, $R^{10}$ is H.

Table 1407. Compounds of formula I.18 wherein $R^1$ is Y-1A, $R^2$ is H, $R^9$ is $CH_3$ and $R^{10}$ is $CH_3$.

Table 1408. Compounds of formula I.18 wherein $R^1$ is Y-1B, $R^2$ is H, $R^9$ is H and $R^{10}$ is H.

Table 1409. Compounds of formula I.18 wherein $R^1$ is Y-1B, $R^2$ is H, $R^9$ is $CH_3$ and $R^{10}$ is H.

Table 1410. Compounds of formula I.18 wherein $R^1$ is Y-1B, $R^2$ is H, $R^9$ is $CH_3$ and $R^{10}$ is $CH_3$.

Table 1411. Compounds of formula I.18 wherein $R^1$ is Y-2A, $R^2$ is H, $R^9$ is H and $R^{10}$ is H.

Table 1412. Compounds of formula I.18 wherein $R^1$ is Y-2A, $R^2$ is H, $R^9$ is $CH_3$ and $R^{10}$ is H.

Table 1413. Compounds of formula I.18 wherein $R^1$ is Y-2A, $R^2$ is H, $R^9$ is $CH_3$ and $R^{10}$ is $CH_3$.

Table 1414. Compounds of formula I.18 wherein $R^1$ is Y-2B, $R^2$ is H, $R^9$ is H and $R^{10}$ is H.

Table 1415. Compounds of formula I.18 wherein $R^1$ is Y-2B, $R^2$ is H, $R^9$ is $CH_3$ and $R^{10}$ is H.

Table 1416. Compounds of formula I.18 wherein $R^1$ is Y-2B, $R^2$ is H, $R^9$ is $CH_3$ and $R^{10}$ is $CH_3$.

Table 1417. Compounds of formula I.18 wherein $R^1$ is Y-3A, $R^2$ is H, $R^9$ is H and $R^{10}$ is H.

Table 1418. Compounds of formula I.18 wherein $R^1$ is Y-3A, $R^2$ is H, $R^9$ is $CH_3$ and $R^{10}$ is H.

Table 1419. Compounds of formula I.18 wherein $R^1$ is Y-3A, $R^2$ is H, $R^9$ is $CH_3$ and $R^{10}$ is $CH_3$.

Table 1420. Compounds of formula I.18 wherein $R^1$ is Y-3B, $R^2$ is H, $R^9$ is H and $R^{10}$ is H.

Table 1421. Compounds of formula I.18 wherein $R^1$ is Y-3B, $R^2$ is H, $R^9$ is $CH_3$ and $R^{10}$ is H.

Table 1422. Compounds of formula I.18 wherein $R^1$ is Y-3B, $R^2$ is H, $R^9$ is $CH_3$ and $R^{10}$ is $CH_3$.

Table 1423. Compounds of formula I.18 wherein $R^1$ is Y-3C, $R^2$ is H, $R^9$ is H and $R^{10}$ is H.

Table 1424. Compounds of formula I.18 wherein $R^1$ is Y-3C, $R^2$ is H, $R^9$ is $CH_3$ and $R^{10}$ is H.

Table 1425. Compounds of formula I.18 wherein $R^1$ is Y-3C, $R^2$ is H, $R^9$ is $CH_3$ and $R^{10}$ is $CH_3$.

Table 1426. Compounds of formula I.18 wherein $R^1$ is Y-3D, $R^2$ is H, $R^9$ is H and $R^{10}$ is H.

Table 1427. Compounds of formula I.18 wherein $R^1$ is Y-3D, $R^2$ is H, $R^9$ is $CH_3$ and $R^{10}$ is H.

Table 1428. Compounds of formula I.18 wherein $R^1$ is Y-3D, $R^2$ is H, $R^9$ is $CH_3$ and $R^{10}$ is $CH_3$.

Table 1429. Compounds of formula I.18 wherein $R^1$ is Y-4A, $R^2$ is H, $R^9$ is H and $R^{10}$ is H.

Table 1430. Compounds of formula I.18 wherein $R^1$ is Y-4A, $R^2$ is H, $R^9$ is $CH_3$ and $R^{10}$ is H.

Table 1431. Compounds of formula I.18 wherein $R^1$ is Y-4A, $R^2$ is H, $R^9$ is $CH_3$ and $R^{10}$ is $CH_3$.

Table 1432. Compounds of formula I.18 wherein $R^1$ is Y-4B, $R^2$ is H, $R^9$ is H and $R^{10}$ is H.

Table 1433. Compounds of formula I.18 wherein $R^1$ is Y-4B, $R^2$ is H, $R^9$ is $CH_3$ and $R^{10}$ is H.

Table 1434. Compounds of formula I.18 wherein $R^1$ is Y-4B, $R^2$ is H, $R^9$ is $CH_3$ and $R^{10}$ is $CH_3$.

Table 1435. Compounds of formula I.18 wherein $R^1$ is Y-4C, $R^2$ is H, $R^9$ is H and $R^{10}$ is H.

Table 1436. Compounds of formula I.18 wherein $R^1$ is Y-4C, $R^2$ is H, $R^9$ is $CH_3$ and $R^{10}$ is H.

Table 1437. Compounds of formula I.18 wherein $R^1$ is Y-4C, $R^2$ is H, $R^9$ is $CH_3$ and $R^{10}$ is $CH_3$.

Table 1438. Compounds of formula I.18 wherein $R^1$ is Y-4D, $R^2$ is H, $R^9$ is H and $R^{10}$ is H.

Table 1439. Compounds of formula I.18 wherein $R^1$ is Y-4D, $R^2$ is H, $R^9$ is $CH_3$ and $R^{10}$ is H.

Table 1440. Compounds of formula I.18 wherein $R^1$ is Y-4D, $R^2$ is H, $R^9$ is $CH_3$ and $R^{10}$ is $CH_3$.

Table 1441. Compounds of formula I.18 wherein $R^1$ is Y-5A, $R^2$ is H, $R^9$ is H and $R^{10}$ is H.

Table 1442. Compounds of formula I.18 wherein $R^1$ is Y-5A, $R^2$ is H, $R^9$ is $CH_3$ and $R^{10}$ is H.

Table 1443. Compounds of formula I.18 wherein $R^1$ is Y-5A, $R^2$ is H, $R^9$ is $CH_3$ and $R^{10}$ is $CH_3$.

Table 1444. Compounds of formula I.18 wherein $R^1$ is Y-5B, $R^2$ is H, $R^9$ is H and $R^{10}$ is H.

Table 1445. Compounds of formula I.18 wherein $R^1$ is Y-5B, $R^2$ is H, $R^9$ is $CH_3$ and $R^{10}$ is H.

Table 1446. Compounds of formula I.18 wherein $R^1$ is Y-5B, $R^2$ is H, $R^9$ is $CH_3$ and $R^{10}$ is $CH_3$.

Table 1447. Compounds of formula I.18 wherein $R^1$ is Y-6A, $R^2$ is H, $R^9$ is H and $R^{10}$ is H.

Table 1448. Compounds of formula I.18 wherein $R^1$ is Y-6A, $R^2$ is H, $R^9$ is $CH_3$ and $R^{10}$ is H.

Table 1449. Compounds of formula I.18 wherein $R^1$ is Y-6A, $R^2$ is H, $R^9$ is $CH_3$ and $R^{10}$ is $CH_3$.

Table 1450. Compounds of formula I.18 wherein $R^1$ is Y-6B, $R^2$ is H, $R^9$ is H and $R^{10}$ is H.

Table 1451. Compounds of formula I.18 wherein $R^1$ is Y-6B, $R^2$ is H, $R^9$ is $CH_3$ and $R^{10}$ is H.

Table 1452. Compounds of formula I.18 wherein $R^1$ is Y-6B, $R^2$ is H, $R^9$ is $CH_3$ and $R^{10}$ is $CH_3$.

Table 1453. Compounds of formula I.18 wherein $R^1$ is Y-8A, $R^2$ is H, $R^9$ is H and $R^{10}$ is H.

Table 1454. Compounds of formula I.18 wherein $R^1$ is Y-8A, $R^2$ is H, $R^9$ is $CH_3$ and $R^{10}$ is H.

Table 1455. Compounds of formula I.18 wherein $R^1$ is Y-8A, $R^2$ is H, $R^9$ is $CH_3$ and $R^{10}$ is $CH_3$.

Table 1456. Compounds of formula I.18 wherein $R^1$ is Y-8B, $R^2$ is H, $R^9$ is H and $R^{10}$ is H.

Table 1457. Compounds of formula I.18 wherein $R^1$ is Y-8B, $R^2$ is H, $R^9$ is $CH_3$ and $R^{10}$ is H.

Table 1458. Compounds of formula I.18 wherein $R^1$ is Y-8B, $R^2$ is H, $R^9$ is $CH_3$ and $R^{10}$ is $CH_3$.

Table 1459. Compounds of formula I.18 wherein $R^1$ is Y-1A, $R^2$ is $CH_3$, $R^9$ is H and $R^{10}$ is H.

Table 1460. Compounds of formula I.18 wherein $R^1$ is Y-1A, $R^2$ is $CH_3$, $R^9$ is $CH_3$ and $R^{10}$ is H.

Table 1461. Compounds of formula I.18 wherein $R^1$ is Y-1A, $R^2$ is $CH_3$, $R^9$ is $CH_3$ and $R^{10}$ is $CH_3$.

Table 1462. Compounds of formula I.18 wherein $R^1$ is Y-1B, $R^2$ is $CH_3$, $R^9$ is H and $R^{10}$ is H.

Table 1463. Compounds of formula I.18 wherein $R^1$ is Y-1B, $R^2$ is $CH_3$, $R^9$ is $CH_3$ and $R^{10}$ is H.

Table 1464. Compounds of formula I.18 wherein $R^1$ is Y-1B, $R^2$ is $CH_3$, $R^9$ is $CH_3$ and $R^{10}$ is $CH_3$.

Table 1465. Compounds of formula I.18 wherein $R^1$ is Y-2A, $R^2$ is $CH_3$, $R^9$ is H and $R^{10}$ is H.

Table 1466. Compounds of formula I.18 wherein $R^1$ is Y-2A, $R^2$ is $CH_3$, $R^9$ is $CH_3$ and $R^{10}$ is H.

Table 1467. Compounds of formula I.18 wherein $R^1$ is Y-2A, $R^2$ is $CH_3$, $R^9$ is $CH_3$ and $R^{10}$ is $CH_3$.

Table 1468. Compounds of formula I.18 wherein $R^1$ is Y-2B, $R^2$ is $CH_3$, $R^9$ is H and $R^{10}$ is H.

Table 1469. Compounds of formula I.18 wherein $R^1$ is Y-2B, $R^2$ is $CH_3$, $R^9$ is $CH_3$ and $R^{10}$ is H.

Table 1470. Compounds of formula I.18 wherein $R^1$ is Y-2B, $R^2$ is $CH_3$, $R^9$ is $CH_3$ and $R^{10}$ is $CH_3$.

Table 1471. Compounds of formula I.18 wherein $R^1$ is Y-3A, $R^2$ is $CH_3$, $R^9$ is H and $R^{10}$ is H.

Table 1472. Compounds of formula I.18 wherein $R^1$ is Y-3A, $R^2$ is $CH_3$, $R^9$ is $CH_3$ and $R^{10}$ is H.

Table 1473. Compounds of formula I.18 wherein $R^1$ is Y-3A, $R^2$ is $CH_3$, $R^9$ is $CH_3$ and $R^{10}$ is $CH_3$.

Table 1474. Compounds of formula I.18 wherein $R^1$ is Y-3B, $R^2$ is $CH_3$, $R^9$ is H and $R^{10}$ is H.

Table 1475. Compounds of formula I.18 wherein $R^1$ is Y-3B, $R^2$ is $CH_3$, $R^9$ is $CH_3$ and $R^{10}$ is H.

Table 1476. Compounds of formula I.18 wherein $R^1$ is Y-3B, $R^2$ is $CH_3$, $R^9$ is $CH_3$ and $R^{10}$ is $CH_3$.

Table 1477. Compounds of formula I.18 wherein $R^1$ is Y-3C, $R^2$ is $CH_3$, $R^9$ is H and $R^{10}$ is H.

Table 1478. Compounds of formula I.18 wherein $R^1$ is Y-3C, $R^2$ is $CH_3$, $R^9$ is $CH_3$ and $R^{10}$ is H.

Table 1479. Compounds of formula I.18 wherein $R^1$ is Y-3C, $R^2$ is $CH_3$, $R^9$ is $CH_3$ and $R^{10}$ is $CH_3$.

Table 1480. Compounds of formula I.18 wherein $R^1$ is Y-3D, $R^2$ is $CH_3$, $R^9$ is H and $R^{10}$ is H.

Table 1481. Compounds of formula I.18 wherein $R^1$ is Y-3D, $R^2$ is $CH_3$, $R^9$ is $CH_3$ and $R^{10}$ is H.

Table 1482. Compounds of formula I.18 wherein $R^1$ is Y-3D, $R^2$ is $CH_3$, $R^9$ is $CH_3$ and $R^{10}$ is $CH_3$.

Table 1483. Compounds of formula I.18 wherein $R^1$ is Y-4A, $R^2$ is $CH_3$, $R^9$ is H and $R^{10}$ is H.

Table 1484. Compounds of formula I.18 wherein $R^1$ is Y-4A, $R^2$ is $CH_3$, $R^9$ is $CH_3$ and $R^{10}$ is H.

Table 1485. Compounds of formula I.18 wherein $R^1$ is Y-4A, $R^2$ is $CH_3$, $R^9$ is $CH_3$ and $R^{10}$ is $CH_3$.

Table 1486. Compounds of formula I.18 wherein $R^1$ is Y-4B, $R^2$ is $CH_3$, $R^9$ is H and $R^{10}$ is H.

Table 1487. Compounds of formula I.18 wherein $R^1$ is Y-4B, $R^2$ is $CH_3$, $R^9$ is $CH_3$ and $R^{10}$ is H.

Table 1488. Compounds of formula I.18 wherein $R^1$ is Y-4B, $R^2$ is $CH_3$, $R^9$ is $CH_3$ and $R^{10}$ is $CH_3$.

Table 1489. Compounds of formula I.18 wherein $R^1$ is Y-4C, $R^2$ is $CH_3$, $R^9$ is H and $R^{10}$ is H.

Table 1490. Compounds of formula I.18 wherein $R^1$ is Y-4C, $R^2$ is $CH_3$, $R^9$ is $CH_3$ and $R^{10}$ is H.

Table 1491. Compounds of formula I.18 wherein $R^1$ is Y-4C, $R^2$ is $CH_3$, $R^9$ is $CH_3$ and $R^{10}$ is $CH_3$.

Table 1492. Compounds of formula I.18 wherein $R^1$ is Y-4D, $R^2$ is $CH_3$, $R^9$ is H and $R^{10}$ is H.

Table 1493. Compounds of formula I.18 wherein $R^1$ is Y-4D, $R^2$ is $CH_3$, $R^9$ is $CH_3$ and $R^{10}$ is H.

Table 1494. Compounds of formula I.18 wherein $R^1$ is Y-4D, $R^2$ is $CH_3$, $R^9$ is $CH_3$ and $R^{10}$ is $CH_3$.

Table 1495. Compounds of formula I.18 wherein $R^1$ is Y-5A, $R^2$ is $CH_3$, $R^9$ is H and $R^{10}$ is H.

Table 1496. Compounds of formula I.18 wherein $R^1$ is Y-5A, $R^2$ is $CH_3$, $R^9$ is $CH_3$ and $R^{10}$ is H.

Table 1497. Compounds of formula I.18 wherein $R^1$ is Y-5A, $R^2$ is $CH_3$, $R^9$ is $CH_3$ and $R^{10}$ is $CH_3$.

Table 1498. Compounds of formula I.18 wherein $R^1$ is Y-5B, $R^2$ is $CH_3$, $R^9$ is H and $R^{10}$ is H.

Table 1499. Compounds of formula I.18 wherein $R^1$ is Y-5B, $R^2$ is $CH_3$, $R^9$ is $CH_3$ and $R^{10}$ is H.

Table 1500. Compounds of formula I.18 wherein $R^1$ is Y-5B, $R^2$ is $CH_3$, $R^9$ is $CH_3$ and $R^{10}$ is $CH_3$.

Table 1501. Compounds of formula I.18 wherein $R^1$ is Y-6A, $R^2$ is $CH_3$, $R^9$ is H and $R^{10}$ is H.

Table 1502. Compounds of formula I.18 wherein $R^1$ is Y-6A, $R^2$ is $CH_3$, $R^9$ is $CH_3$ and $R^{10}$ is H.

Table 1503. Compounds of formula I.18 wherein $R^1$ is Y-6A, $R^2$ is $CH_3$, $R^9$ is $CH_3$ and $R^{10}$ is $CH_3$.

Table 1504. Compounds of formula I.18 wherein $R^1$ is Y-6B, $R^2$ is $CH_3$, $R^9$ is H and $R^{10}$ is H.

Table 1505. Compounds of formula I.18 wherein $R^1$ is Y-6B, $R^2$ is $CH_3$, $R^9$ is $CH_3$ and $R^{10}$ is H.

Table 1506. Compounds of formula I.18 wherein $R^1$ is Y-6B, $R^2$ is $CH_3$, $R^9$ is $CH_3$ and $R^{10}$ is $CH_3$.

Table 1507. Compounds of formula I.18 wherein $R^1$ is Y-8A, $R^2$ is $CH_3$, $R^9$ is H and $R^{10}$ is H.

Table 1508. Compounds of formula I.18 wherein $R^1$ is Y-8A, $R^2$ is $CH_3$, $R^9$ is $CH_3$ and $R^{10}$ is H.

Table 1509. Compounds of formula I.18 wherein $R^1$ is Y-8A, $R^2$ is $CH_3$, $R^9$ is $CH_3$ and $R^{10}$ is $CH_3$.

Table 1510. Compounds of formula I.18 wherein $R^1$ is Y-8B, $R^2$ is $CH_3$, $R^9$ is H and $R^{10}$ is H.

Table 1511. Compounds of formula I.18 wherein $R^1$ is Y-8B, $R^2$ is $CH_3$, $R^9$ is $CH_3$ and $R^{10}$ is H.

Table 1512. Compounds of formula I.18 wherein $R^1$ is Y-8B, $R^2$ is $CH_3$, $R^9$ is $CH_3$ and $R^{10}$ is $CH_3$.

Table 1513. Compounds of formula I.18 wherein $R^1$ is Y-1A, $R^2$ is $C_2H_5$, $R^9$ is H and $R^{10}$ is H.

Table 1514. Compounds of formula I.18 wherein $R^1$ is Y-1A, $R^2$ is $C_2H_5$, $R^9$ is $CH_3$ and $R^{10}$ is H.

Table 1515. Compounds of formula I.18 wherein $R^1$ is Y-1A, $R^2$ is $C_2H_5$, $R^9$ is $CH_3$ and $R^{10}$ is $CH_3$.

Table 1516. Compounds of formula I.18 wherein $R^1$ is Y-1B, $R^2$ is $C_2H_5$, $R^9$ is H and $R^{10}$ is H.

Table 1517. Compounds of formula I.18 wherein $R^1$ is Y-1B, $R^2$ is $C_2H_5$, $R^9$ is $CH_3$ and $R^{10}$ is H.

Table 1518. Compounds of formula I.18 wherein $R^1$ is Y-1B, $R^2$ is $C_2H_5$, $R^9$ is $CH_3$ and $R^{10}$ is $CH_3$.

Table 1519. Compounds of formula I.18 wherein $R^1$ is Y-2A, $R^2$ is $C_2H_5$, $R^9$ is H and $R^{10}$ is H.

Table 1520. Compounds of formula I.18 wherein $R^1$ is Y-2A, $R^2$ is $C_2H_5$, $R^9$ is $CH_3$ and $R^{10}$ is H.

Table 1521. Compounds of formula I.18 wherein $R^1$ is Y-2A, $R^2$ is $C_2H_5$, $R^9$ is $CH_3$ and $R^{10}$ is $CH_3$.

Table 1522. Compounds of formula I.18 wherein $R^1$ is Y-2B, $R^2$ is $C_2H_5$, $R^9$ is H and $R^{10}$ is H.

Table 1523. Compounds of formula I.18 wherein $R^1$ is Y-2B, $R^2$ is $C_2H_5$, $R^9$ is $CH_3$ and $R^{10}$ is H.

Table 1524. Compounds of formula I.18 wherein $R^1$ is Y-2B, $R^2$ is $C_2H_5$, $R^9$ is $CH_3$ and $R^{10}$ is $CH_3$.

Table 1525. Compounds of formula I.18 wherein $R^1$ is Y-3A, $R^2$ is $C_2H_5$, $R^9$ is H and $R^{10}$ is H.

Table 1526. Compounds of formula I.18 wherein $R^1$ is Y-3A, $R^2$ is $C_2H_5$, $R^9$ is $CH_3$ and $R^{10}$ is H.

Table 1527. Compounds of formula I.18 wherein $R^1$ is Y-3A, $R^2$ is $C_2H_5$, $R^9$ is $CH_3$ and $R^{10}$ is $CH_3$.

Table 1528. Compounds of formula I.18 wherein $R^1$ is Y-3B, $R^2$ is $C_2H_5$, $R^9$ is H and $R^{10}$ is H.

Table 1529. Compounds of formula I.18 wherein $R^1$ is Y-3B, $R^2$ is $C_2H_5$, $R^9$ is $CH_3$ and $R^{10}$ is H.

Table 1530. Compounds of formula I.18 wherein $R^1$ is Y-3B, $R^2$ is $C_2H_5$, $R^9$ is $CH_3$ and $R^{10}$ is $CH_3$.

Table 1531. Compounds of formula I.18 wherein $R^1$ is Y-3C, $R^2$ is $C_2H_5$, $R^9$ is H and $R^{10}$ is H.

Table 1532. Compounds of formula I.18 wherein $R^1$ is Y-3C, $R^2$ is $C_2H_5$, $R^9$ is $CH_3$ and $R^{10}$ is H.

Table 1533. Compounds of formula I.18 wherein $R^1$ is Y-3C, $R^2$ is $C_2H_5$, $R^9$ is $CH_3$ and $R^{10}$ is $CH_3$.

Table 1534. Compounds of formula I.18 wherein $R^1$ is Y-3D, $R^2$ is $C_2H_5$, $R^9$ is H and $R^{10}$ is H.

Table 1535. Compounds of formula I.18 wherein $R^1$ is Y-3D, $R^2$ is $C_2H_5$, $R^9$ is $CH_3$ and $R^{10}$ is H.

Table 1536. Compounds of formula I.18 wherein $R^1$ is Y-3D, $R^2$ is $C_2H_5$, $R^9$ is $CH_3$ and $R^{10}$ is $CH_3$.

Table 1537. Compounds of formula I.18 wherein $R^1$ is Y-4A, $R^2$ is $C_2H_5$, $R^9$ is H and $R^{10}$ is H.

Table 1538. Compounds of formula I.18 wherein $R^1$ is Y-4A, $R^2$ is $C_2H_5$, $R^9$ is $CH_3$ and $R^{10}$ is H.

Table 1539. Compounds of formula I.18 wherein $R^1$ is Y-4A, $R^2$ is $C_2H_5$, $R^9$ is $CH_3$ and $R^{10}$ is $CH_3$.

Table 1540. Compounds of formula I.18 wherein $R^1$ is Y-4B, $R^2$ is $C_2H_5$, $R^9$ is H and $R^{10}$ is H.

Table 1541. Compounds of formula I.18 wherein $R^1$ is Y-4B, $R^2$ is $C_2H_5$, $R^9$ is $CH_3$ and $R^{10}$ is H.

Table 1542. Compounds of formula I.18 wherein $R^1$ is Y-4B, $R^2$ is $C_2H_5$, $R^9$ is $CH_3$ and $R^{10}$ is $CH_3$.

Table 1543. Compounds of formula I.18 wherein $R^1$ is Y-4C, $R^2$ is $C_2H_5$, $R^9$ is H and $R^{10}$ is H.

Table 1544. Compounds of formula I.18 wherein $R^1$ is Y-4C, $R^2$ is $C_2H_5$, $R^9$ is $CH_3$ and $R^{10}$ is H.

Table 1545. Compounds of formula I.18 wherein $R^1$ is Y-4C, $R^2$ is $C_2H_5$, $R^9$ is $CH_3$ and $R^{10}$ is $CH_3$.

Table 1546. Compounds of formula I.18 wherein $R^1$ is Y-4D, $R^2$ is $C_2H_5$, $R^9$ is H and $R^{10}$ is H.

Table 1547. Compounds of formula I.18 wherein $R^1$ is Y-4D, $R^2$ is $C_2H_5$, $R^9$ is $CH_3$ and $R^{10}$ is H.

Table 1548. Compounds of formula I.18 wherein $R^1$ is Y-4D, $R^2$ is $C_2H_5$, $R^9$ is $CH_3$ and $R^{10}$ is $CH_3$.

Table 1549. Compounds of formula I.18 wherein $R^1$ is Y-5A, $R^2$ is $C_2H_5$, $R^9$ is H and $R^{10}$ is H.

Table 1550. Compounds of formula I.18 wherein $R^1$ is Y-5A, $R^2$ is $C_2H_5$, $R^9$ is $CH_3$ and $R^{10}$ is H.

Table 1551. Compounds of formula I.18 wherein $R^1$ is Y-5A, $R^2$ is $C_2H_5$, $R^9$ is $CH_3$ and $R^{10}$ is $CH_3$.

Table 1552. Compounds of formula I.18 wherein $R^1$ is Y-5B, $R^2$ is $C_2H_5$, $R^9$ is H and $R^{10}$ is H.

Table 1553. Compounds of formula I.18 wherein $R^1$ is Y-5B, $R^2$ is $C_2H_5$, $R^9$ is $CH_3$ and $R^{10}$ is H.

Table 1554. Compounds of formula I.18 wherein $R^1$ is Y-5B, $R^2$ is $C_2H_5$, $R^9$ is $CH_3$ and $R^{10}$ is $CH_3$.

Table 1555. Compounds of formula I.18 wherein $R^1$ is Y-6A, $R^2$ is $C_2H_5$, $R^9$ is H and $R^{10}$ is H.

Table 1556. Compounds of formula I.18 wherein $R^1$ is Y-6A, $R^2$ is $C_2H_5$, $R^9$ is $CH_3$ and $R^{10}$ is H.

Table 1557. Compounds of formula I.18 wherein $R^1$ is Y-6A, $R^2$ is $C_2H_5$, $R^9$ is $CH_3$ and $R^{10}$ is $CH_3$.

Table 1558. Compounds of formula I.18 wherein $R^1$ is Y-6B, $R^2$ is $C_2H_5$, $R^9$ is H and $R^{10}$ is H.

Table 1559. Compounds of formula I.18 wherein $R^1$ is Y-6B, $R^2$ is $C_2H_5$, $R^9$ is $CH_3$ and $R^{10}$ is H.

Table 1560. Compounds of formula I.18 wherein $R^1$ is Y-6B, $R^2$ is $C_2H_5$, $R^9$ is $CH_3$ and $R^{10}$ is $CH_3$.

Table 1561. Compounds of formula I.18 wherein $R^1$ is Y-8A, $R^2$ is $C_2H_5$, $R^9$ is H and $R^{10}$ is H.

Table 1562. Compounds of formula I.18 wherein $R^1$ is Y-8A, $R^2$ is $C_2H_5$, $R^9$ is $CH_3$ and $R^{10}$ is H.

Table 1563. Compounds of formula I.18 wherein $R^1$ is Y-8A, $R^2$ is $C_2H_5$, $R^9$ is $CH_3$ and $R^{10}$ is $CH_3$.

Table 1564. Compounds of formula I.18 wherein $R^1$ is Y-8B, $R^2$ is $C_2H_5$, $R^9$ is H and $R^{10}$ is H.

Table 1565. Compounds of formula I.18 wherein $R^1$ is Y-8B, $R^2$ is $C_2H_5$, $R^9$ is $CH_3$ and $R^{10}$ is H.

Table 1566. Compounds of formula I.18 wherein $R^1$ is Y-8B, $R^2$ is $C_2H_5$, $R^9$ is $CH_3$ and $R^{10}$ is $CH_3$.

Table 1567. Compounds of formula I.18 wherein $R^1$ is Y-1A, $R^2$ is c-$C_3H_5$, $R^9$ is H and $R^{10}$ is H.

Table 1568. Compounds of formula I.18 wherein $R^1$ is Y-1A, $R^2$ is c-$C_3H_5$, $R^9$ is $CH_3$ and $R^{10}$ is H.

Table 1569. Compounds of formula I.18 wherein $R^1$ is Y-1A, $R^2$ is c-$C_3H_5$, $R^9$ is $CH_3$ and $R^{10}$ is $CH_3$.

Table 1570. Compounds of formula I.18 wherein $R^1$ is Y-1B, $R^2$ is c-$C_3H_5$, $R^9$ is H and $R^{10}$ is H.

Table 1571. Compounds of formula I.18 wherein $R^1$ is Y-1B, $R^2$ is c-$C_3H_5$, $R^9$ is $CH_3$, $R^{10}$ is H.

Table 1572. Compounds of formula I.18 wherein $R^1$ is Y-1B, $R^2$ is c-$C_3H_5$, $R^9$ is $CH_3$ and $R^{10}$ is $CH_3$.

Table 1573. Compounds of formula I.18 wherein $R^1$ is Y-2A, $R^2$ is c-$C_3H_5$, $R^9$ is H and $R^{10}$ is H.

Table 1574. Compounds of formula I.18 wherein $R^1$ is Y-2A, $R^2$ is c-$C_3H_5$, $R^9$ is $CH_3$ and $R^{10}$ is H.

Table 1575. Compounds of formula I.18 wherein $R^1$ is Y-2A, $R^2$ is c-$C_3H_5$, $R^9$ is $CH_3$ and $R^{10}$ is $CH_3$.

Table 1576. Compounds of formula I.18 wherein $R^1$ is Y-2B, $R^2$ is c-$C_3H_5$, $R^9$ is H and $R^{10}$ is H.

Table 1577. Compounds of formula I.18 wherein $R^1$ is Y-2B, $R^2$ is c-$C_3H_5$, $R^9$ is $CH_3$ and $R^{10}$ is H.

Table 1578. Compounds of formula I.18 wherein $R^1$ is Y-2B, $R^2$ is c-$C_3H_5$, $R^9$ is $CH_3$ and $R^{10}$ is $CH_3$.

Table 1579. Compounds of formula I.18 wherein $R^1$ is Y-3A, $R^2$ is c-$C_3H_5$, $R^9$ is H and $R^{10}$ is H.

Table 1580. Compounds of formula I.18 wherein $R^1$ is Y-3A, $R^2$ is c-$C_3H_5$, $R^9$ is $CH_3$ and $R^{10}$ is H.

Table 1581. Compounds of formula I.18 wherein $R^1$ is Y-3A, $R^2$ is c-$C_3H_5$, $R^9$ is $CH_3$ and $R^{10}$ is $CH_3$.

Table 1582. Compounds of formula I.18 wherein $R^1$ is Y-3B, $R^2$ is c-$C_3H_5$, $R^9$ is H and $R^{10}$ is H.

Table 1583. Compounds of formula I.18 wherein $R^1$ is Y-3B, $R^2$ is c-$C_3H_5$, $R^9$ is $CH_3$ and $R^{10}$ is H.

Table 1584. Compounds of formula I.18 wherein $R^1$ is Y-3B, $R^2$ is c-$C_3H_5$, $R^9$ is $CH_3$ and $R^{10}$ is $CH_3$.

Table 1585. Compounds of formula I.18 wherein $R^1$ is Y-3C, $R^2$ is c-$C_3H_5$, $R^9$ is H and $R^{10}$ is H.

Table 1586. Compounds of formula I.18 wherein $R^1$ is Y-3C, $R^2$ is c-$C_3H_5$, $R^9$ is $CH_3$ and $R^{10}$ is H.

Table 1587. Compounds of formula I.18 wherein $R^1$ is Y-3C, $R^2$ is c-$C_3H_5$, $R^9$ is $CH_3$ and $R^{10}$ is $CH_3$.

Table 1588. Compounds of formula I.18 wherein $R^1$ is Y-3D, $R^2$ is c-$C_3H_5$, $R^9$ is H and $R^{10}$ is H.

Table 1589. Compounds of formula I.18 wherein $R^1$ is Y-3D, $R^2$ is c-$C_3H_5$, $R^9$ is $CH_3$ and $R^{10}$ is H.

Table 1590. Compounds of formula I.18 wherein $R^1$ is Y-3D, $R^2$ is c-$C_3H_5$, $R^9$ is $CH_3$ and $R^{10}$ is $CH_3$.

Table 1591. Compounds of formula I.18 wherein $R^1$ is Y-4A, $R^2$ is c-$C_3H_5$, $R^9$ is H and $R^{10}$ is H.

Table 1592. Compounds of formula I.18 wherein $R^1$ is Y-4A, $R^2$ is c-$C_3H_5$, $R^9$ is $CH_3$ and $R^{10}$ is H.

Table 1593. Compounds of formula I.18 wherein $R^1$ is Y-4A, $R^2$ is c-$C_3H_5$, $R^9$ is $CH_3$ and $R^{10}$ is $CH_3$.

Table 1594. Compounds of formula I.18 wherein $R^1$ is Y-4B, $R^2$ is c-$C_3H_5$, $R^9$ is H and $R^{10}$ is H.

Table 1595. Compounds of formula I.18 wherein $R^1$ is Y-4B, $R^2$ is c-$C_3H_5$, $R^9$ is $CH_3$ and $R^{10}$ is H.

Table 1596. Compounds of formula I.18 wherein $R^1$ is Y-4B, $R^2$ is c-$C_3H_5$, $R^9$ is $CH_3$ and $R^{10}$ is $CH_3$.

Table 1597. Compounds of formula I.18 wherein $R^1$ is Y-4C, $R^2$ is c-$C_3H_5$, $R^9$ is H and $R^{10}$ is H.

Table 1598. Compounds of formula I.18 wherein $R^1$ is Y-4C, $R^2$ is c-$C_3H_5$, $R^9$ is $CH_3$ and $R^{10}$ is H.

Table 1599. Compounds of formula I.18 wherein $R^1$ is Y-4C, $R^2$ is c-$C_3H_5$, $R^9$ is $CH_3$ and $R^{10}$ is $CH_3$.

Table 1600. Compounds of formula I.18 wherein $R^1$ is Y-4D, $R^2$ is c-$C_3H_5$, $R^9$ is H and $R^{10}$ is H.

Table 1601. Compounds of formula I.18 wherein $R^1$ is Y-4D, $R^2$ is c-$C_3H_5$, $R^9$ is $CH_3$ and $R^{10}$ is H.

Table 1602. Compounds of formula I.18 wherein $R^1$ is Y-4D, $R^2$ is c-$C_3H_5$, $R^9$ is $CH_3$ and $R^{10}$ is $CH_3$.

Table 1603. Compounds of formula I.18 wherein $R^1$ is Y-5A, $R^2$ is c-$C_3H_5$, $R^9$ is H and $R^{10}$ is H.

Table 1604. Compounds of formula I.18 wherein $R^1$ is Y-5A, $R^2$ is c-$C_3H_5$, $R^9$ is $CH_3$ and $R^{10}$ is H.

Table 1605. Compounds of formula I.18 wherein $R^1$ is Y-5A, $R^2$ is c-$C_3H_5$, $R^9$ is $CH_3$ and $R^{10}$ is $CH_3$.

Table 1606. Compounds of formula I.18 wherein $R^1$ is Y-5B, $R^2$ is c-$C_3H_5$, $R^9$ is H and $R^{10}$ is H.

Table 1607. Compounds of formula I.18 wherein $R^1$ is Y-5B, $R^2$ is c-$C_3H_5$, $R^9$ is $CH_3$ and $R^{10}$ is H.

Table 1608. Compounds of formula I.18 wherein $R^1$ is Y-5B, $R^2$ is c-$C_3H_5$, $R^9$ is $CH_3$ and $R^{10}$ is $CH_3$.

Table 1609. Compounds of formula I.18 wherein $R^1$ is Y-6A, $R^2$ is c-$C_3H_5$, $R^9$ is H and $R^{10}$ is H.

Table 1610. Compounds of formula I.18 wherein $R^1$ is Y-6A, $R^2$ is c-$C_3H_5$, $R^9$ is $CH_3$ and $R^{10}$ is H.

Table 1611. Compounds of formula I.18 wherein $R^1$ is Y-6A, $R^2$ is c-$C_3H_5$, $R^9$ is $CH_3$ and $R^{10}$ is $CH_3$.

Table 1612. Compounds of formula I.18 wherein $R^1$ is Y-6B, $R^2$ is c-$C_3H_5$, $R^9$ is H and $R^{10}$ is H.

Table 1613. Compounds of formula I.18 wherein $R^1$ is Y-6B, $R^2$ is c-$C_3H_5$, $R^9$ is $CH_3$ and $R^{10}$ is H.

Table 1614. Compounds of formula I.18 wherein $R^1$ is Y-6B, $R^2$ is c-$C_3H_5$, $R^9$ is $CH_3$ and $R^{10}$ is $CH_3$.

Table 1615. Compounds of formula I.18 wherein $R^1$ is Y-8A, $R^2$ is c-$C_3H_5$, $R^9$ is H and $R^{10}$ is H.

Table 1616. Compounds of formula I.18 wherein $R^1$ is Y-8A, $R^2$ is c-$C_3H_5$, $R^9$ is $CH_3$ and $R^{10}$ is H.

Table 1617. Compounds of formula I.18 wherein $R^1$ is Y-8A, $R^2$ is c-$C_3H_5$, $R^9$ is $CH_3$ and $R^{10}$ is $CH_3$.

Table 1618. Compounds of formula I.18 wherein $R^1$ is Y-8B, $R^2$ is c-$C_3H_5$, $R^9$ is H and $R^{10}$ is H.

Table 1619. Compounds of formula I.18 wherein $R^1$ is Y-8B, $R^2$ is c-$C_3H_5$, $R^9$ is $CH_3$ and $R^{10}$ is H.

Table 1620. Compounds of formula I.18 wherein $R^1$ is Y-8B, $R^2$ is c-$C_3H_5$, $R^9$ is $CH_3$ and $R^{10}$ is $CH_3$.

Table 1621. Compounds of formula I.25 wherein $R^1$ is Y-1A and $R^2$ is H.

Table 1622. Compounds of formula I.25 wherein $R^1$ is Y-1B and $R^2$ is H.

Table 1623. Compounds of formula I.25 wherein $R^1$ is Y-2A and $R^2$ is H.

Table 1624. Compounds of formula I.25 wherein $R^1$ is Y-2B and $R^2$ is H.

Table 1625. Compounds of formula I.25 wherein $R^1$ is Y-3A and $R^2$ is H.

Table 1626. Compounds of formula I.25 wherein $R^1$ is Y-3B and $R^2$ is H.

Table 1627. Compounds of formula I.25 wherein $R^1$ is Y-3C and $R^2$ is H.

Table 1628. Compounds of formula I.25 wherein $R^1$ is Y-3D and $R^2$ is H.

Table 1629. Compounds of formula I.25 wherein $R^1$ is Y-4A and $R^2$ is H.

Table 1630. Compounds of formula I.25 wherein $R^1$ is Y-4B and $R^2$ is H.

Table 1631. Compounds of formula I.25 wherein $R^1$ is Y-4C and $R^2$ is H.

Table 1632. Compounds of formula I.25 wherein $R^1$ is Y-4D and $R^2$ is H.

Table 1633. Compounds of formula I.25 wherein $R^1$ is Y-5A and $R^2$ is H.

Table 1634. Compounds of formula I.25 wherein $R^1$ is Y-5B and $R^2$ is H.

Table 1635. Compounds of formula I.25 wherein $R^1$ is Y-6A and $R^2$ is H.

Table 1636. Compounds of formula I.25 wherein $R^1$ is Y-6B and $R^2$ is H.

Table 1637. Compounds of formula I.25 wherein $R^1$ is Y-8A and $R^2$ is H.

Table 1638. Compounds of formula I.25 wherein $R^1$ is Y-8B and $R^2$ is H.

Table 1639. Compounds of formula I.25 wherein $R^1$ is Y-1A and $R^2$ is $CH_3$.

Table 1640. Compounds of formula I.25 wherein $R^1$ is Y-1B and $R^2$ is $CH_3$.

Table 1641. Compounds of formula I.25 wherein $R^1$ is Y-2A and $R^2$ is $CH_3$.

Table 1642. Compounds of formula I.25 wherein $R^1$ is Y-2B and $R^2$ is $CH_3$.

Table 1643. Compounds of formula I.25 wherein $R^1$ is Y-3A and $R^2$ is $CH_3$.

Table 1644. Compounds of formula I.25 wherein $R^1$ is Y-3B and $R^2$ is $CH_3$.

Table 1645. Compounds of formula I.25 wherein $R^1$ is Y-3C and $R^2$ is $CH_3$.

Table 1646. Compounds of formula I.25 wherein $R^1$ is Y-3D and $R^2$ is $CH_3$.

Table 1647. Compounds of formula I.25 wherein $R^1$ is Y-4A and $R^2$ is $CH_3$.

Table 1648. Compounds of formula I.25 wherein $R^1$ is Y-4B and $R^2$ is $CH_3$.

Table 1649. Compounds of formula I.25 wherein $R^1$ is Y-4C and $R^2$ is $CH_3$.

Table 1650. Compounds of formula I.25 wherein $R^1$ is Y-4D and $R^2$ is $CH_3$.

Table 1651. Compounds of formula I.25 wherein $R^1$ is Y-5A and $R^2$ is $CH_3$.

Table 1652. Compounds of formula I.25 wherein $R^1$ is Y-5B and $R^2$ is $CH_3$.

Table 1653. Compounds of formula I.25 wherein $R^1$ is Y-6A and $R^2$ is $CH_3$.

Table 1654. Compounds of formula I.25 wherein $R^1$ is Y-6B and $R^2$ is $CH_3$.

Table 1655. Compounds of formula I.25 wherein $R^1$ is Y-8A and $R^2$ is $CH_3$.

Table 1656. Compounds of formula I.25 wherein $R^1$ is Y-8B and $R^2$ is $CH_3$.

Table 1657. Compounds of formula I.25 wherein $R^1$ is Y-1A and $R^2$ is c-$C_3H_5$.

Table 1658. Compounds of formula I.25 wherein $R^1$ is Y-1B and $R^2$ is c-$C_3H_5$.

Table 1659. Compounds of formula I.25 wherein $R^1$ is Y-2A and $R^2$ is c-$C_3H_5$.

Table 1660. Compounds of formula I.25 wherein $R^1$ is Y-2B and $R^2$ is c-$C_3H_5$.

Table 1661. Compounds of formula I.25 wherein $R^1$ is Y-3A and $R^2$ is c-$C_3H_5$.

Table 1662. Compounds of formula I.25 wherein $R^1$ is Y-3B and $R^2$ is c-$C_3H_5$.

Table 1663. Compounds of formula I.25 wherein $R^1$ is Y-3C and $R^2$ is c-$C_3H_5$.

Table 1664. Compounds of formula I.25 wherein $R^1$ is Y-3D and $R^2$ is c-$C_3H_5$.

Table 1665. Compounds of formula I.25 wherein $R^1$ is Y-4A and $R^2$ is c-$C_3H_5$.

Table 1666. Compounds of formula I.25 wherein $R^1$ is Y-4B and $R^2$ is c-$C_3H_5$.

Table 1667. Compounds of formula I.25 wherein $R^1$ is Y-4C and $R^2$ is c-$C_3H_5$.

Table 1668. Compounds of formula I.25 wherein $R^1$ is Y-4D and $R^2$ is c-$C_3H_5$.

Table 1669. Compounds of formula I.25 wherein $R^1$ is Y-5A and $R^2$ is c-$C_3H_5$.

Table 1670. Compounds of formula I.25 wherein $R^1$ is Y-5B and $R^2$ is c-$C_3H_5$.

Table 1671. Compounds of formula I.25 wherein $R^1$ is Y-6A and $R^2$ is c-$C_3H_5$.

Table 1672. Compounds of formula I.25 wherein $R^1$ is Y-6B and $R^2$ is c-$C_3H_5$.

Table 1673. Compounds of formula I.25 wherein $R^1$ is Y-8A and $R^2$ is c-$C_3H_5$.

Table 1674. Compounds of formula I.25 wherein $R^1$ is Y-8B and $R^2$ is c-$C_3H_5$.

Table 1675. Compounds of formula I.26 wherein $R^1$ is Y-1A and $R^2$ is H.

Table 1676. Compounds of formula I.26 wherein $R^1$ is Y-1B and $R^2$ is H.

Table 1677. Compounds of formula I.26 wherein $R^1$ is Y-2A and $R^2$ is H.

Table 1678. Compounds of formula I.26 wherein $R^1$ is Y-2B and $R^2$ is H.

Table 1679. Compounds of formula I.26 wherein $R^1$ is Y-3A and $R^2$ is H.

Table 1680. Compounds of formula I.26 wherein $R^1$ is Y-3B and $R^2$ is H.

Table 1681. Compounds of formula I.26 wherein $R^1$ is Y-3C and $R^2$ is H.

Table 1682. Compounds of formula I.26 wherein $R^1$ is Y-3D and $R^2$ is H.

Table 1683. Compounds of formula I.26 wherein $R^1$ is Y-4A and $R^2$ is H.

Table 1684. Compounds of formula I.26 wherein $R^1$ is Y-4B and $R^2$ is H.

Table 1685. Compounds of formula I.26 wherein $R^1$ is Y-4C and $R^2$ is H.

Table 1686. Compounds of formula I.26 wherein $R^1$ is Y-4D and $R^2$ is H.

Table 1687. Compounds of formula I.26 wherein $R^1$ is Y-5A and $R^2$ is H.

Table 1688. Compounds of formula I.26 wherein $R^1$ is Y-5B and $R^2$ is H.

Table 1689. Compounds of formula I.26 wherein $R^1$ is Y-6A and $R^2$ is H.

Table 1690. Compounds of formula I.26 wherein $R^1$ is Y-6B and $R^2$ is H.

Table 1691. Compounds of formula I.26 wherein $R^1$ is Y-8A and $R^2$ is H.

Table 1692. Compounds of formula I.26 wherein $R^1$ is Y-8B and $R^2$ is H.

Table 1693. Compounds of formula I.26 wherein $R^1$ is Y-1A and $R^2$ is $CH_3$.

Table 1694. Compounds of formula I.26 wherein $R^1$ is Y-1B and $R^2$ is $CH_3$.

Table 1695. Compounds of formula I.26 wherein $R^1$ is Y-2A and $R^2$ is $CH_3$.

Table 1696. Compounds of formula I.26 wherein $R^1$ is Y-2B and $R^2$ is $CH_3$.

Table 1697. Compounds of formula I.26 wherein $R^1$ is Y-3A and $R^2$ is $CH_3$.

Table 1698. Compounds of formula I.26 wherein $R^1$ is Y-3B and $R^2$ is $CH_3$.

Table 1699. Compounds of formula I.26 wherein $R^1$ is Y-3C and $R^2$ is $CH_3$.

Table 1700. Compounds of formula I.26 wherein $R^1$ is Y-3D and $R^2$ is $CH_3$.

Table 1701. Compounds of formula I.26 wherein $R^1$ is Y-4A and $R^2$ is $CH_3$.

Table 1702. Compounds of formula I.26 wherein $R^1$ is Y-4B and $R^2$ is $CH_3$.

Table 1703. Compounds of formula I.26 wherein $R^1$ is Y-4C and $R^2$ is $CH_3$.

Table 1704. Compounds of formula I.26 wherein $R^1$ is Y-4D and $R^2$ is $CH_3$.

Table 1705. Compounds of formula I.26 wherein $R^1$ is Y-5A and $R^2$ is $CH_3$.

Table 1706. Compounds of formula I.26 wherein $R^1$ is Y-5B and $R^2$ is $CH_3$.

Table 1707. Compounds of formula I.26 wherein $R^1$ is Y-6A and $R^2$ is $CH_3$.

Table 1708. Compounds of formula I.26 wherein $R^1$ is Y-6B and $R^2$ is $CH_3$.

Table 1709. Compounds of formula I.26 wherein $R^1$ is Y-8A and $R^2$ is $CH_3$.

Table 1710. Compounds of formula I.26 wherein $R^1$ is Y-8B and $R^2$ is $CH_3$.

Table 1711. Compounds of formula I.26 wherein $R^1$ is Y-1A and $R^2$ is c-$C_3H_5$.

Table 1712. Compounds of formula I.26 wherein $R^1$ is Y-1B and $R^2$ is c-$C_3H_5$.

Table 1713. Compounds of formula I.26 wherein $R^1$ is Y-2A and $R^2$ is c-$C_3H_5$.

Table 1714. Compounds of formula I.26 wherein $R^1$ is Y-2B and $R^2$ is c-$C_3H_5$.

Table 1715. Compounds of formula I.26 wherein $R^1$ is Y-3A and $R^2$ is c-$C_3H_5$.

Table 1716. Compounds of formula I.26 wherein $R^1$ is Y-3B and $R^2$ is c-$C_3H_5$.

Table 1717. Compounds of formula I.26 wherein $R^1$ is Y-3C and $R^2$ is c-$C_3H_5$.

Table 1718. Compounds of formula I.26 wherein $R^1$ is Y-3D and $R^2$ is c-$C_3H_5$.

Table 1719. Compounds of formula I.26 wherein $R^1$ is Y-4A and $R^2$ is c-$C_3H_5$.

Table 1720. Compounds of formula I.26 wherein $R^1$ is Y-4B and $R^2$ is c-$C_3H_5$.

Table 1721. Compounds of formula I.26 wherein $R^1$ is Y-4C and $R^2$ is c-$C_3H_5$.

Table 1722. Compounds of formula I.26 wherein $R^1$ is Y-4D and $R^2$ is c-$C_3H_5$.

Table 1723. Compounds of formula I.26 wherein $R^1$ is Y-5A and $R^2$ is c-$C_3H_5$.

Table 1724. Compounds of formula I.26 wherein $R^1$ is Y-5B and $R^2$ is c-$C_3H_5$.

Table 1725. Compounds of formula I.26 wherein $R^1$ is Y-6A and $R^2$ is c-$C_3H_5$.

Table 1726. Compounds of formula I.26 wherein $R^1$ is Y-6B and $R^2$ is c-$C_3H_5$.

Table 1727. Compounds of formula I.26 wherein $R^1$ is Y-8A and $R^2$ is c-$C_3H_5$.

Table 1728. Compounds of formula I.26 wherein $R^1$ is Y-8B and $R^2$ is c-$C_3H_5$.

Table 1729. Compounds of formula I.27 wherein $R^1$ is Y-1A and $R^2$ is H.

Table 1730. Compounds of formula I.27 wherein $R^1$ is Y-1B and $R^2$ is H.

Table 1731. Compounds of formula I.27 wherein $R^1$ is Y-2A and $R^2$ is H.

Table 1732. Compounds of formula I.27 wherein $R^1$ is Y-2B and $R^2$ is H.

Table 1733. Compounds of formula I.27 wherein $R^1$ is Y-3A and $R^2$ is H.

Table 1734. Compounds of formula I.27 wherein $R^1$ is Y-3B and $R^2$ is H.

Table 1735. Compounds of formula I.27 wherein $R^1$ is Y-3C and $R^2$ is H.

Table 1736. Compounds of formula I.27 wherein $R^1$ is Y-3D and $R^2$ is H.

Table 1737. Compounds of formula I.27 wherein $R^1$ is Y-4A and $R^2$ is H.

Table 1738. Compounds of formula I.27 wherein $R^1$ is Y-4B and $R^2$ is H.

Table 1739. Compounds of formula I.27 wherein $R^1$ is Y-4C and $R^2$ is H.

Table 1740. Compounds of formula I.27 wherein $R^1$ is Y-4D and $R^2$ is H.

Table 1741. Compounds of formula I.27 wherein $R^1$ is Y-5A and $R^2$ is H.

Table 1742. Compounds of formula I.27 wherein $R^1$ is Y-5B and $R^2$ is H.

Table 1743. Compounds of formula I.27 wherein $R^1$ is Y-6A and $R^2$ is H.

Table 1744. Compounds of formula I.27 wherein $R^1$ is Y-6B and $R^2$ is H.

Table 1745. Compounds of formula I.27 wherein $R^1$ is Y-8A and $R^2$ is H.

Table 1746. Compounds of formula I.27 wherein $R^1$ is Y-8B and $R^2$ is H.

Table 1747. Compounds of formula I.27 wherein $R^1$ is Y-1A and $R^2$ is $CH_3$.

Table 1748. Compounds of formula I.27 wherein $R^1$ is Y-1B and $R^2$ is $CH_3$.

Table 1749. Compounds of formula I.27 wherein $R^1$ is Y-2A and $R^2$ is $CH_3$.

Table 1750. Compounds of formula I.27 wherein $R^1$ is Y-2B and $R^2$ is $CH_3$.

Table 1751. Compounds of formula I.27 wherein $R^1$ is Y-3A and $R^2$ is $CH_3$.

Table 1752. Compounds of formula I.27 wherein $R^1$ is Y-3B and $R^2$ is $CH_3$.

Table 1753. Compounds of formula I.27 wherein $R^1$ is Y-3C and $R^2$ is $CH_3$.

Table 1754. Compounds of formula I.27 wherein $R^1$ is Y-3D and $R^2$ is $CH_3$.

Table 1755. Compounds of formula I.27 wherein $R^1$ is Y-4A and $R^2$ is $CH_3$.

Table 1756. Compounds of formula I.27 wherein $R^1$ is Y-4B and $R^2$ is $CH_3$.

Table 1757. Compounds of formula I.27 wherein $R^1$ is Y-4C and $R^2$ is $CH_3$.

Table 1758. Compounds of formula I.27 wherein $R^1$ is Y-4D and $R^2$ is $CH_3$.

Table 1759. Compounds of formula I.27 wherein $R^1$ is Y-5A and $R^2$ is $CH_3$.

Table 1760. Compounds of formula I.27 wherein $R^1$ is Y-5B and $R^2$ is $CH_3$.

Table 1761. Compounds of formula I.27 wherein $R^1$ is Y-6A and $R^2$ is $CH_3$.

Table 1762. Compounds of formula I.27 wherein $R^1$ is Y-6B and $R^2$ is $CH_3$.

Table 1763. Compounds of formula I.27 wherein $R^1$ is Y-8A and $R^2$ is $CH_3$.

Table 1764. Compounds of formula I.27 wherein $R^1$ is Y-8B and $R^2$ is $CH_3$.

Table 1765. Compounds of formula I.27 wherein $R^1$ is Y-1A and $R^2$ is c-$C_3H_5$.

Table 1766. Compounds of formula I.27 wherein $R^1$ is Y-1B and $R^2$ is c-$C_3H_5$.

Table 1767. Compounds of formula I.27 wherein $R^1$ is Y-2A and $R^2$ is c-$C_3H_5$.

Table 1768. Compounds of formula I.27 wherein $R^1$ is Y-2B and $R^2$ is c-$C_3H_5$.

Table 1769. Compounds of formula I.27 wherein $R^1$ is Y-3A and $R^2$ is c-$C_3H_5$.

Table 1770. Compounds of formula I.27 wherein $R^1$ is Y-3B and $R^2$ is c-$C_3H_5$.

Table 1771. Compounds of formula I.27 wherein $R^1$ is Y-3C and $R^2$ is c-$C_3H_5$.

Table 1772. Compounds of formula I.27 wherein $R^1$ is Y-3D and $R^2$ is c-$C_3H_5$.

Table 1773. Compounds of formula I.27 wherein $R^1$ is Y-4A and $R^2$ is c-$C_3H_5$.

Table 1774. Compounds of formula I.27 wherein $R^1$ is Y-4B and $R^2$ is c-$C_3H_5$.

Table 1775. Compounds of formula I.27 wherein $R^1$ is Y-4C and $R^2$ is c-$C_3H_5$.

Table 1776. Compounds of formula I.27 wherein $R^1$ is Y-4D and $R^2$ is c-$C_3H_5$.

Table 1777. Compounds of formula I.27 wherein $R^1$ is Y-5A and $R^2$ is c-$C_3H_5$.

Table 1778. Compounds of formula I.27 wherein $R^1$ is Y-5B and $R^2$ is c-$C_3H_5$.

Table 1779. Compounds of formula I.27 wherein $R^1$ is Y-6A and $R^2$ is c-$C_3H_5$.

Table 1780. Compounds of formula I.27 wherein $R^1$ is Y-6B and $R^2$ is c-$C_3H_5$.

Table 1781. Compounds of formula I.27 wherein $R^1$ is Y-8A and $R^2$ is c-$C_3H_5$.

Table 1782. Compounds of formula I.27 wherein $R^1$ is Y-8B and $R^2$ is c-$C_3H_5$.

Table 1783. Compounds of formula I.28 wherein $R^1$ is Y-1A and $R^2$ is H.

Table 1784. Compounds of formula I.28 wherein $R^1$ is Y-1B and $R^2$ is H.

Table 1785. Compounds of formula I.28 wherein $R^1$ is Y-2A and $R^2$ is H.

Table 1786. Compounds of formula I.28 wherein $R^1$ is Y-2B and $R^2$ is H.

Table 1787. Compounds of formula I.28 wherein $R^1$ is Y-3A and $R^2$ is H.

Table 1788. Compounds of formula I.28 wherein $R^1$ is Y-3B and $R^2$ is H.

Table 1789. Compounds of formula I.28 wherein $R^1$ is Y-3C and $R^2$ is H.

Table 1790. Compounds of formula I.28 wherein $R^1$ is Y-3D and $R^2$ is H.

Table 1791. Compounds of formula I.28 wherein $R^1$ is Y-4A and $R^2$ is H.

Table 1792. Compounds of formula I.28 wherein $R^1$ is Y-4B and $R^2$ is H.

Table 1793. Compounds of formula I.28 wherein $R^1$ is Y-4C and $R^2$ is H.

Table 1794. Compounds of formula I.28 wherein $R^1$ is Y-4D and $R^2$ is H.

Table 1795. Compounds of formula I.28 wherein $R^1$ is Y-5A and $R^2$ is H.

Table 1796. Compounds of formula I.28 wherein $R^1$ is Y-5B and $R^2$ is H.

Table 1797. Compounds of formula I.28 wherein $R^1$ is Y-6A and $R^2$ is H.

Table 1798. Compounds of formula I.28 wherein $R^1$ is Y-6B and $R^2$ is H.

Table 1799. Compounds of formula I.28 wherein $R^1$ is Y-8A and $R^2$ is H.

Table 1800. Compounds of formula I.28 wherein $R^1$ is Y-8B and $R^2$ is H.

Table 1801. Compounds of formula I.28 wherein $R^1$ is Y-1A and $R^2$ is $CH_3$.

Table 1802. Compounds of formula I.28 wherein $R^1$ is Y-1B and $R^2$ is $CH_3$.

Table 1803. Compounds of formula I.28 wherein $R^1$ is Y-2A and $R^2$ is $CH_3$.

Table 1804. Compounds of formula I.28 wherein $R^1$ is Y-2B and $R^2$ is $CH_3$.

Table 1805. Compounds of formula I.28 wherein $R^1$ is Y-3A and $R^2$ is $CH_3$.

Table 1806. Compounds of formula I.28 wherein $R^1$ is Y-3B and $R^2$ is $CH_3$.

Table 1807. Compounds of formula I.28 wherein $R^1$ is Y-3C and $R^2$ is $CH_3$.

Table 1808. Compounds of formula I.28 wherein $R^1$ is Y-3D and $R^2$ is $CH_3$.

Table 1809. Compounds of formula I.28 wherein $R^1$ is Y-4A and $R^2$ is $CH_3$.

Table 1810. Compounds of formula I.28 wherein $R^1$ is Y-4B and $R^2$ is $CH_3$.

Table 1811. Compounds of formula I.28 wherein $R^1$ is Y-4C and $R^2$ is $CH_3$.

Table 1812. Compounds of formula I.28 wherein $R^1$ is Y-4D and $R^2$ is $CH_3$.

Table 1813. Compounds of formula I.28 wherein $R^1$ is Y-5A and $R^2$ is $CH_3$.

Table 1814. Compounds of formula I.28 wherein $R^1$ is Y-5B and $R^2$ is $CH_3$.

Table 1815. Compounds of formula I.28 wherein $R^1$ is Y-6A and $R^2$ is $CH_3$.

Table 1816. Compounds of formula I.28 wherein $R^1$ is Y-6B and $R^2$ is $CH_3$.

Table 1817. Compounds of formula I.28 wherein $R^1$ is Y-8A and $R^2$ is $CH_3$.

Table 1818. Compounds of formula I.28 wherein $R^1$ is Y-8B and $R^2$ is $CH_3$.

Table 1819. Compounds of formula I.28 wherein $R^1$ is Y-1A and $R^2$ is c-$C_3H_5$.

Table 1820. Compounds of formula I.28 wherein $R^1$ is Y-1B and $R^2$ is c-$C_3H_5$.

Table 1821. Compounds of formula I.28 wherein $R^1$ is Y-2A and $R^2$ is c-$C_3H_5$.

Table 1822. Compounds of formula I.28 wherein $R^1$ is Y-2B and $R^2$ is c-$C_3H_5$.

Table 1823. Compounds of formula I.28 wherein $R^1$ is Y-3A and $R^2$ is c-$C_3H_5$.

Table 1824. Compounds of formula I.28 wherein $R^1$ is Y-3B and $R^2$ is c-$C_3H_5$.

Table 1825. Compounds of formula I.28 wherein $R^1$ is Y-3C and $R^2$ is c-$C_3H_5$.

Table 1826. Compounds of formula I.28 wherein $R^1$ is Y-3D and $R^2$ is c-$C_3H_5$.

Table 1827. Compounds of formula I.28 wherein $R^1$ is Y-4A and $R^2$ is c-$C_3H_5$.

Table 1828. Compounds of formula I.28 wherein $R^1$ is Y-4B and $R^2$ is c-$C_3H_5$.

Table 1829. Compounds of formula I.28 wherein $R^1$ is Y-4C and $R^2$ is c-$C_3H_5$.

Table 1830. Compounds of formula I.28 wherein $R^1$ is Y-4D and $R^2$ is c-$C_3H_5$.

Table 1831. Compounds of formula I.28 wherein $R^1$ is Y-5A and $R^2$ is c-$C_3H_5$.

Table 1832. Compounds of formula I.28 wherein $R^1$ is Y-5B and $R^2$ is c-$C_3H_5$.

Table 1833. Compounds of formula I.28 wherein $R^1$ is Y-6A and $R^2$ is c-$C_3H_5$.

Table 1834. Compounds of formula I.28 wherein $R^1$ is Y-6B and $R^2$ is c-$C_3H_5$.

Table 1835. Compounds of formula I.28 wherein $R^1$ is Y-8A and $R^2$ is c-$C_3H_5$.

Table 1836. Compounds of formula I.28 wherein $R^1$ is Y-8B and $R^2$ is c-$C_3H_5$.

Table 1837. Compounds of formula I.29 wherein $R^1$ is Y-1A and $R^2$ is H.

Table 1838. Compounds of formula I.29 wherein $R^1$ is Y-1B and $R^2$ is H.

Table 1839. Compounds of formula I.29 wherein $R^1$ is Y-2A and $R^2$ is H.

Table 1840. Compounds of formula I.29 wherein $R^1$ is Y-2B and $R^2$ is H.

Table 1841. Compounds of formula I.29 wherein $R^1$ is Y-3A and $R^2$ is H.

Table 1842. Compounds of formula I.29 wherein $R^1$ is Y-3B and $R^2$ is H.

Table 1843. Compounds of formula I.29 wherein $R^1$ is Y-3C and $R^2$ is H.

Table 1844. Compounds of formula I.29 wherein $R^1$ is Y-3D and $R^2$ is H.

Table 1845. Compounds of formula I.29 wherein $R^1$ is Y-4A and $R^2$ is H.

Table 1846. Compounds of formula I.29 wherein $R^1$ is Y-4B and $R^2$ is H.

Table 1847. Compounds of formula I.29 wherein $R^1$ is Y-4C and $R^2$ is H.

Table 1848. Compounds of formula I.29 wherein $R^1$ is Y-4D and $R^2$ is H.

Table 1849. Compounds of formula I.29 wherein $R^1$ is Y-5A and $R^2$ is H.

Table 1850. Compounds of formula I.29 wherein $R^1$ is Y-5B and $R^2$ is H.

Table 1851. Compounds of formula I.29 wherein $R^1$ is Y-6A and $R^2$ is H.

Table 1852. Compounds of formula I.29 wherein $R^1$ is Y-6B and $R^2$ is H.

Table 1853. Compounds of formula I.29 wherein $R^1$ is Y-8A and $R^2$ is H.

Table 1854. Compounds of formula I.29 wherein $R^1$ is Y-8B and $R^2$ is H.

Table 1855. Compounds of formula I.29 wherein $R^1$ is Y-1A and $R^2$ is $CH_3$.

Table 1856. Compounds of formula I.29 wherein $R^1$ is Y-1B and $R^2$ is $CH_3$.

Table 1857. Compounds of formula I.29 wherein $R^1$ is Y-2A and $R^2$ is $CH_3$.

Table 1858. Compounds of formula I.29 wherein $R^1$ is Y-2B and $R^2$ is $CH_3$.

Table 1859. Compounds of formula I.29 wherein $R^1$ is Y-3A and $R^2$ is $CH_3$.

Table 1860. Compounds of formula I.29 wherein $R^1$ is Y-3B and $R^2$ is $CH_3$.

Table 1861. Compounds of formula I.29 wherein $R^1$ is Y-3C and $R^2$ is $CH_3$.

Table 1862. Compounds of formula I.29 wherein $R^1$ is Y-3D and $R^2$ is $CH_3$.

Table 1863. Compounds of formula I.29 wherein $R^1$ is Y-4A and $R^2$ is $CH_3$.

Table 1864. Compounds of formula I.29 wherein $R^1$ is Y-4B and $R^2$ is $CH_3$.

Table 1865. Compounds of formula I.29 wherein $R^1$ is Y-4C and $R^2$ is $CH_3$.

Table 1866. Compounds of formula I.29 wherein $R^1$ is Y-4D and $R^2$ is $CH_3$.

Table 1867. Compounds of formula I.29 wherein $R^1$ is Y-5A and $R^2$ is $CH_3$.

Table 1868. Compounds of formula I.29 wherein $R^1$ is Y-5B and $R^2$ is $CH_3$.

Table 1869. Compounds of formula I.29 wherein $R^1$ is Y-6A and $R^2$ is $CH_3$.

Table 1870. Compounds of formula I.29 wherein $R^1$ is Y-6B and $R^2$ is $CH_3$.

Table 1871. Compounds of formula I.29 wherein $R^1$ is Y-8A and $R^2$ is $CH_3$.

Table 1872. Compounds of formula I.29 wherein $R^1$ is Y-8B and $R^2$ is $CH_3$.

Table 1873. Compounds of formula I.29 wherein $R^1$ is Y-1A and $R^2$ is c-$C_3H_5$.

Table 1874. Compounds of formula I.29 wherein $R^1$ is Y-1B and $R^2$ is c-$C_3H_5$.

Table 1875. Compounds of formula I.29 wherein $R^1$ is Y-2A and $R^2$ is c-$C_3H_5$.

Table 1876. Compounds of formula I.29 wherein $R^1$ is Y-2B and $R^2$ is c-$C_3H_5$.

Table 1877. Compounds of formula I.29 wherein $R^1$ is Y-3A and $R^2$ is c-$C_3H_5$.

Table 1878. Compounds of formula I.29 wherein $R^1$ is Y-3B and $R^2$ is c-$C_3H_5$.

Table 1879. Compounds of formula I.29 wherein $R^1$ is Y-3C and $R^2$ is c-$C_3H_5$.

Table 1880. Compounds of formula I.29 wherein $R^1$ is Y-3D and $R^2$ is c-$C_3H_5$.

Table 1881. Compounds of formula I.29 wherein $R^1$ is Y-4A and $R^2$ is c-$C_3H_5$.

Table 1882. Compounds of formula I.29 wherein $R^1$ is Y-4B and $R^2$ is c-$C_3H_5$.

Table 1883. Compounds of formula I.29 wherein $R^1$ is Y-4C and $R^2$ is c-$C_3H_5$.

Table 1884. Compounds of formula I.29 wherein $R^1$ is Y-4D and $R^2$ is c-$C_3H_5$.

Table 1885. Compounds of formula I.29 wherein $R^1$ is Y-5A and $R^2$ is c-$C_3H_5$.

Table 1886. Compounds of formula I.29 wherein $R^1$ is Y-5B and $R^2$ is c-$C_3H_5$.

Table 1887. Compounds of formula I.29 wherein $R^1$ is Y-6A and $R^2$ is c-$C_3H_5$.

Table 1888. Compounds of formula I.29 wherein $R^1$ is Y-6B and $R^2$ is c-$C_3H_5$.

Table 1889. Compounds of formula I.29 wherein $R^1$ is Y-8A and $R^2$ is c-$C_3H_5$.

Table 1890. Compounds of formula I.29 wherein $R^1$ is Y-8B and $R^2$ is c-$C_3H_5$.

Table 1891. Compounds of formula I.30 wherein $R^1$ is Y-1A and $R^2$ is H.

Table 1892. Compounds of formula I.30 wherein $R^1$ is Y-1B and $R^2$ is H.

Table 1893. Compounds of formula I.30 wherein $R^1$ is Y-2A and $R^2$ is H.

Table 1894. Compounds of formula I.30 wherein $R^1$ is Y-2B and $R^2$ is H.

Table 1895. Compounds of formula I.30 wherein $R^1$ is Y-3A and $R^2$ is H.

Table 1896. Compounds of formula I.30 wherein $R^1$ is Y-3B and $R^2$ is H.

Table 1897. Compounds of formula I.30 wherein $R^1$ is Y-3C and $R^2$ is H.

Table 1898. Compounds of formula I.30 wherein $R^1$ is Y-3D and $R^2$ is H.

Table 1899. Compounds of formula I.30 wherein $R^1$ is Y-4A and $R^2$ is H.

Table 1900. Compounds of formula I.30 wherein $R^1$ is Y-4B and $R^2$ is H.

Table 1901. Compounds of formula I.30 wherein $R^1$ is Y-4C and $R^2$ is H.

Table 1902. Compounds of formula I.30 wherein $R^1$ is Y-4D and $R^2$ is H.

Table 1903. Compounds of formula I.30 wherein $R^1$ is Y-5A and $R^2$ is H.

Table 1904. Compounds of formula I.30 wherein $R^1$ is Y-5B and $R^2$ is H.

Table 1905. Compounds of formula I.30 wherein $R^1$ is Y-6A and $R^2$ is H.

Table 1906. Compounds of formula I.30 wherein $R^1$ is Y-6B and $R^2$ is H.

Table 1907. Compounds of formula I.30 wherein $R^1$ is Y-8A and $R^2$ is H.

Table 1908. Compounds of formula I.30 wherein $R^1$ is Y-8B and $R^2$ is H.

Table 1909. Compounds of formula I.30 wherein $R^1$ is Y-1A and $R^2$ is $CH_3$.

Table 1910. Compounds of formula I.30 wherein $R^1$ is Y-1B and $R^2$ is $CH_3$.

Table 1911. Compounds of formula I.30 wherein $R^1$ is Y-2A and $R^2$ is $CH_3$.

Table 1912. Compounds of formula I.30 wherein $R^1$ is Y-2B and $R^2$ is $CH_3$.

Table 1913. Compounds of formula I.30 wherein $R^1$ is Y-3A and $R^2$ is $CH_3$.

Table 1914. Compounds of formula I.30 wherein $R^1$ is Y-3B and $R^2$ is $CH_3$.

Table 1915. Compounds of formula I.30 wherein $R^1$ is Y-3C and $R^2$ is $CH_3$.

Table 1916. Compounds of formula I.30 wherein $R^1$ is Y-3D and $R^2$ is $CH_3$.

Table 1917. Compounds of formula I.30 wherein $R^1$ is Y-4A and $R^2$ is $CH_3$.

Table 1918. Compounds of formula I.30 wherein $R^1$ is Y-4B and $R^2$ is $CH_3$.

Table 1919. Compounds of formula I.30 wherein $R^1$ is Y-4C and $R^2$ is $CH_3$.

Table 1920. Compounds of formula I.30 wherein $R^1$ is Y-4D and $R^2$ is $CH_3$.

Table 1921. Compounds of formula I.30 wherein $R^1$ is Y-5A and $R^2$ is $CH_3$.

Table 1922. Compounds of formula I.30 wherein $R^1$ is Y-5B and $R^2$ is $CH_3$.

Table 1923. Compounds of formula I.30 wherein $R^1$ is Y-6A and $R^2$ is $CH_3$.

Table 1924. Compounds of formula I.30 wherein $R^1$ is Y-6B and $R^2$ is $CH_3$.

Table 1925. Compounds of formula I.30 wherein $R^1$ is Y-8A and $R^2$ is $CH_3$.

Table 1926. Compounds of formula I.30 wherein $R^1$ is Y-8B and $R^2$ is $CH_3$.

Table 1927. Compounds of formula I.30 wherein $R^1$ is Y-1A and $R^2$ is c-$C_3H_5$.

Table 1928. Compounds of formula I.30 wherein $R^1$ is Y-1B and $R^2$ is c-$C_3H_5$.

Table 1929. Compounds of formula I.30 wherein $R^1$ is Y-2A and $R^2$ is c-$C_3H_5$.

Table 1930. Compounds of formula I.30 wherein $R^1$ is Y-2B and $R^2$ is c-$C_3H_5$.

Table 1931. Compounds of formula I.30 wherein $R^1$ is Y-3A and $R^2$ is c-$C_3H_5$.

Table 1932. Compounds of formula I.30 wherein $R^1$ is Y-3B and $R^2$ is c-$C_3H_5$.

Table 1933. Compounds of formula I.30 wherein $R^1$ is Y-3C and $R^2$ is c-$C_3H_5$.

Table 1934. Compounds of formula I.30 wherein $R^1$ is Y-3D and $R^2$ is c-$C_3H_5$.

Table 1935. Compounds of formula I.30 wherein $R^1$ is Y-4A and $R^2$ is c-$C_3H_5$.

Table 1936. Compounds of formula I.30 wherein $R^1$ is Y-4B and $R^2$ is c-$C_3H_5$.

Table 1937. Compounds of formula I.30 wherein $R^1$ is Y-4C and $R^2$ is c-$C_3H_5$.

Table 1938. Compounds of formula I.30 wherein $R^1$ is Y-4D and $R^2$ is c-$C_3H_5$.

Table 1939. Compounds of formula I.30 wherein $R^1$ is Y-5A and $R^2$ is c-$C_3H_5$.

Table 1940. Compounds of formula I.30 wherein $R^1$ is Y-5B and $R^2$ is c-$C_3H_5$.

Table 1941. Compounds of formula I.30 wherein $R^1$ is Y-6A and $R^2$ is c-$C_3H_5$.

Table 1942. Compounds of formula I.30 wherein $R^1$ is Y-6B and $R^2$ is c-$C_3H_5$.

Table 1943. Compounds of formula I.30 wherein $R^1$ is Y-8A and $R^2$ is c-$C_3H_5$.

Table 1944. Compounds of formula I.30 wherein $R^1$ is Y-8B and $R^2$ is c-$C_3H_5$.

Table 1945. Compounds of formula I.37 wherein $R^1$ is Y-1A, R is NH, and $R^2$ is H.

Table 1946. Compounds of formula I.37 wherein $R^1$ is Y-1B, R is NH, and $R^2$ is H.

Table 1947. Compounds of formula I.37 wherein $R^1$ is Y-2A, R is NH, and $R^2$ is H.

Table 1948. Compounds of formula I.37 wherein $R^1$ is Y-2B, R is NH, and $R^2$ is H.

Table 1949. Compounds of formula I.37 wherein $R^1$ is Y-3A, R is NH, and $R^2$ is H.

Table 1950. Compounds of formula I.37 wherein $R^1$ is Y-3B, R is NH, and $R^2$ is H.

Table 1951. Compounds of formula I.37 wherein $R^1$ is Y-3C, R is NH, and $R^2$ is H.

Table 1952. Compounds of formula I.37 wherein $R^1$ is Y-3D, R is NH, and $R^2$ is H.

Table 1953. Compounds of formula I.37 wherein $R^1$ is Y-4A, R is NH, and $R^2$ is H.

Table 1954. Compounds of formula I.37 wherein $R^1$ is Y-4B, R is NH, and $R^2$ is H.

Table 1955. Compounds of formula I.37 wherein $R^1$ is Y-4C, R is NH, and $R^2$ is H.

Table 1956. Compounds of formula I.37 wherein $R^1$ is Y-4D, R is NH, and $R^2$ is H.

Table 1957. Compounds of formula I.37 wherein $R^1$ is Y-5A, R is NH, and $R^2$ is H.

Table 1958. Compounds of formula I.37 wherein $R^1$ is Y-5B, R is NH, and $R^2$ is H.

Table 1959. Compounds of formula I.37 wherein $R^1$ is Y-6A, R is NH, and $R^2$ is H.

Table 1960. Compounds of formula I.37 wherein $R^1$ is Y-6B, R is NH, and $R^2$ is H.

Table 1961. Compounds of formula I.37 wherein $R^1$ is Y-8A, R is NH, and $R^2$ is H.

Table 1962. Compounds of formula I.37 wherein $R^1$ is Y-8B, R is NH, and $R^2$ is H.

Table 1963. Compounds of formula I.37 wherein $R^1$ is Y-1A, R is NH, and $R^2$ is $CH_3$.

Table 1964. Compounds of formula I.37 wherein $R^1$ is Y-1B, R is NH, and $R^2$ is $CH_3$.

Table 1965. Compounds of formula I.37 wherein $R^1$ is Y-2A, R is NH, and $R^2$ is $CH_3$.

Table 1966. Compounds of formula I.37 wherein $R^1$ is Y-2B, R is NH, and $R^2$ is $CH_3$.

Table 1967. Compounds of formula I.37 wherein $R^1$ is Y-3A, R is NH, and $R^2$ is $CH_3$.

Table 1968. Compounds of formula I.37 wherein $R^1$ is Y-3B, R is NH, and $R^2$ is $CH_3$.

Table 1969. Compounds of formula I.37 wherein $R^1$ is Y-3C, R is NH, and $R^2$ is $CH_3$.

Table 1970. Compounds of formula I.37 wherein $R^1$ is Y-3D, R is NH, and $R^2$ is $CH_3$.

Table 1971. Compounds of formula I.37 wherein $R^1$ is Y-4A, R is NH, and $R^2$ is $CH_3$.

Table 1972. Compounds of formula I.37 wherein $R^1$ is Y-4B, R is NH, and $R^2$ is $CH_3$.

Table 1973. Compounds of formula I.37 wherein $R^1$ is Y-4C, R is NH, and $R^2$ is $CH_3$.

Table 1974. Compounds of formula I.37 wherein $R^1$ is Y-4D, R is NH, and $R^2$ is $CH_3$.

Table 1975. Compounds of formula I.37 wherein $R^1$ is Y-5A, R is NH, and $R^2$ is $CH_3$.

Table 1976. Compounds of formula I.37 wherein $R^1$ is Y-5B, R is NH, and $R^2$ is $CH_3$.

Table 1977. Compounds of formula I.37 wherein $R^1$ is Y-6A, R is NH, and $R^2$ is $CH_3$.

Table 1978. Compounds of formula I.37 wherein $R^1$ is Y-6B, R is NH, and $R^2$ is $CH_3$.

Table 1979. Compounds of formula I.37 wherein $R^1$ is Y-8A, R is NH, and $R^2$ is $CH_3$.

Table 1980. Compounds of formula I.37 wherein $R^1$ is Y-8B, R is NH, and $R^2$ is $CH_3$.

Table 1981. Compounds of formula I.37 wherein $R^1$ is Y-1A, R is NH, and $R^2$ is c-$C_3H_5$.

Table 1982. Compounds of formula I.37 wherein $R^1$ is Y-1B, R is NH, and $R^2$ is c-$C_3H_5$.

Table 1983. Compounds of formula I.37 wherein $R^1$ is Y-2A, R is NH, and $R^2$ is c-$C_3H_5$.

Table 1984. Compounds of formula I.37 wherein $R^1$ is Y-2B, R is NH, and $R^2$ is c-$C_3H_5$.

Table 1985. Compounds of formula I.37 wherein $R^1$ is Y-3A, R is NH, and $R^2$ is c-$C_3H_5$.

Table 1986. Compounds of formula I.37 wherein $R^1$ is Y-3B, R is NH, and $R^2$ is c-$C_3H_5$.

Table 1987. Compounds of formula I.37 wherein $R^1$ is Y-3C, R is NH, and $R^2$ is c-$C_3H_5$.

Table 1988. Compounds of formula I.37 wherein $R^1$ is Y-3D, R is NH, and $R^2$ is c-$C_3H_5$.

Table 1989. Compounds of formula I.37 wherein $R^1$ is Y-4A, R is NH, and $R^2$ is c-$C_3H_5$.

Table 1990. Compounds of formula I.37 wherein $R^1$ is Y-4B, R is NH, and $R^2$ is c-$C_3H_5$.

Table 1991. Compounds of formula I.37 wherein $R^1$ is Y-4C, R is NH, and $R^2$ is c-$C_3H_5$.

Table 1992. Compounds of formula I.37 wherein $R^1$ is Y-4D, R is NH, and $R^2$ is c-$C_3H_5$.

Table 1993. Compounds of formula I.37 wherein $R^1$ is Y-5A, R is NH, and $R^2$ is c-$C_3H_5$.

Table 1994. Compounds of formula I.37 wherein $R^1$ is Y-5B, R is NH, and $R^2$ is c-$C_3H_5$.

Table 1995. Compounds of formula I.37 wherein $R^1$ is Y-6A, R is NH, and $R^2$ is c-$C_3H_5$.

Table 1996. Compounds of formula I.37 wherein $R^1$ is Y-6B, R is NH, and $R^2$ is c-$C_3H_5$.

Table 1997. Compounds of formula I.37 wherein $R^1$ is Y-8A, R is NH, and $R^2$ is c-$C_3H_5$.

Table 1998. Compounds of formula I.37 wherein $R^1$ is Y-8B, R is NH, and $R^2$ is c-$C_3H_5$.

Table 1999. Compounds of formula I.37 wherein $R^1$ is Y-1A, R is $NCH_3$ and $R^2$ is H.

Table 2000. Compounds of formula I.37 wherein $R^1$ is Y-1B, R is $NCH_3$ and $R^2$ is H.

Table 2001. Compounds of formula I.37 wherein $R^1$ is Y-2A, R is $NCH_3$ and $R^2$ is H.

Table 2002. Compounds of formula I.37 wherein $R^1$ is Y-2B, R is $NCH_3$ and $R^2$ is H.

Table 2003. Compounds of formula I.37 wherein $R^1$ is Y-3A, R is $NCH_3$ and $R^2$ is H.

Table 2004. Compounds of formula I.37 wherein $R^1$ is Y-3B, R is $NCH_3$ and $R^2$ is H.

Table 2005. Compounds of formula I.37 wherein $R^1$ is Y-3C, R is $NCH_3$ and $R^2$ is H.

Table 2006. Compounds of formula I.37 wherein $R^1$ is Y-3D, R is $NCH_3$ and $R^2$ is H.

Table 2007. Compounds of formula I.37 wherein $R^1$ is Y-4A, R is $NCH_3$ and $R^2$ is H.

Table 2008. Compounds of formula I.37 wherein $R^1$ is Y-4B, R is $NCH_3$ and $R^2$ is H.

Table 2009. Compounds of formula I.37 wherein $R^1$ is Y-4C, R is $NCH_3$ and $R^2$ is H.

Table 2010. Compounds of formula I.37 wherein $R^1$ is Y-4D, R is $NCH_3$ and $R^2$ is H.

Table 2011. Compounds of formula I.37 wherein $R^1$ is Y-5A, R is $NCH_3$ and $R^2$ is H.

Table 2012. Compounds of formula I.37 wherein $R^1$ is Y-5B, R is $NCH_3$ and $R^2$ is H.

Table 2013. Compounds of formula I.37 wherein $R^1$ is Y-6A, R is $NCH_3$ and $R^2$ is H.

Table 2014. Compounds of formula I.37 wherein $R^1$ is Y-6B, R is $NCH_3$ and $R^2$ is H.

Table 2015. Compounds of formula I.37 wherein $R^1$ is Y-8A, R is $NCH_3$ and $R^2$ is H.

Table 2016. Compounds of formula I.37 wherein $R^1$ is Y-8B, R is $NCH_3$ and $R^2$ is H.

Table 2017. Compounds of formula I.37 wherein $R^1$ is Y-1A, R is $NCH_3$ and $R^2$ is $CH_3$.

Table 2018. Compounds of formula I.37 wherein $R^1$ is Y-1B, R is $NCH_3$ and $R^2$ is $CH_3$.

Table 2019. Compounds of formula I.37 wherein $R^1$ is Y-2A, R is $NCH_3$ and $R^2$ is $CH_3$.

Table 2020. Compounds of formula I.37 wherein $R^1$ is Y-2B, R is $NCH_3$ and $R^2$ is $CH_3$.

Table 2021. Compounds of formula I.37 wherein $R^1$ is Y-3A, R is $NCH_3$ and $R^2$ is $CH_3$.

Table 2022. Compounds of formula I.37 wherein $R^1$ is Y-3B, R is $NCH_3$ and $R^2$ is $CH_3$.

Table 2023. Compounds of formula I.37 wherein $R^1$ is Y-3C, R is $NCH_3$ and $R^2$ is $CH_3$.

Table 2024. Compounds of formula I.37 wherein $R^1$ is Y-3D, R is $NCH_3$ and $R^2$ is $CH_3$.

Table 2025. Compounds of formula I.37 wherein $R^1$ is Y-4A, R is $NCH_3$ and $R^2$ is $CH_3$.

Table 2026. Compounds of formula I.37 wherein $R^1$ is Y-4B, R is $NCH_3$ and $R^2$ is $CH_3$.

Table 2027. Compounds of formula I.37 wherein $R^1$ is Y-4C, R is $NCH_3$ and $R^2$ is $CH_3$.

Table 2028. Compounds of formula I.37 wherein $R^1$ is Y-4D, R is $NCH_3$ and $R^2$ is $CH_3$.

Table 2029. Compounds of formula I.37 wherein $R^1$ is Y-5A, R is $NCH_3$ and $R^2$ is $CH_3$.

Table 2030. Compounds of formula I.37 wherein $R^1$ is Y-5B, R is $NCH_3$ and $R^2$ is $CH_3$.

Table 2031. Compounds of formula I.37 wherein $R^1$ is Y-6A, R is $NCH_3$ and $R^2$ is $CH_3$.

Table 2032. Compounds of formula I.37 wherein $R^1$ is Y-6B, R is $NCH_3$ and $R^2$ is $CH_3$.

Table 2033. Compounds of formula I.37 wherein $R^1$ is Y-8A, R is $NCH_3$ and $R^2$ is $CH_3$.

Table 2034. Compounds of formula I.37 wherein $R^1$ is Y-8B, R is $NCH_3$ and $R^2$ is $CH_3$.

Table 2035. Compounds of formula I.37 wherein $R^1$ is Y-1A, R is $NCH_3$ and $R^2$ is c-$C_3H_5$.

Table 2036. Compounds of formula I.37 wherein $R^1$ is Y-1B, R is $NCH_3$ and $R^2$ is c-$C_3H_5$.

Table 2037. Compounds of formula I.37 wherein $R^1$ is Y-2A, R is $NCH_3$ and $R^2$ is c-$C_3H_5$.

Table 2038. Compounds of formula I.37 wherein $R^1$ is Y-2B, R is $NCH_3$ and $R^2$ is c-$C_3H_5$.

Table 2039. Compounds of formula I.37 wherein $R^1$ is Y-3A, R is $NCH_3$ and $R^2$ is c-$C_3H_5$.

Table 2040. Compounds of formula I.37 wherein $R^1$ is Y-3B, R is $NCH_3$ and $R^2$ is c-$C_3H_5$.

Table 2041. Compounds of formula I.37 wherein $R^1$ is Y-3C, R is $NCH_3$ and $R^2$ is c-$C_3H_5$.

Table 2042. Compounds of formula I.37 wherein $R^1$ is Y-3D, R is $NCH_3$ and $R^2$ is c-$C_3H_5$.

Table 2043. Compounds of formula I.37 wherein $R^1$ is Y-4A, R is $NCH_3$ and $R^2$ is c-$C_3H_5$.

Table 2044. Compounds of formula I.37 wherein $R^1$ is Y-4B, R is $NCH_3$ and $R^2$ is c-$C_3H_5$.

Table 2045. Compounds of formula I.37 wherein $R^1$ is Y-4C, R is $NCH_3$ and $R^2$ is c-$C_3H_5$.

Table 2046. Compounds of formula I.37 wherein $R^1$ is Y-4D, R is $NCH_3$ and $R^2$ is c-$C_3H_5$.

Table 2047. Compounds of formula I.37 wherein $R^1$ is Y-5A, R is $NCH_3$ and $R^2$ is c-$C_3H_5$.

Table 2048. Compounds of formula I.37 wherein $R^1$ is Y-5B, R is $NCH_3$ and $R^2$ is c-$C_3H_5$.

Table 2049. Compounds of formula I.37 wherein $R^1$ is Y-6A, R is $NCH_3$ and $R^2$ is c-$C_3H_5$.

Table 2050. Compounds of formula I.37 wherein $R^1$ is Y-6B, R is $NCH_3$ and $R^2$ is c-$C_3H_5$.

Table 2051. Compounds of formula I.37 wherein $R^1$ is Y-8A, R is $NCH_3$ and $R^2$ is c-$C_3H_5$.

Table 2052. Compounds of formula I.37 wherein $R^1$ is Y-8B, R is $NCH_3$ and $R^2$ is c-$C_3H_5$.

Table 2053. Compounds of formula I.37 wherein $R^1$ is Y-1A, R is NCN, and $R^2$ is H.

Table 2054. Compounds of formula I.37 wherein $R^1$ is Y-1B, R is NCN, and $R^2$ is H.

Table 2055. Compounds of formula I.37 wherein $R^1$ is Y-2A, R is NCN, and $R^2$ is H.

Table 2056. Compounds of formula I.37 wherein $R^1$ is Y-2B, R is NCN, and $R^2$ is H.

Table 2057. Compounds of formula I.37 wherein $R^1$ is Y-3A, R is NCN, and $R^2$ is H.

Table 2058. Compounds of formula I.37 wherein $R^1$ is Y-3B, R is NCN, and $R^2$ is H.

Table 2059. Compounds of formula I.37 wherein $R^1$ is Y-3C, R is NCN, and $R^2$ is H.

Table 2060. Compounds of formula I.37 wherein $R^1$ is Y-3D, R is NCN, and $R^2$ is H.

Table 2061. Compounds of formula I.37 wherein $R^1$ is Y-4A, R is NCN, and $R^2$ is H.

Table 2062. Compounds of formula I.37 wherein $R^1$ is Y-4B, R is NCN, and $R^2$ is H.

Table 2063. Compounds of formula I.37 wherein $R^1$ is Y-4C, R is NCN, and $R^2$ is H.

Table 2064. Compounds of formula I.37 wherein $R^1$ is Y-4D, R is NCN, and $R^2$ is H.

Table 2065. Compounds of formula I.37 wherein $R^1$ is Y-5A, R is NCN, and $R^2$ is H.

Table 2066. Compounds of formula I.37 wherein $R^1$ is Y-5B, R is NCN, and $R^2$ is H.

Table 2067. Compounds of formula I.37 wherein $R^1$ is Y-6A, R is NCN, and $R^2$ is H.

Table 2068. Compounds of formula I.37 wherein $R^1$ is Y-6B, R is NCN, and $R^2$ is H.

Table 2069. Compounds of formula I.37 wherein $R^1$ is Y-8A, R is NCN, and $R^2$ is H.

Table 2070. Compounds of formula I.37 wherein $R^1$ is Y-8B, R is NCN, and $R^2$ is H.

Table 2071. Compounds of formula I.37 wherein $R^1$ is Y-1A, R is NCN, and $R^2$ is $CH_3$.

Table 2072. Compounds of formula I.37 wherein $R^1$ is Y-1B, R is NCN, and $R^2$ is $CH_3$.

Table 2073. Compounds of formula I.37 wherein $R^1$ is Y-2A, R is NCN, and $R^2$ is $CH_3$.

Table 2074. Compounds of formula I.37 wherein $R^1$ is Y-2B, R is NCN, and $R^2$ is $CH_3$.

Table 2075. Compounds of formula I.37 wherein $R^1$ is Y-3A, R is NCN, and $R^2$ is $CH_3$.

Table 2076. Compounds of formula I.37 wherein $R^1$ is Y-3B, R is NCN, and $R^2$ is $CH_3$.

Table 2077. Compounds of formula I.37 wherein $R^1$ is Y-3C, R is NCN, and $R^2$ is $CH_3$.

Table 2078. Compounds of formula I.37 wherein $R^1$ is Y-3D, R is NCN, and $R^2$ is $CH_3$.

Table 2079. Compounds of formula I.37 wherein $R^1$ is Y-4A, R is NCN, and $R^2$ is $CH_3$.

Table 2080. Compounds of formula I.37 wherein $R^1$ is Y-4B, R is NCN, and $R^2$ is $CH_3$.

Table 2081. Compounds of formula I.37 wherein $R^1$ is Y-4C, R is NCN, and $R^2$ is $CH_3$.

Table 2082. Compounds of formula I.37 wherein $R^1$ is Y-4D, R is NCN, and $R^2$ is $CH_3$.

Table 2083. Compounds of formula I.37 wherein $R^1$ is Y-5A, R is NCN, and $R^2$ is $CH_3$.

Table 2084. Compounds of formula I.37 wherein $R^1$ is Y-5B, R is NCN, and $R^2$ is $CH_3$.

Table 2085. Compounds of formula I.37 wherein $R^1$ is Y-6A, R is NCN, and $R^2$ is $CH_3$.

Table 2086. Compounds of formula I.37 wherein $R^1$ is Y-6B, R is NCN, and $R^2$ is $CH_3$.

Table 2087. Compounds of formula I.37 wherein $R^1$ is Y-8A, R is NCN, and $R^2$ is $CH_3$.

Table 2088. Compounds of formula I.37 wherein $R^1$ is Y-8B, R is NCN, and $R^2$ is $CH_3$.

Table 2089. Compounds of formula I.37 wherein $R^1$ is Y-1A, R is NCN, and $R^2$ is c-$C_3H_5$.

Table 2090. Compounds of formula I.37 wherein $R^1$ is Y-1B, R is NCN, and $R^2$ is c-$C_3H_5$.

Table 2091. Compounds of formula I.37 wherein $R^1$ is Y-2A, R is NCN, and $R^2$ is c-$C_3H_5$.

Table 2092. Compounds of formula I.37 wherein $R^1$ is Y-2B, R is NCN, and $R^2$ is c-$C_3H_5$.

Table 2093. Compounds of formula I.37 wherein $R^1$ is Y-3A, R is NCN, and $R^2$ is c-$C_3H_5$.

Table 2094. Compounds of formula I.37 wherein $R^1$ is Y-3B, R is NCN, and $R^2$ is c-$C_3H_5$.

Table 2095. Compounds of formula I.37 wherein $R^1$ is Y-3C, R is NCN, and $R^2$ is c-$C_3H_5$.

Table 2096. Compounds of formula I.37 wherein $R^1$ is Y-3D, R is NCN, and $R^2$ is c-$C_3H_5$.

Table 2097. Compounds of formula I.37 wherein $R^1$ is Y-4A, R is NCN, and $R^2$ is c-$C_3H_5$.

Table 2098. Compounds of formula I.37 wherein $R^1$ is Y-4B, R is NCN, and $R^2$ is c-$C_3H_5$.

Table 2099. Compounds of formula I.37 wherein $R^1$ is Y-4C, R is NCN, and $R^2$ is c-$C_3H_5$.

Table 2100. Compounds of formula I.37 wherein $R^1$ is Y-4D, R is NCN, and $R^2$ is c-$C_3H_5$.

Table 2101. Compounds of formula I.37 wherein $R^1$ is Y-5A, R is NCN, and $R^2$ is c-$C_3H_5$.

Table 2102. Compounds of formula I.37 wherein $R^1$ is Y-5B, R is NCN, and $R^2$ is c-$C_3H_5$.

Table 2103. Compounds of formula I.37 wherein $R^1$ is Y-6A, R is NCN, and $R^2$ is c-$C_3H_5$.

Table 2104. Compounds of formula I.37 wherein $R^1$ is Y-6B, R is NCN, and $R^2$ is c-$C_3H_5$.

Table 2105. Compounds of formula I.37 wherein $R^1$ is Y-8A, R is NCN, and $R^2$ is c-$C_3H_5$.

Table 2106. Compounds of formula I.37 wherein $R^1$ is Y-8B, R is NCN, and $R^2$ is c-$C_3H_5$.

Table 2107. Compounds of formula I.38 wherein $R^1$ is Y-1A, R is NH, and $R^2$ is H.

Table 2108. Compounds of formula I.38 wherein $R^1$ is Y-1B, R is NH, and $R^2$ is H.

Table 2109. Compounds of formula I.38 wherein $R^1$ is Y-2A, R is NH, and $R^2$ is H.

Table 2110. Compounds of formula I.38 wherein $R^1$ is Y-2B, R is NH, and $R^2$ is H.

Table 2111. Compounds of formula I.38 wherein $R^1$ is Y-3A, R is NH, and $R^2$ is H.

Table 2112. Compounds of formula I.38 wherein $R^1$ is Y-3B, R is NH, and $R^2$ is H.

Table 2113. Compounds of formula I.38 wherein $R^1$ is Y-3C, R is NH, and $R^2$ is H.

Table 2114. Compounds of formula I.38 wherein $R^1$ is Y-3D, R is NH, and $R^2$ is H.

Table 2115. Compounds of formula I.38 wherein $R^1$ is Y-4A, R is NH, and $R^2$ is H.

Table 2116. Compounds of formula I.38 wherein $R^1$ is Y-4B, R is NH, and $R^2$ is H.

Table 2117. Compounds of formula I.38 wherein $R^1$ is Y-4C, R is NH, and $R^2$ is H.

Table 2118. Compounds of formula I.38 wherein $R^1$ is Y-4D, R is NH, and $R^2$ is H.

Table 2119. Compounds of formula I.38 wherein $R^1$ is Y-5A, R is NH, and $R^2$ is H.

Table 2120. Compounds of formula I.38 wherein $R^1$ is Y-5B, R is NH, and $R^2$ is H.

Table 2121. Compounds of formula I.38 wherein $R^1$ is Y-6A, R is NH, and $R^2$ is H.

Table 2122. Compounds of formula I.38 wherein $R^1$ is Y-6B, R is NH, and $R^2$ is H.

Table 2123. Compounds of formula I.38 wherein $R^1$ is Y-8A, R is NH, and $R^2$ is H.

Table 2124. Compounds of formula I.38 wherein $R^1$ is Y-8B, R is NH, and $R^2$ is H.

Table 2125. Compounds of formula I.38 wherein $R^1$ is Y-1A, R is NH, and $R^2$ is $CH_3$.

Table 2126. Compounds of formula I.38 wherein $R^1$ is Y-1B, R is NH, and $R^2$ is $CH_3$.

Table 2127. Compounds of formula I.38 wherein $R^1$ is Y-2A, R is NH, and $R^2$ is $CH_3$.

Table 2128. Compounds of formula I.38 wherein $R^1$ is Y-2B, R is NH, and $R^2$ is $CH_3$.

Table 2129. Compounds of formula I.38 wherein $R^1$ is Y-3A, R is NH, and $R^2$ is $CH_3$.

Table 2130. Compounds of formula I.38 wherein $R^1$ is Y-3B, R is NH, and $R^2$ is $CH_3$.

Table 2131. Compounds of formula I.38 wherein $R^1$ is Y-3C, R is NH, and $R^2$ is $CH_3$.

Table 2132. Compounds of formula I.38 wherein $R^1$ is Y-3D, R is NH, and $R^2$ is $CH_3$.

Table 2133. Compounds of formula I.38 wherein $R^1$ is Y-4A, R is NH, and $R^2$ is $CH_3$.

Table 2134. Compounds of formula I.38 wherein $R^1$ is Y-4B, R is NH, and $R^2$ is $CH_3$.

Table 2135. Compounds of formula I.38 wherein $R^1$ is Y-4C, R is NH, and $R^2$ is $CH_3$.

Table 2136. Compounds of formula I.38 wherein $R^1$ is Y-4D, R is NH, and $R^2$ is $CH_3$.

Table 2137. Compounds of formula I.38 wherein $R^1$ is Y-5A, R is NH, and $R^2$ is $CH_3$.

Table 2138. Compounds of formula I.38 wherein $R^1$ is Y-5B, R is NH, and $R^2$ is $CH_3$.

Table 2139. Compounds of formula I.38 wherein $R^1$ is Y-6A, R is NH, and $R^2$ is $CH_3$.

Table 2140. Compounds of formula I.38 wherein $R^1$ is Y-6B, R is NH, and $R^2$ is $CH_3$.

Table 2141. Compounds of formula I.38 wherein $R^1$ is Y-8A, R is NH, and $R^2$ is $CH_3$.

Table 2142. Compounds of formula I.38 wherein $R^1$ is Y-8B, R is NH, and $R^2$ is $CH_3$.

Table 2143. Compounds of formula I.38 wherein $R^1$ is Y-1A, R is NH, and $R^2$ is c-$C_3H_5$.

Table 2144. Compounds of formula I.38 wherein $R^1$ is Y-1B, R is NH, and $R^2$ is c-$C_3H_5$.

Table 2145. Compounds of formula I.38 wherein $R^1$ is Y-2A, R is NH, and $R^2$ is c-$C_3H_5$.

Table 2146. Compounds of formula I.38 wherein $R^1$ is Y-2B, R is NH, and $R^2$ is c-$C_3H_5$.

Table 2147. Compounds of formula I.38 wherein $R^1$ is Y-3A, R is NH, and $R^2$ is c-$C_3H_5$.

Table 2148. Compounds of formula I.38 wherein $R^1$ is Y-3B, R is NH, and $R^2$ is c-$C_3H_5$.

Table 2149. Compounds of formula I.38 wherein $R^1$ is Y-3C, R is NH, and $R^2$ is c-$C_3H_5$.

Table 2150. Compounds of formula I.38 wherein $R^1$ is Y-3D, R is NH, and $R^2$ is c-$C_3H_5$.

Table 2151. Compounds of formula I.38 wherein $R^1$ is Y-4A, R is NH, and $R^2$ is c-$C_3H_5$.

Table 2152. Compounds of formula I.38 wherein $R^1$ is Y-4B, R is NH, and $R^2$ is c-$C_3H_5$.

Table 2153. Compounds of formula I.38 wherein $R^1$ is Y-4C, R is NH, and $R^2$ is c-$C_3H_5$.

Table 2154. Compounds of formula I.38 wherein $R^1$ is Y-4D, R is NH, and $R^2$ is c-$C_3H_5$.

Table 2155. Compounds of formula I.38 wherein $R^1$ is Y-5A, R is NH, and $R^2$ is c-$C_3H_5$.

Table 2156. Compounds of formula I.38 wherein $R^1$ is Y-5B, R is NH, and $R^2$ is c-$C_3H_5$.

Table 2157. Compounds of formula I.38 wherein $R^1$ is Y-6A, R is NH, and $R^2$ is c-$C_3H_5$.

Table 2158. Compounds of formula I.38 wherein $R^1$ is Y-6B, R is NH, and $R^2$ is c-$C_3H_5$.

Table 2159. Compounds of formula I.38 wherein $R^1$ is Y-8A, R is NH, and $R^2$ is c-$C_3H_5$.

Table 2160. Compounds of formula I.38 wherein $R^1$ is Y-8B, R is NH, and $R^2$ is c-$C_3H_5$.

Table 2161. Compounds of formula I.38 wherein $R^1$ is Y-1A, R is $NCH_3$ and $R^2$ is H.

Table 2162. Compounds of formula I.38 wherein $R^1$ is Y-1B, R is $NCH_3$ and $R^2$ is H.

Table 2163. Compounds of formula I.38 wherein $R^1$ is Y-2A, R is $NCH_3$ and $R^2$ is H.

Table 2164. Compounds of formula I.38 wherein $R^1$ is Y-2B, R is $NCH_3$ and $R^2$ is H.

Table 2165. Compounds of formula I.38 wherein $R^1$ is Y-3A, R is $NCH_3$ and $R^2$ is H.

Table 2166. Compounds of formula I.38 wherein $R^1$ is Y-3B, R is $NCH_3$ and $R^2$ is H.

Table 2167. Compounds of formula I.38 wherein $R^1$ is Y-3C, R is $NCH_3$ and $R^2$ is H.

Table 2168. Compounds of formula I.38 wherein $R^1$ is Y-3D, R is $NCH_3$ and $R^2$ is H.

Table 2169. Compounds of formula I.38 wherein $R^1$ is Y-4A, R is $NCH_3$ and $R^2$ is H.

Table 2170. Compounds of formula I.38 wherein $R^1$ is Y-4B, R is $NCH_3$ and $R^2$ is H.

Table 2171. Compounds of formula I.38 wherein $R^1$ is Y-4C, R is $NCH_3$ and $R^2$ is H.

Table 2172. Compounds of formula I.38 wherein $R^1$ is Y-4D, R is $NCH_3$ and $R^2$ is H.

Table 2173. Compounds of formula I.38 wherein $R^1$ is Y-5A, R is $NCH_3$ and $R^2$ is H.

Table 2174. Compounds of formula I.38 wherein $R^1$ is Y-5B, R is $NCH_3$ and $R^2$ is H.

Table 2175. Compounds of formula I.38 wherein $R^1$ is Y-6A, R is $NCH_3$ and $R^2$ is H.

Table 2176. Compounds of formula I.38 wherein $R^1$ is Y-6B, R is $NCH_3$ and $R^2$ is H.

Table 2177. Compounds of formula I.38 wherein $R^1$ is Y-8A, R is $NCH_3$ and $R^2$ is H.

Table 2178. Compounds of formula I.38 wherein $R^1$ is Y-8B, R is $NCH_3$ and $R^2$ is H.

Table 2179. Compounds of formula I.38 wherein $R^1$ is Y-1A, R is $NCH_3$ and $R^2$ is $CH_3$.

Table 2180. Compounds of formula I.38 wherein $R^1$ is Y-1B, R is $NCH_3$ and $R^2$ is $CH_3$.

Table 2181. Compounds of formula I.38 wherein $R^1$ is Y-2A, R is $NCH_3$ and $R^2$ is $CH_3$.

Table 2182. Compounds of formula I.38 wherein $R^1$ is Y-2B, R is $NCH_3$ and $R^2$ is $CH_3$.

Table 2183. Compounds of formula I.38 wherein $R^1$ is Y-3A, R is $NCH_3$ and $R^2$ is $CH_3$.

Table 2184. Compounds of formula I.38 wherein $R^1$ is Y-3B, R is $NCH_3$ and $R^2$ is $CH_3$.

Table 2185. Compounds of formula I.38 wherein $R^1$ is Y-3C, R is $NCH_3$ and $R^2$ is $CH_3$.

Table 2186. Compounds of formula I.38 wherein $R^1$ is Y-3D, R is $NCH_3$ and $R^2$ is $CH_3$.

Table 2187. Compounds of formula I.38 wherein $R^1$ is Y-4A, R is $NCH_3$ and $R^2$ is $CH_3$.

Table 2188. Compounds of formula I.38 wherein $R^1$ is Y-4B, R is $NCH_3$ and $R^2$ is $CH_3$.

Table 2189. Compounds of formula I.38 wherein $R^1$ is Y-4C, R is $NCH_3$ and $R^2$ is $CH_3$.

Table 2190. Compounds of formula I.38 wherein $R^1$ is Y-4D, R is $NCH_3$ and $R^2$ is $CH_3$.

Table 2191. Compounds of formula I.38 wherein $R^1$ is Y-5A, R is $NCH_3$ and $R^2$ is $CH_3$.

Table 2192. Compounds of formula I.38 wherein $R^1$ is Y-5B, R is $NCH_3$ and $R^2$ is $CH_3$.

Table 2193. Compounds of formula I.38 wherein $R^1$ is Y-6A, R is $NCH_3$ and $R^2$ is $CH_3$.

Table 2194. Compounds of formula I.38 wherein $R^1$ is Y-6B, R is $NCH_3$ and $R^2$ is $CH_3$.

Table 2195. Compounds of formula I.38 wherein $R^1$ is Y-8A, R is $NCH_3$ and $R^2$ is $CH_3$.

Table 2196. Compounds of formula I.38 wherein $R^1$ is Y-8B, R is $NCH_3$ and $R^2$ is $CH_3$.

Table 2197. Compounds of formula I.38 wherein $R^1$ is Y-1A, R is $NCH_3$ and $R^2$ is c-$C_3H_5$.

Table 2198. Compounds of formula I.38 wherein $R^1$ is Y-1B, R is $NCH_3$ and $R^2$ is c-$C_3H_5$.

Table 2199. Compounds of formula I.38 wherein $R^1$ is Y-2A, R is $NCH_3$ and $R^2$ is c-$C_3H_5$.

Table 2200. Compounds of formula I.38 wherein $R^1$ is Y-2B, R is $NCH_3$ and $R^2$ is c-$C_3H_5$.

Table 2201. Compounds of formula I.38 wherein $R^1$ is Y-3A, R is $NCH_3$ and $R^2$ is c-$C_3H_5$.

Table 2202. Compounds of formula I.38 wherein $R^1$ is Y-3B, R is $NCH_3$ and $R^2$ is c-$C_3H_5$.

Table 2203. Compounds of formula I.38 wherein $R^1$ is Y-3C, R is $NCH_3$ and $R^2$ is c-$C_3H_5$.

Table 2204. Compounds of formula I.38 wherein $R^1$ is Y-3D, R is $NCH_3$ and $R^2$ is c-$C_3H_5$.

Table 2205. Compounds of formula I.38 wherein $R^1$ is Y-4A, R is $NCH_3$ and $R^2$ is c-$C_3H_5$.

Table 2206. Compounds of formula I.38 wherein $R^1$ is Y-4B, R is $NCH_3$ and $R^2$ is c-$C_3H_5$.

Table 2207. Compounds of formula I.38 wherein $R^1$ is Y-4C, R is $NCH_3$ and $R^2$ is c-$C_3H_5$.

Table 2208. Compounds of formula I.38 wherein $R^1$ is Y-4D, R is $NCH_3$ and $R^2$ is c-$C_3H_5$.

Table 2209. Compounds of formula I.38 wherein $R^1$ is Y-5A, R is $NCH_3$ and $R^2$ is c-$C_3H_5$.

Table 2210. Compounds of formula I.38 wherein $R^1$ is Y-5B, R is $NCH_3$ and $R^2$ is c-$C_3H_5$.

Table 2211. Compounds of formula I.38 wherein $R^1$ is Y-6A, R is $NCH_3$ and $R^2$ is c-$C_3H_5$.

Table 2212. Compounds of formula I.38 wherein $R^1$ is Y-6B, R is $NCH_3$ and $R^2$ is c-$C_3H_5$.

Table 2213. Compounds of formula I.38 wherein $R^1$ is Y-8A, R is $NCH_3$ and $R^2$ is c-$C_3H_5$.

Table 2214. Compounds of formula I.38 wherein $R^1$ is Y-8B, R is $NCH_3$ and $R^2$ is c-$C_3H_5$.

Table 2215. Compounds of formula I.38 wherein $R^1$ is Y-1A, R is NCN, and $R^2$ is H.

Table 2216. Compounds of formula I.38 wherein $R^1$ is Y-1B, R is NCN, and $R^2$ is H.

Table 2217. Compounds of formula I.38 wherein $R^1$ is Y-2A, R is NCN, and $R^2$ is H.

Table 2218. Compounds of formula I.38 wherein $R^1$ is Y-2B, R is NCN, and $R^2$ is H.

Table 2219. Compounds of formula I.38 wherein $R^1$ is Y-3A, R is NCN, and $R^2$ is H.

Table 2220. Compounds of formula I.38 wherein $R^1$ is Y-3B, R is NCN, and $R^2$ is H.

Table 2221. Compounds of formula I.38 wherein $R^1$ is Y-3C, R is NCN, and $R^2$ is H.

Table 2222. Compounds of formula I.38 wherein $R^1$ is Y-3D, R is NCN, and $R^2$ is H.

Table 2223. Compounds of formula I.38 wherein $R^1$ is Y-4A, R is NCN, and $R^2$ is H.

Table 2224. Compounds of formula I.38 wherein $R^1$ is Y-4B, R is NCN, and $R^2$ is H.

Table 2225. Compounds of formula I.38 wherein $R^1$ is Y-4C, R is NCN, and $R^2$ is H.

Table 2226. Compounds of formula I.38 wherein $R^1$ is Y-4D, R is NCN, and $R^2$ is H.

Table 2227. Compounds of formula I.38 wherein $R^1$ is Y-5A, R is NCN, and $R^2$ is H.

Table 2228. Compounds of formula I.38 wherein $R^1$ is Y-5B, R is NCN, and $R^2$ is H.

Table 2229. Compounds of formula I.38 wherein $R^1$ is Y-6A, R is NCN, and $R^2$ is H.

Table 2230. Compounds of formula I.38 wherein $R^1$ is Y-6B, R is NCN, and $R^2$ is H.

Table 2231. Compounds of formula I.38 wherein $R^1$ is Y-8A, R is NCN, and $R^2$ is H.

Table 2232. Compounds of formula I.38 wherein $R^1$ is Y-8B, R is NCN, and $R^2$ is H.

Table 2233. Compounds of formula I.38 wherein $R^1$ is Y-1A, R is NCN, and $R^2$ is $CH_3$.

Table 2234. Compounds of formula I.38 wherein $R^1$ is Y-1B, R is NCN, and $R^2$ is $CH_3$.

Table 2235. Compounds of formula I.38 wherein $R^1$ is Y-2A, R is NCN, and $R^2$ is $CH_3$.

Table 2236. Compounds of formula I.38 wherein $R^1$ is Y-2B, R is NCN, and $R^2$ is $CH_3$.

Table 2237. Compounds of formula I.38 wherein $R^1$ is Y-3A, R is NCN, and $R^2$ is $CH_3$.

Table 2238. Compounds of formula I.38 wherein $R^1$ is Y-3B, R is NCN, and $R^2$ is $CH_3$.

Table 2239. Compounds of formula I.38 wherein $R^1$ is Y-3C, R is NCN, and $R^2$ is $CH_3$.

Table 2240. Compounds of formula I.38 wherein $R^1$ is Y-3D, R is NCN, and $R^2$ is $CH_3$.

Table 2241. Compounds of formula I.38 wherein $R^1$ is Y-4A, R is NCN, and $R^2$ is $CH_3$.

Table 2242. Compounds of formula I.38 wherein $R^1$ is Y-4B, R is NCN, and $R^2$ is $CH_3$.

Table 2243. Compounds of formula I.38 wherein $R^1$ is Y-4C, R is NCN, and $R^2$ is $CH_3$.

Table 2244. Compounds of formula I.38 wherein $R^1$ is Y-4D, R is NCN, and $R^2$ is $CH_3$.

Table 2245. Compounds of formula I.38 wherein $R^1$ is Y-5A, R is NCN, and $R^2$ is $CH_3$.

Table 2246. Compounds of formula I.38 wherein $R^1$ is Y-5B, R is NCN, and $R^2$ is $CH_3$.

Table 2247. Compounds of formula I.38 wherein $R^1$ is Y-6A, R is NCN, and $R^2$ is $CH_3$.

Table 2248. Compounds of formula I.38 wherein $R^1$ is Y-6B, R is NCN, and $R^2$ is $CH_3$.

Table 2249. Compounds of formula I.38 wherein $R^1$ is Y-8A, R is NCN, and $R^2$ is $CH_3$.

Table 2250. Compounds of formula I.38 wherein $R^1$ is Y-8B, R is NCN, and $R^2$ is $CH_3$.

Table 2251. Compounds of formula I.38 wherein $R^1$ is Y-1A, R is NCN, and $R^2$ is c-$C_3H_5$.

Table 2252. Compounds of formula I.38 wherein $R^1$ is Y-1B, R is NCN, and $R^2$ is c-$C_3H_5$.

Table 2253. Compounds of formula I.38 wherein $R^1$ is Y-2A, R is NCN, and $R^2$ is c-$C_3H_5$.

Table 2254. Compounds of formula I.38 wherein $R^1$ is Y-2B, R is NCN, and $R^2$ is c-$C_3H_5$.

Table 2255. Compounds of formula I.38 wherein $R^1$ is Y-3A, R is NCN, and $R^2$ is c-$C_3H_5$.

Table 2256. Compounds of formula I.38 wherein $R^1$ is Y-3B, R is NCN, and $R^2$ is c-$C_3H_5$.

Table 2257. Compounds of formula I.38 wherein $R^1$ is Y-3C, R is NCN, and $R^2$ is c-$C_3H_5$.

Table 2258. Compounds of formula I.38 wherein $R^1$ is Y-3D, R is NCN, and $R^2$ is c-$C_3H_5$.

Table 2259. Compounds of formula I.38 wherein $R^1$ is Y-4A, R is NCN, and $R^2$ is c-$C_3H_5$.

Table 2260. Compounds of formula I.38 wherein $R^1$ is Y-4B, R is NCN, and $R^2$ is c-$C_3H_5$.

Table 2261. Compounds of formula I.38 wherein $R^1$ is Y-4C, R is NCN, and $R^2$ is c-$C_3H_5$.

Table 2262. Compounds of formula I.38 wherein $R^1$ is Y-4D, R is NCN, and $R^2$ is c-$C_3H_5$.

Table 2263. Compounds of formula I.38 wherein $R^1$ is Y-5A, R is NCN, and $R^2$ is c-$C_3H_5$.

Table 2264. Compounds of formula I.38 wherein $R^1$ is Y-5B, R is NCN, and $R^2$ is c-$C_3H_5$.

Table 2265. Compounds of formula I.38 wherein $R^1$ is Y-6A, R is NCN, and $R^2$ is c-$C_3H_5$.

Table 2266. Compounds of formula I.38 wherein $R^1$ is Y-6B, R is NCN, and $R^2$ is c-$C_3H_5$.

Table 2267. Compounds of formula I.38 wherein $R^1$ is Y-8A, R is NCN, and $R^2$ is c-$C_3H_5$.

Table 2268. Compounds of formula I.38 wherein $R^1$ is Y-8B, R is NCN, and $R^2$ is c-$C_3H_5$.

Table 2269. Compounds of formula I.39 wherein $R^1$ is Y-1A, R is NH, and $R^2$ is H.

Table 2270. Compounds of formula I.39 wherein $R^1$ is Y-1B, R is NH, and $R^2$ is H.

Table 2271. Compounds of formula I.39 wherein $R^1$ is Y-2A, R is NH, and $R^2$ is H.

Table 2272. Compounds of formula I.39 wherein $R^1$ is Y-2B, R is NH, and $R^2$ is H.

Table 2273. Compounds of formula I.39 wherein $R^1$ is Y-3A, R is NH, and $R^2$ is H.

Table 2274. Compounds of formula I.39 wherein $R^1$ is Y-3B, R is NH, and $R^2$ is H.

Table 2275. Compounds of formula I.39 wherein $R^1$ is Y-3C, R is NH, and $R^2$ is H.

Table 2276. Compounds of formula I.39 wherein $R^1$ is Y-3D, R is NH, and $R^2$ is H.

Table 2277. Compounds of formula I.39 wherein $R^1$ is Y-4A, R is NH, and $R^2$ is H.

Table 2278. Compounds of formula I.39 wherein $R^1$ is Y-4B, R is NH, and $R^2$ is H.

Table 2279. Compounds of formula I.39 wherein $R^1$ is Y-4C, R is NH, and $R^2$ is H.

Table 2280. Compounds of formula I.39 wherein $R^1$ is Y-4D, R is NH, and $R^2$ is H.

Table 2281. Compounds of formula I.39 wherein $R^1$ is Y-5A, R is NH, and $R^2$ is H.

Table 2282. Compounds of formula I.39 wherein $R^1$ is Y-5B, R is NH, and $R^2$ is H.

Table 2283. Compounds of formula I.39 wherein $R^1$ is Y-6A, R is NH, and $R^2$ is H.

Table 2284. Compounds of formula I.39 wherein $R^1$ is Y-6B, R is NH, and $R^2$ is H.

Table 2285. Compounds of formula I.39 wherein $R^1$ is Y-8A, R is NH, and $R^2$ is H.

Table 2286. Compounds of formula I.39 wherein $R^1$ is Y-8B, R is NH, and $R^2$ is H.

Table 2287. Compounds of formula I.39 wherein $R^1$ is Y-1A, R is NH, and $R^2$ is $CH_3$.

Table 2288. Compounds of formula I.39 wherein $R^1$ is Y-1B, R is NH, and $R^2$ is $CH_3$.

Table 2289. Compounds of formula I.39 wherein $R^1$ is Y-2A, R is NH, and $R^2$ is $CH_3$.

Table 2290. Compounds of formula I.39 wherein $R^1$ is Y-2B, R is NH, and $R^2$ is $CH_3$.

Table 2291. Compounds of formula I.39 wherein $R^1$ is Y-3A, R is NH, and $R^2$ is $CH_3$.

Table 2292. Compounds of formula I.39 wherein $R^1$ is Y-3B, R is NH, and $R^2$ is $CH_3$.

Table 2293. Compounds of formula I.39 wherein $R^1$ is Y-3C, R is NH, and $R^2$ is $CH_3$.

Table 2294. Compounds of formula I.39 wherein $R^1$ is Y-3D, R is NH, and $R^2$ is $CH_3$.

Table 2295. Compounds of formula I.39 wherein $R^1$ is Y-4A, R is NH, and $R^2$ is $CH_3$.

Table 2296. Compounds of formula I.39 wherein $R^1$ is Y-4B, R is NH, and $R^2$ is $CH_3$.

Table 2297. Compounds of formula I.39 wherein $R^1$ is Y-4C, R is NH, and $R^2$ is $CH_3$.

Table 2298. Compounds of formula I.39 wherein $R^1$ is Y-4D, R is NH, and $R^2$ is $CH_3$.

Table 2299. Compounds of formula I.39 wherein $R^1$ is Y-5A, R is NH, and $R^2$ is $CH_3$.

Table 2300. Compounds of formula I.39 wherein $R^1$ is Y-5B, R is NH, and $R^2$ is $CH_3$.

Table 2301. Compounds of formula I.39 wherein $R^1$ is Y-6A, R is NH, and $R^2$ is $CH_3$.

Table 2302. Compounds of formula I.39 wherein $R^1$ is Y-6B, R is NH, and $R^2$ is $CH_3$.

Table 2303. Compounds of formula I.39 wherein $R^1$ is Y-8A, R is NH, and $R^2$ is $CH_3$.

Table 2304. Compounds of formula I.39 wherein $R^1$ is Y-8B, R is NH, and $R^2$ is $CH_3$.

Table 2305. Compounds of formula I.39 wherein $R^1$ is Y-1A, R is NH, and $R^2$ is c-$C_3H_5$.

Table 2306. Compounds of formula I.39 wherein $R^1$ is Y-1B, R is NH, and $R^2$ is c-$C_3H_5$.

Table 2307. Compounds of formula I.39 wherein $R^1$ is Y-2A, R is NH, and $R^2$ is c-$C_3H_5$.

Table 2308. Compounds of formula I.39 wherein $R^1$ is Y-2B, R is NH, and $R^2$ is c-$C_3H_5$.

Table 2309. Compounds of formula I.39 wherein $R^1$ is Y-3A, R is NH, and $R^2$ is c-$C_3H_5$.

Table 2310. Compounds of formula I.39 wherein $R^1$ is Y-3B, R is NH, and $R^2$ is c-$C_3H_5$.

Table 2311. Compounds of formula I.39 wherein $R^1$ is Y-3C, R is NH, and $R^2$ is c-$C_3H_5$.

Table 2312. Compounds of formula I.39 wherein $R^1$ is Y-3D, R is NH, and $R^2$ is c-$C_3H_5$.

Table 2313. Compounds of formula I.39 wherein $R^1$ is Y-4A, R is NH, and $R^2$ is c-$C_3H_5$.

Table 2314. Compounds of formula I.39 wherein $R^1$ is Y-4B, R is NH, and $R^2$ is c-$C_3H_5$.

Table 2315. Compounds of formula I.39 wherein $R^1$ is Y-4C, R is NH, and $R^2$ is c-$C_3H_5$.

Table 2316. Compounds of formula I.39 wherein $R^1$ is Y-4D, R is NH, and $R^2$ is c-$C_3H_5$.

Table 2317. Compounds of formula I.39 wherein $R^1$ is Y-5A, R is NH, and $R^2$ is c-$C_3H_5$.

Table 2318. Compounds of formula I.39 wherein $R^1$ is Y-5B, R is NH, and $R^2$ is c-$C_3H_5$.

Table 2319. Compounds of formula I.39 wherein $R^1$ is Y-6A, R is NH, and $R^2$ is c-$C_3H_5$.

Table 2320. Compounds of formula I.39 wherein $R^1$ is Y-6B, R is NH, and $R^2$ is c-$C_3H_5$.

Table 2321. Compounds of formula I.39 wherein $R^1$ is Y-8A, R is NH, and $R^2$ is c-$C_3H_5$.

Table 2322. Compounds of formula I.39 wherein $R^1$ is Y-8B, R is NH, and $R^2$ is c-$C_3H_5$.

Table 2323. Compounds of formula I.39 wherein $R^1$ is Y-1A, R is $NCH_3$ and $R^2$ is H.

Table 2324. Compounds of formula I.39 wherein $R^1$ is Y-1B, R is $NCH_3$ and $R^2$ is H.

Table 2325. Compounds of formula I.39 wherein $R^1$ is Y-2A, R is $NCH_3$ and $R^2$ is H.

Table 2326. Compounds of formula I.39 wherein $R^1$ is Y-2B, R is $NCH_3$ and $R^2$ is H.

Table 2327. Compounds of formula I.39 wherein $R^1$ is Y-3A, R is $NCH_3$ and $R^2$ is H.

Table 2328. Compounds of formula I.39 wherein $R^1$ is Y-3B, R is $NCH_3$ and $R^2$ is H.

Table 2329. Compounds of formula I.39 wherein $R^1$ is Y-3C, R is $NCH_3$ and $R^2$ is H.

Table 2330. Compounds of formula I.39 wherein $R^1$ is Y-3D, R is $NCH_3$ and $R^2$ is H.

Table 2331. Compounds of formula I.39 wherein $R^1$ is Y-4A, R is $NCH_3$ and $R^2$ is H.

Table 2332. Compounds of formula I.39 wherein $R^1$ is Y-4B, R is $NCH_3$ and $R^2$ is H.

Table 2333. Compounds of formula I.39 wherein $R^1$ is Y-4C, R is $NCH_3$ and $R^2$ is H.

Table 2334. Compounds of formula I.39 wherein $R^1$ is Y-4D, R is $NCH_3$ and $R^2$ is H.

Table 2335. Compounds of formula I.39 wherein $R^1$ is Y-5A, R is $NCH_3$ and $R^2$ is H.

Table 2336. Compounds of formula I.39 wherein $R^1$ is Y-5B, R is $NCH_3$ and $R^2$ is H.

Table 2337. Compounds of formula I.39 wherein $R^1$ is Y-6A, R is $NCH_3$ and $R^2$ is H.

Table 2338. Compounds of formula I.39 wherein $R^1$ is Y-6B, R is $NCH_3$ and $R^2$ is H.

Table 2339. Compounds of formula I.39 wherein $R^1$ is Y-8A, R is $NCH_3$ and $R^2$ is H.

Table 2340. Compounds of formula I.39 wherein $R^1$ is Y-8B, R is $NCH_3$ and $R^2$ is H.

Table 2341. Compounds of formula I.39 wherein $R^1$ is Y-1A, R is $NCH_3$ and $R^2$ is $CH_3$.

Table 2342. Compounds of formula I.39 wherein $R^1$ is Y-1B, R is $NCH_3$ and $R^2$ is $CH_3$.

Table 2343. Compounds of formula I.39 wherein $R^1$ is Y-2A, R is $NCH_3$ and $R^2$ is $CH_3$.

Table 2344. Compounds of formula I.39 wherein $R^1$ is Y-2B, R is $NCH_3$ and $R^2$ is $CH_3$.

Table 2345. Compounds of formula I.39 wherein $R^1$ is Y-3A, R is $NCH_3$ and $R^2$ is $CH_3$.

Table 2346. Compounds of formula I.39 wherein $R^1$ is Y-3B, R is $NCH_3$ and $R^2$ is $CH_3$.

Table 2347. Compounds of formula I.39 wherein $R^1$ is Y-3C, R is $NCH_3$ and $R^2$ is $CH_3$.

Table 2348. Compounds of formula I.39 wherein $R^1$ is Y-3D, R is $NCH_3$ and $R^2$ is $CH_3$.

Table 2349. Compounds of formula I.39 wherein $R^1$ is Y-4A, R is $NCH_3$ and $R^2$ is $CH_3$.

Table 2350. Compounds of formula I.39 wherein $R^1$ is Y-4B, R is $NCH_3$ and $R^2$ is $CH_3$.

Table 2351. Compounds of formula I.39 wherein $R^1$ is Y-4C, R is $NCH_3$ and $R^2$ is $CH_3$.

Table 2352. Compounds of formula I.39 wherein $R^1$ is Y-4D, R is $NCH_3$ and $R^2$ is $CH_3$.

Table 2353. Compounds of formula I.39 wherein $R^1$ is Y-5A, R is $NCH_3$ and $R^2$ is $CH_3$.

Table 2354. Compounds of formula I.39 wherein $R^1$ is Y-5B, R is $NCH_3$ and $R^2$ is $CH_3$.

Table 2355. Compounds of formula I.39 wherein $R^1$ is Y-6A, R is $NCH_3$ and $R^2$ is $CH_3$.

Table 2356. Compounds of formula I.39 wherein $R^1$ is Y-6B, R is $NCH_3$ and $R^2$ is $CH_3$.

Table 2357. Compounds of formula I.39 wherein $R^1$ is Y-8A, R is $NCH_3$ and $R^2$ is $CH_3$.

Table 2358. Compounds of formula I.39 wherein $R^1$ is Y-8B, R is $NCH_3$ and $R^2$ is $CH_3$.

Table 2359. Compounds of formula I.39 wherein $R^1$ is Y-1A, R is $NCH_3$ and $R^2$ is c-$C_3H_5$.

Table 2360. Compounds of formula I.39 wherein $R^1$ is Y-1B, R is $NCH_3$ and $R^2$ is c-$C_3H_5$.

Table 2361. Compounds of formula I.39 wherein $R^1$ is Y-2A, R is $NCH_3$ and $R^2$ is c-$C_3H_5$.

Table 2362. Compounds of formula I.39 wherein $R^1$ is Y-2B, R is $NCH_3$ and $R^2$ is c-$C_3H_5$.

Table 2363. Compounds of formula I.39 wherein $R^1$ is Y-3A, R is $NCH_3$ and $R^2$ is c-$C_3H_5$.

Table 2364. Compounds of formula I.39 wherein $R^1$ is Y-3B, R is $NCH_3$ and $R^2$ is c-$C_3H_5$.

Table 2365. Compounds of formula I.39 wherein $R^1$ is Y-3C, R is $NCH_3$ and $R^2$ is c-$C_3H_5$.

Table 2366. Compounds of formula I.39 wherein $R^1$ is Y-3D, R is $NCH_3$ and $R^2$ is c-$C_3H_5$.

Table 2367. Compounds of formula I.39 wherein $R^1$ is Y-4A, R is $NCH_3$ and $R^2$ is c-$C_3H_5$.

Table 2368. Compounds of formula I.39 wherein $R^1$ is Y-4B, R is $NCH_3$ and $R^2$ is c-$C_3H_5$.

Table 2369. Compounds of formula I.39 wherein $R^1$ is Y-4C, R is $NCH_3$ and $R^2$ is c-$C_3H_5$.

Table 2370. Compounds of formula I.39 wherein $R^1$ is Y-4D, R is $NCH_3$ and $R^2$ is c-$C_3H_5$.

Table 2371. Compounds of formula I.39 wherein $R^1$ is Y-5A, R is $NCH_3$ and $R^2$ is c-$C_3H_5$.

Table 2372. Compounds of formula I.39 wherein $R^1$ is Y-5B, R is $NCH_3$ and $R^2$ is c-$C_3H_5$.

Table 2373. Compounds of formula I.39 wherein $R^1$ is Y-6A, R is $NCH_3$ and $R^2$ is c-$C_3H_5$.

Table 2374. Compounds of formula I.39 wherein $R^1$ is Y-6B, R is $NCH_3$ and $R^2$ is c-$C_3H_5$.

Table 2375. Compounds of formula I.39 wherein $R^1$ is Y-8A, R is $NCH_3$ and $R^2$ is c-$C_3H_5$.

Table 2376. Compounds of formula I.39 wherein $R^1$ is Y-8B, R is $NCH_3$ and $R^2$ is c-$C_3H_5$.

Table 2377. Compounds of formula I.39 wherein $R^1$ is Y-1A, R is NCN, and $R^2$ is H.

Table 2378. Compounds of formula I.39 wherein $R^1$ is Y-1B, R is NCN, and $R^2$ is H.

Table 2379. Compounds of formula I.39 wherein $R^1$ is Y-2A, R is NCN, and $R^2$ is H.

Table 2380. Compounds of formula I.39 wherein $R^1$ is Y-2B, R is NCN, and $R^2$ is H.

Table 2381. Compounds of formula I.39 wherein $R^1$ is Y-3A, R is NCN, and $R^2$ is H.

Table 2382. Compounds of formula I.39 wherein $R^1$ is Y-3B, R is NCN, and $R^2$ is H.

Table 2383. Compounds of formula I.39 wherein $R^1$ is Y-3C, R is NCN, and $R^2$ is H.

Table 2384. Compounds of formula I.39 wherein $R^1$ is Y-3D, R is NCN, and $R^2$ is H.

Table 2385. Compounds of formula I.39 wherein $R^1$ is Y-4A, R is NCN, and $R^2$ is H.

Table 2386. Compounds of formula I.39 wherein $R^1$ is Y-4B, R is NCN, and $R^2$ is H.

Table 2387. Compounds of formula I.39 wherein $R^1$ is Y-4C, R is NCN, and $R^2$ is H.

Table 2388. Compounds of formula I.39 wherein $R^1$ is Y-4D, R is NCN, and $R^2$ is H.

Table 2389. Compounds of formula I.39 wherein $R^1$ is Y-5A, R is NCN, and $R^2$ is H.

Table 2390. Compounds of formula I.39 wherein $R^1$ is Y-5B, R is NCN, and $R^2$ is H.

Table 2391. Compounds of formula I.39 wherein $R^1$ is Y-6A, R is NCN, and $R^2$ is H.

Table 2392. Compounds of formula I.39 wherein $R^1$ is Y-6B, R is NCN, and $R^2$ is H.

Table 2393. Compounds of formula I.39 wherein $R^1$ is Y-8A, R is NCN, and $R^2$ is H.

Table 2394. Compounds of formula I.39 wherein $R^1$ is Y-8B, R is NCN, and $R^2$ is H.

Table 2395. Compounds of formula I.39 wherein $R^1$ is Y-1A, R is NCN, and $R^2$ is $CH_3$.

Table 2396. Compounds of formula I.39 wherein $R^1$ is Y-1B, R is NCN, and $R^2$ is $CH_3$.

Table 2397. Compounds of formula I.39 wherein $R^1$ is Y-2A, R is NCN, and $R^2$ is $CH_3$.

Table 2398. Compounds of formula I.39 wherein $R^1$ is Y-2B, R is NCN, and $R^2$ is $CH_3$.

Table 2399. Compounds of formula I.39 wherein $R^1$ is Y-3A, R is NCN, and $R^2$ is $CH_3$.

Table 2400. Compounds of formula I.39 wherein $R^1$ is Y-3B, R is NCN, and $R^2$ is $CH_3$.

Table 2401. Compounds of formula I.39 wherein $R^1$ is Y-3C, R is NCN, and $R^2$ is $CH_3$.

Table 2402. Compounds of formula I.39 wherein $R^1$ is Y-3D, R is NCN, and $R^2$ is $CH_3$.

Table 2403. Compounds of formula I.39 wherein $R^1$ is Y-4A, R is NCN, and $R^2$ is $CH_3$.

Table 2404. Compounds of formula I.39 wherein $R^1$ is Y-4B, R is NCN, and $R^2$ is $CH_3$.

Table 2405. Compounds of formula I.39 wherein $R^1$ is Y-4C, R is NCN, and $R^2$ is $CH_3$.

Table 2406. Compounds of formula I.39 wherein $R^1$ is Y-4D, R is NCN, and $R^2$ is $CH_3$.

Table 2407. Compounds of formula I.39 wherein $R^1$ is Y-5A, R is NCN, and $R^2$ is $CH_3$.

Table 2408. Compounds of formula I.39 wherein $R^1$ is Y-5B, R is NCN, and $R^2$ is $CH_3$.

Table 2409. Compounds of formula I.39 wherein $R^1$ is Y-6A, R is NCN, and $R^2$ is $CH_3$.

Table 2410. Compounds of formula I.39 wherein $R^1$ is Y-6B, R is NCN, and $R^2$ is $CH_3$.

Table 2411. Compounds of formula I.39 wherein $R^1$ is Y-8A, R is NCN, and $R^2$ is $CH_3$.

Table 2412. Compounds of formula I.39 wherein $R^1$ is Y-8B, R is NCN, and $R^2$ is $CH_3$.

Table 2413. Compounds of formula I.39 wherein $R^1$ is Y-1A, R is NCN, and $R^2$ is c-$C_3H_5$.

Table 2414. Compounds of formula I.39 wherein $R^1$ is Y-1B, R is NCN, and $R^2$ is c-$C_3H_5$.

Table 2415. Compounds of formula I.39 wherein $R^1$ is Y-2A, R is NCN, and $R^2$ is c-$C_3H_5$.

Table 2416. Compounds of formula I.39 wherein $R^1$ is Y-2B, R is NCN, and $R^2$ is c-$C_3H_5$.

Table 2417. Compounds of formula I.39 wherein $R^1$ is Y-3A, R is NCN, and $R^2$ is c-$C_3H_5$.

Table 2418. Compounds of formula I.39 wherein $R^1$ is Y-3B, R is NCN, and $R^2$ is c-$C_3H_5$.

Table 2419. Compounds of formula I.39 wherein $R^1$ is Y-3C, R is NCN, and $R^2$ is c-$C_3H_5$.

Table 2420. Compounds of formula I.39 wherein $R^1$ is Y-3D, R is NCN, and $R^2$ is c-$C_3H_5$.

Table 2421. Compounds of formula I.39 wherein $R^1$ is Y-4A, R is NCN, and $R^2$ is c-$C_3H_5$.

Table 2422. Compounds of formula I.39 wherein $R^1$ is Y-4B, R is NCN, and $R^2$ is c-$C_3H_5$.

Table 2423. Compounds of formula I.39 wherein $R^1$ is Y-4C, R is NCN, and $R^2$ is c-$C_3H_5$.

Table 2424. Compounds of formula I.39 wherein $R^1$ is Y-4D, R is NCN, and $R^2$ is c-$C_3H_5$.

Table 2425. Compounds of formula I.39 wherein $R^1$ is Y-5A, R is NCN, and $R^2$ is c-$C_3H_5$.

Table 2426. Compounds of formula I.39 wherein $R^1$ is Y-5B, R is NCN, and $R^2$ is c-$C_3H_5$.

Table 2427. Compounds of formula I.39 wherein $R^1$ is Y-6A, R is NCN, and $R^2$ is c-$C_3H_5$.

Table 2428. Compounds of formula I.39 wherein $R^1$ is Y-6B, R is NCN, and $R^2$ is c-$C_3H_5$.

Table 2429. Compounds of formula I.39 wherein $R^1$ is Y-8A, R is NCN, and $R^2$ is c-$C_3H_5$.

Table 2430. Compounds of formula I.39 wherein $R^1$ is Y-8B, R is NCN, and $R^2$ is c-$C_3H_5$.

Table 2431. Compounds of formula I.40 wherein $R^1$ is Y-1A, R is NH, and $R^2$ is H.

Table 2432. Compounds of formula I.40 wherein $R^1$ is Y-1B, R is NH, and $R^2$ is H.

Table 2433. Compounds of formula I.40 wherein $R^1$ is Y-2A, R is NH, and $R^2$ is H.

Table 2434. Compounds of formula I.40 wherein $R^1$ is Y-2B, R is NH, and $R^2$ is H.

Table 2435. Compounds of formula I.40 wherein $R^1$ is Y-3A, R is NH, and $R^2$ is H.

Table 2436. Compounds of formula I.40 wherein $R^1$ is Y-3B, R is NH, and $R^2$ is H.

Table 2437. Compounds of formula I.40 wherein $R^1$ is Y-3C, R is NH, and $R^2$ is H.

Table 2438. Compounds of formula I.40 wherein $R^1$ is Y-3D, R is NH, and $R^2$ is H.

Table 2439. Compounds of formula I.40 wherein $R^1$ is Y-4A, R is NH, and $R^2$ is H.

Table 2440. Compounds of formula I.40 wherein $R^1$ is Y-4B, R is NH, and $R^2$ is H.

Table 2441. Compounds of formula I.40 wherein $R^1$ is Y-4C, R is NH, and $R^2$ is H.

Table 2442. Compounds of formula I.40 wherein $R^1$ is Y-4D, R is NH, and $R^2$ is H.

Table 2443. Compounds of formula I.40 wherein $R^1$ is Y-5A, R is NH, and $R^2$ is H.

Table 2444. Compounds of formula I.40 wherein $R^1$ is Y-5B, R is NH, and $R^2$ is H.

Table 2445. Compounds of formula I.40 wherein $R^1$ is Y-6A, R is NH, and $R^2$ is H.

Table 2446. Compounds of formula I.40 wherein $R^1$ is Y-6B, R is NH, and $R^2$ is H.

Table 2447. Compounds of formula I.40 wherein $R^1$ is Y-8A, R is NH, and $R^2$ is H.

Table 2448. Compounds of formula I.40 wherein $R^1$ is Y-8B, R is NH, and $R^2$ is H.

Table 2449. Compounds of formula I.40 wherein $R^1$ is Y-1A, R is NH, and $R^2$ is $CH_3$.

Table 2450. Compounds of formula I.40 wherein $R^1$ is Y-1B, R is NH, and $R^2$ is $CH_3$.

Table 2451. Compounds of formula I.40 wherein $R^1$ is Y-2A, R is NH, and $R^2$ is $CH_3$.

Table 2452. Compounds of formula I.40 wherein $R^1$ is Y-2B, R is NH, and $R^2$ is $CH_3$.

Table 2453. Compounds of formula I.40 wherein $R^1$ is Y-3A, R is NH, and $R^2$ is $CH_3$.

Table 2454. Compounds of formula I.40 wherein $R^1$ is Y-3B, R is NH, and $R^2$ is $CH_3$.

Table 2455. Compounds of formula I.40 wherein $R^1$ is Y-3C, R is NH, and $R^2$ is $CH_3$.

Table 2456. Compounds of formula I.40 wherein $R^1$ is Y-3D, R is NH, and $R^2$ is $CH_3$.

Table 2457. Compounds of formula I.40 wherein $R^1$ is Y-4A, R is NH, and $R^2$ is $CH_3$.

Table 2458. Compounds of formula I.40 wherein $R^1$ is Y-4B, R is NH, and $R^2$ is $CH_3$.

Table 2459. Compounds of formula I.40 wherein $R^1$ is Y-4C, R is NH, and $R^2$ is $CH_3$.

Table 2460. Compounds of formula I.40 wherein $R^1$ is Y-4D, R is NH, and $R^2$ is $CH_3$.

Table 2461. Compounds of formula I.40 wherein $R^1$ is Y-5A, R is NH, and $R^2$ is $CH_3$.

Table 2462. Compounds of formula I.40 wherein $R^1$ is Y-5B, R is NH, and $R^2$ is $CH_3$.

Table 2463. Compounds of formula I.40 wherein $R^1$ is Y-6A, R is NH, and $R^2$ is $CH_3$.

Table 2464. Compounds of formula I.40 wherein $R^1$ is Y-6B, R is NH, and $R^2$ is $CH_3$.

Table 2465. Compounds of formula I.40 wherein $R^1$ is Y-8A, R is NH, and $R^2$ is $CH_3$.

Table 2466. Compounds of formula I.40 wherein $R^1$ is Y-8B, R is NH, and $R^2$ is $CH_3$.

Table 2467. Compounds of formula I.40 wherein $R^1$ is Y-1A, R is NH, and $R^2$ is c-$C_3H_5$.

Table 2468. Compounds of formula I.40 wherein $R^1$ is Y-1B, R is NH, and $R^2$ is c-$C_3H_5$.

Table 2469. Compounds of formula I.40 wherein $R^1$ is Y-2A, R is NH, and $R^2$ is c-$C_3H_5$.

Table 2470. Compounds of formula I.40 wherein $R^1$ is Y-2B, R is NH, and $R^2$ is c-$C_3H_5$.

Table 2471. Compounds of formula I.40 wherein $R^1$ is Y-3A, R is NH, and $R^2$ is c-$C_3H_5$.

Table 2472. Compounds of formula I.40 wherein $R^1$ is Y-3B, R is NH, and $R^2$ is c-$C_3H_5$.

Table 2473. Compounds of formula I.40 wherein $R^1$ is Y-3C, R is NH, and $R^2$ is c-$C_3H_5$.

Table 2474. Compounds of formula I.40 wherein $R^1$ is Y-3D, R is NH, and $R^2$ is c-$C_3H_5$.

Table 2475. Compounds of formula I.40 wherein $R^1$ is Y-4A, R is NH, and $R^2$ is c-$C_3H_5$.

Table 2476. Compounds of formula I.40 wherein $R^1$ is Y-4B, R is NH, and $R^2$ is c-$C_3H_5$.

Table 2477. Compounds of formula I.40 wherein $R^1$ is Y-4C, R is NH, and $R^2$ is c-$C_3H_5$.

Table 2478. Compounds of formula I.40 wherein $R^1$ is Y-4D, R is NH, and $R^2$ is c-$C_3H_5$.

Table 2479. Compounds of formula I.40 wherein $R^1$ is Y-5A, R is NH, and $R^2$ is c-$C_3H_5$.

Table 2480. Compounds of formula I.40 wherein $R^1$ is Y-5B, R is NH, and $R^2$ is c-$C_3H_5$.

Table 2481. Compounds of formula I.40 wherein $R^1$ is Y-6A, R is NH, and $R^2$ is c-$C_3H_5$.

Table 2482. Compounds of formula I.40 wherein $R^1$ is Y-6B, R is NH, and $R^2$ is c-$C_3H_5$.

Table 2483. Compounds of formula I.40 wherein $R^1$ is Y-8A, R is NH, and $R^2$ is c-$C_3H_5$.

Table 2484. Compounds of formula I.40 wherein $R^1$ is Y-8B, R is NH, and $R^2$ is c-$C_3H_5$.

Table 2485. Compounds of formula I.40 wherein $R^1$ is Y-1A, R is $NCH_3$ and $R^2$ is H.

Table 2486. Compounds of formula I.40 wherein $R^1$ is Y-1B, R is $NCH_3$ and $R^2$ is H.

Table 2487. Compounds of formula I.40 wherein $R^1$ is Y-2A, R is $NCH_3$ and $R^2$ is H.

Table 2488. Compounds of formula I.40 wherein $R^1$ is Y-2B, R is $NCH_3$ and $R^2$ is H.

Table 2489. Compounds of formula I.40 wherein $R^1$ is Y-3A, R is $NCH_3$ and $R^2$ is H.

Table 2490. Compounds of formula I.40 wherein $R^1$ is Y-3B, R is $NCH_3$ and $R^2$ is H.

Table 2491. Compounds of formula I.40 wherein $R^1$ is Y-3C, R is $NCH_3$ and $R^2$ is H.

Table 2492. Compounds of formula I.40 wherein $R^1$ is Y-3D, R is $NCH_3$ and $R^2$ is H.

Table 2493. Compounds of formula I.40 wherein $R^1$ is Y-4A, R is $NCH_3$ and $R^2$ is H.

Table 2494. Compounds of formula I.40 wherein $R^1$ is Y-4B, R is $NCH_3$ and $R^2$ is H.

Table 2495. Compounds of formula I.40 wherein $R^1$ is Y-4C, R is $NCH_3$ and $R^2$ is H.

Table 2496. Compounds of formula I.40 wherein $R^1$ is Y-4D, R is $NCH_3$ and $R^2$ is H.

Table 2497. Compounds of formula I.40 wherein $R^1$ is Y-5A, R is $NCH_3$ and $R^2$ is H.

Table 2498. Compounds of formula I.40 wherein $R^1$ is Y-5B, R is $NCH_3$ and $R^2$ is H.

Table 2499. Compounds of formula I.40 wherein $R^1$ is Y-6A, R is $NCH_3$ and $R^2$ is H.

Table 2500. Compounds of formula I.40 wherein $R^1$ is Y-6B, R is $NCH_3$ and $R^2$ is H.

Table 2501. Compounds of formula I.40 wherein $R^1$ is Y-8A, R is $NCH_3$ and $R^2$ is H.

Table 2502. Compounds of formula I.40 wherein $R^1$ is Y-8B, R is $NCH_3$ and $R^2$ is H.

Table 2503. Compounds of formula I.40 wherein $R^1$ is Y-1A, R is $NCH_3$ and $R^2$ is $CH_3$.

Table 2504. Compounds of formula I.40 wherein $R^1$ is Y-1B, R is $NCH_3$ and $R^2$ is $CH_3$.

Table 2505. Compounds of formula I.40 wherein $R^1$ is Y-2A, R is $NCH_3$ and $R^2$ is $CH_3$.

Table 2506. Compounds of formula I.40 wherein $R^1$ is Y-2B, R is $NCH_3$ and $R^2$ is $CH_3$.

Table 2507. Compounds of formula I.40 wherein $R^1$ is Y-3A, R is $NCH_3$ and $R^2$ is $CH_3$.

Table 2508. Compounds of formula I.40 wherein $R^1$ is Y-3B, R is $NCH_3$ and $R^2$ is $CH_3$.

Table 2509. Compounds of formula I.40 wherein $R^1$ is Y-3C, R is $NCH_3$ and $R^2$ is $CH_3$.

Table 2510. Compounds of formula I.40 wherein $R^1$ is Y-3D, R is $NCH_3$ and $R^2$ is $CH_3$.

Table 2511. Compounds of formula I.40 wherein $R^1$ is Y-4A, R is $NCH_3$ and $R^2$ is $CH_3$.

Table 2512. Compounds of formula I.40 wherein $R^1$ is Y-4B, R is $NCH_3$ and $R^2$ is $CH_3$.

Table 2513. Compounds of formula I.40 wherein $R^1$ is Y-4C, R is $NCH_3$ and $R^2$ is $CH_3$.

Table 2514. Compounds of formula I.40 wherein $R^1$ is Y-4D, R is $NCH_3$ and $R^2$ is $CH_3$.

Table 2515. Compounds of formula I.40 wherein $R^1$ is Y-5A, R is $NCH_3$ and $R^2$ is $CH_3$.

Table 2516. Compounds of formula I.40 wherein $R^1$ is Y-5B, R is $NCH_3$ and $R^2$ is $CH_3$.

Table 2517. Compounds of formula I.40 wherein $R^1$ is Y-6A, R is $NCH_3$ and $R^2$ is $CH_3$.

Table 2518. Compounds of formula I.40 wherein $R^1$ is Y-6B, R is $NCH_3$ and $R^2$ is $CH_3$.

Table 2519. Compounds of formula I.40 wherein $R^1$ is Y-8A, R is $NCH_3$ and $R^2$ is $CH_3$.

Table 2520. Compounds of formula I.40 wherein $R^1$ is Y-8B, R is $NCH_3$ and $R^2$ is $CH_3$.

Table 2521. Compounds of formula I.40 wherein $R^1$ is Y-1A, R is $NCH_3$ and $R^2$ is c-$C_3H_5$.

Table 2522. Compounds of formula I.40 wherein $R^1$ is Y-1B, R is $NCH_3$ and $R^2$ is c-$C_3H_5$.

Table 2523. Compounds of formula I.40 wherein $R^1$ is Y-2A, R is $NCH_3$ and $R^2$ is c-$C_3H_5$.

Table 2524. Compounds of formula I.40 wherein $R^1$ is Y-2B, R is $NCH_3$ and $R^2$ is c-$C_3H_5$.

Table 2525. Compounds of formula I.40 wherein $R^1$ is Y-3A, R is $NCH_3$ and $R^2$ is c-$C_3H_5$.

Table 2526. Compounds of formula I.40 wherein $R^1$ is Y-3B, R is $NCH_3$ and $R^2$ is c-$C_3H_5$.

Table 2527. Compounds of formula I.40 wherein $R^1$ is Y-3C, R is $NCH_3$ and $R^2$ is c-$C_3H_5$.

Table 2528. Compounds of formula I.40 wherein $R^1$ is Y-3D, R is $NCH_3$ and $R^2$ is c-$C_3H_5$.

Table 2529. Compounds of formula I.40 wherein $R^1$ is Y-4A, R is $NCH_3$ and $R^2$ is c-$C_3H_5$.

Table 2530. Compounds of formula I.40 wherein $R^1$ is Y-4B, R is $NCH_3$ and $R^2$ is c-$C_3H_5$.

Table 2531. Compounds of formula I.40 wherein $R^1$ is Y-4C, R is $NCH_3$ and $R^2$ is c-$C_3H_5$.

Table 2532. Compounds of formula I.40 wherein $R^1$ is Y-4D, R is $NCH_3$ and $R^2$ is c-$C_3H_5$.

Table 2533. Compounds of formula I.40 wherein $R^1$ is Y-5A, R is $NCH_3$ and $R^2$ is c-$C_3H_5$.

Table 2534. Compounds of formula I.40 wherein $R^1$ is Y-5B, R is $NCH_3$ and $R^2$ is c-$C_3H_5$.

Table 2535. Compounds of formula I.40 wherein $R^1$ is Y-6A, R is $NCH_3$ and $R^2$ is c-$C_3H_5$.

Table 2536. Compounds of formula I.40 wherein $R^1$ is Y-6B, R is $NCH_3$ and $R^2$ is c-$C_3H_5$.

Table 2537. Compounds of formula I.40 wherein $R^1$ is Y-8A, R is $NCH_3$ and $R^2$ is c-$C_3H_5$.

Table 2538. Compounds of formula I.40 wherein $R^1$ is Y-8B, R is $NCH_3$ and $R^2$ is c-$C_3H_5$.

Table 2539. Compounds of formula I.40 wherein $R^1$ is Y-1A, R is NCN, and $R^2$ is H.

Table 2540. Compounds of formula I.40 wherein $R^1$ is Y-1B, R is NCN, and $R^2$ is H.

Table 2541. Compounds of formula I.40 wherein $R^1$ is Y-2A, R is NCN, and $R^2$ is H.

Table 2542. Compounds of formula I.40 wherein $R^1$ is Y-2B, R is NCN, and $R^2$ is H.

Table 2543. Compounds of formula I.40 wherein $R^1$ is Y-3A, R is NCN, and $R^2$ is H.

Table 2544. Compounds of formula I.40 wherein $R^1$ is Y-3B, R is NCN, and $R^2$ is H.

Table 2545. Compounds of formula I.40 wherein $R^1$ is Y-3C, R is NCN, and $R^2$ is H.

Table 2546. Compounds of formula I.40 wherein $R^1$ is Y-3D, R is NCN, and $R^2$ is H.

Table 2547. Compounds of formula I.40 wherein $R^1$ is Y-4A, R is NCN, and $R^2$ is H.

Table 2548. Compounds of formula I.40 wherein $R^1$ is Y-4B, R is NCN, and $R^2$ is H.

Table 2549. Compounds of formula I.40 wherein $R^1$ is Y-4C, R is NCN, and $R^2$ is H.

Table 2550. Compounds of formula I.40 wherein $R^1$ is Y-4D, R is NCN, and $R^2$ is H.

Table 2551. Compounds of formula I.40 wherein $R^1$ is Y-5A, R is NCN, and $R^2$ is H.

Table 2552. Compounds of formula I.40 wherein $R^1$ is Y-5B, R is NCN, and $R^2$ is H.

Table 2553. Compounds of formula I.40 wherein $R^1$ is Y-6A, R is NCN, and $R^2$ is H.

Table 2554. Compounds of formula I.40 wherein $R^1$ is Y-6B, R is NCN, and $R^2$ is H.

Table 2555. Compounds of formula I.40 wherein $R^1$ is Y-8A, R is NCN, and $R^2$ is H.

Table 2556. Compounds of formula I.40 wherein $R^1$ is Y-8B, R is NCN, and $R^2$ is H.

Table 2557. Compounds of formula I.40 wherein $R^1$ is Y-1A, R is NCN, and $R^2$ is $CH_3$.

Table 2558. Compounds of formula I.40 wherein $R^1$ is Y-1B, R is NCN, and $R^2$ is $CH_3$.

Table 2559. Compounds of formula I.40 wherein $R^1$ is Y-2A, R is NCN, and $R^2$ is $CH_3$.

Table 2560. Compounds of formula I.40 wherein $R^1$ is Y-2B, R is NCN, and $R^2$ is $CH_3$.

Table 2561. Compounds of formula I.40 wherein $R^1$ is Y-3A, R is NCN, and $R^2$ is $CH_3$.

Table 2562. Compounds of formula I.40 wherein $R^1$ is Y-3B, R is NCN, and $R^2$ is $CH_3$.

Table 2563. Compounds of formula I.40 wherein $R^1$ is Y-3C, R is NCN, and $R^2$ is $CH_3$.

Table 2564. Compounds of formula I.40 wherein $R^1$ is Y-3D, R is NCN, and $R^2$ is $CH_3$.

Table 2565. Compounds of formula I.40 wherein $R^1$ is Y-4A, R is NCN, and $R^2$ is $CH_3$.

Table 2566. Compounds of formula I.40 wherein $R^1$ is Y-4B, R is NCN, and $R^2$ is $CH_3$.

Table 2567. Compounds of formula I.40 wherein $R^1$ is Y-4C, R is NCN, and $R^2$ is $CH_3$.

Table 2568. Compounds of formula I.40 wherein $R^1$ is Y-4D, R is NCN, and $R^2$ is $CH_3$.

Table 2569. Compounds of formula I.40 wherein $R^1$ is Y-5A, R is NCN, and $R^2$ is $CH_3$.

Table 2570. Compounds of formula I.40 wherein $R^1$ is Y-5B, R is NCN, and $R^2$ is $CH_3$.

Table 2571. Compounds of formula I.40 wherein $R^1$ is Y-6A, R is NCN, and $R^2$ is $CH_3$.

Table 2572. Compounds of formula I.40 wherein $R^1$ is Y-6B, R is NCN, and $R^2$ is $CH_3$.

Table 2573. Compounds of formula I.40 wherein $R^1$ is Y-8A, R is NCN, and $R^2$ is $CH_3$.

Table 2574. Compounds of formula I.40 wherein $R^1$ is Y-8B, R is NCN, and $R^2$ is $CH_3$.

Table 2575. Compounds of formula I.40 wherein $R^1$ is Y-1A, R is NCN, and $R^2$ is c-$C_3H_5$.

Table 2576. Compounds of formula I.40 wherein $R^1$ is Y-1B, R is NCN, and $R^2$ is c-$C_3H_5$.

Table 2577. Compounds of formula I.40 wherein $R^1$ is Y-2A, R is NCN, and $R^2$ is c-$C_3H_5$.

Table 2578. Compounds of formula I.40 wherein $R^1$ is Y-2B, R is NCN, and $R^2$ is c-$C_3H_5$.

Table 2579. Compounds of formula I.40 wherein $R^1$ is Y-3A, R is NCN, and $R^2$ is c-$C_3H_5$.

Table 2580. Compounds of formula I.40 wherein $R^1$ is Y-3B, R is NCN, and $R^2$ is c-$C_3H_5$.

Table 2581. Compounds of formula I.40 wherein $R^1$ is Y-3C, R is NCN, and $R^2$ is c-$C_3H_5$.

Table 2582. Compounds of formula I.40 wherein $R^1$ is Y-3D, R is NCN, and $R^2$ is c-$C_3H_5$.

Table 2583. Compounds of formula I.40 wherein $R^1$ is Y-4A, R is NCN, and $R^2$ is c-$C_3H_5$.

Table 2584. Compounds of formula I.40 wherein $R^1$ is Y-4B, R is NCN, and $R^2$ is c-$C_3H_5$.

Table 2585. Compounds of formula I.40 wherein $R^1$ is Y-4C, R is NCN, and $R^2$ is c-$C_3H_5$.

Table 2586. Compounds of formula I.40 wherein $R^1$ is Y-4D, R is NCN, and $R^2$ is c-$C_3H_5$.

Table 2587. Compounds of formula I.40 wherein $R^1$ is Y-5A, R is NCN, and $R^2$ is c-$C_3H_5$.

Table 2588. Compounds of formula I.40 wherein $R^1$ is Y-5B, R is NCN, and $R^2$ is c-$C_3H_5$.

Table 2589. Compounds of formula I.40 wherein $R^1$ is Y-6A, R is NCN, and $R^2$ is c-$C_3H_5$.

Table 2590. Compounds of formula I.40 wherein $R^1$ is Y-6B, R is NCN, and $R^2$ is c-$C_3H_5$.

Table 2591. Compounds of formula I.40 wherein $R^1$ is Y-8A, R is NCN, and $R^2$ is c-$C_3H_5$.

Table 2592. Compounds of formula I.40 wherein $R^1$ is Y-8B, R is NCN, and $R^2$ is c-$C_3H_5$.

Table 2593. Compounds of formula I.41 wherein $R^1$ is Y-1A, R is NH, and $R^2$ is H.

Table 2594. Compounds of formula I.41 wherein $R^1$ is Y-1B, R is NH, and $R^2$ is H.

Table 2595. Compounds of formula I.41 wherein $R^1$ is Y-2A, R is NH, and $R^2$ is H.

Table 2596. Compounds of formula I.41 wherein $R^1$ is Y-2B, R is NH, and $R^2$ is H.

Table 2597. Compounds of formula I.41 wherein $R^1$ is Y-3A, R is NH, and $R^2$ is H.

Table 2598. Compounds of formula I.41 wherein $R^1$ is Y-3B, R is NH, and $R^2$ is H.

Table 2599. Compounds of formula I.41 wherein $R^1$ is Y-3C, R is NH, and $R^2$ is H.

Table 2600. Compounds of formula I.41 wherein $R^1$ is Y-3D, R is NH, and $R^2$ is H.

Table 2601. Compounds of formula I.41 wherein $R^1$ is Y-4A, R is NH, and $R^2$ is H.

Table 2602. Compounds of formula I.41 wherein $R^1$ is Y-4B, R is NH, and $R^2$ is H.

Table 2603. Compounds of formula I.41 wherein $R^1$ is Y-4C, R is NH, and $R^2$ is H.

Table 2604. Compounds of formula I.41 wherein $R^1$ is Y-4D, R is NH, and $R^2$ is H.

Table 2605. Compounds of formula I.41 wherein $R^1$ is Y-5A, R is NH, and $R^2$ is H.

Table 2606. Compounds of formula I.41 wherein $R^1$ is Y-5B, R is NH, and $R^2$ is H.

Table 2607. Compounds of formula I.41 wherein $R^1$ is Y-6A, R is NH, and $R^2$ is H.

Table 2608. Compounds of formula I.41 wherein $R^1$ is Y-6B, R is NH, and $R^2$ is H.

Table 2609. Compounds of formula I.41 wherein $R^1$ is Y-8A, R is NH, and $R^2$ is H.

Table 2610. Compounds of formula I.41 wherein $R^1$ is Y-8B, R is NH, and $R^2$ is H.

Table 2611. Compounds of formula I.41 wherein $R^1$ is Y-1A, R is NH, and $R^2$ is $CH_3$.

Table 2612. Compounds of formula I.41 wherein $R^1$ is Y-1B, R is NH, and $R^2$ is $CH_3$.

Table 2613. Compounds of formula I.41 wherein $R^1$ is Y-2A, R is NH, and $R^2$ is $CH_3$.

Table 2614. Compounds of formula I.41 wherein $R^1$ is Y-2B, R is NH, and $R^2$ is $CH_3$.

Table 2615. Compounds of formula I.41 wherein $R^1$ is Y-3A, R is NH, and $R^2$ is $CH_3$.

Table 2616. Compounds of formula I.41 wherein $R^1$ is Y-3B, R is NH, and $R^2$ is $CH_3$.

Table 2617. Compounds of formula I.41 wherein $R^1$ is Y-3C, R is NH, and $R^2$ is $CH_3$.

Table 2618. Compounds of formula I.41 wherein $R^1$ is Y-3D, R is NH, and $R^2$ is $CH_3$.

Table 2619. Compounds of formula I.41 wherein $R^1$ is Y-4A, R is NH, and $R^2$ is $CH_3$.

Table 2620. Compounds of formula I.41 wherein $R^1$ is Y-4B, R is NH, and $R^2$ is $CH_3$.

Table 2621. Compounds of formula I.41 wherein $R^1$ is Y-4C, R is NH, and $R^2$ is $CH_3$.

Table 2622. Compounds of formula I.41 wherein $R^1$ is Y-4D, R is NH, and $R^2$ is $CH_3$.

Table 2623. Compounds of formula I.41 wherein $R^1$ is Y-5A, R is NH, and $R^2$ is $CH_3$.

Table 2624. Compounds of formula I.41 wherein $R^1$ is Y-5B, R is NH, and $R^2$ is $CH_3$.

Table 2625. Compounds of formula I.41 wherein $R^1$ is Y-6A, R is NH, and $R^2$ is $CH_3$.

Table 2626. Compounds of formula I.41 wherein $R^1$ is Y-6B, R is NH, and $R^2$ is $CH_3$.

Table 2627. Compounds of formula I.41 wherein $R^1$ is Y-8A, R is NH, and $R^2$ is $CH_3$.

Table 2628. Compounds of formula I.41 wherein $R^1$ is Y-8B, R is NH, and $R^2$ is $CH_3$.

Table 2629. Compounds of formula I.41 wherein $R^1$ is Y-1A, R is NH, and $R^2$ is c-$C_3H_5$.

Table 2630. Compounds of formula I.41 wherein $R^1$ is Y-1B, R is NH, and $R^2$ is c-$C_3H_5$.

Table 2631. Compounds of formula I.41 wherein $R^1$ is Y-2A, R is NH, and $R^2$ is c-$C_3H_5$.

Table 2632. Compounds of formula I.41 wherein $R^1$ is Y-2B, R is NH, and $R^2$ is c-$C_3H_5$.

Table 2633. Compounds of formula I.41 wherein $R^1$ is Y-3A, R is NH, and $R^2$ is c-$C_3H_5$.

Table 2634. Compounds of formula I.41 wherein $R^1$ is Y-3B, R is NH, and $R^2$ is c-$C_3H_5$.

Table 2635. Compounds of formula I.41 wherein $R^1$ is Y-3C, R is NH, and $R^2$ is c-$C_3H_5$.

Table 2636. Compounds of formula I.41 wherein $R^1$ is Y-3D, R is NH, and $R^2$ is c-$C_3H_5$.

Table 2637. Compounds of formula I.41 wherein $R^1$ is Y-4A, R is NH, and $R^2$ is c-$C_3H_5$.

Table 2638. Compounds of formula I.41 wherein $R^1$ is Y-4B, R is NH, and $R^2$ is c-$C_3H_5$.

Table 2639. Compounds of formula I.41 wherein $R^1$ is Y-4C, R is NH, and $R^2$ is c-$C_3H_5$.

Table 2640. Compounds of formula I.41 wherein $R^1$ is Y-4D, R is NH, and $R^2$ is c-$C_3H_5$.

Table 2641. Compounds of formula I.41 wherein $R^1$ is Y-5A, R is NH, and $R^2$ is c-$C_3H_5$.

Table 2642. Compounds of formula I.41 wherein $R^1$ is Y-5B, R is NH, and $R^2$ is c-$C_3H_5$.

Table 2643. Compounds of formula I.41 wherein $R^1$ is Y-6A, R is NH, and $R^2$ is c-$C_3H_5$.

Table 2644. Compounds of formula I.41 wherein $R^1$ is Y-6B, R is NH, and $R^2$ is c-$C_3H_5$.

Table 2645. Compounds of formula I.41 wherein $R^1$ is Y-8A, R is NH, and $R^2$ is c-$C_3H_5$.

Table 2646. Compounds of formula I.41 wherein $R^1$ is Y-8B, R is NH, and $R^2$ is c-$C_3H_5$.

Table 2647. Compounds of formula I.41 wherein $R^1$ is Y-1A, R is $NCH_3$ and $R^2$ is H.

Table 2648. Compounds of formula I.41 wherein $R^1$ is Y-1B, R is $NCH_3$ and $R^2$ is H.

Table 2649. Compounds of formula I.41 wherein $R^1$ is Y-2A, R is $NCH_3$ and $R^2$ is H.

Table 2650. Compounds of formula I.41 wherein $R^1$ is Y-2B, R is $NCH_3$ and $R^2$ is H.

Table 2651. Compounds of formula I.41 wherein $R^1$ is Y-3A, R is $NCH_3$ and $R^2$ is H.

Table 2652. Compounds of formula I.41 wherein $R^1$ is Y-3B, R is $NCH_3$ and $R^2$ is H.

Table 2653. Compounds of formula I.41 wherein $R^1$ is Y-3C, R is $NCH_3$ and $R^2$ is H.

Table 2654. Compounds of formula I.41 wherein $R^1$ is Y-3D, R is $NCH_3$ and $R^2$ is H.

Table 2655. Compounds of formula I.41 wherein $R^1$ is Y-4A, R is $NCH_3$ and $R^2$ is H.

Table 2656. Compounds of formula I.41 wherein $R^1$ is Y-4B, R is $NCH_3$ and $R^2$ is H.

Table 2657. Compounds of formula I.41 wherein $R^1$ is Y-4C, R is $NCH_3$ and $R^2$ is H.

Table 2658. Compounds of formula I.41 wherein $R^1$ is Y-4D, R is $NCH_3$ and $R^2$ is H.

Table 2659. Compounds of formula I.41 wherein $R^1$ is Y-5A, R is $NCH_3$ and $R^2$ is H.

Table 2660. Compounds of formula I.41 wherein $R^1$ is Y-5B, R is $NCH_3$ and $R^2$ is H.

Table 2661. Compounds of formula I.41 wherein $R^1$ is Y-6A, R is $NCH_3$ and $R^2$ is H.

Table 2662. Compounds of formula I.41 wherein $R^1$ is Y-6B, R is $NCH_3$ and $R^2$ is H.

Table 2663. Compounds of formula I.41 wherein $R^1$ is Y-8A, R is $NCH_3$ and $R^2$ is H.

Table 2664. Compounds of formula I.41 wherein $R^1$ is Y-8B, R is $NCH_3$ and $R^2$ is H.

Table 2665. Compounds of formula I.41 wherein $R^1$ is Y-1A, R is $NCH_3$ and $R^2$ is $CH_3$.

Table 2666. Compounds of formula I.41 wherein $R^1$ is Y-1B, R is $NCH_3$ and $R^2$ is $CH_3$.

Table 2667. Compounds of formula I.41 wherein $R^1$ is Y-2A, R is $NCH_3$ and $R^2$ is $CH_3$.

Table 2668. Compounds of formula I.41 wherein $R^1$ is Y-2B, R is $NCH_3$ and $R^2$ is $CH_3$.

Table 2669. Compounds of formula I.41 wherein $R^1$ is Y-3A, R is $NCH_3$ and $R^2$ is $CH_3$.

Table 2670. Compounds of formula I.41 wherein $R^1$ is Y-3B, R is $NCH_3$ and $R^2$ is $CH_3$.

Table 2671. Compounds of formula I.41 wherein $R^1$ is Y-3C, R is $NCH_3$ and $R^2$ is $CH_3$.

Table 2672. Compounds of formula I.41 wherein $R^1$ is Y-3D, R is $NCH_3$ and $R^2$ is $CH_3$.

Table 2673. Compounds of formula I.41 wherein $R^1$ is Y-4A, R is $NCH_3$ and $R^2$ is $CH_3$.

Table 2674. Compounds of formula I.41 wherein $R^1$ is Y-4B, R is $NCH_3$ and $R^2$ is $CH_3$.

Table 2675. Compounds of formula I.41 wherein $R^1$ is Y-4C, R is $NCH_3$ and $R^2$ is $CH_3$.

Table 2676. Compounds of formula I.41 wherein $R^1$ is Y-4D, R is $NCH_3$ and $R^2$ is $CH_3$.

Table 2677. Compounds of formula I.41 wherein $R^1$ is Y-5A, R is $NCH_3$ and $R^2$ is $CH_3$.

Table 2678. Compounds of formula I.41 wherein $R^1$ is Y-5B, R is $NCH_3$ and $R^2$ is $CH_3$.

Table 2679. Compounds of formula I.41 wherein $R^1$ is Y-6A, R is $NCH_3$ and $R^2$ is $CH_3$.

Table 2680. Compounds of formula I.41 wherein $R^1$ is Y-6B, R is $NCH_3$ and $R^2$ is $CH_3$.

Table 2681. Compounds of formula I.41 wherein $R^1$ is Y-8A, R is $NCH_3$ and $R^2$ is $CH_3$.

Table 2682. Compounds of formula I.41 wherein $R^1$ is Y-8B, R is $NCH_3$ and $R^2$ is $CH_3$.

Table 2683. Compounds of formula I.41 wherein $R^1$ is Y-1A, R is $NCH_3$ and $R^2$ is c-$C_3H_5$.

Table 2684. Compounds of formula I.41 wherein $R^1$ is Y-1B, R is $NCH_3$ and $R^2$ is c-$C_3H_5$.

Table 2685. Compounds of formula I.41 wherein $R^1$ is Y-2A, R is $NCH_3$ and $R^2$ is c-$C_3H_5$.

Table 2686. Compounds of formula I.41 wherein $R^1$ is Y-2B, R is $NCH_3$ and $R^2$ is c-$C_3H_5$.

Table 2687. Compounds of formula I.41 wherein $R^1$ is Y-3A, R is $NCH_3$ and $R^2$ is c-$C_3H_5$.

Table 2688. Compounds of formula I.41 wherein $R^1$ is Y-3B, R is $NCH_3$ and $R^2$ is c-$C_3H_5$.

Table 2689. Compounds of formula I.41 wherein $R^1$ is Y-3C, R is $NCH_3$ and $R^2$ is c-$C_3H_5$.

Table 2690. Compounds of formula I.41 wherein $R^1$ is Y-3D, R is $NCH_3$ and $R^2$ is c-$C_3H_5$.

Table 2691. Compounds of formula I.41 wherein $R^1$ is Y-4A, R is $NCH_3$ and $R^2$ is c-$C_3H_5$.

Table 2692. Compounds of formula I.41 wherein $R^1$ is Y-4B, R is $NCH_3$ and $R^2$ is c-$C_3H_5$.

Table 2693. Compounds of formula I.41 wherein $R^1$ is Y-4C, R is $NCH_3$ and $R^2$ is c-$C_3H_5$.

Table 2694. Compounds of formula I.41 wherein $R^1$ is Y-4D, R is $NCH_3$ and $R^2$ is c-$C_3H_5$.

Table 2695. Compounds of formula I.41 wherein $R^1$ is Y-5A, R is $NCH_3$ and $R^2$ is c-$C_3H_5$.

Table 2696. Compounds of formula I.41 wherein $R^1$ is Y-5B, R is $NCH_3$ and $R^2$ is c-$C_3H_5$.

Table 2697. Compounds of formula I.41 wherein $R^1$ is Y-6A, R is $NCH_3$ and $R^2$ is c-$C_3H_5$.

Table 2698. Compounds of formula I.41 wherein $R^1$ is Y-6B, R is $NCH_3$ and $R^2$ is c-$C_3H_5$.

Table 2699. Compounds of formula I.41 wherein $R^1$ is Y-8A, R is $NCH_3$ and $R^2$ is c-$C_3H_5$.

Table 2700. Compounds of formula I.41 wherein $R^1$ is Y-8B, R is $NCH_3$ and $R^2$ is c-$C_3H_5$.

Table 2701. Compounds of formula I.41 wherein $R^1$ is Y-1A, R is NCN, and $R^2$ is H.

Table 2702. Compounds of formula I.41 wherein $R^1$ is Y-1B, R is NCN, and $R^2$ is H.

Table 2703. Compounds of formula I.41 wherein $R^1$ is Y-2A, R is NCN, and $R^2$ is H.

Table 2704. Compounds of formula I.41 wherein $R^1$ is Y-2B, R is NCN, and $R^2$ is H.

Table 2705. Compounds of formula I.41 wherein $R^1$ is Y-3A, R is NCN, and $R^2$ is H.

Table 2706. Compounds of formula I.41 wherein $R^1$ is Y-3B, R is NCN, and $R^2$ is H.

Table 2707. Compounds of formula I.41 wherein $R^1$ is Y-3C, R is NCN, and $R^2$ is H.

Table 2708. Compounds of formula I.41 wherein $R^1$ is Y-3D, R is NCN, and $R^2$ is H.

Table 2709. Compounds of formula I.41 wherein $R^1$ is Y-4A, R is NCN, and $R^2$ is H.

Table 2710. Compounds of formula I.41 wherein $R^1$ is Y-4B, R is NCN, and $R^2$ is H.

Table 2711. Compounds of formula I.41 wherein $R^1$ is Y-4C, R is NCN, and $R^2$ is H.

Table 2712. Compounds of formula I.41 wherein $R^1$ is Y-4D, R is NCN, and $R^2$ is H.

Table 2713. Compounds of formula I.41 wherein $R^1$ is Y-5A, R is NCN, and $R^2$ is H.

Table 2714. Compounds of formula I.41 wherein $R^1$ is Y-5B, R is NCN, and $R^2$ is H.

Table 2715. Compounds of formula I.41 wherein $R^1$ is Y-6A, R is NCN, and $R^2$ is H.

Table 2716. Compounds of formula I.41 wherein $R^1$ is Y-6B, R is NCN, and $R^2$ is H.

Table 2717. Compounds of formula I.41 wherein $R^1$ is Y-8A, R is NCN, and $R^2$ is H.

Table 2718. Compounds of formula I.41 wherein $R^1$ is Y-8B, R is NCN, and $R^2$ is H.

Table 2719. Compounds of formula I.41 wherein $R^1$ is Y-1A, R is NCN, and $R^2$ is $CH_3$.

Table 2720. Compounds of formula I.41 wherein $R^1$ is Y-1B, R is NCN, and $R^2$ is $CH_3$.

Table 2721. Compounds of formula I.41 wherein $R^1$ is Y-2A, R is NCN, and $R^2$ is $CH_3$.

Table 2722. Compounds of formula I.41 wherein $R^1$ is Y-2B, R is NCN, and $R^2$ is $CH_3$.

Table 2723. Compounds of formula I.41 wherein $R^1$ is Y-3A, R is NCN, and $R^2$ is $CH_3$.

Table 2724. Compounds of formula I.41 wherein $R^1$ is Y-3B, R is NCN, and $R^2$ is $CH_3$.

Table 2725. Compounds of formula I.41 wherein $R^1$ is Y-3C, R is NCN, and $R^2$ is $CH_3$.

Table 2726. Compounds of formula I.41 wherein $R^1$ is Y-3D, R is NCN, and $R^2$ is $CH_3$.

Table 2727. Compounds of formula I.41 wherein $R^1$ is Y-4A, R is NCN, and $R^2$ is $CH_3$.

Table 2728. Compounds of formula I.41 wherein $R^1$ is Y-4B, R is NCN, and $R^2$ is $CH_3$.

Table 2729. Compounds of formula I.41 wherein $R^1$ is Y-4C, R is NCN, and $R^2$ is $CH_3$.

Table 2730. Compounds of formula I.41 wherein $R^1$ is Y-4D, R is NCN, and $R^2$ is $CH_3$.

Table 2731. Compounds of formula I.41 wherein $R^1$ is Y-5A, R is NCN, and $R^2$ is $CH_3$.

Table 2732. Compounds of formula I.41 wherein $R^1$ is Y-5B, R is NCN, and $R^2$ is $CH_3$.

Table 2733. Compounds of formula I.41 wherein $R^1$ is Y-6A, R is NCN, and $R^2$ is $CH_3$.

Table 2734. Compounds of formula I.41 wherein $R^1$ is Y-6B, R is NCN, and $R^2$ is $CH_3$.

Table 2735. Compounds of formula I.41 wherein $R^1$ is Y-8A, R is NCN, and $R^2$ is $CH_3$.

Table 2736. Compounds of formula I.41 wherein $R^1$ is Y-8B, R is NCN, and $R^2$ is $CH_3$.

Table 2737. Compounds of formula I.41 wherein $R^1$ is Y-1A, R is NCN, and $R^2$ is c-$C_3H_5$.

Table 2738. Compounds of formula I.41 wherein $R^1$ is Y-1B, R is NCN, and $R^2$ is c-$C_3H_5$.

Table 2739. Compounds of formula I.41 wherein $R^1$ is Y-2A, R is NCN, and $R^2$ is c-$C_3H_5$.

Table 2740. Compounds of formula I.41 wherein $R^1$ is Y-2B, R is NCN, and $R^2$ is c-$C_3H_5$.

Table 2741. Compounds of formula I.41 wherein $R^1$ is Y-3A, R is NCN, and $R^2$ is c-$C_3H_5$.

Table 2742. Compounds of formula I.41 wherein $R^1$ is Y-3B, R is NCN, and $R^2$ is c-$C_3H_5$.

Table 2743. Compounds of formula I.41 wherein $R^1$ is Y-3C, R is NCN, and $R^2$ is c-$C_3H_5$.

Table 2744. Compounds of formula I.41 wherein $R^1$ is Y-3D, R is NCN, and $R^2$ is c-$C_3H_5$.

Table 2745. Compounds of formula I.41 wherein $R^1$ is Y-4A, R is NCN, and $R^2$ is c-$C_3H_5$.

Table 2746. Compounds of formula I.41 wherein $R^1$ is Y-4B, R is NCN, and $R^2$ is c-$C_3H_5$.

Table 2747. Compounds of formula I.41 wherein $R^1$ is Y-4C, R is NCN, and $R^2$ is c-$C_3H_5$.

Table 2748. Compounds of formula I.41 wherein $R^1$ is Y-4D, R is NCN, and $R^2$ is c-$C_3H_5$.

Table 2749. Compounds of formula I.41 wherein $R^1$ is Y-5A, R is NCN, and $R^2$ is c-$C_3H_5$.

Table 2750. Compounds of formula I.41 wherein $R^1$ is Y-5B, R is NCN, and $R^2$ is c-$C_3H_5$.

Table 2751. Compounds of formula I.41 wherein $R^1$ is Y-6A, R is NCN, and $R^2$ is c-$C_3H_5$.

Table 2752. Compounds of formula I.41 wherein $R^1$ is Y-6B, R is NCN, and $R^2$ is c-$C_3H_5$.

Table 2753. Compounds of formula I.41 wherein $R^1$ is Y-8A, R is NCN, and $R^2$ is c-$C_3H_5$.

Table 2754. Compounds of formula I.41 wherein $R^1$ is Y-8B, R is NCN, and $R^2$ is c-$C_3H_5$.

Table 2755. Compounds of formula I.42 wherein $R^1$ is Y-1A, R is NH, and $R^2$ is H.

Table 2756. Compounds of formula I.42 wherein $R^1$ is Y-1B, R is NH, and $R^2$ is H.

Table 2757. Compounds of formula I.42 wherein $R^1$ is Y-2A, R is NH, and $R^2$ is H.

Table 2758. Compounds of formula I.42 wherein $R^1$ is Y-2B, R is NH, and $R^2$ is H.

Table 2759. Compounds of formula I.42 wherein $R^1$ is Y-3A, R is NH, and $R^2$ is H.

Table 2760. Compounds of formula I.42 wherein $R^1$ is Y-3B, R is NH, and $R^2$ is H.

Table 2761. Compounds of formula I.42 wherein $R^1$ is Y-3C, R is NH, and $R^2$ is H.

Table 2762. Compounds of formula I.42 wherein $R^1$ is Y-3D, R is NH, and $R^2$ is H.

Table 2763. Compounds of formula I.42 wherein $R^1$ is Y-4A, R is NH, and $R^2$ is H.

Table 2764. Compounds of formula I.42 wherein $R^1$ is Y-4B, R is NH, and $R^2$ is H.

Table 2765. Compounds of formula I.42 wherein $R^1$ is Y-4C, R is NH, and $R^2$ is H.

Table 2766. Compounds of formula I.42 wherein $R^1$ is Y-4D, R is NH, and $R^2$ is H.

Table 2767. Compounds of formula I.42 wherein $R^1$ is Y-5A, R is NH, and $R^2$ is H.

Table 2768. Compounds of formula I.42 wherein $R^1$ is Y-5B, R is NH, and $R^2$ is H.

Table 2769. Compounds of formula I.42 wherein $R^1$ is Y-6A, R is NH, and $R^2$ is H.

Table 2770. Compounds of formula I.42 wherein $R^1$ is Y-6B, R is NH, and $R^2$ is H.

Table 2771. Compounds of formula I.42 wherein $R^1$ is Y-8A, R is NH, and $R^2$ is H.

Table 2772. Compounds of formula I.42 wherein $R^1$ is Y-8B, R is NH, and $R^2$ is H.

Table 2773. Compounds of formula I.42 wherein $R^1$ is Y-1A, R is NH, and $R^2$ is $CH_3$.

Table 2774. Compounds of formula I.42 wherein $R^1$ is Y-1B, R is NH, and $R^2$ is $CH_3$.

Table 2775. Compounds of formula I.42 wherein $R^1$ is Y-2A, R is NH, and $R^2$ is $CH_3$.

Table 2776. Compounds of formula I.42 wherein $R^1$ is Y-2B, R is NH, and $R^2$ is $CH_3$.

Table 2777. Compounds of formula I.42 wherein $R^1$ is Y-3A, R is NH, and $R^2$ is $CH_3$.

Table 2778. Compounds of formula I.42 wherein $R^1$ is Y-3B, R is NH, and $R^2$ is $CH_3$.

Table 2779. Compounds of formula I.42 wherein $R^1$ is Y-3C, R is NH, and $R^2$ is $CH_3$.

Table 2780. Compounds of formula I.42 wherein $R^1$ is Y-3D, R is NH, and $R^2$ is $CH_3$.

Table 2781. Compounds of formula I.42 wherein $R^1$ is Y-4A, R is NH, and $R^2$ is $CH_3$.

Table 2782. Compounds of formula I.42 wherein $R^1$ is Y-4B, R is NH, and $R^2$ is $CH_3$.

Table 2783. Compounds of formula I.42 wherein $R^1$ is Y-4C, R is NH, and $R^2$ is $CH_3$.

Table 2784. Compounds of formula I.42 wherein $R^1$ is Y-4D, R is NH, and $R^2$ is $CH_3$.

Table 2785. Compounds of formula I.42 wherein $R^1$ is Y-5A, R is NH, and $R^2$ is $CH_3$.

Table 2786. Compounds of formula I.42 wherein $R^1$ is Y-5B, R is NH, and $R^2$ is $CH_3$.

Table 2787. Compounds of formula I.42 wherein $R^1$ is Y-6A, R is NH, and $R^2$ is $CH_3$.

Table 2788. Compounds of formula I.42 wherein $R^1$ is Y-6B, R is NH, and $R^2$ is $CH_3$.

Table 2789. Compounds of formula I.42 wherein $R^1$ is Y-8A, R is NH, and $R^2$ is $CH_3$.

Table 2790. Compounds of formula I.42 wherein $R^1$ is Y-8B, R is NH, and $R^2$ is $CH_3$.

Table 2791. Compounds of formula I.42 wherein $R^1$ is Y-1A, R is NH, and $R^2$ is c-$C_3H_5$.

Table 2792. Compounds of formula I.42 wherein $R^1$ is Y-1B, R is NH, and $R^2$ is c-$C_3H_5$.

Table 2793. Compounds of formula I.42 wherein $R^1$ is Y-2A, R is NH, and $R^2$ is c-$C_3H_5$.

Table 2794. Compounds of formula I.42 wherein $R^1$ is Y-2B, R is NH, and $R^2$ is c-$C_3H_5$.

Table 2795. Compounds of formula I.42 wherein $R^1$ is Y-3A, R is NH, and $R^2$ is c-$C_3H_5$.

Table 2796. Compounds of formula I.42 wherein $R^1$ is Y-3B, R is NH, and $R^2$ is c-$C_3H_5$.

Table 2797. Compounds of formula I.42 wherein $R^1$ is Y-3C, R is NH, and $R^2$ is c-$C_3H_5$.

Table 2798. Compounds of formula I.42 wherein $R^1$ is Y-3D, R is NH, and $R^2$ is c-$C_3H_5$.

Table 2799. Compounds of formula I.42 wherein $R^1$ is Y-4A, R is NH, and $R^2$ is c-$C_3H_5$.

Table 2800. Compounds of formula I.42 wherein $R^1$ is Y-4B, R is NH, and $R^2$ is c-$C_3H_5$.

Table 2801. Compounds of formula I.42 wherein $R^1$ is Y-4C, R is NH, and $R^2$ is c-$C_3H_5$.

Table 2802. Compounds of formula I.42 wherein $R^1$ is Y-4D, R is NH, and $R^2$ is c-$C_3H_5$.

Table 2803. Compounds of formula I.42 wherein $R^1$ is Y-5A, R is NH, and $R^2$ is c-$C_3H_5$.

Table 2804. Compounds of formula I.42 wherein $R^1$ is Y-5B, R is NH, and $R^2$ is c-$C_3H_5$.

Table 2805. Compounds of formula I.42 wherein $R^1$ is Y-6A, R is NH, and $R^2$ is c-$C_3H_5$.

Table 2806. Compounds of formula I.42 wherein $R^1$ is Y-6B, R is NH, and $R^2$ is c-$C_3H_5$.

Table 2807. Compounds of formula I.42 wherein $R^1$ is Y-8A, R is NH, and $R^2$ is c-$C_3H_5$.

Table 2808. Compounds of formula I.42 wherein $R^1$ is Y-8B, R is NH, and $R^2$ is c-$C_3H_5$.

Table 2809. Compounds of formula I.42 wherein $R^1$ is Y-1A, R is $NCH_3$ and $R^2$ is H.

Table 2810. Compounds of formula I.42 wherein $R^1$ is Y-1B, R is $NCH_3$ and $R^2$ is H.

Table 2811. Compounds of formula I.42 wherein $R^1$ is Y-2A, R is $NCH_3$ and $R^2$ is H.

Table 2812. Compounds of formula I.42 wherein $R^1$ is Y-2B, R is $NCH_3$ and $R^2$ is H.

Table 2813. Compounds of formula I.42 wherein $R^1$ is Y-3A, R is $NCH_3$ and $R^2$ is H.

Table 2814. Compounds of formula I.42 wherein $R^1$ is Y-3B, R is $NCH_3$ and $R^2$ is H.

Table 2815. Compounds of formula I.42 wherein $R^1$ is Y-3C, R is $NCH_3$ and $R^2$ is H.

Table 2816. Compounds of formula I.42 wherein $R^1$ is Y-3D, R is $NCH_3$ and $R^2$ is H.

Table 2817. Compounds of formula I.42 wherein $R^1$ is Y-4A, R is $NCH_3$ and $R^2$ is H.

Table 2818. Compounds of formula I.42 wherein $R^1$ is Y-4B, R is $NCH_3$ and $R^2$ is H.

Table 2819. Compounds of formula I.42 wherein $R^1$ is Y-4C, R is $NCH_3$ and $R^2$ is H.

Table 2820. Compounds of formula I.42 wherein $R^1$ is Y-4D, R is $NCH_3$ and $R^2$ is H.

Table 2821. Compounds of formula I.42 wherein $R^1$ is Y-5A, R is $NCH_3$ and $R^2$ is H.

Table 2822. Compounds of formula I.42 wherein $R^1$ is Y-5B, R is $NCH_3$ and $R^2$ is H.

Table 2823. Compounds of formula I.42 wherein $R^1$ is Y-6A, R is $NCH_3$ and $R^2$ is H.

Table 2824. Compounds of formula I.42 wherein $R^1$ is Y-6B, R is $NCH_3$ and $R^2$ is H.

Table 2825. Compounds of formula I.42 wherein $R^1$ is Y-8A, R is $NCH_3$ and $R^2$ is H.

Table 2826. Compounds of formula I.42 wherein $R^1$ is Y-8B, R is $NCH_3$ and $R^2$ is H.

Table 2827. Compounds of formula I.42 wherein $R^1$ is Y-1A, R is $NCH_3$ and $R^2$ is $CH_3$.

Table 2828. Compounds of formula I.42 wherein $R^1$ is Y-1B, R is $NCH_3$ and $R^2$ is $CH_3$.

Table 2829. Compounds of formula I.42 wherein $R^1$ is Y-2A, R is $NCH_3$ and $R^2$ is $CH_3$.

Table 2830. Compounds of formula I.42 wherein $R^1$ is Y-2B, R is $NCH_3$ and $R^2$ is $CH_3$.

Table 2831. Compounds of formula I.42 wherein $R^1$ is Y-3A, R is $NCH_3$ and $R^2$ is $CH_3$.

Table 2832. Compounds of formula I.42 wherein $R^1$ is Y-3B, R is $NCH_3$ and $R^2$ is $CH_3$.

Table 2833. Compounds of formula I.42 wherein $R^1$ is Y-3C, R is $NCH_3$ and $R^2$ is $CH_3$.

Table 2834. Compounds of formula I.42 wherein $R^1$ is Y-3D, R is $NCH_3$ and $R^2$ is $CH_3$.

Table 2835. Compounds of formula I.42 wherein $R^1$ is Y-4A, R is $NCH_3$ and $R^2$ is $CH_3$.

Table 2836. Compounds of formula I.42 wherein $R^1$ is Y-4B, R is $NCH_3$ and $R^2$ is $CH_3$.

Table 2837. Compounds of formula I.42 wherein $R^1$ is Y-4C, R is $NCH_3$ and $R^2$ is $CH_3$.

Table 2838. Compounds of formula I.42 wherein $R^1$ is Y-4D, R is $NCH_3$ and $R^2$ is $CH_3$.

Table 2839. Compounds of formula I.42 wherein $R^1$ is Y-5A, R is $NCH_3$ and $R^2$ is $CH_3$.

Table 2840. Compounds of formula I.42 wherein $R^1$ is Y-5B, R is $NCH_3$ and $R^2$ is $CH_3$.

Table 2841. Compounds of formula I.42 wherein $R^1$ is Y-6A, R is $NCH_3$ and $R^2$ is $CH_3$.

Table 2842. Compounds of formula I.42 wherein $R^1$ is Y-6B, R is $NCH_3$ and $R^2$ is $CH_3$.

Table 2843. Compounds of formula I.42 wherein $R^1$ is Y-8A, R is $NCH_3$ and $R^2$ is $CH_3$.

Table 2844. Compounds of formula I.42 wherein $R^1$ is Y-8B, R is $NCH_3$ and $R^2$ is $CH_3$.

Table 2845. Compounds of formula I.42 wherein $R^1$ is Y-1A, R is $NCH_3$ and $R^2$ is c-$C_3H_5$.

Table 2846. Compounds of formula I.42 wherein $R^1$ is Y-1B, R is $NCH_3$ and $R^2$ is c-$C_3H_5$.

Table 2847. Compounds of formula I.42 wherein $R^1$ is Y-2A, R is $NCH_3$ and $R^2$ is c-$C_3H_5$.

Table 2848. Compounds of formula I.42 wherein $R^1$ is Y-2B, R is $NCH_3$ and $R^2$ is c-$C_3H_5$.

Table 2849. Compounds of formula I.42 wherein $R^1$ is Y-3A, R is $NCH_3$ and $R^2$ is c-$C_3H_5$.

Table 2850. Compounds of formula I.42 wherein $R^1$ is Y-3B, R is $NCH_3$ and $R^2$ is c-$C_3H_5$.

Table 2851. Compounds of formula I.42 wherein $R^1$ is Y-3C, R is $NCH_3$ and $R^2$ is c-$C_3H_5$.

Table 2852. Compounds of formula I.42 wherein $R^1$ is Y-3D, R is $NCH_3$ and $R^2$ is c-$C_3H_5$.

Table 2853. Compounds of formula I.42 wherein $R^1$ is Y-4A, R is $NCH_3$ and $R^2$ is c-$C_3H_5$.

Table 2854. Compounds of formula I.42 wherein $R^1$ is Y-4B, R is $NCH_3$ and $R^2$ is c-$C_3H_5$.

Table 2855. Compounds of formula I.42 wherein $R^1$ is Y-4C, R is $NCH_3$ and $R^2$ is c-$C_3H_5$.

Table 2856. Compounds of formula I.42 wherein $R^1$ is Y-4D, R is $NCH_3$ and $R^2$ is c-$C_3H_5$.

Table 2857. Compounds of formula I.42 wherein $R^1$ is Y-5A, R is $NCH_3$ and $R^2$ is c-$C_3H_5$.

Table 2858. Compounds of formula I.42 wherein $R^1$ is Y-5B, R is $NCH_3$ and $R^2$ is c-$C_3H_5$.

Table 2859. Compounds of formula I.42 wherein $R^1$ is Y-6A, R is $NCH_3$ and $R^2$ is c-$C_3H_5$.

Table 2860. Compounds of formula I.42 wherein $R^1$ is Y-6B, R is $NCH_3$ and $R^2$ is c-$C_3H_5$.

Table 2861. Compounds of formula I.42 wherein $R^1$ is Y-8A, R is $NCH_3$ and $R^2$ is c-$C_3H_5$.

Table 2862. Compounds of formula I.42 wherein $R^1$ is Y-8B, R is $NCH_3$ and $R^2$ is c-$C_3H_5$.

Table 2863. Compounds of formula I.42 wherein $R^1$ is Y-1A, R is NCN, and $R^2$ is H.

Table 2864. Compounds of formula I.42 wherein $R^1$ is Y-1B, R is NCN, and $R^2$ is H.

Table 2865. Compounds of formula I.42 wherein $R^1$ is Y-2A, R is NCN, and $R^2$ is H.

Table 2866. Compounds of formula I.42 wherein $R^1$ is Y-2B, R is NCN, and $R^2$ is H.

Table 2867. Compounds of formula I.42 wherein $R^1$ is Y-3A, R is NCN, and $R^2$ is H.

Table 2868. Compounds of formula I.42 wherein $R^1$ is Y-3B, R is NCN, and $R^2$ is H.

Table 2869. Compounds of formula I.42 wherein $R^1$ is Y-3C, R is NCN, and $R^2$ is H.

Table 2870. Compounds of formula I.42 wherein $R^1$ is Y-3D, R is NCN, and $R^2$ is H.

Table 2871. Compounds of formula I.42 wherein $R^1$ is Y-4A, R is NCN, and $R^2$ is H.

Table 2872. Compounds of formula I.42 wherein $R^1$ is Y-4B, R is NCN, and $R^2$ is H.

Table 2873. Compounds of formula I.42 wherein $R^1$ is Y-4C, R is NCN, and $R^2$ is H.

Table 2874. Compounds of formula I.42 wherein $R^1$ is Y-4D, R is NCN, and $R^2$ is H.

Table 2875. Compounds of formula I.42 wherein $R^1$ is Y-5A, R is NCN, and $R^2$ is H.

Table 2876. Compounds of formula I.42 wherein $R^1$ is Y-5B, R is NCN, and $R^2$ is H.

Table 2877. Compounds of formula I.42 wherein $R^1$ is Y-6A, R is NCN, and $R^2$ is H.

Table 2878. Compounds of formula I.42 wherein $R^1$ is Y-6B, R is NCN, and $R^2$ is H.

Table 2879. Compounds of formula I.42 wherein $R^1$ is Y-8A, R is NCN, and $R^2$ is H.

Table 2880. Compounds of formula I.42 wherein $R^1$ is Y-8B, R is NCN, and $R^2$ is H.

Table 2881. Compounds of formula I.42 wherein $R^1$ is Y-1A, R is NCN, and $R^2$ is $CH_3$.

Table 2882. Compounds of formula I.42 wherein $R^1$ is Y-1B, R is NCN, and $R^2$ is $CH_3$.

Table 2883. Compounds of formula I.42 wherein $R^1$ is Y-2A, R is NCN, and $R^2$ is $CH_3$.

Table 2884. Compounds of formula I.42 wherein $R^1$ is Y-2B, R is NCN, and $R^2$ is $CH_3$.

Table 2885. Compounds of formula I.42 wherein $R^1$ is Y-3A, R is NCN, and $R^2$ is $CH_3$.

Table 2886. Compounds of formula I.42 wherein $R^1$ is Y-3B, R is NCN, and $R^2$ is $CH_3$.

Table 2887. Compounds of formula I.42 wherein $R^1$ is Y-3C, R is NCN, and $R^2$ is $CH_3$.

Table 2888. Compounds of formula I.42 wherein $R^1$ is Y-3D, R is NCN, and $R^2$ is $CH_3$.

Table 2889. Compounds of formula I.42 wherein $R^1$ is Y-4A, R is NCN, and $R^2$ is $CH_3$.

Table 2890. Compounds of formula I.42 wherein $R^1$ is Y-4B, R is NCN, and $R^2$ is $CH_3$.

Table 2891. Compounds of formula I.42 wherein $R^1$ is Y-4C, R is NCN, and $R^2$ is $CH_3$.

Table 2892. Compounds of formula I.42 wherein $R^1$ is Y-4D, R is NCN, and $R^2$ is $CH_3$.

Table 2893. Compounds of formula I.42 wherein $R^1$ is Y-5A, R is NCN, and $R^2$ is $CH_3$.

Table 2894. Compounds of formula I.42 wherein $R^1$ is Y-5B, R is NCN, and $R^2$ is $CH_3$.

Table 2895. Compounds of formula I.42 wherein $R^1$ is Y-6A, R is NCN, and $R^2$ is $CH_3$.

Table 2896. Compounds of formula I.42 wherein $R^1$ is Y-6B, R is NCN, and $R^2$ is $CH_3$.

Table 2897. Compounds of formula I.42 wherein $R^1$ is Y-8A, R is NCN, and $R^2$ is $CH_3$.

Table 2898. Compounds of formula I.42 wherein $R^1$ is Y-8B, R is NCN, and $R^2$ is $CH_3$.

Table 2899. Compounds of formula I.42 wherein $R^1$ is Y-1A, R is NCN, and $R^2$ is c-$C_3H_5$.

Table 2900. Compounds of formula I.42 wherein $R^1$ is Y-1B, R is NCN, and $R^2$ is c-$C_3H_5$.

Table 2901. Compounds of formula I.42 wherein $R^1$ is Y-2A, R is NCN, and $R^2$ is c-$C_3H_5$.

Table 2902. Compounds of formula I.42 wherein $R^1$ is Y-2B, R is NCN, and $R^2$ is c-$C_3H_5$.

Table 2903. Compounds of formula I.42 wherein $R^1$ is Y-3A, R is NCN, and $R^2$ is c-$C_3H_5$.

Table 2904. Compounds of formula I.42 wherein $R^1$ is Y-3B, R is NCN, and $R^2$ is c-$C_3H_5$.

Table 2905. Compounds of formula I.42 wherein $R^1$ is Y-3C, R is NCN, and $R^2$ is c-$C_3H_5$.

Table 2906. Compounds of formula I.42 wherein $R^1$ is Y-3D, R is NCN, and $R^2$ is c-$C_3H_5$.

Table 2907. Compounds of formula I.42 wherein $R^1$ is Y-4A, R is NCN, and $R^2$ is c-$C_3H_5$.

Table 2908. Compounds of formula I.42 wherein $R^1$ is Y-4B, R is NCN, and $R^2$ is c-$C_3H_5$.

Table 2909. Compounds of formula I.42 wherein $R^1$ is Y-4C, R is NCN, and $R^2$ is c-$C_3H_5$.

Table 2910. Compounds of formula I.42 wherein $R^1$ is Y-4D, R is NCN, and $R^2$ is c-$C_3H_5$.

Table 2911. Compounds of formula I.42 wherein $R^1$ is Y-5A, R is NCN, and $R^2$ is c-$C_3H_5$.

Table 2912. Compounds of formula I.42 wherein $R^1$ is Y-5B, R is NCN, and $R^2$ is c-$C_3H_5$.

Table 2913. Compounds of formula I.42 wherein $R^1$ is Y-6A, R is NCN, and $R^2$ is c-$C_3H_5$.

Table 2914. Compounds of formula I.42 wherein $R^1$ is Y-6B, R is NCN, and $R^2$ is c-$C_3H_5$.

Table 2915. Compounds of formula I.42 wherein $R^1$ is Y-8A, R is NCN, and $R^2$ is c-$C_3H_5$.

Table 2916. Compounds of formula I.42 wherein $R^1$ is Y-8B, R is NCN, and $R^2$ is c-$C_3H_5$.

Table 2917. Compounds of formula I.43 wherein $R^1$ is Y-1A, R is NH, and $R^2$ is H.

Table 2918. Compounds of formula I.43 wherein $R^1$ is Y-1B, R is NH, and $R^2$ is H.

Table 2919. Compounds of formula I.43 wherein $R^1$ is Y-2A, R is NH, and $R^2$ is H.

Table 2920. Compounds of formula I.43 wherein $R^1$ is Y-2B, R is NH, and $R^2$ is H.

Table 2921. Compounds of formula I.43 wherein $R^1$ is Y-3A, R is NH, and $R^2$ is H.

Table 2922. Compounds of formula I.43 wherein $R^1$ is Y-3B, R is NH, and $R^2$ is H.

Table 2923. Compounds of formula I.43 wherein $R^1$ is Y-3C, R is NH, and $R^2$ is H.

Table 2924. Compounds of formula I.43 wherein $R^1$ is Y-3D, R is NH, and $R^2$ is H.

Table 2925. Compounds of formula I.43 wherein $R^1$ is Y-4A, R is NH, and $R^2$ is H.

Table 2926. Compounds of formula I.43 wherein $R^1$ is Y-4B, R is NH, and $R^2$ is H.

Table 2927. Compounds of formula I.43 wherein $R^1$ is Y-4C, R is NH, and $R^2$ is H.

Table 2928. Compounds of formula I.43 wherein $R^1$ is Y-4D, R is NH, and $R^2$ is H.

Table 2929. Compounds of formula I.43 wherein $R^1$ is Y-5A, R is NH, and $R^2$ is H.

Table 2930. Compounds of formula I.43 wherein $R^1$ is Y-5B, R is NH, and $R^2$ is H.

Table 2931. Compounds of formula I.43 wherein $R^1$ is Y-6A, R is NH, and $R^2$ is H.

Table 2932. Compounds of formula I.43 wherein $R^1$ is Y-6B, R is NH, and $R^2$ is H.

Table 2933. Compounds of formula I.43 wherein $R^1$ is Y-8A, R is NH, and $R^2$ is H.

Table 2934. Compounds of formula I.43 wherein $R^1$ is Y-8B, R is NH, and $R^2$ is H.

Table 2935. Compounds of formula I.43 wherein $R^1$ is Y-1A, R is NH, and $R^2$ is $CH_3$.

Table 2936. Compounds of formula I.43 wherein $R^1$ is Y-1B, R is NH, and $R^2$ is $CH_3$.

Table 2937. Compounds of formula I.43 wherein $R^1$ is Y-2A, R is NH, and $R^2$ is $CH_3$.

Table 2938. Compounds of formula I.43 wherein $R^1$ is Y-2B, R is NH, and $R^2$ is $CH_3$.

Table 2939. Compounds of formula I.43 wherein $R^1$ is Y-3A, R is NH, and $R^2$ is $CH_3$.

Table 2940. Compounds of formula I.43 wherein $R^1$ is Y-3B, R is NH, and $R^2$ is $CH_3$.

Table 2941. Compounds of formula I.43 wherein $R^1$ is Y-3C, R is NH, and $R^2$ is $CH_3$.

Table 2942. Compounds of formula I.43 wherein $R^1$ is Y-3D, R is NH, and $R^2$ is $CH_3$.

Table 2943. Compounds of formula I.43 wherein $R^1$ is Y-4A, R is NH, and $R^2$ is $CH_3$.

Table 2944. Compounds of formula I.43 wherein $R^1$ is Y-4B, R is NH, and $R^2$ is $CH_3$.

Table 2945. Compounds of formula I.43 wherein $R^1$ is Y-4C, R is NH, and $R^2$ is $CH_3$.

Table 2946. Compounds of formula I.43 wherein $R^1$ is Y-4D, R is NH, and $R^2$ is $CH_3$.

Table 2947. Compounds of formula I.43 wherein $R^1$ is Y-5A, R is NH, and $R^2$ is $CH_3$.

Table 2948. Compounds of formula I.43 wherein $R^1$ is Y-5B, R is NH, and $R^2$ is $CH_3$.

Table 2949. Compounds of formula I.43 wherein $R^1$ is Y-6A, R is NH, and $R^2$ is $CH_3$.

Table 2950. Compounds of formula I.43 wherein $R^1$ is Y-6B, R is NH, and $R^2$ is $CH_3$.

Table 2951. Compounds of formula I.43 wherein $R^1$ is Y-8A, R is NH, and $R^2$ is $CH_3$.

Table 2952. Compounds of formula I.43 wherein $R^1$ is Y-8B, R is NH, and $R^2$ is $CH_3$.

Table 2953. Compounds of formula I.43 wherein $R^1$ is Y-1A, R is NH, and $R^2$ is c-$C_3H_5$.

Table 2954. Compounds of formula I.43 wherein $R^1$ is Y-1B, R is NH, and $R^2$ is c-$C_3H_5$.

Table 2955. Compounds of formula I.43 wherein $R^1$ is Y-2A, R is NH, and $R^2$ is c-$C_3H_5$.

Table 2956. Compounds of formula I.43 wherein $R^1$ is Y-2B, R is NH, and $R^2$ is c-$C_3H_5$.

Table 2957. Compounds of formula I.43 wherein $R^1$ is Y-3A, R is NH, and $R^2$ is c-$C_3H_5$.

Table 2958. Compounds of formula I.43 wherein $R^1$ is Y-3B, R is NH, and $R^2$ is c-$C_3H_5$.

Table 2959. Compounds of formula I.43 wherein $R^1$ is Y-3C, R is NH, and $R^2$ is c-$C_3H_5$.

Table 2960. Compounds of formula I.43 wherein $R^1$ is Y-3D, R is NH, and $R^2$ is c-$C_3H_5$.

Table 2961. Compounds of formula I.43 wherein $R^1$ is Y-4A, R is NH, and $R^2$ is c-$C_3H_5$.

Table 2962. Compounds of formula I.43 wherein $R^1$ is Y-4B, R is NH, and $R^2$ is c-$C_3H_5$.

Table 2963. Compounds of formula I.43 wherein $R^1$ is Y-4C, R is NH, and $R^2$ is c-$C_3H_5$.

Table 2964. Compounds of formula I.43 wherein $R^1$ is Y-4D, R is NH, and $R^2$ is c-$C_3H_5$.

Table 2965. Compounds of formula I.43 wherein $R^1$ is Y-5A, R is NH, and $R^2$ is c-$C_3H_5$.

Table 2966. Compounds of formula I.43 wherein $R^1$ is Y-5B, R is NH, and $R^2$ is c-$C_3H_5$.

Table 2967. Compounds of formula I.43 wherein $R^1$ is Y-6A, R is NH, and $R^2$ is c-$C_3H_5$.

Table 2968. Compounds of formula I.43 wherein $R^1$ is Y-6B, R is NH, and $R^2$ is c-$C_3H_5$.

Table 2969. Compounds of formula I.43 wherein $R^1$ is Y-8A, R is NH, and $R^2$ is c-$C_3H_5$.

Table 2970. Compounds of formula I.43 wherein $R^1$ is Y-8B, R is NH, and $R^2$ is c-$C_3H_5$.

Table 2971. Compounds of formula I.43 wherein $R^1$ is Y-1A, R is $NCH_3$ and $R^2$ is H.

Table 2972. Compounds of formula I.43 wherein $R^1$ is Y-1B, R is $NCH_3$ and $R^2$ is H.

Table 2973. Compounds of formula I.43 wherein $R^1$ is Y-2A, R is $NCH_3$ and $R^2$ is H.

Table 2974. Compounds of formula I.43 wherein $R^1$ is Y-2B, R is $NCH_3$ and $R^2$ is H.

Table 2975. Compounds of formula I.43 wherein $R^1$ is Y-3A, R is $NCH_3$ and $R^2$ is H.

Table 2976. Compounds of formula I.43 wherein $R^1$ is Y-3B, R is $NCH_3$ and $R^2$ is H.

Table 2977. Compounds of formula I.43 wherein $R^1$ is Y-3C, R is $NCH_3$ and $R^2$ is H.

Table 2978. Compounds of formula I.43 wherein $R^1$ is Y-3D, R is $NCH_3$ and $R^2$ is H.

Table 2979. Compounds of formula I.43 wherein $R^1$ is Y-4A, R is $NCH_3$ and $R^2$ is H.

Table 2980. Compounds of formula I.43 wherein $R^1$ is Y-4B, R is $NCH_3$ and $R^2$ is H.

Table 2981. Compounds of formula I.43 wherein $R^1$ is Y-4C, R is $NCH_3$ and $R^2$ is H.

Table 2982. Compounds of formula I.43 wherein $R^1$ is Y-4D, R is $NCH_3$ and $R^2$ is H.

Table 2983. Compounds of formula I.43 wherein $R^1$ is Y-5A, R is $NCH_3$ and $R^2$ is H.

Table 2984. Compounds of formula I.43 wherein $R^1$ is Y-5B, R is $NCH_3$ and $R^2$ is H.

Table 2985. Compounds of formula I.43 wherein $R^1$ is Y-6A, R is $NCH_3$ and $R^2$ is H.

Table 2986. Compounds of formula I.43 wherein $R^1$ is Y-6B, R is $NCH_3$ and $R^2$ is H.

Table 2987. Compounds of formula I.43 wherein $R^1$ is Y-8A, R is $NCH_3$ and $R^2$ is H.

Table 2988. Compounds of formula I.43 wherein $R^1$ is Y-8B, R is $NCH_3$ and $R^2$ is H.

Table 2989. Compounds of formula I.43 wherein $R^1$ is Y-1A, R is $NCH_3$ and $R^2$ is $CH_3$.

Table 2990. Compounds of formula I.43 wherein $R^1$ is Y-1B, R is $NCH_3$ and $R^2$ is $CH_3$.

Table 2991. Compounds of formula I.43 wherein $R^1$ is Y-2A, R is $NCH_3$ and $R^2$ is $CH_3$.

Table 2992. Compounds of formula I.43 wherein $R^1$ is Y-2B, R is $NCH_3$ and $R^2$ is $CH_3$.

Table 2993. Compounds of formula I.43 wherein $R^1$ is Y-3A, R is $NCH_3$ and $R^2$ is $CH_3$.

Table 2994. Compounds of formula I.43 wherein $R^1$ is Y-3B, R is $NCH_3$ and $R^2$ is $CH_3$.

Table 2995. Compounds of formula I.43 wherein $R^1$ is Y-3C, R is $NCH_3$ and $R^2$ is $CH_3$.

Table 2996. Compounds of formula I.43 wherein $R^1$ is Y-3D, R is $NCH_3$ and $R^2$ is $CH_3$.

Table 2997. Compounds of formula I.43 wherein $R^1$ is Y-4A, R is $NCH_3$ and $R^2$ is $CH_3$.

Table 2998. Compounds of formula I.43 wherein $R^1$ is Y-4B, R is $NCH_3$ and $R^2$ is $CH_3$.

Table 2999. Compounds of formula I.43 wherein $R^1$ is Y-4C, R is $NCH_3$ and $R^2$ is $CH_3$.

Table 3000. Compounds of formula I.43 wherein $R^1$ is Y-4D, R is $NCH_3$ and $R^2$ is $CH_3$.

Table 3001. Compounds of formula I.43 wherein $R^1$ is Y-5A, R is $NCH_3$ and $R^2$ is $CH_3$.

Table 3002. Compounds of formula I.43 wherein $R^1$ is Y-5B, R is $NCH_3$ and $R^2$ is $CH_3$.

Table 3003. Compounds of formula I.43 wherein $R^1$ is Y-6A, R is $NCH_3$ and $R^2$ is $CH_3$.

Table 3004. Compounds of formula I.43 wherein $R^1$ is Y-6B, R is $NCH_3$ and $R^2$ is $CH_3$.

Table 3005. Compounds of formula I.43 wherein $R^1$ is Y-8A, R is $NCH_3$ and $R^2$ is $CH_3$.

Table 3006. Compounds of formula I.43 wherein $R^1$ is Y-8B, R is $NCH_3$ and $R^2$ is $CH_3$.

Table 3007. Compounds of formula I.43 wherein $R^1$ is Y-1A, R is $NCH_3$ and $R^2$ is c-$C_3H_5$.

Table 3008. Compounds of formula I.43 wherein $R^1$ is Y-1B, R is $NCH_3$ and $R^2$ is c-$C_3H_5$.

Table 3009. Compounds of formula I.43 wherein $R^1$ is Y-2A, R is $NCH_3$ and $R^2$ is c-$C_3H_5$.

Table 3010. Compounds of formula I.43 wherein $R^1$ is Y-2B, R is $NCH_3$ and $R^2$ is c-$C_3H_5$.

Table 3011. Compounds of formula I.43 wherein $R^1$ is Y-3A, R is $NCH_3$ and $R^2$ is c-$C_3H_5$.

Table 3012. Compounds of formula I.43 wherein $R^1$ is Y-3B, R is $NCH_3$ and $R^2$ is c-$C_3H_5$.

Table 3013. Compounds of formula I.43 wherein $R^1$ is Y-3C, R is $NCH_3$ and $R^2$ is c-$C_3H_5$.

Table 3014. Compounds of formula I.43 wherein $R^1$ is Y-3D, R is $NCH_3$ and $R^2$ is c-$C_3H_5$.

Table 3015. Compounds of formula I.43 wherein $R^1$ is Y-4A, R is $NCH_3$ and $R^2$ is c-$C_3H_5$.

Table 3016. Compounds of formula I.43 wherein $R^1$ is Y-4B, R is $NCH_3$ and $R^2$ is c-$C_3H_5$.

Table 3017. Compounds of formula I.43 wherein $R^1$ is Y-4C, R is $NCH_3$ and $R^2$ is c-$C_3H_5$.

Table 3018. Compounds of formula I.43 wherein $R^1$ is Y-4D, R is $NCH_3$ and $R^2$ is c-$C_3H_5$.

Table 3019. Compounds of formula I.43 wherein $R^1$ is Y-5A, R is $NCH_3$ and $R^2$ is c-$C_3H_5$.

Table 3020. Compounds of formula I.43 wherein $R^1$ is Y-5B, R is $NCH_3$ and $R^2$ is c-$C_3H_5$.

Table 3021. Compounds of formula I.43 wherein $R^1$ is Y-6A, R is $NCH_3$ and $R^2$ is c-$C_3H_5$.

Table 3022. Compounds of formula I.43 wherein $R^1$ is Y-6B, R is $NCH_3$ and $R^2$ is c-$C_3H_5$.

Table 3023. Compounds of formula I.43 wherein $R^1$ is Y-8A, R is $NCH_3$ and $R^2$ is c-$C_3H_5$.

Table 3024. Compounds of formula I.43 wherein $R^1$ is Y-8B, R is $NCH_3$ and $R^2$ is c-$C_3H_5$.

Table 3025. Compounds of formula I.43 wherein $R^1$ is Y-1A, R is NCN, and $R^2$ is H.

Table 3026. Compounds of formula I.43 wherein $R^1$ is Y-1B, R is NCN, and $R^2$ is H.

Table 3027. Compounds of formula I.43 wherein $R^1$ is Y-2A, R is NCN, and $R^2$ is H.

Table 3028. Compounds of formula I.43 wherein $R^1$ is Y-2B, R is NCN, and $R^2$ is H.

Table 3029. Compounds of formula I.43 wherein $R^1$ is Y-3A, R is NCN, and $R^2$ is H.

Table 3030. Compounds of formula I.43 wherein $R^1$ is Y-3B, R is NCN, and $R^2$ is H.

Table 3031. Compounds of formula I.43 wherein $R^1$ is Y-3C, R is NCN, and $R^2$ is H.

Table 3032. Compounds of formula I.43 wherein $R^1$ is Y-3D, R is NCN, and $R^2$ is H.

Table 3033. Compounds of formula I.43 wherein $R^1$ is Y-4A, R is NCN, and $R^2$ is H.

Table 3034. Compounds of formula I.43 wherein $R^1$ is Y-4B, R is NCN, and $R^2$ is H.

Table 3035. Compounds of formula I.43 wherein $R^1$ is Y-4C, R is NCN, and $R^2$ is H.

Table 3036. Compounds of formula I.43 wherein $R^1$ is Y-4D, R is NCN, and $R^2$ is H.

Table 3037. Compounds of formula I.43 wherein $R^1$ is Y-5A, R is NCN, and $R^2$ is H.

Table 3038. Compounds of formula I.43 wherein $R^1$ is Y-5B, R is NCN, and $R^2$ is H.

Table 3039. Compounds of formula I.43 wherein $R^1$ is Y-6A, R is NCN, and $R^2$ is H.

Table 3040. Compounds of formula I.43 wherein $R^1$ is Y-6B, R is NCN, and $R^2$ is H.

Table 3041. Compounds of formula I.43 wherein $R^1$ is Y-8A, R is NCN, and $R^2$ is H.

Table 3042. Compounds of formula I.43 wherein $R^1$ is Y-8B, R is NCN, and $R^2$ is H.

Table 3043. Compounds of formula I.43 wherein $R^1$ is Y-1A, R is NCN, and $R^2$ is $CH_3$.

Table 3044. Compounds of formula I.43 wherein $R^1$ is Y-1B, R is NCN, and $R^2$ is $CH_3$.

Table 3045. Compounds of formula I.43 wherein $R^1$ is Y-2A, R is NCN, and $R^2$ is $CH_3$.

Table 3046. Compounds of formula I.43 wherein $R^1$ is Y-2B, R is NCN, and $R^2$ is $CH_3$.

Table 3047. Compounds of formula I.43 wherein $R^1$ is Y-3A, R is NCN, and $R^2$ is $CH_3$.

Table 3048. Compounds of formula I.43 wherein $R^1$ is Y-3B, R is NCN, and $R^2$ is $CH_3$.

Table 3049. Compounds of formula I.43 wherein $R^1$ is Y-3C, R is NCN, and $R^2$ is $CH_3$.

Table 3050. Compounds of formula I.43 wherein $R^1$ is Y-3D, R is NCN, and $R^2$ is $CH_3$.

Table 3051. Compounds of formula I.43 wherein $R^1$ is Y-4A, R is NCN, and $R^2$ is $CH_3$.

Table 3052. Compounds of formula I.43 wherein $R^1$ is Y-4B, R is NCN, and $R^2$ is $CH_3$.

Table 3053. Compounds of formula I.43 wherein $R^1$ is Y-4C, R is NCN, and $R^2$ is $CH_3$.

Table 3054. Compounds of formula I.43 wherein $R^1$ is Y-4D, R is NCN, and $R^2$ is $CH_3$.

Table 3055. Compounds of formula I.43 wherein $R^1$ is Y-5A, R is NCN, and $R^2$ is $CH_3$.

Table 3056. Compounds of formula I.43 wherein $R^1$ is Y-5B, R is NCN, and $R^2$ is $CH_3$.

Table 3057. Compounds of formula I.43 wherein $R^1$ is Y-6A, R is NCN, and $R^2$ is $CH_3$.

Table 3058. Compounds of formula I.43 wherein $R^1$ is Y-6B, R is NCN, and $R^2$ is $CH_3$.

Table 3059. Compounds of formula I.43 wherein $R^1$ is Y-8A, R is NCN, and $R^2$ is $CH_3$.

Table 3060. Compounds of formula I.43 wherein $R^1$ is Y-8B, R is NCN, and $R^2$ is $CH_3$.

Table 3061. Compounds of formula I.43 wherein $R^1$ is Y-1A, R is NCN, and $R^2$ is c-$C_3H_5$.

Table 3062. Compounds of formula I.43 wherein $R^1$ is Y-1B, R is NCN, and $R^2$ is c-$C_3H_5$.

Table 3063. Compounds of formula I.43 wherein $R^1$ is Y-2A, R is NCN, and $R^2$ is c-$C_3H_5$.

Table 3064. Compounds of formula I.43 wherein $R^1$ is Y-2B, R is NCN, and $R^2$ is c-$C_3H_5$.

Table 3065. Compounds of formula I.43 wherein $R^1$ is Y-3A, R is NCN, and $R^2$ is c-$C_3H_5$.

Table 3066. Compounds of formula I.43 wherein $R^1$ is Y-3B, R is NCN, and $R^2$ is c-$C_3H_5$.

Table 3067. Compounds of formula I.43 wherein $R^1$ is Y-3C, R is NCN, and $R^2$ is c-$C_3H_5$.

Table 3068. Compounds of formula I.43 wherein $R^1$ is Y-3D, R is NCN, and $R^2$ is c-$C_3H_5$.

Table 3069. Compounds of formula I.43 wherein $R^1$ is Y-4A, R is NCN, and $R^2$ is c-$C_3H_5$.

Table 3070. Compounds of formula I.43 wherein $R^1$ is Y-4B, R is NCN, and $R^2$ is c-$C_3H_5$.

Table 3071. Compounds of formula I.43 wherein $R^1$ is Y-4C, R is NCN, and $R^2$ is c-$C_3H_5$.

Table 3072. Compounds of formula I.43 wherein $R^1$ is Y-4D, R is NCN, and $R^2$ is c-$C_3H_5$.

Table 3073. Compounds of formula I.43 wherein $R^1$ is Y-5A, R is NCN, and $R^2$ is c-$C_3H_5$.

Table 3074. Compounds of formula I.43 wherein $R^1$ is Y-5B, R is NCN, and $R^2$ is c-$C_3H_5$.

Table 3075. Compounds of formula I.43 wherein $R^1$ is Y-6A, R is NCN, and $R^2$ is c-$C_3H_5$.

Table 3076. Compounds of formula I.43 wherein $R^1$ is Y-6B, R is NCN, and $R^2$ is c-$C_3H_5$.

Table 3077. Compounds of formula I.43 wherein $R^1$ is Y-8A, R is NCN, and $R^2$ is c-$C_3H_5$.

Table 3078. Compounds of formula I.43 wherein $R^1$ is Y-8B, R is NCN, and $R^2$ is c-$C_3H_5$.

Table 3079. Compounds of formula I.44 wherein $R^1$ is Y-1A, R is NH, and $R^2$ is H.

Table 3080. Compounds of formula I.44 wherein $R^1$ is Y-1B, R is NH, and $R^2$ is H.

Table 3081. Compounds of formula I.44 wherein $R^1$ is Y-2A, R is NH, and $R^2$ is H.

Table 3082. Compounds of formula I.44 wherein $R^1$ is Y-2B, R is NH, and $R^2$ is H.

Table 3083. Compounds of formula I.44 wherein $R^1$ is Y-3A, R is NH, and $R^2$ is H.

Table 3084. Compounds of formula I.44 wherein $R^1$ is Y-3B, R is NH, and $R^2$ is H.

Table 3085. Compounds of formula I.44 wherein $R^1$ is Y-3C, R is NH, and $R^2$ is H.

Table 3086. Compounds of formula I.44 wherein $R^1$ is Y-3D, R is NH, and $R^2$ is H.

Table 3087. Compounds of formula I.44 wherein $R^1$ is Y-4A, R is NH, and $R^2$ is H.

Table 3088. Compounds of formula I.44 wherein $R^1$ is Y-4B, R is NH, and $R^2$ is H.

Table 3089. Compounds of formula I.44 wherein $R^1$ is Y-4C, R is NH, and $R^2$ is H.

Table 3090. Compounds of formula I.44 wherein $R^1$ is Y-4D, R is NH, and $R^2$ is H.

Table 3091. Compounds of formula I.44 wherein $R^1$ is Y-5A, R is NH, and $R^2$ is H.

Table 3092. Compounds of formula I.44 wherein $R^1$ is Y-5B, R is NH, and $R^2$ is H.

Table 3093. Compounds of formula I.44 wherein $R^1$ is Y-6A, R is NH, and $R^2$ is H.

Table 3094. Compounds of formula I.44 wherein $R^1$ is Y-6B, R is NH, and $R^2$ is H.

Table 3095. Compounds of formula I.44 wherein $R^1$ is Y-8A, R is NH, and $R^2$ is H.

Table 3096. Compounds of formula I.44 wherein $R^1$ is Y-8B, R is NH, and $R^2$ is H.

Table 3097. Compounds of formula I.44 wherein $R^1$ is Y-1A, R is NH, and $R^2$ is $CH_3$.

Table 3098. Compounds of formula I.44 wherein $R^1$ is Y-1B, R is NH, and $R^2$ is $CH_3$.

Table 3099. Compounds of formula I.44 wherein $R^1$ is Y-2A, R is NH, and $R^2$ is $CH_3$.

Table 3100. Compounds of formula I.44 wherein $R^1$ is Y-2B, R is NH, and $R^2$ is $CH_3$.

Table 3101. Compounds of formula I.44 wherein $R^1$ is Y-3A, R is NH, and $R^2$ is $CH_3$.

Table 3102. Compounds of formula I.44 wherein $R^1$ is Y-3B, R is NH, and $R^2$ is $CH_3$.

Table 3103. Compounds of formula I.44 wherein $R^1$ is Y-3C, R is NH, and $R^2$ is $CH_3$.

Table 3104. Compounds of formula I.44 wherein $R^1$ is Y-3D, R is NH, and $R^2$ is $CH_3$.

Table 3105. Compounds of formula I.44 wherein $R^1$ is Y-4A, R is NH, and $R^2$ is $CH_3$.

Table 3106. Compounds of formula I.44 wherein $R^1$ is Y-4B, R is NH, and $R^2$ is $CH_3$.

Table 3107. Compounds of formula I.44 wherein $R^1$ is Y-4C, R is NH, and $R^2$ is $CH_3$.

Table 3108. Compounds of formula I.44 wherein $R^1$ is Y-4D, R is NH, and $R^2$ is $CH_3$.

Table 3109. Compounds of formula I.44 wherein $R^1$ is Y-5A, R is NH, and $R^2$ is $CH_3$.

Table 3110. Compounds of formula I.44 wherein $R^1$ is Y-5B, R is NH, and $R^2$ is $CH_3$.

Table 3111. Compounds of formula I.44 wherein $R^1$ is Y-6A, R is NH, and $R^2$ is $CH_3$.

Table 3112. Compounds of formula I.44 wherein $R^1$ is Y-6B, R is NH, and $R^2$ is $CH_3$.

Table 3113. Compounds of formula I.44 wherein $R^1$ is Y-8A, R is NH, and $R^2$ is $CH_3$.

Table 3114. Compounds of formula I.44 wherein $R^1$ is Y-8B, R is NH, and $R^2$ is $CH_3$.

Table 3115. Compounds of formula I.44 wherein $R^1$ is Y-1A, R is NH, and $R^2$ is c-$C_3H_5$.

Table 3116. Compounds of formula I.44 wherein $R^1$ is Y-1B, R is NH, and $R^2$ is c-$C_3H_5$.

Table 3117. Compounds of formula I.44 wherein $R^1$ is Y-2A, R is NH, and $R^2$ is c-$C_3H_5$.

Table 3118. Compounds of formula I.44 wherein $R^1$ is Y-2B, R is NH, and $R^2$ is c-$C_3H_5$.

Table 3119. Compounds of formula I.44 wherein $R^1$ is Y-3A, R is NH, and $R^2$ is c-$C_3H_5$.

Table 3120. Compounds of formula I.44 wherein $R^1$ is Y-3B, R is NH, and $R^2$ is c-$C_3H_5$.

Table 3121. Compounds of formula I.44 wherein $R^1$ is Y-3C, R is NH, and $R^2$ is c-$C_3H_5$.

Table 3122. Compounds of formula I.44 wherein $R^1$ is Y-3D, R is NH, and $R^2$ is c-$C_3H_5$.

Table 3123. Compounds of formula I.44 wherein $R^1$ is Y-4A, R is NH, and $R^2$ is c-$C_3H_5$.

Table 3124. Compounds of formula I.44 wherein $R^1$ is Y-4B, R is NH, and $R^2$ is c-$C_3H_5$.

Table 3125. Compounds of formula I.44 wherein $R^1$ is Y-4C, R is NH, and $R^2$ is c-$C_3H_5$.

Table 3126. Compounds of formula I.44 wherein $R^1$ is Y-4D, R is NH, and $R^2$ is c-$C_3H_5$.

Table 3127. Compounds of formula I.44 wherein $R^1$ is Y-5A, R is NH, and $R^2$ is c-$C_3H_5$.

Table 3128. Compounds of formula I.44 wherein $R^1$ is Y-5B, R is NH, and $R^2$ is c-$C_3H_5$.

Table 3129. Compounds of formula I.44 wherein $R^1$ is Y-6A, R is NH, and $R^2$ is c-$C_3H_5$.

Table 3130. Compounds of formula I.44 wherein $R^1$ is Y-6B, R is NH, and $R^2$ is c-$C_3H_5$.

Table 3131. Compounds of formula I.44 wherein $R^1$ is Y-8A, R is NH, and $R^2$ is c-$C_3H_5$.

Table 3132. Compounds of formula I.44 wherein $R^1$ is Y-8B, R is NH, and $R^2$ is c-$C_3H_5$.

Table 3133. Compounds of formula I.44 wherein $R^1$ is Y-1A, R is $NCH_3$ and $R^2$ is H.

Table 3134. Compounds of formula I.44 wherein $R^1$ is Y-1B, R is $NCH_3$ and $R^2$ is H.

Table 3135. Compounds of formula I.44 wherein $R^1$ is Y-2A, R is $NCH_3$ and $R^2$ is H.

Table 3136. Compounds of formula I.44 wherein $R^1$ is Y-2B, R is $NCH_3$ and $R^2$ is H.

Table 3137. Compounds of formula I.44 wherein $R^1$ is Y-3A, R is $NCH_3$ and $R^2$ is H.

Table 3138. Compounds of formula I.44 wherein $R^1$ is Y-3B, R is $NCH_3$ and $R^2$ is H.

Table 3139. Compounds of formula I.44 wherein $R^1$ is Y-3C, R is $NCH_3$ and $R^2$ is H.

Table 3140. Compounds of formula I.44 wherein $R^1$ is Y-3D, R is $NCH_3$ and $R^2$ is H.

Table 3141. Compounds of formula I.44 wherein $R^1$ is Y-4A, R is $NCH_3$ and $R^2$ is H.

Table 3142. Compounds of formula I.44 wherein $R^1$ is Y-4B, R is $NCH_3$ and $R^2$ is H.

Table 3143. Compounds of formula I.44 wherein $R^1$ is Y-4C, R is $NCH_3$ and $R^2$ is H.

Table 3144. Compounds of formula I.44 wherein $R^1$ is Y-4D, R is $NCH_3$ and $R^2$ is H.

Table 3145. Compounds of formula I.44 wherein $R^1$ is Y-5A, R is $NCH_3$ and $R^2$ is H.

Table 3146. Compounds of formula I.44 wherein $R^1$ is Y-5B, R is $NCH_3$ and $R^2$ is H.

Table 3147. Compounds of formula I.44 wherein $R^1$ is Y-6A, R is $NCH_3$ and $R^2$ is H.

Table 3148. Compounds of formula I.44 wherein $R^1$ is Y-6B, R is $NCH_3$ and $R^2$ is H.

Table 3149. Compounds of formula I.44 wherein $R^1$ is Y-8A, R is $NCH_3$ and $R^2$ is H.

Table 3150. Compounds of formula I.44 wherein $R^1$ is Y-8B, R is $NCH_3$ and $R^2$ is H.

Table 3151. Compounds of formula I.44 wherein $R^1$ is Y-1A, R is $NCH_3$ and $R^2$ is $CH_3$.

Table 3152. Compounds of formula I.44 wherein $R^1$ is Y-1B, R is $NCH_3$ and $R^2$ is $CH_3$.

Table 3153. Compounds of formula I.44 wherein $R^1$ is Y-2A, R is $NCH_3$ and $R^2$ is $CH_3$.

Table 3154. Compounds of formula I.44 wherein $R^1$ is Y-2B, R is $NCH_3$ and $R^2$ is $CH_3$.

Table 3155. Compounds of formula I.44 wherein $R^1$ is Y-3A, R is $NCH_3$ and $R^2$ is $CH_3$.

Table 3156. Compounds of formula I.44 wherein $R^1$ is Y-3B, R is $NCH_3$ and $R^2$ is $CH_3$.

Table 3157. Compounds of formula I.44 wherein $R^1$ is Y-3C, R is $NCH_3$ and $R^2$ is $CH_3$.

Table 3158. Compounds of formula I.44 wherein $R^1$ is Y-3D, R is $NCH_3$ and $R^2$ is $CH_3$.

Table 3159. Compounds of formula I.44 wherein $R^1$ is Y-4A, R is $NCH_3$ and $R^2$ is $CH_3$.

Table 3160. Compounds of formula I.44 wherein $R^1$ is Y-4B, R is $NCH_3$ and $R^2$ is $CH_3$.

Table 3161. Compounds of formula I.44 wherein $R^1$ is Y-4C, R is $NCH_3$ and $R^2$ is $CH_3$.

Table 3162. Compounds of formula I.44 wherein $R^1$ is Y-4D, R is $NCH_3$ and $R^2$ is $CH_3$.

Table 3163. Compounds of formula I.44 wherein $R^1$ is Y-5A, R is $NCH_3$ and $R^2$ is $CH_3$.

Table 3164. Compounds of formula I.44 wherein $R^1$ is Y-5B, R is $NCH_3$ and $R^2$ is $CH_3$.

Table 3165. Compounds of formula I.44 wherein $R^1$ is Y-6A, R is $NCH_3$ and $R^2$ is $CH_3$.

Table 3166. Compounds of formula I.44 wherein $R^1$ is Y-6B, R is $NCH_3$ and $R^2$ is $CH_3$.

Table 3167. Compounds of formula I.44 wherein $R^1$ is Y-8A, R is $NCH_3$ and $R^2$ is $CH_3$.

Table 3168. Compounds of formula I.44 wherein $R^1$ is Y-8B, R is $NCH_3$ and $R^2$ is $CH_3$.

Table 3169. Compounds of formula I.44 wherein $R^1$ is Y-1A, R is $NCH_3$ and $R^2$ is c-$C_3H_5$.

Table 3170. Compounds of formula I.44 wherein $R^1$ is Y-1B, R is $NCH_3$ and $R^2$ is c-$C_3H_5$.

Table 3171. Compounds of formula I.44 wherein $R^1$ is Y-2A, R is $NCH_3$ and $R^2$ is c-$C_3H_5$.

Table 3172. Compounds of formula I.44 wherein $R^1$ is Y-2B, R is $NCH_3$ and $R^2$ is c-$C_3H_5$.

Table 3173. Compounds of formula I.44 wherein $R^1$ is Y-3A, R is $NCH_3$ and $R^2$ is c-$C_3H_5$.

Table 3174. Compounds of formula I.44 wherein $R^1$ is Y-3B, R is $NCH_3$ and $R^2$ is c-$C_3H_5$.

Table 3175. Compounds of formula I.44 wherein $R^1$ is Y-3C, R is $NCH_3$ and $R^2$ is c-$C_3H_5$.

Table 3176. Compounds of formula I.44 wherein $R^1$ is Y-3D, R is $NCH_3$ and $R^2$ is c-$C_3H_5$.

Table 3177. Compounds of formula I.44 wherein $R^1$ is Y-4A, R is $NCH_3$ and $R^2$ is c-$C_3H_5$.

Table 3178. Compounds of formula I.44 wherein $R^1$ is Y-4B, R is $NCH_3$ and $R^2$ is c-$C_3H_5$.

Table 3179. Compounds of formula I.44 wherein $R^1$ is Y-4C, R is $NCH_3$ and $R^2$ is c-$C_3H_5$.

Table 3180. Compounds of formula I.44 wherein $R^1$ is Y-4D, R is $NCH_3$ and $R^2$ is c-$C_3H_5$.

Table 3181. Compounds of formula I.44 wherein $R^1$ is Y-5A, R is $NCH_3$ and $R^2$ is c-$C_3H_5$.

Table 3182. Compounds of formula I.44 wherein $R^1$ is Y-5B, R is $NCH_3$ and $R^2$ is c-$C_3H_5$.

Table 3183. Compounds of formula I.44 wherein $R^1$ is Y-6A, R is $NCH_3$ and $R^2$ is c-$C_3H_5$.

Table 3184. Compounds of formula I.44 wherein $R^1$ is Y-6B, R is $NCH_3$ and $R^2$ is c-$C_3H_5$.

Table 3185. Compounds of formula I.44 wherein $R^1$ is Y-8A, R is $NCH_3$ and $R^2$ is c-$C_3H_5$.

Table 3186. Compounds of formula I.44 wherein $R^1$ is Y-8B, R is $NCH_3$ and $R^2$ is c-$C_3H_5$.

Table 3187. Compounds of formula I.44 wherein $R^1$ is Y-1A, R is NCN, and $R^2$ is H.

Table 3188. Compounds of formula I.44 wherein $R^1$ is Y-1B, R is NCN, and $R^2$ is H.

Table 3189. Compounds of formula I.44 wherein $R^1$ is Y-2A, R is NCN, and $R^2$ is H.

Table 3190. Compounds of formula I.44 wherein $R^1$ is Y-2B, R is NCN, and $R^2$ is H.

Table 3191. Compounds of formula I.44 wherein $R^1$ is Y-3A, R is NCN, and $R^2$ is H.

Table 3192. Compounds of formula I.44 wherein $R^1$ is Y-3B, R is NCN, and $R^2$ is H.

Table 3193. Compounds of formula I.44 wherein $R^1$ is Y-3C, R is NCN, and $R^2$ is H.

Table 3194. Compounds of formula I.44 wherein $R^1$ is Y-3D, R is NCN, and $R^2$ is H.

Table 3195. Compounds of formula I.44 wherein $R^1$ is Y-4A, R is NCN, and $R^2$ is H.

Table 3196. Compounds of formula I.44 wherein $R^1$ is Y-4B, R is NCN, and $R^2$ is H.

Table 3197. Compounds of formula I.44 wherein $R^1$ is Y-4C, R is NCN, and $R^2$ is H.

Table 3198. Compounds of formula I.44 wherein $R^1$ is Y-4D, R is NCN, and $R^2$ is H.

Table 3199. Compounds of formula I.44 wherein $R^1$ is Y-5A, R is NCN, and $R^2$ is H.

Table 3200. Compounds of formula I.44 wherein $R^1$ is Y-5B, R is NCN, and $R^2$ is H.

Table 3201. Compounds of formula I.44 wherein $R^1$ is Y-6A, R is NCN, and $R^2$ is H.

Table 3202. Compounds of formula I.44 wherein $R^1$ is Y-6B, R is NCN, and $R^2$ is H.

Table 3203. Compounds of formula I.44 wherein $R^1$ is Y-8A, R is NCN, and $R^2$ is H.

Table 3204. Compounds of formula I.44 wherein $R^1$ is Y-8B, R is NCN, and $R^2$ is H.

Table 3205. Compounds of formula I.44 wherein $R^1$ is Y-1A, R is NCN, and $R^2$ is $CH_3$.

Table 3206. Compounds of formula I.44 wherein $R^1$ is Y-1B, R is NCN, and $R^2$ is $CH_3$.

Table 3207. Compounds of formula I.44 wherein $R^1$ is Y-2A, R is NCN, and $R^2$ is $CH_3$.

Table 3208. Compounds of formula I.44 wherein $R^1$ is Y-2B, R is NCN, and $R^2$ is $CH_3$.

Table 3209. Compounds of formula I.44 wherein $R^1$ is Y-3A, R is NCN, and $R^2$ is $CH_3$.

Table 3210. Compounds of formula I.44 wherein $R^1$ is Y-3B, R is NCN, and $R^2$ is $CH_3$.

Table 3211. Compounds of formula I.44 wherein $R^1$ is Y-3C, R is NCN, and $R^2$ is $CH_3$.

Table 3212. Compounds of formula I.44 wherein $R^1$ is Y-3D, R is NCN, and $R^2$ is $CH_3$.

Table 3213. Compounds of formula I.44 wherein $R^1$ is Y-4A, R is NCN, and $R^2$ is $CH_3$.

Table 3214. Compounds of formula I.44 wherein $R^1$ is Y-4B, R is NCN, and $R^2$ is $CH_3$.

Table 3215. Compounds of formula I.44 wherein $R^1$ is Y-4C, R is NCN, and $R^2$ is $CH_3$.

Table 3216. Compounds of formula I.44 wherein $R^1$ is Y-4D, R is NCN, and $R^2$ is $CH_3$.

Table 3217. Compounds of formula I.44 wherein $R^1$ is Y-5A, R is NCN, and $R^2$ is $CH_3$.

Table 3218. Compounds of formula I.44 wherein $R^1$ is Y-5B, R is NCN, and $R^2$ is $CH_3$.

Table 3219. Compounds of formula I.44 wherein $R^1$ is Y-6A, R is NCN, and $R^2$ is $CH_3$.

Table 3220. Compounds of formula I.44 wherein $R^1$ is Y-6B, R is NCN, and $R^2$ is $CH_3$.

Table 3221. Compounds of formula I.44 wherein $R^1$ is Y-8A, R is NCN, and $R^2$ is $CH_3$.

Table 3222. Compounds of formula I.44 wherein $R^1$ is Y-8B, R is NCN, and $R^2$ is $CH_3$.

Table 3223. Compounds of formula I.44 wherein $R^1$ is Y-1A, R is NCN, and $R^2$ is c-$C_3H_5$.

Table 3224. Compounds of formula I.44 wherein $R^1$ is Y-1B, R is NCN, and $R^2$ is c-$C_3H_5$.

Table 3225. Compounds of formula I.44 wherein $R^1$ is Y-2A, R is NCN, and $R^2$ is c-$C_3H_5$.

Table 3226. Compounds of formula I.44 wherein $R^1$ is Y-2B, R is NCN, and $R^2$ is c-$C_3H_5$.

Table 3227. Compounds of formula I.44 wherein $R^1$ is Y-3A, R is NCN, and $R^2$ is c-$C_3H_5$.

Table 3228. Compounds of formula I.44 wherein $R^1$ is Y-3B, R is NCN, and $R^2$ is c-$C_3H_5$.

Table 3229. Compounds of formula I.44 wherein $R^1$ is Y-3C, R is NCN, and $R^2$ is c-$C_3H_5$.

Table 3230. Compounds of formula I.44 wherein $R^1$ is Y-3D, R is NCN, and $R^2$ is c-$C_3H_5$.

Table 3231. Compounds of formula I.44 wherein $R^1$ is Y-4A, R is NCN, and $R^2$ is c-$C_3H_5$.

Table 3232. Compounds of formula I.44 wherein $R^1$ is Y-4B, R is NCN, and $R^2$ is c-$C_3H_5$.

Table 3233. Compounds of formula I.44 wherein $R^1$ is Y-4C, R is NCN, and $R^2$ is c-$C_3H_5$.

Table 3234. Compounds of formula I.44 wherein $R^1$ is Y-4D, R is NCN, and $R^2$ is c-$C_3H_5$.

Table 3235. Compounds of formula I.44 wherein $R^1$ is Y-5A, R is NCN, and $R^2$ is c-$C_3H_5$.

Table 3236. Compounds of formula I.44 wherein $R^1$ is Y-5B, R is NCN, and $R^2$ is c-$C_3H_5$.

Table 3237. Compounds of formula I.44 wherein $R^1$ is Y-6A, R is NCN, and $R^2$ is c-$C_3H_5$.

Table 3238. Compounds of formula I.44 wherein $R^1$ is Y-6B, R is NCN, and $R^2$ is c-$C_3H_5$.

Table 3239. Compounds of formula I.44 wherein $R^1$ is Y-8A, R is NCN, and $R^2$ is c-$C_3H_5$.

Table 3240. Compounds of formula I.44 wherein $R^1$ is Y-8B, R is NCN, and $R^2$ is c-$C_3H_5$.

Table 3241. Compounds of formula I.45 wherein $R^1$ is Y-1A, R is NH, and $R^2$ is H.

Table 3242. Compounds of formula I.45 wherein $R^1$ is Y-1B, R is NH, and $R^2$ is H.

Table 3243. Compounds of formula I.45 wherein $R^1$ is Y-2A, R is NH, and $R^2$ is H.

Table 3244. Compounds of formula I.45 wherein $R^1$ is Y-2B, R is NH, and $R^2$ is H.

Table 3245. Compounds of formula I.45 wherein $R^1$ is Y-3A, R is NH, and $R^2$ is H.

Table 3246. Compounds of formula I.45 wherein $R^1$ is Y-3B, R is NH, and $R^2$ is H.

Table 3247. Compounds of formula I.45 wherein $R^1$ is Y-3C, R is NH, and $R^2$ is H.

Table 3248. Compounds of formula I.45 wherein $R^1$ is Y-3D, R is NH, and $R^2$ is H.

Table 3249. Compounds of formula I.45 wherein $R^1$ is Y-4A, R is NH, and $R^2$ is H.

Table 3250. Compounds of formula I.45 wherein $R^1$ is Y-4B, R is NH, and $R^2$ is H.

Table 3251. Compounds of formula I.45 wherein $R^1$ is Y-4C, R is NH, and $R^2$ is H.

Table 3252. Compounds of formula I.45 wherein $R^1$ is Y-4D, R is NH, and $R^2$ is H.

Table 3253. Compounds of formula I.45 wherein $R^1$ is Y-5A, R is NH, and $R^2$ is H.

Table 3254. Compounds of formula I.45 wherein $R^1$ is Y-5B, R is NH, and $R^2$ is H.

Table 3255. Compounds of formula I.45 wherein $R^1$ is Y-6A, R is NH, and $R^2$ is H.

Table 3256. Compounds of formula I.45 wherein $R^1$ is Y-6B, R is NH, and $R^2$ is H.

Table 3257. Compounds of formula I.45 wherein $R^1$ is Y-8A, R is NH, and $R^2$ is H.

Table 3258. Compounds of formula I.45 wherein $R^1$ is Y-8B, R is NH, and $R^2$ is H.

Table 3259. Compounds of formula I.45 wherein $R^1$ is Y-1A, R is NH, and $R^2$ is $CH_3$.

Table 3260. Compounds of formula I.45 wherein $R^1$ is Y-1B, R is NH, and $R^2$ is $CH_3$.

Table 3261. Compounds of formula I.45 wherein $R^1$ is Y-2A, R is NH, and $R^2$ is $CH_3$.

Table 3262. Compounds of formula I.45 wherein $R^1$ is Y-2B, R is NH, and $R^2$ is $CH_3$.

Table 3263. Compounds of formula I.45 wherein $R^1$ is Y-3A, R is NH, and $R^2$ is $CH_3$.

Table 3264. Compounds of formula I.45 wherein $R^1$ is Y-3B, R is NH, and $R^2$ is $CH_3$.

Table 3265. Compounds of formula I.45 wherein $R^1$ is Y-3C, R is NH, and $R^2$ is $CH_3$.

Table 3266. Compounds of formula I.45 wherein $R^1$ is Y-3D, R is NH, and $R^2$ is $CH_3$.

Table 3267. Compounds of formula I.45 wherein $R^1$ is Y-4A, R is NH, and $R^2$ is $CH_3$.

Table 3268. Compounds of formula I.45 wherein $R^1$ is Y-4B, R is NH, and $R^2$ is $CH_3$.

Table 3269. Compounds of formula I.45 wherein $R^1$ is Y-4C, R is NH, and $R^2$ is $CH_3$.

Table 3270. Compounds of formula I.45 wherein $R^1$ is Y-4D, R is NH, and $R^2$ is $CH_3$.

Table 3271. Compounds of formula I.45 wherein $R^1$ is Y-5A, R is NH, and $R^2$ is $CH_3$.

Table 3272. Compounds of formula I.45 wherein $R^1$ is Y-5B, R is NH, and $R^2$ is $CH_3$.

Table 3273. Compounds of formula I.45 wherein $R^1$ is Y-6A, R is NH, and $R^2$ is $CH_3$.

Table 3274. Compounds of formula I.45 wherein $R^1$ is Y-6B, R is NH, and $R^2$ is $CH_3$.

Table 3275. Compounds of formula I.45 wherein $R^1$ is Y-8A, R is NH, and $R^2$ is $CH_3$.

Table 3276. Compounds of formula I.45 wherein $R^1$ is Y-8B, R is NH, and $R^2$ is $CH_3$.

Table 3277. Compounds of formula I.45 wherein $R^1$ is Y-1A, R is NH, and $R^2$ is c-$C_3H_5$.

Table 3278. Compounds of formula I.45 wherein $R^1$ is Y-1B, R is NH, and $R^2$ is c-$C_3H_5$.

Table 3279. Compounds of formula I.45 wherein $R^1$ is Y-2A, R is NH, and $R^2$ is c-$C_3H_5$.

Table 3280. Compounds of formula I.45 wherein $R^1$ is Y-2B, R is NH, and $R^2$ is c-$C_3H_5$.

Table 3281. Compounds of formula I.45 wherein $R^1$ is Y-3A, R is NH, and $R^2$ is c-$C_3H_5$.

Table 3282. Compounds of formula I.45 wherein $R^1$ is Y-3B, R is NH, and $R^2$ is c-$C_3H_5$.

Table 3283. Compounds of formula I.45 wherein $R^1$ is Y-3C, R is NH, and $R^2$ is c-$C_3H_5$.

Table 3284. Compounds of formula I.45 wherein $R^1$ is Y-3D, R is NH, and $R^2$ is c-$C_3H_5$.

Table 3285. Compounds of formula I.45 wherein $R^1$ is Y-4A, R is NH, and $R^2$ is c-$C_3H_5$.

Table 3286. Compounds of formula I.45 wherein $R^1$ is Y-4B, R is NH, and $R^2$ is c-$C_3H_5$.

Table 3287. Compounds of formula I.45 wherein $R^1$ is Y-4C, R is NH, and $R^2$ is c-$C_3H_5$.

Table 3288. Compounds of formula I.45 wherein $R^1$ is Y-4D, R is NH, and $R^2$ is c-$C_3H_5$.

Table 3289. Compounds of formula I.45 wherein $R^1$ is Y-5A, R is NH, and $R^2$ is c-$C_3H_5$.

Table 3290. Compounds of formula I.45 wherein $R^1$ is Y-5B, R is NH, and $R^2$ is c-$C_3H_5$.

Table 3291. Compounds of formula I.45 wherein $R^1$ is Y-6A, R is NH, and $R^2$ is c-$C_3H_5$.

Table 3292. Compounds of formula I.45 wherein $R^1$ is Y-6B, R is NH, and $R^2$ is c-$C_3H_5$.

Table 3293. Compounds of formula I.45 wherein $R^1$ is Y-8A, R is NH, and $R^2$ is c-$C_3H_5$.

Table 3294. Compounds of formula I.45 wherein $R^1$ is Y-8B, R is NH, and $R^2$ is c-$C_3H_5$.

Table 3295. Compounds of formula I.45 wherein $R^1$ is Y-1A, R is $NCH_3$ and $R^2$ is H.

Table 3296. Compounds of formula I.45 wherein $R^1$ is Y-1B, R is $NCH_3$ and $R^2$ is H.

Table 3297. Compounds of formula I.45 wherein $R^1$ is Y-2A, R is $NCH_3$ and $R^2$ is H.

Table 3298. Compounds of formula I.45 wherein $R^1$ is Y-2B, R is $NCH_3$ and $R^2$ is H.

Table 3299. Compounds of formula I.45 wherein $R^1$ is Y-3A, R is $NCH_3$ and $R^2$ is H.

Table 3300. Compounds of formula I.45 wherein $R^1$ is Y-3B, R is $NCH_3$ and $R^2$ is H.

Table 3301. Compounds of formula I.45 wherein $R^1$ is Y-3C, R is $NCH_3$ and $R^2$ is H.

Table 3302. Compounds of formula I.45 wherein $R^1$ is Y-3D, R is $NCH_3$ and $R^2$ is H.

Table 3303. Compounds of formula I.45 wherein $R^1$ is Y-4A, R is $NCH_3$ and $R^2$ is H.

Table 3304. Compounds of formula I.45 wherein $R^1$ is Y-4B, R is $NCH_3$ and $R^2$ is H.

Table 3305. Compounds of formula I.45 wherein $R^1$ is Y-4C, R is $NCH_3$ and $R^2$ is H.

Table 3306. Compounds of formula I.45 wherein $R^1$ is Y-4D, R is $NCH_3$ and $R^2$ is H.

Table 3307. Compounds of formula I.45 wherein $R^1$ is Y-5A, R is $NCH_3$ and $R^2$ is H.

Table 3308. Compounds of formula I.45 wherein $R^1$ is Y-5B, R is $NCH_3$ and $R^2$ is H.

Table 3309. Compounds of formula I.45 wherein $R^1$ is Y-6A, R is $NCH_3$ and $R^2$ is H.

Table 3310. Compounds of formula I.45 wherein $R^1$ is Y-6B, R is $NCH_3$ and $R^2$ is H.

Table 3311. Compounds of formula I.45 wherein $R^1$ is Y-8A, R is $NCH_3$ and $R^2$ is H.

Table 3312. Compounds of formula I.45 wherein $R^1$ is Y-8B, R is $NCH_3$ and $R^2$ is H.

Table 3313. Compounds of formula I.45 wherein $R^1$ is Y-1A, R is $NCH_3$ and $R^2$ is $CH_3$.

Table 3314. Compounds of formula I.45 wherein $R^1$ is Y-1B, R is $NCH_3$ and $R^2$ is $CH_3$.

Table 3315. Compounds of formula I.45 wherein $R^1$ is Y-2A, R is $NCH_3$ and $R^2$ is $CH_3$.

Table 3316. Compounds of formula I.45 wherein $R^1$ is Y-2B, R is $NCH_3$ and $R^2$ is $CH_3$.

Table 3317. Compounds of formula I.45 wherein $R^1$ is Y-3A, R is $NCH_3$ and $R^2$ is $CH_3$.

Table 3318. Compounds of formula I.45 wherein $R^1$ is Y-3B, R is $NCH_3$ and $R^2$ is $CH_3$.

Table 3319. Compounds of formula I.45 wherein $R^1$ is Y-3C, R is $NCH_3$ and $R^2$ is $CH_3$.

Table 3320. Compounds of formula I.45 wherein $R^1$ is Y-3D, R is $NCH_3$ and $R^2$ is $CH_3$.

Table 3321. Compounds of formula I.45 wherein $R^1$ is Y-4A, R is $NCH_3$ and $R^2$ is $CH_3$.

Table 3322. Compounds of formula I.45 wherein $R^1$ is Y-4B, R is $NCH_3$ and $R^2$ is $CH_3$.

Table 3323. Compounds of formula I.45 wherein $R^1$ is Y-4C, R is $NCH_3$ and $R^2$ is $CH_3$.

Table 3324. Compounds of formula I.45 wherein $R^1$ is Y-4D, R is $NCH_3$ and $R^2$ is $CH_3$.

Table 3325. Compounds of formula I.45 wherein $R^1$ is Y-5A, R is $NCH_3$ and $R^2$ is $CH_3$.

Table 3326. Compounds of formula I.45 wherein $R^1$ is Y-5B, R is $NCH_3$ and $R^2$ is $CH_3$.

Table 3327. Compounds of formula I.45 wherein $R^1$ is Y-6A, R is $NCH_3$ and $R^2$ is $CH_3$.

Table 3328. Compounds of formula I.45 wherein $R^1$ is Y-6B, R is $NCH_3$ and $R^2$ is $CH_3$.

Table 3329. Compounds of formula I.45 wherein $R^1$ is Y-8A, R is $NCH_3$ and $R^2$ is $CH_3$.

Table 3330. Compounds of formula I.45 wherein $R^1$ is Y-8B, R is $NCH_3$ and $R^2$ is $CH_3$.

Table 3331. Compounds of formula I.45 wherein $R^1$ is Y-1A, R is $NCH_3$ and $R^2$ is c-$C_3H_5$.

Table 3332. Compounds of formula I.45 wherein $R^1$ is Y-1B, R is $NCH_3$ and $R^2$ is c-$C_3H_5$.

Table 3333. Compounds of formula I.45 wherein $R^1$ is Y-2A, R is $NCH_3$ and $R^2$ is c-$C_3H_5$.

Table 3334. Compounds of formula I.45 wherein $R^1$ is Y-2B, R is $NCH_3$ and $R^2$ is c-$C_3H_5$.

Table 3335. Compounds of formula I.45 wherein $R^1$ is Y-3A, R is $NCH_3$ and $R^2$ is c-$C_3H_5$.

Table 3336. Compounds of formula I.45 wherein $R^1$ is Y-3B, R is $NCH_3$ and $R^2$ is c-$C_3H_5$.

Table 3337. Compounds of formula I.45 wherein $R^1$ is Y-3C, R is $NCH_3$ and $R^2$ is c-$C_3H_5$.

Table 3338. Compounds of formula I.45 wherein $R^1$ is Y-3D, R is $NCH_3$ and $R^2$ is c-$C_3H_5$.

Table 3339. Compounds of formula I.45 wherein $R^1$ is Y-4A, R is $NCH_3$ and $R^2$ is c-$C_3H_5$.

Table 3340. Compounds of formula I.45 wherein $R^1$ is Y-4B, R is $NCH_3$ and $R^2$ is c-$C_3H_5$.

Table 3341. Compounds of formula I.45 wherein $R^1$ is Y-4C, R is $NCH_3$ and $R^2$ is c-$C_3H_5$.

Table 3342. Compounds of formula I.45 wherein $R^1$ is Y-4D, R is $NCH_3$ and $R^2$ is c-$C_3H_5$.

Table 3343. Compounds of formula I.45 wherein $R^1$ is Y-5A, R is $NCH_3$ and $R^2$ is c-$C_3H_5$.

Table 3344. Compounds of formula I.45 wherein $R^1$ is Y-5B, R is $NCH_3$ and $R^2$ is c-$C_3H_5$.

Table 3345. Compounds of formula I.45 wherein $R^1$ is Y-6A, R is $NCH_3$ and $R^2$ is c-$C_3H_5$.

Table 3346. Compounds of formula I.45 wherein $R^1$ is Y-6B, R is $NCH_3$ and $R^2$ is c-$C_3H_5$.

Table 3347. Compounds of formula I.45 wherein $R^1$ is Y-8A, R is $NCH_3$ and $R^2$ is c-$C_3H_5$.

Table 3348. Compounds of formula I.45 wherein $R^1$ is Y-8B, R is $NCH_3$ and $R^2$ is c-$C_3H_5$.

Table 3349. Compounds of formula I.45 wherein $R^1$ is Y-1A, R is NCN, and $R^2$ is H.

Table 3350. Compounds of formula I.45 wherein $R^1$ is Y-1B, R is NCN, and $R^2$ is H.

Table 3351. Compounds of formula I.45 wherein $R^1$ is Y-2A, R is NCN, and $R^2$ is H.

Table 3352. Compounds of formula I.45 wherein $R^1$ is Y-2B, R is NCN, and $R^2$ is H.

Table 3353. Compounds of formula I.45 wherein $R^1$ is Y-3A, R is NCN, and $R^2$ is H.

Table 3354. Compounds of formula I.45 wherein $R^1$ is Y-3B, R is NCN, and $R^2$ is H.

Table 3355. Compounds of formula I.45 wherein $R^1$ is Y-3C, R is NCN, and $R^2$ is H.

Table 3356. Compounds of formula I.45 wherein $R^1$ is Y-3D, R is NCN, and $R^2$ is H.

Table 3357. Compounds of formula I.45 wherein $R^1$ is Y-4A, R is NCN, and $R^2$ is H.

Table 3358. Compounds of formula I.45 wherein $R^1$ is Y-4B, R is NCN, and $R^2$ is H.

Table 3359. Compounds of formula I.45 wherein $R^1$ is Y-4C, R is NCN, and $R^2$ is H.

Table 3360. Compounds of formula I.45 wherein $R^1$ is Y-4D, R is NCN, and $R^2$ is H.

Table 3361. Compounds of formula I.45 wherein $R^1$ is Y-5A, R is NCN, and $R^2$ is H.

Table 3362. Compounds of formula I.45 wherein $R^1$ is Y-5B, R is NCN, and $R^2$ is H.

Table 3363. Compounds of formula I.45 wherein $R^1$ is Y-6A, R is NCN, and $R^2$ is H.

Table 3364. Compounds of formula I.45 wherein $R^1$ is Y-6B, R is NCN, and $R^2$ is H.

Table 3365. Compounds of formula I.45 wherein $R^1$ is Y-8A, R is NCN, and $R^2$ is H.

Table 3366. Compounds of formula I.45 wherein $R^1$ is Y-8B, R is NCN, and $R^2$ is H.

Table 3367. Compounds of formula I.45 wherein $R^1$ is Y-1A, R is NCN, and $R^2$ is $CH_3$.

Table 3368. Compounds of formula I.45 wherein $R^1$ is Y-1B, R is NCN, and $R^2$ is $CH_3$.

Table 3369. Compounds of formula I.45 wherein $R^1$ is Y-2A, R is NCN, and $R^2$ is $CH_3$.

Table 3370. Compounds of formula I.45 wherein $R^1$ is Y-2B, R is NCN, and $R^2$ is $CH_3$.

Table 3371. Compounds of formula I.45 wherein $R^1$ is Y-3A, R is NCN, and $R^2$ is $CH_3$.

Table 3372. Compounds of formula I.45 wherein $R^1$ is Y-3B, R is NCN, and $R^2$ is $CH_3$.

Table 3373. Compounds of formula I.45 wherein $R^1$ is Y-3C, R is NCN, and $R^2$ is $CH_3$.

Table 3374. Compounds of formula I.45 wherein $R^1$ is Y-3D, R is NCN, and $R^2$ is $CH_3$.

Table 3375. Compounds of formula I.45 wherein $R^1$ is Y-4A, R is NCN, and $R^2$ is $CH_3$.

Table 3376. Compounds of formula I.45 wherein $R^1$ is Y-4B, R is NCN, and $R^2$ is $CH_3$.

Table 3377. Compounds of formula I.45 wherein $R^1$ is Y-4C, R is NCN, and $R^2$ is $CH_3$.

Table 3378. Compounds of formula I.45 wherein $R^1$ is Y-4D, R is NCN, and $R^2$ is $CH_3$.

Table 3379. Compounds of formula I.45 wherein $R^1$ is Y-5A, R is NCN, and $R^2$ is $CH_3$.

Table 3380. Compounds of formula I.45 wherein $R^1$ is Y-5B, R is NCN, and $R^2$ is $CH_3$.

Table 3381. Compounds of formula I.45 wherein $R^1$ is Y-6A, R is NCN, and $R^2$ is $CH_3$.

Table 3382. Compounds of formula I.45 wherein $R^1$ is Y-6B, R is NCN, and $R^2$ is $CH_3$.

Table 3383. Compounds of formula I.45 wherein $R^1$ is Y-8A, R is NCN, and $R^2$ is $CH_3$.

Table 3384. Compounds of formula I.45 wherein $R^1$ is Y-8B, R is NCN, and $R^2$ is $CH_3$.

Table 3385. Compounds of formula I.45 wherein $R^1$ is Y-1A, R is NCN, and $R^2$ is c-$C_3H_5$.

Table 3386. Compounds of formula I.45 wherein $R^1$ is Y-1B, R is NCN, and $R^2$ is c-$C_3H_5$.

Table 3387. Compounds of formula I.45 wherein $R^1$ is Y-2A, R is NCN, and $R^2$ is c-$C_3H_5$.

Table 3388. Compounds of formula I.45 wherein $R^1$ is Y-2B, R is NCN, and $R^2$ is c-$C_3H_5$.

Table 3389. Compounds of formula I.45 wherein $R^1$ is Y-3A, R is NCN, and $R^2$ is c-$C_3H_5$.

Table 3390. Compounds of formula I.45 wherein $R^1$ is Y-3B, R is NCN, and $R^2$ is c-$C_3H_5$.

Table 3391. Compounds of formula I.45 wherein $R^1$ is Y-3C, R is NCN, and $R^2$ is c-$C_3H_5$.

Table 3392. Compounds of formula I.45 wherein $R^1$ is Y-3D, R is NCN, and $R^2$ is c-$C_3H_5$.

Table 3393. Compounds of formula I.45 wherein $R^1$ is Y-4A, R is NCN, and $R^2$ is c-$C_3H_5$.

Table 3394. Compounds of formula I.45 wherein $R^1$ is Y-4B, R is NCN, and $R^2$ is c-$C_3H_5$.

Table 3395. Compounds of formula I.45 wherein $R^1$ is Y-4C, R is NCN, and $R^2$ is c-$C_3H_5$.

Table 3396. Compounds of formula I.45 wherein $R^1$ is Y-4D, R is NCN, and $R^2$ is c-$C_3H_5$.

Table 3397. Compounds of formula I.45 wherein $R^1$ is Y-5A, R is NCN, and $R^2$ is c-$C_3H_5$.

Table 3398. Compounds of formula I.45 wherein $R^1$ is Y-5B, R is NCN, and $R^2$ is c-$C_3H_5$.

Table 3399. Compounds of formula I.45 wherein $R^1$ is Y-6A, R is NCN, and $R^2$ is c-$C_3H_5$.

Table 3400. Compounds of formula I.45 wherein $R^1$ is Y-6B, R is NCN, and $R^2$ is c-$C_3H_5$.

Table 3401. Compounds of formula I.45 wherein $R^1$ is Y-8A, R is NCN, and $R^2$ is c-$C_3H_5$.

Table 3402. Compounds of formula I.45 wherein $R^1$ is Y-8B, R is NCN, and $R^2$ is c-$C_3H_5$.

Table 3403. Compounds of formula I.46 wherein $R^1$ is Y-1A, R is NH, and $R^2$ is H.

Table 3404. Compounds of formula I.46 wherein $R^1$ is Y-1B, R is NH, and $R^2$ is H.

Table 3405. Compounds of formula I.46 wherein $R^1$ is Y-2A, R is NH, and $R^2$ is H.

Table 3406. Compounds of formula I.46 wherein $R^1$ is Y-2B, R is NH, and $R^2$ is H.

Table 3407. Compounds of formula I.46 wherein $R^1$ is Y-3A, R is NH, and $R^2$ is H.

Table 3408. Compounds of formula I.46 wherein $R^1$ is Y-3B, R is NH, and $R^2$ is H.

Table 3409. Compounds of formula I.46 wherein $R^1$ is Y-3C, R is NH, and $R^2$ is H.

Table 3410. Compounds of formula I.46 wherein $R^1$ is Y-3D, R is NH, and $R^2$ is H.

Table 3411. Compounds of formula I.46 wherein $R^1$ is Y-4A, R is NH, and $R^2$ is H.

Table 3412. Compounds of formula I.46 wherein $R^1$ is Y-4B, R is NH, and $R^2$ is H.

Table 3413. Compounds of formula I.46 wherein $R^1$ is Y-4C, R is NH, and $R^2$ is H.

Table 3414. Compounds of formula I.46 wherein $R^1$ is Y-4D, R is NH, and $R^2$ is H.

Table 3415. Compounds of formula I.46 wherein $R^1$ is Y-5A, R is NH, and $R^2$ is H.

Table 3416. Compounds of formula I.46 wherein $R^1$ is Y-5B, R is NH, and $R^2$ is H.

Table 3417. Compounds of formula I.46 wherein $R^1$ is Y-6A, R is NH, and $R^2$ is H.

Table 3418. Compounds of formula I.46 wherein $R^1$ is Y-6B, R is NH, and $R^2$ is H.

Table 3419. Compounds of formula I.46 wherein $R^1$ is Y-8A, R is NH, and $R^2$ is H.

Table 3420. Compounds of formula I.46 wherein $R^1$ is Y-8B, R is NH, and $R^2$ is H.

Table 3421. Compounds of formula I.46 wherein $R^1$ is Y-1A, R is NH, and $R^2$ is $CH_3$.

Table 3422. Compounds of formula I.46 wherein $R^1$ is Y-1B, R is NH, and $R^2$ is $CH_3$.

Table 3423. Compounds of formula I.46 wherein $R^1$ is Y-2A, R is NH, and $R^2$ is $CH_3$.

Table 3424. Compounds of formula I.46 wherein $R^1$ is Y-2B, R is NH, and $R^2$ is $CH_3$.

Table 3425. Compounds of formula I.46 wherein $R^1$ is Y-3A, R is NH, and $R^2$ is $CH_3$.

Table 3426. Compounds of formula I.46 wherein $R^1$ is Y-3B, R is NH, and $R^2$ is $CH_3$.

Table 3427. Compounds of formula I.46 wherein $R^1$ is Y-3C, R is NH, and $R^2$ is $CH_3$.

Table 3428. Compounds of formula I.46 wherein $R^1$ is Y-3D, R is NH, and $R^2$ is $CH_3$.

Table 3429. Compounds of formula I.46 wherein $R^1$ is Y-4A, R is NH, and $R^2$ is $CH_3$.

Table 3430. Compounds of formula I.46 wherein $R^1$ is Y-4B, R is NH, and $R^2$ is $CH_3$.

Table 3431. Compounds of formula I.46 wherein $R^1$ is Y-4C, R is NH, and $R^2$ is $CH_3$.

Table 3432. Compounds of formula I.46 wherein $R^1$ is Y-4D, R is NH, and $R^2$ is $CH_3$.

Table 3433. Compounds of formula I.46 wherein $R^1$ is Y-5A, R is NH, and $R^2$ is $CH_3$.

Table 3434. Compounds of formula I.46 wherein $R^1$ is Y-5B, R is NH, and $R^2$ is $CH_3$.

Table 3435. Compounds of formula I.46 wherein $R^1$ is Y-6A, R is NH, and $R^2$ is $CH_3$.

Table 3436. Compounds of formula I.46 wherein $R^1$ is Y-6B, R is NH, and $R^2$ is $CH_3$.

Table 3437. Compounds of formula I.46 wherein $R^1$ is Y-8A, R is NH, and $R^2$ is $CH_3$.

Table 3438. Compounds of formula I.46 wherein $R^1$ is Y-8B, R is NH, and $R^2$ is $CH_3$.

Table 3439. Compounds of formula I.46 wherein $R^1$ is Y-1A, R is NH, and $R^2$ is c-$C_3H_5$.

Table 3440. Compounds of formula I.46 wherein $R^1$ is Y-1B, R is NH, and $R^2$ is c-$C_3H_5$.

Table 3441. Compounds of formula I.46 wherein $R^1$ is Y-2A, R is NH, and $R^2$ is c-$C_3H_5$.

Table 3442. Compounds of formula I.46 wherein $R^1$ is Y-2B, R is NH, and $R^2$ is c-$C_3H_5$.

Table 3443. Compounds of formula I.46 wherein $R^1$ is Y-3A, R is NH, and $R^2$ is c-$C_3H_5$.

Table 3444. Compounds of formula I.46 wherein $R^1$ is Y-3B, R is NH, and $R^2$ is c-$C_3H_5$.

Table 3445. Compounds of formula I.46 wherein $R^1$ is Y-3C, R is NH, and $R^2$ is c-$C_3H_5$.

Table 3446. Compounds of formula I.46 wherein $R^1$ is Y-3D, R is NH, and $R^2$ is c-$C_3H_5$.

Table 3447. Compounds of formula I.46 wherein $R^1$ is Y-4A, R is NH, and $R^2$ is c-$C_3H_5$.

Table 3448. Compounds of formula I.46 wherein $R^1$ is Y-4B, R is NH, and $R^2$ is c-$C_3H_5$.

Table 3449. Compounds of formula I.46 wherein $R^1$ is Y-4C, R is NH, and $R^2$ is c-$C_3H_5$.

Table 3450. Compounds of formula I.46 wherein $R^1$ is Y-4D, R is NH, and $R^2$ is c-$C_3H_5$.

Table 3451. Compounds of formula I.46 wherein $R^1$ is Y-5A, R is NH, and $R^2$ is c-$C_3H_5$.

Table 3452. Compounds of formula I.46 wherein $R^1$ is Y-5B, R is NH, and $R^2$ is c-$C_3H_5$.

Table 3453. Compounds of formula I.46 wherein $R^1$ is Y-6A, R is NH, and $R^2$ is c-$C_3H_5$.

Table 3454. Compounds of formula I.46 wherein $R^1$ is Y-6B, R is NH, and $R^2$ is c-$C_3H_5$.

Table 3455. Compounds of formula I.46 wherein $R^1$ is Y-8A, R is NH, and $R^2$ is c-$C_3H_5$.

Table 3456. Compounds of formula I.46 wherein $R^1$ is Y-8B, R is NH, and $R^2$ is c-$C_3H_5$.

Table 3457. Compounds of formula I.46 wherein $R^1$ is Y-1A, R is $NCH_3$ and $R^2$ is H.

Table 3458. Compounds of formula I.46 wherein $R^1$ is Y-1B, R is $NCH_3$ and $R^2$ is H.

Table 3459. Compounds of formula I.46 wherein $R^1$ is Y-2A, R is $NCH_3$ and $R^2$ is H.

Table 3460. Compounds of formula I.46 wherein $R^1$ is Y-2B, R is $NCH_3$ and $R^2$ is H.

Table 3461. Compounds of formula I.46 wherein $R^1$ is Y-3A, R is $NCH_3$ and $R^2$ is H.

Table 3462. Compounds of formula I.46 wherein $R^1$ is Y-3B, R is $NCH_3$ and $R^2$ is H.

Table 3463. Compounds of formula I.46 wherein $R^1$ is Y-3C, R is $NCH_3$ and $R^2$ is H.

Table 3464. Compounds of formula I.46 wherein $R^1$ is Y-3D, R is $NCH_3$ and $R^2$ is H.

Table 3465. Compounds of formula I.46 wherein $R^1$ is Y-4A, R is $NCH_3$ and $R^2$ is H.

Table 3466. Compounds of formula I.46 wherein $R^1$ is Y-4B, R is $NCH_3$ and $R^2$ is H.

Table 3467. Compounds of formula I.46 wherein $R^1$ is Y-4C, R is $NCH_3$ and $R^2$ is H.

Table 3468. Compounds of formula I.46 wherein $R^1$ is Y-4D, R is $NCH_3$ and $R^2$ is H.

Table 3469. Compounds of formula I.46 wherein $R^1$ is Y-5A, R is $NCH_3$ and $R^2$ is H.

Table 3470. Compounds of formula I.46 wherein $R^1$ is Y-5B, R is $NCH_3$ and $R^2$ is H.

Table 3471. Compounds of formula I.46 wherein $R^1$ is Y-6A, R is $NCH_3$ and $R^2$ is H.

Table 3472. Compounds of formula I.46 wherein $R^1$ is Y-6B, R is $NCH_3$ and $R^2$ is H.

Table 3473. Compounds of formula I.46 wherein $R^1$ is Y-8A, R is $NCH_3$ and $R^2$ is H.

Table 3474. Compounds of formula I.46 wherein $R^1$ is Y-8B, R is $NCH_3$ and $R^2$ is H.

Table 3475. Compounds of formula I.46 wherein $R^1$ is Y-1A, R is $NCH_3$ and $R^2$ is $CH_3$.

Table 3476. Compounds of formula I.46 wherein $R^1$ is Y-1B, R is $NCH_3$ and $R^2$ is $CH_3$.

Table 3477. Compounds of formula I.46 wherein $R^1$ is Y-2A, R is $NCH_3$ and $R^2$ is $CH_3$.

Table 3478. Compounds of formula I.46 wherein $R^1$ is Y-2B, R is $NCH_3$ and $R^2$ is $CH_3$.

Table 3479. Compounds of formula I.46 wherein $R^1$ is Y-3A, R is $NCH_3$ and $R^2$ is $CH_3$.

Table 3480. Compounds of formula I.46 wherein $R^1$ is Y-3B, R is $NCH_3$ and $R^2$ is $CH_3$.

Table 3481. Compounds of formula I.46 wherein $R^1$ is Y-3C, R is $NCH_3$ and $R^2$ is $CH_3$.

Table 3482. Compounds of formula I.46 wherein $R^1$ is Y-3D, R is $NCH_3$ and $R^2$ is $CH_3$.

Table 3483. Compounds of formula I.46 wherein $R^1$ is Y-4A, R is $NCH_3$ and $R^2$ is $CH_3$.

Table 3484. Compounds of formula I.46 wherein $R^1$ is Y-4B, R is $NCH_3$ and $R^2$ is $CH_3$.

Table 3485. Compounds of formula I.46 wherein $R^1$ is Y-4C, R is $NCH_3$ and $R^2$ is $CH_3$.

Table 3486. Compounds of formula I.46 wherein $R^1$ is Y-4D, R is $NCH_3$ and $R^2$ is $CH_3$.

Table 3487. Compounds of formula I.46 wherein $R^1$ is Y-5A, R is $NCH_3$ and $R^2$ is $CH_3$.

Table 3488. Compounds of formula I.46 wherein $R^1$ is Y-5B, R is $NCH_3$ and $R^2$ is $CH_3$.

Table 3489. Compounds of formula I.46 wherein $R^1$ is Y-6A, R is $NCH_3$ and $R^2$ is $CH_3$.

Table 3490. Compounds of formula I.46 wherein $R^1$ is Y-6B, R is $NCH_3$ and $R^2$ is $CH_3$.

Table 3491. Compounds of formula I.46 wherein $R^1$ is Y-8A, R is $NCH_3$ and $R^2$ is $CH_3$.

Table 3492. Compounds of formula I.46 wherein $R^1$ is Y-8B, R is $NCH_3$ and $R^2$ is $CH_3$.

Table 3493. Compounds of formula I.46 wherein $R^1$ is Y-1A, R is $NCH_3$ and $R^2$ is c-$C_3H_5$.

Table 3494. Compounds of formula I.46 wherein $R^1$ is Y-1B, R is $NCH_3$ and $R^2$ is c-$C_3H_5$.

Table 3495. Compounds of formula I.46 wherein $R^1$ is Y-2A, R is $NCH_3$ and $R^2$ is c-$C_3H_5$.

Table 3496. Compounds of formula I.46 wherein $R^1$ is Y-2B, R is $NCH_3$ and $R^2$ is c-$C_3H_5$.

Table 3497. Compounds of formula I.46 wherein $R^1$ is Y-3A, R is $NCH_3$ and $R^2$ is c-$C_3H_5$.

Table 3498. Compounds of formula I.46 wherein $R^1$ is Y-3B, R is $NCH_3$ and $R^2$ is c-$C_3H_5$.

Table 3499. Compounds of formula I.46 wherein $R^1$ is Y-3C, R is $NCH_3$ and $R^2$ is c-$C_3H_5$.

Table 3500. Compounds of formula I.46 wherein $R^1$ is Y-3D, R is $NCH_3$ and $R^2$ is c-$C_3H_5$.

Table 3501. Compounds of formula I.46 wherein $R^1$ is Y-4A, R is $NCH_3$ and $R^2$ is c-$C_3H_5$.

Table 3502. Compounds of formula I.46 wherein $R^1$ is Y-4B, R is $NCH_3$ and $R^2$ is c-$C_3H_5$.

Table 3503. Compounds of formula I.46 wherein $R^1$ is Y-4C, R is $NCH_3$ and $R^2$ is c-$C_3H_5$.

Table 3504. Compounds of formula I.46 wherein $R^1$ is Y-4D, R is $NCH_3$ and $R^2$ is c-$C_3H_5$.

Table 3505. Compounds of formula I.46 wherein $R^1$ is Y-5A, R is $NCH_3$ and $R^2$ is c-$C_3H_5$.

Table 3506. Compounds of formula I.46 wherein $R^1$ is Y-5B, R is $NCH_3$ and $R^2$ is c-$C_3H_5$.

Table 3507. Compounds of formula I.46 wherein $R^1$ is Y-6A, R is $NCH_3$ and $R^2$ is c-$C_3H_5$.

Table 3508. Compounds of formula I.46 wherein $R^1$ is Y-6B, R is $NCH_3$ and $R^2$ is c-$C_3H_5$.

Table 3509. Compounds of formula I.46 wherein $R^1$ is Y-8A, R is $NCH_3$ and $R^2$ is c-$C_3H_5$.

Table 3510. Compounds of formula I.46 wherein $R^1$ is Y-8B, R is $NCH_3$ and $R^2$ is c-$C_3H_5$.

Table 3511. Compounds of formula I.46 wherein $R^1$ is Y-1A, R is NCN, and $R^2$ is H.

Table 3512. Compounds of formula I.46 wherein $R^1$ is Y-1B, R is NCN, and $R^2$ is H.

Table 3513. Compounds of formula I.46 wherein $R^1$ is Y-2A, R is NCN, and $R^2$ is H.

Table 3514. Compounds of formula I.46 wherein $R^1$ is Y-2B, R is NCN, and $R^2$ is H.

Table 3515. Compounds of formula I.46 wherein $R^1$ is Y-3A, R is NCN, and $R^2$ is H.

Table 3516. Compounds of formula I.46 wherein $R^1$ is Y-3B, R is NCN, and $R^2$ is H.

Table 3517. Compounds of formula I.46 wherein $R^1$ is Y-3C, R is NCN, and $R^2$ is H.

Table 3518. Compounds of formula I.46 wherein $R^1$ is Y-3D, R is NCN, and $R^2$ is H.

Table 3519. Compounds of formula I.46 wherein $R^1$ is Y-4A, R is NCN, and $R^2$ is H.

Table 3520. Compounds of formula I.46 wherein $R^1$ is Y-4B, R is NCN, and $R^2$ is H.

Table 3521. Compounds of formula I.46 wherein $R^1$ is Y-4C, R is NCN, and $R^2$ is H.

Table 3522. Compounds of formula I.46 wherein $R^1$ is Y-4D, R is NCN, and $R^2$ is H.

Table 3523. Compounds of formula I.46 wherein $R^1$ is Y-5A, R is NCN, and $R^2$ is H.

Table 3524. Compounds of formula I.46 wherein $R^1$ is Y-5B, R is NCN, and $R^2$ is H.

Table 3525. Compounds of formula I.46 wherein $R^1$ is Y-6A, R is NCN, and $R^2$ is H.

Table 3526. Compounds of formula I.46 wherein $R^1$ is Y-6B, R is NCN, and $R^2$ is H.

Table 3527. Compounds of formula I.46 wherein $R^1$ is Y-8A, R is NCN, and $R^2$ is H.
Table 3528. Compounds of formula I.46 wherein $R^1$ is Y-8B, R is NCN, and $R^2$ is H.
Table 3529. Compounds of formula I.46 wherein $R^1$ is Y-1A, R is NCN, and $R^2$ is $CH_3$.
Table 3530. Compounds of formula I.46 wherein $R^1$ is Y-1B, R is NCN, and $R^2$ is $CH_3$.
Table 3531. Compounds of formula I.46 wherein $R^1$ is Y-2A, R is NCN, and $R^2$ is $CH_3$.
Table 3532. Compounds of formula I.46 wherein $R^1$ is Y-2B, R is NCN, and $R^2$ is $CH_3$.
Table 3533. Compounds of formula I.46 wherein $R^1$ is Y-3A, R is NCN, and $R^2$ is $CH_3$.
Table 3534. Compounds of formula I.46 wherein $R^1$ is Y-3B, R is NCN, and $R^2$ is $CH_3$.
Table 3535. Compounds of formula I.46 wherein $R^1$ is Y-3C, R is NCN, and $R^2$ is $CH_3$.
Table 3536. Compounds of formula I.46 wherein $R^1$ is Y-3D, R is NCN, and $R^2$ is $CH_3$.
Table 3537. Compounds of formula I.46 wherein $R^1$ is Y-4A, R is NCN, and $R^2$ is $CH_3$.
Table 3538. Compounds of formula I.46 wherein $R^1$ is Y-4B, R is NCN, and $R^2$ is $CH_3$.
Table 3539. Compounds of formula I.46 wherein $R^1$ is Y-4C, R is NCN, and $R^2$ is $CH_3$.
Table 3540. Compounds of formula I.46 wherein $R^1$ is Y-4D, R is NCN, and $R^2$ is $CH_3$.
Table 3541. Compounds of formula I.46 wherein $R^1$ is Y-5A, R is NCN, and $R^2$ is $CH_3$.
Table 3542. Compounds of formula I.46 wherein $R^1$ is Y-5B, R is NCN, and $R^2$ is $CH_3$.
Table 3543. Compounds of formula I.46 wherein $R^1$ is Y-6A, R is NCN, and $R^2$ is $CH_3$.
Table 3544. Compounds of formula I.46 wherein $R^1$ is Y-6B, R is NCN, and $R^2$ is $CH_3$.
Table 3545. Compounds of formula I.46 wherein $R^1$ is Y-8A, R is NCN, and $R^2$ is $CH_3$.
Table 3546. Compounds of formula I.46 wherein $R^1$ is Y-8B, R is NCN, and $R^2$ is $CH_3$.
Table 3547. Compounds of formula I.46 wherein $R^1$ is Y-1A, R is NCN, and $R^2$ is c-$C_3H_5$.
Table 3548. Compounds of formula I.46 wherein $R^1$ is Y-1B, R is NCN, and $R^2$ is c-$C_3H_5$.
Table 3549. Compounds of formula I.46 wherein $R^1$ is Y-2A, R is NCN, and $R^2$ is c-$C_3H_5$.
Table 3550. Compounds of formula I.46 wherein $R^1$ is Y-2B, R is NCN, and $R^2$ is c-$C_3H_5$.
Table 3551. Compounds of formula I.46 wherein $R^1$ is Y-3A, R is NCN, and $R^2$ is c-$C_3H_5$.
Table 3552. Compounds of formula I.46 wherein $R^1$ is Y-3B, R is NCN, and $R^2$ is c-$C_3H_5$.
Table 3553. Compounds of formula I.46 wherein $R^1$ is Y-3C, R is NCN, and $R^2$ is c-$C_3H_5$.
Table 3554. Compounds of formula I.46 wherein $R^1$ is Y-3D, R is NCN, and $R^2$ is c-$C_3H_5$.
Table 3555. Compounds of formula I.46 wherein $R^1$ is Y-4A, R is NCN, and $R^2$ is c-$C_3H_5$.
Table 3556. Compounds of formula I.46 wherein $R^1$ is Y-4B, R is NCN, and $R^2$ is c-$C_3H_5$.
Table 3557. Compounds of formula I.46 wherein $R^1$ is Y-4C, R is NCN, and $R^2$ is c-$C_3H_5$.
Table 3558. Compounds of formula I.46 wherein $R^1$ is Y-4D, R is NCN, and $R^2$ is c-$C_3H_5$.
Table 3559. Compounds of formula I.46 wherein $R^1$ is Y-5A, R is NCN, and $R^2$ is c-$C_3H_5$.
Table 3560. Compounds of formula I.46 wherein $R^1$ is Y-5B, R is NCN, and $R^2$ is c-$C_3H_5$.
Table 3561. Compounds of formula I.46 wherein $R^1$ is Y-6A, R is NCN, and $R^2$ is c-$C_3H_5$.
Table 3562. Compounds of formula I.46 wherein $R^1$ is Y-6B, R is NCN, and $R^2$ is c-$C_3H_5$.
Table 3563. Compounds of formula I.46 wherein $R^1$ is Y-8A, R is NCN, and $R^2$ is c-$C_3H_5$.
Table 3564. Compounds of formula I.46 wherein $R^1$ is Y-8B, R is NCN, and $R^2$ is c-$C_3H_5$.
Table 3565. Compounds of formula I.47 wherein $R^1$ is Y-1A, R is NH, and $R^2$ is H.
Table 3566. Compounds of formula I.47 wherein $R^1$ is Y-1B, R is NH, and $R^2$ is H.
Table 3567. Compounds of formula I.47 wherein $R^1$ is Y-2A, R is NH, and $R^2$ is H.
Table 3568. Compounds of formula I.47 wherein $R^1$ is Y-2B, R is NH, and $R^2$ is H.
Table 3569. Compounds of formula I.47 wherein $R^1$ is Y-3A, R is NH, and $R^2$ is H.
Table 3570. Compounds of formula I.47 wherein $R^1$ is Y-3B, R is NH, and $R^2$ is H.
Table 3571. Compounds of formula I.47 wherein $R^1$ is Y-3C, R is NH, and $R^2$ is H.
Table 3572. Compounds of formula I.47 wherein $R^1$ is Y-3D, R is NH, and $R^2$ is H.
Table 3573. Compounds of formula I.47 wherein $R^1$ is Y-4A, R is NH, and $R^2$ is H.
Table 3574. Compounds of formula I.47 wherein $R^1$ is Y-4B, R is NH, and $R^2$ is H.
Table 3575. Compounds of formula I.47 wherein $R^1$ is Y-4C, R is NH, and $R^2$ is H.
Table 3576. Compounds of formula I.47 wherein $R^1$ is Y-4D, R is NH, and $R^2$ is H.
Table 3577. Compounds of formula I.47 wherein $R^1$ is Y-5A, R is NH, and $R^2$ is H.
Table 3578. Compounds of formula I.47 wherein $R^1$ is Y-5B, R is NH, and $R^2$ is H.
Table 3579. Compounds of formula I.47 wherein $R^1$ is Y-6A, R is NH, and $R^2$ is H.
Table 3580. Compounds of formula I.47 wherein $R^1$ is Y-6B, R is NH, and $R^2$ is H.
Table 3581. Compounds of formula I.47 wherein $R^1$ is Y-8A, R is NH, and $R^2$ is H.
Table 3582. Compounds of formula I.47 wherein $R^1$ is Y-8B, R is NH, and $R^2$ is H.
Table 3583. Compounds of formula I.47 wherein $R^1$ is Y-1A, R is NH, and $R^2$ is $CH_3$.
Table 3584. Compounds of formula I.47 wherein $R^1$ is Y-1B, R is NH, and $R^2$ is $CH_3$.
Table 3585. Compounds of formula I.47 wherein $R^1$ is Y-2A, R is NH, and $R^2$ is $CH_3$.
Table 3586. Compounds of formula I.47 wherein $R^1$ is Y-2B, R is NH, and $R^2$ is $CH_3$.
Table 3587. Compounds of formula I.47 wherein $R^1$ is Y-3A, R is NH, and $R^2$ is $CH_3$.
Table 3588. Compounds of formula I.47 wherein $R^1$ is Y-3B, R is NH, and $R^2$ is $CH_3$.
Table 3589. Compounds of formula I.47 wherein $R^1$ is Y-3C, R is NH, and $R^2$ is $CH_3$.
Table 3590. Compounds of formula I.47 wherein $R^1$ is Y-3D, R is NH, and $R^2$ is $CH_3$.
Table 3591. Compounds of formula I.47 wherein $R^1$ is Y-4A, R is NH, and $R^2$ is $CH_3$.
Table 3592. Compounds of formula I.47 wherein $R^1$ is Y-4B, R is NH, and $R^2$ is $CH_3$.

Table 3593. Compounds of formula I.47 wherein $R^1$ is Y-4C, R is NH, and $R^2$ is $CH_3$.

Table 3594. Compounds of formula I.47 wherein $R^1$ is Y-4D, R is NH, and $R^2$ is $CH_3$.

Table 3595. Compounds of formula I.47 wherein $R^1$ is Y-5A, R is NH, and $R^2$ is $CH_3$.

Table 3596. Compounds of formula I.47 wherein $R^1$ is Y-5B, R is NH, and $R^2$ is $CH_3$.

Table 3597. Compounds of formula I.47 wherein $R^1$ is Y-6A, R is NH, and $R^2$ is $CH_3$.

Table 3598. Compounds of formula I.47 wherein $R^1$ is Y-6B, R is NH, and $R^2$ is $CH_3$.

Table 3599. Compounds of formula I.47 wherein $R^1$ is Y-8A, R is NH, and $R^2$ is $CH_3$.

Table 3600. Compounds of formula I.47 wherein $R^1$ is Y-8B, R is NH, and $R^2$ is $CH_3$.

Table 3601. Compounds of formula I.47 wherein $R^1$ is Y-1A, R is NH, and $R^2$ is c-$C_3H_5$.

Table 3602. Compounds of formula I.47 wherein $R^1$ is Y-1B, R is NH, and $R^2$ is c-$C_3H_5$.

Table 3603. Compounds of formula I.47 wherein $R^1$ is Y-2A, R is NH, and $R^2$ is c-$C_3H_5$.

Table 3604. Compounds of formula I.47 wherein $R^1$ is Y-2B, R is NH, and $R^2$ is c-$C_3H_5$.

Table 3605. Compounds of formula I.47 wherein $R^1$ is Y-3A, R is NH, and $R^2$ is c-$C_3H_5$.

Table 3606. Compounds of formula I.47 wherein $R^1$ is Y-3B, R is NH, and $R^2$ is c-$C_3H_5$.

Table 3607. Compounds of formula I.47 wherein $R^1$ is Y-3C, R is NH, and $R^2$ is c-$C_3H_5$.

Table 3608. Compounds of formula I.47 wherein $R^1$ is Y-3D, R is NH, and $R^2$ is c-$C_3H_5$.

Table 3609. Compounds of formula I.47 wherein $R^1$ is Y-4A, R is NH, and $R^2$ is c-$C_3H_5$.

Table 3610. Compounds of formula I.47 wherein $R^1$ is Y-4B, R is NH, and $R^2$ is c-$C_3H_5$.

Table 3611. Compounds of formula I.47 wherein $R^1$ is Y-4C, R is NH, and $R^2$ is c-$C_3H_5$.

Table 3612. Compounds of formula I.47 wherein $R^1$ is Y-4D, R is NH, and $R^2$ is c-$C_3H_5$.

Table 3613. Compounds of formula I.47 wherein $R^1$ is Y-5A, R is NH, and $R^2$ is c-$C_3H_5$.

Table 3614. Compounds of formula I.47 wherein $R^1$ is Y-5B, R is NH, and $R^2$ is c-$C_3H_5$.

Table 3615. Compounds of formula I.47 wherein $R^1$ is Y-6A, R is NH, and $R^2$ is c-$C_3H_5$.

Table 3616. Compounds of formula I.47 wherein $R^1$ is Y-6B, R is NH, and $R^2$ is c-$C_3H_5$.

Table 3617. Compounds of formula I.47 wherein $R^1$ is Y-8A, R is NH, and $R^2$ is c-$C_3H_5$.

Table 3618. Compounds of formula I.47 wherein $R^1$ is Y-8B, R is NH, and $R^2$ is c-$C_3H_5$.

Table 3619. Compounds of formula I.47 wherein $R^1$ is Y-1A, R is $NCH_3$ and $R^2$ is H.

Table 3620. Compounds of formula I.47 wherein $R^1$ is Y-1B, R is $NCH_3$ and $R^2$ is H.

Table 3621. Compounds of formula I.47 wherein $R^1$ is Y-2A, R is $NCH_3$ and $R^2$ is H.

Table 3622. Compounds of formula I.47 wherein $R^1$ is Y-2B, R is $NCH_3$ and $R^2$ is H.

Table 3623. Compounds of formula I.47 wherein $R^1$ is Y-3A, R is $NCH_3$ and $R^2$ is H.

Table 3624. Compounds of formula I.47 wherein $R^1$ is Y-3B, R is $NCH_3$ and $R^2$ is H.

Table 3625. Compounds of formula I.47 wherein $R^1$ is Y-3C, R is $NCH_3$ and $R^2$ is H.

Table 3626. Compounds of formula I.47 wherein $R^1$ is Y-3D, R is $NCH_3$ and $R^2$ is H.

Table 3627. Compounds of formula I.47 wherein $R^1$ is Y-4A, R is $NCH_3$ and $R^2$ is H.

Table 3628. Compounds of formula I.47 wherein $R^1$ is Y-4B, R is $NCH_3$ and $R^2$ is H.

Table 3629. Compounds of formula I.47 wherein $R^1$ is Y-4C, R is $NCH_3$ and $R^2$ is H.

Table 3630. Compounds of formula I.47 wherein $R^1$ is Y-4D, R is $NCH_3$ and $R^2$ is H.

Table 3631. Compounds of formula I.47 wherein $R^1$ is Y-5A, R is $NCH_3$ and $R^2$ is H.

Table 3632. Compounds of formula I.47 wherein $R^1$ is Y-5B, R is $NCH_3$ and $R^2$ is H.

Table 3633. Compounds of formula I.47 wherein $R^1$ is Y-6A, R is $NCH_3$ and $R^2$ is H.

Table 3634. Compounds of formula I.47 wherein $R^1$ is Y-6B, R is $NCH_3$ and $R^2$ is H.

Table 3635. Compounds of formula I.47 wherein $R^1$ is Y-8A, R is $NCH_3$ and $R^2$ is H.

Table 3636. Compounds of formula I.47 wherein $R^1$ is Y-8B, R is $NCH_3$ and $R^2$ is H.

Table 3637. Compounds of formula I.47 wherein $R^1$ is Y-1A, R is $NCH_3$ and $R^2$ is $CH_3$.

Table 3638. Compounds of formula I.47 wherein $R^1$ is Y-1B, R is $NCH_3$ and $R^2$ is $CH_3$.

Table 3639. Compounds of formula I.47 wherein $R^1$ is Y-2A, R is $NCH_3$ and $R^2$ is $CH_3$.

Table 3640. Compounds of formula I.47 wherein $R^1$ is Y-2B, R is $NCH_3$ and $R^2$ is $CH_3$.

Table 3641. Compounds of formula I.47 wherein $R^1$ is Y-3A, R is $NCH_3$ and $R^2$ is $CH_3$.

Table 3642. Compounds of formula I.47 wherein $R^1$ is Y-3B, R is $NCH_3$ and $R^2$ is $CH_3$.

Table 3643. Compounds of formula I.47 wherein $R^1$ is Y-3C, R is $NCH_3$ and $R^2$ is $CH_3$.

Table 3644. Compounds of formula I.47 wherein $R^1$ is Y-3D, R is $NCH_3$ and $R^2$ is $CH_3$.

Table 3645. Compounds of formula I.47 wherein $R^1$ is Y-4A, R is $NCH_3$ and $R^2$ is $CH_3$.

Table 3646. Compounds of formula I.47 wherein $R^1$ is Y-4B, R is $NCH_3$ and $R^2$ is $CH_3$.

Table 3647. Compounds of formula I.47 wherein $R^1$ is Y-4C, R is $NCH_3$ and $R^2$ is $CH_3$.

Table 3648. Compounds of formula I.47 wherein $R^1$ is Y-4D, R is $NCH_3$ and $R^2$ is $CH_3$.

Table 3649. Compounds of formula I.47 wherein $R^1$ is Y-5A, R is $NCH_3$ and $R^2$ is $CH_3$.

Table 3650. Compounds of formula I.47 wherein $R^1$ is Y-5B, R is $NCH_3$ and $R^2$ is $CH_3$.

Table 3651. Compounds of formula I.47 wherein $R^1$ is Y-6A, R is $NCH_3$ and $R^2$ is $CH_3$.

Table 3652. Compounds of formula I.47 wherein $R^1$ is Y-6B, R is $NCH_3$ and $R^2$ is $CH_3$.

Table 3653. Compounds of formula I.47 wherein $R^1$ is Y-8A, R is $NCH_3$ and $R^2$ is $CH_3$.

Table 3654. Compounds of formula I.47 wherein $R^1$ is Y-8B, R is $NCH_3$ and $R^2$ is $CH_3$.

Table 3655. Compounds of formula I.47 wherein $R^1$ is Y-1A, R is $NCH_3$ and $R^2$ is c-$C_3H_5$.

Table 3656. Compounds of formula I.47 wherein $R^1$ is Y-1B, R is $NCH_3$ and $R^2$ is c-$C_3H_5$.

Table 3657. Compounds of formula I.47 wherein $R^1$ is Y-2A, R is $NCH_3$ and $R^2$ is c-$C_3H_5$.

Table 3658. Compounds of formula I.47 wherein $R^1$ is Y-2B, R is $NCH_3$ and $R^2$ is c-$C_3H_5$.

Table 3659. Compounds of formula I.47 wherein $R^1$ is Y-3A, R is $NCH_3$ and $R^2$ is c-$C_3H_5$.

Table 3660. Compounds of formula I.47 wherein $R^1$ is Y-3B, R is $NCH_3$ and $R^2$ is c-$C_3H_5$.

Table 3661. Compounds of formula I.47 wherein $R^1$ is Y-3C, R is $NCH_3$ and $R^2$ is c-$C_3H_5$.

Table 3662. Compounds of formula I.47 wherein $R^1$ is Y-3D, R is $NCH_3$ and $R^2$ is c-$C_3H_5$.

Table 3663. Compounds of formula I.47 wherein $R^1$ is Y-4A, R is $NCH_3$ and $R^2$ is c-$C_3H_5$.

Table 3664. Compounds of formula I.47 wherein $R^1$ is Y-4B, R is $NCH_3$ and $R^2$ is c-$C_3H_5$.

Table 3665. Compounds of formula I.47 wherein $R^1$ is Y-4C, R is $NCH_3$ and $R^2$ is c-$C_3H_5$.

Table 3666. Compounds of formula I.47 wherein $R^1$ is Y-4D, R is $NCH_3$ and $R^2$ is c-$C_3H_5$.

Table 3667. Compounds of formula I.47 wherein $R^1$ is Y-5A, R is $NCH_3$ and $R^2$ is c-$C_3H_5$.

Table 3668. Compounds of formula I.47 wherein $R^1$ is Y-5B, R is $NCH_3$ and $R^2$ is c-$C_3H_5$.

Table 3669. Compounds of formula I.47 wherein $R^1$ is Y-6A, R is $NCH_3$ and $R^2$ is c-$C_3H_5$.

Table 3670. Compounds of formula I.47 wherein $R^1$ is Y-6B, R is $NCH_3$ and $R^2$ is c-$C_3H_5$.

Table 3671. Compounds of formula I.47 wherein $R^1$ is Y-8A, R is $NCH_3$ and $R^2$ is c-$C_3H_5$.

Table 3672. Compounds of formula I.47 wherein $R^1$ is Y-8B, R is $NCH_3$ and $R^2$ is c-$C_3H_5$.

Table 3673. Compounds of formula I.47 wherein $R^1$ is Y-1A, R is NCN, and $R^2$ is H.

Table 3674. Compounds of formula I.47 wherein $R^1$ is Y-1B, R is NCN, and $R^2$ is H.

Table 3675. Compounds of formula I.47 wherein $R^1$ is Y-2A, R is NCN, and $R^2$ is H.

Table 3676. Compounds of formula I.47 wherein $R^1$ is Y-2B, R is NCN, and $R^2$ is H.

Table 3677. Compounds of formula I.47 wherein $R^1$ is Y-3A, R is NCN, and $R^2$ is H.

Table 3678. Compounds of formula I.47 wherein $R^1$ is Y-3B, R is NCN, and $R^2$ is H.

Table 3679. Compounds of formula I.47 wherein $R^1$ is Y-3C, R is NCN, and $R^2$ is H.

Table 3680. Compounds of formula I.47 wherein $R^1$ is Y-3D, R is NCN, and $R^2$ is H.

Table 3681. Compounds of formula I.47 wherein $R^1$ is Y-4A, R is NCN, and $R^2$ is H.

Table 3682. Compounds of formula I.47 wherein $R^1$ is Y-4B, R is NCN, and $R^2$ is H.

Table 3683. Compounds of formula I.47 wherein $R^1$ is Y-4C, R is NCN, and $R^2$ is H.

Table 3684. Compounds of formula I.47 wherein $R^1$ is Y-4D, R is NCN, and $R^2$ is H.

Table 3685. Compounds of formula I.47 wherein $R^1$ is Y-5A, R is NCN, and $R^2$ is H.

Table 3686. Compounds of formula I.47 wherein $R^1$ is Y-5B, R is NCN, and $R^2$ is H.

Table 3687. Compounds of formula I.47 wherein $R^1$ is Y-6A, R is NCN, and $R^2$ is H.

Table 3688. Compounds of formula I.47 wherein $R^1$ is Y-6B, R is NCN, and $R^2$ is H.

Table 3689. Compounds of formula I.47 wherein $R^1$ is Y-8A, R is NCN, and $R^2$ is H.

Table 3690. Compounds of formula I.47 wherein $R^1$ is Y-8B, R is NCN, and $R^2$ is H.

Table 3691. Compounds of formula I.47 wherein $R^1$ is Y-1A, R is NCN, and $R^2$ is $CH_3$.

Table 3692. Compounds of formula I.47 wherein $R^1$ is Y-1B, R is NCN, and $R^2$ is $CH_3$.

Table 3693. Compounds of formula I.47 wherein $R^1$ is Y-2A, R is NCN, and $R^2$ is $CH_3$.

Table 3694. Compounds of formula I.47 wherein $R^1$ is Y-2B, R is NCN, and $R^2$ is $CH_3$.

Table 3695. Compounds of formula I.47 wherein $R^1$ is Y-3A, R is NCN, and $R^2$ is $CH_3$.

Table 3696. Compounds of formula I.47 wherein $R^1$ is Y-3B, R is NCN, and $R^2$ is $CH_3$.

Table 3697. Compounds of formula I.47 wherein $R^1$ is Y-3C, R is NCN, and $R^2$ is $CH_3$.

Table 3698. Compounds of formula I.47 wherein $R^1$ is Y-3D, R is NCN, and $R^2$ is $CH_3$.

Table 3699. Compounds of formula I.47 wherein $R^1$ is Y-4A, R is NCN, and $R^2$ is $CH_3$.

Table 3700. Compounds of formula I.47 wherein $R^1$ is Y-4B, R is NCN, and $R^2$ is $CH_3$.

Table 3701. Compounds of formula I.47 wherein $R^1$ is Y-4C, R is NCN, and $R^2$ is $CH_3$.

Table 3702. Compounds of formula I.47 wherein $R^1$ is Y-4D, R is NCN, and $R^2$ is $CH_3$.

Table 3703. Compounds of formula I.47 wherein $R^1$ is Y-5A, R is NCN, and $R^2$ is $CH_3$.

Table 3704. Compounds of formula I.47 wherein $R^1$ is Y-5B, R is NCN, and $R^2$ is $CH_3$.

Table 3705. Compounds of formula I.47 wherein $R^1$ is Y-6A, R is NCN, and $R^2$ is $CH_3$.

Table 3706. Compounds of formula I.47 wherein $R^1$ is Y-6B, R is NCN, and $R^2$ is $CH_3$.

Table 3707. Compounds of formula I.47 wherein $R^1$ is Y-8A, R is NCN, and $R^2$ is $CH_3$.

Table 3708. Compounds of formula I.47 wherein $R^1$ is Y-8B, R is NCN, and $R^2$ is $CH_3$.

Table 3709. Compounds of formula I.47 wherein $R^1$ is Y-1A, R is NCN, and $R^2$ is c-$C_3H_5$.

Table 3710. Compounds of formula I.47 wherein $R^1$ is Y-1B, R is NCN, and $R^2$ is c-$C_3H_5$.

Table 3711. Compounds of formula I.47 wherein $R^1$ is Y-2A, R is NCN, and $R^2$ is c-$C_3H_5$.

Table 3712. Compounds of formula I.47 wherein $R^1$ is Y-2B, R is NCN, and $R^2$ is c-$C_3H_5$.

Table 3713. Compounds of formula I.47 wherein $R^1$ is Y-3A, R is NCN, and $R^2$ is c-$C_3H_5$.

Table 3714. Compounds of formula I.47 wherein $R^1$ is Y-3B, R is NCN, and $R^2$ is c-$C_3H_5$.

Table 3715. Compounds of formula I.47 wherein $R^1$ is Y-3C, R is NCN, and $R^2$ is c-$C_3H_5$.

Table 3716. Compounds of formula I.47 wherein $R^1$ is Y-3D, R is NCN, and $R^2$ is c-$C_3H_5$.

Table 3717. Compounds of formula I.47 wherein $R^1$ is Y-4A, R is NCN, and $R^2$ is c-$C_3H_5$.

Table 3718. Compounds of formula I.47 wherein $R^1$ is Y-4B, R is NCN, and $R^2$ is c-$C_3H_5$.

Table 3719. Compounds of formula I.47 wherein $R^1$ is Y-4C, R is NCN, and $R^2$ is c-$C_3H_5$.

Table 3720. Compounds of formula I.47 wherein $R^1$ is Y-4D, R is NCN, and $R^2$ is c-$C_3H_5$.

Table 3721. Compounds of formula I.47 wherein $R^1$ is Y-5A, R is NCN, and $R^2$ is c-$C_3H_5$.

Table 3722. Compounds of formula I.47 wherein $R^1$ is Y-5B, R is NCN, and $R^2$ is c-$C_3H_5$.

Table 3723. Compounds of formula I.47 wherein $R^1$ is Y-6A, R is NCN, and $R^2$ is c-$C_3H_5$.

Table 3724. Compounds of formula I.47 wherein $R^1$ is Y-6B, R is NCN, and $R^2$ is c-$C_3H_5$.

Table 3725. Compounds of formula I.47 wherein $R^1$ is Y-8A, R is NCN, and $R^2$ is c-$C_3H_5$.

Table 3726. Compounds of formula I.47 wherein $R^1$ is Y-8B, R is NCN, and $R^2$ is c-$C_3H_5$.

Table 3727. Compounds of formula I.48 wherein $R^1$ is Y-1A, R is NH, and $R^2$ is H.

Table 3728. Compounds of formula I.48 wherein $R^1$ is Y-1B, R is NH, and $R^2$ is H.

Table 3729. Compounds of formula I.48 wherein $R^1$ is Y-2A, R is NH, and $R^2$ is H.

Table 3730. Compounds of formula I.48 wherein $R^1$ is Y-2B, R is NH, and $R^2$ is H.

Table 3731. Compounds of formula I.48 wherein $R^1$ is Y-3A, R is NH, and $R^2$ is H.

Table 3732. Compounds of formula I.48 wherein $R^1$ is Y-3B, R is NH, and $R^2$ is H.

Table 3733. Compounds of formula I.48 wherein $R^1$ is Y-3C, R is NH, and $R^2$ is H.

Table 3734. Compounds of formula I.48 wherein $R^1$ is Y-3D, R is NH, and $R^2$ is H.

Table 3735. Compounds of formula I.48 wherein $R^1$ is Y-4A, R is NH, and $R^2$ is H.

Table 3736. Compounds of formula I.48 wherein $R^1$ is Y-4B, R is NH, and $R^2$ is H.

Table 3737. Compounds of formula I.48 wherein $R^1$ is Y-4C, R is NH, and $R^2$ is H.

Table 3738. Compounds of formula I.48 wherein $R^1$ is Y-4D, R is NH, and $R^2$ is H.

Table 3739. Compounds of formula I.48 wherein $R^1$ is Y-5A, R is NH, and $R^2$ is H.

Table 3740. Compounds of formula I.48 wherein $R^1$ is Y-5B, R is NH, and $R^2$ is H.

Table 3741. Compounds of formula I.48 wherein $R^1$ is Y-6A, R is NH, and $R^2$ is H.

Table 3742. Compounds of formula I.48 wherein $R^1$ is Y-6B, R is NH, and $R^2$ is H.

Table 3743. Compounds of formula I.48 wherein $R^1$ is Y-8A, R is NH, and $R^2$ is H.

Table 3744. Compounds of formula I.48 wherein $R^1$ is Y-8B, R is NH, and $R^2$ is H.

Table 3745. Compounds of formula I.48 wherein $R^1$ is Y-1A, R is NH, and $R^2$ is $CH_3$.

Table 3746. Compounds of formula I.48 wherein $R^1$ is Y-1B, R is NH, and $R^2$ is $CH_3$.

Table 3747. Compounds of formula I.48 wherein $R^1$ is Y-2A, R is NH, and $R^2$ is $CH_3$.

Table 3748. Compounds of formula I.48 wherein $R^1$ is Y-2B, R is NH, and $R^2$ is $CH_3$.

Table 3749. Compounds of formula I.48 wherein $R^1$ is Y-3A, R is NH, and $R^2$ is $CH_3$.

Table 3750. Compounds of formula I.48 wherein $R^1$ is Y-3B, R is NH, and $R^2$ is $CH_3$.

Table 3751. Compounds of formula I.48 wherein $R^1$ is Y-3C, R is NH, and $R^2$ is $CH_3$.

Table 3752. Compounds of formula I.48 wherein $R^1$ is Y-3D, R is NH, and $R^2$ is $CH_3$.

Table 3753. Compounds of formula I.48 wherein $R^1$ is Y-4A, R is NH, and $R^2$ is $CH_3$.

Table 3754. Compounds of formula I.48 wherein $R^1$ is Y-4B, R is NH, and $R^2$ is $CH_3$.

Table 3755. Compounds of formula I.48 wherein $R^1$ is Y-4C, R is NH, and $R^2$ is $CH_3$.

Table 3756. Compounds of formula I.48 wherein $R^1$ is Y-4D, R is NH, and $R^2$ is $CH_3$.

Table 3757. Compounds of formula I.48 wherein $R^1$ is Y-5A, R is NH, and $R^2$ is $CH_3$.

Table 3758. Compounds of formula I.48 wherein $R^1$ is Y-5B, R is NH, and $R^2$ is $CH_3$.

Table 3759. Compounds of formula I.48 wherein $R^1$ is Y-6A, R is NH, and $R^2$ is $CH_3$.

Table 3760. Compounds of formula I.48 wherein $R^1$ is Y-6B, R is NH, and $R^2$ is $CH_3$.

Table 3761. Compounds of formula I.48 wherein $R^1$ is Y-8A, R is NH, and $R^2$ is $CH_3$.

Table 3762. Compounds of formula I.48 wherein $R^1$ is Y-8B, R is NH, and $R^2$ is $CH_3$.

Table 3763. Compounds of formula I.48 wherein $R^1$ is Y-1A, R is NH, and $R^2$ is c-$C_3H_5$.

Table 3764. Compounds of formula I.48 wherein $R^1$ is Y-1B, R is NH, and $R^2$ is c-$C_3H_5$.

Table 3765. Compounds of formula I.48 wherein $R^1$ is Y-2A, R is NH, and $R^2$ is c-$C_3H_5$.

Table 3766. Compounds of formula I.48 wherein $R^1$ is Y-2B, R is NH, and $R^2$ is c-$C_3H_5$.

Table 3767. Compounds of formula I.48 wherein $R^1$ is Y-3A, R is NH, and $R^2$ is c-$C_3H_5$.

Table 3768. Compounds of formula I.48 wherein $R^1$ is Y-3B, R is NH, and $R^2$ is c-$C_3H_5$.

Table 3769. Compounds of formula I.48 wherein $R^1$ is Y-3C, R is NH, and $R^2$ is c-$C_3H_5$.

Table 3770. Compounds of formula I.48 wherein $R^1$ is Y-3D, R is NH, and $R^2$ is c-$C_3H_5$.

Table 3771. Compounds of formula I.48 wherein $R^1$ is Y-4A, R is NH, and $R^2$ is c-$C_3H_5$.

Table 3772. Compounds of formula I.48 wherein $R^1$ is Y-4B, R is NH, and $R^2$ is c-$C_3H_5$.

Table 3773. Compounds of formula I.48 wherein $R^1$ is Y-4C, R is NH, and $R^2$ is c-$C_3H_5$.

Table 3774. Compounds of formula I.48 wherein $R^1$ is Y-4D, R is NH, and $R^2$ is c-$C_3H_5$.

Table 3775. Compounds of formula I.48 wherein $R^1$ is Y-5A, R is NH, and $R^2$ is c-$C_3H_5$.

Table 3776. Compounds of formula I.48 wherein $R^1$ is Y-5B, R is NH, and $R^2$ is c-$C_3H_5$.

Table 3777. Compounds of formula I.48 wherein $R^1$ is Y-6A, R is NH, and $R^2$ is c-$C_3H_5$.

Table 3778. Compounds of formula I.48 wherein $R^1$ is Y-6B, R is NH, and $R^2$ is c-$C_3H_5$.

Table 3779. Compounds of formula I.48 wherein $R^1$ is Y-8A, R is NH, and $R^2$ is c-$C_3H_5$.

Table 3780. Compounds of formula I.48 wherein $R^1$ is Y-8B, R is NH, and $R^2$ is c-$C_3H_5$.

Table 3781. Compounds of formula I.48 wherein $R^1$ is Y-1A, R is $NCH_3$ and $R^2$ is H.

Table 3782. Compounds of formula I.48 wherein $R^1$ is Y-1B, R is $NCH_3$ and $R^2$ is H.

Table 3783. Compounds of formula I.48 wherein $R^1$ is Y-2A, R is $NCH_3$ and $R^2$ is H.

Table 3784. Compounds of formula I.48 wherein $R^1$ is Y-2B, R is $NCH_3$ and $R^2$ is H.

Table 3785. Compounds of formula I.48 wherein $R^1$ is Y-3A, R is $NCH_3$ and $R^2$ is H.

Table 3786. Compounds of formula I.48 wherein $R^1$ is Y-3B, R is $NCH_3$ and $R^2$ is H.

Table 3787. Compounds of formula I.48 wherein $R^1$ is Y-3C, R is $NCH_3$ and $R^2$ is H.

Table 3788. Compounds of formula I.48 wherein $R^1$ is Y-3D, R is $NCH_3$ and $R^2$ is H.

Table 3789. Compounds of formula I.48 wherein $R^1$ is Y-4A, R is $NCH_3$ and $R^2$ is H.

Table 3790. Compounds of formula I.48 wherein $R^1$ is Y-4B, R is $NCH_3$ and $R^2$ is H.

Table 3791. Compounds of formula I.48 wherein $R^1$ is Y-4C, R is $NCH_3$ and $R^2$ is H.

Table 3792. Compounds of formula I.48 wherein $R^1$ is Y-4D, R is $NCH_3$ and $R^2$ is H.

Table 3793. Compounds of formula I.48 wherein $R^1$ is Y-5A, R is $NCH_3$ and $R^2$ is H.

Table 3794. Compounds of formula I.48 wherein $R^1$ is Y-5B, R is $NCH_3$ and $R^2$ is H.

Table 3795. Compounds of formula I.48 wherein $R^1$ is Y-6A, R is $NCH_3$ and $R^2$ is H.

Table 3796. Compounds of formula I.48 wherein $R^1$ is Y-6B, R is $NCH_3$ and $R^2$ is H.

Table 3797. Compounds of formula I.48 wherein $R^1$ is Y-8A, R is $NCH_3$ and $R^2$ is H.

Table 3798. Compounds of formula I.48 wherein $R^1$ is Y-8B, R is $NCH_3$ and $R^2$ is H.

Table 3799. Compounds of formula I.48 wherein $R^1$ is Y-1A, R is $NCH_3$ and $R^2$ is $CH_3$.

Table 3800. Compounds of formula I.48 wherein $R^1$ is Y-1B, R is $NCH_3$ and $R^2$ is $CH_3$.

Table 3801. Compounds of formula I.48 wherein $R^1$ is Y-2A, R is $NCH_3$ and $R^2$ is $CH_3$.

Table 3802. Compounds of formula I.48 wherein $R^1$ is Y-2B, R is $NCH_3$ and $R^2$ is $CH_3$.

Table 3803. Compounds of formula I.48 wherein $R^1$ is Y-3A, R is $NCH_3$ and $R^2$ is $CH_3$.

Table 3804. Compounds of formula I.48 wherein $R^1$ is Y-3B, R is $NCH_3$ and $R^2$ is $CH_3$.

Table 3805. Compounds of formula I.48 wherein $R^1$ is Y-3C, R is $NCH_3$ and $R^2$ is $CH_3$.

Table 3806. Compounds of formula I.48 wherein $R^1$ is Y-3D, R is $NCH_3$ and $R^2$ is $CH_3$.

Table 3807. Compounds of formula I.48 wherein $R^1$ is Y-4A, R is $NCH_3$ and $R^2$ is $CH_3$.

Table 3808. Compounds of formula I.48 wherein $R^1$ is Y-4B, R is $NCH_3$ and $R^2$ is $CH_3$.

Table 3809. Compounds of formula I.48 wherein $R^1$ is Y-4C, R is $NCH_3$ and $R^2$ is $CH_3$.

Table 3810. Compounds of formula I.48 wherein $R^1$ is Y-4D, R is $NCH_3$ and $R^2$ is $CH_3$.

Table 3811. Compounds of formula I.48 wherein $R^1$ is Y-5A, R is $NCH_3$ and $R^2$ is $CH_3$.

Table 3812. Compounds of formula I.48 wherein $R^1$ is Y-5B, R is $NCH_3$ and $R^2$ is $CH_3$.

Table 3813. Compounds of formula I.48 wherein $R^1$ is Y-6A, R is $NCH_3$ and $R^2$ is $CH_3$.

Table 3814. Compounds of formula I.48 wherein $R^1$ is Y-6B, R is $NCH_3$ and $R^2$ is $CH_3$.

Table 3815. Compounds of formula I.48 wherein $R^1$ is Y-8A, R is $NCH_3$ and $R^2$ is $CH_3$.

Table 3816. Compounds of formula I.48 wherein $R^1$ is Y-8B, R is $NCH_3$ and $R^2$ is $CH_3$.

Table 3817. Compounds of formula I.48 wherein $R^1$ is Y-1A, R is $NCH_3$ and $R^2$ is c-$C_3H_5$.

Table 3818. Compounds of formula I.48 wherein $R^1$ is Y-1B, R is $NCH_3$ and $R^2$ is c-$C_3H_5$.

Table 3819. Compounds of formula I.48 wherein $R^1$ is Y-2A, R is $NCH_3$ and $R^2$ is c-$C_3H_5$.

Table 3820. Compounds of formula I.48 wherein $R^1$ is Y-2B, R is $NCH_3$ and $R^2$ is c-$C_3H_5$.

Table 3821. Compounds of formula I.48 wherein $R^1$ is Y-3A, R is $NCH_3$ and $R^2$ is c-$C_3H_5$.

Table 3822. Compounds of formula I.48 wherein $R^1$ is Y-3B, R is $NCH_3$ and $R^2$ is c-$C_3H_5$.

Table 3823. Compounds of formula I.48 wherein $R^1$ is Y-3C, R is $NCH_3$ and $R^2$ is c-$C_3H_5$.

Table 3824. Compounds of formula I.48 wherein $R^1$ is Y-3D, R is $NCH_3$ and $R^2$ is c-$C_3H_5$.

Table 3825. Compounds of formula I.48 wherein $R^1$ is Y-4A, R is $NCH_3$ and $R^2$ is c-$C_3H_5$.

Table 3826. Compounds of formula I.48 wherein $R^1$ is Y-4B, R is $NCH_3$ and $R^2$ is c-$C_3H_5$.

Table 3827. Compounds of formula I.48 wherein $R^1$ is Y-4C, R is $NCH_3$ and $R^2$ is c-$C_3H_5$.

Table 3828. Compounds of formula I.48 wherein $R^1$ is Y-4D, R is $NCH_3$ and $R^2$ is c-$C_3H_5$.

Table 3829. Compounds of formula I.48 wherein $R^1$ is Y-5A, R is $NCH_3$ and $R^2$ is c-$C_3H_5$.

Table 3830. Compounds of formula I.48 wherein $R^1$ is Y-5B, R is $NCH_3$ and $R^2$ is c-$C_3H_5$.

Table 3831. Compounds of formula I.48 wherein $R^1$ is Y-6A, R is $NCH_3$ and $R^2$ is c-$C_3H_5$.

Table 3832. Compounds of formula I.48 wherein $R^1$ is Y-6B, R is $NCH_3$ and $R^2$ is c-$C_3H_5$.

Table 3833. Compounds of formula I.48 wherein $R^1$ is Y-8A, R is $NCH_3$ and $R^2$ is c-$C_3H_5$.

Table 3834. Compounds of formula I.48 wherein $R^1$ is Y-8B, R is $NCH_3$ and $R^2$ is c-$C_3H_5$.

Table 3835. Compounds of formula I.48 wherein $R^1$ is Y-1A, R is NCN, and $R^2$ is H.

Table 3836. Compounds of formula I.48 wherein $R^1$ is Y-1B, R is NCN, and $R^2$ is H.

Table 3837. Compounds of formula I.48 wherein $R^1$ is Y-2A, R is NCN, and $R^2$ is H.

Table 3838. Compounds of formula I.48 wherein $R^1$ is Y-2B, R is NCN, and $R^2$ is H.

Table 3839. Compounds of formula I.48 wherein $R^1$ is Y-3A, R is NCN, and $R^2$ is H.

Table 3840. Compounds of formula I.48 wherein $R^1$ is Y-3B, R is NCN, and $R^2$ is H.

Table 3841. Compounds of formula I.48 wherein $R^1$ is Y-3C, R is NCN, and $R^2$ is H.

Table 3842. Compounds of formula I.48 wherein $R^1$ is Y-3D, R is NCN, and $R^2$ is H.

Table 3843. Compounds of formula I.48 wherein $R^1$ is Y-4A, R is NCN, and $R^2$ is H.

Table 3844. Compounds of formula I.48 wherein $R^1$ is Y-4B, R is NCN, and $R^2$ is H.

Table 3845. Compounds of formula I.48 wherein $R^1$ is Y-4C, R is NCN, and $R^2$ is H.

Table 3846. Compounds of formula I.48 wherein $R^1$ is Y-4D, R is NCN, and $R^2$ is H.

Table 3847. Compounds of formula I.48 wherein $R^1$ is Y-5A, R is NCN, and $R^2$ is H.

Table 3848. Compounds of formula I.48 wherein $R^1$ is Y-5B, R is NCN, and $R^2$ is H.

Table 3849. Compounds of formula I.48 wherein $R^1$ is Y-6A, R is NCN, and $R^2$ is H.

Table 3850. Compounds of formula I.48 wherein $R^1$ is Y-6B, R is NCN, and $R^2$ is H.

Table 3851. Compounds of formula I.48 wherein $R^1$ is Y-8A, R is NCN, and $R^2$ is H.

Table 3852. Compounds of formula I.48 wherein $R^1$ is Y-8B, R is NCN, and $R^2$ is H.

Table 3853. Compounds of formula I.48 wherein $R^1$ is Y-1A, R is NCN, and $R^2$ is $CH_3$.

Table 3854. Compounds of formula I.48 wherein $R^1$ is Y-1B, R is NCN, and $R^2$ is $CH_3$.

Table 3855. Compounds of formula I.48 wherein $R^1$ is Y-2A, R is NCN, and $R^2$ is $CH_3$.

Table 3856. Compounds of formula I.48 wherein $R^1$ is Y-2B, R is NCN, and $R^2$ is $CH_3$.

Table 3857. Compounds of formula I.48 wherein $R^1$ is Y-3A, R is NCN, and $R^2$ is $CH_3$.

Table 3858. Compounds of formula I.48 wherein $R^1$ is Y-3B, R is NCN, and $R^2$ is $CH_3$.

Table 3859. Compounds of formula I.48 wherein $R^1$ is Y-3C, R is NCN, and $R^2$ is $CH_3$.

Table 3860. Compounds of formula I.48 wherein $R^1$ is Y-3D, R is NCN, and $R^2$ is $CH_3$.

Table 3861. Compounds of formula I.48 wherein $R^1$ is Y-4A, R is NCN, and $R^2$ is $CH_3$.

Table 3862. Compounds of formula I.48 wherein $R^1$ is Y-4B, R is NCN, and $R^2$ is $CH_3$.

Table 3863. Compounds of formula I.48 wherein $R^1$ is Y-4C, R is NCN, and $R^2$ is $CH_3$.

Table 3864. Compounds of formula I.48 wherein $R^1$ is Y-4D, R is NCN, and $R^2$ is $CH_3$.

Table 3865. Compounds of formula I.48 wherein $R^1$ is Y-5A, R is NCN, and $R^2$ is $CH_3$.

Table 3866. Compounds of formula I.48 wherein $R^1$ is Y-5B, R is NCN, and $R^2$ is $CH_3$.

Table 3867. Compounds of formula I.48 wherein $R^1$ is Y-6A, R is NCN, and $R^2$ is $CH_3$.

Table 3868. Compounds of formula I.48 wherein $R^1$ is Y-6B, R is NCN, and $R^2$ is $CH_3$.

Table 3869. Compounds of formula I.48 wherein $R^1$ is Y-8A, R is NCN, and $R^2$ is $CH_3$.

Table 3870. Compounds of formula I.48 wherein $R^1$ is Y-8B, R is NCN, and $R^2$ is $CH_3$.

Table 3871. Compounds of formula I.48 wherein $R^1$ is Y-1A, R is NCN, and $R^2$ is c-$C_3H_5$.

Table 3872. Compounds of formula I.48 wherein $R^1$ is Y-1B, R is NCN, and $R^2$ is c-$C_3H_5$.

Table 3873. Compounds of formula I.48 wherein $R^1$ is Y-2A, R is NCN, and $R^2$ is c-$C_3H_5$.

Table 3874. Compounds of formula I.48 wherein $R^1$ is Y-2B, R is NCN, and $R^2$ is c-$C_3H_5$.

Table 3875. Compounds of formula I.48 wherein $R^1$ is Y-3A, R is NON, and $R^2$ is c-$C_3H_5$.

Table 3876. Compounds of formula I.48 wherein $R^1$ is Y-3B, R is NON, and $R^2$ is c-$C_3H_5$.

Table 3877. Compounds of formula I.48 wherein $R^1$ is Y-3C, R is NON, and $R^2$ is c-$C_3H_5$.

Table 3878. Compounds of formula I.48 wherein $R^1$ is Y-31D, R is NON, and $R^2$ is c-$C_3H_5$.

Table 3879. Compounds of formula I.48 wherein $R^1$ is Y-4A, R is NON, and $R^2$ is c-$C_3H_5$.

Table 3880. Compounds of formula I.48 wherein $R^1$ is Y-4B, R is NON, and $R^2$ is c-$C_3H_5$.

Table 3881. Compounds of formula I.48 wherein $R^1$ is Y-4C, R is NON, and $R^2$ is c-$C_3H_5$.

Table 3882. Compounds of formula I.48 wherein $R^1$ is Y-41D, R is NON, and $R^2$ is c-$C_3H_5$.

Table 3883. Compounds of formula I.48 wherein $R^1$ is Y-5A, R is NON, and $R^2$ is c-$C_3H_5$.

Table 3884. Compounds of formula I.48 wherein $R^1$ is Y-5B, R is NON, and $R^2$ is c-$C_3H_5$.

Table 3885. Compounds of formula I.48 wherein $R^1$ is Y-6A, R is NON, and $R^2$ is c-$C_3H_5$.

Table 3886. Compounds of formula I.48 wherein $R^1$ is Y-6B, R is NON, and $R^2$ is c-$C_3H_5$.

Table 3887. Compounds of formula I.48 wherein $R^1$ is Y-8A, R is NON, and $R^2$ is c-$C_3H_5$.

Table 3888. Compounds of formula I.48 wherein $R^1$ is Y-8B, R is NON, and $R^2$ is c-$C_3H_5$.

TABLE B

| Line | $B^2$ | $B^3$ | $B^4$ | Ar | D |
|---|---|---|---|---|---|
| 1 | CH | CH | CH | $Ar^1$ | $R^{11}$-1 |
| 2 | CH | CH | CH | $Ar^1$ | $R^{11}$-2 |
| 3 | CH | CH | CH | $Ar^1$ | $R^{11}$-3 |
| 4 | CH | CH | CH | $Ar^1$ | $R^{11}$-5 |
| 5 | CH | CH | CH | $Ar^1$ | $R^{11}$-6 |
| 6 | CH | CH | CH | $Ar^1$ | $R^{11}$-7 |
| 7 | CH | CH | CH | $Ar^1$ | $R^{11}$-8 |
| 8 | CH | CH | CH | $Ar^1$ | $R^{11}$-9 |
| 9 | CH | CH | CH | $Ar^1$ | $R^{11}$-10 |
| 10 | CH | CH | CH | $Ar^1$ | $R^{11}$-11 |
| 11 | CH | CH | CH | $Ar^1$ | $R^{11}$-12 |
| 12 | CH | CH | CH | $Ar^1$ | $R^{11}$-13 |
| 13 | CH | CH | CH | $Ar^1$ | $R^{11}$-14 |
| 14 | CH | CH | CH | $Ar^1$ | $R^{11}$-15 |
| 15 | CH | CH | CH | $Ar^1$ | $R^{11}$-16 |
| 16 | CH | CH | CH | $Ar^1$ | $R^{11}$-17 |
| 17 | CH | CH | CH | $Ar^1$ | $R^{11}$-18 |
| 18 | CH | CH | CH | $Ar^1$ | $R^{11}$-19 |
| 19 | CH | CH | CH | $Ar^1$ | $R^{11}$-20 |
| 20 | CH | CH | CH | $Ar^1$ | $R^{11}$-21 |
| 21 | CH | CH | CH | $Ar^1$ | $R^{11}$-22 |
| 22 | CH | CH | CH | $Ar^1$ | $R^{11}$-23 |
| 23 | CH | CH | CH | $Ar^1$ | $R^{11}$-25 |
| 24 | CH | CH | CH | $Ar^1$ | $R^{11}$-26 |
| 25 | CH | CH | CH | $Ar^1$ | $R^{11}$-27 |
| 26 | CH | CH | CH | $Ar^1$ | $R^{11}$-28 |
| 27 | CH | CH | CH | $Ar^1$ | $R^{11}$-29 |
| 28 | CH | CH | CH | $Ar^1$ | $A^{11}$-1 |
| 29 | CH | CH | CH | $Ar^1$ | $A^{11}$-2 |
| 30 | CH | CH | CH | $Ar^1$ | $A^{11}$-3 |
| 31 | CH | CH | CH | $Ar^2$ | $R^{11}$-1 |
| 32 | CH | CH | CH | $Ar^2$ | $R^{11}$-2 |
| 33 | CH | CH | CH | $Ar^2$ | $R^{11}$-3 |
| 34 | CH | CH | CH | $Ar^2$ | $R^{11}$-5 |
| 35 | CH | CH | CH | $Ar^2$ | $R^{11}$-6 |
| 36 | CH | CH | CH | $Ar^2$ | $R^{11}$-7 |
| 37 | CH | CH | CH | $Ar^2$ | $R^{11}$-8 |
| 38 | CH | CH | CH | $Ar^2$ | $R^{11}$-9 |
| 39 | CH | CH | CH | $Ar^2$ | $R^{11}$-10 |
| 40 | CH | CH | CH | $Ar^2$ | $R^{11}$-11 |
| 41 | CH | CH | CH | $Ar^2$ | $R^{11}$-12 |
| 42 | CH | CH | CH | $Ar^2$ | $R^{11}$-13 |
| 43 | CH | CH | CH | $Ar^2$ | $R^{11}$-14 |
| 44 | CH | CH | CH | $Ar^2$ | $R^{11}$-15 |
| 45 | CH | CH | CH | $Ar^2$ | $R^{11}$-16 |
| 46 | CH | CH | CH | $Ar^2$ | $R^{11}$-17 |
| 47 | CH | CH | CH | $Ar^2$ | $R^{11}$-18 |
| 48 | CH | CH | CH | $Ar^2$ | $R^{11}$-19 |
| 49 | CH | CH | CH | $Ar^2$ | $R^{11}$-20 |
| 50 | CH | CH | CH | $Ar^2$ | $R^{11}$-21 |
| 51 | CH | CH | CH | $Ar^2$ | $R^{11}$-22 |
| 52 | CH | CH | CH | $Ar^2$ | $R^{11}$-23 |
| 53 | CH | CH | CH | $Ar^2$ | $R^{11}$-25 |
| 54 | CH | CH | CH | $Ar^2$ | $R^{11}$-26 |
| 55 | CH | CH | CH | $Ar^2$ | $R^{11}$-27 |
| 56 | CH | CH | CH | $Ar^2$ | $R^{11}$-28 |
| 57 | CH | CH | CH | $Ar^2$ | $R^{11}$-29 |
| 58 | CH | CH | CH | $Ar^2$ | $A^{11}$-1 |
| 59 | CH | CH | CH | $Ar^2$ | $A^{11}$-2 |
| 60 | CH | CH | CH | $Ar^2$ | $A^{11}$-3 |
| 61 | CH | CH | CH | $Ar^3$ | $R^{11}$-1 |
| 62 | CH | CH | CH | $Ar^3$ | $R^{11}$-2 |
| 63 | CH | CH | CH | $Ar^3$ | $R^{11}$-3 |
| 64 | CH | CH | CH | $Ar^3$ | $R^{11}$-5 |
| 65 | CH | CH | CH | $Ar^3$ | $R^{11}$-6 |
| 66 | CH | CH | CH | $Ar^3$ | $R^{11}$-7 |
| 67 | CH | CH | CH | $Ar^3$ | $R^{11}$-8 |
| 68 | CH | CH | CH | $Ar^3$ | $R^{11}$-9 |
| 69 | CH | CH | CH | $Ar^3$ | $R^{11}$-10 |
| 70 | CH | CH | CH | $Ar^3$ | $R^{11}$-11 |
| 71 | CH | CH | CH | $Ar^3$ | $R^{11}$-12 |
| 72 | CH | CH | CH | $Ar^3$ | $R^{11}$-13 |
| 73 | CH | CH | CH | $Ar^3$ | $R^{11}$-14 |
| 74 | CH | CH | CH | $Ar^3$ | $R^{11}$-15 |
| 75 | CH | CH | CH | $Ar^3$ | $R^{11}$-16 |
| 76 | CH | CH | CH | $Ar^3$ | $R^{11}$-17 |
| 77 | CH | CH | CH | $Ar^3$ | $R^{11}$-18 |
| 78 | CH | CH | CH | $Ar^3$ | $R^{11}$-19 |

TABLE B-continued

| Line | $B^2$ | $B^3$ | $B^4$ | Ar | D |
|---|---|---|---|---|---|
| 79 | CH | CH | CH | $Ar^3$ | $R^{11}$-20 |
| 80 | CH | CH | CH | $Ar^3$ | $R^{11}$-21 |
| 81 | CH | CH | CH | $Ar^3$ | $R^{11}$-22 |
| 82 | CH | CH | CH | $Ar^3$ | $R^{11}$-23 |
| 83 | CH | CH | CH | $Ar^3$ | $R^{11}$-25 |
| 84 | CH | CH | CH | $Ar^3$ | $R^{11}$-26 |
| 85 | CH | CH | CH | $Ar^3$ | $R^{11}$-27 |
| 86 | CH | CH | CH | $Ar^3$ | $R^{11}$-28 |
| 87 | CH | CH | CH | $Ar^3$ | $R^{11}$-29 |
| 88 | CH | CH | CH | $Ar^3$ | $A^{11}$-1 |
| 89 | CH | CH | CH | $Ar^3$ | $A^{11}$-2 |
| 90 | CH | CH | CH | $Ar^3$ | $A^{11}$-3 |
| 91 | CH | CH | CH | $Ar^4$ | $R^{11}$-1 |
| 92 | CH | CH | CH | $Ar^4$ | $R^{11}$-2 |
| 93 | CH | CH | CH | $Ar^4$ | $R^{11}$-3 |
| 94 | CH | CH | CH | $Ar^4$ | $R^{11}$-5 |
| 95 | CH | CH | CH | $Ar^4$ | $R^{11}$-6 |
| 96 | CH | CH | CH | $Ar^4$ | $R^{11}$-7 |
| 97 | CH | CH | CH | $Ar^4$ | $R^{11}$-8 |
| 98 | CH | CH | CH | $Ar^4$ | $R^{11}$-9 |
| 99 | CH | CH | CH | $Ar^4$ | $R^{11}$-10 |
| 100 | CH | CH | CH | $Ar^4$ | $R^{11}$-11 |
| 101 | CH | CH | CH | $Ar^4$ | $R^{11}$-12 |
| 102 | CH | CH | CH | $Ar^4$ | $R^{11}$-13 |
| 103 | CH | CH | CH | $Ar^4$ | $R^{11}$-14 |
| 104 | CH | CH | CH | $Ar^4$ | $R^{11}$-15 |
| 105 | CH | CH | CH | $Ar^4$ | $R^{11}$-16 |
| 106 | CH | CH | CH | $Ar^4$ | $R^{11}$-17 |
| 107 | CH | CH | CH | $Ar^4$ | $R^{11}$-18 |
| 108 | CH | CH | CH | $Ar^4$ | $R^{11}$-19 |
| 109 | CH | CH | CH | $Ar^4$ | $R^{11}$-20 |
| 110 | CH | CH | CH | $Ar^4$ | $R^{11}$-21 |
| 111 | CH | CH | CH | $Ar^4$ | $R^{11}$-22 |
| 112 | CH | CH | CH | $Ar^4$ | $R^{11}$-23 |
| 113 | CH | CH | CH | $Ar^4$ | $R^{11}$-25 |
| 114 | CH | CH | CH | $Ar^4$ | $R^{11}$-26 |
| 115 | CH | CH | CH | $Ar^4$ | $R^{11}$-27 |
| 116 | CH | CH | CH | $Ar^4$ | $R^{11}$-28 |
| 117 | CH | CH | CH | $Ar^4$ | $R^{11}$-29 |
| 118 | CH | CH | CH | $Ar^4$ | $A^{11}$-1 |
| 119 | CH | CH | CH | $Ar^4$ | $A^{11}$-2 |
| 120 | CH | CH | CH | $Ar^4$ | $A^{11}$-3 |
| 121 | CH | CH | CH | $Ar^{10}$ | $R^{11}$-1 |
| 122 | CH | CH | CH | $Ar^{10}$ | $R^{11}$-2 |
| 123 | CH | CH | CH | $Ar^{10}$ | $R^{11}$-3 |
| 124 | CH | CH | CH | $Ar^{10}$ | $R^{11}$-5 |
| 125 | CH | CH | CH | $Ar^{10}$ | $R^{11}$-6 |
| 126 | CH | CH | CH | $Ar^{10}$ | $R^{11}$-7 |
| 127 | CH | CH | CH | $Ar^{10}$ | $R^{11}$-8 |
| 128 | CH | CH | CH | $Ar^{10}$ | $R^{11}$-9 |
| 129 | CH | CH | CH | $Ar^{10}$ | $R^{11}$-10 |
| 130 | CH | CH | CH | $Ar^{10}$ | $R^{11}$-11 |
| 131 | CH | CH | CH | $Ar^{10}$ | $R^{11}$-12 |
| 132 | CH | CH | CH | $Ar^{10}$ | $R^{11}$-13 |
| 133 | CH | CH | CH | $Ar^{10}$ | $R^{11}$-14 |
| 134 | CH | CH | CH | $Ar^{10}$ | $R^{11}$-15 |
| 135 | CH | CH | CH | $Ar^{10}$ | $R^{11}$-16 |
| 136 | CH | CH | CH | $Ar^{10}$ | $R^{11}$-17 |
| 137 | CH | CH | CH | $Ar^{10}$ | $R^{11}$-18 |
| 138 | CH | CH | CH | $Ar^{10}$ | $R^{11}$-19 |
| 139 | CH | CH | CH | $Ar^{10}$ | $R^{11}$-20 |
| 140 | CH | CH | CH | $Ar^{10}$ | $R^{11}$-21 |
| 141 | CH | CH | CH | $Ar^{10}$ | $R^{11}$-22 |
| 142 | CH | CH | CH | $Ar^{10}$ | $R^{11}$-23 |
| 143 | CH | CH | CH | $Ar^{10}$ | $R^{11}$-25 |
| 144 | CH | CH | CH | $Ar^{10}$ | $R^{11}$-26 |
| 145 | CH | CH | CH | $Ar^{10}$ | $R^{11}$-27 |
| 146 | CH | CH | CH | $Ar^{10}$ | $R^{11}$-28 |
| 147 | CH | CH | CH | $Ar^{10}$ | $R^{11}$-29 |
| 148 | CH | CH | CH | $Ar^{10}$ | $A^{11}$-1 |
| 149 | CH | CH | CH | $Ar^{10}$ | $A^{11}$-2 |
| 150 | CH | CH | CH | $Ar^{10}$ | $A^{11}$-3 |
| 151 | CH | CH | CH | $Ar^{17}$ | $R^{11}$-1 |
| 152 | CH | CH | CH | $Ar^{17}$ | $R^{11}$-2 |
| 153 | CH | CH | CH | $Ar^{17}$ | $R^{11}$-3 |
| 154 | CH | CH | CH | $Ar^{17}$ | $R^{11}$-5 |
| 155 | CH | CH | CH | $Ar^{17}$ | $R^{11}$-6 |
| 156 | CH | CH | CH | $Ar^{17}$ | $R^{11}$-7 |
| 157 | CH | CH | CH | $Ar^{17}$ | $R^{11}$-8 |
| 158 | CH | CH | CH | $Ar^{17}$ | $R^{11}$-9 |
| 159 | CH | CH | CH | $Ar^{17}$ | $R^{11}$-10 |
| 160 | CH | CH | CH | $Ar^{17}$ | $R^{11}$-11 |
| 161 | CH | CH | CH | $Ar^{17}$ | $R^{11}$-12 |
| 162 | CH | CH | CH | $Ar^{17}$ | $R^{11}$-13 |
| 163 | CH | CH | CH | $Ar^{17}$ | $R^{11}$-14 |
| 164 | CH | CH | CH | $Ar^{17}$ | $R^{11}$-15 |
| 165 | CH | CH | CH | $Ar^{17}$ | $R^{11}$-16 |
| 166 | CH | CH | CH | $Ar^{17}$ | $R^{11}$-17 |
| 167 | CH | CH | CH | $Ar^{17}$ | $R^{11}$-18 |
| 168 | CH | CH | CH | $Ar^{17}$ | $R^{11}$-19 |
| 169 | CH | CH | CH | $Ar^{17}$ | $R^{11}$-20 |
| 170 | CH | CH | CH | $Ar^{17}$ | $R^{11}$-21 |
| 171 | CH | CH | CH | $Ar^{17}$ | $R^{11}$-22 |
| 172 | CH | CH | CH | $Ar^{17}$ | $R^{11}$-23 |
| 173 | CH | CH | CH | $Ar^{17}$ | $R^{11}$-25 |
| 174 | CH | CH | CH | $Ar^{17}$ | $R^{11}$-26 |
| 175 | CH | CH | CH | $Ar^{17}$ | $R^{11}$-27 |
| 176 | CH | CH | CH | $Ar^{17}$ | $R^{11}$-28 |
| 177 | CH | CH | CH | $Ar^{17}$ | $R^{11}$-29 |
| 178 | CH | CH | CH | $Ar^{17}$ | $A^{11}$-1 |
| 179 | CH | CH | CH | $Ar^{17}$ | $A^{11}$-2 |
| 180 | CH | CH | CH | $Ar^{17}$ | $A^{11}$-3 |
| 181 | CH | CH | CH | $Ar^{18}$ | $R^{11}$-1 |
| 182 | CH | CH | CH | $Ar^{18}$ | $R^{11}$-2 |
| 183 | CH | CH | CH | $Ar^{18}$ | $R^{11}$-3 |
| 184 | CH | CH | CH | $Ar^{18}$ | $R^{11}$-5 |
| 185 | CH | CH | CH | $Ar^{18}$ | $R^{11}$-6 |
| 186 | CH | CH | CH | $Ar^{18}$ | $R^{11}$-7 |
| 187 | CH | CH | CH | $Ar^{18}$ | $R^{11}$-8 |
| 188 | CH | CH | CH | $Ar^{18}$ | $R^{11}$-9 |
| 189 | CH | CH | CH | $Ar^{18}$ | $R^{11}$-10 |
| 190 | CH | CH | CH | $Ar^{18}$ | $R^{11}$-11 |
| 191 | CH | CH | CH | $Ar^{18}$ | $R^{11}$-12 |
| 192 | CH | CH | CH | $Ar^{18}$ | $R^{11}$-13 |
| 193 | CH | CH | CH | $Ar^{18}$ | $R^{11}$-14 |
| 194 | CH | CH | CH | $Ar^{18}$ | $R^{11}$-15 |
| 195 | CH | CH | CH | $Ar^{18}$ | $R^{11}$-16 |
| 196 | CH | CH | CH | $Ar^{18}$ | $R^{11}$-17 |
| 197 | CH | CH | CH | $Ar^{18}$ | $R^{11}$-18 |
| 198 | CH | CH | CH | $Ar^{18}$ | $R^{11}$-19 |
| 199 | CH | CH | CH | $Ar^{18}$ | $R^{11}$-20 |
| 200 | CH | CH | CH | $Ar^{18}$ | $R^{11}$-21 |
| 201 | CH | CH | CH | $Ar^{18}$ | $R^{11}$-22 |
| 202 | CH | CH | CH | $Ar^{18}$ | $R^{11}$-23 |
| 203 | CH | CH | CH | $Ar^{18}$ | $R^{11}$-25 |
| 204 | CH | CH | CH | $Ar^{18}$ | $R^{11}$-26 |
| 205 | CH | CH | CH | $Ar^{18}$ | $R^{11}$-27 |
| 206 | CH | CH | CH | $Ar^{18}$ | $R^{11}$-28 |
| 207 | CH | CH | CH | $Ar^{18}$ | $R^{11}$-29 |
| 208 | CH | CH | CH | $Ar^{18}$ | $A^{11}$-1 |
| 209 | CH | CH | CH | $Ar^{18}$ | $A^{11}$-2 |
| 210 | CH | CH | CH | $Ar^{18}$ | $A^{11}$-3 |

As used herein, the term "compound(s) of the present invention" or "compound(s) according to the invention" refers to the compound(s) of formula (I) as defined above, which are also referred to as "compound(s) of formula I" or "compound(s) I" or "formula I compound(s)", and includes their salts, tautomers, stereoisomers, and N-oxides.

Mixtures

The invention also relates to a mixture of at least one compound of the invention with at least one mixing partner. Preferred are binary mixtures of one compound of the invention as component I with one mixing partner herein as component II. Preferred weight ratios for such binary mixtures are from 5000:1 to 1:5000, preferably from 1000:1 to 1:1000, more preferably from 100:1 to 1:100, particularly from 10:1 to 1:10. In such binary mixtures, components I and II may be used in equal amounts, or an excess of component I, or an excess of component II may be used.

Mixing partners can be selected from pesticides, in particular insecticides, nematicides, and acaricides, fungicides, herbicides, plant growth regulators, fertilizers. Preferred mixing partners are insecticides, nematicides, and fungicides.

The following list M of pesticides, grouped according the Mode of Action Classification of the Insecticide Resistance Action Committee (IRAC), together with which the compounds of the invention can be used and with which potential synergistic effects might be produced, illustrates the possible combinations:

M.1 AChE inhibitors: aldicarb, alanycarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thiofanox, trimethacarb, XMC, xylylcarb, triazamate; acephate, azamethiphos, azinphos-ethyl, azinphosmethyl, cadusafos, chlorethoxyfos, chlorfenvinphos, chlormephos, chlorpyrifos, chlorpyrifos-methyl, coumaphos, cyanophos, demeton-S-methyl, diazinon, dichlorvos/DDVP, dicrotophos, dimethoate, dimethylvinphos, disulfoton, EPN, ethion, ethoprophos, famphur, fenamiphos, fenitrothion, fenthion, fosthiazate, heptenophos, imicyafos, isofenphos, isopropyl O-(methoxyaminothio-phosphoryl) salicylate, isoxathion, malathion, mecarbam, methamidophos, methidathion, mevinphos, monocrotophos, naled, omethoate, oxydemeton-methyl, parathion, parathion-methyl, phenthoate, phorate, phosalone, phosmet, phosphamidon, phoxim, pirimiphos-methyl, profenofos, propetamphos, prothiofos, pyraclofos, pyridaphenthion, quinalphos, sulfotep, tebupirimfos, temephos, terbufos, tetrachlorvinphos, thiometon, triazophos, trichlorfon, vamidothion;

M.2. GABA-gated chloride channel antagonists: cyclodiene organochlorine compounds: endo-sulfan, chlordane; phenylpyrazoles: ethiprole, fipronil, flufiprole, pyrafluprole, pyriprole;

M.3 Sodium channel modulators: pyrethroids: acrinathrin, allethrin, d-cis-trans allethrin, d-trans allethrin, bifenthrin, kappa-bifenthrin, bioallethrin, bioallethrin S-cylclopentenyl, bioresmethrin, cycloprothrin, cyfluthrin, beta-cyfluthrin, cyhalothrin, lambda-cyhalothrin, gamma-cyhalothrin, cypermethrin, alpha-cypermethrin, beta-cypermethrin, theta-cypermethrin, zeta-cypermethrin, cyphenothrin, deltamethrin, empenthrin, esfenvalerate, etofenprox, fenpropathrin, fenvalerate, flucythrinate, flumethrin, tau-fluvalinate, halfenprox, heptafluthrin, imiprothrin, meperfluthrin,metofluthrin, momfluorothrin, epsilon-momfluorothrin, permethrin, phenothrin, prallethrin, profluthrin, pyrethrin (pyrethrum), resmethrin, silafluofen, tefluthrin, kappa-tefluthrin, tetramethylfluthrin, tetramethrin, tralomethrin, transfluthrin; sodium channel modulatorse.g.: DDT, methoxychlor;

M.4 nAChR agonists: neonicotinoids: acetamiprid, clothianidin, cycloxaprid, dinotefuran, imidacloprid, nitenpyram, thiacloprid, thiamethoxam; 4,5-Dihydro-N-nitro-1-(2-oxiranylmethyl)-1H-imidazol-2-amine, (2E-)-1-[(6-Chloropyridin-3-yl)methyl]-N'-nitro-2-pentylidenehydrazinecarboximidamide; 1-[(6-Chloropyridin-3-yl)methyl]-7-methyl-8-nitro-5-propoxy-1,2,3,5,6,7-hexahydroimidazo[1,2-a]pyridine; nicotine; sulfoxaflor; flupyradifurone; triflumezopyrim, (3R)-3-(2-chlorothiazol-5-yl)-8-methyl-5-oxo-6-phenyl-2,3-dihydrothiazolo[3,2-a]pyrimidin-8-ium-7-olate, (3S)-3-(6-chloro-3-pyridyl)-8-methyl-5-oxo-6-phenyl-2,3-dihydrothiazolo[3,2-a]pyrimidin-8-ium-7-olate, (3S)-8-methyl-5-oxo-6-phenyl-3-pyrimidin-5-yl-2,3-dihydrothiazolo[3,2-a]pyrimidin-8-ium-7-olate, (3R)-3-(2-chlorothiazol-5-yl)-8-methyl-5-oxo-6-[3-(trifluoromethyl)phenyl]-2,3-dihydrothiazolo[3,2-a]pyrimidin-8-ium-7-olate; (3R)-3-(2-chlorothiazol-5-yl)-6-(3,5-dichlorophenyl)-8-methyl-5-oxo-2,3-dihydrothiazolo[3,2-a]pyrimidin-8-ium-7-olate, (3R)-3-(2-chlorothiazol-5-yl)-8-ethyl-5-oxo-6-phenyl-2,3-dihydrothiazolo[3,2-a]pyrimidin-8-ium-7-olate;

M.5 Nicotinic acetylcholine receptor allosteric activators: spinosad, spinetoram;

M.6 Chloride channel activators: abamectin, emamectin benzoate, ivermectin, lepimectin, milbemectin;

M.7 Juvenile hormone mimicse.g.: hydroprene, kinoprene, methoprene; fenoxycarb, pyriproxyfen;

M.8 miscellaneous multi-site inhibitors: $CH_3Br$, other alkyl halides, chloropicrin, sulfuryl fluoride, borax, tartar emetic;

M.9 Chordotonal organ TRPV channel modulators: pymetrozine; pyrifluquinazon;

M.10 Mite growth inhibitors: clofentezine, hexythiazox, diflovidazin, etoxazole;

M.11 Microbial disruptors of insect midgut membranes: *Bacillus thuringiensis, Bacillus sphaericus*, and insecticdal proteins they producee.g.: *Bacillus thuringiensis* subsp. *israelensis, Bacillus sphaericus, Bacillus thuringiensis* subsp. *aizawai, Bacillus thuringiensis* subsp. kurstaki, *Bacillus thuringiensis* subsp. *tenebrionis*, Bt crop proteins: Cry1Ab, Cry1Ac, Cry1Fa, Cry2Ab, mCry3A, Cry3Ab, Cry3Bb, Cry34/35Ab1;

M.12 Inhibitors of mitochondrial ATP synthase: diafenthiuron, organotin miticidese.g.: azocyclotin, cyhexatin, fenbutatin oxide, propargite, tetradifon;

M.13 Uncouplers of oxidative phosphorylation via disruption of the proton gradient: chlorfenapyr, DNOC, sulfluramid;

M.14 nAChR channel blockers: nereistoxin analogues bensultap, cartap hydrochloride, thiocyclam, thiosultap-sodium;

M.15 Inhibitors of the chitin biosynthesis type Oe.g.: bistrifluron, chlorfluazuron, diflubenzuron, flucycloxuron, flufenoxuron, hexaflumuron, lufenuron, novaluron, noviflumuron, teflubenzuron, triflumuron;

M.16 Inhibitors of the chitin biosynthesis type 1: buprofezin;

M.17 Moulting disruptors: Dipteran, cyromazine;

M.18 Ecdyson receptor agonistse.g.: methoxyfenozide, tebufenozide, halofenozide, fufenozide, chromafenozide;

M.19 Octopamin receptor agonists: amitraz;

M.20 Mitochondrial complex III electron transport inhibitors: hydramethylnon, acequinocyl, fluacrypyrim; bifenazate;

M.21 METI acaricides and insecticidese.g.: fenazaquin, fenpyroximate, pyrimidifen, pyridaben, tebufenpyrad, tolfenpyrad, rotenone;

M.22 Voltage-dependent sodium channel blockers: indoxacarb, metaflumizone, 2-[2-(4-cyanophenyl)-1-[3-(trifluoromethyl)phenyl]ethylidene]-N-[4-(difluoromethoxy)phenyl]-hydrazinecarboxamide, N-(3-chloro-2-methylphenyl)-2-[(4-chlorophenyl)[4-[methyl(methylsulfonyl)amino]phenyl]methylene]-hydrazinecarboxamide;

M.23 Inhibitors of the of acetyl CoA carboxylasee.g.: spirodiclofen, spiromesifen, spirotetramat; spiropidion;

M.24 Mitochondrial complex IV electron transport inhibitors: e.g.aluminium phosphide, calcium phosphide, zinc phosphide, cyanide;

M.25 Mitochondrial complex II electron transport inhibitorse.g.: cyenopyrafen, cyflumetofen;

M.28 Ryanodine receptor-modulators: flubendiamide, chlorantraniliprole, cyantraniliprole, tetra-niliprole, (R)-3-chloro-N1-{2-methyl-4-[1,2,2,2-tetrafluoro-1-(trifluoromethyl)ethyl]phenyl}-N2-(1-methyl-2-methylsulfonylethyl)phthalamid, (S)-3-chloro-N1-{2-methyl-4-[1,2,2,2-tetrafluoro-1-(trifluoromethyl)ethyl]phenyl}-N2-(1-methyl-2-methylsulfonylethyl) phthalamide, cyclaniliprole, methyl-2-[3,5-dibromo-2-({[3-bromo-1-(3-chlorpyridin-2-yl)-1H-pyrazol-5-yl]carbonyl}-amino)benzoyl]-1,2-dimethylhydrazinecarboxylate; N-[2-(5-amino-1,3,4-thiadiazol-2-yl)-4-chloro-6-methylphenyl]-3-bromo-1-(3-chloro-2-pyridinyl)-1H-pyrazole-5-carboxamide; 3-chloro-1-(3-chloro-2-pyridinyl)-N-[2,4-dichloro-6-[[(1-cyano-1-methylethyl)amino]carbonyl]phenyl]-1H-pyrazole-5-carboxamide; tetrachlorantraniliprole; N-[4-chloro-2-[[(1,1-dimethylethyl)amino]carbonyl]-6-methylphenyl]-1-(3-chloro-2-pyridinyl)-3-(fluoromethoxy)-1H-pyrazole-5-carboxamide; cyhalodiamide;

M.29: Chordotonal organ Modulators: flonicamid;

M.UN. Unknown mode of action: afidopyropen, afoxolaner, azadirachtin, amidoflumet, benzoximate, broflanilide, bromopropylate, chinomethionat, cryolite, dicloromezotiaz, dicofol, dimpropyridaz, flufenerim, flometoquin, fluensulfone, fluhexafon, fluopyram, fluralaner, metaldehyde, metoxadiazone, piperonyl butoxide, pyflubumide, pyridalyl, tioxazafen, 11-(4-chloro-2,6-dimethylphenyl)-12-hydroxy-1,4-dioxa-9-azadispiro[4.2.4.2]-tetradec-11-en-10-one, 3-(4'-fluoro-2,4-dimethylbiphenyl-3-yl)-4-hydroxy-8-oxa-1-azaspiro[4.5]dec-3-en-2-one, 1-[2-fluoro-4-methyl-5-[(2,2,2-trifluoroethyl)sulfinyl]phenyl]-3-(trifluoromethyl)-1H-1,2,4-triazole-5-amine, actives on basis of *Bacillus firmus* (Votivo, I-1582); flupyrimin; fluazaindolizine; 4-[5-(3,5-dichlorophenyl)-5-(trifluoromethyl)-4H-isoxazol-3-yl]-2-methyl-N-(1-oxothietan-3-yl)benzamide; fluxametamide; 5-[3-[2,6-dichloro-4-(3,3-dichloroallyloxy)phenoxy]propoxy]-1H-pyrazole; 4-cyano-N-[2-cyano-5-[[2,6-dibromo-4-[1,2,2,3,3,3-hexafluoro-1-(trifluoromethyl)-propyl]phenyl]carbamoyl]phenyl]-2-methyl-benzamide; 4-cyano-3-[(4-cyano-2-methyl-benzoyl)amino]-N-[2,6-dichloro-4-[1,2,2,3,3,3-hexafluoro-1-(trifluoromethyl)propyl]phenyl]-2-fluoro-benzamide; N-[5-[[2-chloro-6-cyano-4-[1,2,2,3,3,3-hexafluoro-1-(trifluoromethyl)propyl]phenyl]carbamoyl]-2-cyano-phenyl]-4-cyano-2-methyl-benzamide; N-[5-[[2-bromo-6-chloro-4-[2,2,2-trifluoro-1-hydroxy-1-(trifluoromethyl)ethyl]phenyl]carbamoyl]-2-cyano-phenyl]-4-cyano-2-methyl-benzamide; N-[5-[[2-bromo-6-chloro-4-[1,2,2,3,3,3-hexafluoro-1-(trifluoromethyl)propyl]phenyl]carbamoyl]-2-cyano-phenyl]-4-cyano-2-methyl-benzamide; 4-cyano-N-[2-cyano-5-[[2,6-dichloro-4-[1,2,2,3,3,3-hexafluoro-1-(trifluoromethyl)-propyl]phenyl]carbamoyl]phenyl]-2-methyl-benzamide; 4-cyano-N-[2-cyano-5-[[2,6-dichloro-4-[1,2,2,2-tetrafluoro-1-(trifluoromethyl)ethyl]phenyl]carbamoyl]phenyl]-2-methyl-benzamide; N-[5-[[2-bromo-6-chloro-4-[1,2,2,2-tetrafluoro-1-(trifluoromethyl)ethyl]phenyl]carbamoyl]-2-cyano-phenyl]-4-cyano-2-methyl-benzamide; 2-(1,3-dioxan-2-yl)-6-[2-(3-pyridinyl)-5-thiazolyl]-pyridine; 2-[6-[2-(5-fluoro-3-pyridinyl)-5-thiazolyl]-2-pyridinyl]-pyrimidine; 2-[6-[2-(3-pyridinyl)-5-thiazolyl]-2-pyridinyl]-pyrimidine; N-methylsulfonyl-6-[2-(3-pyridyl)thiazol-5-yl]pyridine-2-carboxamide; N-methylsulfonyl-6-[2-(3-pyridyl)thiazol-5-yl]pyridine-2-carboxamide; 1-[(6-chloro-3-pyridinyl)methyl]-1,2,3,5,6,7-hexahydro-5-methoxy-7-methyl-8-nitro-imidazo[1,2-a]pyridine; 1-[(6-chloropyridin-3-yl)methyl]-7-methyl-8-nitro-1,2,3,5,6,7-hexahydroimidazo[1,2-a]pyridin-5-ol; N-(1-methylethyl)-2-(3-pyridinyl)-2H-indazole-4-carboxamide; N-cyclopropyl-2-(3-pyridinyl)-2H-indazole-4-carboxamide; N-cyclohexyl-2-(3-pyridinyl)-2H-indazole-4-carboxamide; 2-(3-pyridinyl)-N-(2,2,2-trifluoroethyl)-2H-indazole-4-carboxamide; 2-(3-pyridinyl)-N-[(tetrahydro-2-furanyl)methyl]-2H-indazole-5-carboxamide; methyl 2-[[2-(3-pyridinyl)-2H-indazol-5-yl]carbonyl]hydrazinecarboxylate; N-[(2,2-difluorocyclopropyl)methyl]-2-(3-pyridinyl)-2H-indazole-5-carboxamide; N-(2,2-difluoropropyl)-2-(3-pyridinyl)-2H-indazole-5-carboxamide; 2-(3-pyridinyl)-N-(2-pyrimidinylmethyl)-2H-indazole-5-carboxamide; N-[(5-methyl-2-pyrazinyl)methyl]-2-(3-pyridinyl)-2H-indazole-5-carboxamide, tyclopyrazoflor; sarolaner, lotilaner; N-[4-chloro-3-[[(phenylmethyl)amino]carbonyl]phenyl]-1-methyl-3-(1,1,2,2,2-pentafluoroethyl)-4-(trifluoromethyl)-1H-pyrazole-5-carboxamide; 2-(3-ethylsulfonyl-2-pyridyl)-3-methyl-6-(trifluoromethyl)imidazo[4,5-b]pyridine, 2-[3-ethylsulfonyl-5-(trifluoromethyl)-2-pyridyl]-3-methyl-6-(trifluoromethyl)imidazo[4,5-b]pyridine; Isocycloseram; N-[4-chloro-3-(cyclopropylcarbamoyl)phenyl]-2-methyl-5-(1,1,2,2,2-pentafluoroethyl)-4-(trifluoromethyl)pyrazole-3-carboxamide, N-[4-chloro-3-[(1-cyanocyclopropyl)carbamoyl]phenyl]-2-methyl-5-(1,1,2,2,2-pentafluoroethyl)-4-(trifluoromethyl)pyrazole-3-carboxamide; acynonapyr; benzpyrimoxan; tigolaner; oxazosulfyl; [(2S,3R,4R,5S,6S)-3,5-dimethoxy-6-methyl-4-propoxy-tetrahydropyran-2-yl] N-[4-[1-[4-(trifluoromethoxy)phenyl]-1,2,4-triazol-3-yl]phenyl]carbamate; [(2S,3R,4R,5S,6S)-3,4,5-trimethoxy-6-methyl-tetrahydropyran-2-yl] N-[4-[1-[4-(trifluoromethoxy)phenyl]-1,2,4-triazol-3-yl]phenyl]carbamate; [(2S,3R,4R,5S,6S)-3,5-dimethoxy-6-methyl-4-propoxy-tetrahydropyran-2-yl] N-[4-[1-[4-(1,1,2,2,2-pentafluoroethoxy)phenyl]-1,2,4-triazol-3-yl]phenyl]carbamate; [(2S,3R,4R,5S,6S)-3,4,5-trimethoxy-6-methyl-tetrahydropyran-2-yl] N-[4-[1-[4-(1,1,2,2,2-pentafluoroethoxy)phenyl]-1,2,4-triazol-3-yl]phenyl]carbamate; (2Z)-3-(2-isopropylphenyl)-2-[(E)-[4-[1-[4-(trifluoromethoxy)phenyl]-1,2,4-triazol-3-yl]phenyl]methylenehydrazono]thiazolidin-4-one, (2Z)-3-(2-isopropylphenyl)-2-[(E)-[4-[1-[4-(1,1,2,2,2-pentafluoroethoxy)phenyl]-1,2,4-triazol-3-yl]phenyl]methylenehydrazono]thiazolidin-4-one; 2-(6-chloro-3-ethylsulfonyl-imidazo[1,2-a]pyridin-2-yl)-3-methyl-6-(trifluoromethyl)imidazo[4,5-b]pyridine, 2-(6-bromo-3-ethylsulfonyl-imidazo[1,2-a]pyridin-2-yl)-3-methyl-6-(trifluoromethyl)imidazo[4,5-b]pyridine, 2-(3-ethylsulfonyl-6-iodo-imidazo[1,2-a]pyridin-2-yl)-3-methyl-6-(trifluoromethyl)imidazo[4,5-b]pyridine, 2-[3-ethylsulfonyl-6-(trifluoromethyl)imidazo[1,2-a]pyridin-2-yl]-3-methyl-6-(trifluoromethyl)imidazo[4,5-b]pyridine, 2-(7-chloro-3-ethylsulfonyl-imidazo[1,2-a]pyridin-2-yl)-3-methyl-6-(trifluoromethyl)imidazo[4,5-b]pyridine, 2-(3-ethylsulfonyl-7-iodo-imidazo[1, 2-a]pyridin-2-yl)-3-methyl-6-(trifluoromethyl)imidazo[4,5-b]pyridine, 3-ethylsulfonyl-6-iodo-2-[3-methyl-6-(trifluoromethyl)imidazo[4,5-b]pyridin-2-yl]imidazo[1,2-a]pyridine-8-carbonitrile, 2-[3-ethylsulfonyl-8-fluoro-6-(trifluoromethyl)imidazo[1,2-a]pyridin-2-yl]-3-methyl-6-(trifluoromethyl)imidazo[4,5-b]pyridine, 2-[3-ethylsulfonyl-7-(trifluoromethyl)imidazo[1,2-a]pyridin-2-yl]-3-methyl-6-(trifluoromethylsulfinyl)imidazo[4,5-b]pyridine, 2-[3-ethylsulfonyl-7-(trifluoromethyl)imidazo[1,2-a]pyridin-2-yl]-3-methyl-6-(trifluoromethyl)imidazo[4,5-c]pyridine, 2-(6-bromo-3-ethylsulfonyl-imidazo[1,2-a]pyridin-2-yl)-6-(trifluoromethyl)pyrazolo[4,3-c]pyridine.

The commercially available compounds M listed above may be found in The Pesticide Manual, 18th Edition, C. MacBean, British Crop Protection Council (2018), or http://bcpcdata.com/pesticide-manual.html, http://www.alanwood.net/pesticides.

The active compounds described by IUPAC nomenclature are known from CN103814937; WO2013/003977, WO2007/101369, WO2018/177970, CN10171577, CN102126994, WO2007/101540, WO2007/043677, WO2011/085575, WO2008/134969, WO2012/034403, WO2006/089633, WO2008/067911, WO2006/043635, WO2009/124707, WO2013/050317, WO2010/060379, WO2010/127926, WO2010/006713, WO2012/000896, WO2007/101369, WO2012/143317, WO2015/038503, EP2910126, WO2015/059039, WO2015/190316, WO2012/126766, WO2009/102736, WO2013/116053, WO2018/052136.

The following list of fungicides, in conjunction with which the compounds of the invention can be used, illustrates the possible combinations:

A) Respiration Inhibitors

Inhibitors of complex III at $Q_o$ site: azoxystrobin, coumethoxystrobin, coumoxystrobin, dimoxystrobin, enestroburin, fenaminstrobin, fenoxystrobin/flufenoxystrobin, fluoxastrobin, kresoxim-methyl, mandestrobin, metominostrobin, orysastrobin, picoxystrobin, pyraclostrobin, pyrametostrobin, pyraoxystrobin, trifloxystrobin, 2-(2-(3-(2,6-dichlorophenyl)-1-methyl-allylidene-aminooxymethyl)-phenyl)-2-methoxy-imino-N-methyl-acetamide, pyribencarb, triclopyricarb/chlorodincarb, famoxadone, fenamidone, methyl-N-[2-[(1,4-dimethyl-5-phenyl-pyrazol-3-yl)oxylmethyl]phenyl]-N-methoxy-carbamate, metyltetrapole, (Z,2E)-5-[1-(2,4-dichloro-phenyl)pyrazol-3-yl]-oxy-2-methoxyimino-N,3-dimethyl-pent-3-enamide, (Z,2E)-5-[1-(4-chlorophenyl)pyrazol-3-yl]oxy-2-methoxyimino-N,3-dimethyl-pent-3-enamide, pyriminostrobin, bifujunzhi, 2-(ortho-((2,5-dimethylphenyl-oxymethylen)phenyl)-3-methoxy-acrylic acid methylester;

inhibitors of complex III at $Q_i$ site: cyazofamid, amisulbrom, [(6S,7R,8R)-8-benzyl-3-[(3-hydroxy-4-methoxy-pyridine-2-carbonyl)amino]-6-methyl-4,9-dioxo-1,5-dioxonan-7-yl] 2-methylpropanoate, fenpicoxamid, florylpicoxamid;

inhibitors of complex II: benodanil, benzovindiflupyr, bixafen, boscalid, carboxin, fenfuram, fluopyram, flutolanil, fluxapyroxad, furametpyr, isofetamid, isopyrazam, mepronil, oxycarboxin, penflufen, penthiopyrad), pydiflumetofen, pyraziflumid, sedaxane, tecloftalam, thifluzamide, in-pyrfluxam, pyrapropoyne, fluindapyr, N-[2-[2-chloro-4-(trifluoromethyl)phenoxy]phenyl]-3-(difluoromethyl)-5-fluoro-1-methyl-pyrazole-4-carboxamide, methyl (E)-2-[2-[(5-cyano-2-methyl-phenoxy)methyl]phenyl]-3-methoxy-prop-2-enoate, isoflucypram, 2-(difluoromethyl)-N-(1,1,3-trimethyl-indan-4-yl)pyridine-3-carboxamide, 2-(difluoromethyl)-N-[(3R)-1,1,3-trimethylindan-4-yl]pyridine-3-carboxamide, 2-(difluoromethyl)-N-(3-ethyl-1,1-dimethyl-indan-4-yl)pyridine-3-carboxamide, 2-(difluoromethyl)-N-[(3R)-3-ethyl-1,1-dimethyl-indan-4-yl]pyridine-3-carboxamide, 2-(difluoromethyl)-N-(1,1-dimethyl-3-propyl-indan-4-yl)pyridine-3-carboxamide, 2-(difluoromethyl)-N-[(3R)-1,1-dimethyl-3-propyl-indan-4-yl]pyridine-3-carboxamide, 2-(difluoromethyl)-N-(3-isobutyl-1,1-dimethyl-indan-4-yl)pyridine-3-carboxamide, 2-(difluoromethyl)-N-[(3R)-3-isobutyl-1,1-dimethyl-indan-4-yl]pyridine-3-carboxamide;

other respiration inhibitors: diflumetorim; nitrophenyl derivates: binapacryl, dinobuton, dinocap, fluazinam, meptyldinocap, ferimzone; organometal compounds: fentin salts, e.g. fentin-acetate, fentin chloride, fentin hydroxide; ametoctradin; silthiofam;

B) Sterol Biosynthesis Inhibitors (SBI Fungicides)

C14 demethylase inhibitors: triazoles: azaconazole, bitertanol, bromuconazole, cypro-conazole, difenoconazole, diniconazole, diniconazole-M, epoxiconazole, fenbuconazole, fluquinconazole, flusilazole, flutriafol, hexaconazole, imibenconazole, ipconazole, metconazole, myclobutanil, oxpoconazole, paclobutrazole, penconazole, propiconazole, prothioconazole, simeconazole, tebuconazole, tetraconazole, triadimefon, triadimenol, triticonazole, uniconazole, 2-(2,4-difluorophenyl)-1,1-difluoro-3-(tetrazol-1-yl)-1-[5-[4-(2,2,2-trifluoroethoxy)phenyl]-2-pyridyl]propan-2-ol, 2-(2,4-difluorophenyl)-1,1-difluoro-3-(tetrazol-1-yl)-1-[5-[4-(trifluoromethoxy)phenyl]-2-pyridyl]propan-2-ol, 4-[[6-[2-(2,4-difluorophenyl)-1,1-difluoro-2-hydroxy-3-(5-sulfanyl-1,2,4-triazol-1-yl)propyl]-3-pyridyl]oxy]benzonitrile, ipfentrifluconazole, mefentrifluconazole, 2-(chloromethyl)-2-methyl-5-(p-tolylmethyl)-1-(1,2,4-triazol-1-ylmethyl)cyclopentanol; imidazoles: imazalil, pefurazoate, prochloraz, triflumizol; pyrimidines, pyridines, piperazines: fenarimol, pyrifenox, triforine, [3-(4-chloro-2-fluoro-phenyl)-5-(2,4-difluoro-phenyl)isoxazol-4-yl]-(3-pyridyl)methanol;

Delta14-reductase inhibitors: aldimorph, dodemorph, dodemorph-acetate, fenpropimorph, tridemorph, fenpropidin, piperalin, spiroxamine;

Inhibitors of 3-keto reductase: fenhexamid;

Other Sterol biosynthesis inhibitors: chlorphenomizole;

C) Nucleic Acid Synthesis Inhibitors phenylamides or acyl amino acid fungicides: benalaxyl, benalaxyl-M, kiralaxyl, metalaxyl, metalaxyl-M, ofurace, oxadixyl;

other nucleic acid synthesis inhibitors: hymexazole, octhilinone, oxolinic acid, bupirimate, 5-fluorocytosine, 5-fluoro-2-(p-tolylmethoxy)pyrimidin-4-amine, 5-fluoro-2-(4-fluorophenyl-methoxy)pyrimidin-4-amine, 5-fluoro-2-(4-chlorophenylmethoxy)pyrimidin-4 amine;

D) Inhibitors of Cell Division and Cytoskeleton tubulin inhibitors: benomyl, carbendazim, fuberidazole, thiabendazole, thiophanate-methyl, pyridachlometyl, N-ethyl-2-[(3-ethynyl-8-methyl-6-quinolyl)oxy]butanamide, N-ethyl-2-[(3-ethynyl-8-methyl-6-quinolyl)oxy]-2-methylsulfanyl-acetamide, 2-[(3-ethynyl-8-methyl-6-quinol-yl)oxy]-N-(2-fluoroethyl)butanamide, 2-[(3-ethynyl-8-methyl-6-quinolyl)oxy]-N-(2-fluoroethyl)-2-methoxy-acetamide, 2-[(3-ethynyl-8-methyl- 6-quinolyl)oxy]-N-propyl-butanamide, 2-[(3-ethynyl-8-methyl-6-quinolyl)oxy]-2-methoxy-N-propyl-acetamide, 2-[(3-ethynyl-8-methyl-6-quinolyl)oxy]-2-methylsulfanyl-N-propyl-acetamide, 2-[(3-ethynyl-8-methyl-6-quinolyl)oxy]-N-(2-fluoroethyl)-2-methylsulfanyl-acetamide, 4-(2-bromo-4-fluoro-phenyl)-N-(2-chloro-6-fluoro-phenyl)-2,5-dimethyl-pyrazol-3-amine;

other cell division inhibitors: diethofencarb, ethaboxam, pencycuron, fluopicolide, zoxamide, metrafenone, pyriofenone, phenamacril;

E) Inhibitors of Amino Acid and Protein Synthesis methionine synthesis inhibitors: cyprodinil, mepanipyrim, pyrimethanil;

protein synthesis inhibitors: blasticidin-S, kasugamycin, kasugamycin hydrochloride-hydrate, mildiomycin, streptomycin, oxytetracyclin;

F) Signal Transduction Inhibitors

MAP/histidine kinase inhibitors: fluoroimid, iprodione, procymidone, vinclozolin, fludioxonil;

G protein inhibitors: quinoxyfen;

G) Lipid and Membrane Synthesis Inhibitors

Phospholipid biosynthesis inhibitors: edifenphos, iprobenfos, pyrazophos, isoprothiolane;

lipid peroxidation: dicloran, quintozene, tecnazene, tolclofos-methyl, biphenyl, chloroneb, etridiazole, zinc thiazole;

phospholipid biosynthesis and cell wall deposition: dimethomorph, flumorph, mandipropamid, pyrimorph, benthiavalicarb, iprovalicarb, valifenalate;

compounds affecting cell membrane permeability and fatty acids: propamocarb;

inhibitors of oxysterol binding protein: oxathiapiprolin, fluoxapiprolin, 4-[1-[2-[3-(difluoro-methyl)-5-methyl-pyrazol-1-yl]acetyl]-4-piperidyl]-N-tetralin-1-yl-pyridine-2-carboxamide, 4-[1-[2-[3,5-bis(difluoromethyl)pyrazol-1-yl]acetyl]-4-piperidyl]-N-tetralin-1-yl-pyridine-2-carboxamide, 4-[1-[2-[3-(difluoromethyl)-5-(trifluoromethyl)pyrazol-1-yl]acetyl]-4-piperidyl]-N-tetralin-1-yl-pyridine-2-carboxamide, 4-[1-[2-[5-cyclopropyl-3-(difluoromethyl)pyrazol-1-yl]acetyl]-4-piperidyl]-N-tetralin-1-yl-pyridine-2-carboxamide, 4-[1-[2-[5-methyl-3-(trifluoromethyl)pyrazol-1-yl]acetyl]-4-piperidyl]-N-tetralin-1-yl-pyridine-2-carboxamide, 4-[1-[2-[5-(difluoromethyl)-3-(trifluoromethyl)pyrazol-1-yl]acetyl]-4-piperidyl]-N-tetralin-1-yl-pyridine-2-carboxamide, 4-[1-[2-[3,5-bis(trifluoromethyl)pyrazol-1-yl]acetyl]-4-piperidyl]-N-tetralin-1-yl-pyridine-2-carboxamide, (4-[1-[2-[5-cyclopropyl-3-(trifluoromethyl)pyrazol-1-yl]acetyl]-4-piperidyl]-N-tetralin-1-yl-pyridine-2-carboxamide;

H) Inhibitors with Multi Site Action inorganic active substances: Bordeaux mixture, copper, copper acetate, copper hydroxide, copper oxychloride, basic copper sulfate, sulfur;

thio- and dithiocarbamates: ferbam, mancozeb, maneb, metam, metiram, propineb, thiram, zineb, ziram;

organochlorine compounds: anilazine, chlorothalonil, captafol, captan, folpet, dichlofluanid, dichlorophen, hexachlorobenzene, pentachlorphenole and its salts, phthalide, tolylfluanid;

guanidines and others: guanidine, dodine, dodine free base, guazatine, guazatine-acetate, iminoctadine, iminoctadine-triacetate, iminoctadine-tris(albesilate), dithianon, 2,6-dimethyl-1H,5H-[1,4]dithiino[2,3-c:5,6-c']dipyrrole-1,3,5,7(2H,6H)-tetraone;

I) Cell Wall Synthesis Inhibitors inhibitors of glucan synthesis: validamycin, polyoxin B;

melanin synthesis inhibitors: pyroquilon, tricyclazole, carpropamid, dicyclomet, fenoxanil;

J) Plant Defence Inducers acibenzolar-S-methyl, probenazole, isotianil, tiadinil, prohexadione-calcium; phosphonates: fosetyl, fosetyl-aluminum, phosphorous acid and its salts, calcium phosphonate, potassium phosphonate, potassium or sodium bicarbonate, 4-cyclopropyl-N-(2,4-dimethoxy-phenyl)thiadiazole-5-carboxamide;

K) Unknown Mode of Action bronopol, chinomethionat, cyflufenamid, cymoxanil, dazomet, debacarb, diclocymet, diclo-mezine, difenzoquat, difenzoquat-methylsulfate, diphenylamin, fenitropan, fenpyrazamine, flu-metover, flusulfamide, flutianil, harpin, methasulfocarb, nitrapyrin, nitrothal-isopropyl, tolprocarb, oxin-copper, proquinazid, tebufloquin, tecloftalam, triazoxide, N'-(4-(4-chloro-3-trifluoromethyl-phenoxy)-2,5-dimethyl-phenyl)-N-ethyl-N-methyl formamidine, N'-(4-(4-fluoro-3-trifluoromethyl-phenoxy)-2,5-dimethyl-phenyl)-N-ethyl-N-methyl formamidine, N'-[4-[[3-[(4-chlorophenyl)methyl]-1,2,4-thiadiazol-5-yl]oxy]-2,5-dimethyl-phenyl]-N-ethyl-N-methyl-formamidine, N'-(5-bromo-6-indan-2-yloxy-2-methyl-3-pyridyl)-N-ethyl-N-methyl-formamidine, N'-[5-bromo-6-[1-(3,5-difluorophenyl)ethoxy]-2-methyl-3-pyridyl]-N-ethyl-N-methyl-formamidine, N'-[5-bromo-6-(4-isopropylcyclohexoxy)-2-methyl-3-pyridyl]-N-ethyl-N-methyl-formamidine, N'-[5-bromo-2-methyl-6-(1-phenylethoxy)-3-pyridyl]-N-ethyl-N-methyl-formamidine, N'-(2-methyl-5-trifluoromethyl-4-(3-trimethylsilanyl-propoxy)-phenyl)-N-ethyl-N-methyl formamidine, N'-(5-difluoromethyl-2-methyl-4-(3-trimethylsilanyl-propoxy)-phenyl)-N-ethyl-N-methyl formamidine, 2-(4-chloro-phenyl)-N-[4-(3,4-dimethoxy-phenyl)-isoxazol-5-yl]-2-prop-2-ynyloxy-acetamide, 3-[5-(4-chloro-phenyl)-2,3-dimethyl-isoxazolidin-3-yl]-pyridine (pyrisoxazole) 3-[5-(4-methylphenyl)-2,3-dimethyl-isoxazolidin-3 yl]-pyridine, 5-chloro-1-(4,6-dimethoxy-pyrimidin-2-yl)-2-methyl-1H-benzoimidazole, ethyl (Z)-3-amino-2-cyano-3-phenyl-prop-2-enoate (K.1.40), picarbutrazox, pentyl N-[6-[[(Z)-[(1-methyltetrazol-5-yl)-phenyl-methylene]amino]oxymethyl]-2-pyridyl]carbamate, but-3-ynyl N-[6-[[(Z)-[(1-methyltetrazol-5-yl)-phenyl-methylene]amino]oxymethyl]-2-pyridyl]carbamate, ipflufenoquin, quinofumelin, benziothiazolinone, bromothalonil, 2-(6-benzyl-2-pyridyl)quinazoline, 2-[6-(3-fluoro-4-methoxy-phenyl)-5-methyl-2-pyridyl]quinazoline, dichlobentiazox, N'-(2,5-dimethyl-4-phenoxy-phenyl)-N-ethyl-N-methyl-formamidine, pyrifenamine, fluopimomide, N-[5-bromo-2-methyl-6-(1-methyl-2-propoxy-ethoxy)-3-pyridyl]-N-ethyl-N-methyl-formamidine;

The fungicides described by common names, their preparation and their activity e.g. against harmful fungi is known (cf.: http://www.alanwood.net/pesticides/); these substances are commercially available.

The active substances referred to as component 2, their preparation and their activity e.g. against harmful fungi is known (cf.: http://www.alanwood.net/pesticides/); these substances are commercially available. The compounds described by IUPAC nomenclature, their preparation and their pesticidal activity are also known (cf. Can. J. Plant Sci. 48(6), 587-94, 1968; EP 141 317; EP 152 031; EP 226 917; EP 243 970; EP 256 503; EP 428 941; EP 532 022; EP 1 028

125; EP 1 035 122; EP 1 201 648; EP 1122 244, JP 2002316902; DE 19650197; DE 10021412; DE 102005009458; U.S. Pat. Nos. 3,296,272; 3,325,503; WO 98/46608; WO 99/14187; WO 99/24413; WO 99/27783; WO 00/29404; WO 00/46148; WO 00/65913; WO 01/54501; WO 01/56358; WO 02/22583; WO 02/40431; WO 03/10149; WO 03/11853; WO 03/14103; WO 03/16286; WO 03/53145; WO 03/61388; WO 03/66609; WO 03/74491; WO 04/49804; WO 04/83193; WO 05/120234; WO 05/123689; WO 05/123690; WO 05/63721; WO 05/87772; WO 05/87773; WO 06/15866; WO 06/87325; WO 06/87343; WO 07/82098; WO 07/90624, WO 10/139271, WO 11/028657, WO 12/168188, WO 07/006670, WO 11/77514; WO 13/047749, WO 10/069882, WO 13/047441, WO 03/16303, WO 09/90181, WO 13/007767, WO 13/010862, WO 13/127704, WO 13/024009, WO 13/24010, WO 13/047441, WO 13/162072, WO 13/092224, WO 11/135833, CN 1907024, CN 1456054, CN 103387541, CN 1309897, WO 12/84812, CN 1907024, WO 09094442, WO 14/60177, WO 13/116251, WO 08/013622, WO 15/65922, WO 94/01546, EP 2865265, WO 07/129454, WO 12/165511, WO 11/081174, WO 13/47441). Some compounds are identified by their CAS Registry Number.

Biopesticides

Suitable mixing partners for the compounds of the invention also include biopesticides.

Biopesticides have been defined as a form of pesticides based on micro-organisms (bacteria, fungi, viruses, nematodes, etc.) or natural products (compounds, e.g. metabolites, proteins, or extracts from biological or other natural sources) (U.S. Environmental Protection Agency: http://www.epa.gov/pesticides/biopesticides/). Biopesticides fall into two major classes, microbial and biochemical pesticides:

(1) Microbial pesticides consist of bacteria, fungi or viruses (and often include the metabolites that bacteria and fungi produce). Entomopathogenic nematodes are also classified as microbial pesticides, even though they are multi-cellular.

(2) Biochemical pesticides are naturally occurring substances or or structurally-similar and functionally identical to a naturally-occurring substance and extracts from biological sources that control pests or provide other crop protection uses as defined below, but have non-toxic mode of actions (e.g. growth or developmental regulation, attractants, repellents or defence activators (e.g. induced resistance) and are relatively non-toxic to mammals.

The following list of biopesticides, in conjunction with which the compounds of the invention can be used, illustrates the possible combinations:

L) Biopesticides

L1) Microbial pesticides with fungicidal, bactericidal, viricidal and/or plant defense activator activity: *Ampelomyces quisqualis, Aspergillus flavus, Aureobasidium pullulans, Bacillus altitudinis, B. amyloliquefaciens, B. amyloliquefaciens* ssp. *plantarum* (*B. velezensis*), *B. megaterium, B. mojavensis, B. mycoides, B. pumilus, B. simplex, B. solisalsi, B. subtilis, B. subtilis* var. *amyloliquefaciens, B. velezensis, Candida oleophila, C. saitoana, Clavibacter michiganensis* (bacteriophages), *Coniothyrium minitans, Cryphonectria parasitica, Cryptococcus albidus, Dilophosphora alopecuri, Fusarium oxysporum, Clonostachys rosea* f. *catenulate* (*Gliocladium catenulatum*), *Gliocladium roseum, Lysobacter antibioticus, L. enzymogenes,*

*Metschnikowia fructicola, Microdochium dimerum, Microsphaeropsis ochracea, Muscodor albus, Paenibacillus alvei, Paenibacillus epiphyticus, P. polymyxa, Pantoea vagans, Penicillium bilaiae, Phlebiopsis gigantea, Pseudomonas* sp., *Pseudomonas chloraphis, Pseudozyma flocculosa, Pichia anomala, Pythium oligandrum, Sphaerodes mycoparasitica, Streptomyces griseoviridis, S. lydicus, S. violaceusniger, Talaromyces flavus, Trichoderma asperelloides, T. asperellum, T. atroviride, T. fertile, T. gamsii, T. harmatum, T. harzianum, T. polysporum, T. stromaticum, T. virens, T. viride, Typhula phacorrhiza, Ulocladium oudemansii, Verticillium* dahlia, zucchini yellow mosaic virus (avirulent strain);

L2) Biochemical pesticides with fungicidal, bactericidal, viricidal and/or plant defense activator activity: harpin protein, *Reynoutria sachalinensis* extract;

L3) Microbial pesticides with insecticidal, acaricidal, molluscidal and/or nematicidal activity: *Agrobacterium radiobacter, Bacillus cereus, B. firmus, B. thuringiensis, B. thuringiensis* ssp. *aizawai*, B. t. ssp. *israelensis*, B. t. ssp. *galleriae*, B. t. ssp. *kurstaki*, B. t. ssp. *tenebrionis, Beauveria bassiana, B. brongniartii, Burkholderia* spp., *Chromobacterium subtsugae, Cydia pomonella granulovirus* (CpGV), *Cryptophlebia leucotreta* granulovirus (CrleGV), *Flavobacterium* spp., *Helicoverpa armigera* nucleopolyhedrovirus (HearNPV), *Helicoverpa zea* nucleopolyhedrovirus (HzNPV), *Helicoverpa zea* single capsid nucleopolyhedrovirus (HzSNPV), *Heterorhabditis bacteriophora, Isaria fumosorosea, Lecanicillium longisporum, L. muscarium, Metarhizium anisopliae, M. anisopliae* var. *anisopliae, M. anisopliae* var. *acridum, Nomuraea rileyi, Paecilomyces fumosoroseus, P. lilacinus, Paenibacillus popilliae, Pasteuria* spp., *P. nishizawae, P. penetrans, P. ramosa, P. thornea, P. usgae, Pseudomonas fluorescens, Spodoptera littoralis* nucleopolyhedrovirus (SpliNPV), *Steinernema carpocapsae, S. feltiae, S. kraussei, Streptomyces galbus, S. microflavus;*

L4) Biochemical pesticides with insecticidal, acaricidal, molluscidal, pheromone and/or nematicidal activity: L-carvone, citral, (E,Z)-7,9-dodecadien-1-yl acetate, ethyl formate, (E,Z)-2,4-ethyl decadienoate (pear ester), (Z,Z,E)-7,11,13-hexadecatrienal, heptyl butyrate, isopropyl myristate, lavanulyl senecioate, cis-jasmone, 2-methyl 1-butanol, methyl eugenol, methyl jasmonate, (E,Z)-2,13-octadecadien-1-ol, (E,Z)-2,13-octadecadien-1-ol acetate, (E,Z)-3,13-octadecadien-1-ol, (R)-1-octen-3-ol, pentatermanone, (E,Z,Z)-3,8,11-tetradecatrienyl acetate, (Z,E)-9,12-tetradecadien-1-yl acetate, (Z)-7-tetradecen-2-one, (Z)-9-tetradecen-1-yl acetate, (Z)-11-tetradecenal, (Z)-11-tetradecen-1-ol, extract of *Chenopodium ambrosiodes*, Neem oil, Quillay extract;

L5) Microbial pesticides with plant stress reducing, plant growth regulator, plant growth promoting and/or yield enhancing activity: *Azospirillum amazonense, A. brasilense, A. lipoferum, A. irakense, A. halopraeferens, Bradyrhizobium* spp., *B. elkanii, B. japonicum, B. liaoningense, B. lupini, Delftia acidovorans, Glomus intraradices, Mesorhizobium* spp., *Rhizobium leguminosarum* bv. *phaseoli*, R. I. bv. *trifolii*, R. I. bv. *viciae, R. tropici, Sinorhizobium meliloti;*

The biopesticides from group L1) and/or L2) may also have insecticidal, acaricidal, molluscidal, pheromone, nematicidal, plant stress reducing, plant growth regulator, plant growth promoting and/or yield enhancing activity. The biopesticides from group L3) and/or L4) may also have fungicidal, bactericidal, viricidal, plant defense activator, plant stress reducing, plant growth regulator, plant growth promoting and/or yield enhancing activity. The biopesticides from group L5) may also have fungicidal, bactericidal, viricidal, plant defense activator, insecticidal, acaricidal, molluscidal, pheromone and/or nematicidal activity.

Many of these biopesticides have been deposited under deposition numbers mentioned herein (the prefices e.g. ATCC or DSM refer to the acronym of the respective culture collection, for details see e.g. here: http://www.wfcc.info/ccinfo/collection/by acronym/), are referred to in literature, registered and/or are commercially available: mixtures of *Aureobasidium pullulans* DSM 14940 and DSM 14941 isolated in 1989 in Konstanz, Germany (e.g. blastospores in BlossomProtect® from bio-ferm GmbH, Austria), *Azospirillum brasilense* Sp245 originally isolated in wheat reagion of South Brazil (Passo Fundo) at least prior to 1980 (BR 11005; e.g. GELFIX® Gramineas from BASF Agricultural Specialties Ltd., Brazil), *A. brasilense* strains Ab-V5 and Ab-V6 (e.g. in AzoMax from Novozymes BioAg Produtos papra Agricultura Ltda., Quattro Barras, Brazil or Simbiose-Maiz® from Simbiose-Agro, Brazil; Plant Soil 331, 413-425, 2010), *Bacillus amyloliquefaciens* strain AP-188 (NRRL B-50615 and B-50331; U.S. Pat. No. 8,445,255); *B. amyloliquefaciens* ssp. *plantarum* strains formerly also sometimes referred to as *B. subtilis*, recently together with *B. methylotrophicus*, and *B. velezensis* classified as *B. velezensis* (Int. J. Syst. Evol. Microbiol. 66, 1212-1217, 2016): B. a. ssp. *plantarum* or *B. velezensis* D747 isolated from air in Kikugawa-shi, Japan (US 20130236522 A1; FERM BP-8234; e.g. Double Nickel™ 55 WDG from Certis LLC, USA), B. a. ssp. *plantarum* or *B. velezensis* FZB24 isolated from soil in Brandenburg, Germany (also called SB3615; DSM 96-2; J. Plant Dis. Prot. 105, 181-197, 1998; e.g. Taegro® from Novozyme Biologicals, Inc., USA), B. a. ssp. *plantarum* or *B. velezensis* FZB42 isolated from soil in Brandenburg, Germany (DSM 23117; J. Plant Dis. Prot. 105, 181-197, 1998; e.g. RhizoVital® 42 from AbiTEP GmbH, Germany), B. a. ssp. *plantarum* or *B. velezensis* MB1600 isolated from *faba* bean in Sutton Bonington, Nottinghamshire, U.K. at least before 1988 (also called 1430; NRRL B-50595; US 2012/0149571 A1; e.g. Integral® from BASF Corp., USA), B. a. ssp. *plantarum* or *B. velezensis* QST-713 isolated from peach orchard in 1995 in California, U.S.A. (NRRL B-21661; e.g. Serenade® MAX from Bayer Crop Science LP, USA), B. a. ssp. *plantarum* or *B. velezensis* TJ1000 isolated in 1992 in South Dakoda, U.S.A. (also called 1BE; ATCC BAA-390; CA 2471555 A1; e.g. QuickRoots™ from TJ Technologies, Watertown, SD, USA); *B. firmus* CNCM 1-1582, a variant of parental strain EIP-N1 (CNCM 1-1556) isolated from soil of central plain area of Israel (WO 2009/126473, U.S. Pat. No. 6,406,690; e.g. Votivo® from Bayer CropScience LP, USA), *B. pumilus* GHA 180 isolated from apple tree rhizosphere in Mexico (IDAC 260707-01; e.g. PRO-MIX® BX from Premier Horticulture, Quebec, Canada), *B. pumilus* INR-7 otherwise referred to as BU-F22 and BU-F33 isolated at least before 1993 from cucumber infested by *Erwinia tracheiphila* (NRRL B-50185, NRRL B-50153; U.S. Pat. No. 8,445,255), *B. pumilus* KFP9F isolated from the rhizosphere of grasses in South Africa at least before 2008 (NRRL B-50754; WO 2014/029697; e.g. BAC-UP or FUSION-P from BASF Agricultural Specialities (Pty) Ltd., South Africa), *B. pumilus* QST 2808 was isolated from soil collected in Pohnpei, Federated States of Micronesia, in 1998 (NRRL B-30087; e.g. Sonata® or Ballad® Plus from Bayer Crop Science LP, USA), *B. simplex* ABU 288 (NRRL B-50304; U.S. Pat. No. 8,445,255), *B. subtilis* FB17 also called UD 1022 or UD10-22 isolated from red beet roots in North America (ATCC PTA-11857; System. Appl. Microbiol. 27, 372-379, 2004; US2010/0260735; WO 2011/109395); *B. thuringiensis* ssp. *aizawai* ABTS-1857 isolated from soil taken from a lawn in Ephraim, Wis., U.S.A., in 1987 (also called ABG-6346; ATCC SD-1372; e.g. XenTari® from BioFa AG, Munsingen, Germany), B. t. ssp. *kurstaki* ABTS-351 identical to HD-1 isolated in 1967 from diseased Pink Bollworm black larvae in Brownsville, Texas, U.S.A. (ATCC SD-1275; e.g. Dipel® DF from Valent BioSciences, IL, USA), B. t. ssp. kurstaki SB4 isolated from *E. saccharina* larval cadavers (NRRL B-50753; e.g. Beta Pro® from BASF Agricultural Specialities (Pty) Ltd., South Africa), B. t. ssp. *tenebrionis* NB-176-1, a mutant of strain NB-125, a wild type strain isolated in 1982 from a dead pupa of the beetle *Tenebrio molitor* (DSM 5480; EP 585 215 B1; e.g. Novodor® from Valent BioSciences, Switzerland), *Beauveria bassiana* GHA (ATCC 74250; e.g. BotaniGard® 22WGP from Laverlam Int. Corp., USA), *B. bassiana* JW-1 (ATCC 74040; e.g. Naturalis® from CBC (Europe) S.r., Italy), *B. bassiana* PPRI 5339 isolated from the larva of the tortoise beetle *Conchyloctenia punctata* (NRRL 50757; e.g. BroadBand® from BASF Agricultural Specialities (Pty) Ltd., South Africa), *Bradyrhizobium elkanii* strains SEMIA 5019 (also called 29W) isolated in Rio de Janeiro, Brazil and SEMIA 587 isolated in 1967 in the State of Rio Grande do Sul, from an area previously inoculated with a North American isolate, and used in commercial inoculants since 1968 (Appl. Environ. Microbiol. 73(8), 2635, 2007; e.g. GELFIX 5 from BASF Agricultural Specialties Ltd., Brazil), *B. japonicum* 532c isolated from Wisconsin field in U.S.A. (Nitragin 61A152; Can. J. Plant. Sci. 70, 661-666, 1990; e.g. in Rhizoflo®, Histick®, Hicoat® Super from BASF Agricultural Specialties Ltd., Canada), *B. japonicum* E-109 variant of strain USDA 138 (INTA E109, SEMIA 5085; Eur. J. Soil Biol. 45, 28-35, 2009; Biol. Fertil. Soils 47, 81-89, 2011); *B. japonicum* strains deposited at SEMIA known from Appl. Environ. Microbiol. 73(8), 2635, 2007: SEMIA 5079 isolated from soil in Cerrados region, Brazil by Embrapa-Cerrados used in commercial inoculants since 1992 (CPAC 15; e.g. GELFIX 5 or ADHERE 60 from BASF Agricultural Specialties Ltd., Brazil), *B. japonicum* SEMIA 5080 obtained under lab conditions by Embrapa-Cerrados in Brazil and used in commercial inoculants since 1992, being a natural variant of SEMIA 586 (CB1809) originally isolated in U.S.A. (CPAC 7; e.g. GELFIX 5 or ADHERE 60 from BASF Agricultural Specialties Ltd., Brazil); *Burkholderia* sp. A396 isolated from soil in Nikko, Japan, in 2008 (NRRL B-50319; WO 2013/032693; Marrone Bio Innovations, Inc., USA), *Coniothyrium minitans* CON/M/91-08 isolated from oilseed rape (WO 1996/021358; DSM 9660; e.g. Contans® WG, Intercept® WG from Bayer CropScience AG, Germany), harpin (alpha-beta) protein (Science 257, 85-88, 1992; e.g. Messenger™ or HARP-N-Tek from Plant Health Care plc, U.K.), *Helicoverpa armigera* nucleopolyhedrovirus (HearNPV) (J. Invertebrate Pathol. 107, 112-126, 2011; e.g. Helicovex® from Adermatt Biocontrol, Switzerland; Diplomata® from Koppert, Brazil; Vivus® Max from AgBiTech Pty Ltd., Queensland, Australia), *Helicoverpa zea* single capsid nucleopolyhedrovirus (HzSNPV) (e.g. Gemstar® from Certis LLC, USA), *Helicoverpa zea* nucleopolyhedrovirus ABA-NPV-U (e.g. Heligen® from AgBiTech Pty Ltd., Queensland, Australia), *Heterorhabditis bacterio-*

*phora* (e.g. Nemasys® G from BASF Agricultural Specialities Limited, UK), *Isaria fumosorosea* Apopka-97 isolated from mealy bug on gynura in Apopka, Florida, U.S.A. (ATCC 20874; Biocontrol Science Technol. 22(7), 747-761, 2012; e.g. PFR-97™ or PreFeRal® from Certis LLC, USA), *Metarhizium anisopliae* var. anisopliae F52 also called 275 or V275 isolated from codling moth in Austria (DSM 3884, ATCC 90448; e.g. Met52® Novozymes Biologicals BioAg Group, Canada), *Metschnikowia fructicola* 277 isolated from grapes in the central part of Israel (U.S. Pat. No. 6,994,849; NRRL Y-30752; e.g. formerly Shemer® from Agrogreen, Israel), *Paecilomyces ilacinus* 251 isolated from infected nematode eggs in the Philippines (AGAL 89/030550; WO1991/02051; Crop Protection 27, 352-361, 2008; e.g. BioAct® from Bayer CropScience AG, Germany and MeloCon® from Certis, USA), *Paenibacillus alvei* NAS6G6 isolated from the rhizosphere of grasses in South Africa at least before 2008 (WO 2014/029697; NRRL B-50755; e.g. BAC-UP from BASF Agricultural Specialities (Pty) Ltd., South Africa), *Paenibacillus* strains isolated from soil samples from a variety of European locations including Germany: *P. epiphyticus* Lu17015 (WO 2016/020371; DSM 26971), *P. polymyxa* ssp. *plantarum* Lu16774 (WO 2016/020371; DSM 26969), P. p. ssp. *plantarum* strain Lu17007 (WO 2016/020371; DSM 26970); Pasteuria nishizawae Pn1 isolated from a soybean field in the mid-2000s in Illinois, U.S.A. (ATCC SD-5833; Federal Register 76(22), 5808, Feb. 2, 2011; e.g. Clariva™ PN from Syngenta Crop Protection, LLC, USA), *Penicillium bilaiae* (also called *P. bilail*) strains ATCC 18309 (=ATCC 74319), ATCC 20851 and/or ATCC 22348 (=ATCC 74318) originally isolated from soil in Alberta, Canada (Fertilizer Res. 39, 97-103, 1994; Can. J. Plant Sci. 78(1), 91-102, 1998; U.S. Pat. No. 5,026,417, WO 1995/017806; e.g. Jump Start®, Provide® from Novozymes Biologicals BioAg Group, Canada), *Reynoutria sachalinensis* extract (EP 0307510 B1; e.g Regalia® SC from Marrone BioInnovations, Davis, Calif., USA or Milsana® from BioFa AG, Germany), *Steinernema carpocapsae* (e.g. Millenium® from BASF Agricultural Specialities Limited, UK), *S. feltiae* (e.g. Nemashield® from BioWorks, Inc., USA; Nemasys® from BASF Agricultural Specialities Limited, UK), *Streptomyces microflavus* NRRL B-50550 (WO 2014/124369; Bayer CropScience, Germany), *Trichoderma* asperelloides JM41R isolated in South Africa (NRRL 50759; also referred to as *T. fertile*; e.g. Trichoplus® from BASF Agricultural Specialities (Pty) Ltd., South Africa), *T. harzianum* T-22 also called KRL-AG2 (ATCC 20847; BioControl 57, 687-696, 2012; e.g. Plantshield® from BioWorks Inc., USA or SabrEx™ from Advanced Biological Marketing Inc., Van Wert, OH, USA).

According to the invention, the solid material (dry matter) of the biopesticides (with the exception of oils e.g. Neem oil) are considered as active components (e.g. to be obtained after drying or evaporation of the extraction or suspension medium in case of liquid formulations of the microbial pesticides).

In accordance with the invention, the weight ratios and percentages used herein for a biological extract e.g. Quillay extract are based on the total weight of the dry content (solid material) of the respective extract(s).

The total weight ratios of compositions comprising at least one microbial pesticide in the form of viable microbial cells including dormant forms, can be determined using the amount of CFU of the respective microorganism to calculate the total weight of the respective active component with the following equation that $1\times10^{10}$ CFU equals one gram of total weight of the respective active component. Colony forming unit is measure of viable microbial cells, in particular fungal and bacterial cells. In addition, here "CFU" may also be understood as the number of (juvenile) individual nematodes in case of (entomopathogenic) nematode biopesticides, e.g. *Steinernema feltiae*.

When mixtures comprising microbial pesticides are employed in crop protection, the application rates range from $1\times10^6$ to $5\times10^{16}$ (or more) CFU/ha, preferably from $1\times10^8$ to $1\times10^{13}$ CFU/ha, and even more preferably from $1\times10^9$ to $5\times10^{15}$ CFU/ha and in particular from $1\times10^{12}$ to $5\times10^{14}$ CFU/ha. In the case of nematodes as microbial pesticides (e.g. *Steinernema feltiae*), the application rates regularly range from $1\times10^5$ to $1\times10^{12}$ (or more), preferably from $1\times10^8$ to $1\times10^{11}$, more preferably from $5\times10^8$ to $1\times10^{10}$ individuals (e.g. in the form of eggs, juvenile or any other live stages, preferably in an infective juvenile stage) per ha.

When mixtures comprising microbial pesticides are employed in seed treatment, the application rates generally range from $1\times10^1$ to $1\times10^{12}$ (or more) CFU/seed, preferably from $1\times10^6$ to $1\times10^9$ CFU/seed. Furthermore, the application rates with respect to seed treatment generally range from $1\times10^7$ to $1\times10^{14}$ (or more) CFU per 100 kg of seed, preferably from $1\times10^9$ to $1\times10^{12}$ CFU per 100 kg of seed.

The invention also relates to agrochemical compositions comprising an auxiliary and at least one compound of the invention or a mixture thereof.

An agrochemical composition comprises a pesticidally effective amount of a compound of the invention or a mixture thereof.

The compounds of the invention or the mixtures thereof can be converted into customary types of agro-chemical compositions, e.g. solutions, emulsions, suspensions, dusts, powders, pastes, granules, pressings, capsules, and mixtures thereof. Examples for composition types are suspensions (e.g. SC, OD, FS), emulsifiable concentrates (e.g. EC), emulsions (e.g. EW, EO, ES, ME), capsules (e.g. CS, ZC), pastes, pastilles, wettable powders or dusts (e.g. WP, SP, WS, DP, DS), pressings (e.g. BR, TB, DT), granules (e.g. WG, SG, GR, FG, GG, MG), insecticidal articles (e.g. LN), as well as gel formulations for the treatment of plant propagation materials e.g. seeds (e.g. GF). These and further compositions types are defined in the "Catalogue of pesticide formulation types and international coding system", Technical Monograph No. 2,6th Ed. May 2008, CropLife International.

The compositions are prepared in a known manner, e.g. described by Mollet and Grube-mann, Formulation technology, Wiley VCH, Weinheim, 2001; or Knowles, New developments in crop protection product formulation, Agrow Reports DS243, T&F Informa, London, 2005.

Examples for suitable auxiliaries are solvents, liquid carriers, solid carriers or fillers, surfactants, dispersants, emulsifiers, wetters, adjuvants, solubilizers, penetration enhancers, protective colloids, adhesion agents, thickeners, humectants, repellents, attractants, feeding stimulants, compatibilizers, bactericides, anti-freezing agents, anti-foaming agents, colorants, tackifiers and binders.

Suitable solvents and liquid carriers are water and organic solvents, e.g. mineral oil fractions of medium to high boiling point, e.g. kerosene, diesel oil; oils of vegetable or animal origin; hydrocarbons, e.g. toluene, paraffin, tetrahydronaphthalene, alkylated naphthalenes; alcohols, e.g. ethanol, propanol, butanol, benzylalcohol, cyclohexanol; glycols; DMSO; ketones, e.g. cyclohexanone; esters, e.g. lactates, carbonates, fatty acid esters, gamma-butyrolactone; fatty acids; phosphonates; amines; amides, e.g. N-methylpyrrolidone, fatty acid dimethylamides; and mixtures thereof.

Suitable solid carriers or fillers are mineral earths, e.g. silicates, silica gels, talc, kaolins, limestone, lime, chalk, clays, dolomite, diatomaceous earth, bentonite, $CaSO_4$, $MgSO_4$, MgO; polysaccharide powders, e.g. cellulose, starch; fertilizers, e.g. $(NH_4)_2SO_4$, $(NH_4)_3PO_4$, $NH_4NO_3$, ureas; products of vegetable origin, e.g. cereal meal, tree bark meal, wood meal, nutshell meal, and mixtures thereof.

Suitable surfactants are surface-active compounds, e.g. anionic, cationic, nonionic and amphoteric surfactants, block polymers, polyelectrolytes, and mixtures thereof. Such surfactants can be used as emusifier, dispersant, solubilizer, wetter, penetration enhancer, protective colloid, or adjuvant. Examples of surfactants are listed in McCutcheon's, Vol. 1: Emulsifiers & Detergents, McCutcheon's Directories, Glen Rock, USA, 2008 (International or North American Ed.).

Suitable anionic surfactants are alkali, alkaline earth or ammonium salts of sulfonates, sulfates, phosphates, carboxylates, and mixtures thereof. Examples of sulfonates are alkylarylsulfonates, diphenylsulfonates, alpha-olefin sulfonates, lignine sulfonates, sulfonates of fatty acids and oils, sulfonates of ethoxylated alkylphenols, sulfonates of alkoxylated arylphenols, sulfonates of condensed naphthalenes, sulfonates of dodecyl- and tridecylbenzenes, sulfonates of naphthalenes and alkylnaphthalenes, sulfosuccinates or sulfosuccinamates. Examples of sulfates are sulfates of fatty acids and oils, of ethoxylated alkylphenols, of alcohols, of ethoxylated alcohols, or of fatty acid esters. Examples of phosphates are phosphate esters. Examples of carboxylates are alkyl carboxylates, and carboxylated alcohol or alkylphenol ethoxylates.

Suitable nonionic surfactants are alkoxylates, N-substituted fatty acid amides, amine oxides, esters, sugar-based surfactants, polymeric surfactants, and mixtures thereof. Examples of alkoxylates are compounds e.g. alcohols, alkylphenols, amines, amides, arylphenols, fatty acids or fatty acid esters which have been alkoxylated with 1 to 50 equivalents. Ethylene oxide and/or propylene oxide may be employed for the alkoxylation, preferably ethylene oxide. Examples of N-substituted fatty acid amides are fatty acid glucamides or fatty acid alkanolamides. Examples of esters are fatty acid esters, glycerol esters or monoglycerides. Examples of sugar-based surfactants are sorbitans, ethoxylated sorbitans, sucrose and glucose esters or alkylpolyglucosi-des. Examples of polymeric surfactants are homo- or copolymers of vinylpyrrolidone, vinylalcohols, or vinylacetate.

Suitable cationic surfactants are quaternary surfactants, e.g. quaternary ammonium compounds with one or two hydrophobic groups, or salts of long-chain primary amines. Suitable amphoteric surfactants are alkylbetains and imidazolines. Suitable block polymers are block polymers of the A-B or A-B-A type comprising blocks of polyethylene oxide and polypropylene oxide, or of the A-B-C type comprising alkanol, polyethylene oxide and polypropylene oxide. Suitable polyelectrolytes are polyacids or polybases. Examples of polyacids are alkali salts of polyacrylic acid or polyacid comb polymers. Examples of polybases are polyvinylamines or polyethyleneamines.

Suitable adjuvants are compounds, which have a neglectable or even no pesticidal activity themselves, and which improve the biological performance of the compounds of the invention on the target. Examples are surfactants, mineral or vegetable oils, and other auxilaries. Further examples are listed by Knowles, Adjuvants and additives, Agrow Reports DS256, T&F Informa UK, 2006, chapter 5.

Suitable thickeners are polysaccharides (e.g. xanthan gum, carboxymethylcellulose), an organic clays (organically modified or unmodified), polycarboxylates, and silicates.

Suitable bactericides are bronopol and isothiazolinone derivatives e.g. alkylisothiazoli-nones and benzisothiazolinones.

Suitable anti-freezing agents are ethylene glycol, propylene glycol, urea and glycerin.

Suitable anti-foaming agents are silicones, long chain alcohols, and salts of fatty acids.

Suitable colorants (e.g. in red, blue, or green) are pigments of low water solubility and water-soluble dyes. Examples are inorganic colorants (e.g. iron oxide, titan oxide, iron hexacyanofer-rate) and organic colorants (e.g. alizarin-, azo-, and phthalocyanine colorants).

Suitable tackifiers or binders are polyvinylpyrrolidons, polyvinylacetates, polyvinyl alcohols, polyacrylates, biological or synthetic waxes, and cellulose ethers.

Examples for composition types and their preparation are:

i) Water-Soluble Concentrates (SL, LS)

10-60 wt % of a compound I according to the invention and 5-15 wt % wetting agent (e.g. alcohol alkoxylates) are dissolved in water and/or in a water-soluble solvent (e.g. alcohols) up to 100 wt %.

The active substance dissolves upon dilution with water.

ii) Dispersible Concentrates (DC)

5-25 wt % of a compound I according to the invention and 1-10 wt % dispersant (e.g. polyvinylpyrrolidone) are dissolved in up to 100 wt % organic solvent (e.g. cyclohexanone). Dilution with water gives a dispersion.

iii) Emulsifiable Concentrates (EC)

15-70 wt % of a compound I according to the invention and 5-10 wt % emulsifiers (e.g. calcium dodecylbenzenesulfonate and castor oil ethoxylate) are dissolved in up to 100 wt % water-insoluble organic solvent (e.g. aromatic hydrocarbon). Dilution with water gives an emulsion.

iv) Emulsions (EW, EO, ES)

5-40 wt % of a compound I according to the invention and 1-10 wt % emulsifiers (e.g. calcium dodecylbenzenesulfonate and castor oil ethoxylate) are dissolved in 20-40 wt % water-insoluble organic solvent (e.g. aromatic hydrocarbon). This mixture is introduced into up to 100 wt % water by means of an emulsifying machine and made into a homogeneous emulsion. Dilution with water gives an emulsion.

v) Suspensions (SC, OD, FS)

In an agitated ball mill, 20-60 wt % of a compound I according to the invention are comminuted with addition of 2-10 wt % dispersants and wetting agents (e.g. sodium lignosulfonate and alcohol ethoxylate), 0.1-2 wt % thickener (e.g. xanthan gum) and up to 100 wt % water to give a fine active substance suspension. Dilution with water gives a stable suspension of the active substance. For FS type composition up to 40 wt % binder (e.g. polyvinylalcohol) is added.

vi) Water-Dispersible Granules and Water-Soluble Granules (WG, SG)

50-80 wt % of a compound I according to the invention are ground finely with addition of up to 100 wt % dispersants and wetting agents (e.g. sodium lignosulfonate and alcohol ethoxylate) and prepared as water-dispersible or water-soluble granules by means of technical appliances (e.g. extrusion, spray tower, fluidized bed). Dilution with water gives a stable dispersion or solution of the active substance.

vii) Water-Dispersible Powders and Water-Soluble Powders (WP, SP, WS)

50-80 wt % of a compound I according to the invention are ground in a rotor-stator mill with addition of 1-5 wt % dispersants (e.g. sodium lignosulfonate), 1-3 wt % wetting agents (e.g. alcohol ethoxylate) and up to 100 wt % solid carrier, e.g. silica gel. Dilution with water gives a stable dispersion or solution of the active substance.

viii) Gel (GW, GF)

In an agitated ball mill, 5-25 wt % of a compound I according to the invention are comminuted with addition of 3-10 wt % dispersants (e.g. sodium lignosulfonate), 1-5 wt % thickener (e.g. carboxymethylcellulose) and up to 100 wt % water to give a fine suspension of the active substance. Dilution with water gives a stable suspension of the active substance.

ix) Microemulsion (ME)

5-20 wt % of a compound I according to the invention are added to 5-30 wt % organic solvent blend (e.g. fatty acid dimethylamide and cyclohexanone), 10-25 wt % surfactant blend (e.g. alcohol ethoxylate and arylphenol ethoxylate), and water up to 100%. This mixture is stirred for 1 h to produce spontaneously a thermodynamically stable microemulsion.

x) Microcapsules (CS)

An oil phase comprising 5-50 wt % of a compound I according to the invention, 0-40 wt % water insoluble organic solvent (e.g. aromatic hydrocarbon), 2-15 wt % acrylic monomers (e.g. methylmethacrylate, methacrylic acid and a di- or triacrylate) are dispersed into an aqueous solution of a protective colloid (e.g. polyvinyl alcohol). Radical polymerization initiated by a radical initiator results in the formation of poly(meth)acrylate microcapsules. Alternatively, an oil phase comprising 5-50 wt % of a compound I according to the invention, 0-40 wt % water insoluble organic solvent (e.g. aromatic hydrocarbon), and an isocyanate monomer (e.g. diphenylmethene-4,4'-diisocyanatae) are dispersed into an aqueous solution of a protective colloid (e.g. polyvinyl alcohol). The addition of a polyamine (e.g. hexamethylenediamine) results in the formation of a polyurea microcapsule. The monomers amount to 1-10 wt %. The wt % relate to the total CS composition.

xi) Dustable Powders (DP, DS)

1-10 wt % of a compound I according to the invention are ground finely and mixed intimately with up to 100 wt % solid carrier, e.g. finely divided kaolin.

xii) Granules (GR, FG)

0.5-30 wt % of a compound I according to the invention is ground finely and associated with up to 100 wt % solid carrier (e.g. silicate). Granulation is achieved by extrusion, spray-drying or the fluidized bed.

xiii) Ultra-Low Volume Liquids (UL)

1-50 wt % of a compound I according to the invention are dissolved in up to 100 wt % organic solvent, e.g. aromatic hydrocarbon.

The compositions types i) to xi) may optionally comprise further auxiliaries, e.g. 0.1-1 wt % bactericides, 5-15 wt % anti-freezing agents, 0.1-1 wt % anti-foaming agents, and 0.1-1 wt % colorants.

The agrochemical compositions generally comprise between 0.01 and 95%, preferably between 0.1 and 90%, and most preferably between 0.5 and 75%, by weight of active substance.

The active substances are employed in a purity of from 90% to 100%, preferably from 95% to 100% (according to NMR spectrum).

Various types of oils, wetters, adjuvants, fertilizer, or micronutrients, and other pesticides (e.g. herbicides, insecticides, fungicides, growth regulators, safeners) may be added to the active substances or the compositions comprising them as premix or, if appropriate not until immediately prior to use (tank mix). These agents can be admixed with the compositions according to the invention in a weight ratio of 1:100 to 100:1, preferably 1:10 to 10:1.

The user applies the composition according to the invention usually from a predosage device, a knapsack sprayer, a spray tank, a spray plane, or an irrigation system. Usually, the agrochemical composition is made up with water, buffer, and/or further auxiliaries to the desired application concentration and the ready-to-use spray liquor or the agrochemical composition according to the invention is thus obtained. Usually, 20 to 2000 liters, preferably 50 to 400 liters, of the ready-to-use spray liquor are applied per hectare of agricultural useful area.

According to one embodiment, individual components of the composition of the invention e.g. parts of a kit or parts of a binary or ternary mixture may be mixed by the user himself in a spray tank and further auxiliaries may be added, if appropriate.

In a further embodiment, either individual components of the composition according to the invention or partially premixed components, e.g. components comprising compounds of the invention and/or mixing partners as defined above, may be mixed by the user in a spray tank and further auxiliaries and additives may be added.

In a further embodiment, either individual components of the composition according to the invention or partially premixed components, e.g. components comprising compounds of the invention and/or mixing partners as defined above, can be applied jointly (e.g. after tank mix) or consecutively.

The compounds of the invention are suitable for use in protecting crops, plants, plant propagation materials, e.g. seeds, or soil or water, in which the plants are growing, from attack or infestation by animal pests. Therefore, the invention also relates to a plant protection method, which comprises contacting crops, plants, plant propagation materials, e.g. seeds, or soil or water, in which the plants are growing, to be protected from attack or infestation by animal pests, with a pesticidally effective amount of a compound of the invention.

The compounds of the invention are also suitable for use in combating or controlling animal pests. Therefore, the invention also relates to a method of combating or controlling animal pests, which comprises contacting the animal pests, their habitat, breeding ground, or food supply, or the crops, plants, plant propagation materials, e.g. seeds, or soil, or the area, material or environment in which the animal pests are growing or may grow, with a pesticidally effective amount of a compound of the invention.

The compounds of the invention are effective through both contact and ingestion. Furthermore, the compounds of the invention can be applied to any and all developmental stages, e.g. egg, larva, pupa, and adult.

The compounds of the invention can be applied as such or in form of compositions comprising them as defined above. Furthermore, the compounds of the invention can be applied together with a mixing partner or in form of compositions comprising said mixtures. The components of said mixture can be applied simultaneously, jointly or separately, or in succession, that is immediately one after another and thereby creating the mixture “in situ” on the desired location, e.g. the plant, the sequence, in the case of separate application, generally not having any effect on the result of the control measures.

The application can be carried out both before and after the infestation of the crops, plants, plant propagation materials, e.g. seeds, soil, or the area, material or environment by the pests.

Suitable application methods include i.a. soil treatment, seed treatment, in furrow application, and foliar application. Soil treatment methods include drenching the soil, drip irrigation (drip application onto the soil), dipping roots, tubers or bulbs, or soil injection. Seed treatment techniques include seed dressing, seed coating, seed dusting, seed soaking, and seed pelleting. In furrow applications typically include the steps of making a furrow in cultivated land, seeding the furrow with seeds, applying the pesticidally active compound to the furrow, and closing the furrow. Foliar application refers to the application of the pesticidally active compound to plant foliage, e.g. through spray equipment. For foliar applications, it can be advantageous to modify the behavior of the pests by use of pheromones in combination with the compounds of the invention. Suitable pheromones for specific crops and pests are known and publicly available from databases of pheromones and semiochemicals, e.g. http://www.pherobase.com.

As used herein, the term "contacting" includes both direct contact (applying the compounds/compositions directly on the animal pest or plant—typically to the foliage, stem or roots of the plant) and indirect contact (applying the compounds/compositions to the locus, i.e. habitat, breeding ground, plant, seed, soil, area, material, or environment in which a pest is growing or may grow, of the animal pest or plant).

The term "animal pest" includes arthropods, gastropods, and nematodes. Preferred animal pests according to the invention are arthropods, preferably insects and arachnids, in particular insects. Insects, which are of particular relevance for crops, are typically referred to as crop insect pests.

The term "crop" refers to both, growing and harvested crops.

The term "plant" includes cereals, e.g. durum and other wheat, rye, barley, triticale, oats, rice, or maize (fodder maize and sugar maize/sweet and field corn); beet, e.g. sugar beet, or fodder beet; fruits, e.g. pomes, stone fruits, or soft fruits, e.g. apples, pears, plums, peaches, nectarines, almonds, cherries, papayas, strawberries, raspberries, blackberries or gooseberries; leguminous plants, e.g. beans, lentils, peas, alfalfa, or soybeans; oil plants, e.g. rapeseed (oilseed rape), turnip rape, mustard, olives, sunflowers, coconut, cocoa beans, castor oil plants, oil palms, ground nuts, or soybeans; cucurbits, e.g. squashes, pumpkins, cucumber or melons; fiber plants, e.g. cotton, flax, hemp, or jute; citrus fruit, e.g. oranges, lemons, grapefruits or mandarins; vegetables, e.g. eggplant, spinach, lettuce (e.g. iceberg lettuce), chicory, cabbage, asparagus, cabbages, carrots, onions, garlic, leeks, tomatoes, potatoes, cucurbits or sweet peppers; lauraceous plants, e.g. avocados, cinnamon, or camphor; energy and raw material plants, e.g. corn, soybean, rapeseed, sugar cane or oil palm; tobacco; nuts, e.g. walnuts; pistachios; coffee; tea; bananas; vines; hop; sweet leaf (*Stevia*); natural rubber plants or ornamental and forestry plants, shrubs, broad-leaved trees or evergreens, *eucalyptus*; turf; lawn; grass. Preferred plants include potatoes sugar beets, tobacco, wheat, rye, barley, oats, rice, corn, cotton, soybeans, rapeseed, legumes, sunflowers, coffee, or sugar cane; fruits; vines; ornamentals; or vegetables, e.g. cucumbers, tomatoes, beans or squashes.

The term "cultivated plants" is to be understood as including plants which have been modified by mutagenesis or genetic engineering in order to provide a new trait to a plant or to modify an already present trait.

Mutagenesis includes techniques of random mutagenesis using X-rays or mutagenic chemicals, but also techniques of targeted mutagenesis, in order to create mutations at a specific locus of a plant genome. Targeted mutagenesis techniques frequently use oligonucleotides or proteins like CRISPR/Cas, zinc-finger nucleases, TALENs or meganucleases to achieve the targeting effect.

Genetic engineering usually uses recombinant DNA techniques to create modifications in a plant genome which under natural circumstances cannot readily be obtained by cross breeding, mutagenesis or natural recombination. Typically, one or more genes are integrated into the genome of a plant in order to add a trait or improve a trait. These integrated genes are also referred to as transgenes in the art, while plant comprising such transgenes are referred to as transgenic plants. The process of plant transformation usually produces several transformation events, which differ in the genomic locus in which a transgene has been integrated. Plants comprising a specific transgene on a specific genomic locus are usually described as comprising a specific "event", which is referred to by a specific event name. Traits which have been introduced in plants or have been modified include in particular herbicide tolerance, insect resistance, increased yield and tolerance to abiotic conditions, like drought.

Herbicide tolerance has been created by using mutagenesis as well as using genetic engineering. Plants which have been rendered tolerant to ALS inhibitor herbicides by conventional methods of mutagenesis and breeding comprise plant varieties commercially available under the name Clearfield®.

Herbicide tolerance has been created to glyphosate, glufosinate, 2,4-D, dicamba, oxynil herbicides, like bromoxynil and ioxynil, sulfonylurea herbicides, ALS inhibitor herbicides and HPPD inhibitors, like isoxaflutole and mesotrione.

Transgenes which have been used to provide herbicide tolerance traits comprise: for tolerance to glyphosate: cp4 epsps, epsps grg23ace5, mepsps, 2mepsps, gat4601, gat4621 and goxv247, for tolerance to glufosinate: pat and bar, for tolerance to 2,4-D: aad-1 and aad-12, for tolerance to dicamba: dmo, for tolerance to oxynil herbicies: bxn, for tolerance to sulfonylurea herbicides: zm-hra, csr1-2, gm-hra, S4-HrA, for tolerance to ALS inhibitor herbicides: csr1-2, for tolerance to HPPD inhibitor herbicides: hppdPF, W336 and avhppd-03.

Transgenic corn events comprising herbicide tolerance genes are e.g., but not excluding others, DAS40278, MON801, MON802, MON809, MON810, MON832, MON87411, MON87419, MON87427, MON88017, MON89034, NK603, GA21, MZHGOJG, HCEM485, VCO-Ø1981-5, 676, 678, 680, 33121, 4114, 59122, 98140, Bt10, Bt176, CBH-351, DBT418, DLL25, MS3, MS6, MZIR098, T25, TC1507 and TC6275.

Transgenic soybean events comprising herbicide tolerance genes are e.g., but not excluding others, GTS 40-3-2, MON87705, MON87708, MON87712, MON87769, MON89788, A2704-12, A2704-21, A5547-127, A5547-35, DP356043, DAS44406-6, DAS68416-4, DAS-81419-2, GU262, SYHTØH2, W62, W98, FG72 and CV127.

Transgenic cotton events comprising herbicide tolerance genes are e.g., but not excluding others, 19-51a, 31707, 42317, 81910, 281-24-236, 3006-210-23, BXN10211, BXN10215, BXN10222, BXN10224, MON1445, MON1698, MON88701, MON88913, GHB119, GHB614, LLCotton25, T303-3 and T304-40.

Transgenic canola events comprising herbicide tolerance genes are e.g., but not excluding others, MON88302, HCR-1, HCN10, HCN28, HCN92, MS1, MS8, PHY14, PHY23, PHY35, PHY36, RF1, RF2 and RF3.

Insect resistance has mainly been created by transferring bacterial genes for insecticidal proteins to plants. Transgenes which have most frequently been used are toxin genes of *Bacillus* spec. and synthetic variants thereof, like cry1A, cry1Ab, cry1Ab-Ac, cry1Ac, cry1A.105, cry1F, cry1Fa2, cry2Ab2, cry2Ae, mcry3A, ecry3.1Ab, cry3Bb1, cry34Ab1, cry35Ab1, cry9C, vip3A(a), vip3Aa20. However, also genes of plant origin have been transferred to other plants. In particular genes coding for protease inhibitors, like CpTI and pinII. A further approach uses transgenes in order to produce double stranded RNA in plants to target and down-regulate insect genes. An example for such a transgene is dvsnf7.

Transgenic corn events comprising genes for insecticidal proteins or double stranded RNA are e.g., but not excluding others, Bt10, Bt11, Bt176, MON801, MON802, MON809, MON810, MON863, MON87411, MON88017, MON89034, 33121, 4114, 5307, 59122, TC1507, TC6275, CBH-351, MIR162, DBT418 and MZIR098.

Transgenic soybean events comprising genes for insecticidal proteins are e.g., but not excluding others, MON87701, MON87751 and DAS-81419.

Transgenic cotton events comprising genes for insecticidal proteins are e.g., but not excluding others, SGK321, MON531, MON757, MON1076, MON15985, 31707, 31803, 31807, 31808, 42317, BNLA-601, Event1, COT67B, COT102, T303-3, T304-40, GFM Cry1A, GK12, MLS 9124, 281-24-236, 3006-210-23, GHB119 and SGK321.

Increased yield has been created by increasing ear biomass using the transgene athb17, being present in corn event MON87403, or by enhancing photosynthesis using the transgene bbx32, being present in the soybean event MON87712.

Cultivated plants comprising a modified oil content have been created by using the transgenes: gm-fad2-1, Pj.D6D, Nc.Fad3, fad2-1A and fatb1-A. Soybean events comprising at least one of these genes are: 260-05, MON87705 and MON87769.

Tolerance to abiotic conditions, in particular to tolerance to drought, has been created by using the transgene cspB, comprised by the corn event MON87460 and by using the transgene Hahb-4, comprised by soybean event IND-00410-5.

Traits are frequently combined by combining genes in a transformation event or by combining different events during the breeding process. Preferred combination of traits are herbicide tolerance to different groups of herbicides, insect tolerance to different kind of insects, in particular tolerance to lepidopteran and coleopteran insects, herbicide tolerance with one or several types of insect resistance, herbicide tolerance with increased yield as well as a combination of herbicide tolerance and tolerance to abiotic conditions.

Plants comprising singular or stacked traits as well as the genes and events providing these traits are known (http://www.isaaa.org/gmapprovaldatabase) and (http://cera-amc.ora/GMCropDatabase).

Further information on specific events and methods to detect them can be found for canola events MS1, MS8, RF3, GT73, MON88302, KK179 in WO01/031042, WO01/041558, WO01/041558, WO02/036831, WO11/153186, WO13/003558, for cotton events MON1445, MON15985, MON531(MON15985), LLCotton25, MON88913, COT102, 281-24-236, 3006-210-23, COT67B, GHB614, T304-40, GHB119, MON88701, 81910 in WO02/034946, WO02/100163, WO02/100163, WO03/013224, WO04/072235, WO04/039986, WO05/103266, WO05/103266, WO06/128573, WO07/017186, WO08/122406, WO08/151780, WO12/134808, WO13/112527, for corn events GA21, MON810, DLL25, TC1507, MON863, MIR604, LY038, MON88017, 3272, 59122, NK603, MIR162, MON89034, 98140, 32138, MON87460, 5307, 4114, MON87427, DAS40278, MON87411, 33121, MON87403, MON87419 in WO98/044140, US02/102582, US03/126634, WO04/099447, WO04/011601, WO05/103301, WO05/061720, WO05/059103, WO06/098952, WO06/039376, US2007/292854, WO07/142840, WO07/140256, WO08/112019, WO09/103049, WO09/111263, WO10/077816, WO11/084621, WO11/062904, WO11/022469, WO13/169923, WO14/116854, WO15/053998, WO15/142571, for potato events E12, F10, J3, J55, V11, X17, Y9 in WO14/178910, WO14/178913, WO14/178941, WO14/179276, WO16/183445, WO17/062831, WO17/062825, for rice events LLRICE06, LLRICE601, LLRICE62 in WO00/026345, WO00/026356, WO00/026345 for soybean events H7-1, MON89788, A2704-12, A5547-127, DP305423, DP356043, MON87701, MON87769, CV127, MON87705, DAS68416-4, MON87708, MON87712, SYHT0H2, DAS81419, DAS81419×DAS44406-6, MON87751 in WO04/074492, WO06/130436, WO06/108674, WO06/108675, WO08/054747, WO08/002872, WO09/064652, WO09/102873, WO10/080829, WO10/037016, WO11/066384, WO11/034704, WO12/051199, WO12/082548, WO13/016527, WO13/016516, WO14/201235.

The use of compositions according to the invention on cultivated plants may result in effects which are specific to a cultivated plant comprising a certain gene or event. These effects may comprise enhanced yield, enhanced resistance or tolerance to insects, nematodes, fungal, bacterial, *mycoplasma*, viral or viroid pathogens as well as early vigour, early or delayed ripening, cold or heat tolerance as well as changed amino acid or fatty acid spectrum or content.

It has been found that the pesticidal activity of the compounds of the invention may be enhanced by the insecticidal trait of a modified plant. Furthermore, it has been found that the compounds of the invention are suitable for preventing insects to become resistant to the insecticidal trait or for combating pests, which already have become resistant to the insecticidal trait of a modified plant. Moreover, the compounds of the invention are suitable for combating pests, against which the insecticidal trait is not effective, so that a complementary insecticidal activity can advantageously be used.

The term "plant propagation material" refers to all the generative parts of the plant e.g. seeds and vegetative plant material e.g. cuttings and tubers (e.g. potatoes), which can be used for the multiplication of the plant. This includes seeds, roots, fruits, tubers, bulbs, rhizomes, shoots, sprouts and other parts of plants. Seedlings and young plants, which are to be transplanted after germination or after emergence from soil, may also be included. These plant propagation materials may be treated prophylactically with a plant protection compound either at or before planting or transplanting.

The term "seed" embraces seeds and plant propagules of all kinds including but not limited to true seeds, seed pieces, suckers, corms, bulbs, fruit, tubers, grains, cuttings, cut shoots and the like, and means in a preferred embodiment true seeds.

In general, “pesticidally effective amount” means the amount of active ingredient needed to achieve an observable effect on growth, including the effects of necrosis, death, retardation, prevention, and removal, destruction, or otherwise diminishing the occurrence and activity of the target organism. The pesticidally effective amount can vary for the various compounds/compositions used in the invention. A pesticidally effective amount of the compositions will also vary according to the prevailing conditions e.g. desired pesticidal effect and duration, weather, target species, locus, mode of application.

In the case of soil treatment, in furrow application or of application to the pests dwelling place or nest, the quantity of active ingredient ranges from 0.0001 to 500 g per 100 $m^2$, preferably from 0.001 to 20 g per 100 $m^2$.

For use in treating crop plants, e.g. by foliar application, the rate of application of the active ingredients of this invention may be in the range of 0.0001 g to 4000 g per hectare, e.g. from 1 g to 2 kg per hectare or from 1 g to 750 g per hectare, desirably from 1 g to 100 g per hectare, more desirably from 10 g to 50 g per hectare, e.g., 10 to 20 g per hectare, 20 to 30 g per hectare, 30 to 40 g per hectare, or 40 to 50 g per hectare.

The compounds of the invention are particularly suitable for use in the treatment of seeds in order to protect the seeds from insect pests, in particular from soil-living insect pests, and the resulting seedling's roots and shoots against soil pests and foliar insects. The invention therefore also relates to a method for the protection of seeds from insects, in particular from soil insects, and of the seedling's roots and shoots from insects, in particular from soil and foliar insects, said method comprising treating the seeds before sowing and/or after pregermination with a compound of the invention. The protection of the seedling's roots and shoots is preferred. More preferred is the protection of seedling's shoots from piercing and sucking insects, chewing insects and nematodes.

The term “seed treatment” comprises e.g. seed dressing, seed coating, seed dusting, seed soaking, seed pelleting, and in-furrow application methods. Preferably, the seed treatment application of the active compound is carried out by spraying or by dusting the seeds before sowing of the plants and before emergence of the plants.

The invention also comprises seeds coated with or containing the active compound. The term “coated with and/or containing” generally signifies that the active ingredient is for the most part on the surface of the propagation product at the time of application, although a greater or lesser part of the ingredient may penetrate into the propagation product, depending on the method of application. When the said propagation product is (re)planted, it may absorb the active ingredient.

Suitable seed is e.g. seed of cereals, root crops, oil crops, vegetables, spices, ornamentals, e.g. seed of durum and other wheat, barley, oats, rye, maize (fodder maize and sugar maize/sweet and field corn), soybeans, oil crops, crucifers, cotton, sunflowers, bananas, rice, oilseed rape, turnip rape, sugarbeet, fodder beet, eggplants, potatoes, grass, lawn, turf, fodder grass, tomatoes, leeks, pumpkin/squash, cabbage, iceberg lettuce, pepper, cucumbers, melons, *Brassica* species, melons, beans, peas, garlic, onions, carrots, tuberous plants e.g. potatoes, sugar cane, tobacco, grapes, petunias, geranium/pelargoniums, pansies and *impatiens.*

In addition, the active compound may also be used for the treatment of seeds from plants, which have been modified by mutagenisis or genetic engineering, and which e.g. tolerate the action of herbicides or fungicides or insecticides.

Conventional seed treatment formulations include e.g. flowable concentrates FS, solutions LS, suspoemulsions (SE), powders for dry treatment DS, water dispersible powders for slurry treatment WS, water-soluble powders SS and emulsion ES and EC and gel formulation GF. These formulations can be applied to the seed diluted or undiluted. Application to the seeds is carried out before sowing, either directly on the seeds or after having pregerminated the latter. Preferably, the formulations are applied such that germination is not included.

The active substance concentrations in ready-to-use formulations, which may be obtained after two-to-tenfold dilution, are preferably from 0.01 to 60% by weight, more preferably from 0.1 to 40% by weight.

In a preferred embodiment a FS formulation is used for seed treatment. Typically, a FS formulation may comprise 1-800 g/l of active ingredient, 1-200 g/l Surfactant, 0 to 200 g/l antifreezing agent, 0 to 400 g/l of binder, 0 to 200 g/l of a pigment and up to 1 liter of a solvent, preferably water.

Especially preferred FS formulations of the compounds of the invention for seed treatment usually comprise from 0.1 to 80% by weight (1 to 800 g/l) of the active ingredient, from 0.1 to 20% by weight (1 to 200 g/l) of at least one surfactant, e.g. 0.05 to 5% by weight of a wetter and from 0.5 to 15% by weight of a dispersing agent, up to 20% by weight, e.g. from 5 to 20% of an anti-freeze agent, from 0 to 15% by weight, e.g. 1 to 15% by weight of a pigment and/or a dye, from 0 to 40% by weight, e.g. 1 to 40% by weight of a binder (sticker/adhesion agent), optionally up to 5% by weight, e.g. from 0.1 to 5% by weight of a thickener, optionally from 0.1 to 2% of an anti-foam agent, and optionally a preservative e.g. a biocide, antioxidant or the like, e.g. in an amount from 0.01 to 1% by weight and a filler/vehicle up to 100% by weight.

In the treatment of seed, the application rates of the compounds of the invention are generally from 0.1 g to 10 kg per 100 kg of seed, preferably from 1 g to 5 kg per 100 kg of seed, more preferably from 1 g to 1000 g per 100 kg of seed and in particular from 1 g to 200 g per 100 kg of seed, e.g. from 1 g to 100 g or from 5 g to 100 g per 100 kg of seed.

The invention therefore also relates to seed comprising a compound of the invention, or an agriculturally useful salt thereof, as defined herein. The amount of the compound of the invention or the agriculturally useful salt thereof will in general vary from 0.1 g to 10 kg per 100 kg of seed, preferably from 1 g to 5 kg per 100 kg of seed, in particular from 1 g to 1000 g per 100 kg of seed. For specific crops e.g. lettuce the rate can be higher.

The compounds of the invention may also be used for improving the health of a plant. Therefore, the invention also relates to a method for improving plant health by treating a plant, plant propagation material and/or the locus where the plant is growing or is to grow with an effective and non-phytotoxic amount of a compound of the invention.

As used herein “an effective and non-phytotoxic amount” means that the compound is used in a quantity which allows to obtain the desired effect but which does not give rise to any phytotoxic symptom on the treated plant or on the plant grown from the treated propagule or treated soil.

“Plant health” is defined as a condition of the plant and/or its products which is determined by several aspects alone or in combination with each other e.g. yield (e.g. increased biomass and/or increased content of valuable ingredients), quality (e.g. improved content or composition of certain ingredients or shelf life), plant vigour (e.g. improved plant growth and/or greener leaves ("greening effect"), tolerance to abiotic (e.g. drought) and/or biotic stress (e.g. disease) and production efficiency (e.g., harvesting efficiency, processability).

The above identified indicators for the health condition of a plant may be interdependent and may result from each other. Each indicator is defined in the art and can be determined by methods known to a skilled person.

The compounds of the invention are also suitable for use against non-crop insect pests. For use against said non-crop pests, compounds of the invention can be used as bait composition, gel, general insect spray, aerosol, as ultra-low volume application and bed net (impregnated or surface applied). Furthermore, drenching and rodding methods can be used.

As used herein, the term "non-crop insect pest" refers to pests, which are particularly relevant for non-crop targets, e.g. ants, termites, wasps, flies, ticks, mosquitoes, bed bugs, crickets, or cockroaches.

The bait can be a liquid, a solid or a semisolid preparation (e.g. a gel). The bait employed in the composition is a product, which is sufficiently attractive to incite insects e.g. ants, termites, wasps, flies, mosquitoes, crickets etc. or cockroaches to eat it. The attractiveness can be manipulated by using feeding stimulants or sex pheromones. Food stimulants are preferably chosen from animal and/or plant proteins (meat-, fish- or blood meal, insect parts, egg yolk), from fats and oils of animal and/or plant origin, or mono-, oligo- or polyorganosaccharides, especially from sucrose, lactose, fructose, dextrose, glucose, starch, pectin or even molasses or honey. Fresh or decaying parts of fruits, crops, plants, animals, insects or specific parts thereof can also serve as a feeding stimulant. Sex pheromones are known to be more insect specific. Specific pheromones are known (http://www.pherobase.com).

For use in bait compositions, the typical content of active ingredient is from 0.001 wt % to 15 wt %, desirably from 0.001 wt % to 5 wt % of active compound.

Formulations of the compounds of the invention as aerosols (e.g in spray cans), oil sprays or pump sprays are highly suitable for professional or non-professional users for controlling pests e.g. flies, fleas, ticks, bed bugs, mosquitoes or cockroaches. Aerosol recipes are preferably composed of the active compound, solvents, furthermore auxiliaries e.g. emulsifiers, perfume oils, if appropriate stabilizers, and, if required, propellants.

The oil spray formulations differ from the aerosol recipes in that no propellants are used.

For use in spray compositions, the content of active ingredient is from 0.001 to 80 wt %, preferably from 0.01 to 50 wt % and most preferably from 0.01 to 15 wt %.

The compounds of the invention and its respective compositions can also be used in mosquito and fumigating coils, smoke cartridges, vaporizer plates or long-term vaporizers and also in moth papers, moth pads or other heat-independent vaporizer systems.

Methods to control infectious diseases transmitted by insects (e.g. malaria, dengue and yellow fever, lymphatic filariasis, and leishmaniasis) with compounds of the invention and its respective compositions also comprise treating surfaces of huts and houses, air spraying and impregnation of curtains, tents, clothing items, bed nets, tsetse-fly trap. Insecticidal compositions for application to fibers, fabric, knitgoods, nonwovens, netting material or foils and tarpaulins preferably comprise a mixture including the insecticide, optionally a repellent and at least one binder.

The compounds of the invention and its compositions can be used for protecting wooden materials e.g. trees, board fences, sleepers, frames, artistic artifacts, etc. and buildings, but also construction materials, furniture, leathers, fibers, vinyl articles, electric wires and cables etc. from ants, termites and/or wood or textile destroying beetles, and for controlling ants and termites from doing harm to crops or human beings (e.g. when the pests invade into houses and public facilities or nest in yards, orchards or parks).

Customary application rates in the protection of materials are, e.g., from 0.001 g to 2000 g or from 0.01 g to 1000 g of active compound per $m^2$ treated material, desirably from 0.1 g to 50 g per $m^2$.

Insecticidal compositions for use in the impregnation of materials typically contain from 0.001 to 95 wt %, preferably from 0.1 to 45 wt %, and more preferably from 1 to 25 wt % of at least one repellent and/or insecticide.

The compounds of the invention are especially suitable for efficiently combating animal pests e.g. arthropods, gastropods and nematodes including:

insects from the order of Lepidoptera, e.g. *Achroia grisella, Acleris* spp. e.g. *A. fimbriana, A. gloverana, A. variana; Acrolepiopsis assectella, Acronicta major, Adoxophyes* spp. e.g. *A. cyrtosema, A. orana; Aedia leucomelas, Agrotis* spp. e.g. *A. exclamationis, A. fucosa, A. ipsilon, A. orthogoma, A. segetum, A. subterranea; Alabama argillacea, Aleurodicus dispersus, Alsophila pometaria, Ampelophaga rubiginosa, Amyelois transitella, Anacampsis sarcitella, Anagasta kuehniella, Anarsia lineatella, Anisota senatoria, Antheraea pernyi, Anticarsia* (=*Thermesia*) spp. e.g. *A. gemmatalis; Apamea* spp., *Aproaerema modicella, Archips* spp. e.g. *A. argyrospila, A. fuscocupreanus, A. rosana, A. xyloseanus; Argyresthia conjugella, Argyroploce* spp., *Argyrotaenia* spp. e.g. *A. velutinana; Athetis mindara, Austroasca viridigrisea, Autographa gamma, Autographa nigrisigna, Barathra brassicae, Bedellia* spp., *Bonagota salubricola, Borbo cinnara, Bucculatrix thurberiella, Bupalus piniarius, Busseola* spp., *Cacoecia* spp. e.g. *C. murinana, C. podana; Cactoblastis cactorum, Cadra cautella, Calingo braziliensis, Caloptilis theivora, Capua reticulana, Carposina* spp. e.g. *C. niponensis, C. sasakii; Cephus* spp., *Chaetocnema aridula, Cheimatobia brumata, Chilo* spp. e.g. *C. Indicus, C. suppressalis, C. partellus; Choreutis pariana, Choristoneura* spp. e.g. *C. conflictana, C. fumiferana, C. longicellana, C. murinana, C. occidentalis, C. rosaceana; Chrysodeixis* (=*Pseudoplusia*) spp. e.g. *C. eriosoma, C. includens; Cirphis unipuncta, Clysia ambiguella, Cnaphalocerus* spp., *Cnaphalocrocis medinalis, Cnephasia* spp., *Cochylis hospes, Coleophora* spp., *Colias eurytheme, Conopomorpha* spp., *Conotrachelus* spp., *Copitarsia* spp., *Corcyra cephalonica, Crambus caliginosellus, Crambus teterrellus, Crocidosema* (=*Epinotia*) *aporema, Cydalima* (=*Diaphania*) *perspectalis, Cydia* (=*Carpocapsa*) spp. e.g. *C. pomonella, C. latiferreana; Dalaca noctuides, Datana integerrima, Dasychira pinicola, Dendrolimus* spp. e.g. *D. pini, D. spectabilis, D. sibiricus; Desmia funeralis, Diaphania* spp. e.g. *D. nitidalis, D. hyalinata; Diatraea grandiosella, Diatraea saccharalis, Diphthera festiva, Earias* spp. e.g. *E. insulana, E. vittella; Ecdytolopha aurantianu, Egira* (=*Xylomyges*) *curialis, Elasmopalpus lignosellus, Eldana saccharina, Endopiza viteana, Ennomos sub-*

*signaria, Eoreuma loftini, Ephestia* spp. e.g. *E. cautella, E. elutella, E. kuehniella; Epinotia aporema, Epiphyas postvittana, Erannis tiliaria, Erionota thrax, Etiella* spp., *Eulia* spp., *Eupoecilia ambiguella, Euproctis chrysorrhoea, Euxoa* spp., *Evetria bouliana, Faronta albilinea, Feltia* spp. e.g. *F. subterranean; Galleria mellonella, Gracillaria* spp., *Grapholita* spp. e.g. *G. funebrana, G. molesta, G. inopinata; Halysidota* spp., *Harrisina americana, Hedylepta* spp., *Helicoverpa* spp. e.g. *H. armigera* (=*Heliothis armigera*), *H. zea* (=*Heliothis zea*); *Heliothis* spp. e.g. *H. assulta, H. subflexa, H. virescens; Hellula* spp. e.g. *H. undalis, H. rogatalis; Helocoverpa gelotopoeon, Hemileuca oliviae, Herpetogramma licarsisalis, Hibernia defoliaria, Hofmannophila pseudospretella, Homoeosoma electellum, Homona magnanima, Hypena scabra, Hyphantria cunea, Hyponomeuta padella, Hyponomeuta malinellus, Kakivoria flavofasciata, Keiferia lycopersicella, Lambdina fiscellaria fiscellaria, Lambdina fiscellaria lugubrosa, Lamprosema indicata, Laspeyresia molesta, Leguminivora glycinivorella, Lerodea eufala, Leucinodes orbonalis, Leucoma salicis, Leucoptera* spp. e.g. *L. coffeella, L. scitella; Leuminivora lycinivorella, Lithocolletis blancardella, Lithophane antennata, Llattia octo* (=*Amyna axis*), *Lobesia botrana, Lophocampa* spp., *Loxagrotis albicosta, Loxostege* spp. e.g. *L. sticticalis, L. cereralis; Lymantria* spp. e.g. *L. dispar, L. monacha; Lyonetia clerkella, Lyonetia prunifoliella, Malacosoma* spp. e.g. *M. americanum, M. californicum, M. constrictum, M. neustria; Mamestra* spp. e.g. *M. brassicae, M. configurata; Mamstra brassicae, Manduca* spp. e.g. *M. quinquemaculata, M. sexta; Marasmia* spp, *Marmara* spp., *Maruca testulalis, Megalopyge lanata, Melanchra picta, Melanitis leda, Mocis* spp. e.g. *M. lapites, M. repanda; Mocis latipes, Monochroa fragariae, Mythimna separata, Nemapogon cloacella, Neoleucinodes elegantalis, Nepytia* spp., *Nymphula* spp., *Oiketicus* spp., *Omiodes indicata, Omphisa anastomosalis, Operophtera brumata, Orgyia pseudotsugata, Oria* spp., *Orthaga thyrisalis, Ostrinia* spp. e.g. *O. nubilalis; Oulema oryzae, Paleacrita vernata, Panolis flammea, Parnara* spp., *Papaipema nebris, Papilio cresphontes, Paramyelois transitella, Paranthrene regalis, Paysandisia archon, Pectinophora* spp. e.g. *P. gossypiella; Peridroma saucia, Perileucoptera* spp., e.g. *P. coffeella; Phalera bucephala, Phryganidia californica, Phthorimaea* spp. e.g. *P. operculella; Phyllocnistis citrella, Phyllonorycter* spp. e.g. *P. blancardella, P. crataegella, P. issikii, P. ringoniella; Pieris* spp. e.g. *P. brassicae, P. rapae, P. napi; Pilocrocis tripunctata, Plathypena scabra, Platynota* spp. e.g. *P. flavedana, P. idaeusalis, P. stultana; Platyptilia carduidactyla, Plebejus argus, Plodia interpunctella, Plusia* spp., *Plutella maculipennis, Plutella xylostella, Pontia protodica, Prays* spp., *Prodenia* spp., *Proxenus lepigone, Pseudaletia* spp. e.g. *P. sequax, P. unipuncta; Pyrausta nubilalis, Rachiplusia nu, Richia albicosta, Rhizobius ventralis, Rhyacionia frustrana, Sabulodes aegrotata, Schizura concinna, Schoenobius* spp., *Schreckensteinia festaliella, Scirpophaga* spp. e.g. *S. incertulas, S. innotata; Scotia segetum, Sesamia* spp. e.g. *S. inferens, Seudyra subflava, Sitotroga cerealella, Sparganothis pilleriana, Spilonota lechriaspis, S. ocellina, Spodoptera* (=*Lamphygma*) spp. e.g. *S. cosmoides, S. eridania, S. exigua, S. frugiperda, S. latisfascia, S. littoralis, S. litura, S. omithogalli; Stigmella* spp., *Stomopteryx subsecivella, Strymon bazochii, Sylepta derogata, Synanthedon* spp. e.g. *S. exitiosa, Tecia solanivora, Telehin licus, Thaumatopoea pityocampa, Thaumatotibia* (=*Cryptophlebia*) *leucotreta, Thaumetopoea pityocampa, Thecla* spp., *Theresimima ampelophaga, Thyrinteina* spp, *Tildenia inconspicuella, Tinea* spp. e.g. *T. cloacella, T. pellionella; Tineola bisselliella, Tortrix* spp. e.g. *T. viridana; Trichophaga tapetzella, Trichoplusia* spp. e.g. *T. ni; Tuta* (=*Scrobipalpula*) *absoluta, Udea* spp. e.g. *U. rubigalis, U. rubigalis; Virachola* spp., *Yponomeuta padella*, and *Zeiraphera canadensis;* insects from the order of Coleoptera, e.g. *Acalymma vittatum, Acanthoscehdes obtectus, Adoretus* spp., *Agelastica alni, Agrilus* spp. e.g. *A. anxius, A. planipennis, A. sinuatus; Agriotes* spp. e.g. *A. fuscicollis, A. lineatus, A. obscurus; Alphitobius diaperinus, Amphimallus solstitialis, Anisandrus dispar, Anisoplia austriaca, Anobium punctatum, Anomala corpulenta, Anomala rufocuprea, Anoplophora* spp. e.g. *A. glabripennis; Anthonomus* spp. e.g. *A. eugenii, A. grandis, A. pomorum; Anthrenus* spp., *Aphthona euphoridae, Apion* spp., *Apogonia* spp., *Athous haemorrhoidalis, Atomaria* spp. e.g. *A. linearis; Attagenus* spp., *Aulacophora femoralis, Blastophagus piniperda, Blitophaga undata, Bruchidius obtectus, Bruchus* spp. e.g. *B. lentis, B. pisorum, B. rufimanus; Byctiscus betulae, Callidiellum rufipenne, Callopistria floridensis, Callosobruchus chinensis, Cameraria ohridella, Cassida nebulosa, Cerotoma trifurcata, Cetonia aurata, Ceuthorhynchus* spp. e.g. *C. assimilis, C. napi; Chaetocnema tibialis, Cleonus mendicus, Conoderus* spp. e.g. *C. vespertinus; Conotrachelus nenuphar, Cosmopolites* spp., *Costelytra zealandica, Crioceris asparagi, Cryptolestes ferrugineus, Cryptorhynchus lapathi, Ctenicera* spp. e.g. *C. destructor; Curculio* spp., *Cylindrocopturus* spp., *Cyclocephala* spp., *Dactylispa balyi, Dectes texanus, Dermestes* spp., *Diabrotica* spp. e.g. *D. undecimpunctata, D. speciosa, D. longicornis, D. semipunctata, D. virgifera; Diaprepes abbreviates, Dichocrocis* spp., *Dicladispa armigera, Diloboderus abderus, Diocalandra frumenti* (*Diocalandra stigmaticollis*), *Enaphalodes rufulus, Epilachna* spp. e.g. *E. varivestis, E. vigintioctomaculata; Epitrix* spp. e.g. *E. hirtipennis, E. similaris; Eutheola humilis, Eutinobothrus brasiliensis, Faustinus cubae, Gibbium psylloides, Gnathocerus cornutus, Hellula undalis, Heteronychus arator, Hylamorpha elegans, Hylobius abietis, Hylotrupes bajulus, Hypera* spp. e.g. *H. brunneipennis, H. postica; Hypomeces squamosus, Hypothenemus* spp., *Ips typographus, Lachnosterna consanguinea, Lasioderma serricorne, Latheticus oryzae, Lathridius* spp., *Lema* spp. e.g. *L. bilineata, L. melanopus; Leptinotarsa* spp. e.g. *L. decemlineata; Leptispa pygmaea, Limonius californicus, Lissorhoptrus oryzophilus, Lixus* spp., *Luperodes* spp., *Lyctus* spp. e.g. *L. bruneus; Liogenys fuscus, Macrodactylus* spp. e.g. *M. subspinosus; Maladera matrida, Megaplatypus mutates, Megascelis* spp., *Melanotus communis, Meligethes* spp. e.g. *M. aeneus; Melolontha* spp. e.g. *M. hippocastani, M. melolontha; Metamasius hemipterus, Microtheca* spp., *Migdolus* spp. e.g. *M. fryanus, Monochamus* spp. e.g. *M. alternatus; Naupactus xanthographus, Niptus hololeucus, Oberia brevis, Oemona hirta, Oryctes rhinoceros, Oryzaephilus surinamensis, Oryzaphagus oryzae, Otiorrhynchus sulcatus, Otiorrhynchus ovatus, Otiorrhynchus sulcatus, Oulema melanopus, Oulema oryzae,*

*Oxycetonia jucunda, Phaedon* spp. e.g. *P. brassicae, P. cochleariae; Phoracantha recurva, Phyllobius pyri, Phyllopertha horticola, Phyllophaga* spp. e.g. *P. helleri; Phyllotreta* spp. e.g. *P. chrysocephala, P. nemorum, P. striolata, P. vittula; Phyllopertha horticola, Popillia japonica, Premnotrypes* spp., *Psacothea hilaris, Psylliodes chrysocephala, Prostephanus truncates, Psylliodes* spp., *Ptinus* spp., *Pulga saltona, Rhizopertha dominica, Rhynchophorus* spp. e.g. *R. billineatus, R. ferrugineus, R. palmarum, R. phoenicis, R. vulneratus; Saperda candida, Scolytus schevyrewi, Scyphophorus acupunctatus, Sitona lineatus, Sitophilus* spp. e.g. *S. granaria, S. oryzae, S. zeamais; Sphenophorus* spp. e.g. *S. levis; Stegobium paniceum, Sternechus* spp. e.g. *S. subsignatus; Strophomorphus ctenotus, Symphyletes* spp., *Tanymecus* spp., *Tenebrio molitor, Tenebrioides mauretanicus, Tribolium* spp. e.g. *T. castaneum; Trogoderma* spp., *Tychius* spp., *Xylotrechus* spp. e.g. *X. pyrrhoderus*; and, *Zabrus* spp. e.g. *Z. tenebrioides;* insects from the order of Diptera e.g. *Aedes* spp. e.g. *A. aegypti, A. albopictus, A. vexans; Anastrepha ludens, Anopheles* spp. e.g. *A. albimanus, A. crucians, A. freeborni, A. gambiae, A. leucosphyrus, A. maculipennis, A. minimus, A. quadrimaculatus, A. sinensis; Bactrocera invadens, Bibio hortulanus, Calliphora erythrocephala, Calliphora vicina, Ceratitis capitata, Chrysomyia* spp. e.g. *C. bezziana, C. hominivorax, C. macellaria; Chrysops atlanticus, Chrysops discalis, Chrysops silacea, Cochliomyia* spp. e.g. *C. hominivorax; Contarinia* spp. e.g. *C. sorghicola; Cordylobia anthropophaga, Culex* spp. e.g. *C. nigripalpus, C. pipiens, C. quinquefasciatus, C. tarsalis, C. tritaeniorhynchus; Culicoides furens, Culiseta inornata, Culiseta melanura, Cuterebra* spp., *Dacus cucurbitae, Dacus oleae, Dasineura brassicae, Dasineura oxycoccana, Delia* spp. e.g. *D. antique, D. coarctata, D. platura, D. radicum; Dermatobia hominis, Drosophila* spp. e.g. *D. suzukii, Fannia* spp. e.g. *F. canicularis; Gastraphilus* spp. e.g. *G. intestinalis; Geomyza tipunctata, Glossina* spp. e.g. *G. fuscipes, G. morsitans, G. palpalis, G. tachinoides; Haematobia irritans, Haplodiplosis equestris, Hippelates* spp., *Hylemyia* spp. e.g. *H. platura; Hypoderma* spp. e.g. *H. lineata; Hyppobosca* spp., *Hydrellia philippina, Leptoconops torrens, Liriomyza* spp. e.g. *L. sativae, L. trifolii; Lucilia* spp. e.g. *L. caprina, L. cuprina, L. sericata; Lycoria pectoralis, Mansonia titillanus, Mayetiola* spp. e.g. *M. destructor; Musca* spp. e.g. *M. autumnalis, M. domestica; Muscina stabulans, Oestrus* spp. e.g. *O. ovis; Opomyza florum, Oscinella* spp. e.g. *O. frit; Orseolia oryzae, Pegomya hysocyami, Phlebotomus argentipes, Phorbia* spp. e.g. *P. antiqua, P. brassicae, P. coarctata; Phytomyza gymnostoma, Prosimulium mixtum, Psila rosae, Psorophora columbiae, Psorophora discolor, Rhagoletis* spp. e.g. *R. cerasi, R. cingulate, R. indifferens, R. mendax, R. pomonella; Rivellia quadrifasciata, Sarcophaga* spp. e.g. *S. haemorrhoidalis; Simulium vittatum, Sitodiplosis mosellana, Stomoxys* spp. e.g. *S. calcitrans; Tabanus* spp. e.g. *T. atratus, T. bovinus, T. lineola, T. similis; Tannia* spp., *Thecodiplosis japonensis, Tipula oleracea, Tipula paludosa*, and *Wohlfahrtia* spp;

insects from the order of Thysanoptera e.g., *Baliothrips biformis, Dichromothrips corbetti, Dichromothrips* ssp., *Echinothrips americanus, Enneothrips flavens, Frankliniella* spp. e.g. *F. fusca, F. occidentalis, F. tritici; Heliothrips* spp., *Hercinothrips femoralis, Kakothrips* spp., *Microcephalothrips abdominalis, Neohydatothrips samayunkur, Pezothrips kellyanus, Rhipiphorothrips cruentatus, Scirtothrips* spp. e.g. *S. citri, S. dorsalis, S. perseae; Stenchaetothrips* spp, *Taeniothrips cardamoni, Taeniothrips inconsequens, Thrips* spp. e.g. *T. imagines, T. hawaiiensis, T. oryzae, T. palmi, T. parvispinus, T. tabaci;* insects from the order of Hemiptera e.g., *Acizziajamatonica, Acrosternum* spp. e.g. *A. hilare; Acyrthosipon* spp. e.g. *A. onobrychis, A. pisum; Adelges laricis, Adelges tsugae, Adelphocoris* spp., e.g. *A. rapidus, A. superbus; Aeneolamia* spp., *Agonoscena* spp., *Aulacorthum solani, Aleurocanthus woglumi, Aleurodes* spp., *Aleurodicus disperses, Aleurolobus barodensis, Aleurothrixus* spp., *Amrasca* spp., *Anasa tristis, Antestiopsis* spp., *Anuraphis cardui, Aonidiella* spp., *Aphanostigma piri, Aphidula nasturtii, Aphis* spp. e.g. *A. craccivora, A. fabae, A. forbesi, A. gossypii, A. grossulariae, A. maidiradicis, A. pomi, A. sambuci, A. schneideri, A. spiraecola; Arboridia apicalis, Arilus critatus, Aspidiella* spp., *Aspidiotus* spp., *Atanus* spp., *Aulacaspis yasumatsui, Aulacorthum solani, Bactericera cockerelli* (*Paratrioza cockerelli*), *Bemisia* spp. e.g. *B. argentifolii, B. tabaci* (*Aleurodes tabaci*); *Blissus* spp. e.g. *B. leucopterus; Brachycaudus* spp. e.g. *B. cardui, B. helichrysi, B. persicae, B. prunicola; Brachycolus* spp., *Brachycorynella asparagi, Brevicoryne brassicae, Cacopsylla* spp. e.g. *C. fulguralis, C. pyricola* (*Psylla piri*); *Calligypona marginata, Calocoris* spp., *Campylomma livida, Capitophorus horni, Carneocephala fulgida, Cavelerius* spp., *Ceraplastes* spp., *Ceratovacuna lanigera, Ceroplastes ceriferus, Cerosipha gossypii, Chaetosiphon fragaefolii, Chionaspis tegalensis, Chlorita onukii, Chromaphis juglandicola, Chrysomphalus ficus, Cicadulina mbila, Cimex* spp. e.g. *C. hemipterus, C. lectularius; Coccomytilus halli, Coccus* spp. e.g. *C. hesperidum, C. pseudomagnoliarum; Corythucha arcuata, Creontiades dilutus, Cryptomyzus ribis, Chrysomphalus aonidum, Cryptomyzus ribis, Ctenarytaina spatulata, Cyrtopeltis notatus, Dalbulus* spp., *Dasynus piperis, Dialeurodes* spp. e.g. *D. citrifolii; Dalbulus maidis, Diaphorina* spp. e.g. *D. citri; Diaspis* spp. e.g. *D. bromeliae; Dichelops furcatus, Diconocoris hewetti, Doralis* spp., *Dreyfusia nordmannianae, Dreyfusia piceae, Drosicha* spp., *Dysaphis* spp. e.g. *D. plantaginea, D. pyri, D. radicola; Dysaulacorthum pseudosolani, Dysdercus* spp. e.g. *D. cingulatus, D. intermedius; Dysmicoccus spp., Edessa* spp., *Geocoris* spp., *Empoasca* spp. e.g. *E. fabae, E. solana; Epidiaspis leperii, Eriosoma* spp. e.g. *E. lanigerum, E. pyricola; Erythroneura* spp., *Eurygaster* spp. e.g. *E. integriceps; Euscelis bilobatus, Euschistus* spp. e.g. *E. heros, E. impictiventris, E. servus; Fiorinia theae, Geococcus coffeae, Glycaspis brimblecombei, Halyomorpha* spp. e.g. *H. halys; Heliopeltis* spp., *Homalodisca vitripennis* (=*H. coagulata*), *Horcias nobilellus, Hyalopterus pruni, Hyperomyzus lactucae, Icerya* spp. e.g. *I. purchase; Idiocerus* spp., *Idioscopus* spp., *Laodelphax striatellus, Lecanium* spp., *Lecanoideus floccissimus, Lepidosaphes* spp. e.g. *L. ulmi; Leptocorisa* spp., *Leptoglossus phyllopus, Lipaphis erysimi, Lygus* spp. e.g. *L. hesperus, L. lineolaris, L. pratensis; Maconellicoccus hirsutus, Marchalina hellenica, Macropes excavatus, Macrosiphum* spp. e.g. *M. rosae, M. avenae, M. euphorbiae; Macrosteles quadrilineatus, Mahanarva fimbriolata, Megacopta cribraria, Megoura viciae, Melanaphis pyrarius, Melanaphis sacchari,*

*Melanocallis* (=*Tinocallis*) *caryaefoliae, Metcafiella* spp., *Metopolophium dirhodum, Monellia costalis, Monelliopsis pecanis, Myzocallis coryli, Murgantia* spp., *Myzus* spp. e.g. *M. ascalonicus, M. cerasi, M. nicotianae, M. persicae, M. varians; Nasonovia ribis-nigri, Neotoxoptera formosana, Neomegalotomus* spp, *Nephotettix* spp. e.g. *N. malayanus, N. nigropictus, N. parvus, N. virescens; Nezara* spp. e.g. *N. viridula; Nilaparvata lugens, Nysius huttoni, Oebalus* spp. e.g. *O. pugnax; Oncometopia* spp., *Orthezia praelonga, Oxycaraenus hyalinipennis, Parabemisia myricae, Parlatoria* spp., *Parthenolecanium* spp. e.g. *P. corni, P. persicae; Pemphigus* spp. e.g. *P. bursarius, P. populivenae; Peregrinus maidis, Perkinsiella saccharicida, Phenacoccus* spp. e.g. *P. aceris, P. gossypii; Phloeomyzus passerinii, Phorodon humuli, Phylloxera* spp. e.g. *P. devastatrix, Piesma quadrata, Piezodorus* spp. e.g. *P. guildinii; Pinnaspis aspidistrae, Planococcus* spp. e.g. *P. citri, P. ficus; Prosapia bicincta, Protopulvinaria pyriformis, Psallus seriatus, Pseudacysta persea, Pseudaulacaspis pentagona, Pseudococcus* spp. e.g. *P. comstocki; Psylla* spp. e.g. *P. mali; Pteromalus* spp., *Pulvinaria amygdali, Pyrilla* spp., *Quadraspidiotus* spp., e.g. *Q. perniciosus; Quesada gigas, Rastrococcus* spp., *Reduvius senilis, Rhizoecus americanus, Rhodnius* spp., *Rhopalomyzus ascalonicus, Rhopalosiphum* spp. e.g. *R. pseudobrassicas, R. insertum, R. maidis, R. padi; Sagatodes* spp., *Sahlbergella singularis, Saissetia* spp., *Sappaphis mala, Sappaphis mali, Scaptocoris* spp., *Scaphoides titanus, Schizaphis graminum, Schizoneura lanuginosa, Scotinophora* spp., *Selenaspidus articulatus, Sitobion avenae, Sogata* spp., *Sogatella furcifera, Solubea insularis, Spissistilus festinus* (=*Stictocephala festina*), *Stephanitis nashi, Stephanitis pyrioides, Stephanitis takeyai, Tenalaphara malayensis, Tetraleurodes perseae, Therioaphis maculate, Thyanta* spp. e.g. *T. accerra, T. perditor; Tibraca* spp., *Tomaspis* spp., *Toxoptera* spp. e.g. *T. aurantii; Trialeurodes* spp. e.g. *T. abutilonea, T. ricini, T. vaporariorum; Triatoma* spp., *Trioza* spp., *Typhlocyba* spp., *Unaspis* spp. e.g. *U. citri, U. yanonensis*; and *Viteus vitifolii,*

Insects from the order Hymenoptera e.g. *Acanthomyops interjectus, Athalia rosae, Atta* spp. e.g. *A. capiguara, A. cephalotes, A. cephalotes, A. laevigata, A. robusta, A. sexdens, A. texana, Bombus* spp., *Brachymyrmex* spp., *Camponotus* spp. e.g. *C. floridanus, C. pennsylvanicus, C. modoc; Cardiocondyla nuda, Chalibion* sp, *Crematogaster* spp., *Dasymutilla occidentalis, Diprion* spp., *Dolichovespula maculata, Dorymyrmex* spp., *Dryocosmus kuriphilus, Formica* spp., *Hoplocampa* spp. e.g. *H. minuta, H. testudinea; Iridomyrmex humilis, Lasius* spp. e.g. *L. niger, Linepithema humile, Liometopum* spp., *Leptocybe invasa, Monomorium* spp. e.g. *M. pharaonis, Monomorium, Nylandria fulva, Pachycondyla chinensis, Paratrechina longicornis, Paravespula* spp., e.g. *P. germanica, P. pennsylvanica, P. vulgaris; Pheidole* spp. e.g. *P. megacephala; Pogonomyrmex* spp. e.g. *P. barbatus, P. californicus, Polistes rubiginosa, Prenolepis impairs, Pseudomyrmex gracilis, Schelipron* spp., *Sirex cyaneus, Solenopsis* spp. e.g. *S. geminata, S. invicta, S. molesta, S. richteri. S. xyloni. Sphecius speciosus, Sphex* spp., *Tapinoma* spp. e.g. *T. melanocephalum, T. sessile; Tetramorium* spp. e.g. *T. caespitum, T. bicarinatum, Vespa* spp. e.g. *V. crabro; Vespula* spp. e.g. *V. squamosal; Wasmannia auropunctata, Xylocopa* sp;

Insects from the order Orthoptera e.g. *Acheta domesticus, Calliptamus italicus, Chortoicetes terminifera, Ceuthophilus* spp., *Diastrammena asynamora, Dociostaurus maroccanus, Gryllotalpa* spp. e.g. *G. africana, G. gryllotalpa; Gryllus* spp., *Hieroglyphus daganensis, Kraussaria angulifera, Locusta* spp. e.g. *L. migratoria, L. pardalina; Melanoplus* spp. e.g. *M. bivittatus, M. femurrubrum, M. mexicanus, M. sanguinipes, M. spretus; Nomadacris septemfasciata, Oedaleus senegalensis, Scapteriscus* spp., *Schistocerca* spp. e.g. *S. americana, S. gregaria, Stemopelmatus* spp., *Tachycines asynamorus*, and *Zonozerus variegatus;*

Pests from the Class Arachnida e.g. Acari, e.g. of the families Argasidae, Ixodidae and Sarcoptidae, e.g. *Amblyomma* spp. (e.g. *A. americanum, A. variegatum, A. maculatum*), *Argas* spp. e.g. *A. persicu*), *Boophilus* spp. e.g. *B. annulatus, B. decoloratus, B. microplus, Dermacentor* spp. e.g. *D. silvarum, D. andersoni, D. variabilis, Hyalomma* spp. e.g. *H. truncatum, Ixodes* spp. e.g. *I. ricinus, I. rubicundus, I. scapularis, I. holocyclus, I. pacificus, Rhipicephalus sanguineus, Ornithodorus* spp. e.g. *O. moubata, O. hermsi, O. turicata, Ornithonyssus bacoti, Otobius megnini, Dermanyssus gallinae, Psoroptes* spp. e.g. *P. ovis, Rhipicephalus* spp. e.g. *R. sanguineus, R. appendiculatus, Rhipicephalus evertsi, Rhizoglyphus* spp., *Sarcoptes* spp. e.g. *S. scabiei*; and Family Eriophyidae including Aceria spp. e.g. *A. sheldoni, A. anthocoptes, Acallitus* spp., *Aculops* spp. e.g. *A. lycopersici, A. pelekassi; Aculus* spp. e.g. *A. schlechtendali; Colomerus vitis, Epitrimerus pyri, Phyllocoptruta oleivora; Eriophytes ribis* and *Eriophyes* spp. e.g. *Eriophyes sheldoni*; Family Tarsonemidae including *Hemitarsonemus* spp., *Phytonemus pallidus* and *Polyphagotarsonemus latus, Stenotarsonemus* spp. *Steneotarsonemus spinki*; Family Tenuipalpidae including *Brevipalpus* spp. e.g. *B. phoenicis*; Family Tetranychidae including *Eotetranychus* spp., *Eutetranychus* spp., *Oligonychus* spp., *Petrobia latens, Tetranychus* spp. e.g. *T. cinnabarinus, T. evansi, T. kanzawai, T, pacificus, T. phaseulus, T. telarius* and *T. urticae; Bryobia praetiosa; Panonychus* spp. e.g. *P. ulmi, P. citri; Metatetranychus* spp. and *Oligonychus* spp. e.g. *O. pratensis, O. perseae, Vasates lycopersici; Raoiella indica*, Family Carpoglyphidae including *Carpoglyphus* spp.; *Penthaleidae* spp. e.g. Halotydeus destructor; Family Demodicidae with species e.g. *Demodex* spp.; Family Trombicidea including *Trombicula* spp.; Family Macronyssidae including *Ornothonyssus* spp.; Family Pyemotidae including *Pyemotes tritici; Tyrophagus putrescentiae*; Family Acaridae including *Acarus siro*; Family Araneida including *Latrodectus mactans, Tegenaria agrestis, Chiracanthium* sp, *Lycosa* sp *Achaearanea tepidariorum* and *Loxosceles reclusa;*

Pests from the Phylum Nematoda, e.g. plant parasitic nematodes e.g. root-knot nematodes, *Meloidogyne* spp. e.g. *M. hapla, M. incognita, M. javanica*; cyst-forming nematodes, *Globodera* spp. e.g. *G. rostochiensis; Heterodera* spp. e.g. *H. avenae, H. glycines, H. schachtii, H. trifolii*; Seed gall nematodes, *Anguina* spp.; Stem and foliar nematodes, *Aphelenchoides* spp. e.g. *A. besseyi*; Sting nematodes, *Belonolaimus* spp. e.g. *B. longicaudatus*; Pine nematodes, *Bursaphelenchus* spp. e.g. *B. lignicolus, B. xylophilus*; Ring nematodes, *Criconema* spp., *Criconemella* spp. e.g. *C. xenoplax* and *C. ornata*; and, *Criconemoides* spp. e.g. *Criconemoides informis; Mesocriconema* spp.; Stem and bulb nematodes, *Ditylenchus* spp. e.g. *D. destructor, D. dipsaci*; Awl nematodes, *Dolichodorus* spp.; Spiral nematodes, *Heliocotylenchus multicinctus*; Sheath and sheathoid nematodes, *Hemicycliophora* spp. and *Hemicriconemoides* spp.; *Hirshmanniella* spp.; Lance nematodes, *Hoploaimus* spp.; False rootknot nematodes, *Nacobbus* spp.; Needle nematodes, *Longidorus* spp. e.g. *L. elongatus*; Lesion nematodes, *Pratylenchus* spp. e.g. *P. brachyurus, P. neglectus, P. penetrans, P. curvitatus, P. goodeyi*; Burrowing nematodes, *Radopholus* spp. e.g. *R. similis; Rhadopholus* spp.; *Rhodopholus* spp.; Reniform nematodes, *Rotylenchus* spp. e.g. *R. robustus, R. reniformis; Scutellonema* spp.; Stubby-root nematode, *Trichodorus* spp. e.g. *T. obtusus, T. primitivus; Paratrichodorus* spp. e.g. *P. minor*; Stunt nematodes, *Tylenchorhynchus* spp. e.g. *T. claytoni, T. dubius*; Citrus nematodes, *Tylenchulus* spp. e.g. *T. semipenetrans*; Dagger nematodes, *Xiphinema* spp.; and other plant parasitic nematode species;

Insects from the order Blattodea e.g. *Macrotermes* spp. e.g. *M. natalensis; Cornitermes cumulans, Procornitermes* spp., *Globitermes sulfureus, Neocapritermes* spp. e.g. *N. opacus, N. parvus; Odontotermes* spp., *Nasutitermes* spp. e.g. *N. corniger; Coptotermes* spp. e.g. *C. formosanus, C. gestroi, C. acinaciformis; Reticulitermes* spp. e.g. *R. hesperus, R. tibialis, R. speratus, R. flavipes, R. grassei, R. lucifugus, R. virginicus; Heterotermes* spp. e.g. *H. aureus, H. longiceps, H. tenuis; Cryptotermes* spp. e.g. *C. brevis, C. cavifrons; Incisitermes* spp. e.g. *I. minor, I. snyderi; Marginitermes hubbardi, Kalotermes flavicollis, Neotermes* spp. e.g. *N. castaneus, Zootermopsis* spp. e.g. *Z. angusticollis, Z. nevadensis, Mastotermes* spp. e.g. *M. darwiniensis; Blatta* spp. e.g. *B. orientalis, B. lateralis; Blattella* spp. e.g. *B. asahinae, B. germanica; Rhyparobia maderae, Panchlora nivea, Periplaneta* spp. e.g. *P. americana, P. australasiae, P. brunnea, P. fuliginosa, P. japonica; Supella longipalpa, Parcoblatta pennsylvanica, Eurycotis floridana, Pycnoscelus surinamensis,*

Insects from the order Siphonoptera e.g. *Cediopsylla simples, Ceratophyllus* spp., *Ctenocephalides* spp. e.g. *C. felis, C. canis, Xenopsylla cheopis, Pulex irritans, Trichodectes canis, Tunga penetrans*, and *Nosopsyllus fasciatus,*

Insects from the order Thysanura e.g. *Lepisma saccharina, Ctenolepisma urbana*, and *Thermobia domestica,*

Pests from the class Chilopoda e.g. *Geophilus* spp., *Scutigera* spp. e.g. *Scutigera coleoptrata;*

Pests from the class Diplopoda e.g. *Blaniulus guttulatus, Julus* spp., *Narceus* spp., Pests from the class Symphyla e.g. *Scutigerella immaculata,*

Insects from the order Dermaptera, e.g. *Forficula auricularia,*

Insects from the order Collembola, e.g. *Onychiurus* spp., e.g. *Onychiurus armatus,*

Pests from the order Isopoda e.g., *Armadillidium vulgare, Oniscus asellus, Porcellio scaber,*

Insects from the order Phthiraptera, e.g. *Damalinia* spp., *Pediculus* spp. e.g. *Pediculus humanus* capitis, *Pediculus humanus* corporis, *Pediculus humanus humanus; Pthirus pubis, Haematopinus* spp. e.g. *Haematopinus eurysternus, Haematopinus suis; Linognathus* spp. e.g. *Linognathus vituli; Bovicola bovis, Menopon gallinae, Menacanthus stramineus* and *Solenopotes capillatus, Trichodectes* spp., Further pest species which may be controlled by compounds I include: from the Phylum Mollusca, class Bivalvia, e.g., *Dreissena* spp.; class Gastropoda, e.g., Anon spp., *Biomphalaria* spp., *Bulinus* spp., *Deroceras* spp., Galba spp., *Lymnaea* spp., *Oncomelania* spp., *Pomacea canaliclata, Succinea* spp.; from the class of the helminths, e.g., *Ancylostoma duodenale, Ancylostoma ceylanicum, Acylostoma braziliensis, Ancylostoma* spp., *Ascaris lumbricoides, Ascaris* spp., *Brugia malayi, Brugia timori, Bunostomum* spp., *Chabertia* spp., *Clonorchis* spp., *Cooperia* spp., *Dicrocoelium* spp., *Dictyocaulus filaria, Diphyllobothrium latum, Dracunculus medinensis, Echinococcus granulosus, Echinococcus multilocularis, Enterobius vermicularis, Faciola* spp., *Haemonchus* spp. e.g. *Haemonchus contortus; Heterakis* spp., *Hymenolepis nana, Hyostrongulus* spp., *Loa Loa, Nematodirus* spp., *Oesophagostomum* spp., *Opisthorchis* spp., *Onchocerca volvulus, Ostertagia* spp., *Paragonimus* spp., *Schistosomen* spp., *Strongyloides fuelleborni, Strongyloides stercoralis, Stronyloides* spp., *Taenia saginata, Taenia solium, Trichinella spiralis, Trichinella nativa, Trichinella britovi, Trichinella nelsoni, Trichinella pseudopsiralis, Trichostrongulus* spp., *Trichuris trichiura, Wuchereria bancrofti.*

The compounds of the invention are particularly suitable for efficiently combating insects from the sub-order of Auchenorrhyncha, e.g. *Amrasca biguttula, Empoasca* spp., *Nephotettix virescens, Sogatella furcifera, Mahanarva* spp., *Laodelphax striatellus, Nilaparvata lugens, Diaphorina citri;*

Lepidoptera, e.g. *Helicoverpa* spp., *Heliothis virescens, Lobesia botrana, Ostrinia nubilalis, Plutella xylostella, Pseudoplusia includens, Scirpophaga incertulas, Spodoptera* spp., *Trichoplusia ni, Tuta absoluta, Cnaphalocrocis medialis, Cydia pomonella, Chilo suppressalis, Anticarsia gemmatalis, Agrotis ipsilon, Chrysodeixis includens;*

True bugs, e.g. *Lygus* spp., Stink bugs such as *Euschistus* spp., *Halyomorpha halys, Nezara viridula, Piezodorus guildinii, Dichelops furcatus;*

Thrips, e.g. *Frankliniella* spp., *Thrips* spp., *Dichromothrips corbettii;*

Aphids, e.g. *Acyrthosiphon pisum, Aphis* spp., *Myzus persicae, Rhopalosiphum* spp., *Schizaphis graminum, Megoura viciae;*

Whiteflies, e.g. *Trialeurodes vaporariorum, Bemisia* spp.;

Coleoptera, e.g. *Phyllotreta* spp., *Melanotus* spp., *Meligethes aeneus, Leptinotarsa decimlineata, Ceutorhynchus* spp., *Diabrotica* spp., *Anthonomus grandis, Atomaria linearia, Agriotes* spp., *Epilachna* spp.;

Flies, e.g. *Delia* spp., *Ceratitis* capitate, *Bactrocera* spp., *Liriomyza* spp.;

Coccoidea, e.g. *Aonidiella aurantia*, Ferrisia virgate;

Anthropods of class Arachnida (Mites), e.g. *Penthaleus major, Tetranychus* spp.;

Nematodes, e.g. *Heterodera glycines, Meloidogyne* sp., *Pratylenchus* spp., *Caenorhabditis elegans.*

The compounds of the invention are suitable for use in treating or protecting animals against infestation or infection by parasites. Therefore, the invention also relates to the use of a compound of the invention for the manufacture of a medicament for the treatment or protection of animals against infestation or infection by parasites. Furthermore, the invention relates to a method of treating or protecting animals against infestation and infection by parasites, which comprises orally, topically or parenterally administering or applying to the animals a parasiticidally effective amount of a compound of the invention.

The invention also relates to the non-therapeutic use of compounds of the invention for treating or protecting animals against infestation and infection by parasites. Moreover, the invention relates to a non-therapeutic method of treating or protecting animals against infestation and infection by parasites, which comprises applying to a locus a parasiticidally effective amount of a compound of the invention.

The compounds of the invention are further suitable for use in combating or controlling parasites in and on animals. Furthermore, the invention relates to a method of combating or controlling parasites in and on animals, which comprises contacting the parasites with a parasitically effective amount of a compound of the invention.

The invention also relates to the non-therapeutic use of compounds of the invention for controlling or combating parasites. Moreover, the invention relates to a non-therapeutic method of combating or controlling parasites, which comprises applying to a locus a parasiticidally effective amount of a compound of the invention.

The compounds of the invention can be effective through both contact (via soil, glass, wall, bed net, carpet, blankets or animal parts) and ingestion (e.g. baits). Furthermore, the compounds of the invention can be applied to any and all developmental stages.

The compounds of the invention can be applied as such or in form of compositions comprising the compounds of the invention.

The compounds of the invention can also be applied together with a mixing partner, which acts against pathogenic parasites, e.g. with synthetic coccidiosis compounds, polyetherantibiotics e.g. Amprolium, Robenidin, Toltrazuril, Monensin, Salinomycin, Maduramicin, Lasalocid, Narasin or Semduramicin, or with other mixing partners as defined above, or in form of compositions comprising said mixtures.

The compounds of the invention and compositions comprising them can be applied orally, parenterally or topically, e.g. dermally. The compounds of the invention can be systemically or non-systemically effective.

The application can be carried out prophylactically, therapeutically or non-therapeutically. Furthermore, the application can be carried out preventively to places at which occurrence of the parasites is expected.

As used herein, the term “contacting” includes both direct contact (applying the compounds/compositions directly on the parasite, including the application directly on the animal or excluding the application directly on the animal, e.g. at it’s locus for the latter) and indirect contact (applying the compounds/compositions to the locus of the parasite). The contact of the parasite through application to its locus is an example of a non-therapeutic use of the compounds of the invention.

The term “locus” means the habitat, food supply, breeding ground, area, material or environment in which a parasite is growing or may grow outside of the animal.

As used herein, the term “parasites” includes endo- and ectoparasites. In some embodiments of the invention, endoparasites can be preferred. In other embodiments, ectoparasites can be preferred. Infestations in warm-blooded animals and fish include lice, biting lice, ticks, nasal bots, keds, biting flies, muscoid flies, flies, myiasitic fly larvae, chiggers, gnats, mosquitoes and fleas.

The compounds of the invention are especially useful for combating parasites of the following orders and species, respectively:

fleas (Siphonaptera), e.g. *Ctenocephalides felis, C. canis, Xenopsylla cheopis, Pulex irritans, Tunga penetrans*, and *Nosopsyllus fasciatus*; cockroaches (*Blattaria*—Blattodea), e.g. *Blattella germanica, B. asahinae, Periplaneta americana, P. japonica, P. brunnea, P. fuligginosa, P. australasiae*, and *Blatta orientalis*; flies, mosquitoes (Diptera), e.g. *Aedes aegypti, A. albopictus, A. vexans, Anastrepha ludens, Anopheles maculipennis, A. crucians, A. albimanus, A. gambiae, A. freeborni, A. leucosphyrus, A. minimus, A. quadrimaculatus, Calliphora vicina, Chrysomya bezziana, C. hominivorax, C. macellaria, Chrysops discalis, C. silacea, C. atlanticus, Cochliomyia hominivorax, Cordylobia anthropophaga, Culicoides furens, Culex pipiens, C. nigripalpus, C. quinquefasciatus, C. tarsalis, Culiseta inornata, C. melanura, Dermatobia hominis, Fannia canicularis, Gasterophilus intestinalis, Glossina morsitans, G. palpalis, G. fuscipes, G. tachinoides, Haematobia irritans, Haplodiplosis equestris, Hippelates* spp., *Hypoderma lineata, Leptoconops torrens, Lucilia caprina, L. cuprina, L. sericata, Lycoria pectoralis, Mansonia* spp., *Musca domestica, M. stabulans, Oestrus ovis, Phlebotomus argentipes, Psorophora columbiae, P. discolor, Prosimulium mixtum, Sarcophaga* spp., *S. haemorrhoidalis, Simulium vittatum, Stomoxys calcitrans, Tabanus bovinus, T. atratus, T. lineola*, and *T. similis*; lice (Phthiraptera), e.g. *Pediculus humanus* capitis, *P. humanus humanus, Pthirus pubis, Haematopinus eurysternus, H. suis, Linognathus vituli, Bovicola bovis, Menopon gallinae, Menacanthus stramineus*, and *Solenopotes capillatus*; ticks and parasitic mites (Parasitiformes): ticks (Ixodida), e.g. *Ixodes scapularis, I. holocyclus, I. pacificus, Rhiphicephalus sanguineus, Dermacentor andersoni, D. variabilis, Amblyomma americanum, A. maculatum, Ornithodorus hermsi, O. turicata* and parasitic mites (Mesostigmata), e.g. *Ornithonyssus bacoti, Dermanyssus gallinae*; Actinedida (Prostigmata) and Acaridida (Astigmata), e.g. *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp., and *Laminosioptes* spp; Bugs (Heteropterida): *Cimex lectularius, C. hemipterus, Reduvius senilis, Triatoma* spp., *Rhodnius* ssp., *Panstrongylus* ssp., and *Arilus critatus; Anoplurida*, e.g. *Haematopinus* spp., *Linognathus* spp., *Pediculus* spp., *Phtirus* spp., and *Solenopotes* spp.; Mallophagida (suborders Arnblycerina and Ischnocerina), e.g. *Trimenopon* spp., *Menopon* spp., *Trinoton* spp., *Bovicola* spp., *Werneckiella* spp., *Lepikentron* spp., *Trichodectes* spp., and *Felicola* spp.; Roundworms Nematoda: Wipeworms and Trichinosis (Trichosyringida), e.g. Trichinellidae (*Trichinella* spp.), (Trichuridae) *Trichuris* spp., *Capillaria* spp.; Rhabditida, e.g. *Rhabditis* spp., *Strongyloides* spp., *Helicephalobus* spp.; Strongylida, e.g. *Strongylus* spp., *Ancylostoma* spp., *Necator americanus, Bunostomum* spp. (Hookworm), *Trichostrongylus* spp., *Haemonchus contortus, Ostertagia* spp., *Cooperia* spp., *Nematodirus* spp., *Dictyocaulus* spp., *Cyathostoma* spp., *Oesophagostomum* spp., *Stephanurus dentatus, Ollulanus* spp., *Chabertia* spp., *Stephanurus dentatus, Syngamus trachea, Ancylostoma* spp., *Uncinaria* spp., *Globocephalus* spp., *Necator* spp., *Metastrongylus* spp., *Muellerius capillaris, Protostrongylus* spp., *Angiostrongylus* spp., *Parelaphostrongylus* spp., *Aleurostrongylus abstrusus*, and *Dioctophyma renale*; Intestinal roundworms (Ascaridida), e.g. *Ascaris lumbricoides, Ascaris suum, Ascaridia galli, Parascaris equorum, Enterobius vermicularis* (Threadworm), *Toxocara canis, Toxascaris leonine, Skrjabinema* spp., and

*Oxyuris equi; Camallanida*, e.g. *Dracunculus medinensis* (guinea worm); Spirurida, e.g. *Thelazia* spp., *Wuchereria* spp., *Brugia* spp., *Onchocerca* spp., *Dirofilari* spp., *Dipetalonema* spp., *Setaria* spp., *Elaeophora* spp., *Spirocerca lupi*, and *Habronema* spp.; Thorny headed worms (Acanthocephala), e.g. *Acanthocephalus* spp., *Macracanthorhynchus hirudinaceus* and *Oncicola* spp.; Planarians (Plathelminthes): Flukes (Trematoda), e.g. *Faciola* spp., *Fascioloides magna, Paragonimus* spp., *Dicrocoelium* spp., *Fasciolopsis buski, Clonorchis sinensis, Schistosoma* spp., *Trichobilharzia* spp., *Alaria alata, Paragonimus* spp., and *Nanocyetes* spp.; Cercomeromorpha, in particular Cestoda (Tapeworms), e.g. *Diphyllobothrium* spp., *Tenia* spp., *Echinococcus* spp., *Dipylidium caninum, Multiceps* spp., *Hymenolepis* spp., *Mesocestoides* spp., *Vampirolepis* spp., *Moniezia* spp., *Anoplocephala* spp., *Sirometra* spp., *Anoplocephala* spp., and *Hymenolepis* spp.

The term "animal" includes warm-blooded animals (including humans) and fish. Preferred are mammals, e.g. cattle, sheep, swine, camels, deer, horses, pigs, poultry, rabbits, goats, dogs and cats, water buffalo, donkeys, fallow deer and reindeer, and also in fur-bearing animals e.g. mink, chinchilla and raccoon, birds e.g. hens, geese, turkeys and ducks and fish e.g. fresh- and salt-water fish e.g. trout, carp and eels. Particularly preferred are domestic animals, e.g. dogs or cats.

Generally, "parasiticidally effective amount" means the amount of active ingredient needed to achieve an observable effect on growth, including the effects of necrosis, death, retardation, prevention, and removal, destruction, or otherwise diminishing the occurrence and activity of the target organism. The parasiticidally effective amount can vary for the various compounds/compositions used in the invention. A parasiticidally effective amount of the compositions will also vary according to the prevailing conditions e.g. desired parasiticidal effect and duration, target species, mode of application.

Generally, it is favorable to apply the compounds of the invention in total amounts of 0.5 mg/kg to 100 mg/kg per day, preferably 1 mg/kg to 50 mg/kg per day.

For oral administration to warm-blooded animals, the compounds I may be formulated as animal feeds, animal feed premixes, animal feed concentrates, pills, solutions, pastes, suspensions, drenches, gels, tablets, boluses and capsules. In addition, the compounds I may be administered to the animals in their drinking water. For oral administration, the dosage form chosen should provide the animal with 0.01 mg/kg to 100 mg/kg of animal body weight per day of the compounds I, preferably with 0.5 mg/kg to 100 mg/kg of animal body weight per day.

Alternatively, the compounds I may be administered to animals parenterally, e.g., by intraruminal, intramuscular, intravenous or subcutaneous injection. The compounds I may be dispersed or dissolved in a physiologically acceptable carrier for subcutaneous injection. Alternatively, the compounds I may be formulated into an implant for subcutaneous administration. In addition the compounds I may be transdermally administered to animals. For parenteral administration, the dosage form chosen should provide the animal with 0.01 mg/kg to 100 mg/kg of animal body weight per day of the compounds I.

The compounds I may also be applied topically to the animals in the form of dips, dusts, powders, collars, medallions, sprays, shampoos, spot-on and pour-on formulations and in ointments or oil-in-water or water-in-oil emulsions. For topical application, dips and sprays usually contain 0.5 ppm to 5,000 ppm and preferably 1 ppm to 3,000 ppm of the compounds I. In addition, the compounds I may be formulated as ear tags for animals, particularly quadrupeds e.g. cattle and sheep.

Suitable preparations are:

- Solutions e.g. oral solutions, concentrates for oral administration after dilution, solutions for use on the skin or in body cavities, pouring-on formulations, gels;
- Emulsions and suspensions for oral or dermal administration; semi-solid preparations;
- Formulations in which the active compound is processed in an ointment base or in an oil-in-water or water-in-oil emulsion base;
- Solid preparations e.g. powders, premixes or concentrates, granules, pellets, tablets, boluses, capsules; aerosols and inhalants, and active compound-containing shaped articles.

Compositions suitable for injection are prepared by dissolving the active ingredient in a suitable solvent and optionally adding further auxiliaries e.g. acids, bases, buffer salts, preservatives, and solubilizers. Suitable auxiliaries for injection solutions are known in the art. The solutions are filtered and filled sterile.

Oral solutions are administered directly. Concentrates are administered orally after prior dilution to the use concentration. Oral solutions and concentrates are prepared according to the state of the art and as described above for injection solutions, sterile procedures not being necessary.

Solutions for use on the skin are trickled on, spread on, rubbed in, sprinkled on or sprayed on. Solutions for use on the skin are prepared according to the state of the art and according to what is described above for injection solutions, sterile procedures not being necessary.

Gels are applied to or spread on the skin or introduced into body cavities. Gels are prepared by treating solutions which have been prepared as described in the case of the injection solutions with sufficient thickener that a clear material having an ointment-like consistency results. Suitable thickeners are known in the art.

Pour-on formulations are poured or sprayed onto limited areas of the skin, the active compound penetrating the skin and acting systemically. Pour-on formulations are prepared by dissolving, suspending or emulsifying the active compound in suitable skin-compatible solvents or solvent mixtures. If appropriate, other auxiliaries e.g. colorants, bioabsorption-promoting substances, antioxidants, light stabilizers, adhesives are added. Suitable such auxiliaries are known in the art.

Emulsions can be administered orally, dermally or as injections. Emulsions are either of the water-in-oil type or of the oil-in-water type. They are prepared by dissolving the active compound either in the hydrophobic or in the hydrophilic phase and homogenizing this with the solvent of the other phase with the aid of suitable emulsifiers and, if appropriate, other auxiliaries e.g. colorants, absorption-promoting substances, preservatives, antioxidants, light stabilizers, viscosity-enhancing substances. Suitable hydrophobic phases (oils), suitable hydrophilic phases, suitable emulsifiers, and suitable further auxiliaries for emulsions are known in the art.

Suspensions can be administered orally or topically/dermally. They are prepared by suspending the active compound in a suspending agent, if appropriate with addition of other auxiliaries e.g. wetting agents, colorants, bioabsorption-promoting substances, preservatives, antioxidants, light stabilizers. Suitable suspending agents, and suitable other auxiliaries for suspensions including wetting agents are known in the art.

Semi-solid preparations can be administered orally or topically/dermally. They differ from the suspensions and emulsions described above only by their higher viscosity.

For the production of solid preparations, the active compound is mixed with suitable excipients, if appropriate with addition of auxiliaries, and brought into the desired form. Suitable auxiliaries for this purpose are known in the art.

The compositions which can be used in the invention can comprise generally from about 0.001 to 95% of the compound of the invention.

Ready-to-use preparations contain the compounds acting against parasites, preferably ectoparasites, in concentrations of 10 ppm to 80% by weight, preferably from 0.1 to 65% by weight, more preferably from 1 to 50% by weight, most preferably from 5 to 40% by weight.

Preparations which are diluted before use contain the compounds acting against ectoparasites in concentrations of 0.5 to 90% by weight, preferably of 1 to 50% by weight.

Furthermore, the preparations comprise the compounds of formula I against endoparasites in concentrations of 10 ppm to 2% by weight, preferably of 0.05 to 0.9% by weight, very particularly preferably of 0.005 to 0.25% by weight.

Topical application may be conducted with compound-containing shaped articles e.g. collars, medallions, ear tags, bands for fixing at body parts, and adhesive strips and foils.

Generally it is favorable to apply solid formulations which release compounds of the invention in total amounts of 10 mg/kg to 300 mg/kg, preferably 20 mg/kg to 200 mg/kg, most preferably 25 mg/kg to 160 mg/kg body weight of the treated animal in the course of three weeks.

EXAMPLES

Synthesis Examples

With appropriate modification of the starting materials, the procedures as described in the preparation examples below were used to obtain further compounds of formula I. The compounds obtained in this manner are listed in the table C that follows, together with physical data.

Compounds can be characterized e.g. by coupled High Performance Liquid Chromatography/mass spectrometry (HPLC/MS), by $^1$H-NMR and/or by their melting points.

Analytical HPLC—Method 1: Agilent Eclipse Plus C18, 50×4.6 mm, ID 5 μm; Elution: A=10 mM Amm. Formate (0.1% Formic Acid), B=Acetonitrile (0.1% Formic Acid), Flow=1.2 ml/min. at 30° C.; Gradient: 10% B to 100% B=3 min, hold for 1 min, 1 min-10% B. Run Time=5.01 min.

Analytical HPLC—Method 2: Kinetex XB C18 1,7μ 50×2.1 mm; A=Water+0.1% TFA, B=Acetonitrile, Flow=0.8 ml/min-1.0 ml/min in 1.5 min. at 60° C.; Gradient: 5% B to 100% B=1.5 min.

Preparative HPLC—Method 3: SunFire C18 5 μm, 50×100 mm; A=Water+2% TFA, B=Acetonitrile, Flow=128 ml/min; Gradient Narrow A: 1% B to 20% in 7.50 min, from 7.50 min to 7.60 min to 96% solvent B.

Preparative HPLC—Method 4: SunFire C18 5 μm, 50×100 mm; A=Water+2% TFA, B=Acetonitrile, Flow=128 ml/min; Gradient LM-Narrow F: 50% B in 7.50 min, 95% to 97% from 7.50 min to 11.0 min.

$^1$H-NMR: The signals are characterized by chemical shift (ppm, δ [delta]) vs. tetramethylsilane respectively, $CDCl_3$ for $^{13}$C-NMR, by their multiplicity and by their integral (relative number of hydrogen atoms given). The following abbreviations are used to characterize the multiplicity of the signals: m=multiplet, q=quartet, t=triplet, d=doublet and s=singlet.

Abbreviations used are: d for day(s), h for hour(s), min for minute(s), r.t./room temperature for 20-25° C., Rt for retention time; DMSO for dimethyl sulfoxide, OAc for acetate, EtOAc for ethyl acetate.

Example C-5

N-[2-[4-[(E)-[(Z)-[3-(2-isopropyl-5-methyl-phenyl)-4-oxo-thiazolidin-2-ylidene]hydrazono]methyl]phenyl]pyrimidin-4-yl]-4-(trifluoromethyl)benzamide (C-5)

Step 1: 4-(4-aminopyrimidin-2-yl)benzaldehyde

A solution of 2-chloropyrimidin-4-amine (1.500 g), (4-formylphenyl)boronic acid (2.328 g), cesium fluoride (1.935 g), palladium acetate (0.130 g), triphenylphosphine-3,3',3''-trisulfonic acid trisodium salt (0.645 g) in acetonitrile/water (1:3, 22 mL) was set under argon atmosphere. The reaction mixture was stirred for 16 h at 100° C. The reaction mixture was cooled down and water was added. The resulting precipitate was filtered and subjected to silica gel flash column chromatography, eluting with a gradient of EtOAc and cyclohexane to obtain the title compound as a solid (2.00 g). HPLC/MS (method 2): Rt: 0.551 min; m/z=199.9 $(M+1)^+$.

Step 2: N-[2-(4-formylphenyl)pyrimidin-4-yl]-4-(trifluoromethyl)benzamide

To solution of 4-(4-aminopyrimidin-2-yl)benzaldehyde (0.700 g) in pyridine (20 mL) 4-(trifluoromethyl)benzoyl chloride (0.832 g) was added at 0° C. After stirring 16 h at room temperature, ethyl acetate (20 mL) was added. The resulting precipitate was was subjected to silica gel flash column chromatography eluting with a gradient of EtOAc and methanol to obtain the title compound as a solid (0.400 g). HPLC/MS (method 2): Rt: 1.143 min; m/z=371.9 $(M+1)^+$.

Step 3: Synthesis of N-[2-[4-[(E)-[(2-isopropyl-5-methyl-phenyl)carbamothioylhydrazono]methyl]phenyl]pyrimidin-4-yl]-4-(trifluoromethyl)benzamide To a solution of N-[2-(4-formylphenyl)pyrimidin-4-yl]-4-(trifluoromethyl)benzamide (0.200 g) in ethanol (5 mL) 1-amino-3-(2-isopropyl-5-methyl-phenyl)thiourea (0.135 g) was added. The reaction mixture was stirred for 5 h at reflux temperature and subsequently stirred for 16 h at room temperature. The reaction mixture was cooled down and the resulting precipitate was filtered and washed with cold ethanol to obtain the title compound as a solid (0.170 g). HPLC/MS (method 2): Rt: 1.457 min; m/z=577.0 $(M+1)^+$. 1H NMR (400 MHz, Acetone-d6) δ 10.80 (s, 1H), 10.48 (s, 1H), 9.65 (s, 1H), 8.86 (d, J=5.5 Hz, 1H), 8.49 (d, J=8.5 Hz, 2H), 8.34 (s, 1H), 8.34-8.30 (m, 2H), 8.25 (d, J=5.6 Hz, 1H), 8.02 (d, J=8.5 Hz, 2H), 7.93 (d, J=8.2 Hz, 2H), 7.30-7.19 (m, 2H), 7.13-7.08 (m, 1H), 3.21 (hept, J=7.0 Hz, 1H), 2.31 (s, 3H), 1.23 (d, J=6.9 Hz, 6H).

Step 4, example C-5: N-[2-[4-[(E)-[(Z)-[3-(2-isopropyl-5-methyl-phenyl)-4-oxo-thiazolidin-2-ylidene]hydrazono]methyl]phenyl]pyrimidin-4-yl]-4-(trifluoromethyl)benzamide N-[2-[4-[(E)-[(2-isopropyl-5-methyl-phenyl)carbamothioylhydrazono]methyl]phenyl]pyrimidin-4-yl]-4-(trifluoromethyl)benzamide (0.100 g) and methyl 2-bromoacetate (0.03 mL) were dissolved in ethanol (3.0 mL) and stirred for and stirred for 4 h at reflux temperature. After stirring 16 h at room temperature, the resulting precipitate was filtered and washed with cold ethanol to obtain the title compound as a solid (0.090 g). HPLC/MS (method 2): Rt: 1.488 min; m/z=617.2 $(M+1)^+$.

Example C-12

N-[6-[4-[(E)-[(2Z)-2-(2-isopropylphenyl)imino-4-oxo-thiazolidin-3-yl]iminomethyl]phenyl]pyrimidin-4-yl]-4-(trifluoromethoxy)benzamide (C-12)

Step 1: 4-(6-aminopyrimidin-4-yl)benzaldehyde

A solution of 6-chloropyrimidin-4-amine (3.500 g), (4-formylphenyl)boronic acid (4.456 g), cesium fluoride (4.514 g), palladium acetate (0.288 g), triphenylphosphine-3,3',3"-trisulfonic acid trisodium salt (0.921 g) in acetonitrile/water (1:3, 100 mL) was set under argon atmosphere. The reaction mixture was stirred for 72 h at 100° C. The reaction mixture was cooled down and methanol was added. The resulting precipitate was removed and the filtrate was concentrated. Methanol was added and the resulted precipitate was subjected to preparative HPLC (Method 3) to obtain the title compound as a solid (2.50 g). HPLC/MS (method 2): Rt: 0.509 min; m/z=199.9 $(M+1)^+$. 1H NMR (400 MHz, DMSO-d6) δ 10.10 (s, 1H), 8.65 (d, J=1.0 Hz, 1H), 8.15-8.06 (m, 4H), 7.97 (s, 2H), 7.02 (d, J=1.0 Hz, 1H).

Step 2: N-[6-(4-formylphenyl)pyrimidin-4-yl]-4-(trifluoromethoxy)benzamide

To solution of 4-(6-aminopyrimidin-4-yl)benzaldehyde (1.200 g) in pyridine (30 mL) 4-(trifluoromethyl)benzoyl chloride (1.550 g) was added at 0° C. After stirring 16 h at room temperature, ethyl acetate was added and the mixture was extracted with brine. The organic phase was dried over sodium sulfate, and the residue obtained was subjected to silica gel flash column chromatography eluting with a gradient of EtOAc and cyclohexane to obtain the title compound as a solid (0.370 g). HPLC/MS (method 2): Rt: 1.22 min; m/z=387.8 $(M+1)^+$. 1H NMR (500 MHz, Methanol-d4) δ 10.10 (s, 1H), 8.99 (d, J=1.2 Hz, 1H), 8.86 (d, J=1.3 Hz, 1H), 8.35-8.30 (m, 2H), 8.16-8.07 (m, 4H), 7.46 (d, J=8.4 Hz, 2H), 7.39-7.34 (m, 2H).

Step 3, example C-12: N-[6-[4-[(E)-[(2Z)-2-(2-isopropylphenyl)imino-4-oxo-thiazolidin-3-yl]iminomethyl]phenyl]pyrimidin-4-yl]-4-(trifluoromethoxy)benzamide N-[6-(4-formylphenyl)pyrimidin-4-yl]-4-(trifluoromethoxy)benzamide (0.100 g) and (2E)-3-amino-2-(2-isopropylphenyl)imino-thiazolidin-4-one (0.071 g) were dissolved in acetic acid (5.0 mL) and stirred for 16 h at room temperature. The mixture was extracted with EtOAc and water. The organic phase was dried over sodium sulfate, and the residue obtained was subjected to preparative HPLC (Method 4) to obtain the title compound as a solid (0.036 g). HPLC/MS (method 2): Rt: 1.489 min; m/z=619.2 (M+1)+. 1H NMR (400 MHz, Chloroform-d) b 8.98 (s, 1H), 8.95 (d, J=1.2 Hz, 1H), 8.84 (d, J=1.2 Hz, 1H), 8.31 (s, 1H), 8.21-8.17 (m, 2H), 8.04-8.00 (m, 2H), 7.89-7.84 (m, 2H), 7.50-7.47 (m, 2H), 7.40-7.31 (m, 3H), 7.17 (dt, J=7.8, 1.0 Hz, 1H), 4.02 (d, J=1.7 Hz, 2H), 2.82 (h, J=6.8 Hz, 1H), 1.23 (t, J=6.9 Hz, 6H).

Example C-13

4-(trifluoromethoxy)-N-[6-[4-[(E)-[(2S,3R,4R,5S,6S)-3,4,5-trimethoxy-6-methyl-tetrahydropyran-2-yl]oxyiminomethyl]phenyl]pyrimidin-4-yl]benzamide (C-13)

N-[6-(4-formylphenyl)pyrimidin-4-yl]-4-(trifluoromethoxy)benzamide (0.100 g) and O-[(2S,3R,4R,5S,6S)-3,4,5-trimethoxy-6-methyl-tetrahydropyran-2-yl]hydroxylamine (0.086 g) were dissolved in ethanol (5.0 mL) and stirred for 4 h at 80° C. and then 16 h at room temperature. The mixture was extracted with EtOAc and brine. The organic phase was dried over sodium sulfate, and the residue obtained was subjected to silica gel flash column chromatography eluting with a gradient of EtOAc and cyclohexane to obtain the title compound as a solid (0.060 g). HPLC/MS (method 2): Rt: 1.344 min; m/z=591 (M+1)+. 1H NMR (400 MHz, Chloroform-d) b 9.46 (s, 1H), 8.88 (dd, J=26.4, 1.2 Hz, 2H), 8.19 (d, J=3.5 Hz, 2H), 8.09-8.03 (m, 2H), 7.76 (d, J=8.4 Hz, 2H), 7.39-7.35 (m, 2H), 5.68 (d, J=2.0 Hz, 1H), 3.76 (dd, J=3.3, 2.0 Hz, 1H), 3.69 (dq, J=9.4, 6.1 Hz, 1H), 3.57 (s, 3H), 3.55 (s, 3H), 3.54 (s, 3H), 3.53-3.44 (m, 2H), 3.21 (t, J=9.4 Hz, 1H), 1.32 (d, J=6.2 Hz, 3H).

By analogous procedures to the procedures described above for example C-5, C-12, C-13 the examples of formula I as listed in Table C were prepared.

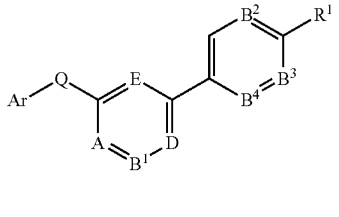

(I)

TABLE C

| Compound | Ar | Q | A | $B^1$ | D | E | $B^2$ | $B^3$ | $B^4$ | $R^1$ | $t_R$, $M^+$ (min; /) |
|---|---|---|---|---|---|---|---|---|---|---|---|
| C-1. | 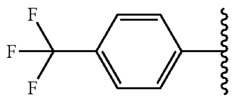 | 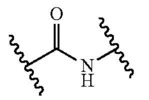 [SMILES: *NC(*)=O] | CH | CH | N | N | CH | CH | CH | 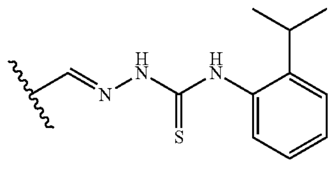 [SMILES: */C=N/NC(=S)Nc1ccccc1C(C)C] | 1.427; 563.2 |

TABLE C-continued
| Compound | Ar | Q | A | $B^1$ | D | E | $B^2$ | $B^3$ | $B^4$ | $R^1$ | $t_R$, $M^+$ (min; /) |
|---|---|---|---|---|---|---|---|---|---|---|---|
| C-2. | 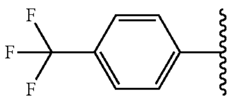 [SMILES: *c1ccc(C(F)(F)F)cc1] | 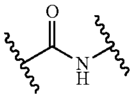 [SMILES: *NC(*)=O] | CH | CH | N | N | CH | CH | CH | 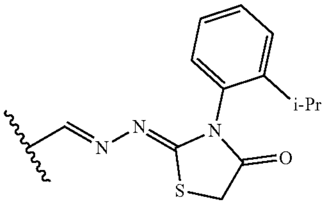 [SMILES: */C=N/N=C1\SCC(=O)N1c1ccccc1C(C)C] | 1.467; 603 |
| C-3. | 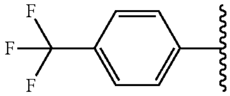 [SMILES: *c1ccc(C(F)(F)F)cc1] | 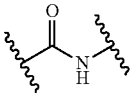 [SMILES: *NC(*)=O] | CH | CH | N | N | CH | CH | CH | 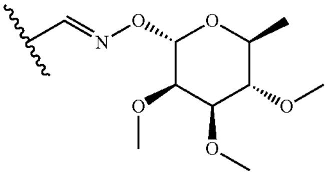 [SMILES: */C=N/O[C@@H]1O[C@@H](C)[C@H](OC)[C@@H](OC)[C@H]1OC] | 1.366; 575 |
| C-4. | 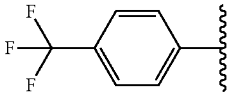 | 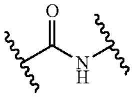 [SMILES: *NC(*)=O] | CH | CH | N | N | CH | CH | CH | 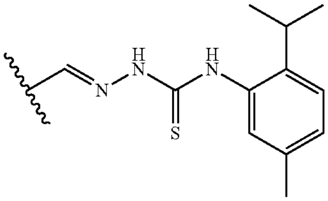 [SMILES: */C=N/NC(=S)Nc1cc(C)ccc1C(C)C] | 1.457; 577 |
| C-5. | 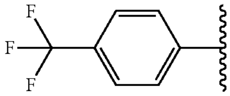 [SMILES: *c1ccc(C(F)(F)F)cc1] | 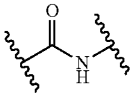 [SMILES: *NC(*)=O] | CH | CH | N | N | CH | CH | CH | 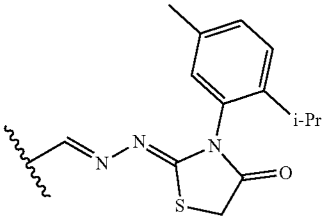 [SMILES: */C=N/N=C1\SCC(=O)N1c1cc(C)ccc1C(C)C] | 1.489; 617 |
| C-6. | 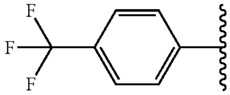 | 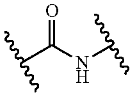 | CH | N | N | CH | CH | CH | CH | 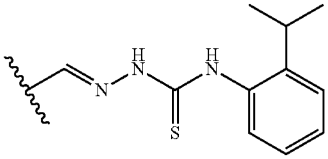 [SMILES: */C=N/NC(=S)Nc1ccccc1C(C)C] | 1.28; 563.2 |
| C-7. | 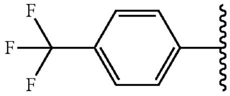 [SMILES: *c1ccc(C(F)(F)F)cc1] | 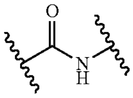 [SMILES: *NC(*)=O] | CH | N | N | CH | CH | CH | CH | 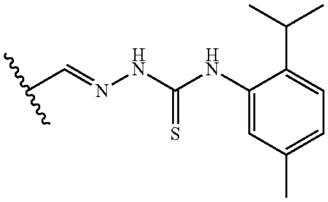 [SMILES: */C=N/NC(=S)Nc1cc(C)ccc1C(C)C] | 1.312; 577 |
| C-8. | 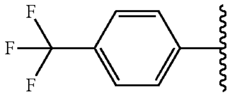 [SMILES: *c1ccc(C(F)(F)F)cc1] | 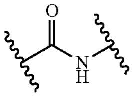 [SMILES: *NC(*)=O] | CH | N | N | CH | CH | CH | CH | 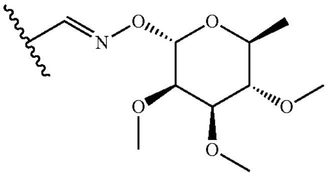 [SMILES: */C=N/O[C@@H]1O[C@@H](C)[C@H](OC)[C@@H](OC)[C@H]1OC] | 1.194; 575 |

TABLE C-continued
| Compound | Ar | Q | A | $B^1$ | D | E | $B^2$ | $B^3$ | $B^4$ | $R^1$ | $t_R$, $M^+$ (min; /) |
|---|---|---|---|---|---|---|---|---|---|---|---|
| C-9. | 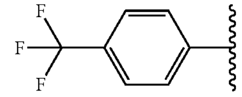 | 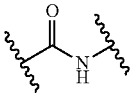 [SMILES: *NC(*)=O] | CH | N | N | CH | CH | CH | CH | 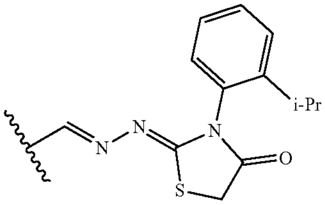 [SMILES: */C=N/N=C1\SCC(=O)N1c1ccccc1C(C)C] | 1.331; 603.2 |
| C-10 | 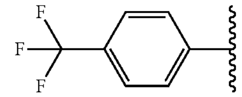 [SMILES: *c1ccc(C(F)(F)F)cc1] | 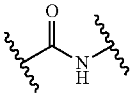 [SMILES: *NC(*)=O] | CH | N | N | CH | CH | CH | CH | 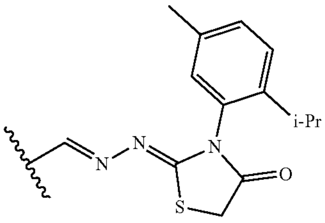 [SMILES: */C=N/N=C1\SCC(=O)N1c1cc(C)ccc1C(C)C] | 1.371; 617 |
| C-11 | 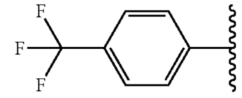 | 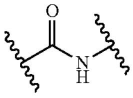 [SMILES: *NC(*)=O] | CH | N | N | CH | CH | CH | CH | 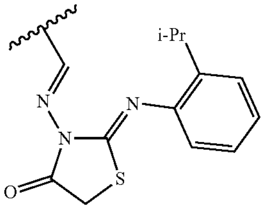 [SMILES: */C=N/N1C(=O)CS/C1=N\c1ccccc1C(C)C] | 1.34; 603.1 |
| C-12 | 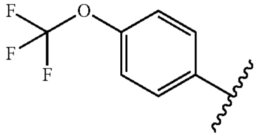 [SMILES: *c1ccc(OC(F)(F)F)cc1] | 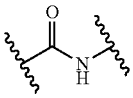 [SMILES: *NC(*)=O] | N | CH | N | CH | CH | CH | CH | 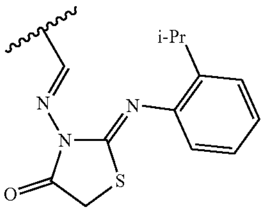 [SMILES: */C=N/N1C(=O)CS/C1=N\c1ccccc1C(C)C] | 1.489; 619.2 |
| C-13 | 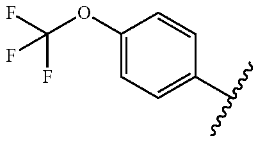 [SMILES: *c1ccc(OC(F)(F)F)cc1] | 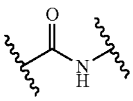 [SMILES: *NC(*)=O] | N | CH | N | CH | CH | CH | CH | 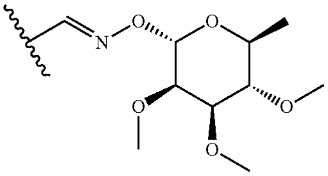 [SMILES: */C=N/O[C@@H]1O[C@@H](C)[C@H](OC)[C@@H](OC)[C@H]1OC] | 1.363; 575 |
| C-14 | 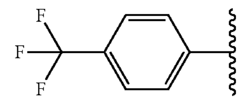 [SMILES: *c1ccc(C(F)(F)F)cc1] | 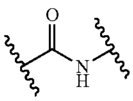 [SMILES: *NC(*)=O] | N | CH | N | CH | CH | CH | CH | 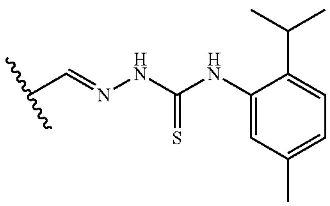 [SMILES: */C=N/NC(=S)Nc1cc(C)ccc1C(C)C] | 1.424; 577 |
| C-15 | 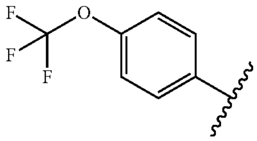 [SMILES: *c1ccc(OC(F)(F)F)cc1] | 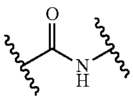 [SMILES: *NC(*)=O] | N | CH | N | CH | CH | CH | CH | 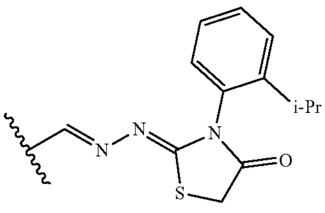 [SMILES: */C=N/N=C1\SCC(=O)N1c1ccccc1C(C)C] | 1.468; 619.1 |

TABLE C-continued
| Compound | Ar | Q | A | $B^1$ | D | E | $B^2$ | $B^3$ | $B^4$ | $R^1$ | $t_R$, $M^+$ (min; /) |
|---|---|---|---|---|---|---|---|---|---|---|---|
| C-16 | 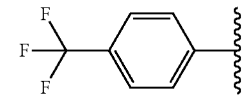 | 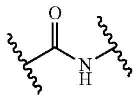 [SMILES: *NC(*)=O] | N | CH | N | CH | CH | CH | CH | 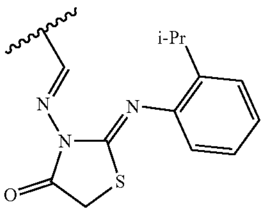 [SMILES: */C=N/N1C(=O)CS/C1=N\c1ccccc1C(C)C] | 1.469; 603.2 |
| C-17 | 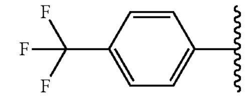 [SMILES: *c1ccc(C(F)(F)F)cc1] | 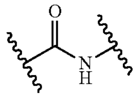 [SMILES: *NC(*)=O] | N | CH | N | CH | CH | CH | CH | 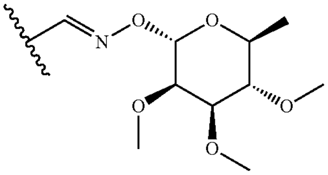 [SMILES: */C=N/O[C@@H]1O[C@@H](C)[C@H](OC)[C@@H](OC)[C@H]1OC] | 1.321; 575 |
| C-18 | 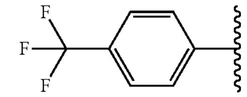 | 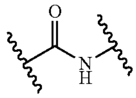 [SMILES: *NC(*)=O] | N | CH | N | CH | CH | CH | CH | 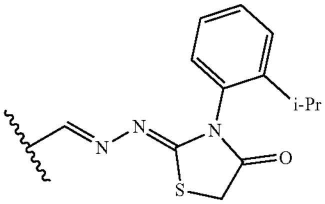 [SMILES: */C=N/N=C1\SCC(=O)N1c1ccccc1C(C)C] | 1.435; 602.9 |
| C-19 | 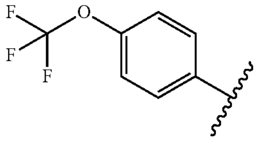 [SMILES: *c1ccc(OC(F)(F)F)cc1] | 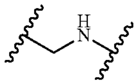 [SMILES: *CN*] | N | CH | N | CH | CH | CH | CH | 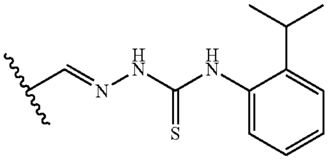 [SMILES: */C=N/NC(=S)Nc1ccccc1C(C)C] | 2.187; 565 |
| C-20 | 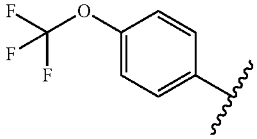 [SMILES: *c1ccc(OC(F)(F)F)cc1] | 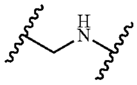 | N | CH | N | CH | CH | CH | CH | 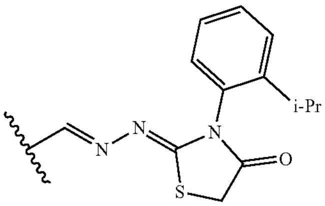 [SMILES: */C=N/N=C1\SCC(=O)N1c1ccccc1C(C)C] | 2.187; 603 |
| C-21 | 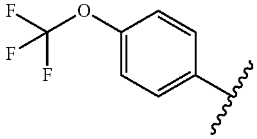 [SMILES: *c1ccc(OC(F)(F)F)cc1] | 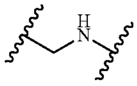 [SMILES: *CN*] | N | CH | N | CH | CH | CH | CH | 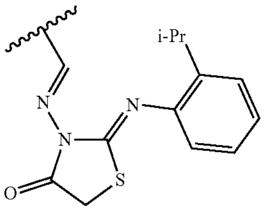 [SMILES: */C=N/N1C(=O)CS/C1=N\c1ccccc1C(C)C] | 2.304; 653.55 |
| C-22 | 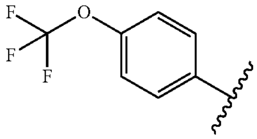 [SMILES: *c1ccc(OC(F)(F)F)cc1] | 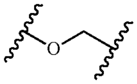 [SMILES: *CO*] | N | CH | N | CH | CH | CH | CH | 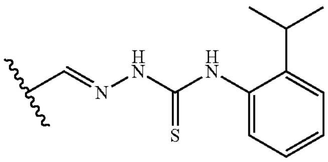 [SMILES: */C=N/NC(=S)Nc1ccccc1C(C)C] | 2.219; 566 |

TABLE C-continued
| Compound | Ar | Q | A | $B^1$ | D | E | $B^2$ | $B^3$ | $B^4$ | $R^1$ | $t_R$, $M^+$ (min; /) |
|---|---|---|---|---|---|---|---|---|---|---|---|
| C-23 | 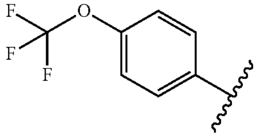 [SMILES: *c1ccc(OC(F)(F)F)cc1] | 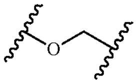 [SMILES: *CO*] | N | CH | N | CH | CH | CH | CH | 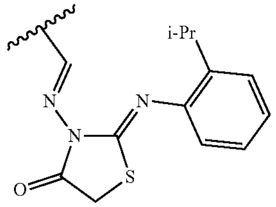 [SMILES: */C=N/N1C(=O)CS/C1=N\c1ccccc1C(C)C] | 2.325; 606 |
| C-24 | 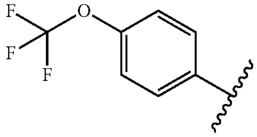 [SMILES: *c1ccc(OC(F)(F)F)cc1] | 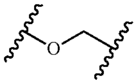 [SMILES: *CO*] | N | CH | N | CH | CH | CH | CH | 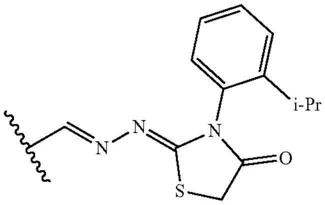 [SMILES: */C=N/N=C1\SCC(=O)N1c1ccccc1C(C)C] | 2.261; 604 |
| C-25 | 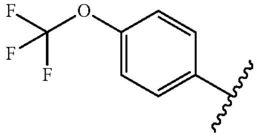 [SMILES: *c1ccc(OC(F)(F)F)cc1] | 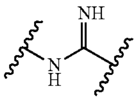 [SMILES: *NC(*)=N] | N | CH | N | CH | CH | CH | CH | 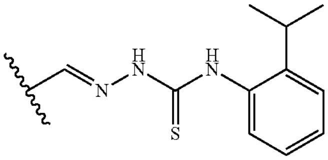 | 2.261; 576 |
| C-26 | 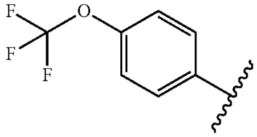 [SMILES: *c1ccc(OC(F)(F)F)cc1] | 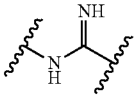 [SMILES: *NC(*)=N] | N | CH | N | CH | CH | CH | CH | 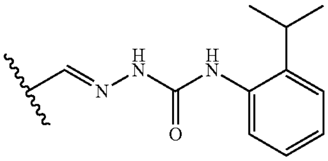 | 2.251; 560 |
| C-27 | 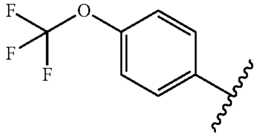 [SMILES: *c1ccc(OC(F)(F)F)cc1] | 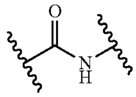 | N | CH | N | CH | CH | CH | CH | 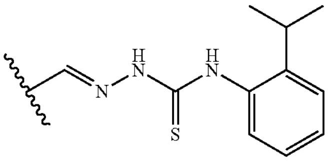 | 2.219; 577 |
| C-28 | 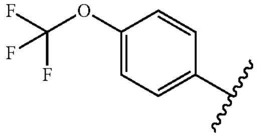 [SMILES: *c1ccc(OC(F)(F)F)cc1] | 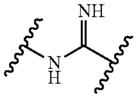 [SMILES: *NC(*)=N] | N | CH | N | CH | CH | CH | CH | 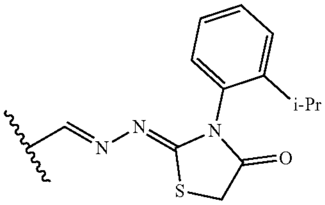 [SMILES: */C=N/N=C1\SCC(=O)N1c1ccccc1C(C)C] | 2.368; 616 |
| C-29 | 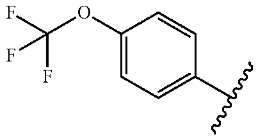 [SMILES: *c1ccc(OC(F)(F)F)cc1] | 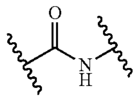 [SMILES: *NC(*)=O] | N | CH | N | CH | CH | CH | CH | 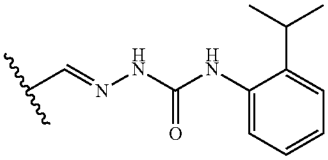 [SMILES: */C=N/NC(=O)Nc1ccccc1C(C)C] | 2.432; 561 |
| C-30 | 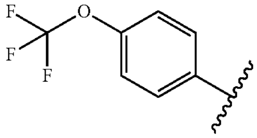 [SMILES: *c1ccc(OC(F)(F)F)cc1] | 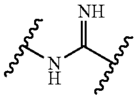 [SMILES: *NC(*)=N] | N | CH | N | CH | CH | CH | CH | 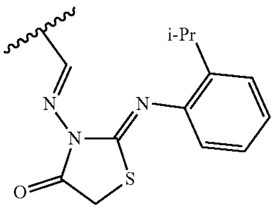 [SMILES: */C=N/N1C(=O)CS/C1=N\c1ccccc1C(C)C] | 2.42; 618 |

TABLE C-continued
| Compound | Ar | Q | A | $B^1$ | D | E | $B^2$ | $B^3$ | $B^4$ | $R^1$ | $t_R$, $M^+$ (min; /) |
|---|---|---|---|---|---|---|---|---|---|---|---|
| C-31 | 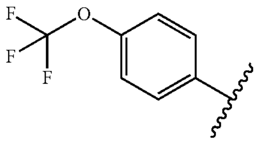 [SMILES: *c1ccc(OC(F)(F)F)cc1] | 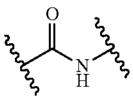 [SMILES: *NC(*)=O] | N | CH | N | CH | CH | CH | CH | 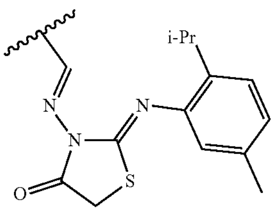 [SMILES: */C=N/N1C(=O)CS/C1=N\c1cc(C)ccc1C(C)C] | 2.432; 633 |
| C-32 | 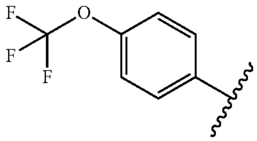 [SMILES: *c1ccc(OC(F)(F)F)cc1] | 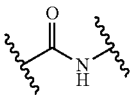 [SMILES: *NC(*)=O] | N | CH | CH | CH | CH | CH | CH | 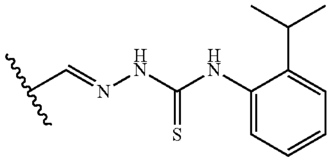 [SMILES: */C=N/NC(=S)Nc1ccccc1C(C)C] | 2.133; 578 |
| C-33 | 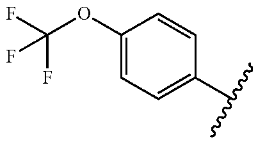 [SMILES: *c1ccc(OC(F)(F)F)cc1] | 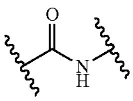 [SMILES: *NC(*)=O] | CH | N | CH | CH | CH | CH | CH | 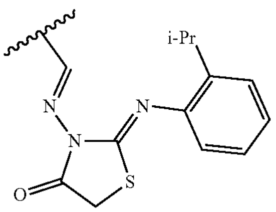 [SMILES: */C=N/N1C(=O)CS/C1=N\c1ccccc1C(C)C] | 2.24; 618 |
| C-34 | 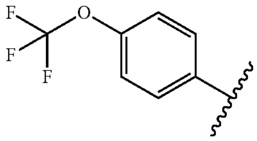 [SMILES: *c1ccc(OC(F)(F)F)cc1] | 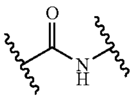 | CH | N | CH | CH | CH | CH | CH | 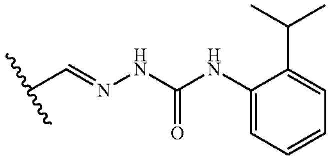 | 2.091; 562 |
| C-35 | 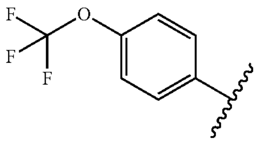 [SMILES: *c1ccc(OC(F)(F)F)cc1] | 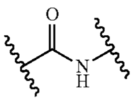 [SMILES: *NC(*)=O] | CH | N | CH | CH | CH | CH | CH | 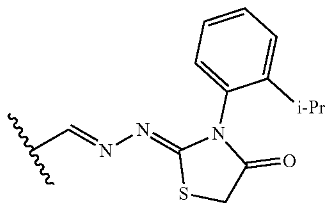 [SMILES: */C=N/N=C1\SCC(=O)N1c1ccccc1C(C)C] | 2.112; 616 |
| C-36 | 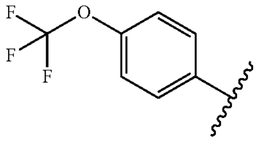 [SMILES: *c1ccc(OC(F)(F)F)cc1] | 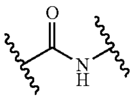 [SMILES: *NC(*)=O] | N | CH | CH | CH | CH | CH | CH | 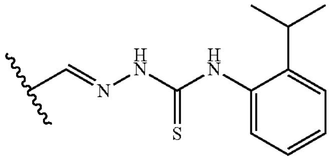 [SMILES: */C=N/NC(=S)Nc1ccccc1C(C)C] | 2.005; 578 |
| C-37 | 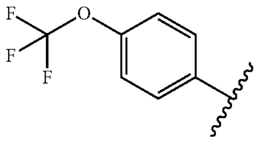 [SMILES: *c1ccc(OC(F)(F)F)cc1] | 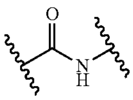 [SMILES: *NC(*)=O] | N | CH | CH | CH | CH | CH | CH | 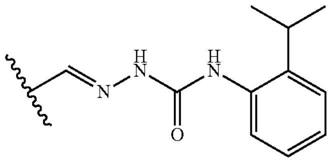 [SMILES: */C=N/NC(=O)Nc1ccccc1C(C)C] | 2.283; 567 |

TABLE C-continued
| Compound | Ar | Q | A | $B^1$ | D | E | $B^2$ | $B^3$ | $B^4$ | $R^1$ | $t_R$, $M^+$ (min; /) |
|---|---|---|---|---|---|---|---|---|---|---|---|
| C-38 | 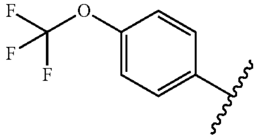 [SMILES: *c1ccc(OC(F)(F)F)cc1] | 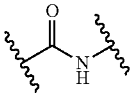 [SMILES: *NC(*)=O] | N | CH | CH | CH | CH | CH | CH | 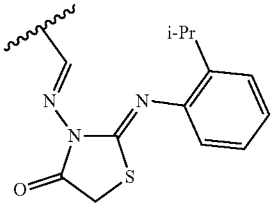 [SMILES: */C=N/N1C(=O)CS/C1=N\c1ccccc1C(C)C] | 2.112; 618 |
| C-39 | 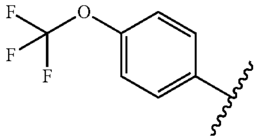 [SMILES: *c1ccc(OC(F)(F)F)cc1] | 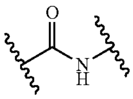 | CH | N | CH | CH | CH | CH | CH | 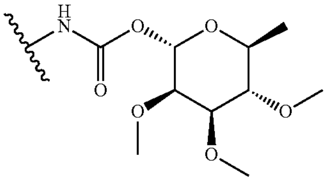 [SMILES: *NC(=O)O[C@@H]1O[C@@H](C)[C@H](OC)[C@@H](OC)[C@H]1OC] | 1.867; 604 |
| C-40 | 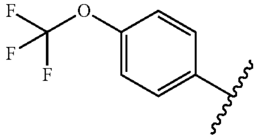 [SMILES: *c1ccc(OC(F)(F)F)cc1] | 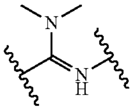 [SMILES: */N=C(/*)N(C)C] | N | CH | N | CH | CH | CH | CH | 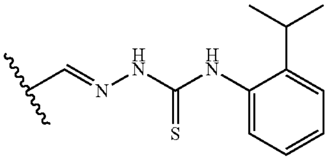 [SMILES: */C=N/NC(=S)Nc1ccccc1C(C)C] | 2.091; 604 |
| C-41 | 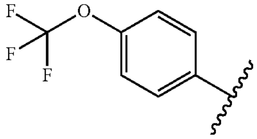 [SMILES: *c1ccc(OC(F)(F)F)cc1] | 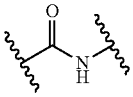 | N | CH | CH | CH | CH | CH | CH | 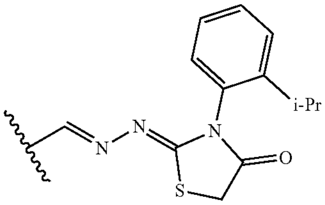 [SMILES: */C=N/N=C1\SCC(=O)N1c1ccccc1C(C)C] | 2.219; 616 |
| C-42 | 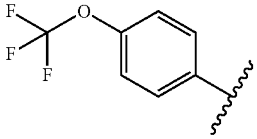 [SMILES: *c1ccc(OC(F)(F)F)cc1] | 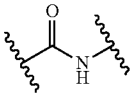 [SMILES: *NC(*)=O] | N | CH | CH | CH | CH | CH | CH | 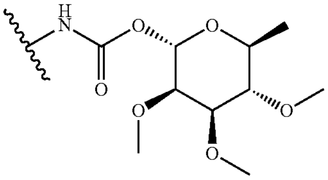 [SMILES: *NC(=O)O[C@@H]1O[C@@H](C)[C@H](OC)[C@@H](OC)[C@H]1OC] | 2.017; 607 |
| C-43 | 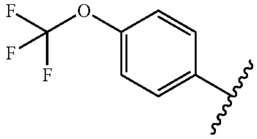 [SMILES: *c1ccc(OC(F)(F)F)cc1] | 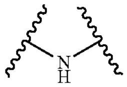 | N | CH | N | CH | CH | CH | CH | 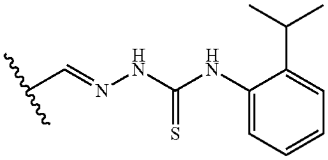 [SMILES: */C=N/NC(=S)Nc1ccccc1C(C)C] | 2.251; 551 |
| C-44 | 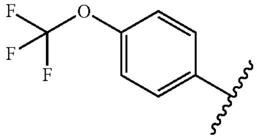 [SMILES: *c1ccc(OC(F)(F)F)cc1] | 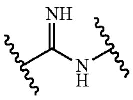 [SMILES: *NC(*)=N] | N | CH | CH | CH | CH | CH | CH | 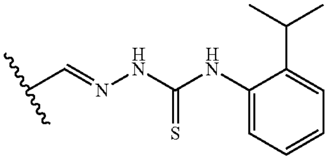 [SMILES: */C=N/NC(=S)Nc1ccccc1C(C)C] | 2.204; 576 |
| C-45 | 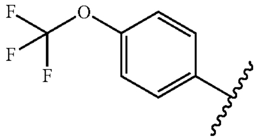 [SMILES: *c1ccc(OC(F)(F)F)cc1] | 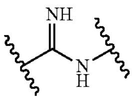 [SMILES: *NC(*)=N] | N | CH | CH | CH | CH | CH | CH | 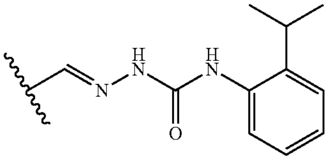 [SMILES: */C=N/NC(=O)Nc1ccccc1C(C)C] | 2.2; 561 |

TABLE C-continued

| Compound | Ar | Q | A | $B^1$ | D | E | $B^2$ | $B^3$ | $B^4$ | $R^1$ | $t_R$, $M^+$ (min; /) |
|---|---|---|---|---|---|---|---|---|---|---|---|
| C-46 | 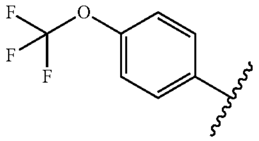 [SMILES: *c1ccc(OC(F)(F)F)cc1] | 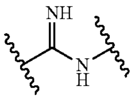 [SMILES: *NC(*)=N] | N | CH | CH | CH | CH | CH | CH | 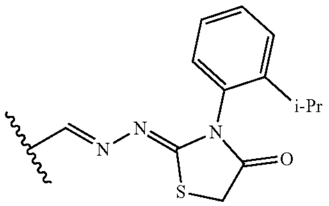 [SMILES: */C=N/N=C1\SCC(=O)N1c1ccccc1C(C)C] | 2.132; 617 |

Biological Examples

If not otherwise specified, the test solutions are prepared as follows:

The active compound is dissolved at the desired concentration in a mixture of 1:1 (vol:vol) distilled water:acetone. The test solution is prepared at the day of use.

Test solutions are prepared in general at concentrations of 1000 ppm, 500 ppm, 300 ppm, 100 ppm and 30 ppm (wt/vol).

B.1. Boll Weevil (*Anthonomus grandis*)

For evaluating control of boll weevil (*Anthonomus grandis*) the test unit consisted of 96-well-microtiter plates containing an insect diet and 5-10 *A. grandis* eggs.

The compounds were formulated using a solution containing 75% v/v water and 25% v/v DMSO. Different concentrations of formulated compounds were sprayed onto the insect diet at 5 μl, using a custom built micro atomizer, at two replications.

After application, microtiter plates were incubated at about 25±1° C. and about 75±5% relative humidity for 5 days. Egg and larval mortality was then visually assessed.

In this test, the following compounds at 2500 ppm showed over 75% mortality in comparison with untreated controls: C-24, C-25, C-26, C-27, C-28, C-29, C-30, C-31.

B.2. Diamond Back Moth (*Plutella xylostella*)

The active compound is dissolved at the desired concentration in a mixture of 1:1 (vol:vol) distilled water:acetone. Surfactant (Alkamuls® EL 620) is added at a rate of 0.1% (vol/vol). The test solution is prepared at the day of use.

Leaves of cabbage were dipped in test solution and air-dried. Treated leaves were placed in petri dish enlined with moist filter paper and inoculated with ten $3^{rd}$ instar larvae. Mortality was recorded 72 hours after treatment. Feeding damages were also recorded using a scale of 0-100%.

In this test, the following compounds at 500 ppm showed over 75% mortality in comparison with untreated controls: C-1, C-2, C-4, C-6, C-7, C-9, C-10, C-11, C-12, C-14, C-15, C-16, C-18, C-19, C-20, C-21, C-22, C-23, C-26, C-27, C-28, C-29, C-30, C-31, C-32, C-33, C-34, C-35, C-36, C-37, C-38, C-40, C-41, C-43, C-44, C-45, C-46.

B.3 Silverleaf Whitefly (*Bemisia argentifolih*) (Adults)

The active compounds were formulated in cyclohexanone as a 10,000 ppm solution supplied in tubes. The tubes were inserted into an automated electrostatic sprayer equipped with an atomizing nozzle and they served as stock solutions for which lower dilutions were made in 50% acetone:50% water (v/v). A non-ionic surfactant (Kinetic®) was included in the solution at a volume of 0.01% (v/v).

Cotton plants at the cotyledon stage (one plant per pot) were sprayed by an automated electrostatic plant sprayer equipped with an atomizing spray nozzle. The plants were dried in the sprayer fume hood and then removed from the sprayer. Each pot was placed into a plastic cup and about 10 to 12 whitefly adults (approximately 3-5 days old) were introduced. The insects were collected using an aspirator and a nontoxic Tygon® tubing connected to a barrier pipette tip. The tip, containing the collected insects, was then gently inserted into the soil containing the treated plant, allowing insects to crawl out of the tip to reach the foliage for feeding. Cups were covered with a reusable screened lid. Test plants were maintained in a growth room at about 25° C. and about 20-40% relative humidity for 3 days, avoiding direct exposure to fluorescent light (24-hour photoperiod) to prevent trapping of heat inside the cup. Mortality was assessed 3 days after treatment, compared to untreated control plants.

In this test, the following compounds at 300 ppm showed over 75% mortality in comparison with untreated controls: C-25.

B.4. Southern Armyworm (*Spodoptera eridania*), 2nd Instar Larvae

The active compounds were formulated in cyclohexanone as a 10,000 ppm solution supplied in tubes. The tubes were inserted into an automated electrostatic sprayer equipped with an atomizing nozzle and they served as stock solutions for which lower dilutions were made in 50% acetone:50% water (v/v). A nonionic surfactant (Kinetic®) was included in the solution at a volume of 0.01% (v/v).

Lima bean plants (variety Sieva) were grown 2 plants to a pot and selected for treatment at the $1^{st}$ true leaf stage. Test solutions were sprayed onto the foliage by an automated electrostatic plant sprayer equipped with an atomizing spray nozzle. The plants were dried in the sprayer fume hood and then removed from the sprayer. Each pot was placed into perforated plastic bags with a zip closure. About 10 to 11 armyworm larvae were placed into the bag and the bags zipped closed. Test plants were maintained in a growth room at about 25° C. and about 20-40% relative humidity for 4 days, avoiding direct exposure to fluorescent light (24 hour photoperiod) to prevent trapping of heat inside the bags. Mortality and reduced feeding were assessed 4 days after treatment, compared to untreated control plants.

In this test, the following compounds at 500 ppm showed over 75% mortality in comparison with untreated controls: C-4, C-7, C-9, C-10, C-11, C-12, C-14, C-15, C-18, C-19, C-20, C-21, C-22, C-23, C-24, C-25, C-26, C-27, C-28, C-30.

B.5. Tobacco Budworm (*Heliothis virescens*)

For evaluating control of tobacco budworm (*Heliothis virescens*) the test unit consisted of 96-well-microtiter plates containing an insect diet and 15-25 *H. virescens* eggs.

The compounds were formulated using a solution containing 75% v/v water and 25% v/v DMSO. Different concentrations of formulated compounds were sprayed onto the insect diet at 10 μl, using a custom built micro atomizer, at two replications.

After application, microtiter plates were incubated at about 28±1° C. and about 80±5% relative humidity for 5 days. Egg and larval mortality was then visually assessed.

In this test, the following compounds at 2500 ppm showed over 75% mortality in comparison with untreated controls: C-1, C-2, C-4, C-5, C-6, C-7, C-8, C-9, C-10, C-11, C-12, C-13, C-14, C-15, C-18, C-19, C-20, C-21, C-22, C-23, C-24, C-25, C-26, C-27, C-28, C-29, C-30, C-31, C-32, C-33, C-34, C-35, C-36, C-37, C-38, C-39, C-40, C-41, C-42, C-43, C-44, C-45, C-46.

B.6. Yellow Fever Mosquito (*Aedes aegypti*)

For evaluating control of yellow fever mosquito (*Aedes aegypti*) the test unit consisted of 96-well-microtiter plates containing 200 μl of tap water per well and 5-15 freshly hatched *A. aegypti* larvae. The active compounds were formulated using a solution containing 75% (v/v) water and 25% (v/v) DMSO. Different concentrations of formulated compounds or mixtures were sprayed onto the insect diet at 2.5 μl, using a custom built micro atomizer, at two replications.

After application, microtiter plates were incubated at 28+1° C., 80+5% RH for 2 days. Larval mortality was then visually assessed.

In this test, the following compounds at 2500 ppm showed over 75% mortality in comparison with untreated controls: C-2, C-4, C-5, C-6, C-7, C-8, C-9, C-10, C-17, C-18, C-20, C-21, C-23, C-24, C-25, C-26, C-27, C-28, C-29, C-30, C-31, C-32, C-33, C-34, C-35, C-36, C-37, C-38, C-39, C-40, C-41, C-42, C-43, C-45, C-46.

B.7. Orchid Thrips (*Dichromothrips corbetti*)

*Dichromothrips corbetti* adults used for bioassay were obtained from a colony maintained continuously under laboratory conditions. For testing purposes, the test compound is diluted in a 1:1 mixture of acetone:water (vol:vol), plus Kinetic® HV at a rate of 0.01% v/v.

Thrips potency of each compound was evaluated by using a floral-immersion technique. All petals of individual, intact orchid flowers were dipped into treatment solution and allowed to dry in Petri dishes. Treated petals were placed into individual re-sealable plastic along with about 20 adult thrips. All test arenas were held under continuous light and a temperature of about 28° C. for duration of the assay. After 3 days, the numbers of live thrips were counted on each petal. The percent mortality was recorded 72 hours after treatment.

In this test, the following compounds at 500 ppm showed over 75% mortality in comparison with untreated controls: C-6, C-7, C-9, C-10, C-11, C-12, C-14, C-15, C-16, C-18, C-22, C-23, C-24, C-25, C-27, C-28, C-30, C-31, C-33, C-34, C-35, C-36, C-38, C-40, C-41, C-44, C-46.

B.9. Western Flower Thrips (*Frankliniella occidentalis*)

The active compounds were formulated by a Tecan liquid handler in 100% cyclohexanone as a 10,000 ppm solution supplied in tubes. The 10,000 ppm solution was serially diluted in 100% cyclohexanone to make interim solutions. These served as stock solutions for which final dilutions were made by the Tecan in 50% acetone:50% water (v/v) into 10 or 20 ml glass vials. A nonionic surfactant (Kinetic®) was included in the solution at a volume of 0.01% (v/v). The vials were then inserted into an automated electrostatic sprayer equipped with an atomizing nozzle for application to plants/insects.

Small (~2" in height) cotton plants are sprayed with test compounds at concentrations ranging from 300 to 0.01 ppm in acetone/water through the automated VPS. After drying, cotton leaves are removed and circular leaf discs (~1 cm diameter) are punched from the treated surface and transferred to clean 20 mL scintillation vials. Ten Western flower thrips (FRANOC) are aspirated into each scintillation vial. The vials with the leaf discs and thrips are kept in an upright incubator at 25° C. and 50% relative humidity with a 14:10 light:dark photoperiod. Each treatment is replicated twice.

Thrips mortality is assessed at 2 DAT (days after treatment), counting all thrips both dead and alive. [The average absolute mortality is calculated for each treatment.]

In this test, the following compounds at 300 ppm showed over 75% mortality in comparison with untreated controls: C-12, C-15, C-18, C-24, C-27, C-28, C-30.

We claim:

1. A compound of the formula I

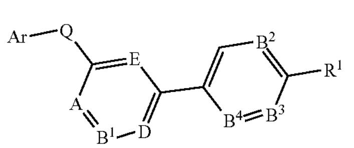

(I)

wherein

A is N or $CR^A$;

$B^1$ is N or $CR^{B1}$;

D is N or $CR^D$;

E is N or $CR^E$;

wherein at least one of the A, $B^1$, E, and D is N; and when A and D are N, $B^1$ is $CR^{B1}$;

$B^2$ is N or $CR^{B2}$;

$B^3$ is N or $CR^{B3}$;

$B^4$ is N or $CR^{B4}$;

provided that at least one of the $B^2$, $B^3$, and $B^4$ is other than N;

$R^A$, $R^D$, $R^{B1}$, and $R^E$ independently of each other are H, halogen, $N_3$, OH, CN, $NO_2$, —SCN, —$SF_5$, $C_1$-$C_6$-alkyl, $C_1$-$C_6$-alkoxy, $C_2$-$C_6$-alkenyl, tri-$C_1$-$C_6$-alkylsilyl, $C_2$-$C_6$-alkynyl, $C_1$-$C_6$-alkoxy-$C_1$-$C_4$-alkyl, $C_1$-$C_6$-alkoxy-$C_1$-$C_4$-alkoxy, $C_3$-$C_6$-cycloalkyl, $C_3$-$C_6$-cycloalkoxy, $C_3$-$C_6$-cycloalkyl-$C_1$-$C_4$-alkyl, $C_1$-$C_4$-alkyl-$C_3$-$C_6$-cycloalkoxy, which moieties are unsubstituted or substituted with halogen, C(═O)—$OR^a$, $NR^bR^c$, $C_1$-$C_6$-alkylene-$NR^bR^c$, O-$C_1$-$C_6$-alkylene-$NR^bR^c$, $C_1$-$C_6$-alkylene-CN, NH-$C_1$-$C_6$-alkylene-$NR^bR^c$, C(═O)—$NR^bR^c$, C(═O)—$R^d$, $SO_2NR^bR^c$, or $S(═O)_mR^e$, phenyl, phenoxy, phenylcarbonyl, phenylthio, or —$CH_2$-phenyl, wherein the phenyl rings are unsubstituted or substituted with $R^f$;

$R^{B2}$, $R^{B3}$, and $R^{B4}$ independently of each other are H, halogen, $N_3$, OH, CN, $NO_2$, —SCN, —$SF_5$, $C_1$-$C_6$-alkyl, $C_1$-$C_6$-alkoxy, $C_2$-$C_6$-alkenyl, tri-$C_1$-$C_6$-alkylsilyl, $C_2$-$C_6$-alkynyl, $C_1$-$C_6$-alkoxy-$C_1$-$C_4$-alkyl, $C_1$-$C_6$-alkoxy-$C_1$-$C_4$-alkoxy, $C_3$-$C_6$-cycloalkyl, $C_3$-$C_6$-cycloalkoxy, $C_3$-$C_6$-cycloalkyl-$C_1$-$C_4$-alkyl, $C_1$-$C_4$-alkyl-$C_3$-$C_6$-cycloalkoxy, which moieties are unsubstituted or substituted with halogen, C(═O)—$OR^a$, $NR^bR^c$, $C_1$-$C_6$-alkylene-$NR^bR^c$, O-$C_1$-$C_6$-alkylene-$NR^bR^c$, $C_1$-$C_6$-alkylene-CN, NH-$C_1$-$C_6$-alkylene-$NR^bR^c$, C(═O)—$NR^bR^c$, C(═O)—$R^d$, $SO_2NR^bR^c$, or $S(═O)_mR^e$, phenyl, phenoxy, phenylcarbonyl, phenylthio, or —$CH_2$-phenyl, wherein the phenyl rings are unsubstituted or substituted with $R^f$;

Q is —$C(R^4R^5)$—O—, —C(═O)—O—, —$S(═O)_m$—$C(R^7R^8)$—, —$N(R^2)$—$S(═O)_m$—, —$N(R^2)$—C $(R^9R^{10})$—, —C(=O)—C($R^{19}R^{20}$)—, —N($R^2$)—, —N($R^2$)—C(=O)—, —N($R^2$)—C(=S)—, —C($R^{13}R^{14}$)—C($R^{15}R^{16}$)—, —N=C(X)—, —N($R^2$)—C(=NR)—, or —C($R^{17}$)=C($R^{18}$)—; wherein Ar is bound to either side of Q;

m is 0, 1, or 2;

X is H, halogen, $SR^7$, $OR^8$, or $N(R^8)_2$;

R is H, CN, $C_1$-$C_6$-alkyl, $C_2$-$C_6$-alkenyl, $C_2$-$C_6$-alkynyl, or $C_3$-$C_6$-cycloalkyl, which moieties are unsubstituted or substituted with halogen, $OR^8$, $N(R^3)_2$;

$R^3$ is H, $C_1$-$C_6$-alkyl, $C_1$-$C_6$-alkoxy-$C_1$-$C_4$-alkyl;

$R^2$ is H, $C_1$-$C_6$-alkyl, $C_2$-$C_6$-alkenyl, $C_2$-$C_6$-alkynyl, $C_1$-$C_6$-alkoxy-$C_1$-$C_4$-alkyl, $C_3$-$C_6$-cycloalkyl, $C_3$-$C_6$-cycloalkyl-$C_1$-$C_4$-alkyl, $C_3$-$C_6$-cycloalkoxy-$C_1$-$C_4$-alkyl, which moieties are unsubstituted or substituted with halogen C(=O)—$OR^a$, $C_1$-$C_6$-alkylene-$NR^bR^c$, $C_1$-$C_6$-alkylene-CN, C(=O)—$NR^bR^c$, C(=O)—$R^d$, $SO_2NR^bR^c$, $S(=O)_mR^e$, phenyl, or —$CH_2$-phenyl, wherein the phenyl rings are unsubstituted or substituted with $R^f$;

$R^4$, $R^5$, $R^7$, $R^8$, $R^9$, $R^{10}$, $R^{13}$, $R^{14}$, $R^{15}$, $R^{16}$, $R^{17}$, $R^{18}$, $R^{19}$, $R^{20}$ are, identical or different, H, halogen, $C_1$-$C_6$-alkyl, $C_2$-$C_6$-alkenyl, $C_2$-$C_6$-alkynyl, $C_1$-$C_6$-alkoxy-$C_1$-$C_4$-alkyl, $C_3$-$C_6$-cycloalkyl, $C_3$-$C_6$-cycloalkyl-$C_1$-$C_4$-alkyl, $C_3$-$C_6$-cycloalkoxy-$C_1$-$C_4$-alkyl, which moieties are unsubstituted or substituted with halogen, C(=O)—$OR^a$, $C_1$-$C_6$-alkylene-$NR^bR^c$, $C_1$-$C_6$-alkylene-CN, C(=O)—$NR^bR^c$, C(=O)—$R^d$, $SO_2NR^bR^c$, $S(=O)_mR^e$, phenyl, or —$CH_2$-phenyl, wherein the phenyl rings are unsubstituted or substituted with $R^f$;

Ar is phenyl or 5- or 6-membered hetaryl or 1,3-benzodioxole, which are unsubstituted or substituted with $R^{Ar}$, wherein $R^{Ar}$ is halogen, $N_3$, OH, CN, $NO_2$, —SCN, —$SF_5$, $C_1$-$C_6$-alkyl, $C_1$-$C_6$-alkoxy, $C_2$-$C_6$-alkenyl, tri-$C_1$-$C_6$-alkylsilyl, $C_2$-$C_6$-alkynyl, $C_1$-$C_6$-alkoxy-$C_1$-$C_4$-alkyl, $C_1$-$C_6$-alkoxy-$C_1$-$C_4$-alkoxy, $C_3$-$C_6$-cycloalkyl, $C_3$-$C_6$-cycloalkoxy, $C_3$-$C_6$-cycloalkyl-$C_1$-$C_4$-alkyl, $C_3$-$C_6$-cycloalkoxy-$C_1$-$C_4$-alkyl, which moieties are unsubstituted or substituted with halogen, C(=O)—$OR^a$, $NR^bR^c$, $C_1$-$C_6$-alkylene-$NR^bR^c$, O—$C_1$-$C_6$-alkylene-$NR^bR^c$, $C_1$-$C_6$-alkylene-CN, NH—$C_1$-$C_6$-alkylene-$NR^bR^c$, C(=O)—$NR^bR^c$, C(=O)—$R^d$, $SO_2NR^bR^c$, or $S(=O)_mR^e$, phenyl, phenoxy, phenylcarbonyl, phenylthio or —$CH_2$-phenyl, wherein phenyl rings are unsubstituted or substituted with $R^f$;

$R^1$ is a moiety of formula Y—Z—T—$R^{11}$ or Y—Z—T—$R^{12}$; wherein

Y is —$CR^{ya}$=N—, wherein the N is bound to Z;
—$NR^{yc}$—C(=O)—, wherein C(=O) is bound to Z; or
—$NR^{yc}$—C(=S)—, wherein C(=S) is bound to Z;

Z is a single bond;
—$NR^{zc}$—C(=O)—, wherein C(=O) is bound to T;
—$NR^{zc}$—C(=S)—, wherein C(=S) is bound to T;
—N=C(S—$R^{za}$)—, wherein T is bound to the carbon atom;
—O—C(=O)—, wherein T is bound to the carbon atom; or
—$NR^{zc}$—C(S—$R^{za}$)=, wherein T is bound to the carbon atom;

Provided that when Y is —$NR^{yc}$—C(=O)— or —$NR^{yc}$—C(=S)—, then Z is other than a single bond;

T is O, N or N—$R^T$;

$R^{11}$ is $C_1$-$C_6$-alkyl, $C_2$-$C_6$-alkenyl, $C_2$-$C_6$-alkynyl, $C_1$-$C_6$-alkoxy-$C_1$-$C_4$-alkyl, $C_3$-$C_6$-cycloalkyl, $C_3$-$C_6$-cycloalkyl-$C_1$-$C_4$-alkyl, $C_1$-$C_4$-alkyl-$C_3$-$C_6$-cycloalkoxy, which moieties are unsubstituted or substituted with halogen, $C_1$-$C_6$-alkylene-$NR^bR^c$, $C_1$-$C_6$-alkylene-CN, C(=O)—$NR^bR^c$, C(=O)—$R^d$, aryl, aryl-carbonyl, aryl-$C_1$-$C_4$-alkyl, aryloxy-$C_1$-$C_4$-alkyl, hetaryl, carbonyl-hetaryl, hetaryl-$C_1$-$C_4$-alkyl or hetaryloxy-$C_1$-$C_4$-alkyl, wherein the phenyl and hetaryl rings are unsubstituted or substituted with $R^g$ and wherein the hetaryl is a 5- or 6-membered monocyclic hetaryl or a 8-, 9- or 10-membered bicyclic hetaryl;

$R^{12}$ is a radical of the formula $A^1$;

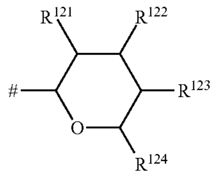
($A^1$)

wherein # indicates the point of attachment to T;

$R^{121}$, $R^{122}$, $R^{123}$are, identical or different, H, halogen, $C_1$-$C_6$-alkyl, $C_2$-$C_6$-alkenyl, $C_2$-$C_6$-alkynyl, $C_1$-$C_6$-alkoxy-$C_1$-$C_4$-alkyl, $C_1$-$C_6$-alkoxy, $C_2$-$C_6$-alkenyloxy, $C_2$-$C_6$-alkynyloxy, $C_1$-$C_6$-alkoxy-$C_1$-$C_4$-alkoxy, $C_1$-$C_6$-alkylcarbonlyoxy, $C_1$-$C_6$-alkenylcarbonlyoxy, $C_3$-$C_6$-cycloalkylcarbonlyoxy, which moieties are unsubstituted or substituted with halogen, or $NR^bR^c$, or one of $R^{121}$, $R^{122}$, $R^{123}$ may also be oxo;

$R^{124}$ is H, $C_1$-$C_6$-alkyl, $C_1$-$C_6$-alkoxy-$C_1$-$C_4$-alkyl, $C_1$-$C_6$-alkoxy, or $C_2$-$C_6$-alkenyloxy, which moieties are unsubstituted or substituted with halogen;

and where $R^{ya}$ is H, halogen, $C_1$-$C_6$-alkyl, $C_1$-$C_6$-alkoxy, $C_2$-$C_6$-alkenyl, $C_2$-$C_6$-alkynyl, $C_1$-$C_6$-alkoxy-$C_1$-$C_4$-alkyl, $C_3$-$C_6$-cycloalkyl, $C_1$-$C_4$-alkyl-$C_3$-$C_6$-cycloalkyl, $C_1$-$C_4$-alkyl-$C_3$-$C_6$-cycloalkoxy, which moieties are unsubstituted or substituted with halogen, C(=O)—$OR^a$, $C_1$-$C_6$-alkylene-$NR^bR^c$, $C_1$-$C_6$-alkylene-CN, C(=O)—$NR^bR^c$, C(=O)—$R^d$, $SO_2NR^bR^c$, $S(=O)_mR^e$, phenyl, or —$CH_2$-phenyl, wherein the phenyl rings are unsubstituted or substituted with $R^f$;

$R^{yc}$, $R^{zc}$ are, identical or different, H, $C_1$-$C_6$-alkyl, $C_2$-$C_6$-alkenyl, $C_2$-$C_6$-alkynyl, $C_1$-$C_4$-alkyl-$C_1$-$C_6$-alkoxy, $C_3$-$C_6$-cycloalkyl, $C_1$-$C_4$-alkyl-$C_3$-$C_6$-cycloalkyl, or $C_1$-$C_4$-alkyl-$C_3$-$C_6$-cycloalkoxy, which moieties are unsubstituted or substituted with halogen;

$R^T$ is H, $C_1$-$C_6$-alkyl, $C_2$-$C_6$-alkenyl, $C_2$-$C_6$-alkynyl, $C_1$-$C_4$-alkyl-$C_1$-$C_6$-alkoxy, $C_3$-$C_6$-cycloalkyl, $C_3$-$C_6$-cycloalkyl-$C_1$-$C_4$-alkyl, $C_3$-$C_6$-cyclo-alkoxy-$C_1$-$C_4$-alkyl, which moieties are unsubstituted or substituted with halogen, C(=O)—$OR^a$, $C_1$-$C_6$-alkylene-$NR^bR^c$, $C_1$-$C_6$-alkylene-CN, C(=O)—$NR^bR^c$, C(=O)—$R^d$, $SO_2NR^bR^c$, $S(=O)_mR^e$, phenyl, or —$CH_2$-phenyl, wherein the phenyl rings are unsubstituted or substituted with $R^f$;

$R^{zc}$ together with $R^T$ if present, may form $C_1$-$C_6$-alkylene or a linear $C_2$-$C_6$-alkenylene group, where in the linear $C_1$-$C_6$-alkylene and the linear $C_2$-$C_6$-alkenylene a $CH_2$ moiety may be replaced by a carbonyl or a C═N—R' and/or wherein 1 or 2 $CH_2$ moieties may be replaced by O or S and/or wherein the linear $C_1$-$C_6$-alkylene and the linear $C_2$-$C_6$-alkenylene may be unsubstituted or substituted with $R^h$;

$R^{za}$ is H, $C_1$-$C_6$-alkyl, $C_1$-$C_6$-alkoxy, $C_2$-$C_6$-alkenyl, tri-$C_1$-$C_6$-alkylsilyl, $C_2$-$C_6$-alkynyl, $C_1$-$C_4$-alkyl-$C_1$-$C_6$-alkoxy, $C_3$-$C_6$-cycloalkyl, $C_1$-$C_4$-alkyl-$C_3$-$C_6$-cycloalkoxy, $C_1$-$C_4$-alkyl-$C_3$-$C_6$-cycloalkyl, which moieties are unsubstituted or substituted with halogen, $C_1$-$C_6$-alkylene-$NR^bR^c$, $C_1$-$C_6$-alkylene-CN, C(═O)—$NR^bR^c$, C(═O)—$R^d$, phenyl, phenylcarbonyl, or —$CH_2$-phenyl, wherein the phenyl rings are unsubstituted or substituted with $R^f$;

$R^{za}$ together with $R^T$ if present, may form $C_1$-$C_6$-alkylene or a linear $C_2$-$C_6$-alkenylene group, where in the linear $C_1$-$C_6$-alkylene and the linear $C_2$-$C_6$-alkenylene a $CH_2$ moiety may be replaced by a carbonyl or a C═N-R' and/or wherein 1 or 2 $CH_2$ moieties may be replaced by O or S and/or wherein the linear $C_1$-$C_6$-alkylene and the linear $C_2$-$C_6$-alkenylene may be unsubstituted or substituted with $R^h$;

$R^a$, $R^b$ and $R^c$ are, identical or different, H, $C_1$-$C_6$-alkyl, $C_2$-$C_6$-alkenyl, $C_2$-$C_6$-alkynyl, $C_1$-$C_6$-alkoxy-$C_1$-$C_4$-alkyl, $C_3$-$C_6$-cycloalkyl, $C_3$-$C_6$-cycloalkyl-$C_1$-$C_4$-alkyl, $C_3$-$C_6$-cycloalkoxy-$C_1$-$C_4$-alkyl, which moieties are unsubstituted or substituted with halogen, $C_1$-$C_6$-alkylene-CN, phenyl, or —$CH_2$-phenyl, wherein the phenyl rings are unsubstituted or substituted with $R^f$;

$R^d$ is H, $C_1$-$C_6$-alkyl, $C_2$-$C_6$-alkenyl, $C_2$-$C_6$-alkynyl, $C_1$-$C_6$-alkoxy-$C_1$-$C_4$-alkyl, $C_3$-$C_6$-cycloalkyl, $C_3$-$C_6$-cycloalkyl-$C_1$-$C_4$-alkyl, $C_3$-$C_6$-cyclo-alkoxy-$C_1$-$C_4$-alkyl, which moieties are unsubstituted or substituted with halogen, phenyl, or —$CH_2$-phenyl, wherein the phenyl rings are unsubstituted or substituted with $R^f$;

$R^e$ is $C_1$-$C_6$-alkyl, $C_3$-$C_6$-cycloalkyl, $C_3$-$C_6$-cycloalkyl-$C_1$-$C_4$-alkyl, which moieties are unsubstituted or substituted with halogen, phenyl and —$CH_2$-phenyl, wherein the phenyl rings are unsubstituted or substituted with $R^f$;

$R^f$ is halogen, $N_3$, OH, CN, $NO_2$, —SCN, —$SF_5$, $C_1$-$C_6$-alkyl, $C_1$-$C_6$-alkoxy, $C_2$-$C_6$-alkenyl, tri-$C_1$-$C_6$-alkylsilyl, $C_2$-$C_6$-alkynyl, $C_1$-$C_6$-alkoxy-$C_1$-$C_4$-alkyl, $C_1$-$C_6$-alkoxy-$C_1$-$C_4$-alkoxy, $C_3$-$C_6$-cycloalkyl, $C_3$-$C_6$-cycloalkoxy, $C_3$-$C_6$-cycloalkyl-$C_1$-$C_4$-alkyl, $C_3$-$C_6$-cycloalkoxyx-$C_1$-$C_4$-alkyl, which moieties are unsubstituted or substituted with halogen, C(═O)—$OR^a$, $NR^bR^c$, $C_1$-$C_6$-alkylene-$NR^bR^c$, O—$C_1$-$C_6$-alkylene-$NR^bR^c$, $C_1$-$C_6$-alkylene-CN, NH—$C_1$-$C_6$-alkylene-$NR^bR^c$, C(═O)—$NR^bR^c$, C(═O)—$R^d$, $SO_2NR^bR^c$, or $S(═O)_mR^e$;

$R^g$ is halogen, $N_3$, OH, CN, $NO_2$, —SCN, —$SF_5$, $C_1$-$C_6$-alkyl, $C_1$-$C_6$-alkoxy, $C_2$-$C_6$-alkenyl, tri-$C_1$-$C_6$-alkylsilyl, $C_2$-$C_6$-alkynyl, $C_1$-$C_6$-alkoxy-$C_1$-$C_4$-alkyl, $C_1$-$C_6$-alkoxy-$C_1$-$C_4$-alkoxy, $C_3$-$C_6$-cycloalkyl, $C_3$-$C_6$-cycloalkoxy, $C_3$-$C_6$-cycloalkyl-$C_1$-$C_4$-alkyl, $C_3$-$C_6$-cycloalkoxy-$C_1$-$C_4$-alkyl, which moieties are unsubstituted or substituted with halogen, C(═O)—$OR^a$, $NR^bR^c$, $C_1$-$C_6$-alkylene-$NR^bR^c$, O—$C_1$-$C_6$-alkylene-$NR^bR^c$, $C_1$-$C_6$-alkylene-CN, NH—$C_1$-$C_6$-alkylene-$NR^bR^c$, C(═O)—$NR^bR^c$, C(═O)—$R^d$, $SO_2NR^bR^c$, or $S(═O)_mR^e$;

$R^h$ is halogen, OH, $C_1$-$C_6$-alkyl, $C_3$-$C_6$-cycloalkyl, or CN;

and the N-oxides, stereoisomers, tautomers, and agriculturally or veterinarily acceptable salts thereof.

2. The compound of formula I according to claim 1, wherein A is N.

3. The compound of formula I according to claim 1, wherein A and D are N.

4. The compound of formula I according to claim 1, wherein $B^1$ is N.

5. The compound of formula I according to claim 1, wherein $B^1$ and D are N.

6. The compound of formula I according to claim 1, wherein E and D are N.

7. The compound of formula I according to claim 1, wherein Q is —C($R^4R^5$)—O—, —N($R^2$)—C($R^9R^{10}$)—, —N($R^2$)—, —N($R^2$)—C(═O)—, —N═C(X)—, or —N($R^2$)—C(═NR)—; wherein Ar is bound to either side of Q.

8. The compound of formula I according to claim 1, wherein $R^1$ are formulas YZT-1 to YZT-9,  wherein denotes attachment to the remaining part of the compound;

YZT-1

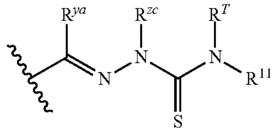

YZT-2

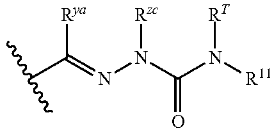

YZT-3

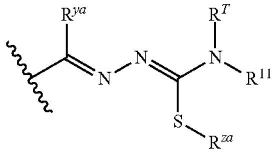

YZT-4

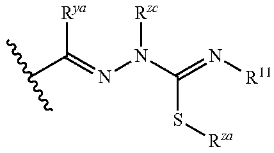

YZT-5

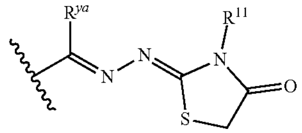

YZT-6

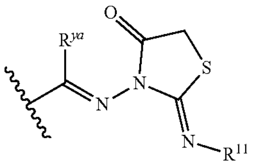

YZT-8

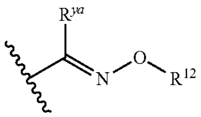

-continued
YZT-9
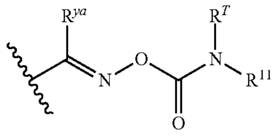
wherein $R^{11}$, $R^{12}$, $R^T$, $R^{ya}$, $R^{yc}$, $R^{za}$ and $R^{zc}$ are as defined in claim 1.
9. The compound of formula I according to claim 1, wherein Ar is a formula Ar-1 to Ar-22
Ar-1
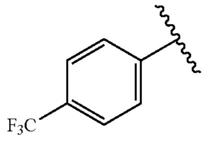
Ar-2
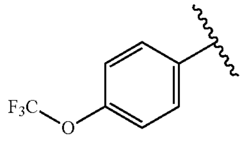
Ar-3
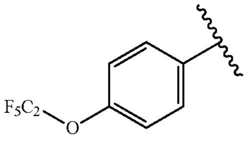
Ar-4
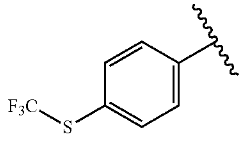
Ar-5
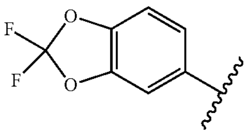
Ar-6
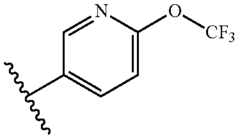
Ar-7
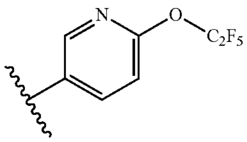
Ar-8
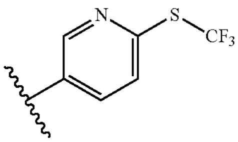
-continued
Ar-9
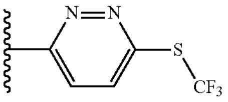
Ar-10
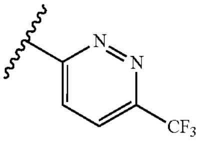
Ar-11
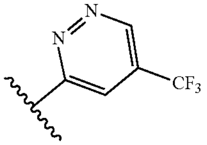
Ar-12
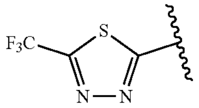
Ar-13
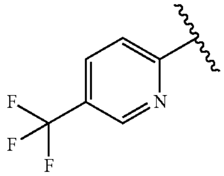
Ar-14
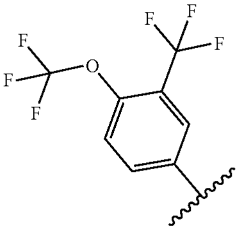
Ar-15
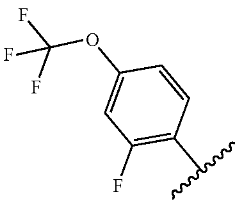
Ar-16
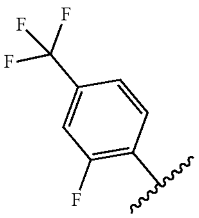

-continued

Ar-17

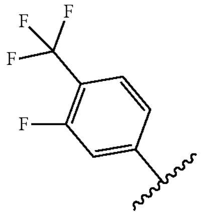

Ar-18

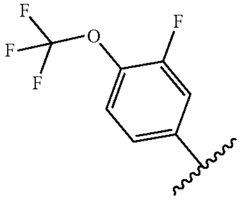

Ar-19

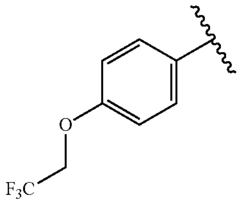

Ar-20

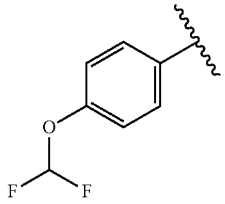

-continued

Ar-21

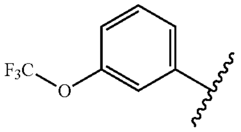

Ar-22

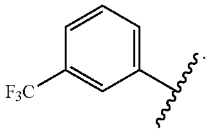

10. A composition, comprising a compound of formula I according to claim 1, an N-oxide or an agriculturally acceptable salt thereof, and a further active substance.

11. A method for combating or controlling invertebrate pests, comprising contacting said pest or its food supply, habitat or breeding grounds with a pesticidally effective amount of at least one compound according to claim 1.

12. A method for protecting growing plants from attack or infestation by invertebrate pests, which method comprises contacting a plant, or soil or water wherein the plant is growing, with a pesticidally effective amount of at least one compound according to claim 1.

13. A seed comprising a compound according to claim 1, or the enantiomers, diastereomers or salts thereof, in an amount of from 0.1 g to 10 kg per 100 kg of seed.

14. A method for treating or protecting an animal from infestation or infection by invertebrate pests comprising bringing the animal in contact with a pesticidally effective amount of at least one compound of the formula I according to claim 1, a stereoisomer thereof and/or at least one veterinarily acceptable salt thereof.

* * * * *